US012486254B2

(12) United States Patent
Rodzinak et al.

(10) Patent No.: US 12,486,254 B2
(45) Date of Patent: Dec. 2, 2025

12
(54) URACIL DERIVATIVES FOR STIMULATING READ-THROUGH OF PREMATURE TERMINATION CODONS

(71) Applicants: Southern Research Institute, Birmingham, AL (US); UAB Research Foundation, Birmingham, AL (US)

(72) Inventors: Kevin Jay Rodzinak, Moody, AL (US); Terry Smalley, Greensboro, NC (US); Robert Hunter, Garner, NC (US); John P. Tillotson, Birmingham, AL (US); Corinne E. Augelli-Szafran, Homewood, AL (US); Bini Mathew, Hoover, AL (US); David Bedwell, Hoover, AL (US); Steven Rowe, Birmingham, AL (US)

(73) Assignees: SOUTHERN RESEARCH INSTITUTE, Birmingham, AL (US); UAB RESEARCH FOUNDATION, Birmingham, AL (US)

( * ) Notice: Subject to any disclaimer, the term of this patent is extended or adjusted under 35 U.S.C. 154(b) by 1 day.

(21) Appl. No.: 18/114,977

(22) Filed: Feb. 27, 2023

(65) Prior Publication Data

US 2023/0416231 A1 Dec. 28, 2023

Related U.S. Application Data

(60) Provisional application No. 63/314,145, filed on Feb. 25, 2022.

(51) Int. Cl.

*C07D 403/06* (2006.01)
*C07D 403/14* (2006.01)
*C07D 409/14* (2006.01)
*C07D 413/14* (2006.01)
*C07D 417/14* (2006.01)

(52) U.S. Cl.

CPC ......... *C07D 403/06* (2013.01); *C07D 403/14* (2013.01); *C07D 409/14* (2013.01); *C07D 413/14* (2013.01); *C07D 417/14* (2013.01)

(58) Field of Classification Search

CPC .............. A61K 2300/00; A61K 31/137; A61K 31/443; A61K 31/505; A61K 31/506; A61K 31/522; A61K 45/06; C07D 239/545; C07D 401/06; C07D 401/12; C07D 401/14; C07D 403/06; C07D 403/14; C07D 409/06; C07D 409/14; C07D 413/14; C07D 417/14

See application file for complete search history.

(56) References Cited

U.S. PATENT DOCUMENTS

2003/0199533 A1 10/2003 Curry

OTHER PUBLICATIONS

Pranke et. al. (Factors influencing readthrough therapy for frequent cystic fibrosis premature termination codons, Cystic Fibrosis, ERJ Open Res 2018, 4) (Year: 2017).*

CAS Registry File (790266-16-9, obtained from the internet Sep. 30, 2024, entered into STN Nov. 29, 2004) (Year: 2004).*

Smith et. al. ("Identification of Compounds That Promote Readthrough of Premature Termination Codons in the CFTR", SLAS Discovery, 26(2)) (Year: 2021).*

Bedwell, D. M., et al. (1997). Suppression of a CFTR premature stop mutation in a bronchial epithelial cell line. Nature medicine, 3(11), 1280-1284.

Clancy JP, et al. No detectable improvements in cystic fibrosis transmembrane conductance regulator by nasal aminoglycosides in patients with cystic fibrosis with stop mutations. (2007) Am J Respir Cell Mol Biol ;37:57-66.

Clancy, J. P., et al. (2001). Evidence that systemic gentamicin suppresses premature stop mutations in patients with cystic fibrosis. American journal of respiratory and critical care medicine, 163(7), 1683-1692.

Howard, M., Frizzell, R. & Bedwell, D. Aminoglycoside antibiotics restore CFTR function by overcoming premature stop mutations. Nat Med 2, 467-469 (1996).

Kerem, E., et al. Cystic Fibrosis Ataluren Study Group (2014). Ataluren for the treatment of nonsense-mutation cystic fibrosis: a randomised, double-blind, placebo-controlled phase 3 trial. The Lancet. Respiratory medicine, 2(7), 539-547.

PubChem-SID-111294171, Modify Date: Mar. 6, 2011 (Mar. 6, 2011), p. 2, figure.

PubChem-SID-366949150, Modify Date: May 25, 2018 (May 25, 2018), p. 2, figure.

PubChem-SID-379933795, Modify Date: Jun. 3, 2019 (Jun. 3, 2019), p. 2, figure.

Sermet-Gaudelus, I., et al. (2007) In vitroprediction of stop-codon suppression by intravenous gentamicin in patients with cystic fibrosis: a pilot study. BMC Med 5, 5.

(Continued)

*Primary Examiner* — Jeffrey H Murray
*Assistant Examiner* — Daniel John Burkett
(74) *Attorney, Agent, or Firm* — Ballard Spahr LLP

(57) ABSTRACT

The present disclosure is concerned with substituted uracil compounds, pharmaceutical compositions comprising the compounds, and methods of treating disorders associated with the presence of a premature termination codon such as, for example, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer, using the compounds. This abstract is intended as a scanning tool for purposes of searching in the particular art and is not intended to be limiting of the present invention.

2 Claims, 2 Drawing Sheets

(56) References Cited

OTHER PUBLICATIONS

Sloane, P. A., & Rowe, S. M. (2010). Cystic fibrosis transmembrane conductance regulator protein repair as a therapeutic strategy in cystic fibrosis. Current opinion in pulmonary medicine, 16(6), 591-597.
Welsh, M. J., & Smith, A. E. (1993). Molecular mechanisms of CFTR chloride channel dysfunction in cystic fibrosis. Cell, 73(7), 1251-1254.
Wilschanski M, et al. (2000) A pilot study of the effect of gentamicin on nasal potential difference measurements in cystic fibrosis patients carrying stop mutations. Am J Respir Crit Care Med. 161:860-865.
Wilschanski, M.; et al. (2003) Gentamicin-Induced Correction of CFTR Function in Patients with Cystic Fibrosis and CFTR Stop Mutations. N. Engl. J. Med. , 349, 1433-1441.

* cited by examiner

URACIL DERIVATIVES FOR STIMULATING READ-THROUGH OF PREMATURE TERMINATION CODONS

CROSS-REFERENCE TO RELATED APPLICATIONS

This Application claims the benefit of U.S. Application No. 63/314,145, filed on Feb. 25, 2022, the contents of which are incorporated herein by reference in their entirety.

STATEMENT REGARDING FEDERALLY SPONSORED RESEARCH

This invention was made with government support under DK072482 awarded by the National Institutes of Health. The government has certain rights in the invention.

STATEMENT REGARDING SPONSORED RESEARCH

Background

Cystic fibrosis (CF) is an autosomal recessive disorder caused by mutations in the gene encoding the CF transmembrane conductance regulator (CFTR), an anion channel primarily localized to the apical membranes of secretory epithelial cells lining the airways and multiple organs. Among the most common mutation class, premature termination codons (PTCs) in CFTR lead to translation termination due to an in-frame nonsense mutation in the coding sequence, resulting in nonfunctional CFTR protein (Welsh et al. (1993) *Cell* 73: 1251-1254). PTCs are the proximate cause of ~11% of CF causing alleles and many other genetic diseases (Sloane et al. (2010) *Current opinion in pulmonary medicine* 16: 591-7).

Efforts to develop treatments for CF patients with nonsense mutations have focused on strategies to promote termination suppression (also known as translational read-through) of PTCs. Translational read-through is accomplished when an amino acid carried by near-cognate aminoacyl tRBA is inserted into a polypeptide chain at the erroneous stop codon, allowing translation to continue, and partially restoring full-length, functional protein (Bedwell et al. (1997) *Nat Med* 3: 1280-1284; Howard et al. (1996) *Nat Med* 2: 467-469). Several pharmacologic approaches to induce read-through have been discovered, yet none has yielded an optimal combination of efficacy and safety. For instance, in vitro work has demonstrated that certain aminoglycosides can promote read-through and have been tested in clinical trials with mixed results (Clancy et al. (2001) *Am J Respir Crit Care Med* 163: 1683-1692; Clancy et al. (2007) *Am J Respir Cell Mol Biol* 37: 57-66; Wilschanski et al. (2003) *N Engl J Med* 349: 1433-1441; Wilschanki et al. (2000) *Am J Respir Crit Care Med* 161: 860-865; Sermet-Gaudelus et al. (2007) *BMC Med* 5: 5), but are not well-suited for long-term use. Synthetic aminoglycoside derivatives optimized for translation suppression of the eukaryotic ribosome have exhibited improved read-through and reduced toxicity when compared in vitro. Ataluren (formerly PTC 124) is an orally bioavailable small molecule that induces read-through. In a subset analysis, ataluren demonstrated a modest treatment bebefit in CF patients not using chronic inhalaed tobramycin, which interferes with its effect (Kerem et al. (2014) *Lancet Respir Med* 2: 539-47), a finding currently under prospective evaluation.

Despite the significance of premature termination mutations in CF, as well as in other genetic diseases and cancers, pharmacological strategies specific to these mutations has remained elusive. Thus, there remains a need for a compounds and compositions to stimulate read-through of premature termination codons, and methods of making and using same. These needs and others are met by the present invention.

SUMMARY

In accordance with the purpose(s) of the invention, as embodied and broadly described herein, the invention, in one aspect, relates to substituted uracil compounds, pharmaceutical compositions containing the compounds, and methods of using the compounds in, for example, the prevention and treatment of disorders associated with the presence of a premature termination codon such as, for example, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer.

Thus, in one aspect, disclosed are compounds having a structure represented by a formula:

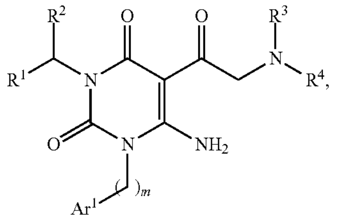

wherein m is 1 or 2; wherein $R^1$ is selected from C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein each occurrence of $R^{10a}$, when present, is independently selected from hydrogen and C1-C4 alkyl; wherein each occurrence of $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein each of $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O (C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

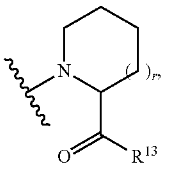

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when $R^4$ is —$(CR^{10a}R^{10b})_nC(O)R^{11}$, —$CH(R^{12})Ar^2$ or $Ar^2$, or when $R^3$ and $R^4$ together comprise a heterocycle having a structure represented by a formula:

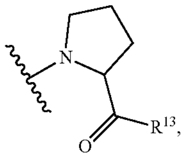

then $R^1$ is $Cy^1$ or $R^1$ and $R^2$ together comprise a C3-C6 cycloalkyl or a C3-C6 heterocycloalkyl, and provided that when $R^1$ is C1-C3 alkyl, $R^3$ and $R^4$ together comprise a heterocycle having a structure represented by a formula:

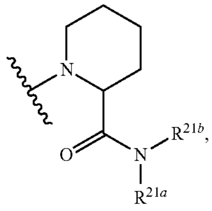

and $Ar^1$ is phenyl, then either (i) $Ar^1$ is substituted with at least one non-hydrogen group; or (ii) at least one of $R^{21a}$ and $R^{21b}$ is hydrogen, or a pharmaceutically acceptable salt thereof.

Also disclosed are compounds selected from:

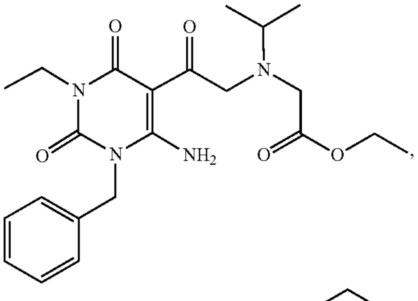

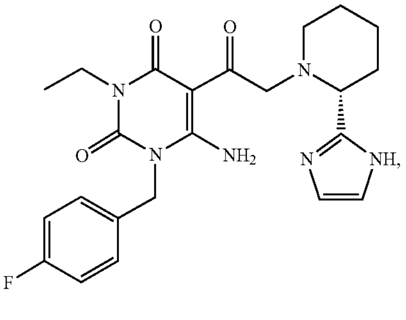

-continued
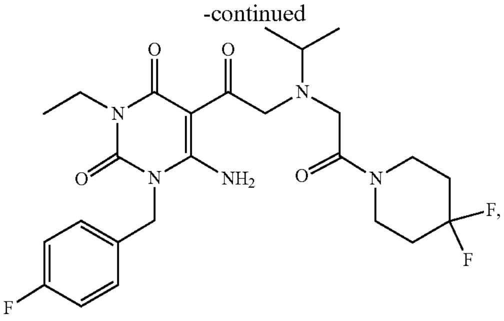
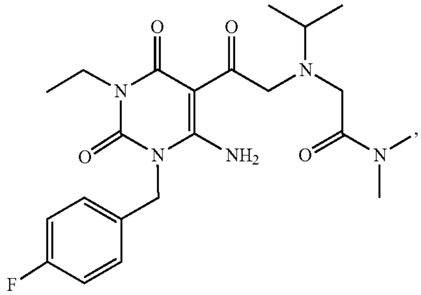
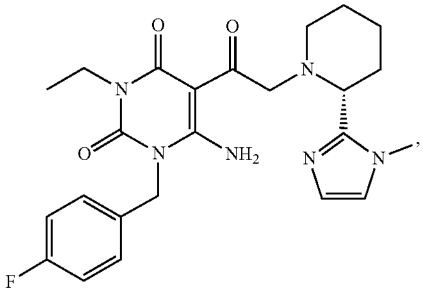
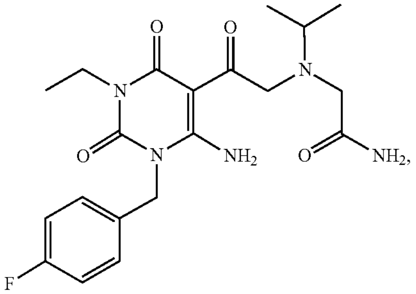
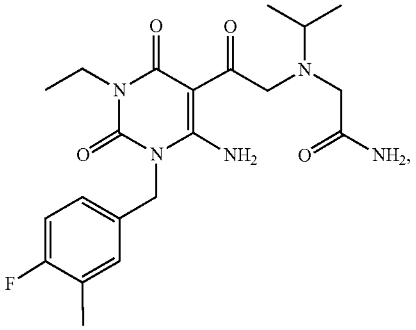
-continued
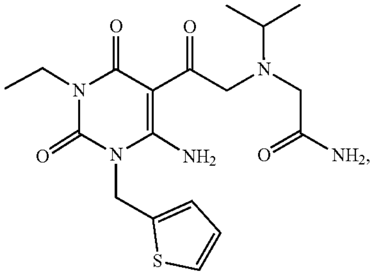
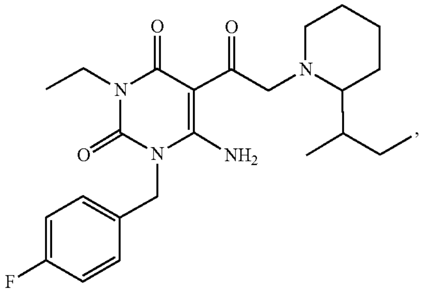
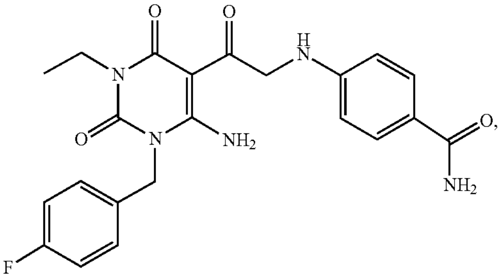
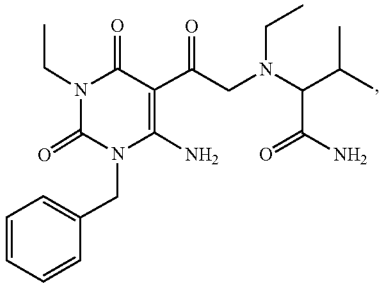
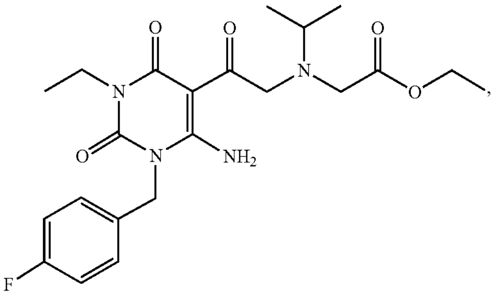
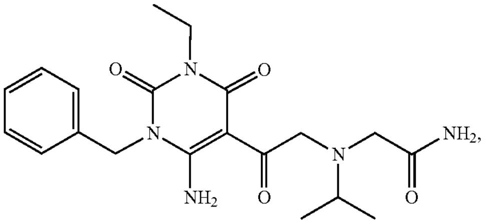

-continued
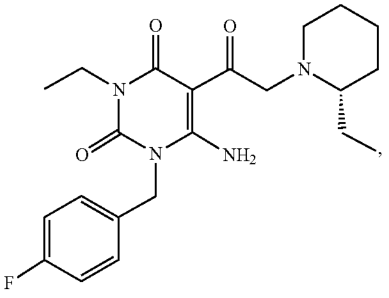
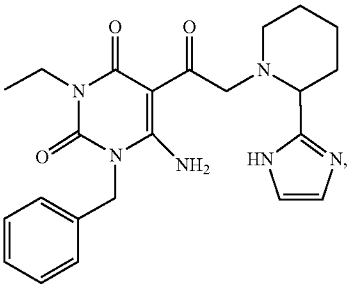
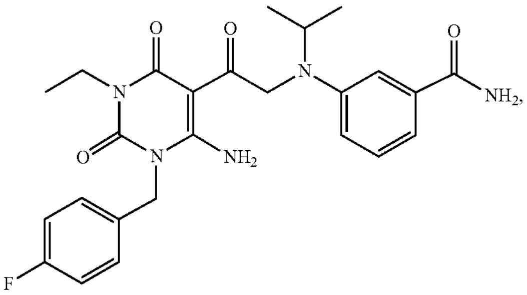
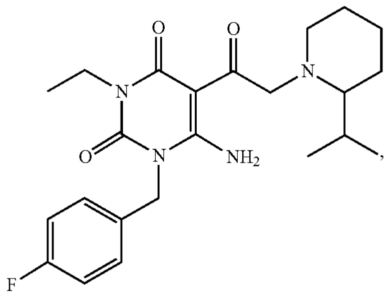
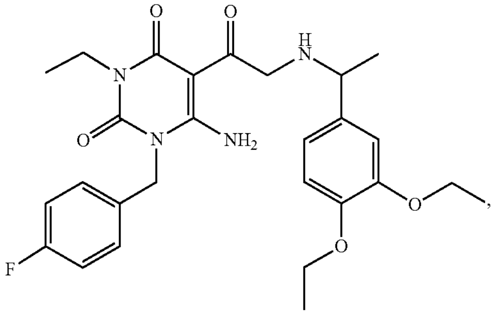
-continued
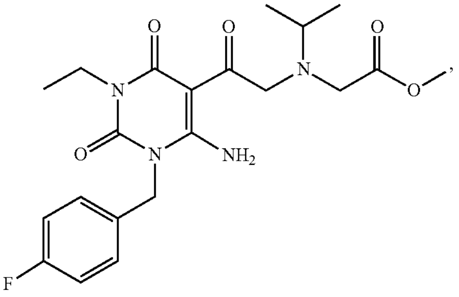
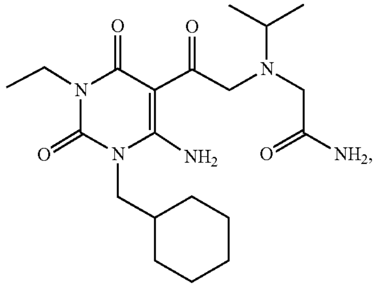
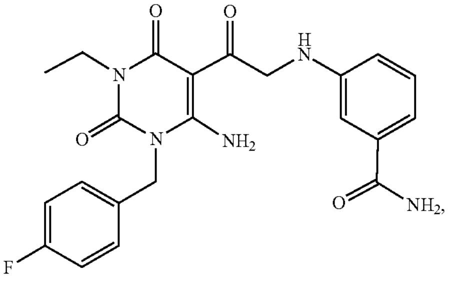
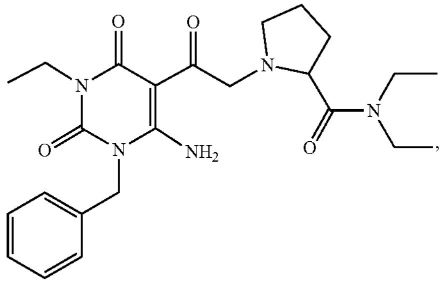
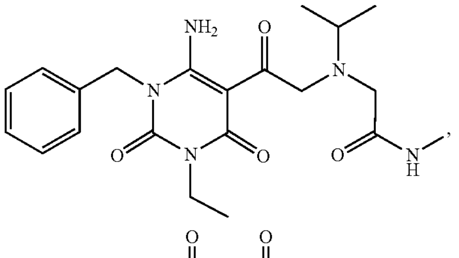
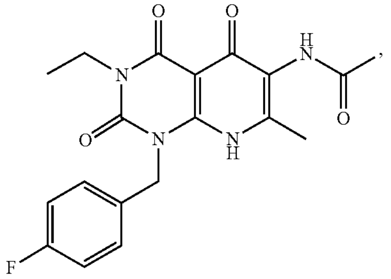

-continued
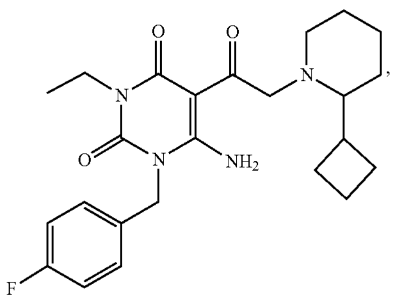
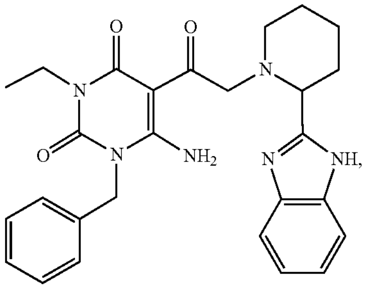
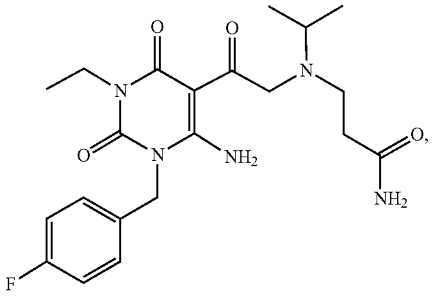
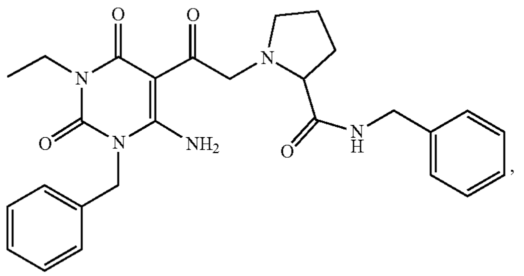
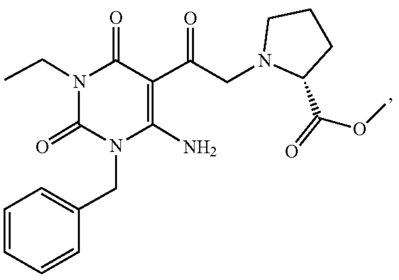
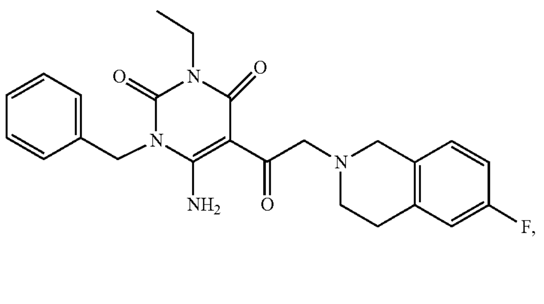
-continued
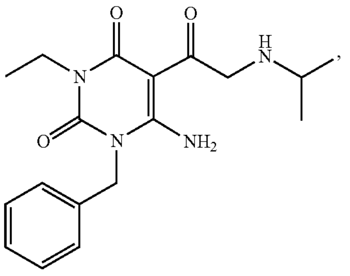
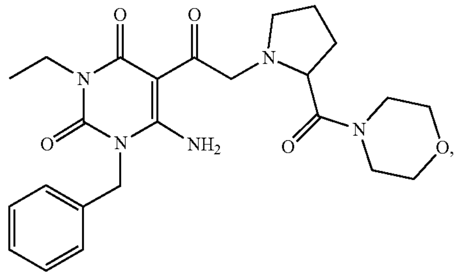
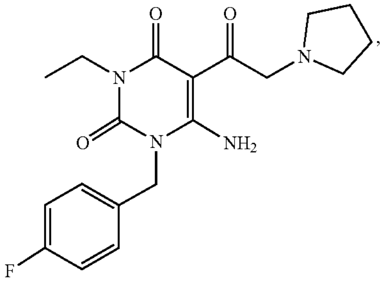
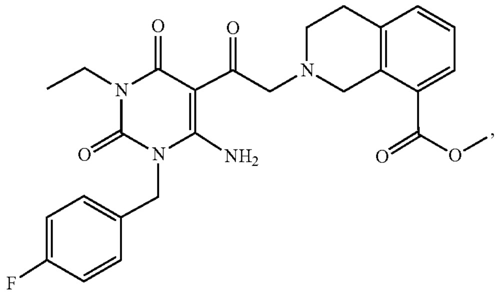
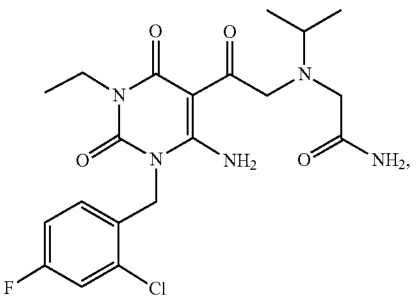
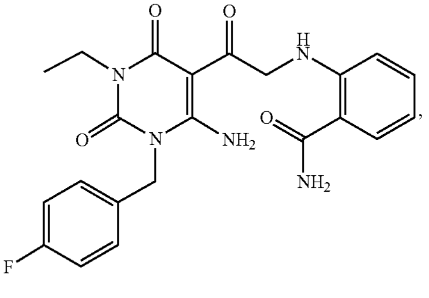

-continued
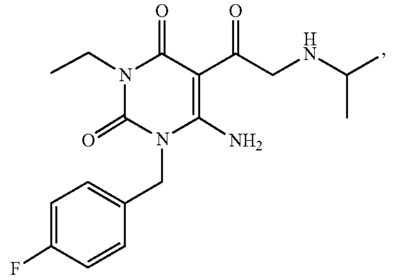
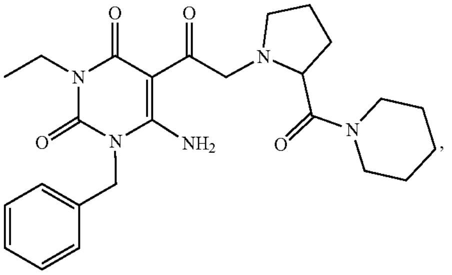
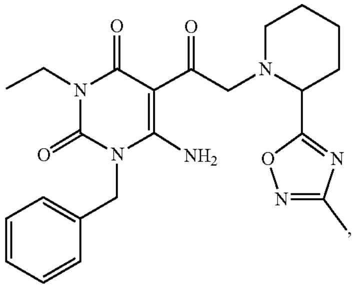
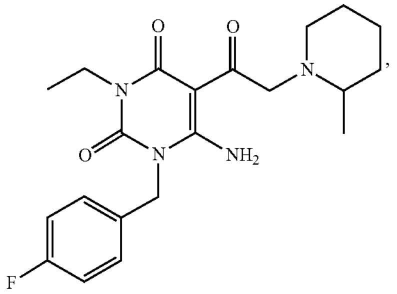
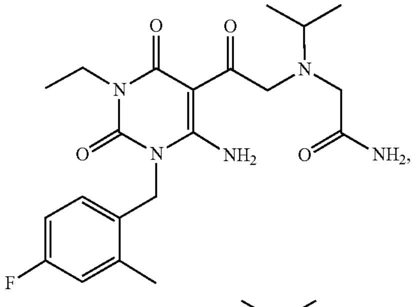
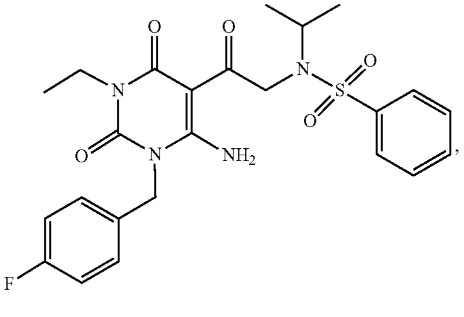
-continued
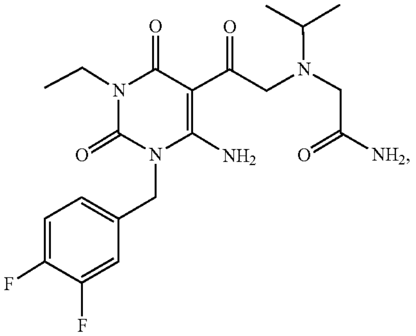
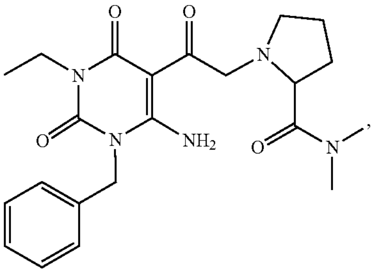
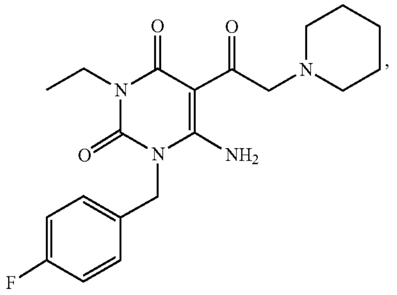
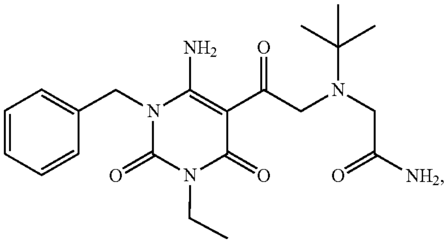
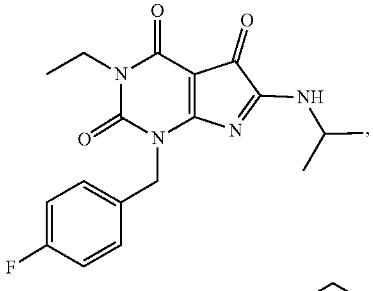
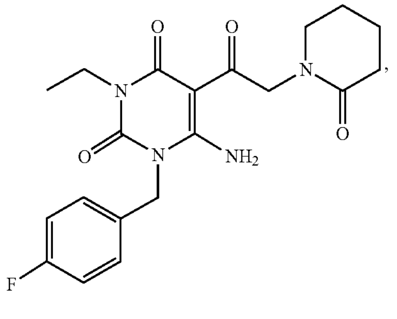

-continued
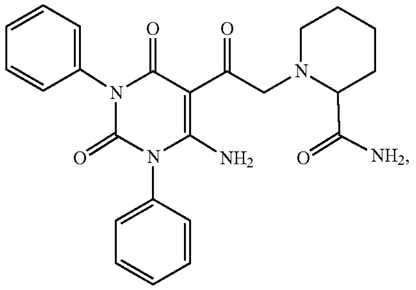
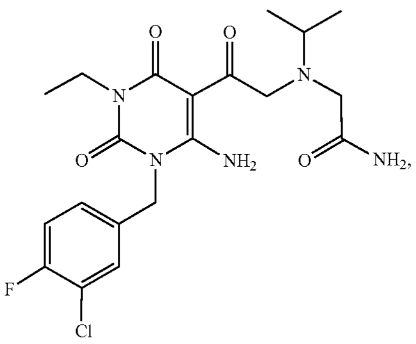
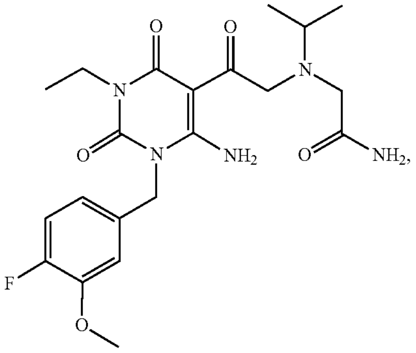
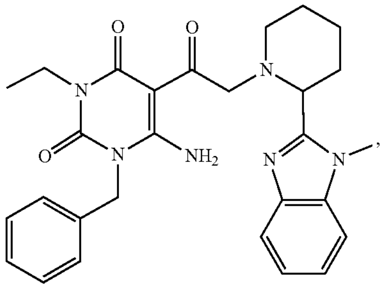
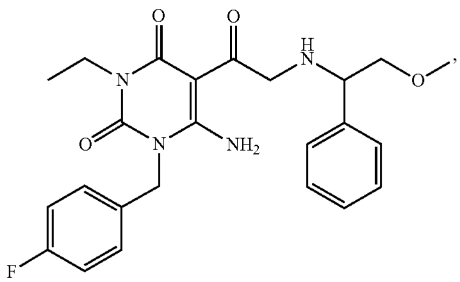
-continued
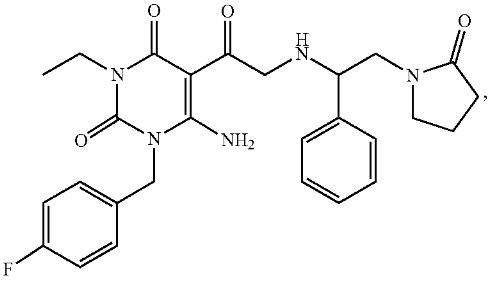
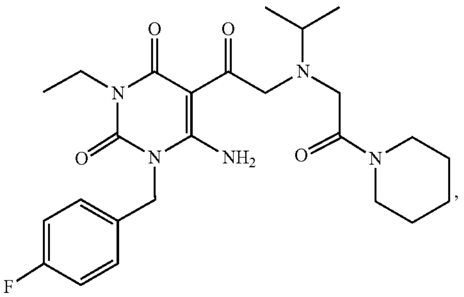
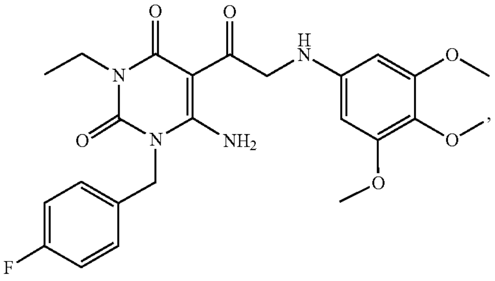
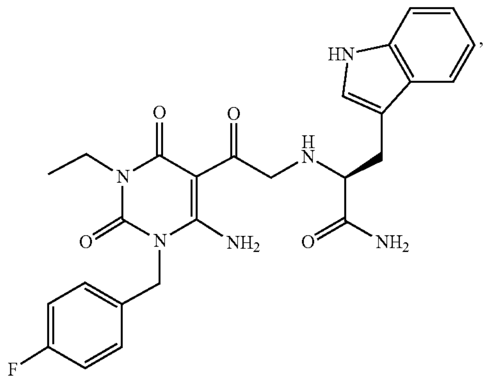
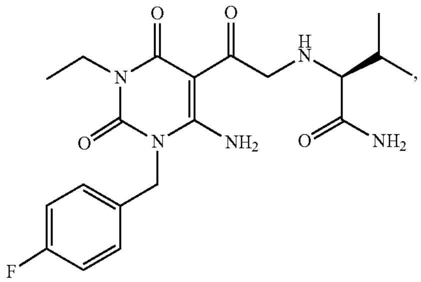

-continued
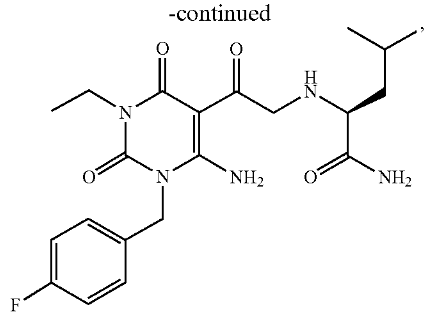
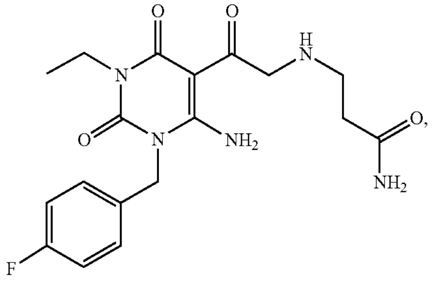
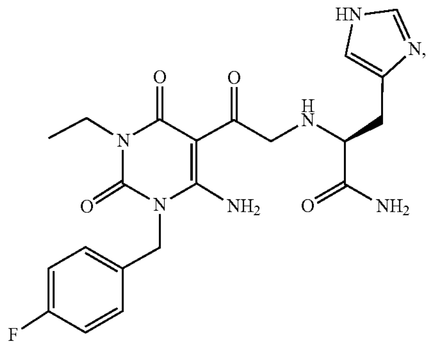
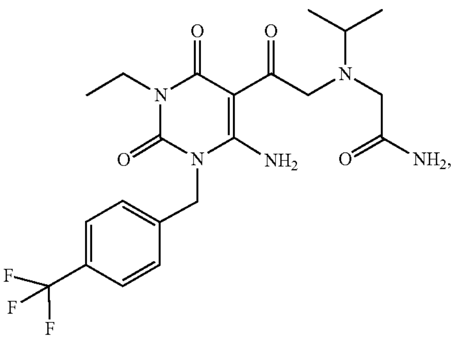
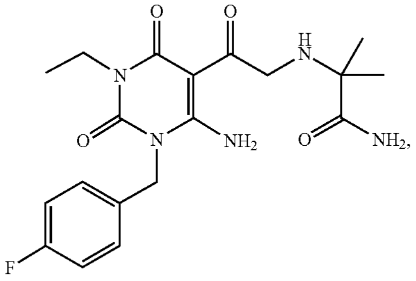
-continued
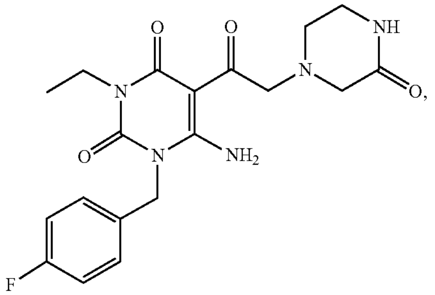
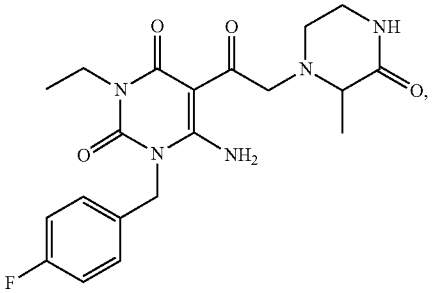
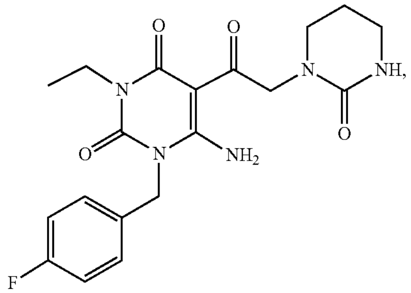
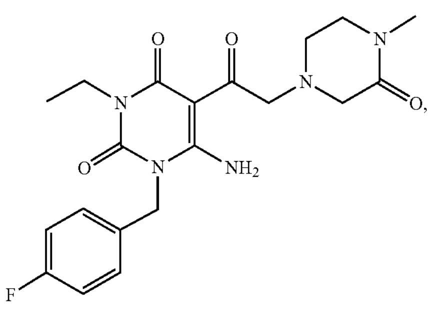
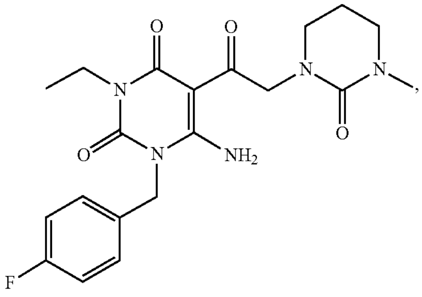

-continued
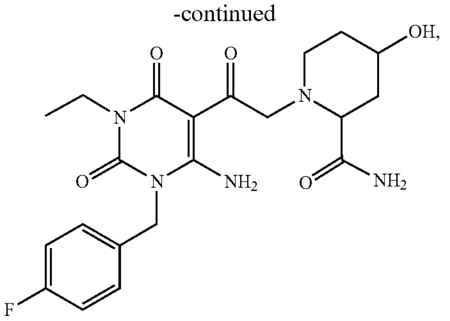
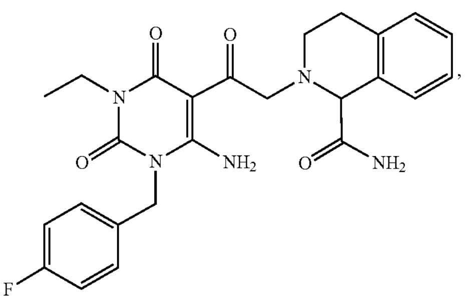
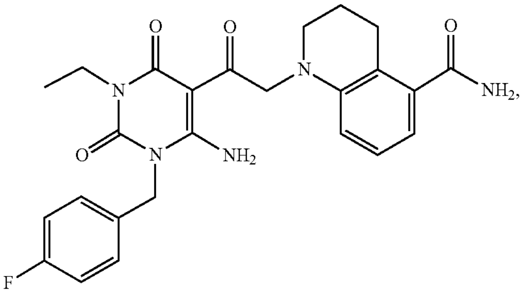
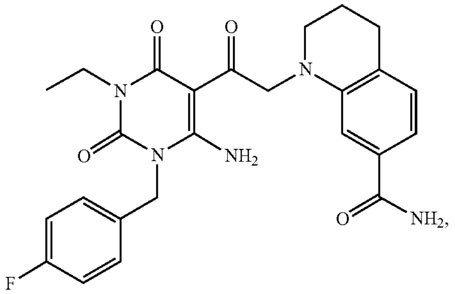
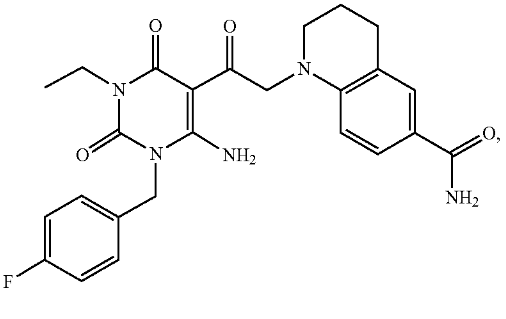
-continued
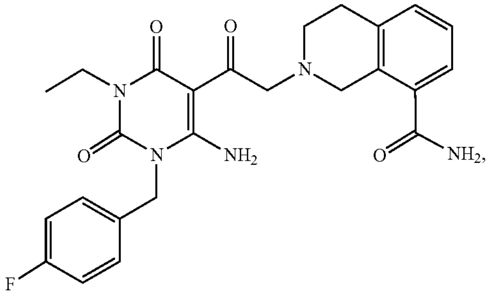
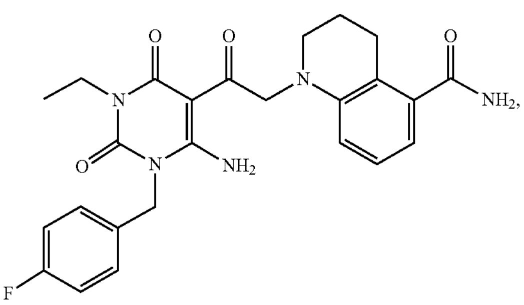
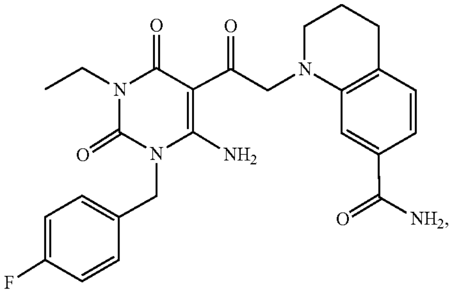
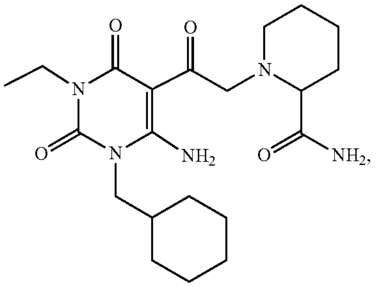
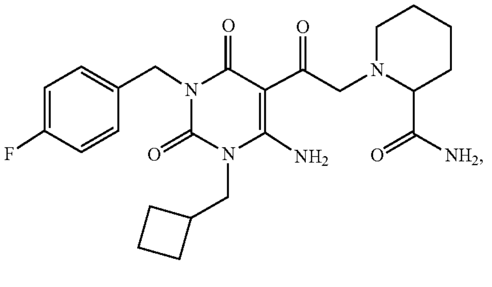
and -continued

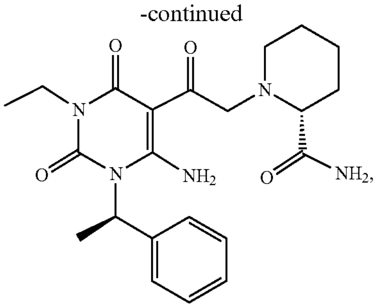

or a pharmaceutically acceptable salt thereof.

Also disclosed are pharmaceutical compositions comprising a therapeutically effective of a compound having a structure represented by a formula:

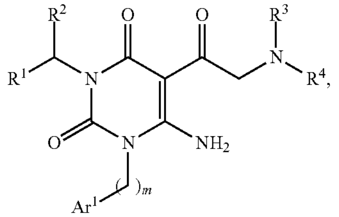

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$, when present, is independently selected from hydrogen and C1-C4 alkyl; wherein $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

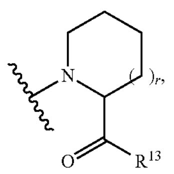

wherein r is 0 or 1; and wherein $R^{13}$ is selected from C1-C4 alkoxy and —$NR^{21a}R^{21b}$; wherein each of $R^{21a}$ and $R^{21b}$ when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.
Also disclosed are pharmaceutical compositions comprising a therapeutically effective amount of a compound selected from:
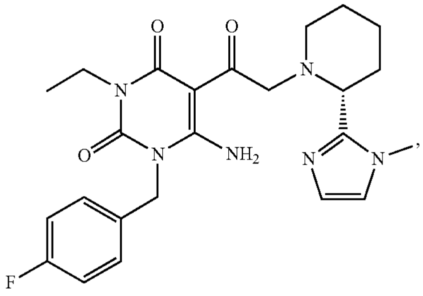
,
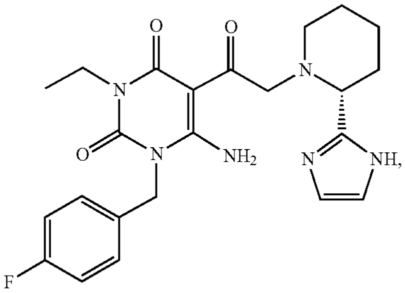
,
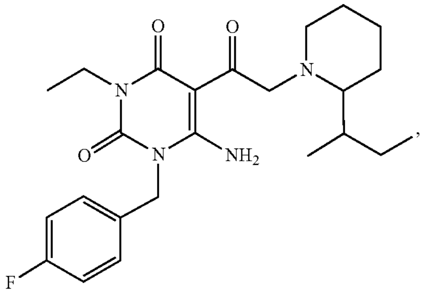
,
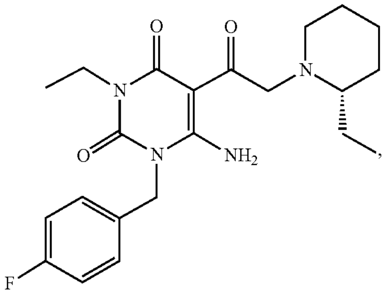
,
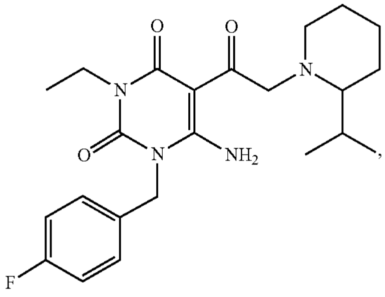
,
-continued
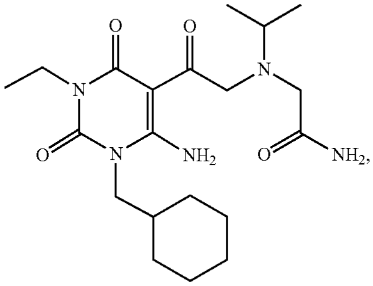
,
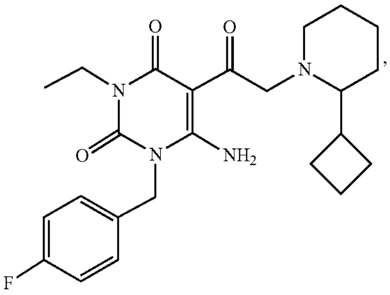
,
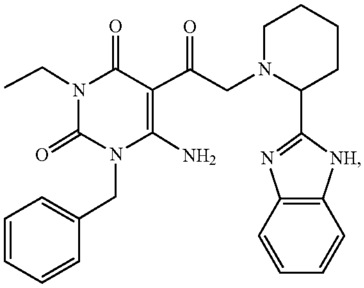
,
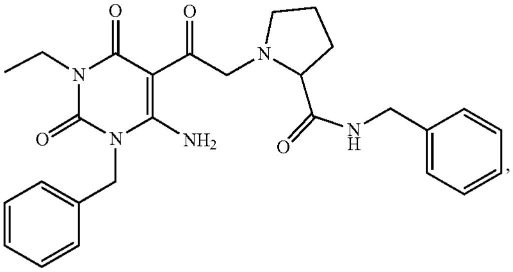
,
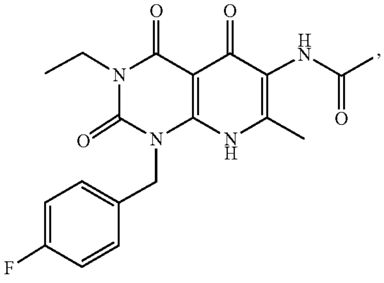
,
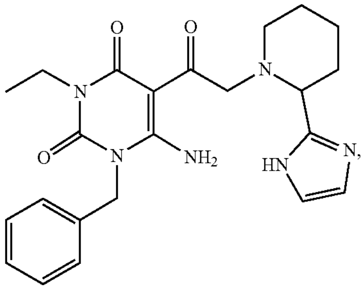
, -continued
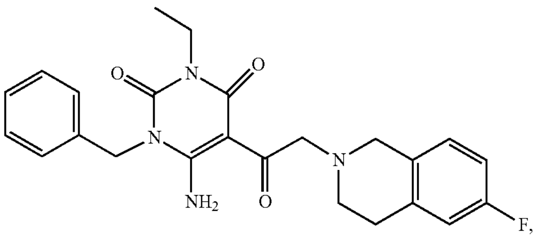
,
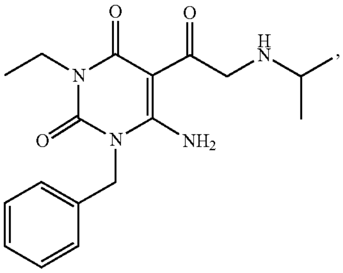
,
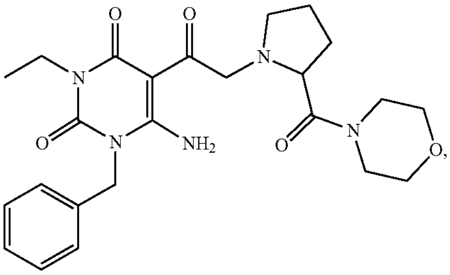
,
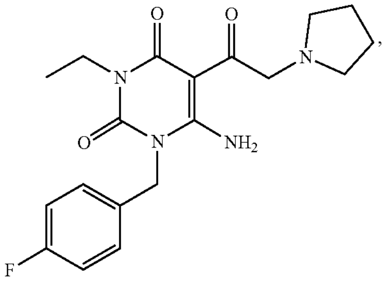
,
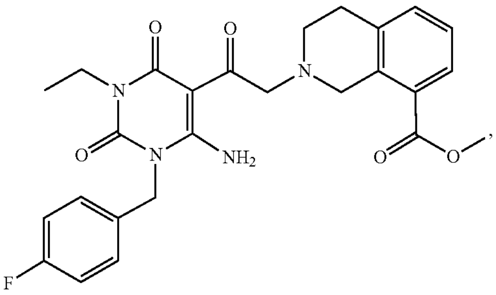
,
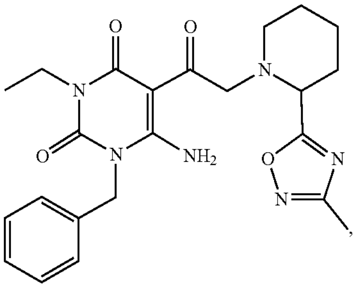
,
-continued
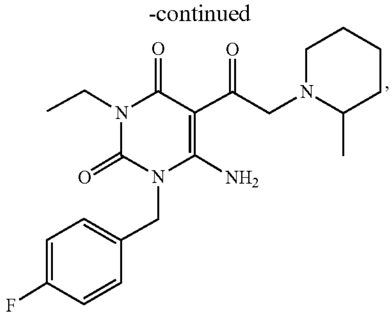
,
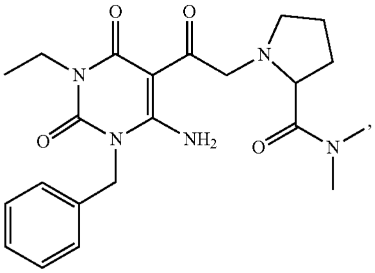
,
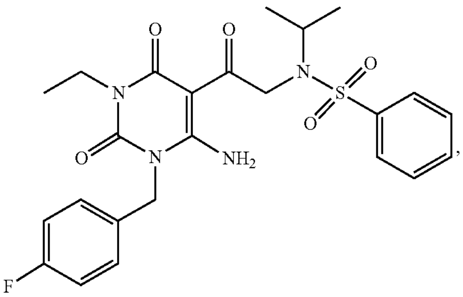
,
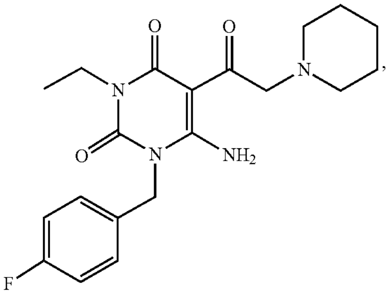
,
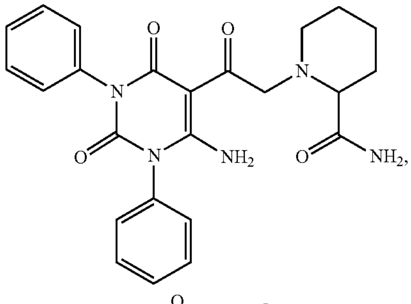
,
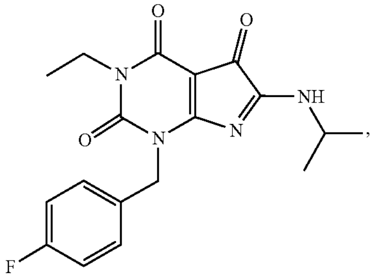
, -continued
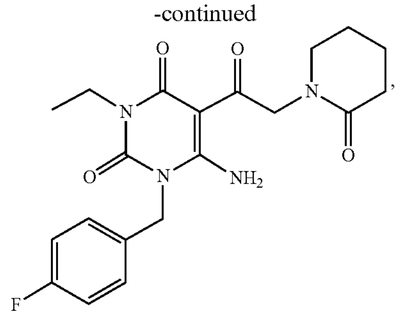
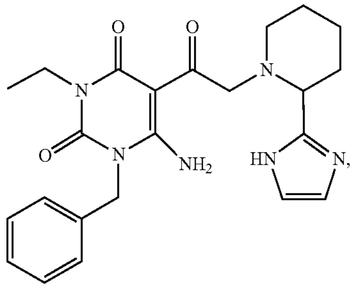
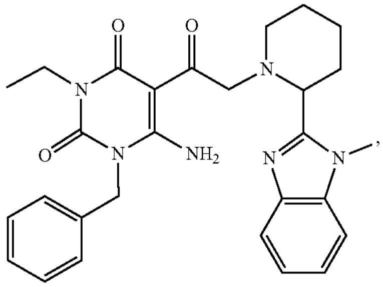
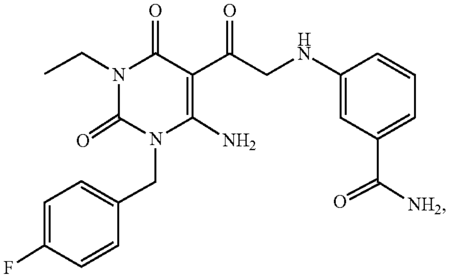
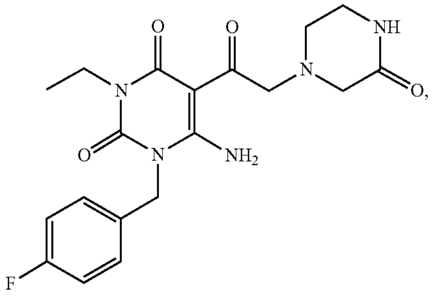
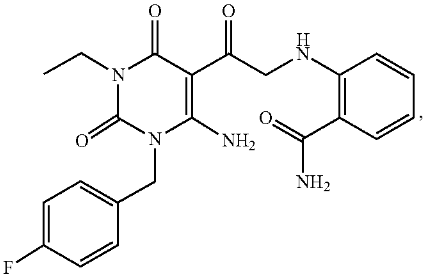
-continued
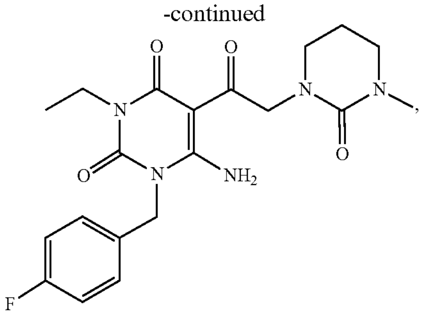
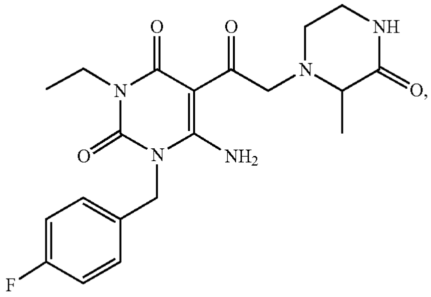
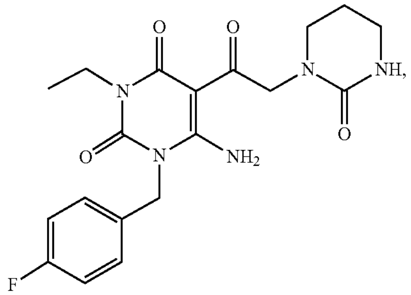
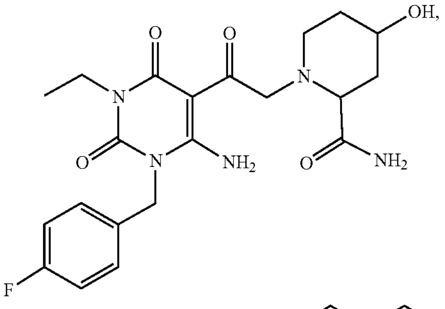
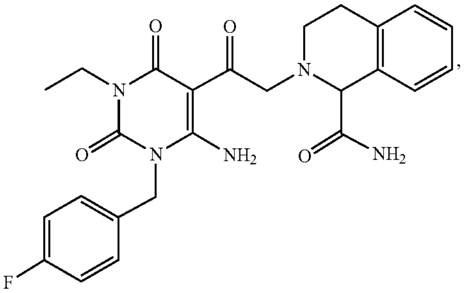

-continued

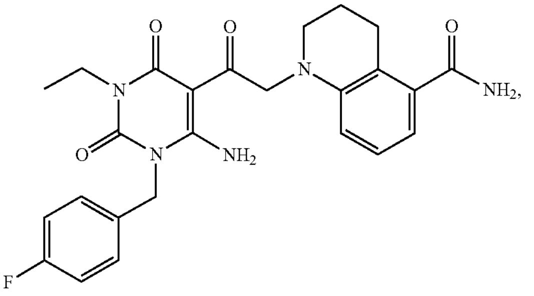

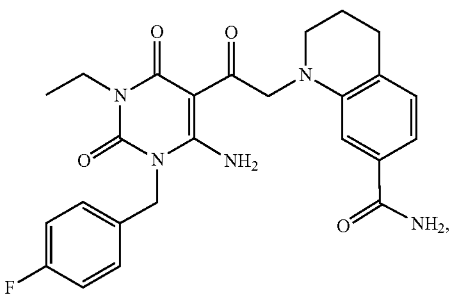

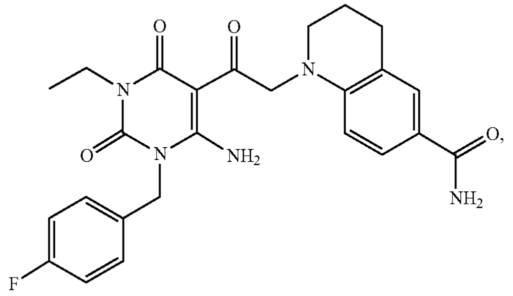

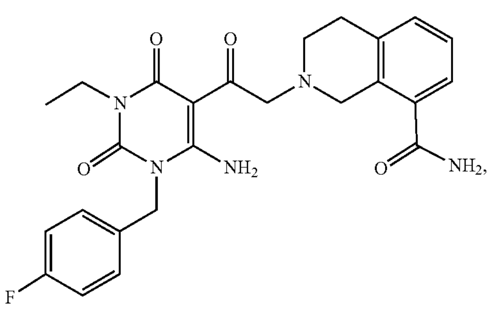

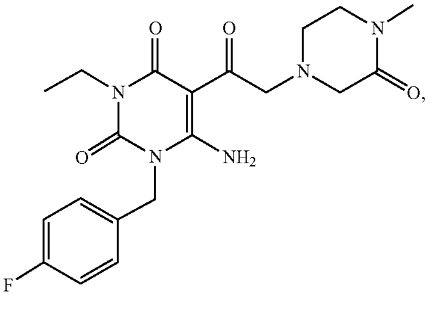

-continued

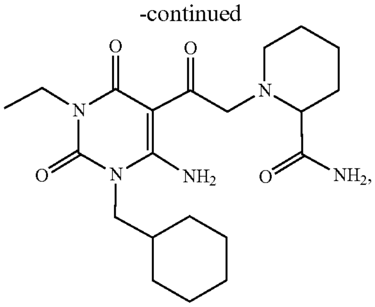

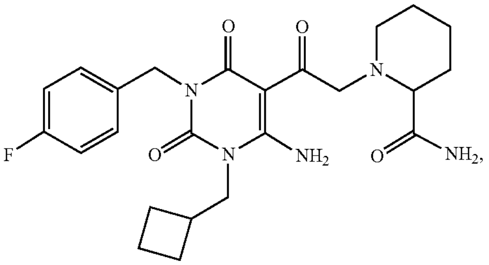

and

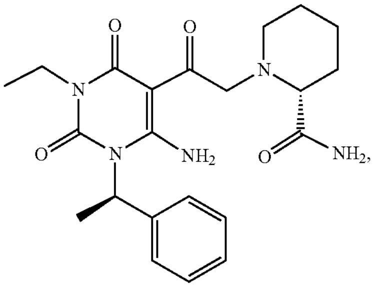

or a pharmaceutically acceptable salt thereof, and a pharmaceutically acceptable carrier.

Also disclosed are methods for modulating read-through of a premature termination codon in a subject in need thereof, the method comprising administering to the subject an effective amount of a compound having a structure represented by a formula:

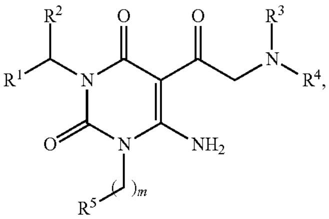

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$, when present, is independently selected from hydrogen and C1-C4 alkyl; wherein $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

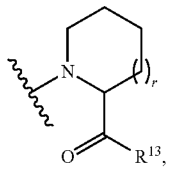

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^5$ is selected from $Ar^1$ and $Cy^6$; wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are methods for modulating read-through of a premature termination codon in a subject in need thereof, the method comprising administering to the subject an effective amount of a compound selected from:

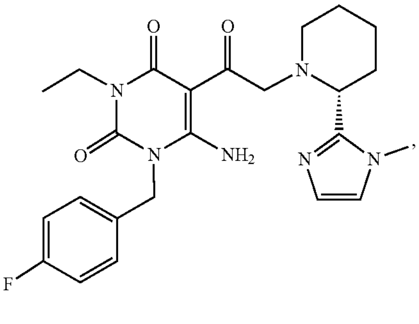

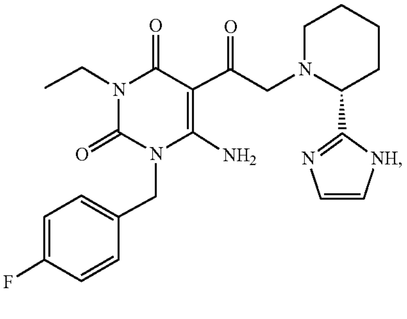

-continued
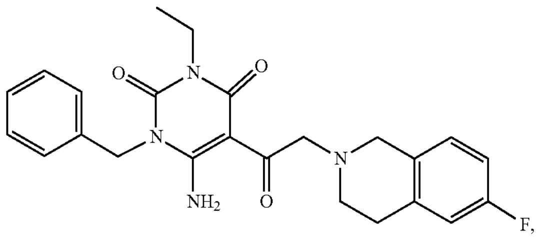
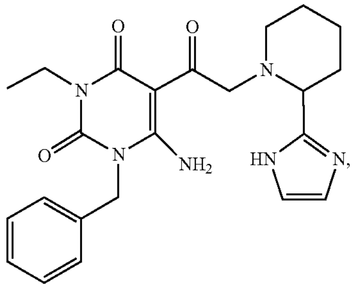
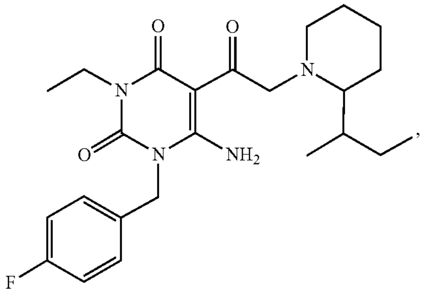
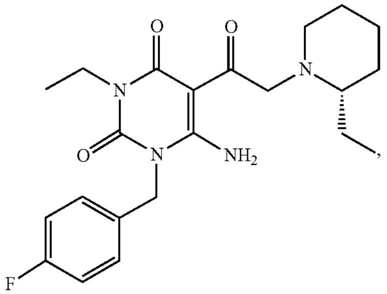
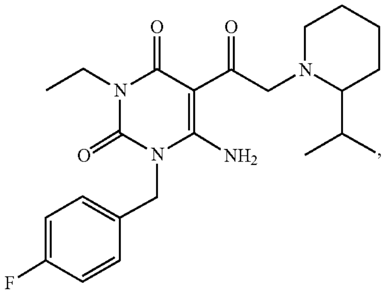
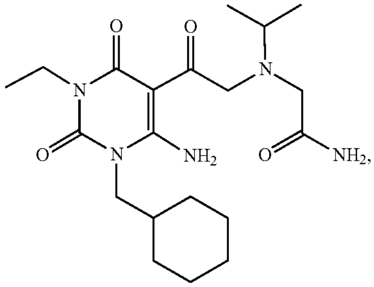
-continued
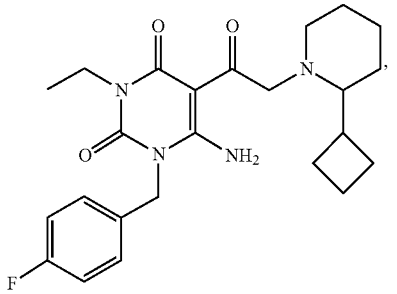
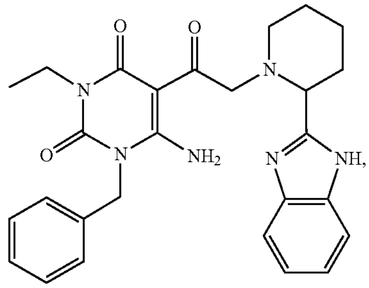
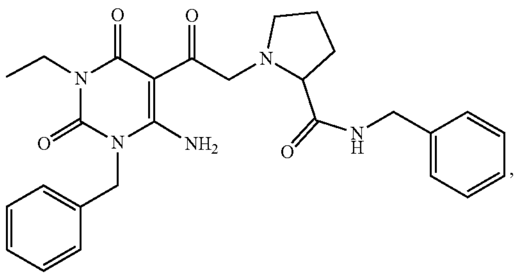
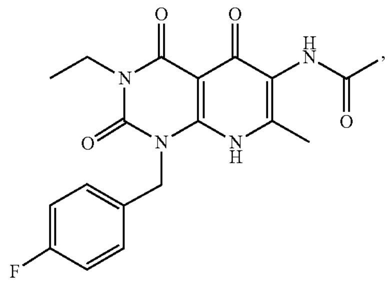
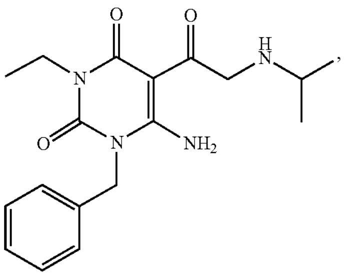
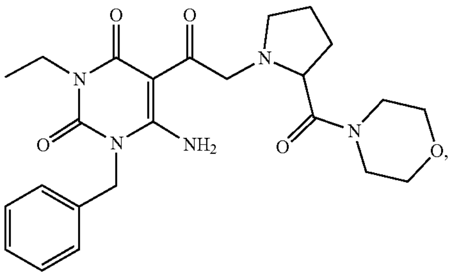

-continued
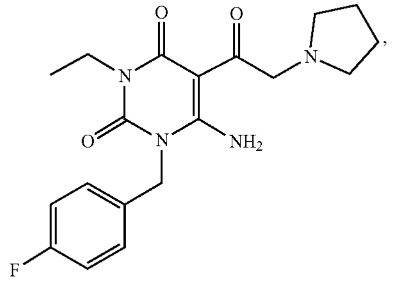
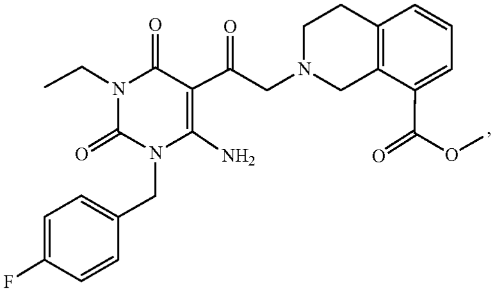
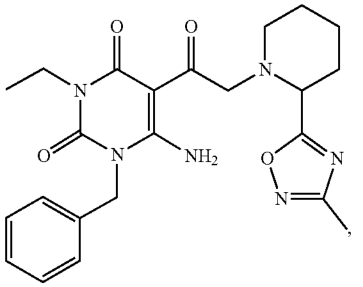
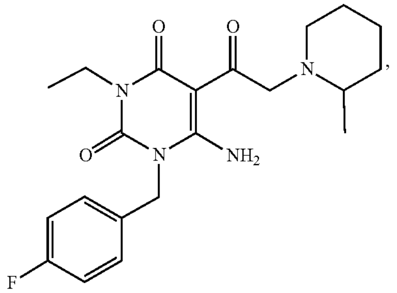
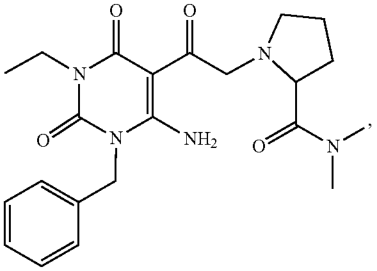
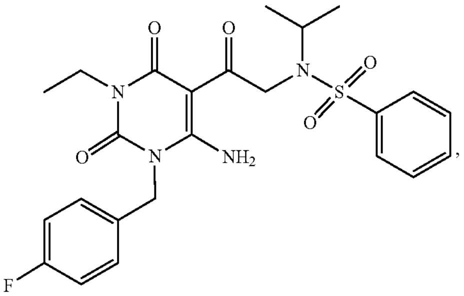
-continued
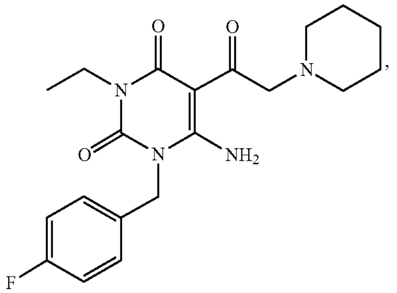
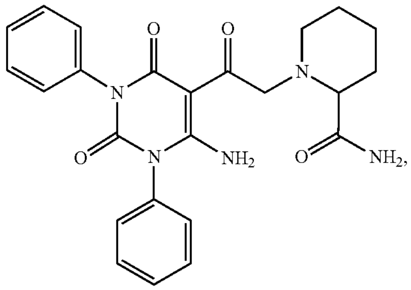
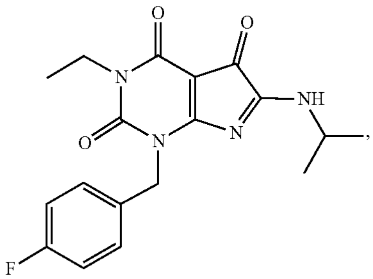
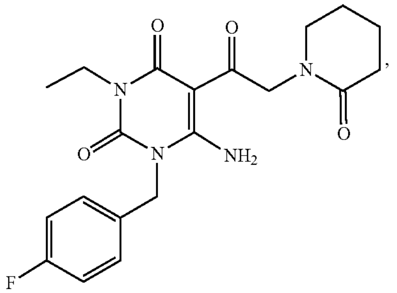
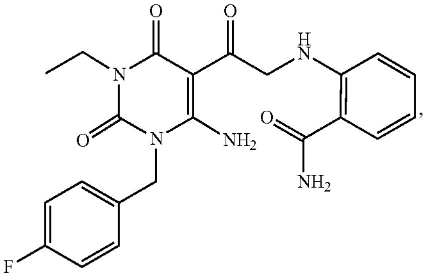
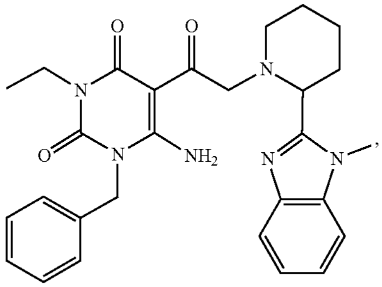

-continued
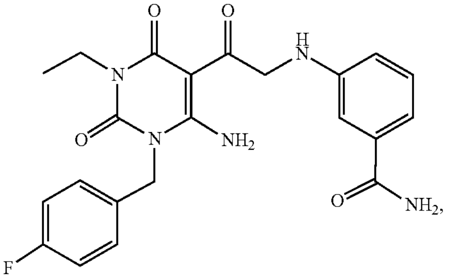
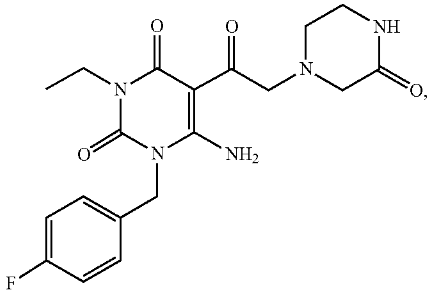
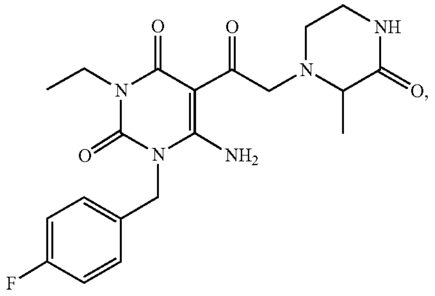
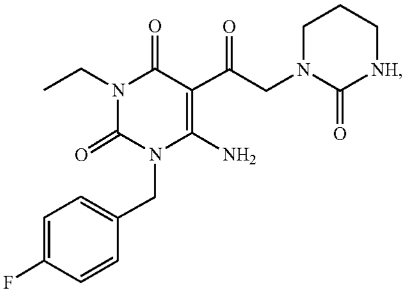
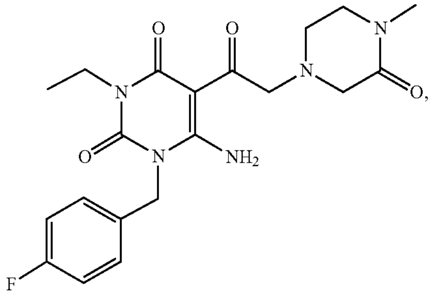
-continued
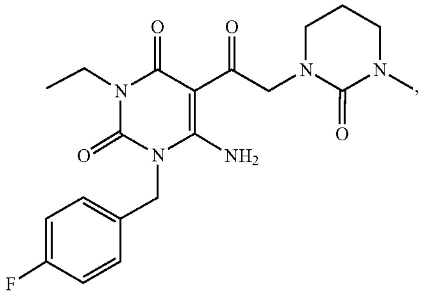
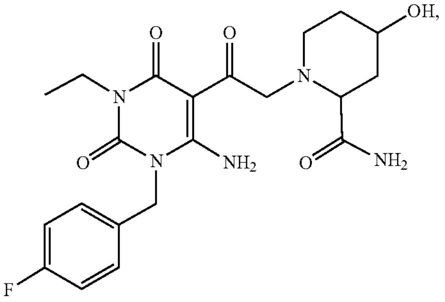
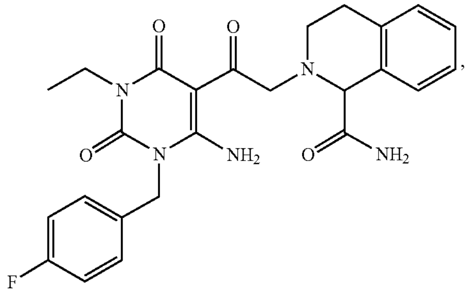
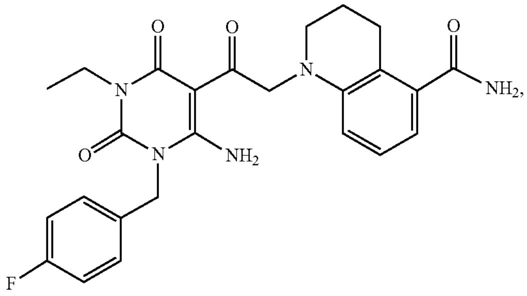
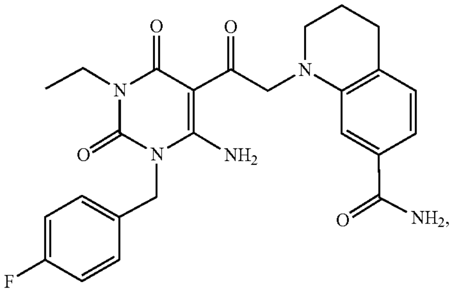

-continued

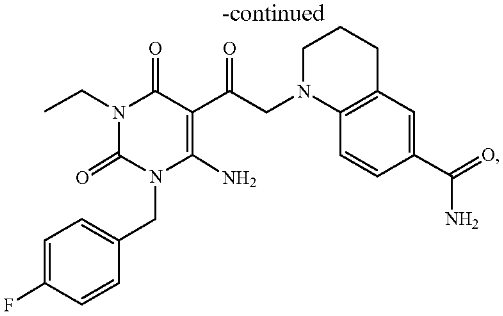

, and

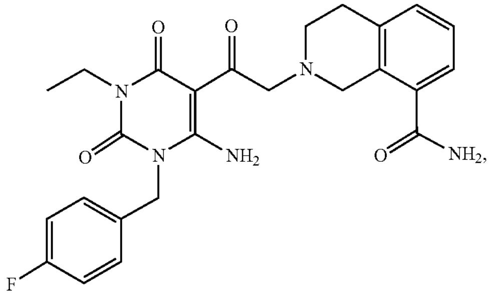

, or a pharmaceutically acceptable salt thereof.

Also disclosed are methods for modulating read-through of a premature termination codon in a cell, the method comprising contacting the cell with an effective amount of a compound having a structure represented by a formula:

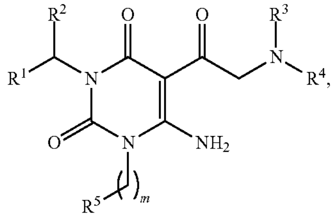

, wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$, when present, is independently selected from hydrogen and C1-C4 alkyl; wherein $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

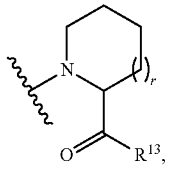

, wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^5$ is selected from $Ar^1$ and $Cy^6$; wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are methods for modulating read-through of a premature termination codon in a cell, the method comprising contacting the cell with an effective amount of a compound selected from:

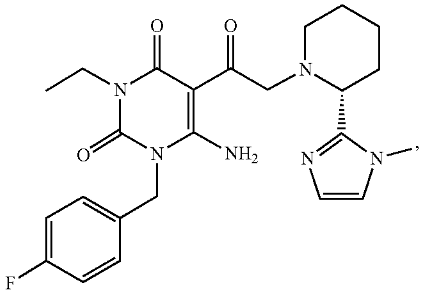

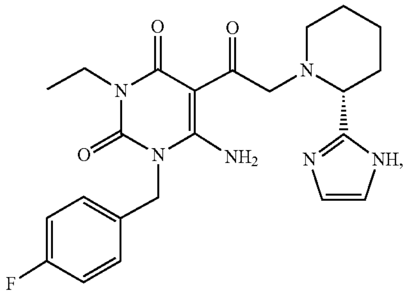

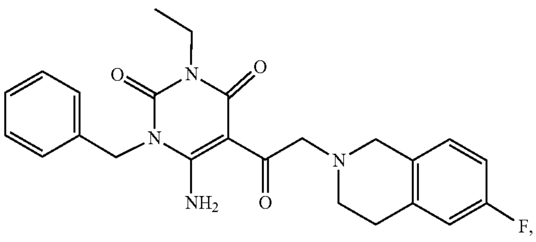

-continued

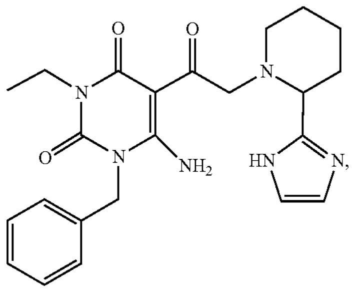

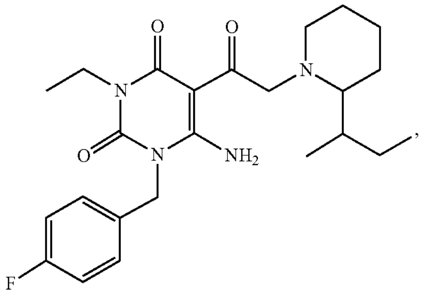

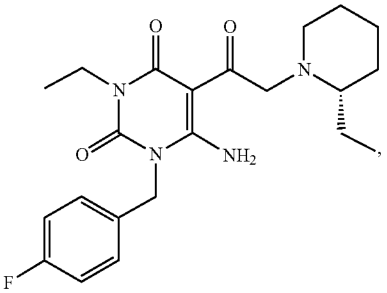

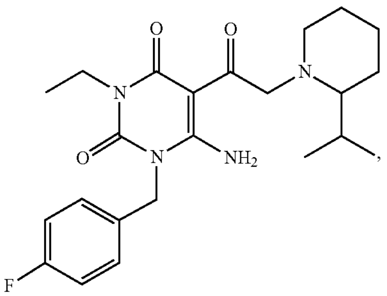

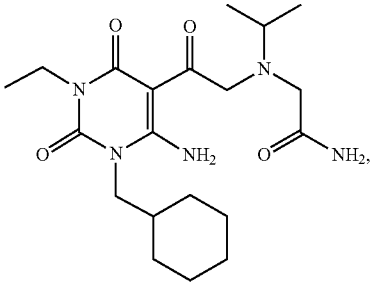

-continued
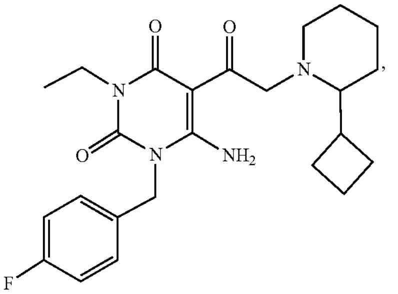
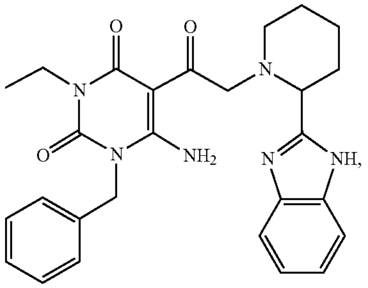
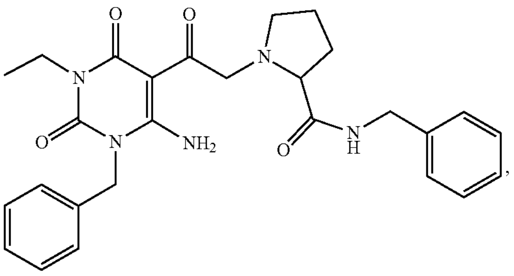
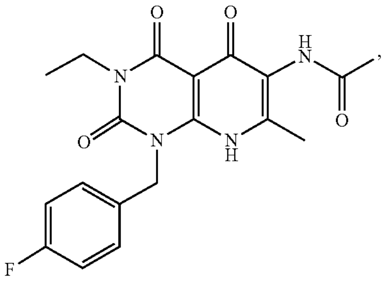
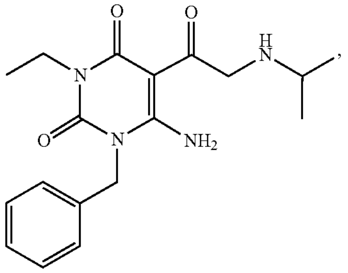
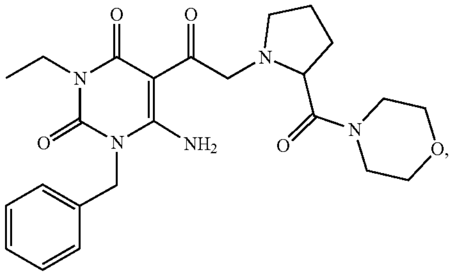
-continued
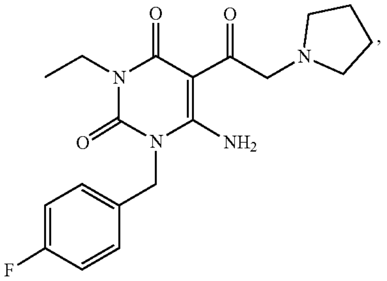
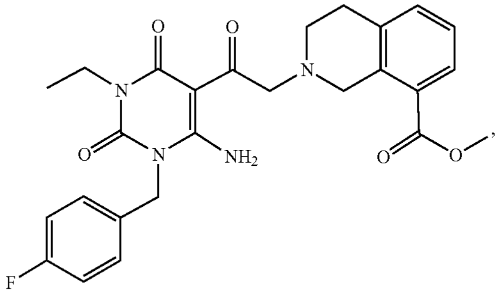
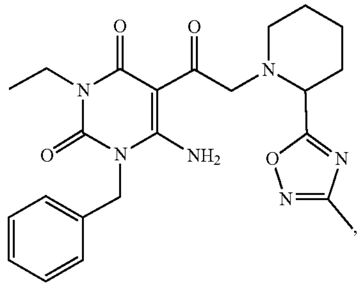
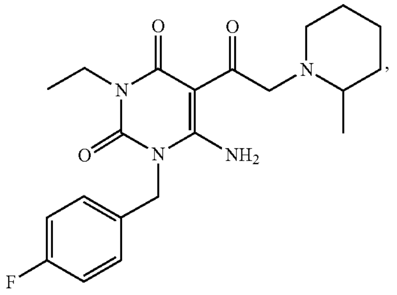
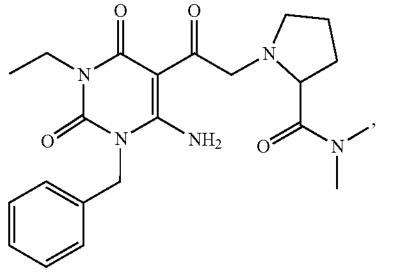
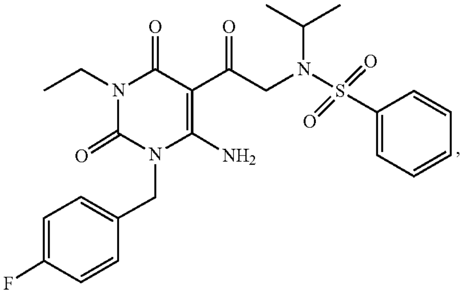

-continued
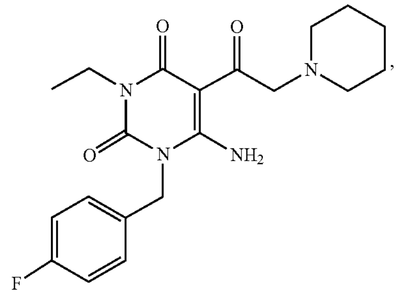
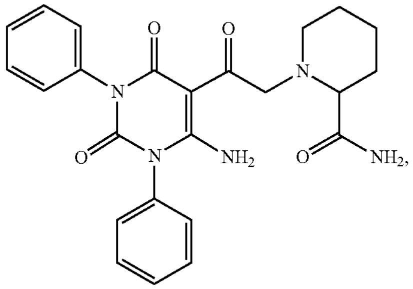
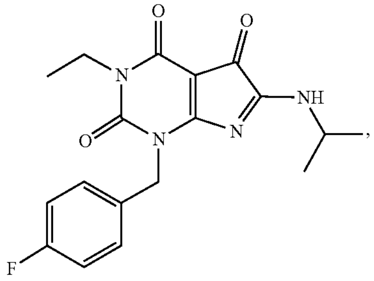
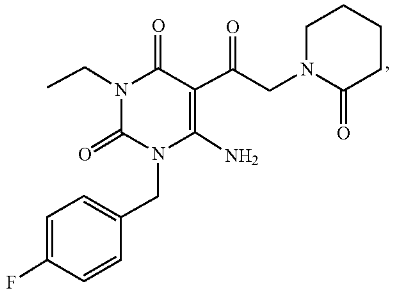
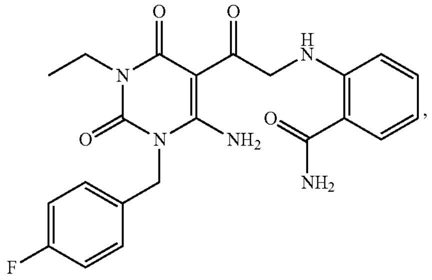
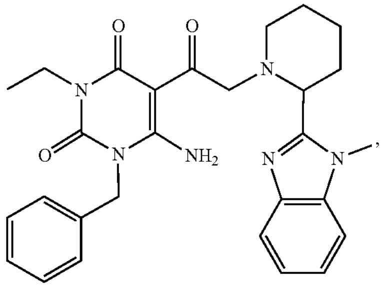
-continued
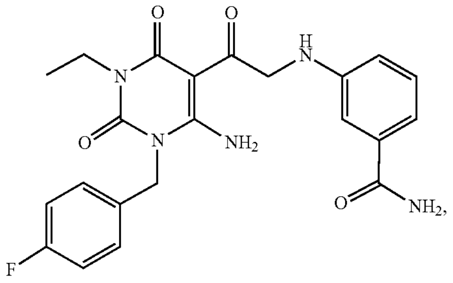
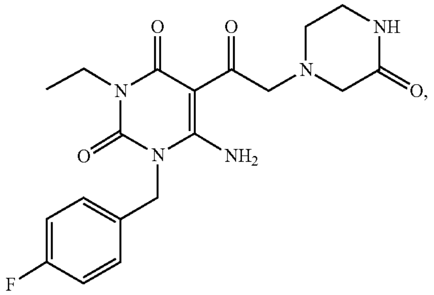
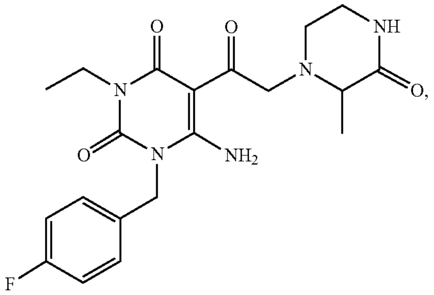
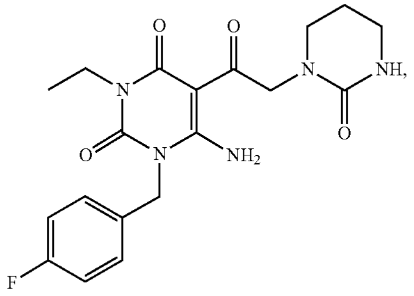
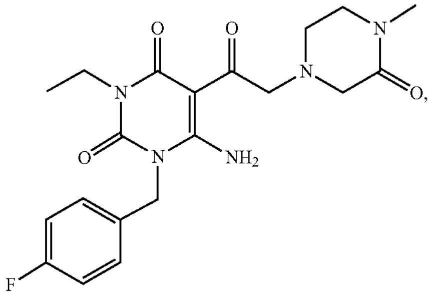

-continued

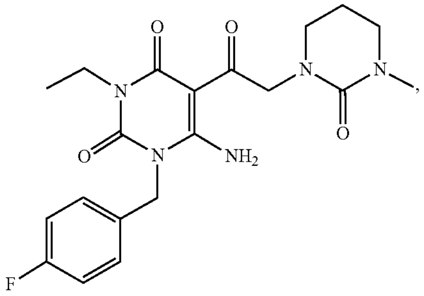

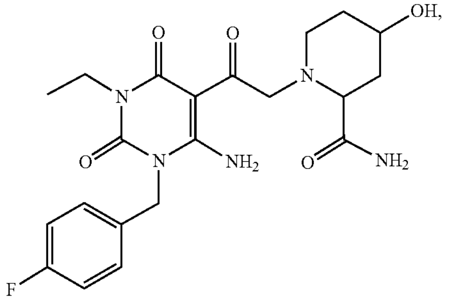

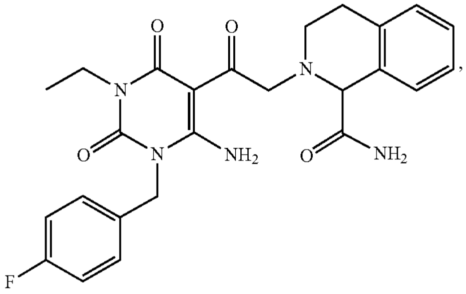

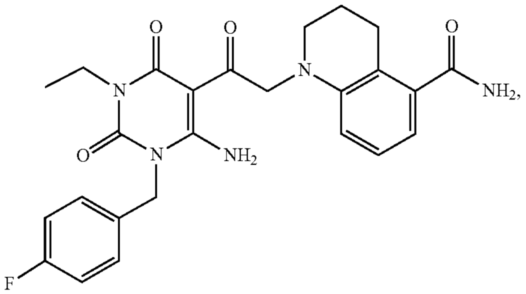

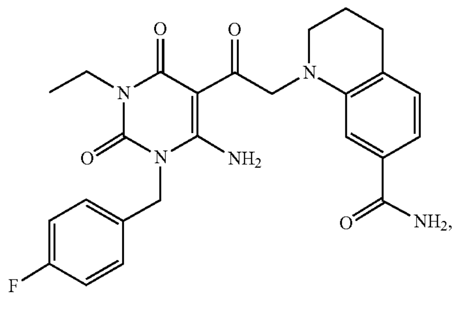

-continued

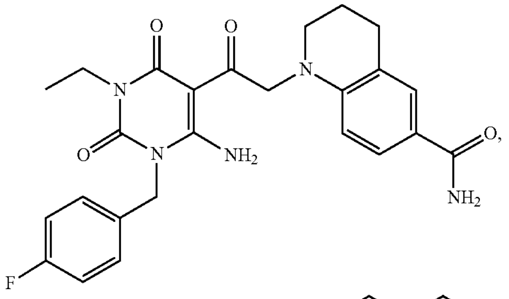

and

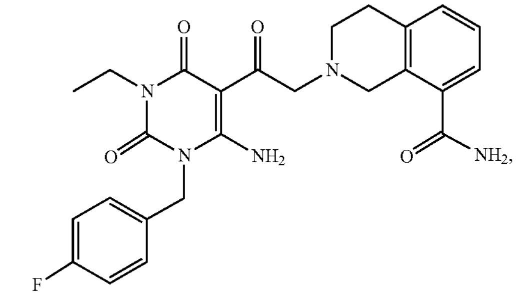

or a pharmaceutically acceptable salt thereof.

Also disclosed are methods for treating a disorder associated with the presence of a premature termination codon in a subject in need thereof, the method comprising administering to the subject an effective amount of a compound having a structure represented by a formula:

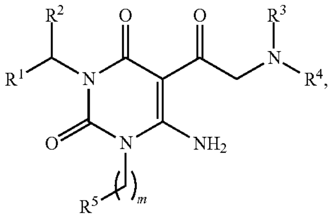

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$ when present, is independently selected from hydrogen and C1-C4 alkyl; wherein $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

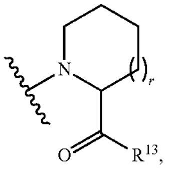

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^5$ is selected from $Ar^1$ and $Cy^6$; wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are methods for treating a disorder associated with the presence of a premature termination codon in a subject in need thereof, the method comprising administering to the subject an effective amount of a compound selected from:

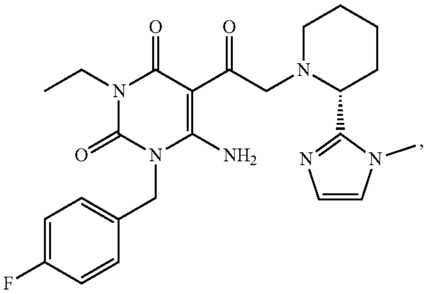

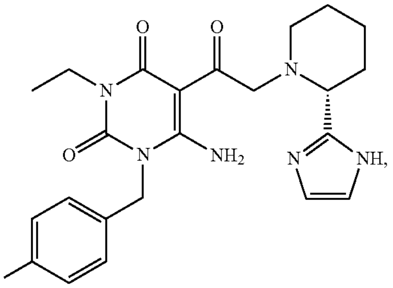

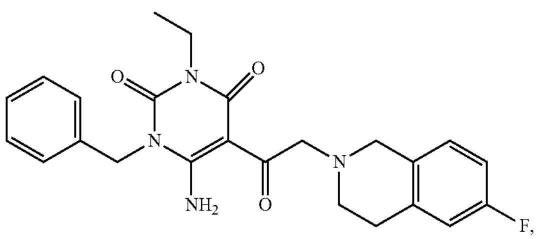

-continued
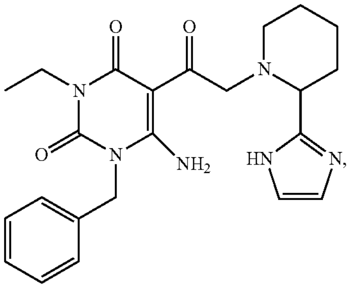
,
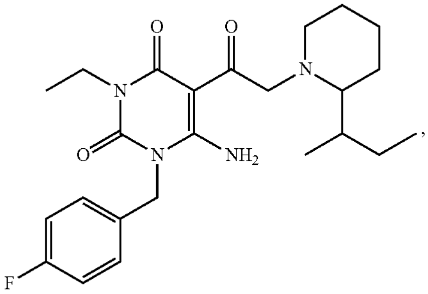
,
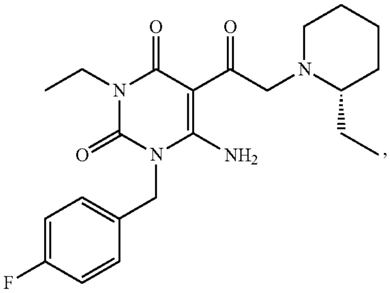
,
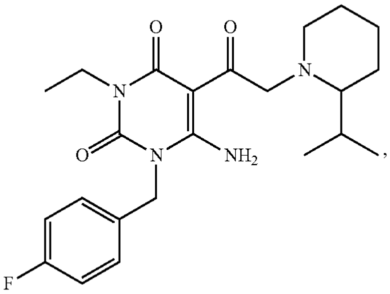
,
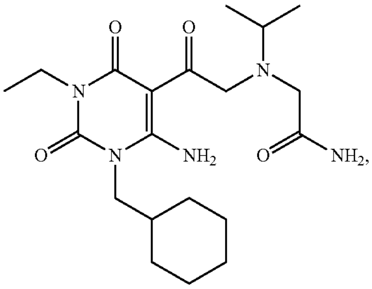
,
-continued
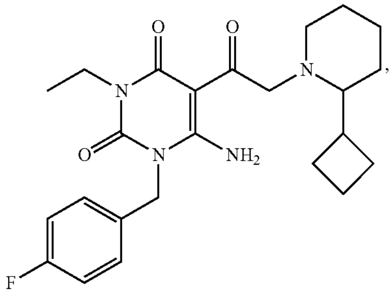
,
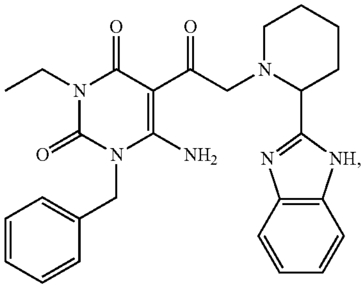
,
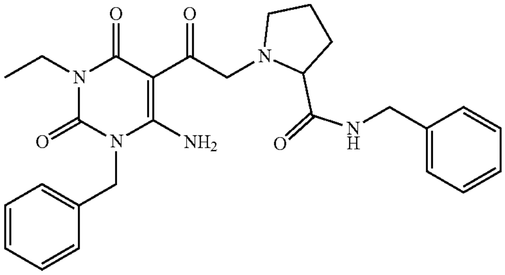
,
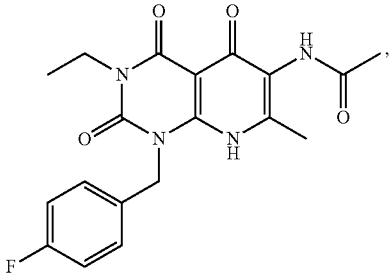
,
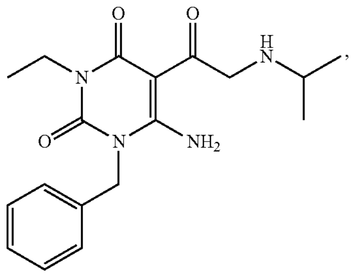
,
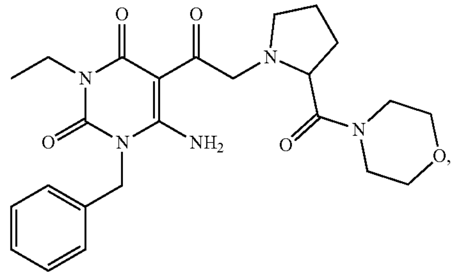
, -continued
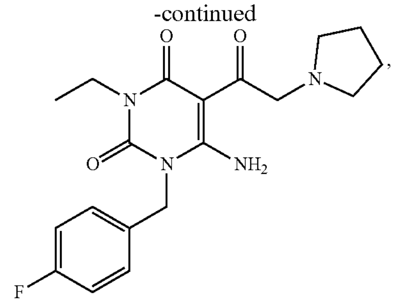
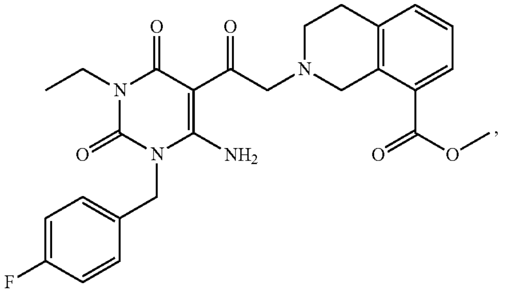
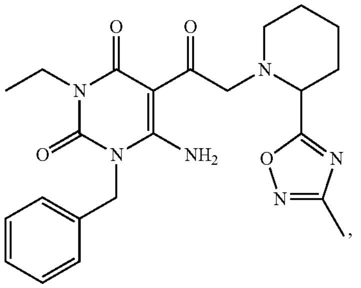
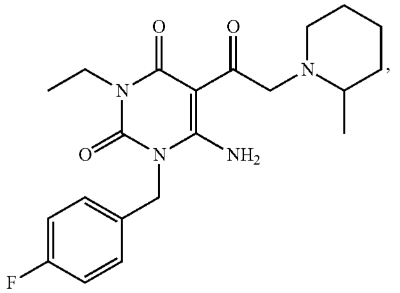
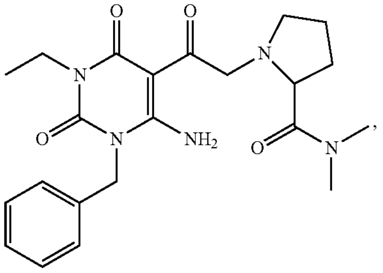
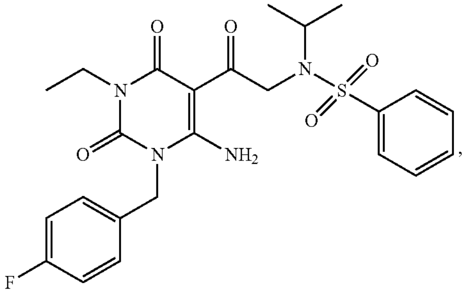
-continued
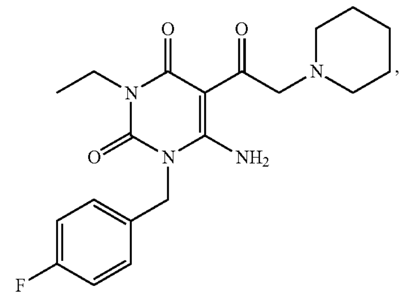
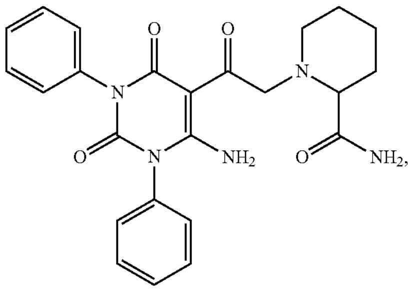
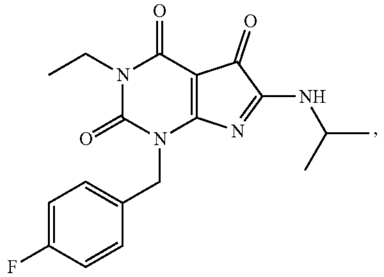
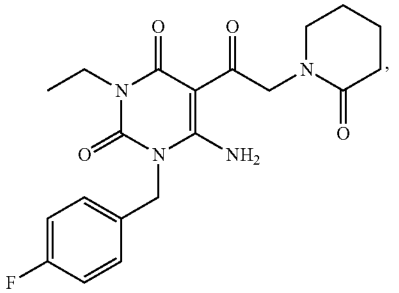
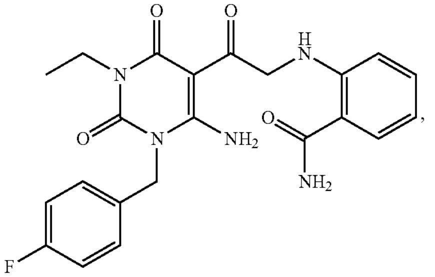
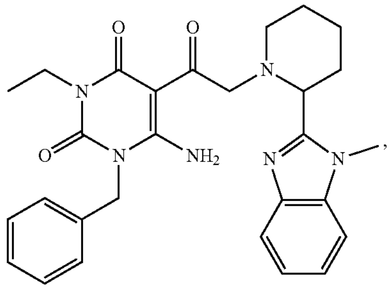

-continued
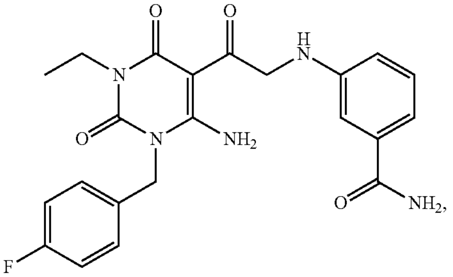
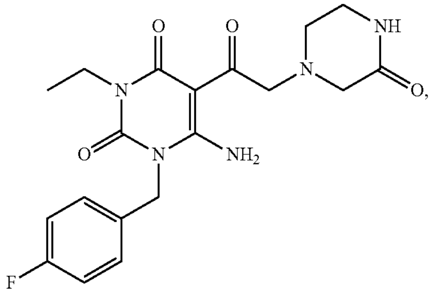
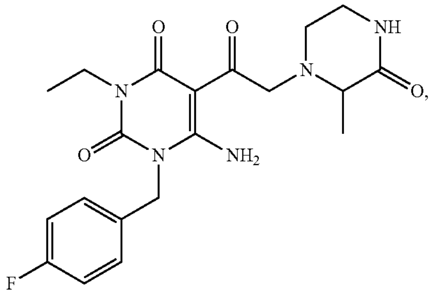
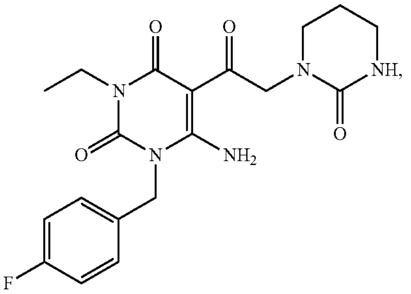
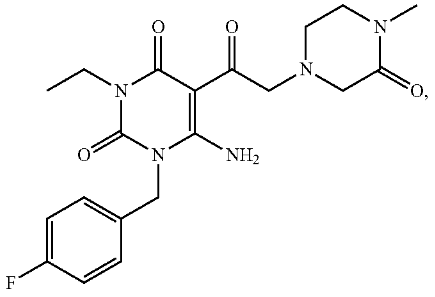
-continued
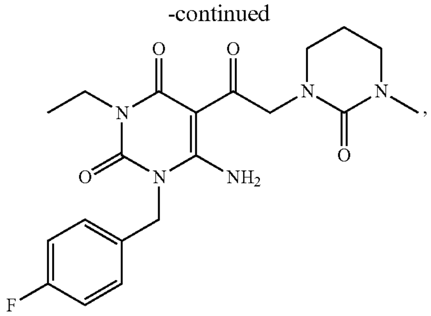
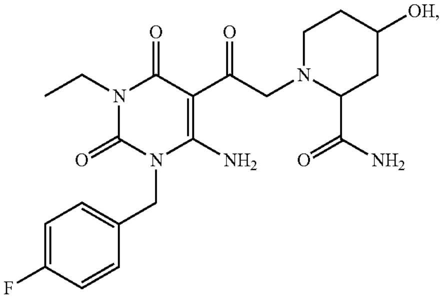
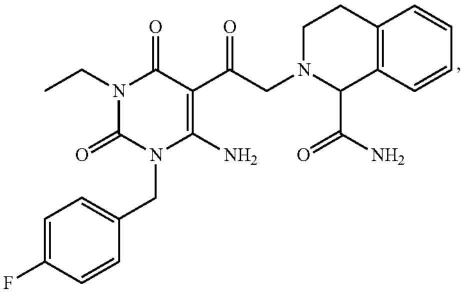
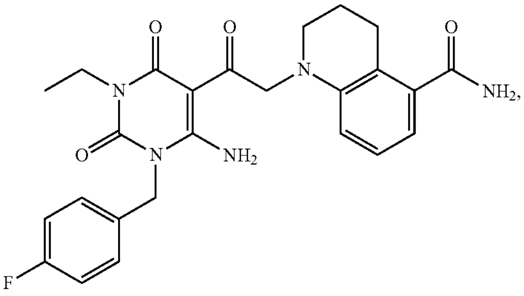
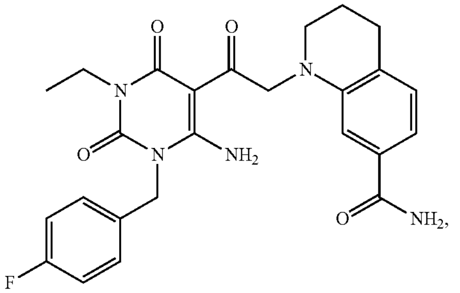

-continued

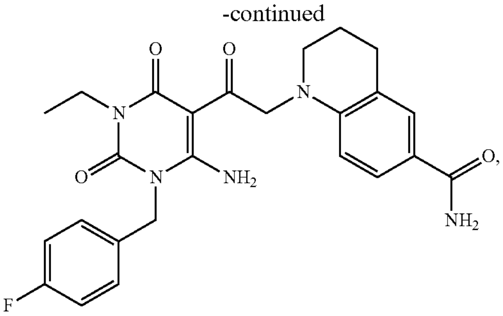

, and

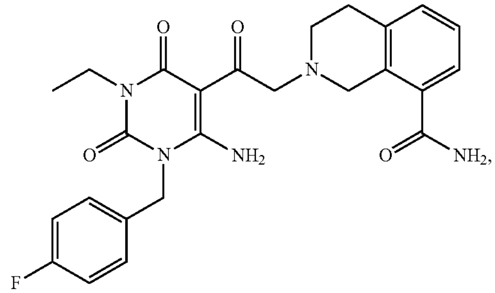

, or a pharmaceutically acceptable salt thereof.

Also disclosed are methods for treating a disorder in a subject identified as having a premature termination codon, the method comprising administering to the subject an effective amount of a compound having a structure represented by a formula:

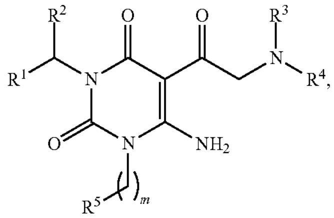

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$, when present, is independently selected from hydrogen and C1-C4 alkyl; wherein $R^{10a}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

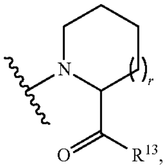

wherein r is 0 or 1; and wherein $R^{13}$ is selected from C1-C4 alkoxy and —$NR^{21a}R^{21b}$; wherein each of $R^{21a}$ and $R^{21b}$ when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^5$ is selected from $Ar^1$ and $Cy^6$; wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are methods for treating a disorder in a subject identified as having a premature termination codon, the method comprising administering to the subject an effective amount of a compound selected from:

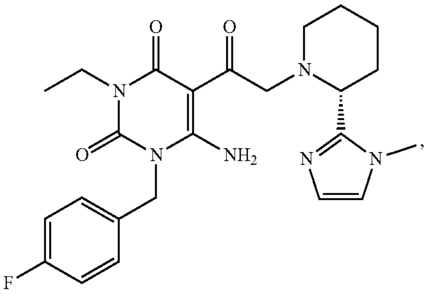

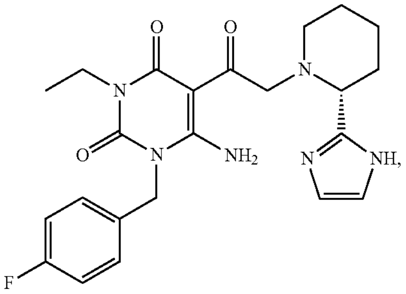

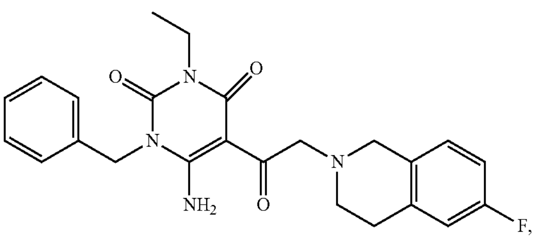

-continued

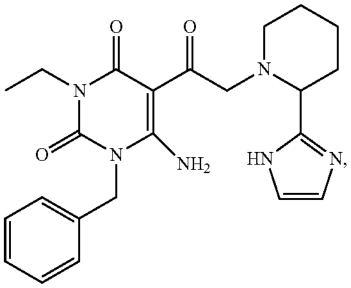

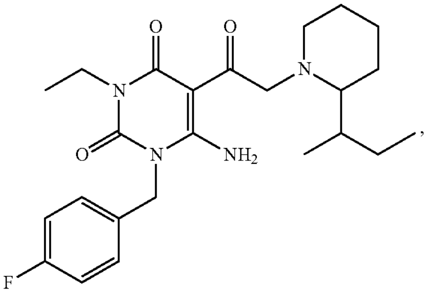

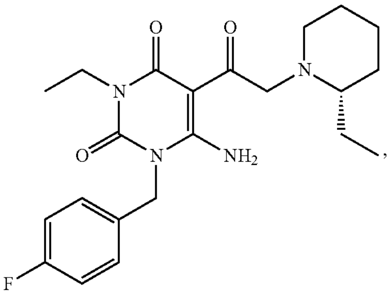

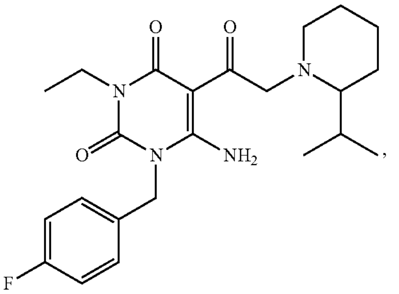

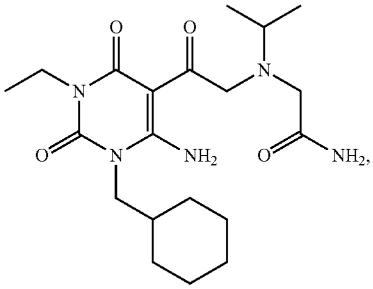

-continued
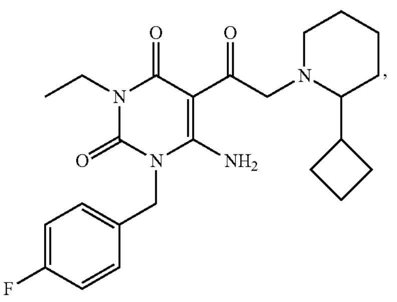
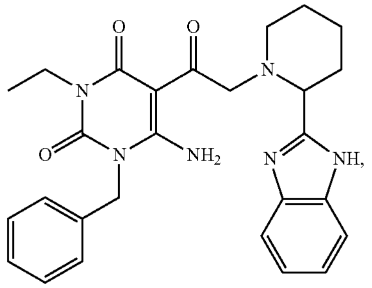
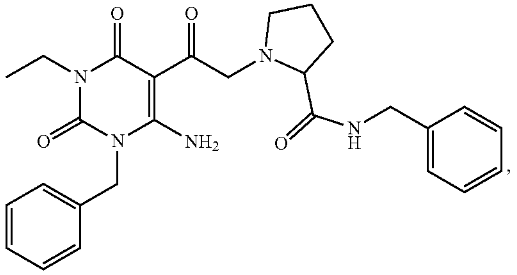
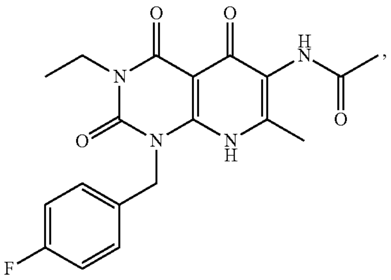
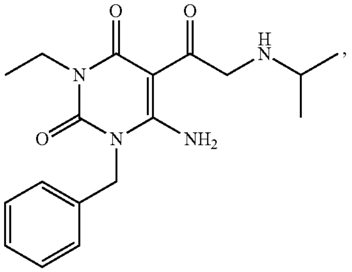
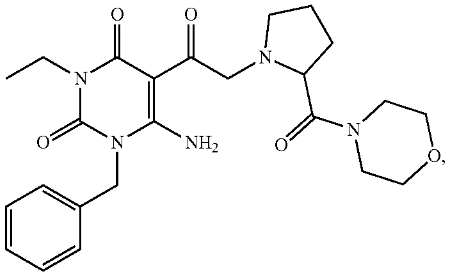
-continued
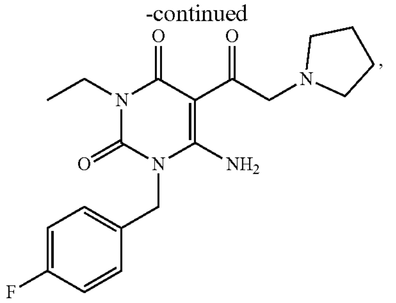
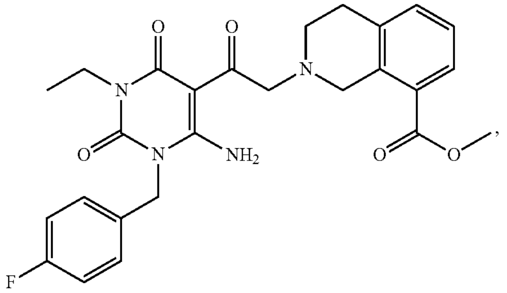
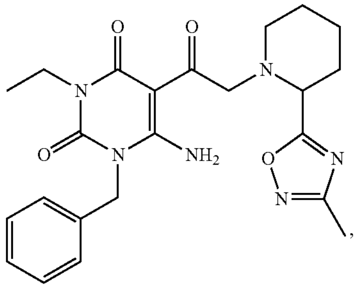
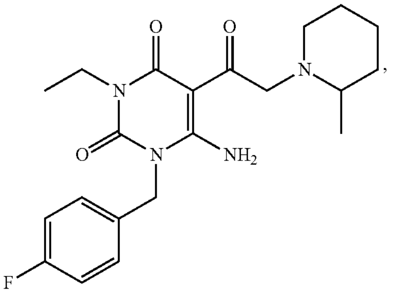
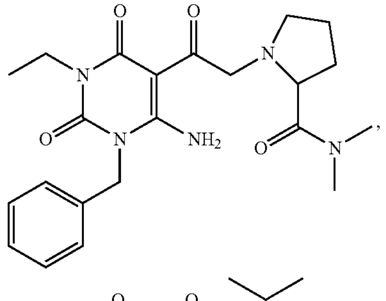
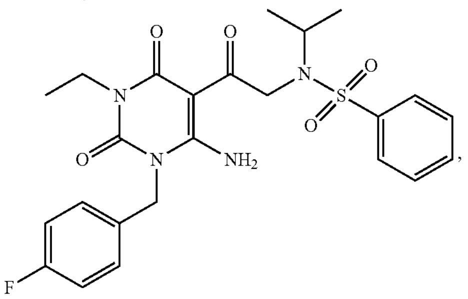

-continued
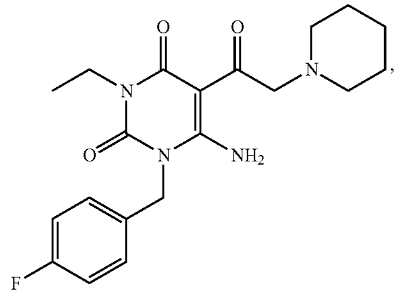
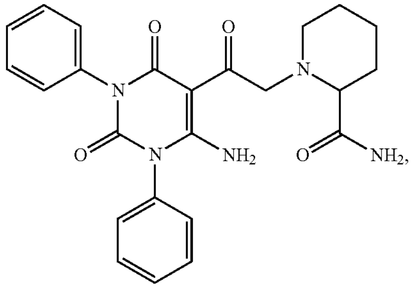
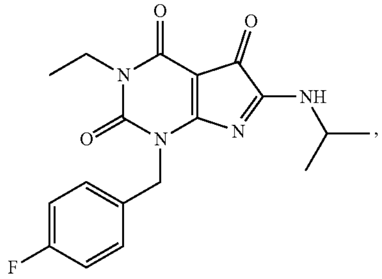
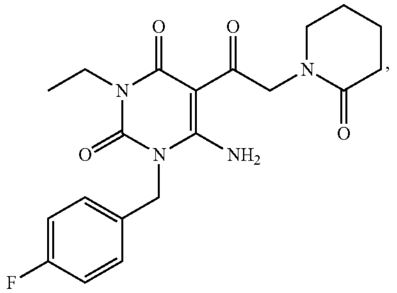
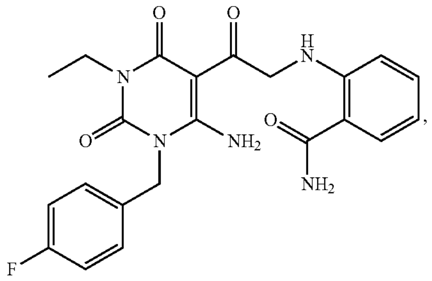
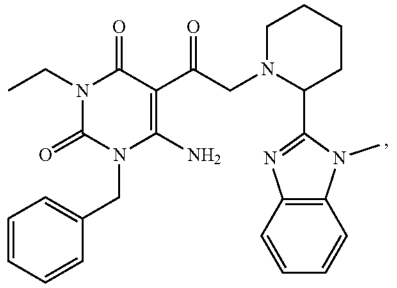
-continued
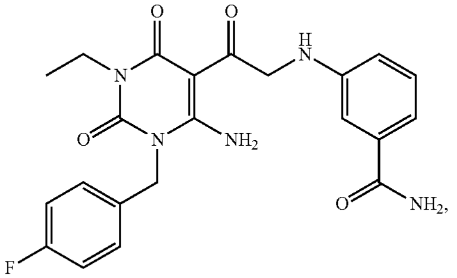
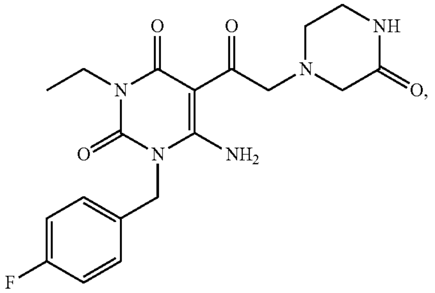
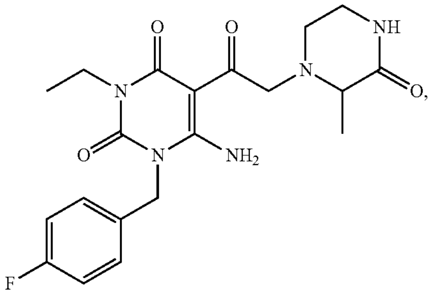
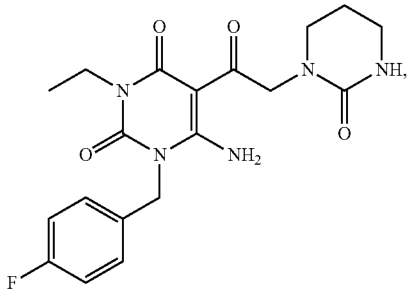
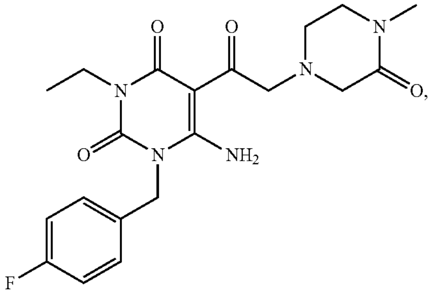

-continued

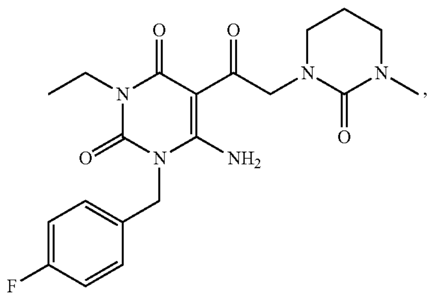

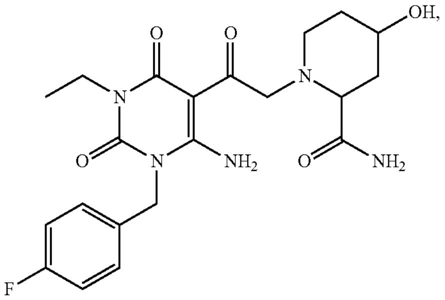

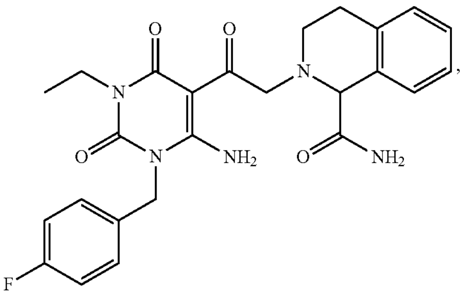

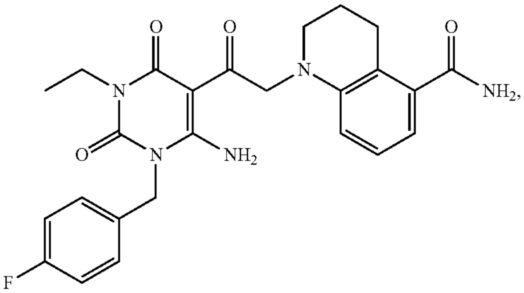

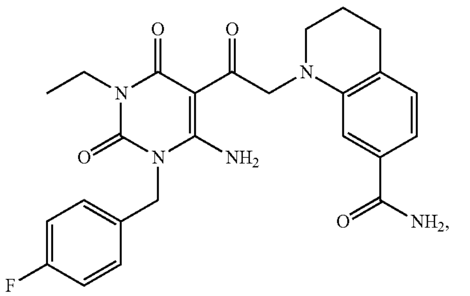

-continued

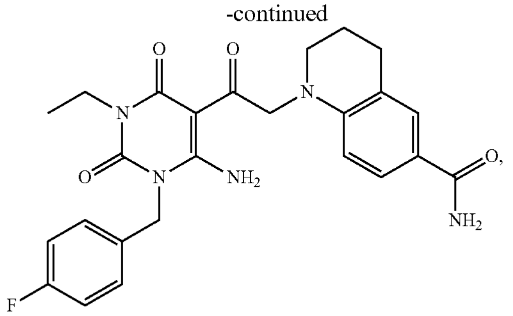

and

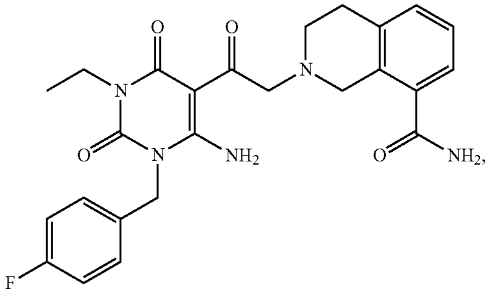

or a pharmaceutically acceptable salt thereof.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
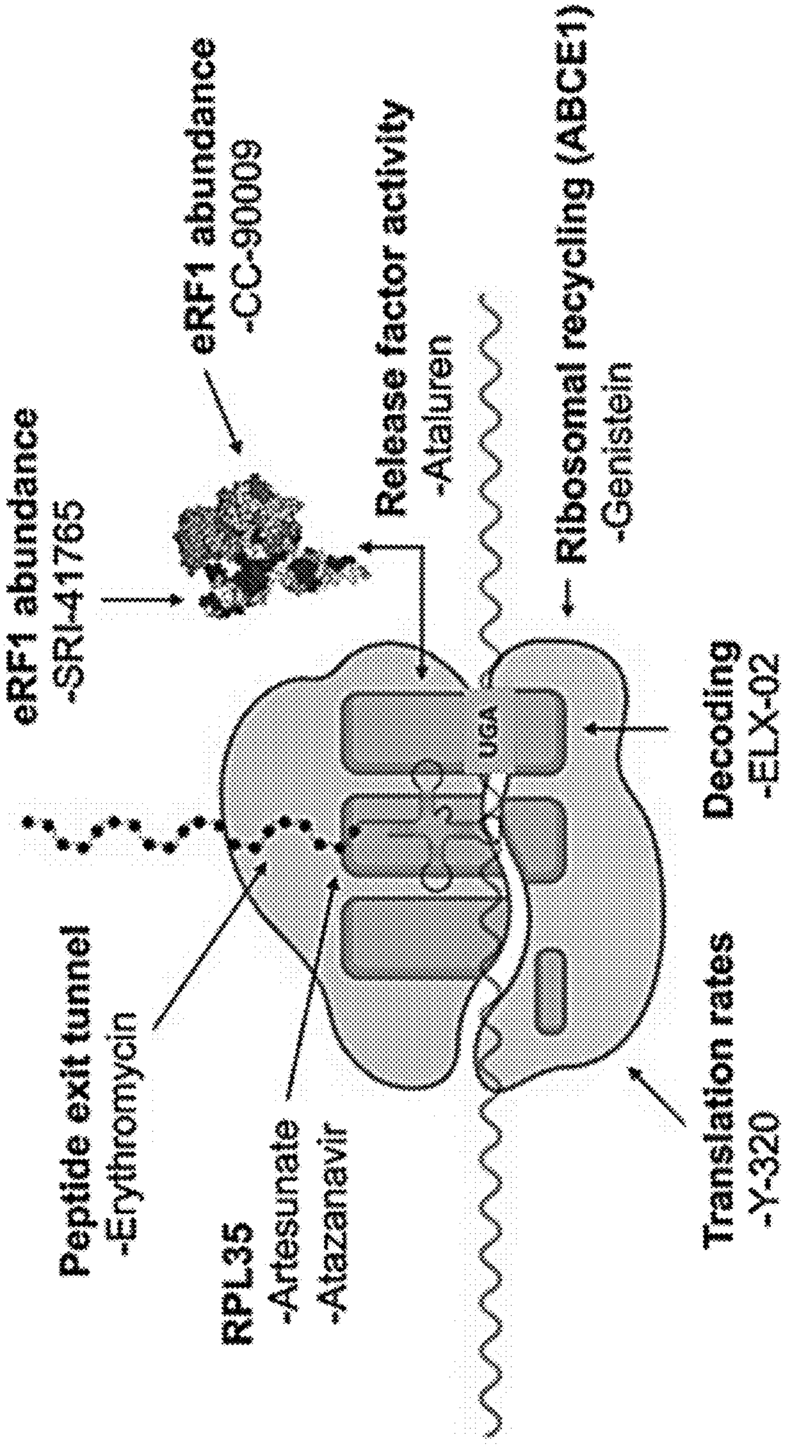
FIG. 1 shows a representative schematic illustrating that different compound classes induce PTC readthrough by distinct mechanisms.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

As used herein, "$EC_{50}$" is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, "$CC_{50}$" is intended to refer to the concentration of a substance (e.g., a compound or a drug) that is required for 50% reduction of cell viability. In one aspect, a $CC_{50}$ can refer to the concentration of a substance that is required for 50% reduction of cell viability in vivo, as further defined elsewhere herein. In a further aspect, $CC_{50}$ can refer to the concentration of a substance that is required for 50% reduction of cell viability in vitro, as further defined elsewhere herein.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form, which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions that can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radioactively labeled forms, isomers, solvates and combinations thereof. The "combinations" mentioned in this context are refer to derivatives falling within at least two of the groups: pharmaceutically acceptable salts, prodrugs, deuterated forms, radioactively labeled forms, isomers, and solvates. Examples of radioactively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids that are present in different states of order that are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in treating disorders associated with the presence of a premature termination codon such as, for example, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer.

In one aspect, the disclosed compounds modulate read-through of a premature termination codon.

In one aspect, the compounds of the invention are useful in modulating read-through of a premature termination codon in a subject (e.g., a mammal). In a further aspect, the compounds of the invention are useful in modulating read-through of a premature termination codon in at least one cell.

In one aspect, the compound has an $EC_{50}$ of less than 10 μM. In a further aspect, the compound has an $EC_{50}$ of less than 8 μM. In a still further aspect, the compound has an $EC_{50}$ of less than 6 μM. In yet a further aspect, the compound has an $EC_{50}$ of less than 4 μM. In an even further aspect, the compound has an $EC_{50}$ of less than 2 μM. In a still further aspect, the compound has an $EC_{50}$ of less than 1 μM. In yet a further aspect, the compound has an $EC_{50}$ of less than 0.8 μM. In an even further aspect, the compound has an $EC_{50}$ of less than 0.6 μM. In a still further aspect, the compound has an $EC_{50}$ of less than 0.4 μM. In yet a further aspect, the compound has an $EC_{50}$ of less than 0.2 μM. In an even further aspect, the compound has an $EC_{50}$ of less than 0.1 μM.

In one aspect, the compounds of the invention are useful in the treatment of a disorder associated with the presence of a premature termination codon, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

I. Structure

In one aspect, disclosed are compounds having a structure represented by a formula:

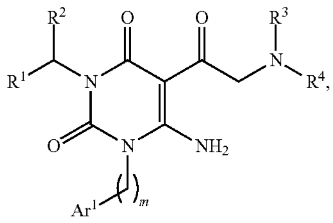

wherein m is 1 or 2; wherein $R^1$ is selected from C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein each occurrence of $R^{10a}$, when present, is independently selected from hydrogen and C1-C4 alkyl; wherein each occurrence of $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O (C1-C4 alkyl), and —$(CH_2)_q$$Cy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

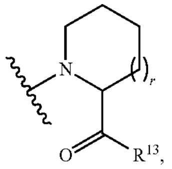

wherein r is 0 or 1; and wherein $R^{13}$ is selected from C1-C4 alkoxy and —$NR^{21a}R^{21b}$; wherein each of $R^{21a}$ and $R^{21b}$ when present, is independently selected from hydrogen, C1-C8 alkyl, C1-C8 haloalkyl, and —$(CH_2)_s$$Cy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when $R^4$ is —$(CR^{10a}R^{10b})_n$C(O)$R^{11}$, —CH($R^{12}$)$Ar^2$, or $Ar^2$, or when $R^3$ and $R^4$ together comprise a heterocycle having a structure represented by a formula:

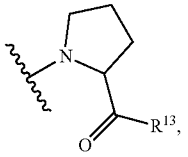

then $R^1$ is $Cy^1$ or $R^1$ and $R^2$ together comprise a C3-C6 cycloalkyl or a C3-C6 heterocycloalkyl, and provided that when $R^1$ is C1-C3 alkyl, $R^3$ and $R^4$ together comprise a heterocycle having a structure represented by a formula:

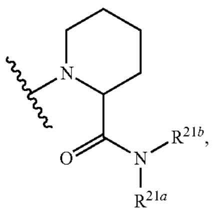

and $Ar^1$ is phenyl, then either (i) $Ar^1$ is substituted with at least one non-hydrogen group; or (ii) at least one of $R^{21a}$ and $R^{21b}$ is hydrogen, or a pharmaceutically acceptable salt thereof.

Also disclosed are compounds selected from:

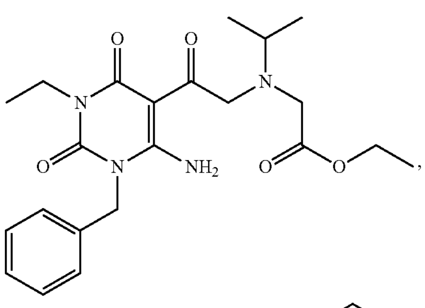

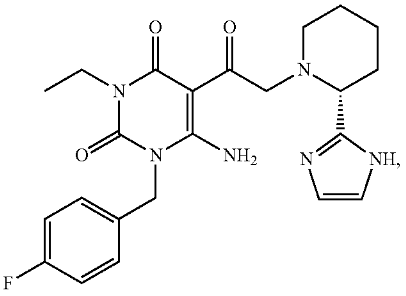

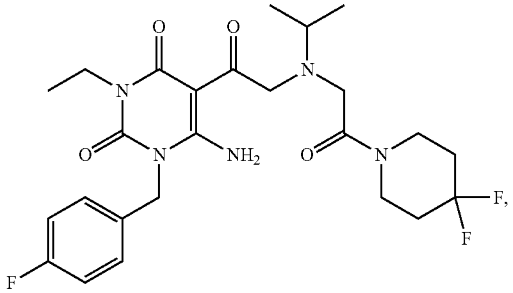

-continued
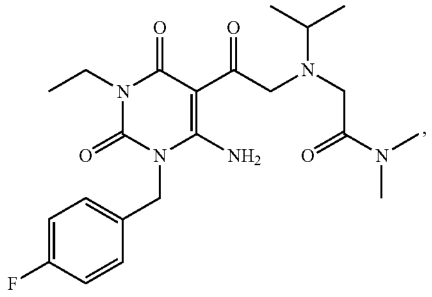
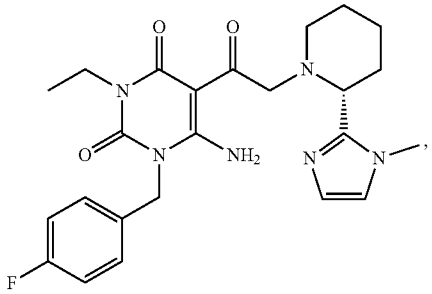
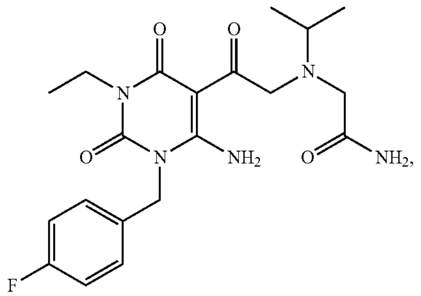
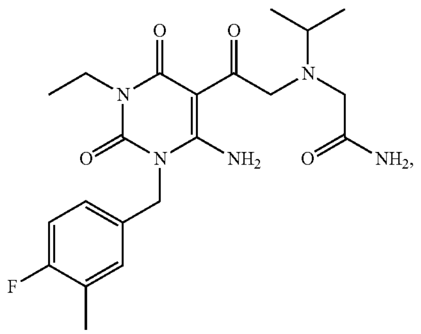
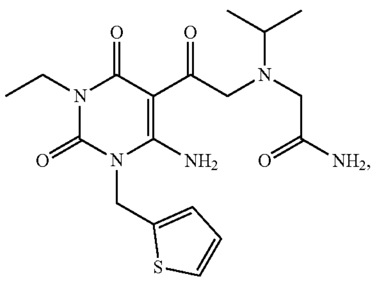
-continued
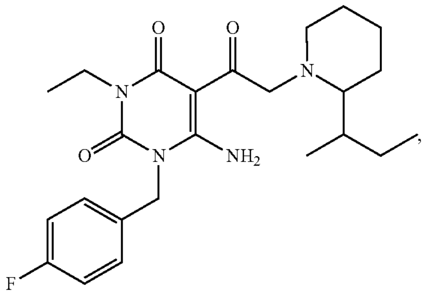
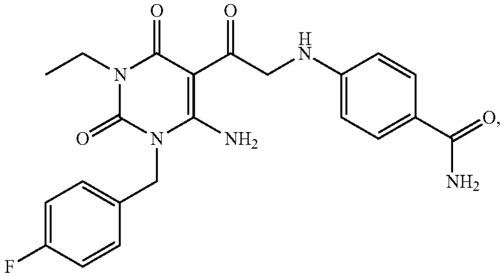
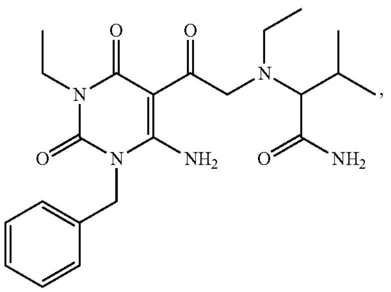
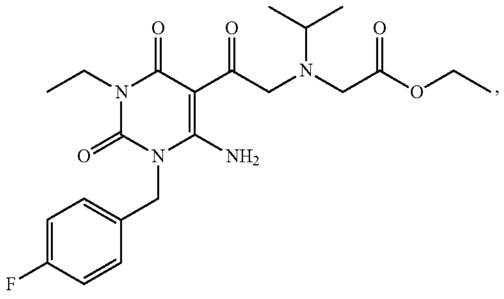
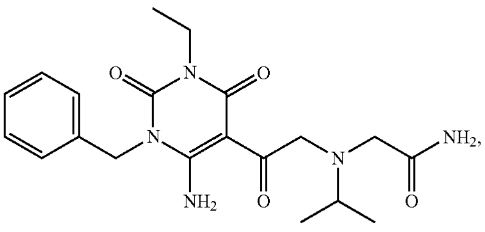
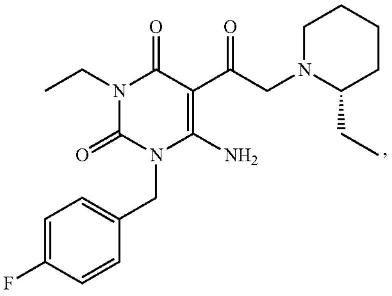

-continued
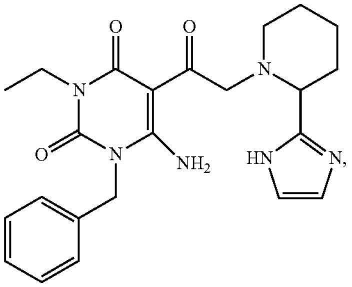
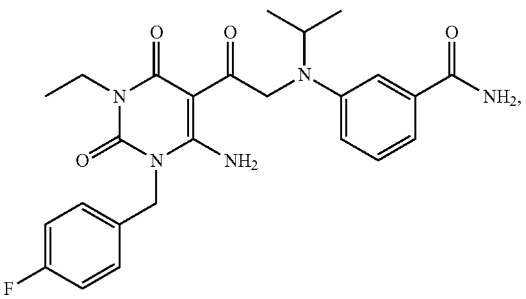
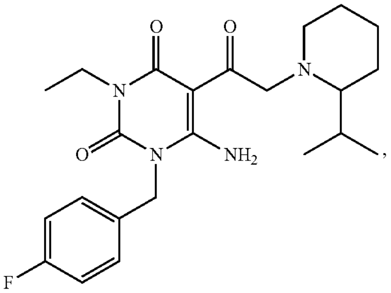
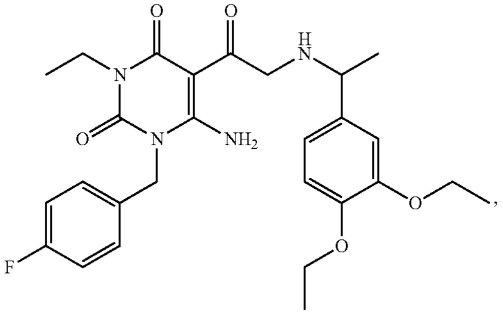
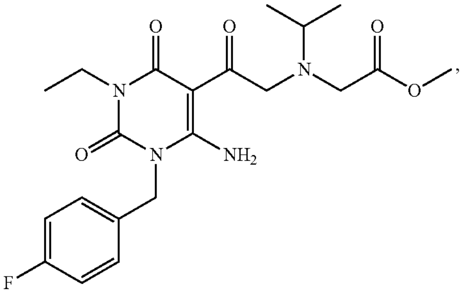
-continued
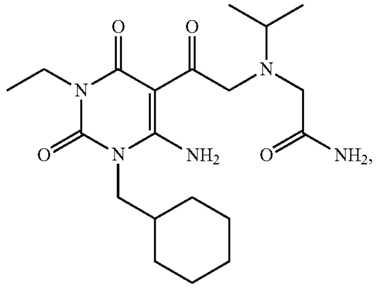
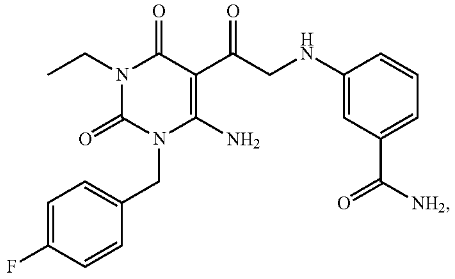
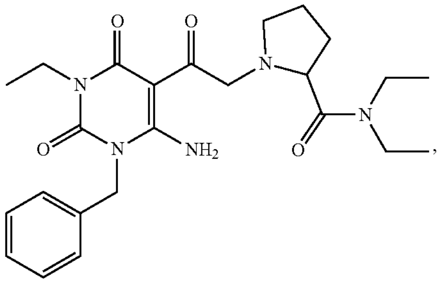
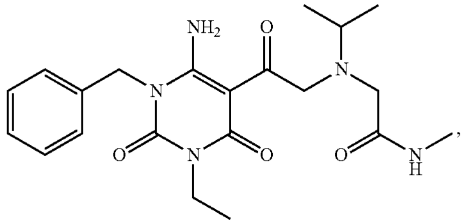
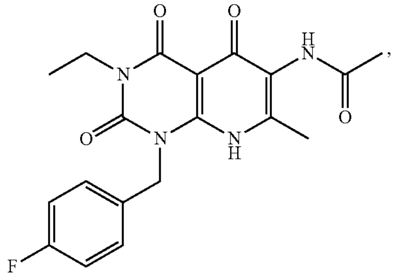
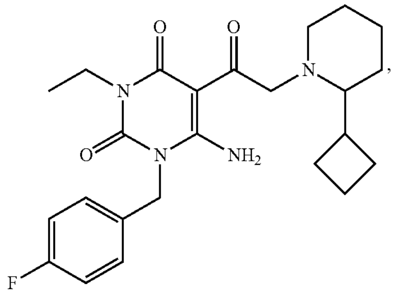

-continued
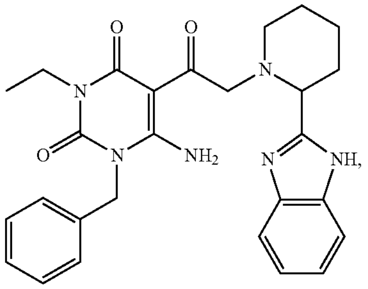
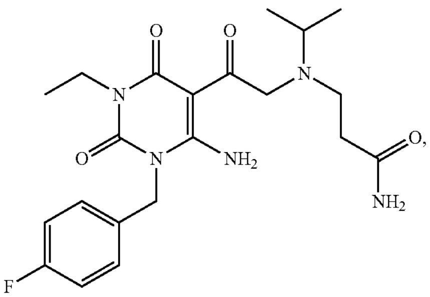
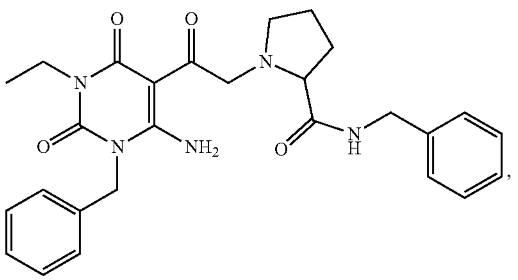
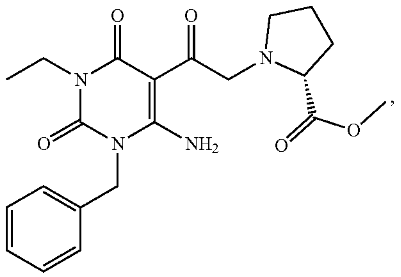
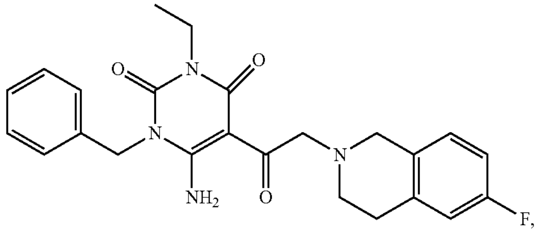
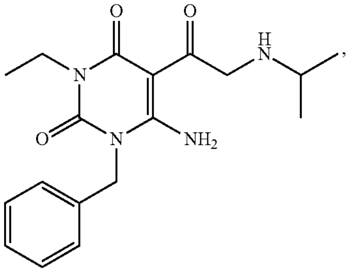
-continued
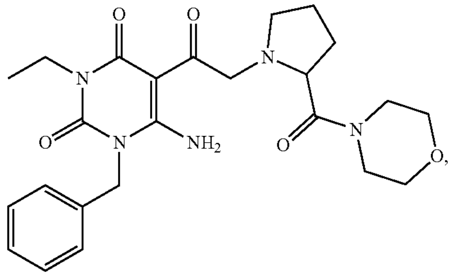
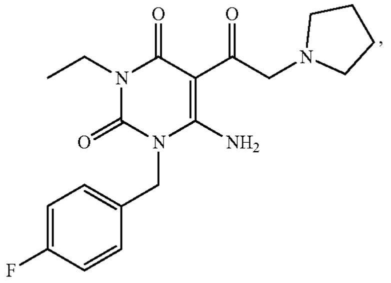
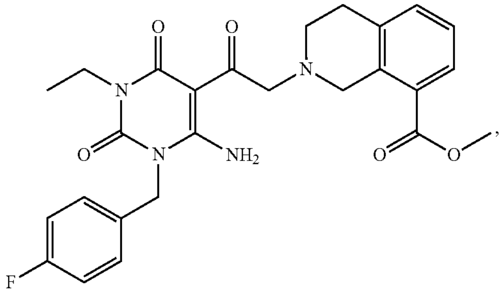
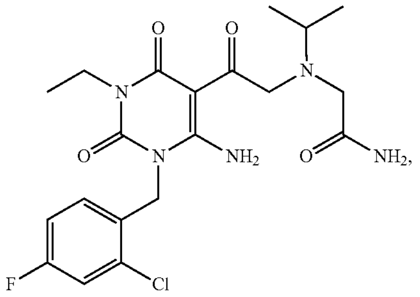
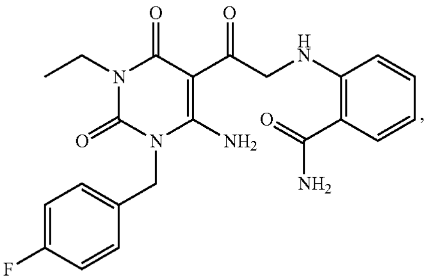
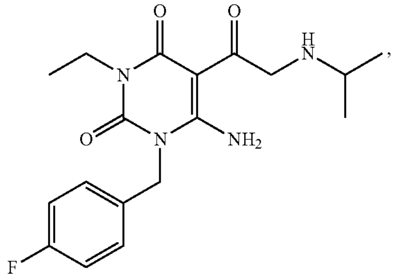

-continued
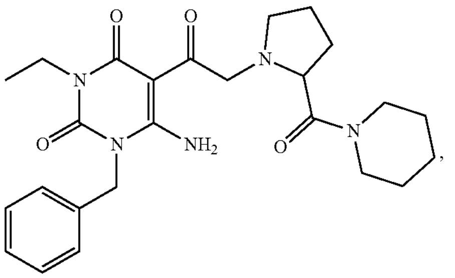
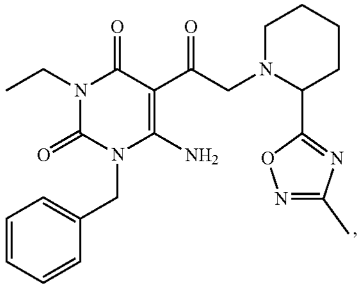
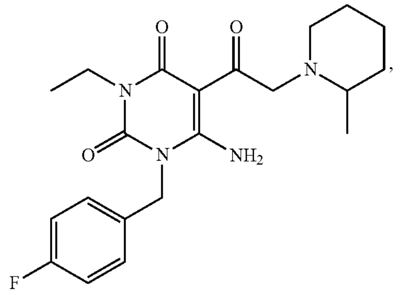
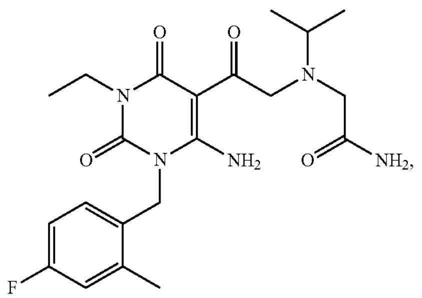
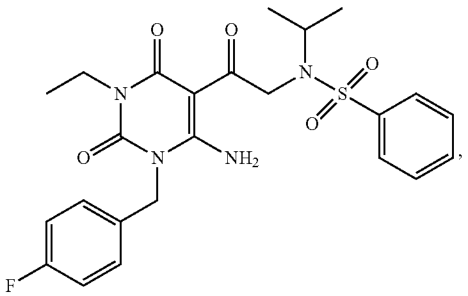
-continued
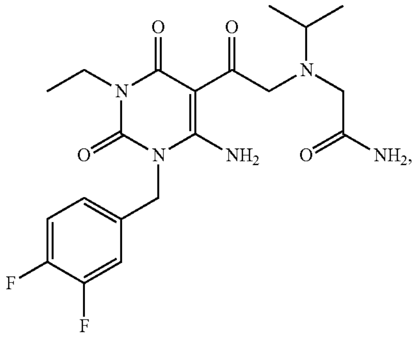
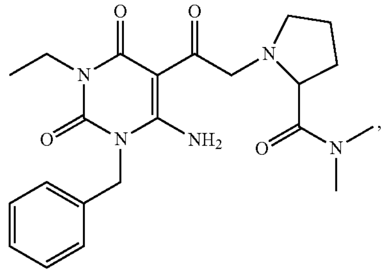
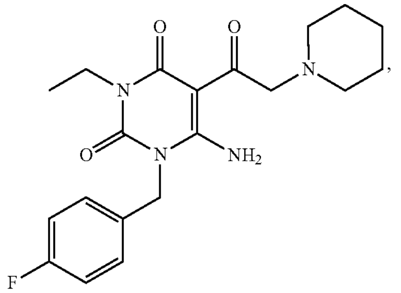
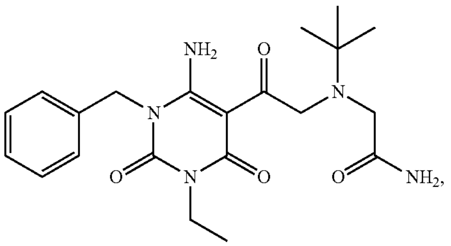
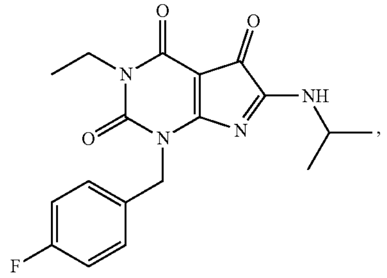
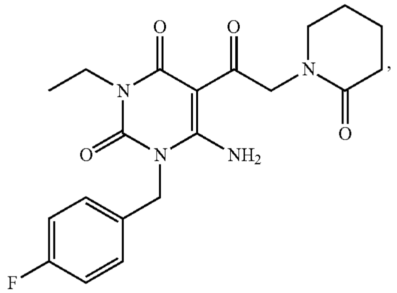

-continued
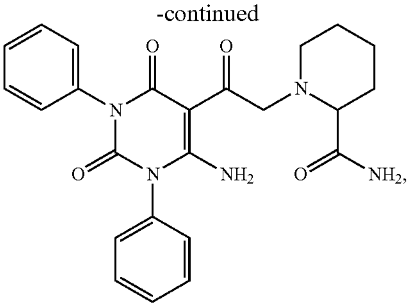
,
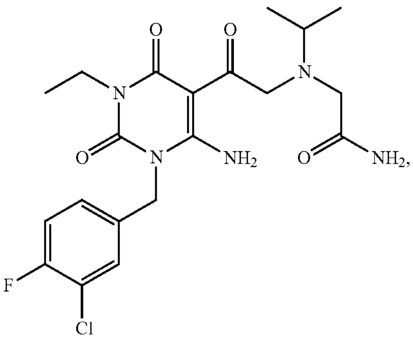
,
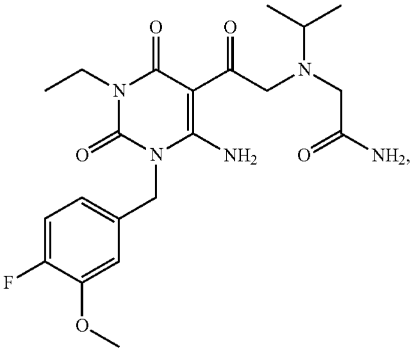
,
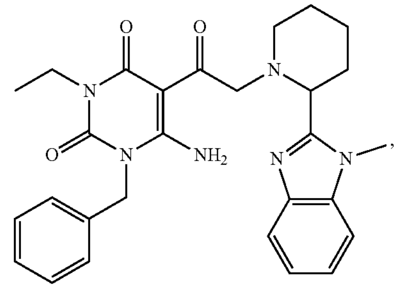
,
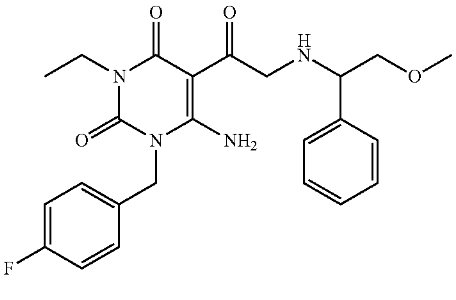
,
-continued
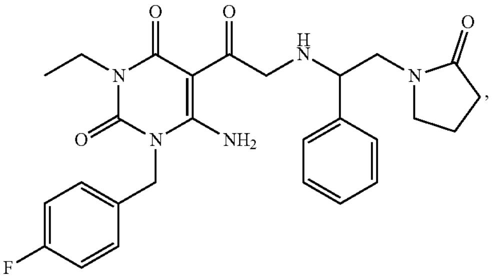
,
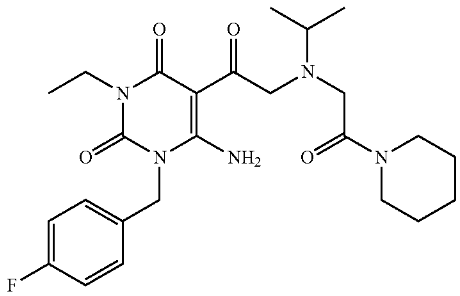
,
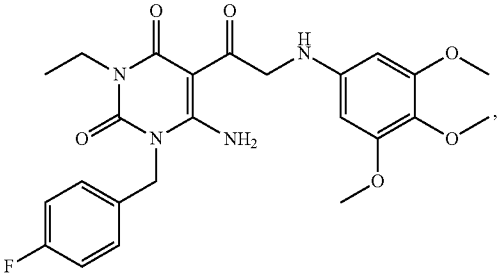
,
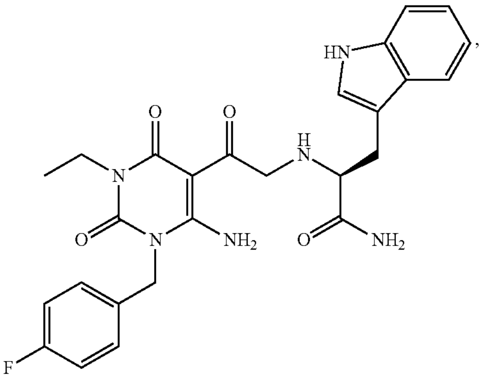
,
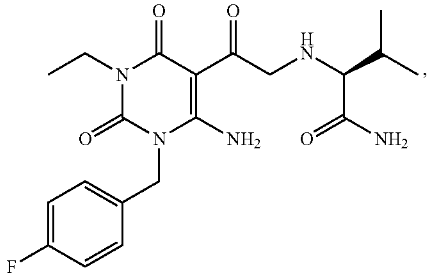
, -continued
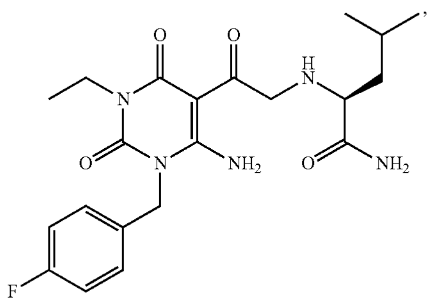
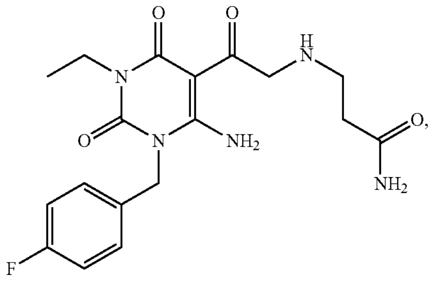
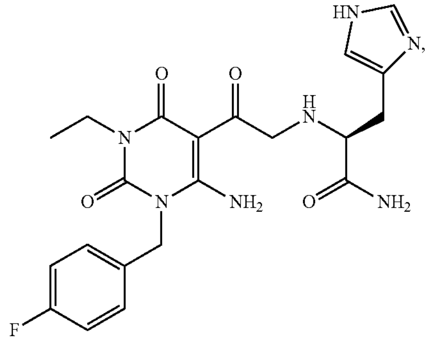
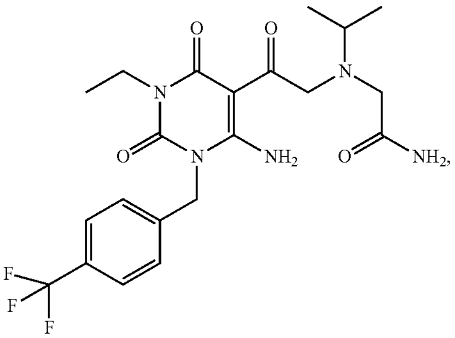
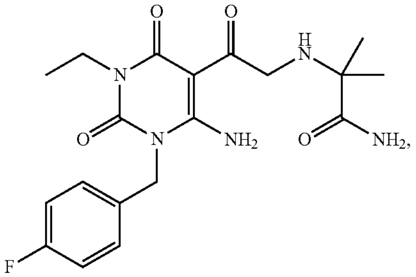
-continued
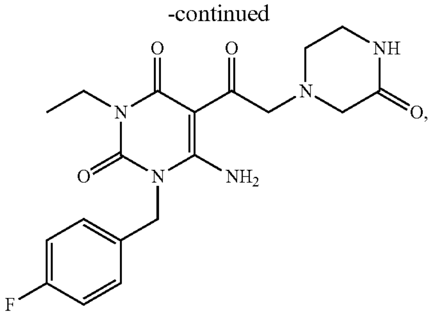
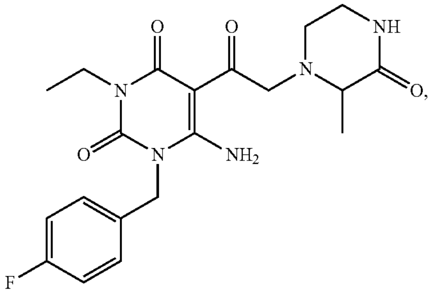
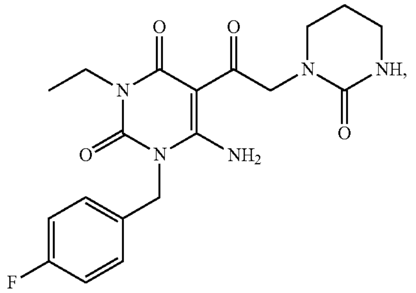
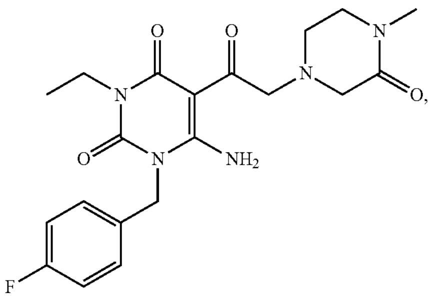
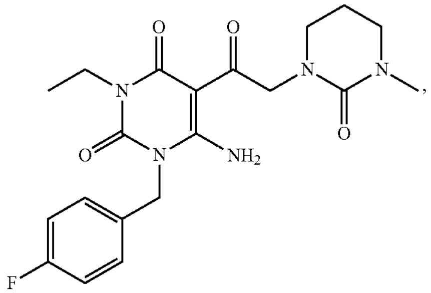

-continued
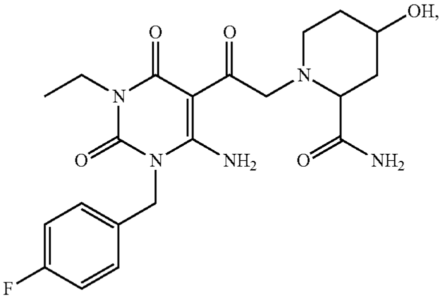
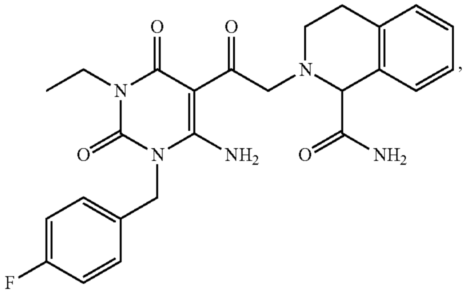
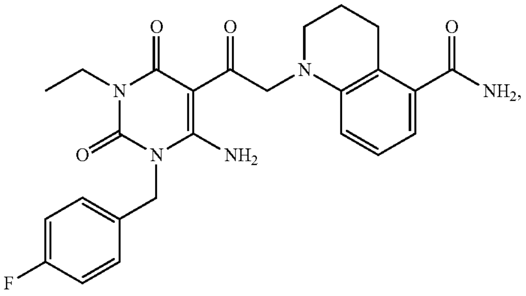
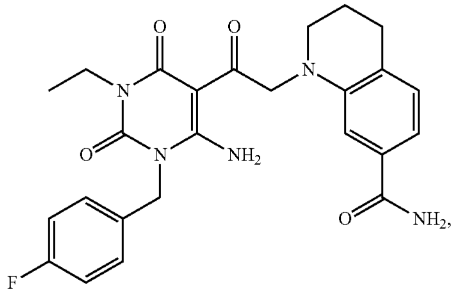
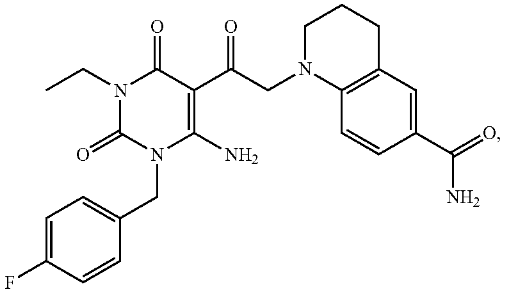
-continued
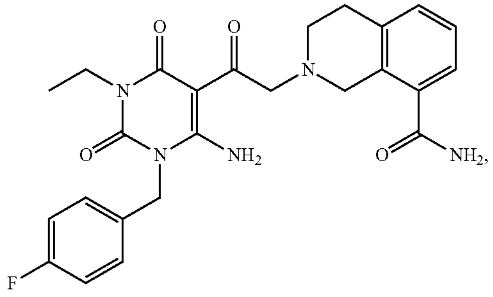
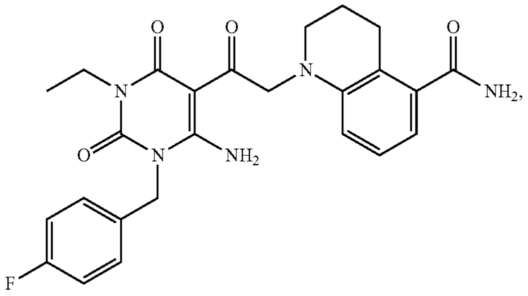
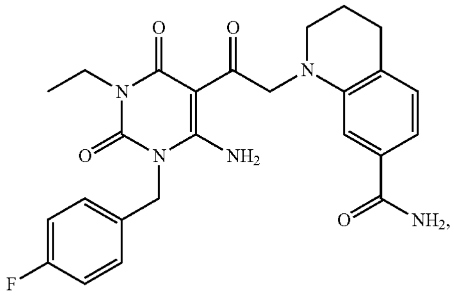
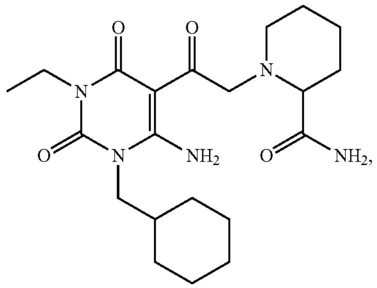
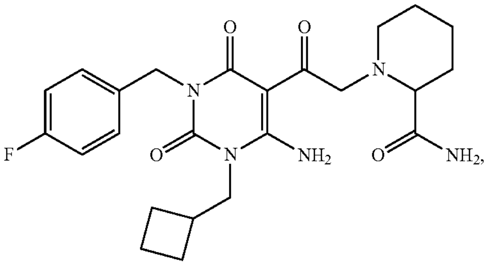
and -continued

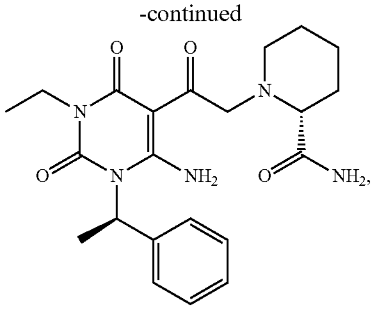

or a pharmaceutically acceptable salt thereof.

Also disclosed are compounds having a structure represented by a formula:

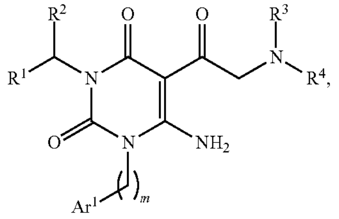

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$, when present, is independently selected from hydrogen and C1-C4 alkyl; wherein $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

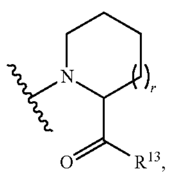

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In various aspects, the compound is not:
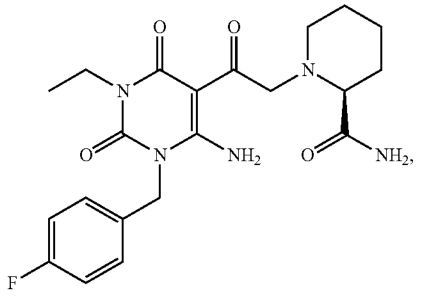
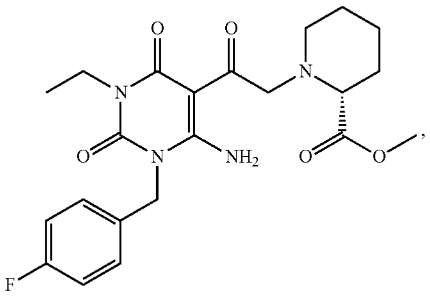
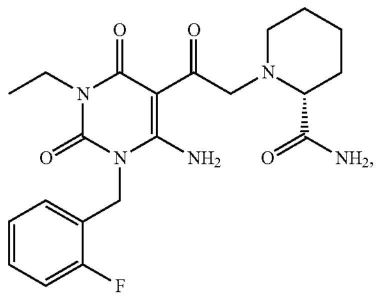
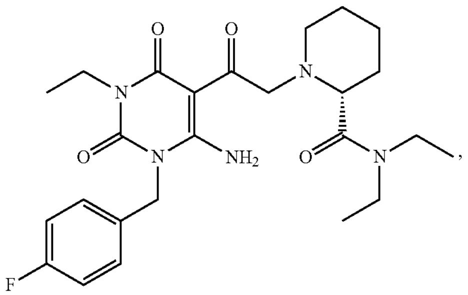
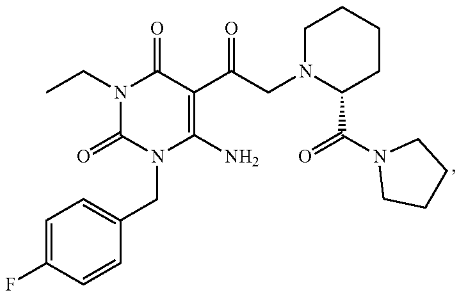
-continued
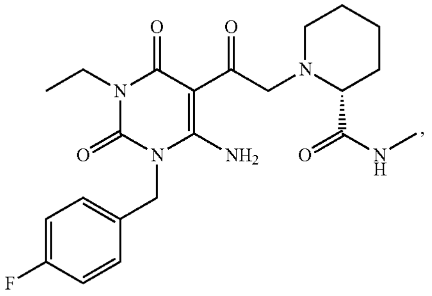
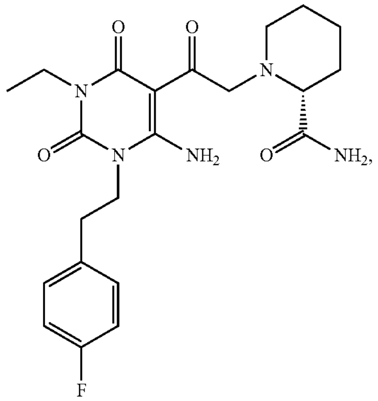
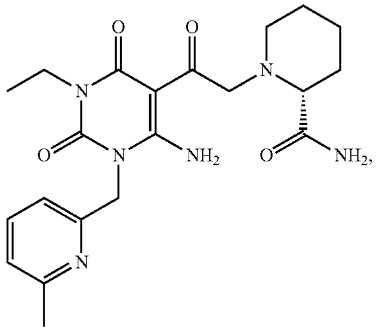
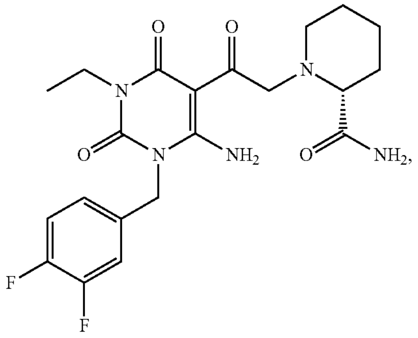
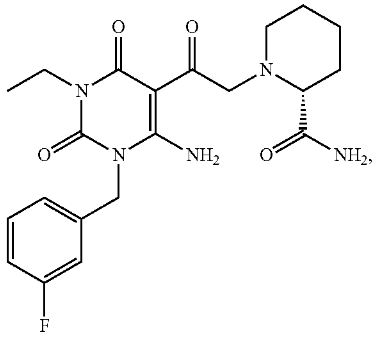

-continued
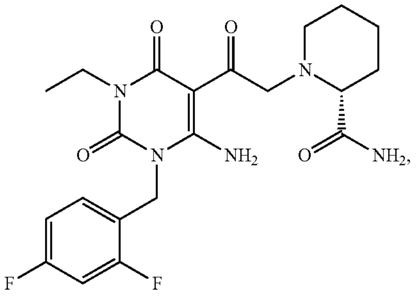
,
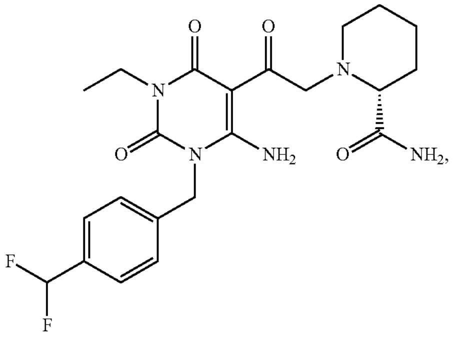
,
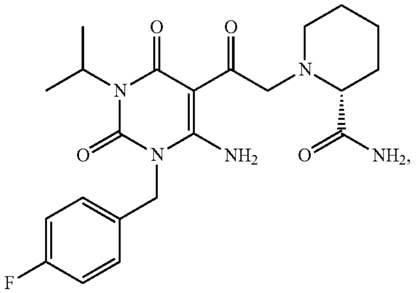
,
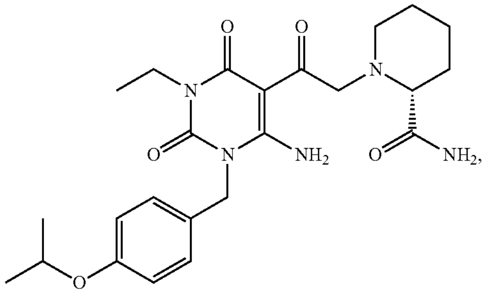
,
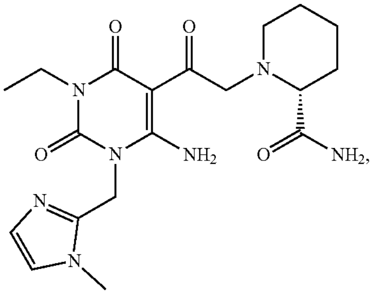
,
-continued
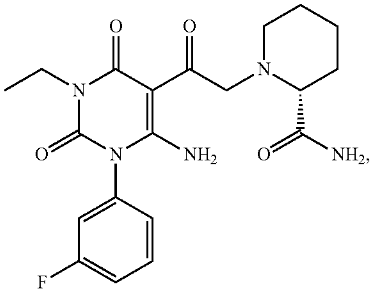
,
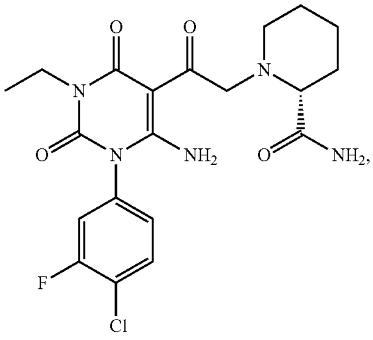
,
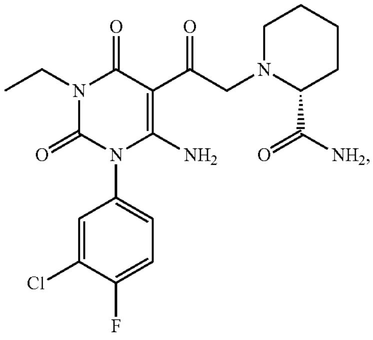
,
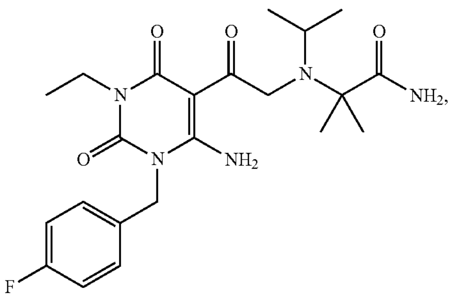
,
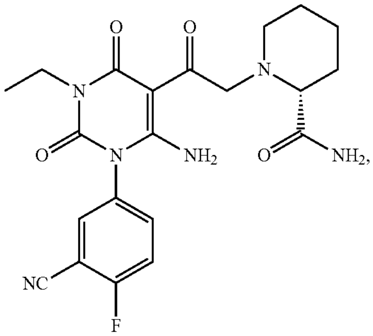
, -continued

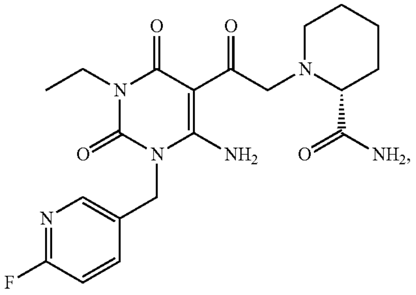

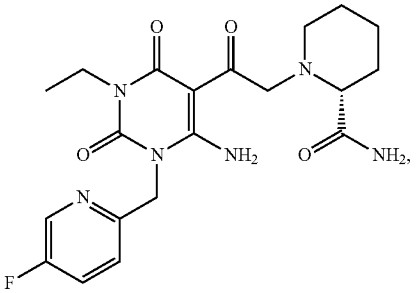

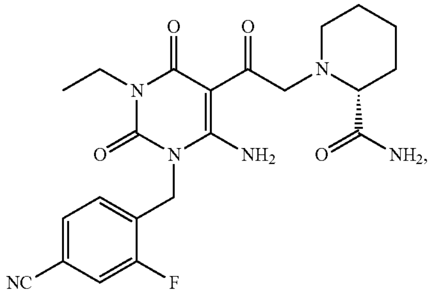

or

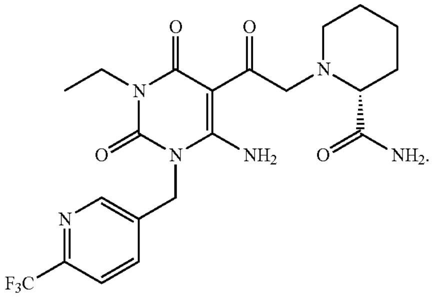

In various aspects, the compound has a structure represented by a formula:

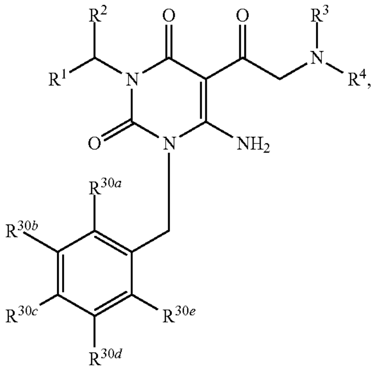

wherein each of $R^{30a}$, $R^{30b}$, $R^{30c}$, $R^{30d}$, and $R^{30e}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl).

In various aspects, the compound has a structure represented by a formula:

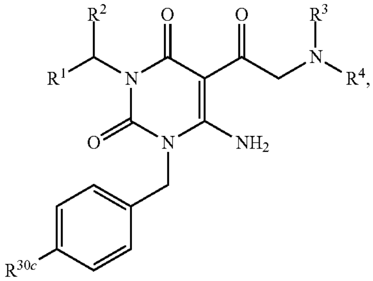

In various aspects, the compound has a structure represented by a formula:

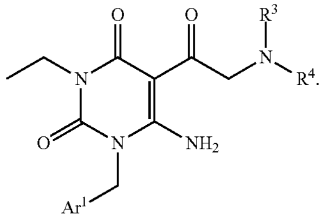

In various aspects, the compound has a structure represented by a formula:

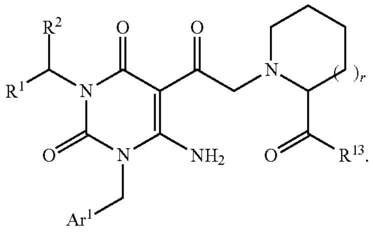

In various aspects, the compound has a structure represented by a formula:

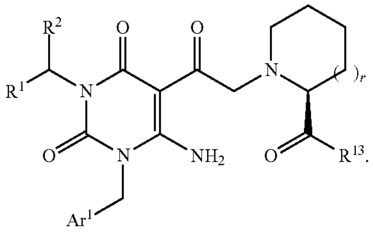

In various aspects, the compound has a structure represented by a formula:

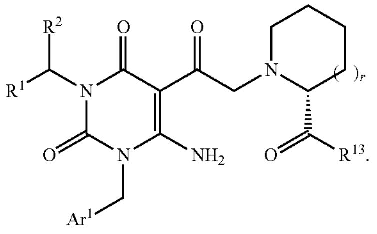

In various aspects, the compound has a structure represented by a formula:

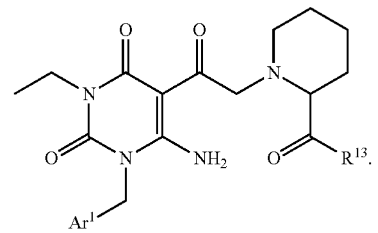

In various aspects, the compound has a structure represented by a formula:

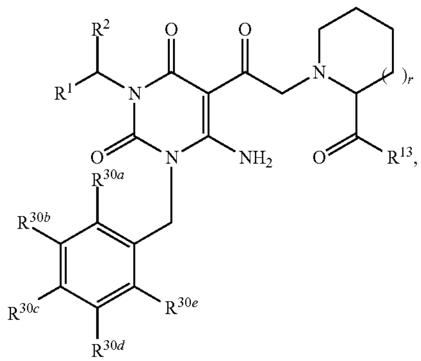

wherein each of $R^{30a}$, $R^{30b}$, $R^{30c}$, $R^{30d}$, and $R^{30e}$ are independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl).

In various aspects, the compound has a structure represented by a formula:

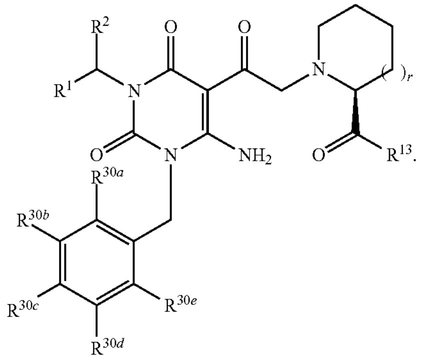

In various aspects, the compound has a structure represented by a formula:

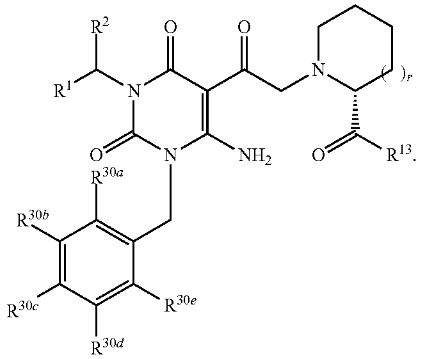

In various aspects, the compound has a structure represented by a formula:

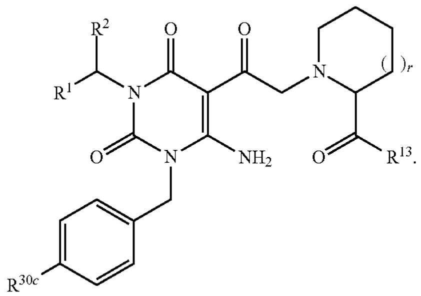

In various aspects, the compound has a structure represented by a formula:

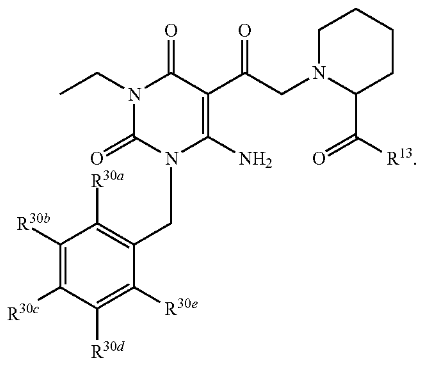

In various aspects, the compound has a structure represented by a formula:

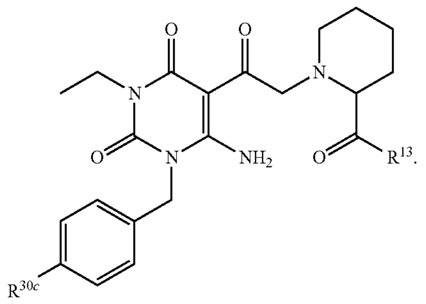

In various aspects, the compound has a structure represented by a formula:

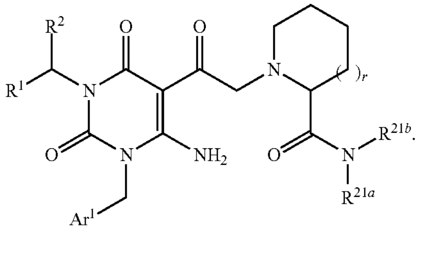

In various aspects, the compound has a structure represented by a formula:

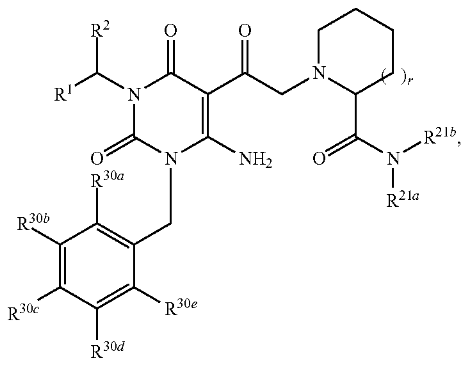

wherein each of $R^{30a}$, $R^{30b}$, $R^{30c}$, $R^{30d}$, and $R^{30e}$ are independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl).

In various aspects, the compound has a structure represented by a formula:

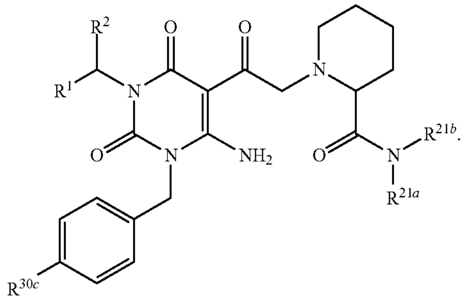

In various aspects, the compound has a structure represented by a formula:

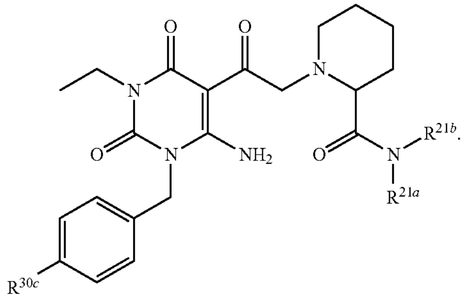

In various aspects, the compound is selected from:
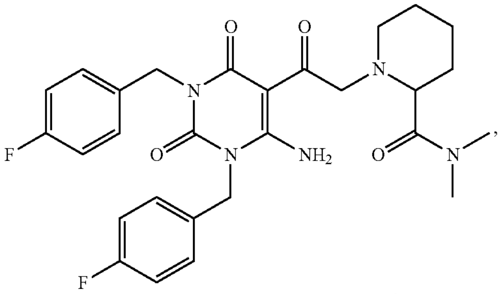
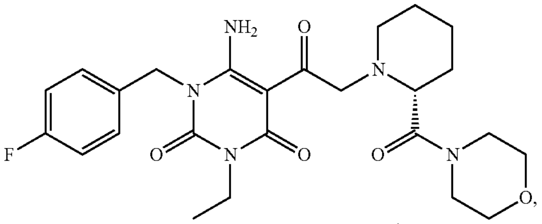
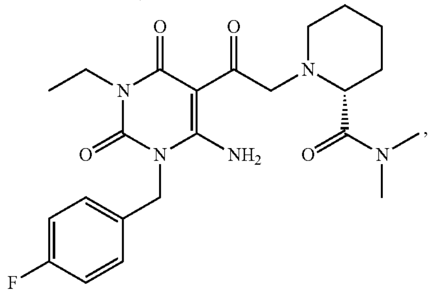
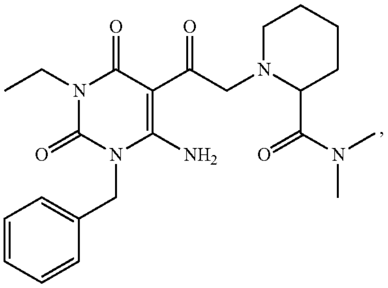
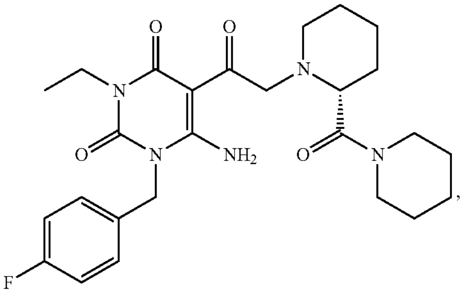
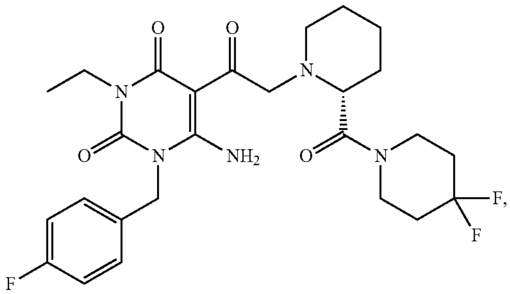
-continued
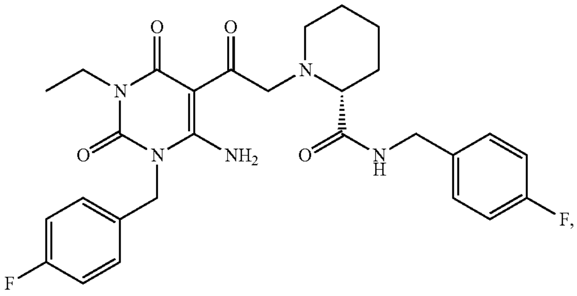
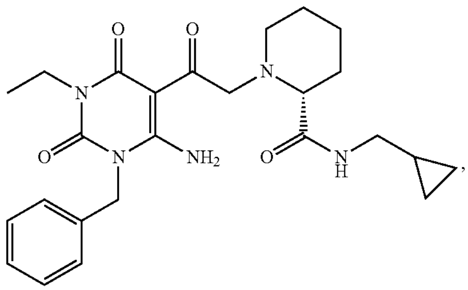
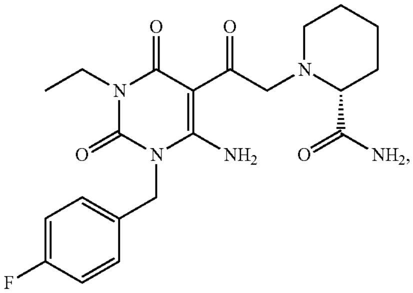
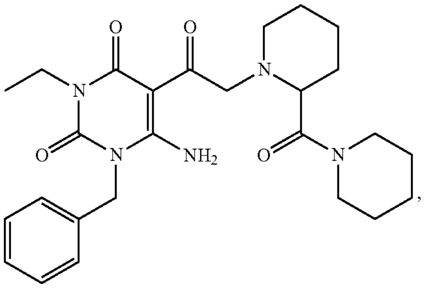
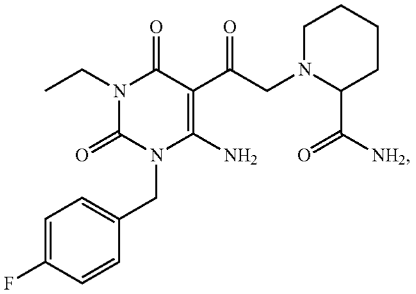

-continued
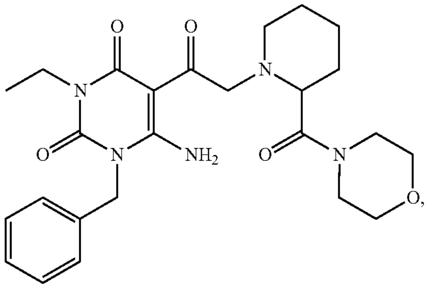
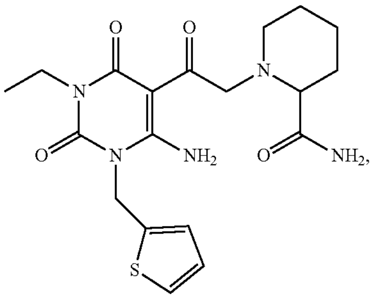
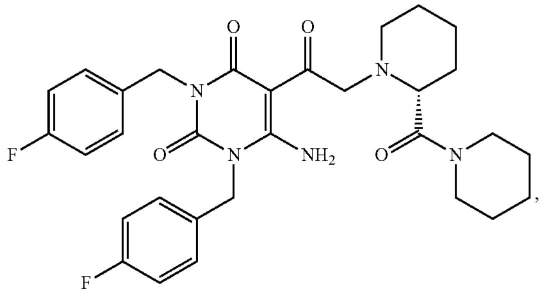
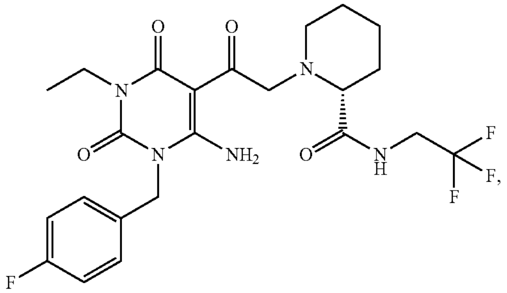
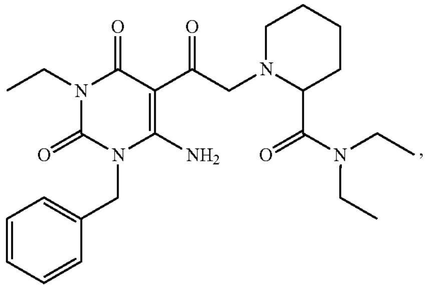
-continued
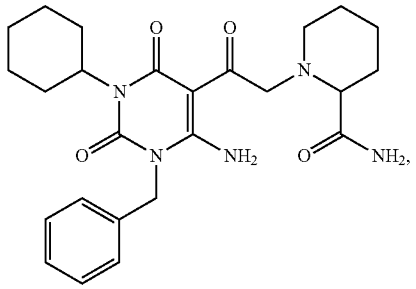
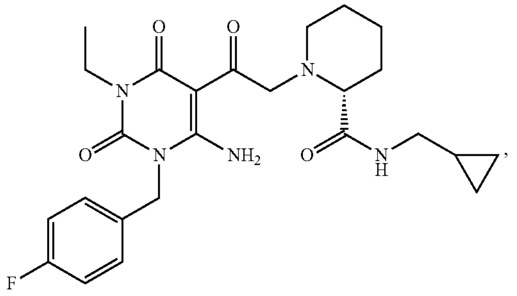
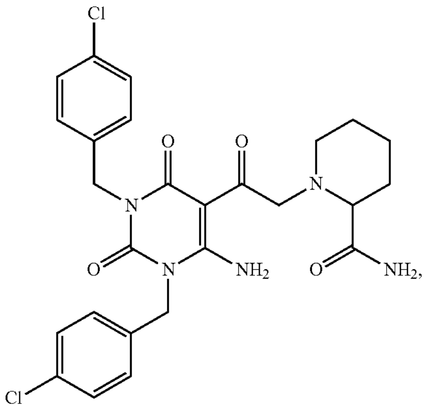
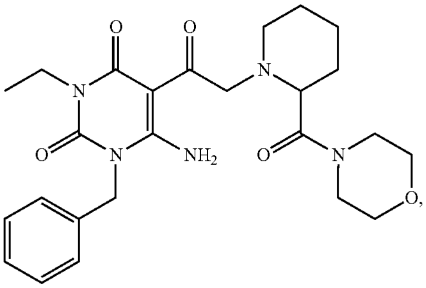
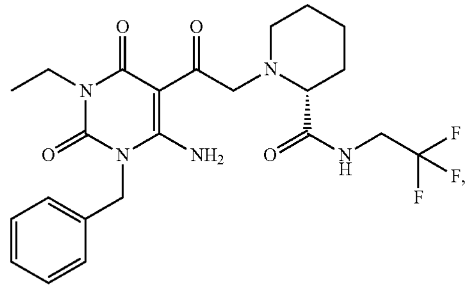

-continued
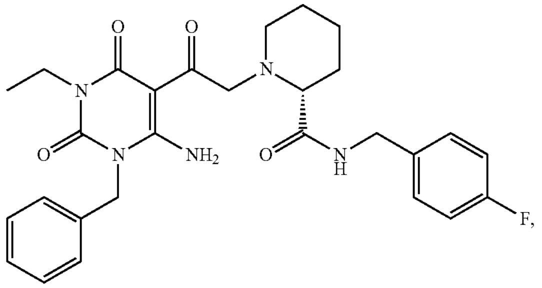
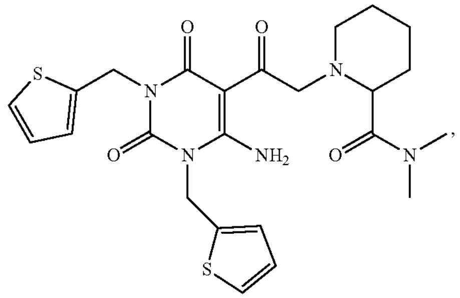
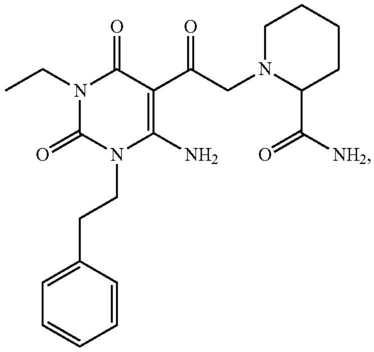
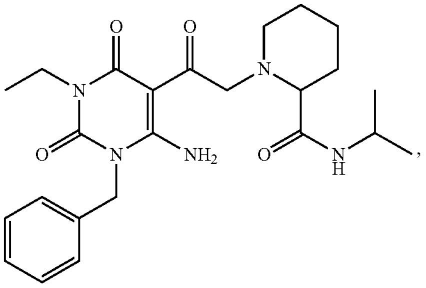
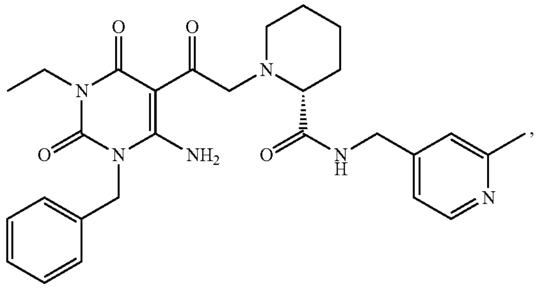
-continued
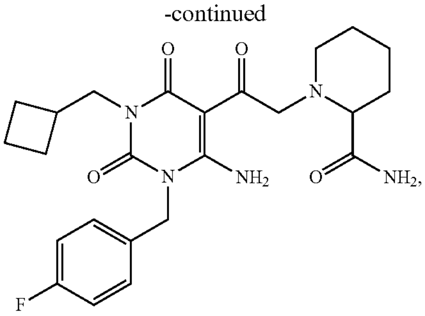
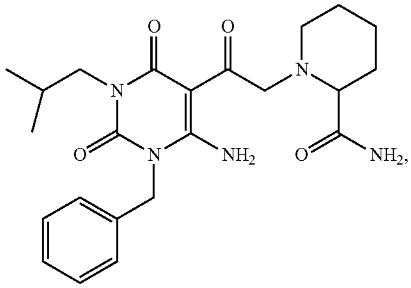
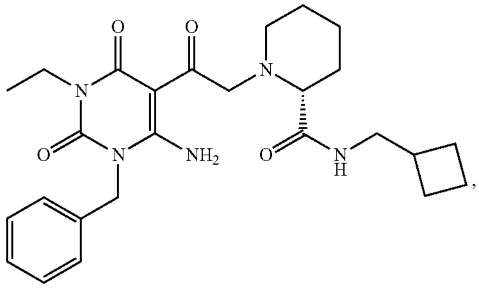
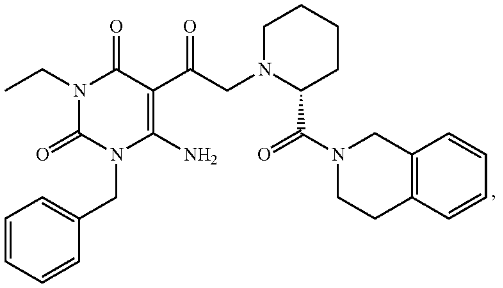
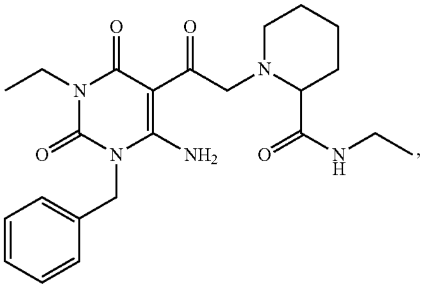
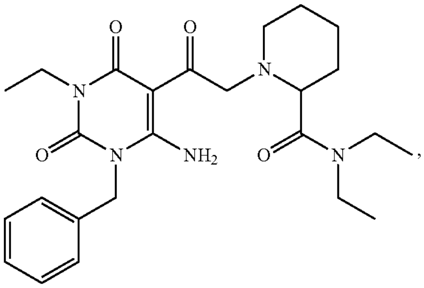

-continued
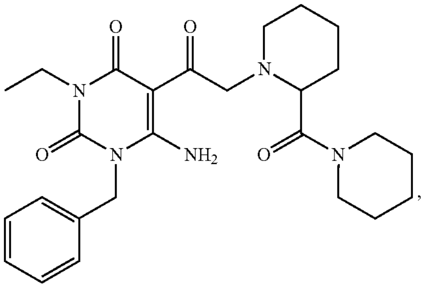
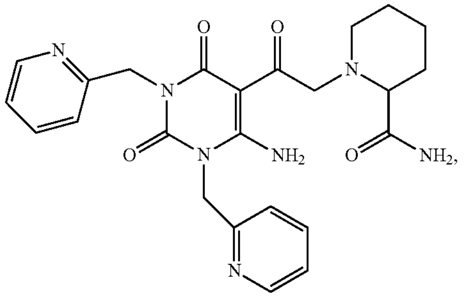
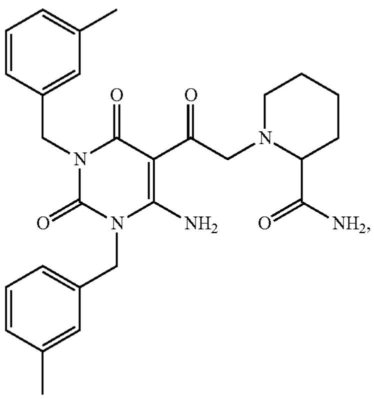
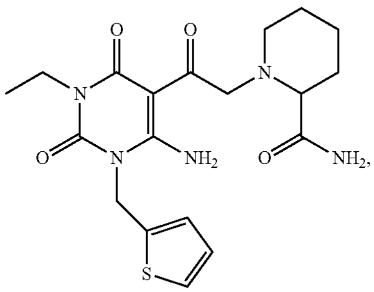
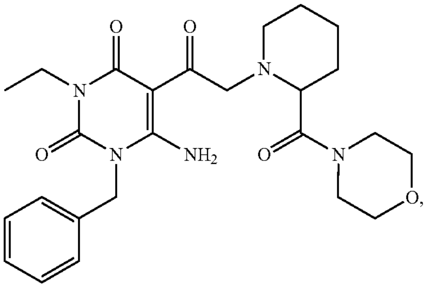
-continued
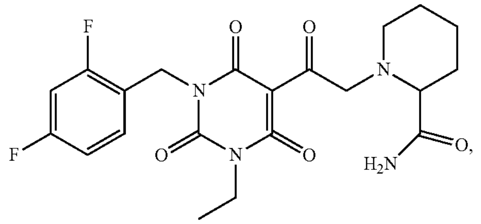
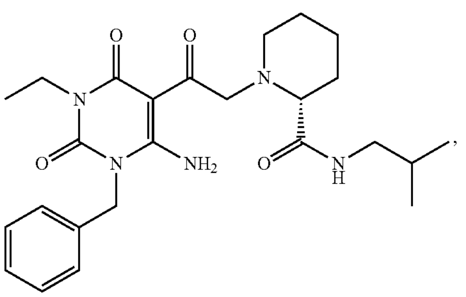
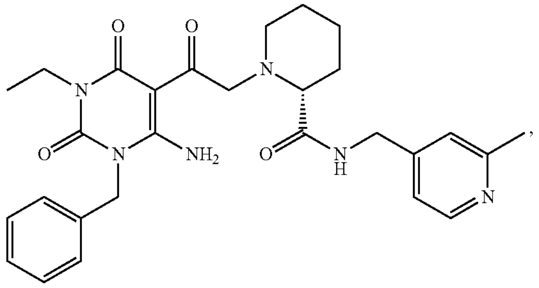
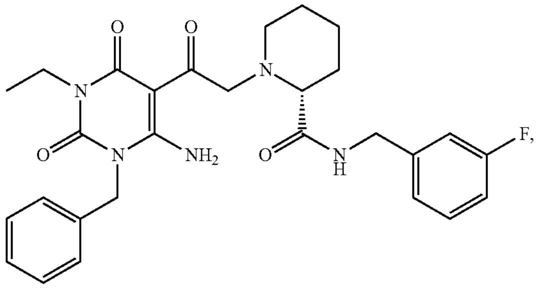
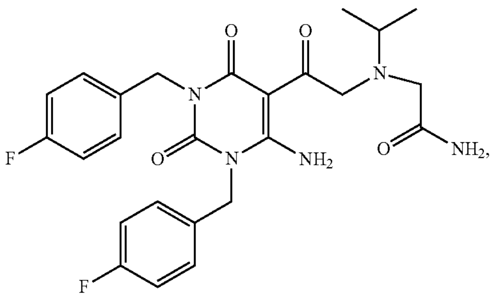
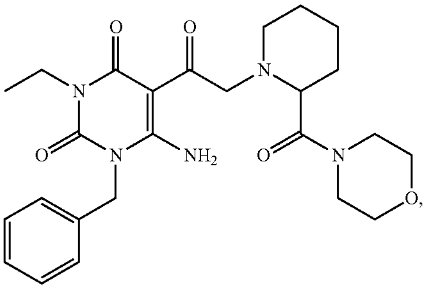

-continued
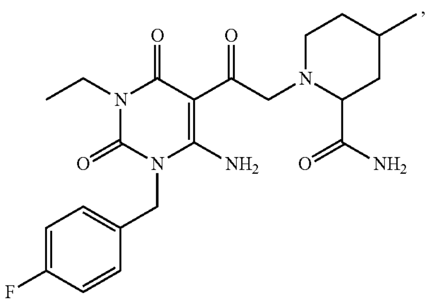
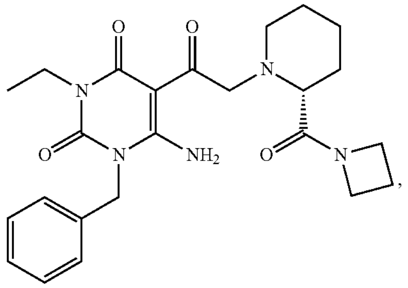
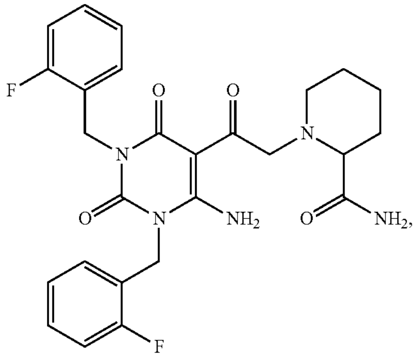
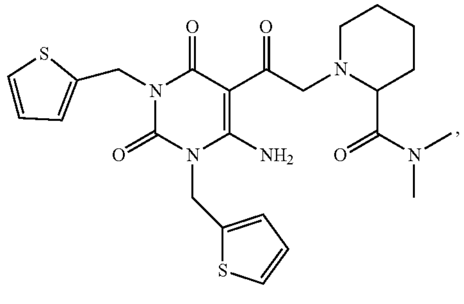
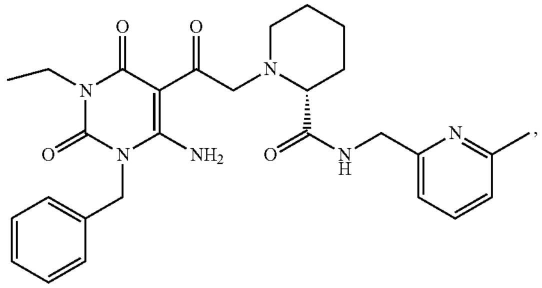
-continued
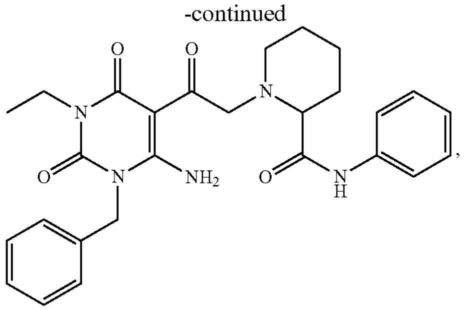
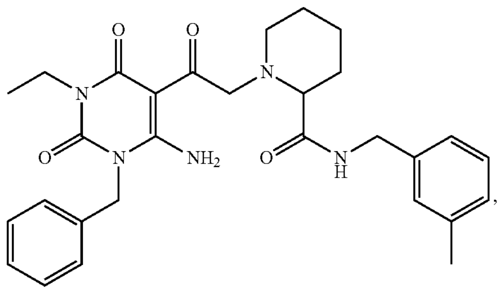
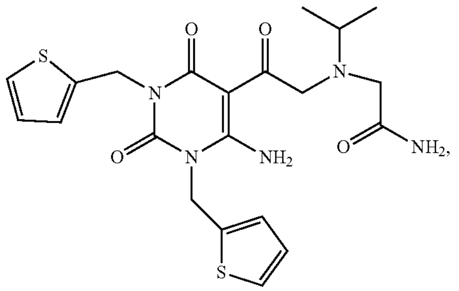
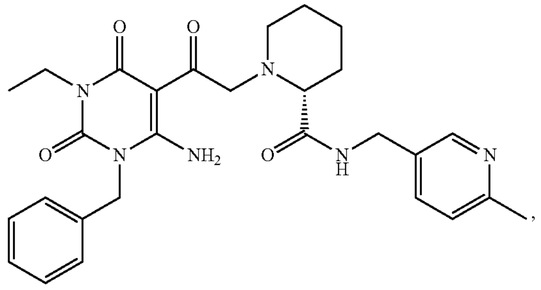
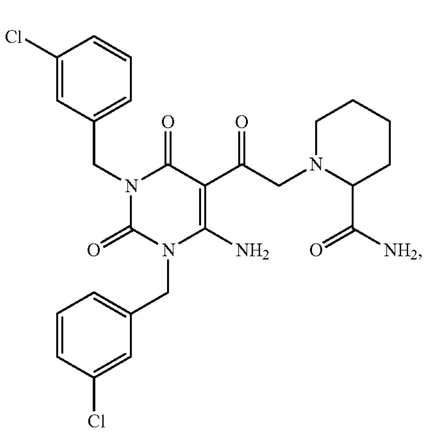

-continued
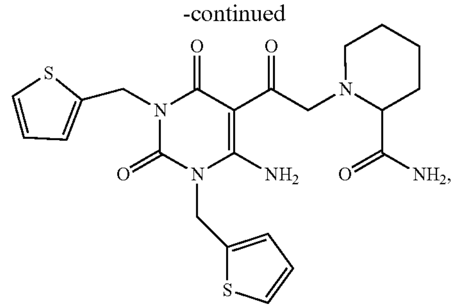
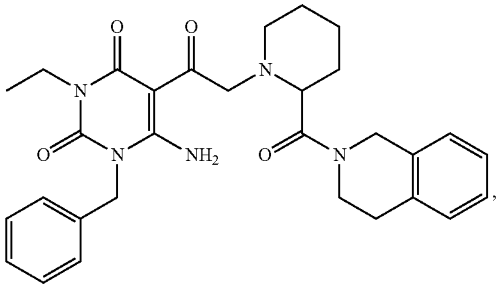
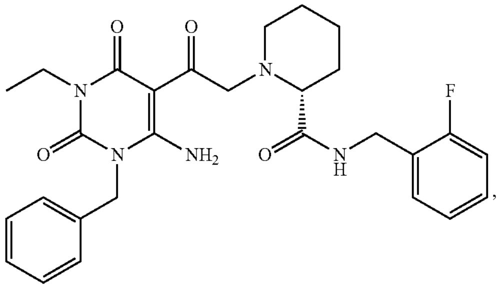
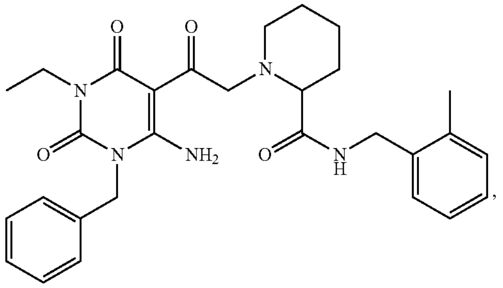
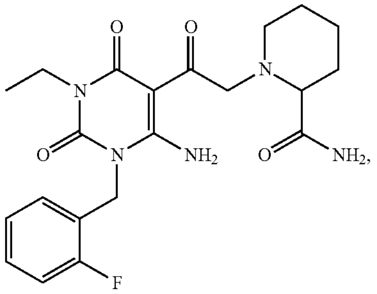
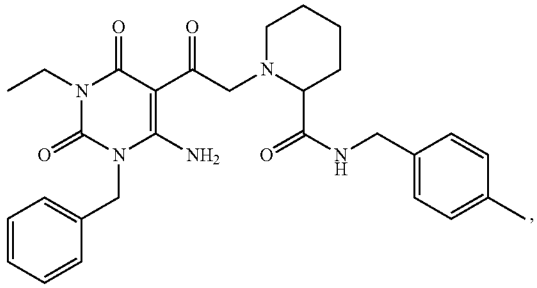
-continued
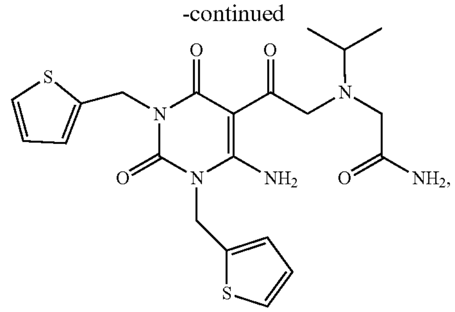
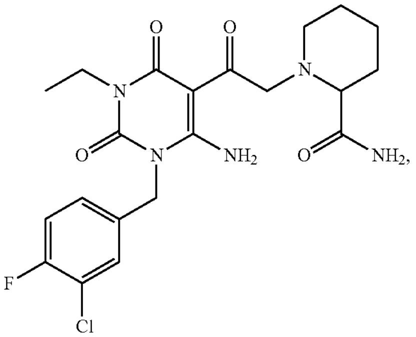
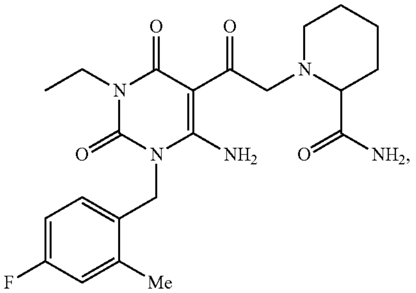
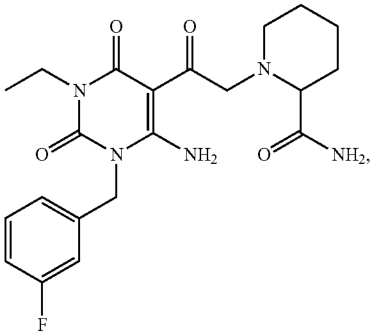
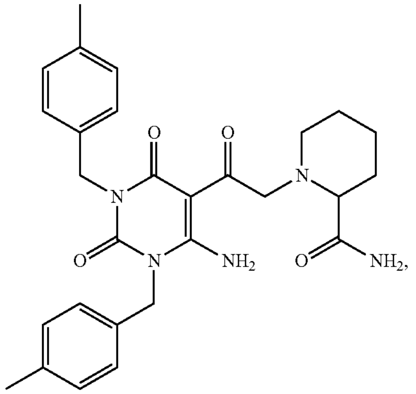

-continued
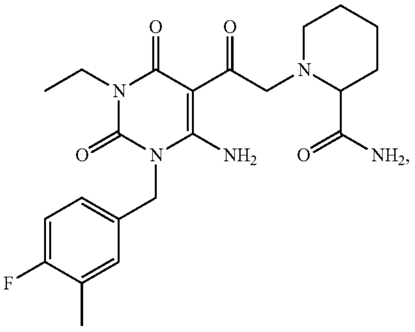
,
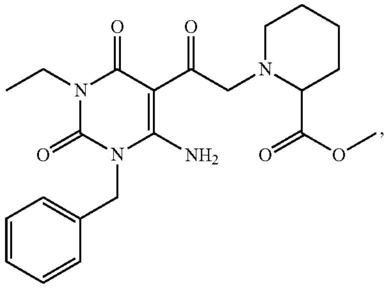
,
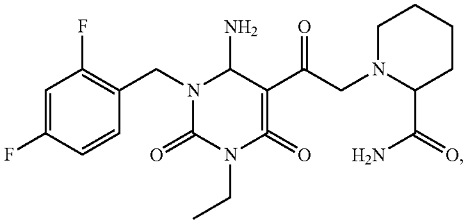
,
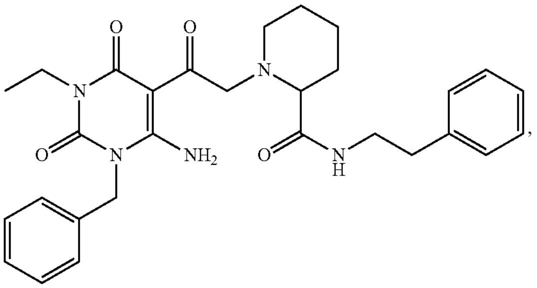
,
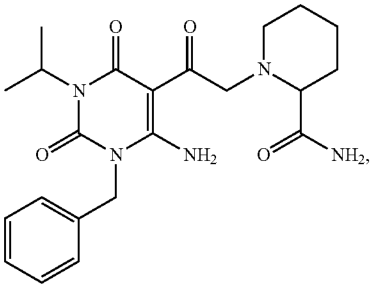
,
-continued
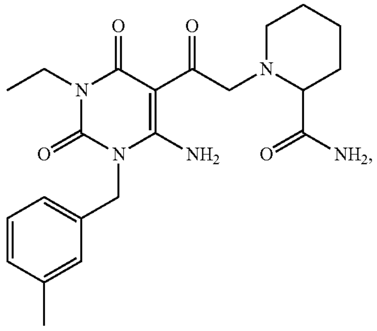
,
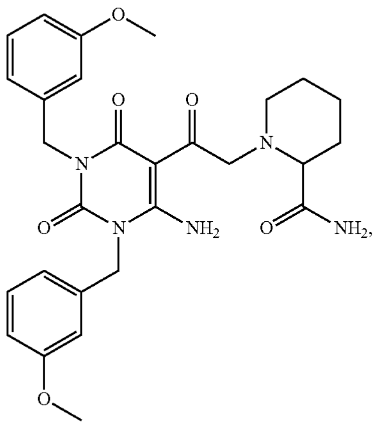
,
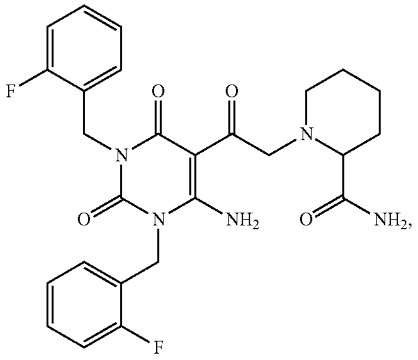
,
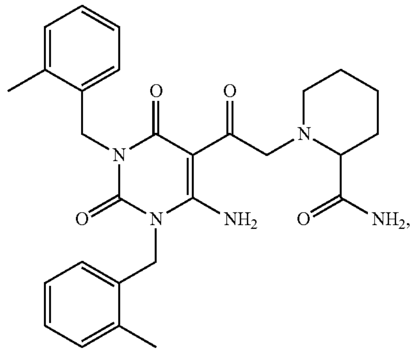
, -continued
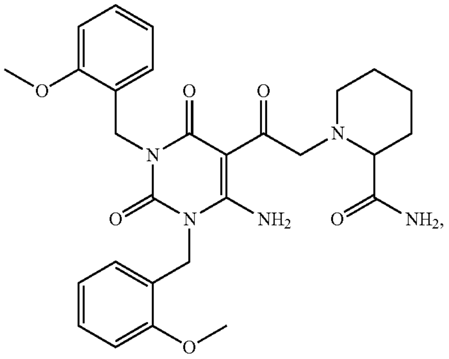
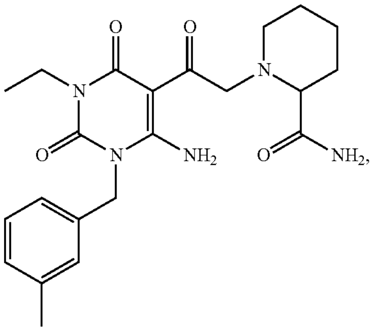
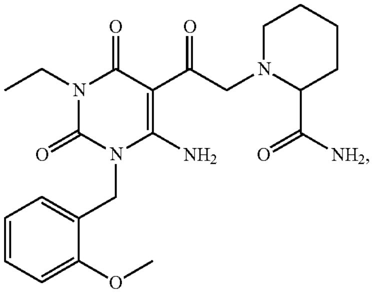
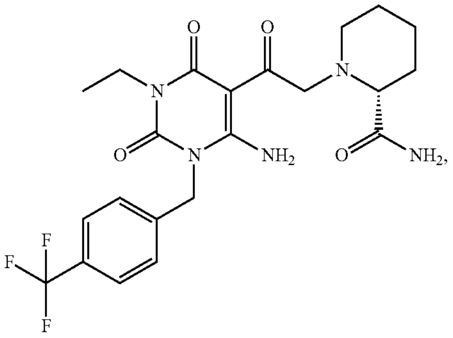
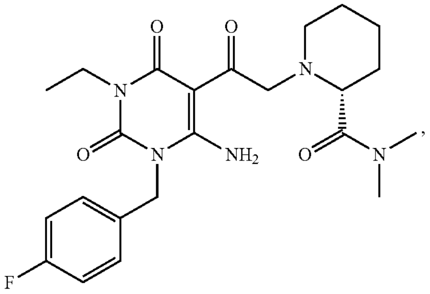
-continued
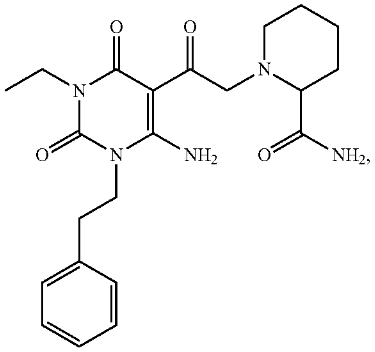
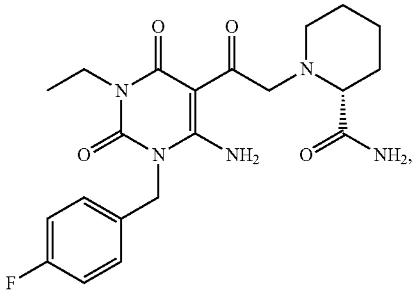
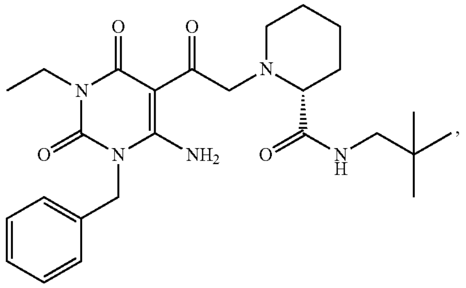
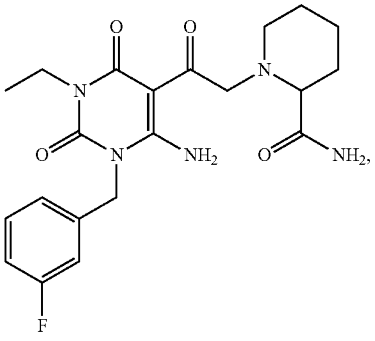
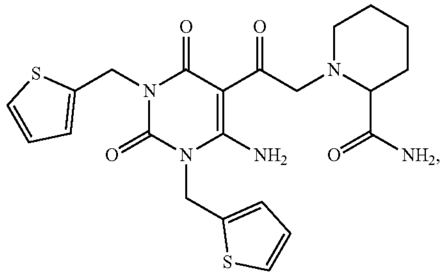

-continued
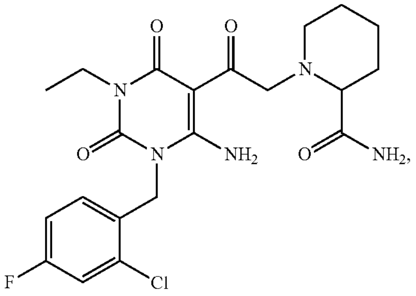
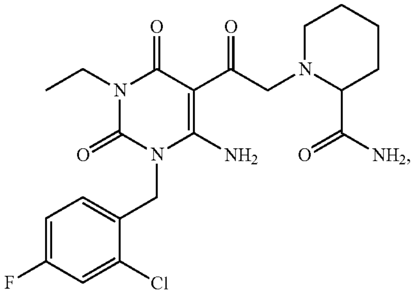
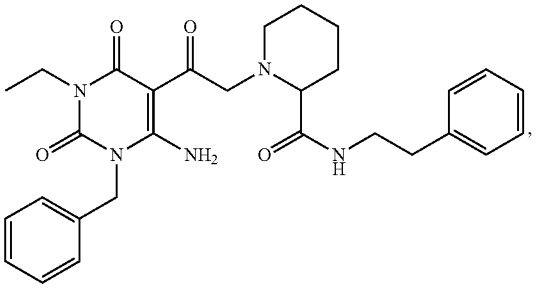
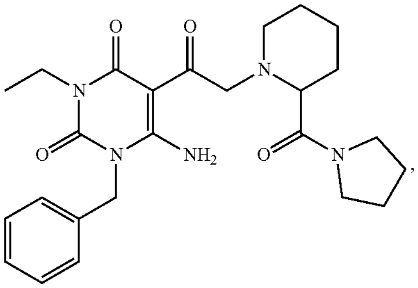
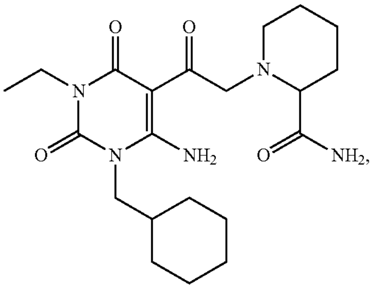
-continued
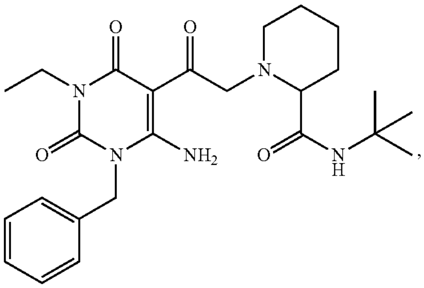
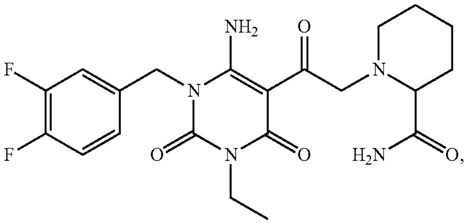
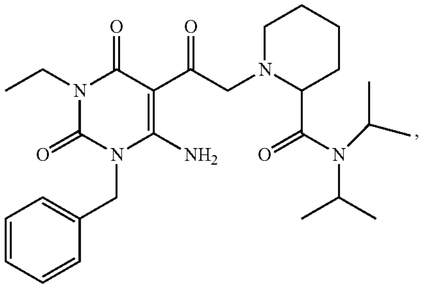
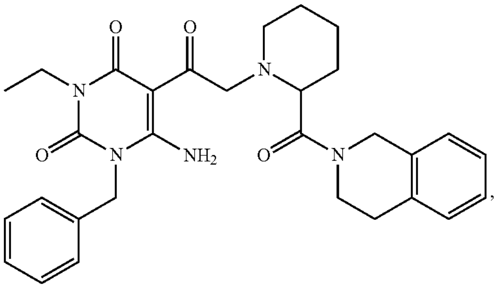
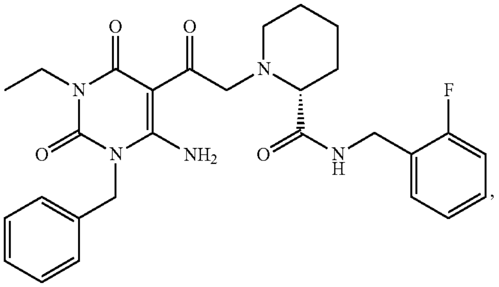
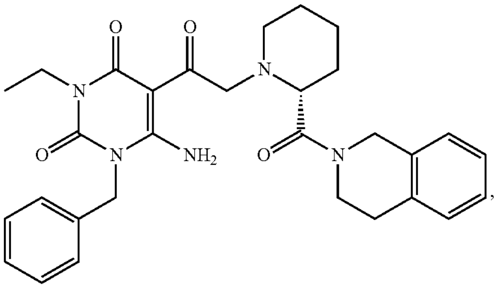

-continued
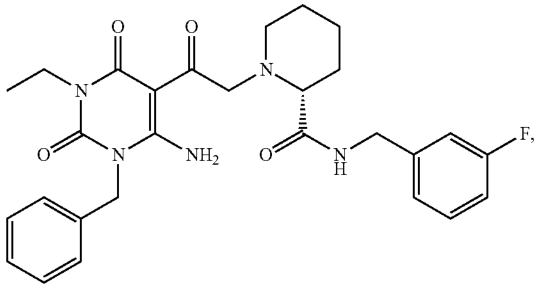
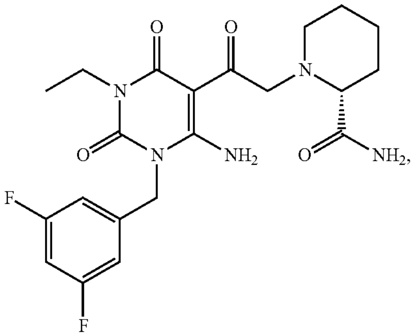
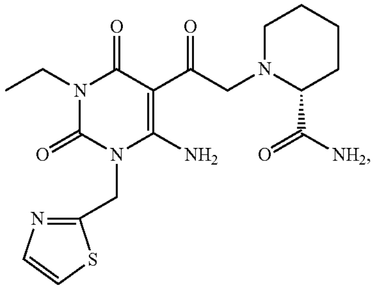
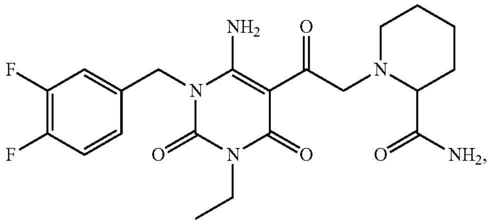
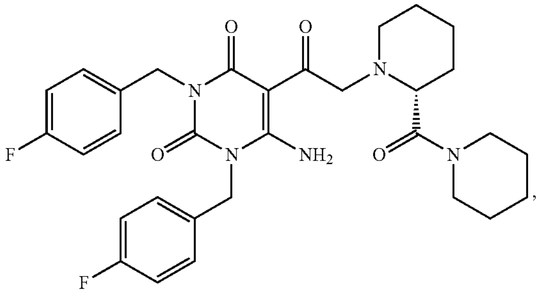
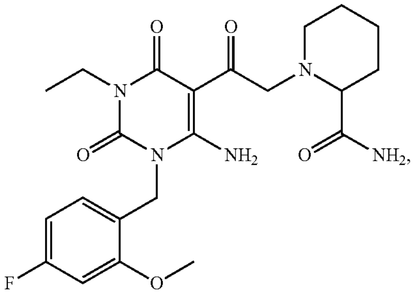
-continued
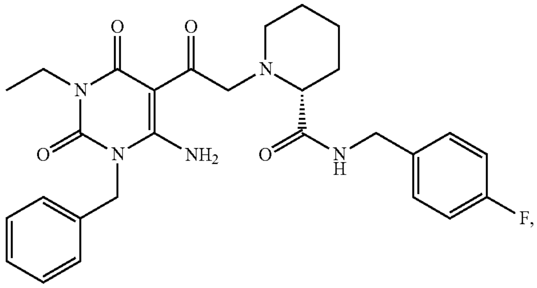
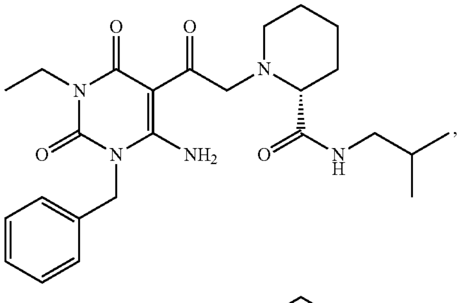
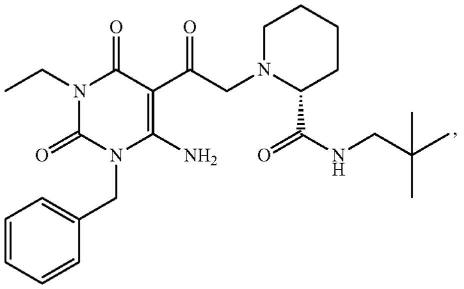
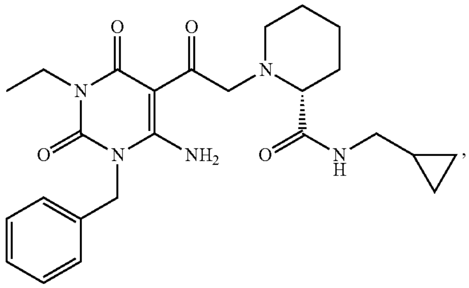
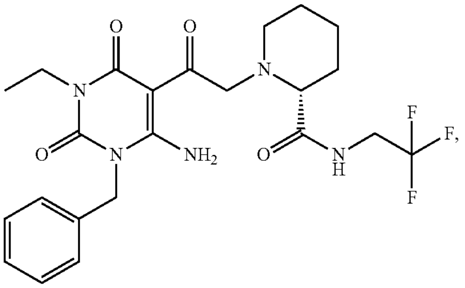
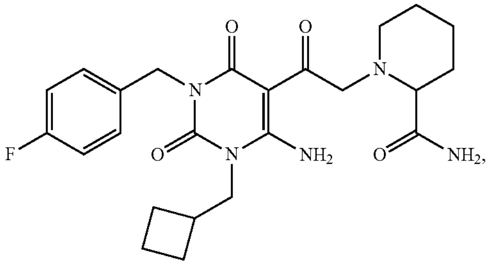

-continued
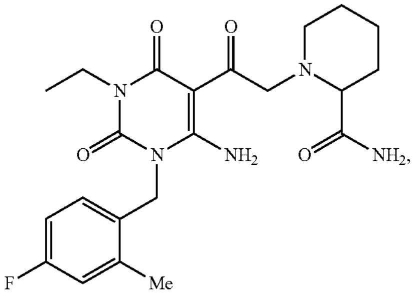
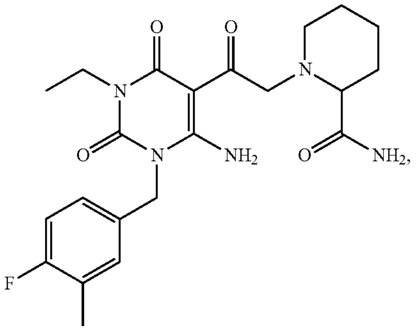
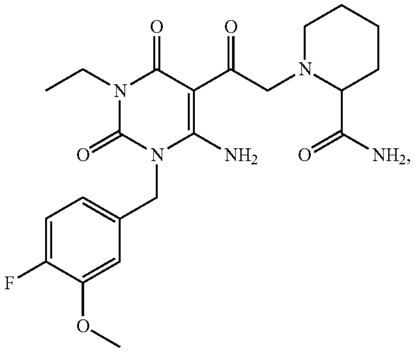
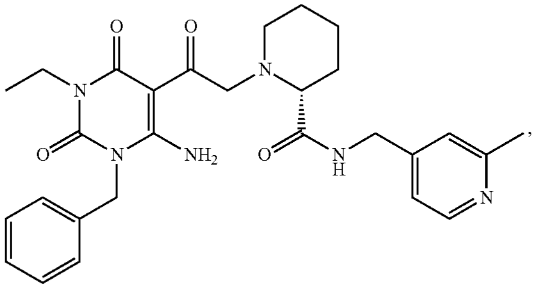
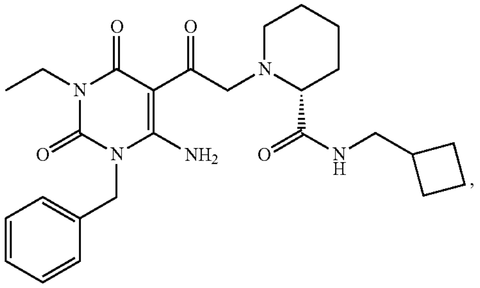
-continued
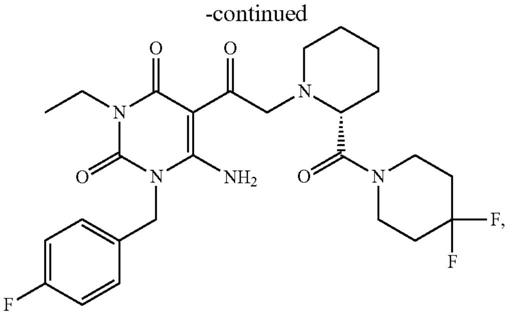
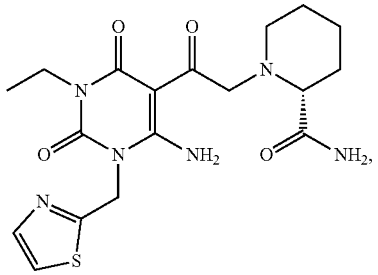
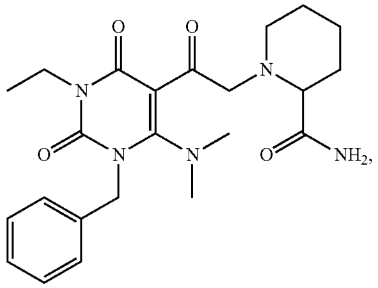
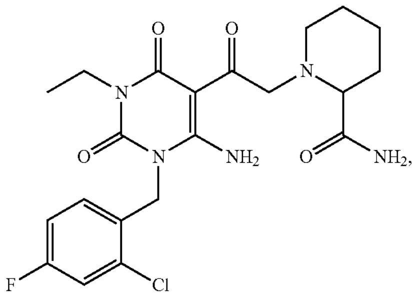
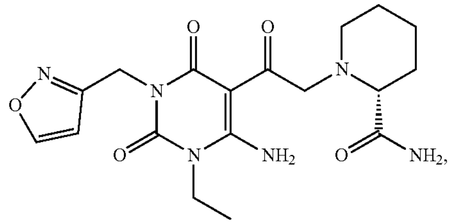
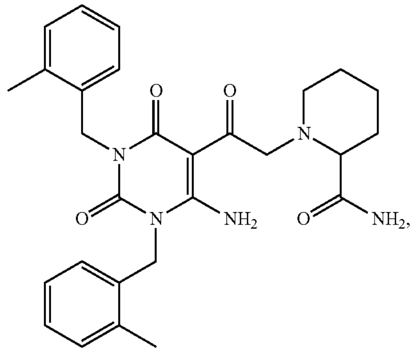

-continued
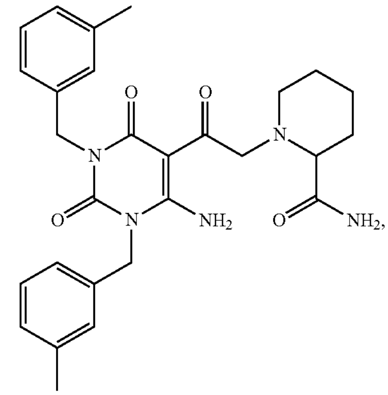
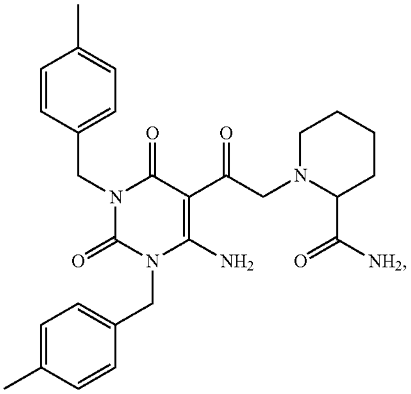
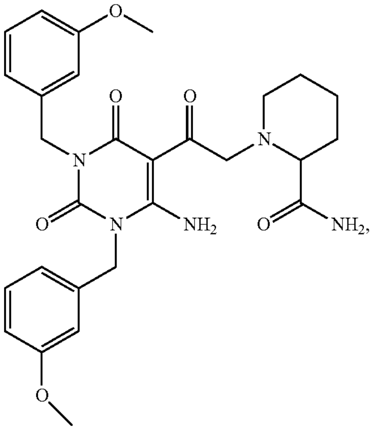
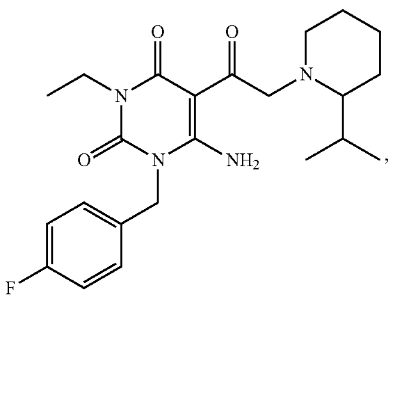
-continued
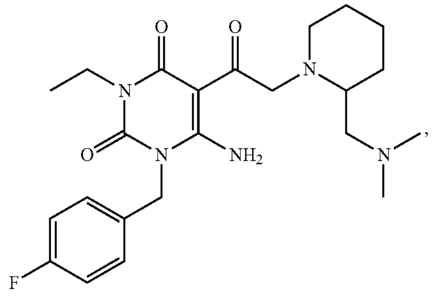
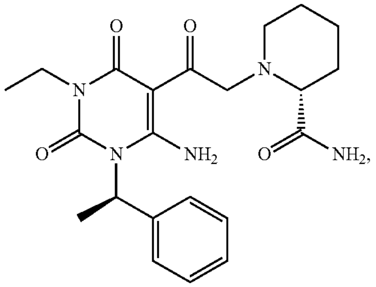
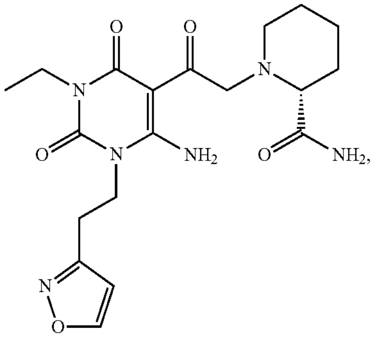
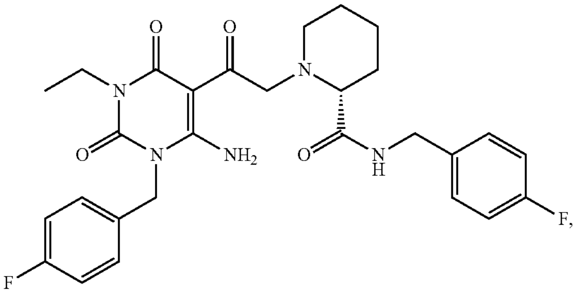
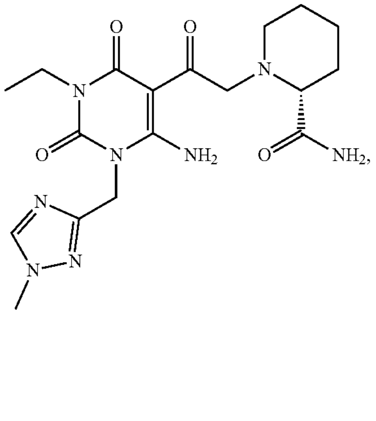

-continued

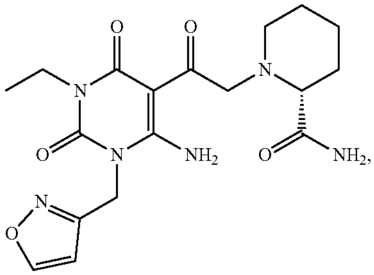

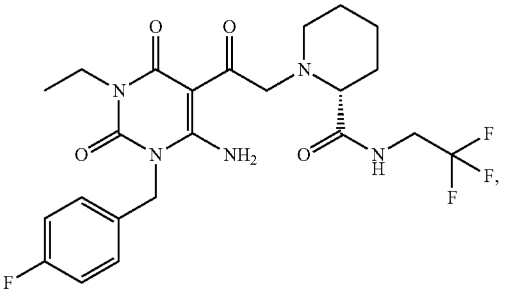

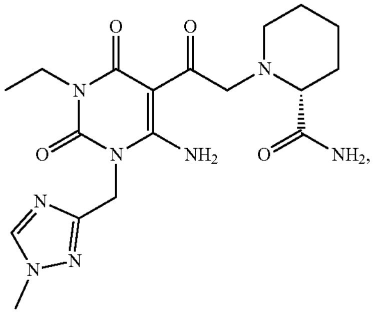

and

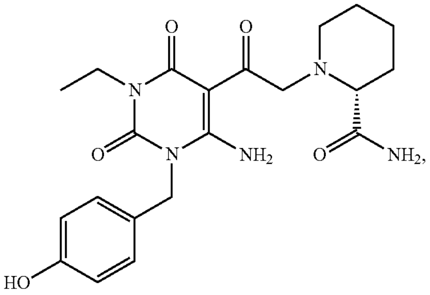

In various aspects, the compound is:

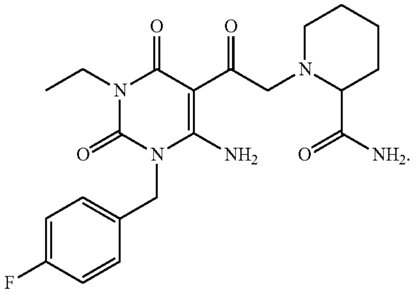 [SMILES: CCn1c(=O)c(C(=O)CN2CCCCC2C(N)=O)c(N)n(Cc2ccc(F)cc2)c1=O]

In various aspects, the compound is:

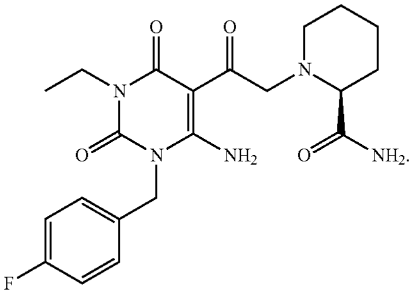 [SMILES: CCn1c(=O)c(C(=O)CN2CCCC[C@H]2C(N)=O)c(N)n(Cc2ccc(F)cc2)c1=O]

In various aspects, the compound is:

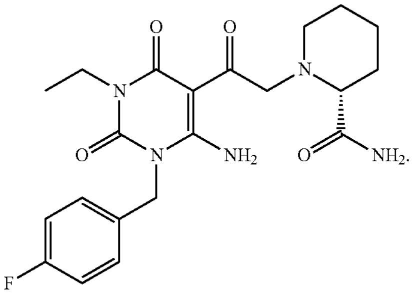 [SMILES: CCn1c(=O)c(C(=O)CN2CCCC[C@@H]2C(N)=O)c(N)n(Cc2ccc(F)cc2)c1=O]

In various aspects, $R^1$ is $Cy^1$. In a further aspect, $Cy^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$ is C6-C14 aryl para-substituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, m is 1 or 2. In a further aspect, m is 1. In a still further aspect, m is 2.

In various aspects, n, when present, is 1 or 2. In a further aspect, n, when present, is 1. In a still further aspect, n, when present, is 2.

In various aspects, o, when present, is 0 or 1. In a further aspect, o, when present, is 0. In a still further aspect, o, when present, is 1.

In various aspects, p, when present, is 0, 1, or 2. In a further aspect, p, when present, is 0 or 1. In a still further aspect, p, when present, is 1 or 2. In yet a further aspect, p, when present, is 0 or 2. In an even further aspect, p, when present, is 0. In a still further aspect, p, when present, is 1. In yet a further aspect, p, when present, is 2.

In various aspects, r is 0 or 1. In a further aspect, r is 0. In a still further aspect, r is 1.

In various aspects, s, when present, is 0, 1, or 2. In a further aspect, s, when present, is 0 or 1. In a still further aspect, s, when present, is 1 or 2. In yet a further aspect, s, when present, is 0 or 2. In an even further aspect, s, when present, is 0. In a still further aspect, s, when present, is 1. In yet a further aspect, s, when present, is 2.

a. $R^1$ and $R^2$ Groups

In one aspect, $R^1$ is selected from C1-C3 alkyl and $Cy^1$, and $R^2$ is selected from hydrogen and C1-C4 alkyl, or $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, $R^1$ is selected from C1-C3 alkyl and $Cy^1$. In a further aspect, $R^1$ is selected from methyl, ethyl, and $Cy^1$. In a still further aspect, $R^1$ is selected from methyl and $Cy^1$.

In various aspects, $R^1$ is C1-C3 alkyl. In a further aspect, $R^1$ is selected from methyl and ethyl. In a still further aspect, $R^1$ is ethyl. In yet a further aspect, $R^1$ is methyl.

In various aspects, $R^1$ is $Cy^1$.

In various aspects, $R^2$ is selected from hydrogen and C1-C4 alkyl. In a further aspect, $R^2$ is selected from hydrogen, methyl, ethyl, n-propyl, and isopropyl. In a still further aspect, $R^2$ is selected from hydrogen, methyl, and ethyl. In yet a further aspect, $R^2$ is selected from hydrogen and ethyl. In an even further aspect, $R^2$ is selected from hydrogen and methyl.

In various aspects, $R^2$ is hydrogen.

In various aspects, $R^2$ is C1-C4 alkyl. In a further aspect, $R^2$ is selected from methyl, ethyl, n-propyl, and isopropyl. In a still further aspect, $R^2$ is selected from methyl and ethyl. In yet a further aspect, $R^2$ is ethyl. In an even further aspect, $R^2$ is methyl.

In various aspects, $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^1$ and $R^2$ together comprise a C3-C6 cycloalkyl or a C3-C6 heterocycloalkyl, and are substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^1$ and $R^2$ together comprise a C3-C6 cycloalkyl or a C3-C6 heterocycloalkyl, and are substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^1$ and $R^2$ together comprise a C3-C6 cycloalkyl or a C3-C6 heterocycloalkyl, and are monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^1$ and $R^2$ together comprise a C3-C6 cycloalkyl or a C3-C6 heterocycloalkyl, and are unsubstituted.

In various aspects, $R^1$ and $R^2$ together comprise a C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^1$ and $R^2$ together comprise a C3-C6 cycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^1$ and $R^2$ together comprise a C3-C6 cycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^1$ and $R^2$ together comprise a C3-C6 cycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^1$ and $R^2$ together comprise an unsubstituted C3-C6 cycloalkyl.

In various aspects, $R^1$ and $R^2$ together comprise a cyclohexyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^1$ and $R^2$ together comprise a cyclohexyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^1$ and $R^2$ together comprise a cyclohexyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^1$ and $R^2$ together comprise a cyclohexyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^1$ and $R^2$ together comprise an unsubstituted cyclohexyl.

In various aspects, $R^1$ and $R^2$ together comprise a C3-C6 heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 heterocycloalkyls include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, $R^1$ and $R^2$ together comprise a C3-C6 heterocycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^1$ and $R^2$ together comprise a C3-C6 heterocycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^1$ and $R^2$ together comprise a C3-C6 heterocycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^1$ and $R^2$ together comprise an unsubstituted C3-C6 heterocycloalkyl.

b. $R^3$ and $R^4$ Groups

In one aspect, $R^3$ is selected from hydrogen and C1-C4 alkyl, and $R^4$ is selected from —$(CR^{10a}R^{10b})_nC(O)R^{11}$, —$CH(R^{12})Ar^2$, and $Ar^2$, or $R^3$ and $R^4$ together comprise a heterocycle having a structure represented by a formula:

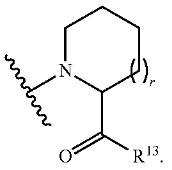

In various aspects, $R^3$ is selected from hydrogen and C1-C4 alkyl. In a further aspect, $R^3$ is selected from hydrogen, methyl, ethyl, n-propyl, and isopropyl. In a still further aspect, $R^3$ is selected from hydrogen, methyl, and ethyl. In yet a further aspect, $R^3$ is selected from hydrogen and ethyl. In an even further aspect, $R^3$ is selected from hydrogen and methyl.

In various aspects, $R^3$ is hydrogen.

In various aspects, $R^3$ is C1-C4 alkyl. In a further aspect, $R^3$ is selected from methyl, ethyl, n-propyl, and isopropyl. In a still further aspect, $R^3$ is selected from methyl and ethyl. In yet a further aspect, $R^3$ is ethyl. In an even further aspect, $R^3$ is methyl.

In various aspects, $R^3$ is isopropyl.

In various aspects, $R^4$ is selected from —$(CR^{10a}R^{10b})_nC(O)R^{11}$, —$CH(R^{12})Ar^2$, and $Ar^2$. In a further aspect, $R^4$ is selected from —$(CR^{10a}R^{10b})_nC(O)R^{11}$ and $Ar^2$. In a still further aspect, $R^4$ is selected from —$CH(R^{12})Ar^2$ and $Ar^2$. In yet a further aspect, $R^4$ is selected from —$(CR^{10a}R^{10b})_nC(O)R^{11}$ and —$CH(R^{12})Ar^2$.

In various aspects, $R^4$ is —$(CR^{10a}R^{10b})_nC(O)R^{11}$. In a further aspect, $R^4$ is —$(CH_2)_nC(O)R^{11}$. In a still further aspect, $R^4$ is —$CH_2CH_2C(O)R^{11}$. In yet a further aspect, $R^4$ is —$CH_2C(O)R^{11}$.

In various aspects, $R^4$ is —$CH_2C(O)R^{11}$. In a further aspect, $R^4$ is —$CH_2C(O)NR^{20a}R^{20b}$.

In various aspects, $R^4$ is —$CH(R^{12})Ar^2$. In a further aspect, $R^4$ is —$CH_2Ar^2$.

In various aspects, $R^4$ is $Ar^2$.

In various aspects, $R^3$ and $R^4$ together comprise a heterocycle having a structure represented by a formula:

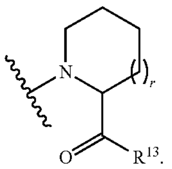

In various further aspect, $R^{13}$ is —$NR^{21a}R^{21b}$. In a still further aspect, each of $R^{21a}$ and $R^{21b}$, when present, is independently selected from hydrogen, C1-C8 alkyl, C1-C8 haloalkyl, and —$(CH_2)_sCy^5$. In yet a further aspect, each of $R^{21a}$ and $R^{21b}$, when present, is hydrogen. In an even further aspect, $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, $R^3$ and $R^4$ together comprise a heterocycle having a structure represented by a formula:

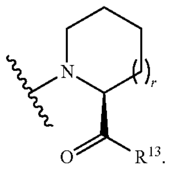

In various aspects, $R^3$ and $R^4$ together comprise a heterocycle having a structure represented by a formula:

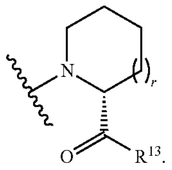

In various aspects, $R^3$ and $R^4$ together comprise a heterocycle having a structure represented by a formula:

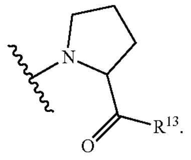

In various aspects, $R^3$ and $R^4$ together comprise a heterocycle having a structure represented by a formula:

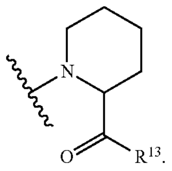

c. $R^5$ Groups

In one aspect, $R^5$ is selected from $Ar^1$ and $Cy^6$. In a further aspect, $R^5$ is $Ar^1$. In a still further aspect, $R^5$ is $Cy^6$.

d. $R^{10A}$ Groups

In one aspect, each occurrence of $R^{10a}$, when present, is independently selected from hydrogen and C1-C4 alkyl. In a further aspect, each occurrence of $R^{10a}$, when present, is independently selected from hydrogen, methyl, ethyl, n-propyl, and isopropyl. In a still further aspect, each occurrence of $R^{10a}$, when present, is independently selected from hydrogen, methyl, and ethyl. In yet a further aspect, each occurrence of $R^{10a}$, when present, is independently selected from hydrogen and ethyl. In an even further aspect, each occurrence of $R^{10a}$, when present, is independently selected from hydrogen and methyl.

In various aspects, each occurrence of $R^{10a}$, when present, is hydrogen.

In various aspects, each occurrence of $R^{10a}$, when present, is independently C1-C4 alkyl. In a further aspect, each occurrence of $R^{10a}$, when present, is independently selected from methyl, ethyl, n-propyl, and isopropyl. In a still further aspect, each occurrence of $R^{10a}$, when present, is independently selected from methyl and ethyl. In yet a further aspect, each occurrence of $R^{10a}$, when present, is ethyl. In an even further aspect, each occurrence of $R^{10a}$, when present, is methyl.

e. $R^{10B}$ Groups

In one aspect, each occurrence of $R^{10b}$, when present, is independently selected from hydrogen, C1-C4 alkyl, —(C1-C4 alkyl)O(C1-C4 alkyl), and —$(CH_2)_oCy^2$. In a further aspect, each occurrence of $R^{10b}$, when present, is independently selected from hydrogen, methyl, ethyl, n-propyl, isopropyl, —$CH_2OCH_3$, —$CH_2OCH_2CH_3$, —$CH_2CH_2OCH_3$, —$CH_2OCH(CH_3)_2$, —$CH_2OCH_2CH_2CH_3$, —$CH_2Cy^2$ and —$Cy^2$. In a still further aspect, each occurrence of $R^{10b}$, when present, is independently selected from hydrogen, methyl, ethyl, —$CH_2OCH_3$, —$CH_2OCH_2CH_3$, —$CH_2CH_2OCH_3$, —$CH_2Cy^2$ and —$Cy^2$. In yet a further aspect, each occurrence of $R^{10b}$, when present, is independently selected from hydrogen, methyl, —$CH_2OCH_3$, —$CH_2Cy^2$ and —$Cy^2$.

In various aspects, each occurrence of $R^{10b}$, when present, is hydrogen.

In various aspects, each occurrence of $R^{10b}$, when present, is independently selected from hydrogen and C1-C4 alkyl. In a further aspect, each occurrence of $R^{10b}$, when present, is independently selected from hydrogen, methyl, ethyl, n-propyl, and isopropyl. In a still further aspect, each occurrence of $R^{10b}$, when present, is independently selected from hydrogen, methyl, and ethyl. In yet a further aspect, each occurrence of $R^{10b}$, when present, is independently selected from hydrogen and methyl.

In various aspects, each occurrence of $R^{10b}$, when present, is independently selected from hydrogen and —(C1-C4 alkyl)O(C1-C4 alkyl). In a further aspect, each occurrence of $R^{10b}$, when present, is independently selected from hydrogen, —$CH_2OCH_3$, —$CH_2OCH_2CH_3$, —$CH_2CH_2OCH_3$, —$CH_2OCH(CH_3)_2$, and —$CH_2OCH_2CH_2CH_3$. In a still further aspect, each occurrence of $R^{10b}$, when present, is independently selected from hydrogen, —$CH_2OCH_3$, —$CH_2OCH_2CH_3$, and —$CH_2CH_2OCH_3$. In yet a further aspect, each occurrence of $R^{10b}$, when present, is independently selected from hydrogen and —$CH_2OCH_3$.

In various aspects, each occurrence of $R^{10b}$, when present, is independently selected from hydrogen and —$(CH_2)_oCy^2$. In a further aspect, each occurrence of $R^{10b}$, when present, is independently selected from hydrogen, —$CH_2Cy^2$, and —$Cy^2$. In a still further aspect, each occurrence of $R^{10b}$, when present, is independently selected from hydrogen and —$Cy^2$.

f. $R^{11}$ Groups

In one aspect, $R^{11}$, when present, is selected from C1-C4 alkoxy and —$NR^{20a}R^{20b}$. In a further aspect, $R^{11}$, when present, is selected from —$OCH_3$, —$OCH_2CH_3$, —$OCH(CH_3)_2$, —$OCH_2CH_2CH_3$, and —$NR^{20a}R^{20b}$. In a still further aspect, $R^{11}$, when present, is selected from —$OCH_3$, —$OCH_2CH_3$, and —$NR^{20a}R^{20b}$. In yet a further aspect, $R^{11}$, when present, is selected from —$OCH_3$ and —$NR^{20a}R^{20b}$.

In various aspects, $R^{11}$, when present, is C1-C4 alkoxy. In a further aspect, $R^{11}$, when present, is selected from —$OCH_3$, —$OCH_2CH_3$, —$OCH(CH_3)_2$, and —$OCH_2CH_2CH_3$. In a still further aspect, $R^{11}$, when present, is selected from —$OCH_3$ and —$OCH_2CH_3$. In yet a further aspect, $R^{11}$, when present, is —$OCH_3$.

In various aspects, $R^{11}$, when present, is —$NR^{20a}R^{20b}$.

g. $R^{12}$ Groups

In one aspect, $R^{12}$, when present, is selected from hydrogen, C1-C4 alkyl, —(C1-C4 alkyl)O(C1-C4 alkyl), and —$(CH_2)_qCy^4$. In a further aspect, $R^{12}$, when present, is independently selected from hydrogen, methyl, ethyl, n-propyl, isopropyl, —$CH_2OCH_3$, —$CH_2OCH_2CH_3$, —$CH_2CH_2OCH_3$, —$CH_2OCH(CH_3)_2$, —$CH_2OCH_2CH_2CH_3$, —$CH_2Cy^4$ and —$Cy^4$. In a still further aspect, $R^{12}$, when present, is independently selected from hydrogen, methyl, ethyl, —$CH_2OCH_3$, —$CH_2OCH_2CH_3$, —$CH_2CH_2OCH_3$, —$CH_2Cy^4$ and —$Cy^4$. In yet a further aspect, $R^{12}$, when present, is independently selected from hydrogen, methyl, —$CH_2OCH_3$, —$CH_2Cy^4$ and —$Cy^4$.

In various aspects, $R^{12}$, when present, is hydrogen.

In various aspects, $R^{12}$, when present, is independently selected from hydrogen and C1-C4 alkyl. In a further aspect, $R^{12}$, when present, is independently selected from hydrogen, methyl, ethyl, n-propyl, and isopropyl. In a still further aspect, $R^{12}$, when present, is independently selected from hydrogen, methyl, and ethyl. In yet a further aspect, $R^{12}$, when present, is independently selected from hydrogen and methyl.

In various aspects, $R^{12}$, when present, is independently selected from hydrogen and —(C1-C4 alkyl)O(C1-C4 alkyl). In a further aspect, $R^{12}$, when present, is independently selected from hydrogen, —$CH_2OCH_3$, —$CH_2OCH_2CH_3$, —$CH_2CH_2OCH_3$, —$CH_2OCH(CH_3)_2$, and —$CH_2OCH_2CH_2CH_3$. In a still further aspect, $R^{12}$, when present, is independently selected from hydrogen, —$CH_2OCH_3$, —$CH_2OCH_2CH_3$, and —$CH_2CH_2OCH_3$. In yet a further aspect, $R^{12}$, when present, is independently selected from hydrogen and —$CH_2OCH_3$.

In various aspects, $R^{12}$, when present, is independently selected from hydrogen and —$(CH_2)_qCy^4$. In a further aspect, $R^{12}$, when present, is independently selected from hydrogen, —$CH_2Cy^4$, and —$Cy^4$. In a still further aspect, $R^{12}$, when present, is independently selected from hydrogen and —$Cy^4$.

h. $R^{13}$ Groups

In one aspect, $R^{13}$ is selected from C1-C4 alkoxy and —$NR^{21a}R^{21b}$. In a further aspect, $R^{13}$ is selected from —$OCH_3$, —$OCH_2CH_3$, —$OCH(CH_3)_2$, —$OCH_2CH_2CH_3$, and —$NR^{21a}R^{21b}$. In a still further aspect, $R^{13}$ is selected from —$OCH_3$, —$OCH_2CH_3$, and —$NR^{21a}R^{21b}$. In yet a further aspect, $R^{13}$ is selected from —$OCH_3$ and —$NR^{21a}R^{21b}$.

In various aspects, $R^{13}$ is C1-C4 alkoxy. In a further aspect, $R^{13}$ is selected from —$OCH_3$, —$OCH_2CH_3$, —$OCH(CH_3)_2$, and —$OCH_2CH_2CH_3$. In a still further aspect, $R^{13}$ is selected from —$OCH_3$ and —$OCH_2CH_3$. In yet a further aspect, $R^{13}$ is —$OCH_3$.

In various aspects, $R^{13}$ is —$NR^{21a}R^{21b}$.

i. $R^{20A}$ and $R^{20B}$ Groups

In one aspect, each of $R^{20a}$ and $R^{20b}$, when present, is independently selected from hydrogen, C1-C8 alkyl, C1-C8 haloalkyl, and —$(CH_2)_pCy^3$, or $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, each of $R^{20a}$ and $R^{20b}$, when present, is independently selected from hydrogen, C1-C8 alkyl, C1-C8 haloalkyl, and —$(CH_2)_pCy^3$. In a further aspect, each of $R^{20a}$ and $R^{20b}$, when present, is independently selected from hydrogen, C1-C4 alkyl, C1-C4 haloalkyl, and —$(CH_2)_p$ $Cy^3$. In a still further aspect, each of $R^{20a}$ and $R^{20b}$, when present, is independently selected from hydrogen, methyl, ethyl, n-propyl, isopropyl, —$CF_3$, —$CHF_2$, —$CH_2F$, —$CCl_3$, —$CHCl_2$, —$CH_2Cl$, —$CH_2CH_2F$, —$CH_2CH_2Cl$, —$CH(CH_2F)(CH_3)$, —$CH(CH_2Cl)(CH_3)$, —$CH_2CH_2CH_2F$, —$CH_2CH_2CH_2Cl$, —$Cy^3$, —$CH_2Cy^3$, and —$CH_2CH_2Cy^3$. In yet a further aspect, each of $R^{20a}$ and $R^{20b}$, when present, is independently selected from hydrogen, methyl, ethyl, —$CF_3$, —$CHF_2$, —$CH_2F$, —$CCl_3$, —$CHCl_2$, —$CH_2Cl$, —$CH_2CH_2F$, —$CH_2CH_2Cl$, —$Cy^3$, —$CH_2Cy^3$, and —$CH_2CH_2Cy^3$. In an even further aspect, each of $R^{20a}$ and $R^{20b}$, when present, is independently selected from hydrogen, methyl, —$CF_3$, —$CHF_2$, —$CH_2F$, —$CCl_3$, —$CHCl_2$, —$CH_2Cl$, —$Cy^3$, and —$CH_2Cy^3$.

In various aspects, each of $R^{20a}$ and $R^{20b}$, when present, is independently selected from hydrogen and C1-C8 alkyl. In a further aspect, each of $R^{20a}$ and $R^{20b}$, when present, is independently selected from hydrogen and C1-C4 alkyl. In a still further aspect, each of $R^{20a}$ and $R^{20b}$, when present, is independently selected from hydrogen, methyl, ethyl, n-propyl, and isopropyl. In yet a further aspect, each of $R^{20a}$ and $R^{20b}$, when present, is independently selected from hydrogen, methyl, and ethyl. In an even further aspect, each of $R^{20a}$ and $R^{20b}$, when present, is independently selected from hydrogen and methyl.

In various aspects, each of $R^{20a}$ and $R^{20b}$, when present, is independently selected from hydrogen and C1-C8 haloalkyl. In a further aspect, each of $R^{20a}$ and $R^{20b}$, when present, is independently selected from hydrogen and C1-C4 haloalkyl. In a still further aspect, each of $R^{20a}$ and $R^{20b}$, when present, is independently selected from hydrogen, —$CF_3$, —$CHF_2$, —$CH_2F$, —$CCl_3$, —$CHCl_2$, —$CH_2Cl$, —$CH_2CH_2F$, —$CH_2CH_2Cl$, —$CH(CH_2F)(CH_3)$, —$CH(CH_2Cl)(CH_3)$, —$CH_2CH_2CH_2F$, and —$CH_2CH_2CH_2Cl$. In yet a further aspect, each of $R^{20a}$ and $R^{20b}$, when present, is independently selected from hydrogen, —$CF_3$, —$CHF_2$, —$CH_2F$, —$CCl_3$, —$CHCl_2$, —$CH_2Cl$, —$CH_2CH_2F$, and —$CH_2CH_2Cl$. In an even further aspect, each of $R^{20a}$ and $R^{20b}$, when present, is independently selected from hydrogen, —$CF_3$, —$CHF_2$, —$CH_2F$, —$CCl_3$, —$CHCl_2$, and —$CH_2Cl$.

In various aspects, each of $R^{20a}$ and $R^{20b}$, when present, is independently selected from hydrogen and —$(CH_2)_pCy^3$. In a further aspect, each of $R^{20a}$ and $R^{20b}$, when present, is independently selected from hydrogen, —$Cy^3$, —$CH_2Cy^3$, and —$CH_2CH_2Cy^3$. In a still further aspect, each of $R^{20a}$ and $R^{20b}$, when present, is independently selected from hydrogen, —$Cy^3$, and —$CH_2Cy^3$. In yet a further aspect, each of $R^{20a}$ and $R^{20b}$, when present, is independently selected from hydrogen and —$Cy^3$.

In various aspects, each of $R^{20a}$ and $R^{20b}$, when present, is hydrogen.

In various aspects, $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of 5- to 10-membered heterocycles include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, $R^{20a}$ and $R^{20b}$, when present, together comprise a 5- to 10-membered heterocycle substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{20a}$ and $R^{20b}$, when present, together comprise a 5- to 10-membered heterocycle substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{20a}$ and $R^{20b}$, when present, together comprise a 5- to 10-membered heterocycle monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{20a}$ and $R^{20b}$, when present, together comprise an unsubstituted 5- to 10-membered heterocycle.

In various aspects, $R^{20a}$ and $R^{20b}$, when present, together comprise piperidinyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{20a}$ and $R^{20b}$, when present, together comprise a piperidinyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{20a}$ and $R^{20b}$ when present, together comprise a piperidinyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{20a}$ and $R^{20b}$ when present, together comprise a piperidinyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{20a}$ and $R^{20b}$ when present, together comprise an unsubstituted piperidinyl.

In various aspects, $R^{20a}$ and $R^{20b}$, when present, together comprise a morpholinyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{20a}$ and $R^{20b}$, when present, together comprise a morpholinyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{20a}$ and $R^{20b}$ when present, together comprise a morpholinyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{20a}$ and $R^{20b}$ when present, together comprise a morpholinyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{20a}$ and $R^{20b}$ when present, together comprise an unsubstituted morpholinyl.

j. $R^{21A}$ and $R^{21B}$ Groups

In one aspect, each of $R^{21a}$ and $R^{21b}$ when present, is independently selected from hydrogen, C1-C8 alkyl, C1-C8 haloalkyl, and —$(CH_2)_s$$Cy^5$, or $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, each of $R^{21a}$ and $R^{21b}$, when present, is independently selected from hydrogen, C1-C8 alkyl, C1-C8 haloalkyl, and —$(CH_2)_s$$Cy^5$. In a further aspect, each of $R^{21a}$ and $R^{21b}$, when present, is independently selected from hydrogen, C1-C4 alkyl, C1-C4 haloalkyl, and —$(CH_2)_s$ $Cy^5$. In a still further aspect, each of $R^{21a}$ and $R^{21b}$, when present, is independently selected from hydrogen, methyl, ethyl, n-propyl, isopropyl, —$CF_3$, —$CHF_2$, —$CH_2F$, —$CCl_3$, —$CHCl_2$, —$CH_2Cl$, —$CH_2CH_2F$, —$CH_2CH_2Cl$, —$CH(CH_2F)(CH_3)$, —$CH(CH_2Cl)(CH_3)$, —$CH_2CH_2CH_2F$, —$CH_2CH_2CH_2Cl$, -$Cy^5$, —$CH_2Cy^5$, and —$CH_2CH_2Cy^5$. In yet a further aspect, each of $R^{21a}$ and $R^{21b}$, when present, is independently selected from hydrogen, methyl, ethyl, —$CF_3$, —$CHF_2$, —$CH_2F$, —$CCl_3$, —$CHCl_2$, —$CH_2Cl$, —$CH_2CH_2F$, —$CH_2CH_2Cl$, -$Cy^3$, —$CH_2Cy^3$, and —$CH_2CH_2Cy^3$. In an even further aspect, each of $R^{21a}$ and $R^{21b}$, when present, is independently selected from hydrogen, methyl, —$CF_3$, —$CHF_2$, —$CH_2F$, —$CCl_3$, —$CHCl_2$, —$CH_2Cl$, -$Cy^3$, and —$CH_2Cy^3$.

In various aspects, each of $R^{21a}$ and $R^{21b}$, when present, is independently selected from hydrogen and C1-C8 alkyl. In a further aspect, each of $R^{21a}$ and $R^{21b}$, when present, is independently selected from hydrogen and C1-C4 alkyl. In a still further aspect, each of $R^{21a}$ and $R^{21b}$, when present, is independently selected from hydrogen, methyl, ethyl, n-propyl, and isopropyl. In yet a further aspect, each of $R^{21a}$ and $R^{21b}$, when present, is independently selected from hydrogen, methyl, and ethyl. In an even further aspect, each of $R^{21a}$ and $R^{21b}$, when present, is independently selected from hydrogen and methyl.

In various aspects, each of $R^{21a}$ and $R^{21b}$, when present, is independently selected from hydrogen and C1-C8 haloalkyl. In a further aspect, each of $R^{21a}$ and $R^{21b}$, when present, is independently selected from hydrogen and C1-C4 haloalkyl. In a still further aspect, each of $R^{21a}$ and $R^{21b}$, when present, is independently selected from hydrogen, —$CF_3$, —$CHF_2$, —$CH_2F$, —$CCl_3$, —$CHCl_2$, —$CH_2Cl$, —$CH_2CH_2F$, —$CH_2CH_2Cl$, —$CH(CH_2F)(CH_3)$, —$CH(CH_2Cl)(CH_3)$, —$CH_2CH_2CH_2F$, and —$CH_2CH_2CH_2C1$. In yet a further aspect, each of $R^{21a}$ and $R^{21b}$, when present, is independently selected from hydrogen, —$CF_3$, —$CHF_2$, —$CH_2F$, —$CCl_3$, —$CHCl_2$, —$CH_2Cl$, —$CH_2CH_2F$, and —$CH_2CH_2C1$. In an even further aspect, each of $R^{21a}$ and $R^{21b}$ when present, is independently selected from hydrogen, —$CF_3$, —$CHF_2$, —$CH_2F$, —$CCl_3$, —$CHCl_2$, and —$CH_2Cl$.

In various aspects, each of $R^{21a}$ and $R^{21b}$, when present, is independently selected from hydrogen and —$(CH_2)_s$$Cy^5$. In a further aspect, each of $R^{21a}$ and $R^{21b}$, when present, is independently selected from hydrogen, -$Cy^5$, —$CH_2Cy^5$, and —$CH_2CH_2Cy^5$. In a still further aspect, each of $R^{21a}$ and $R^{21b}$, when present, is independently selected from hydrogen, -$Cy^5$, and —$CH_2Cy^5$. In yet a further aspect, each of $R^{21a}$ and $R^{21b}$, when present, is independently selected from hydrogen and —$Cy^5$.

In various aspects, each of $R^{21a}$ and $R^{21b}$, when present, is hydrogen.

In various aspects, $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of 5- to 10-membered heterocycles include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, $R^{21a}$ and $R^{21b}$, when present, together comprise a 5- to 10-membered heterocycle substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{21a}$ and $R^{21b}$, when present, together comprise a 5- to 10-membered heterocycle substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{21a}$ and $R^{21b}$, when present, together comprise a 5- to 10-membered heterocycle monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{21a}$ and $R^{21b}$, when present, together comprise an unsubstituted 5- to 10-membered heterocycle.

In various aspects, $R^{21a}$ and $R^{21b}$, when present, together comprise piperidinyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{21a}$ and $R^{21b}$ when present, together comprise a piperidinyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{21a}$ and $R^{21b}$, when present, together comprise a piperidinyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{21a}$ and $R^{21b}$, when present, together comprise a piperidinyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{21a}$ and $R^{21b}$, when present, together comprise an unsubstituted piperidinyl.

In various aspects, $R^{21a}$ and $R^{21b}$, when present, together comprise a morpholinyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{21a}$ and $R^{21b}$, when present, together comprise a morpholinyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{21a}$ and $R^{21b}$, when present, together comprise a morpholinyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{21a}$ and $R^{21b}$, when present, together comprise a morpholinyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{21a}$ and $R^{21b}$, when present, together comprise an unsubstituted morpholinyl.

k. $R^{30A}$, $R^{30B}$, $R^{30C}$, $R^{30D}$, and $R^{30E}$ Groups

In one aspect, each of $R^{30a}$, $R^{30b}$, $R^{30c}$, $R^{30d}$, and $R^{30e}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl). Thus, in various aspects, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, methyl, ethyl, n-propyl, i-propyl, ethenyl, propenyl, isopropenyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, —$CH(CH_3)CH_2CN$, —$CH_2OH$, —$CH_2CH_2OH$, —$CH_2CH_2CH_2OH$, —$CH(CH_3)CH_2OH$, —$OCF_3$, —$OCH_2CF_3$, —$OCH_2CH_2CF_3$, —$OCH(CH_3)CF_3$, —$OCH_3$, —$OCH_2CH_3$, —$OCH_2CH_2CH_3$, —$OCH(CH_3)CH_3$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, —$CH(CH_3)CH_2NH_2$, —C(O)$NH_2$, —C(O)$NHCH_3$, —C(O)$NHCH_2CH_3$, —C(O)$NHCH(CH_3)_2$, —C(O)$NHCH_2CH_2CH_3$, —C(O)$N(CH_3)_2$, —C(O)$N(CH_3)(CH_2CH_3)$, —C(O)$N(CH_2CH_3)_2$, —C(O)$N(CH_3)(CH(CH_3)_2)$, and —C(O)$N(CH_3)(CH_2CH_2CH_3)$. In a further aspect, each of $R^{30a}$, $R^{30b}$, $R^{30c}$, $R^{30d}$, and $R^{30e}$ is independently selected from hydrogen, —F, —C1, —$NH_2$, —CN, —OH, —$NO_2$, methyl, ethyl, ethenyl, —$CH_2F$, —$CH_2Cl$, —$CH_2CH_2F$, —$CH_2CH_2Cl$, —$CH_2CN$, —$CH_2CH_2CN$, —$CH_2OH$, —$CH_2CH_2OH$, —$OCF_3$, —$OCH_2CF_3$, —$OCH_3$, —$OCH_2CH_3$, —$NHCH_3$, —$NHCH_2CH_3$, —$N(CH_3)_2$, —$N(CH_2CH_3)_2$, —$N(CH_3)(CH_2CH_3)$, —$CH_2NH_2$, —$CH_2CH_2NH_2$, —C(O)$NH_2$, —C(O)$NHCH_3$, —C(O)$NHCH_2CH_3$, —C(O)$N(CH_3)_2$, —C(O)$N(CH_3)(CH_2CH_3)$, and —C(O)$N(CH_2CH_3)_2$. In a still further aspect, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, methyl, —$CH_2F$, —$CH_2Cl$, —$CH_2CN$, —$CH_2OH$, —$OCF_3$, —$OCH_2CF_3$, —$OCH_3$, —$NHCH_3$, —$N(CH_3)_2$, —$CH_2NH_2$, —C(O)$NH_2$, —C(O)$NHCH_3$, and —C(O)$N(CH_3)_2$.

In various aspects, each of $R^{30a}$, $R^{30b}$, $R^{30c}$, $R^{30d}$, and $R^{30e}$ is independently selected from hydrogen, halogen, —CN, —$NH_2$, —OH, —$NO_2$, C1-C4 alkyl, and C2-C4 alkenyl. Thus, in various further aspects, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, methyl, ethyl, n-propyl, i-propyl, ethenyl, propenyl, and isopropenyl. In a further aspect, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, methyl, ethyl, and ethenyl. In a still further aspect, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, and methyl.

In various aspects, each of $R^{30a}$, $R^{30b}$, $R^{30c}$, $R^{30d}$, and $R^{30e}$ is independently selected from hydrogen, C1-C4 alkyl, and C2-C4 alkenyl. Thus, in various further aspects, each of $R^{30a}$, $R^{30b}$, $R^{30c}$, $R^{30d}$, and $R^{30e}$ is independently selected from hydrogen, methyl, ethyl, n-propyl, i-propyl, ethenyl, propenyl, and isopropenyl. In a further aspect, each of $R^{30a}$, $R^{30b}$, $R^{30c}$, $R^{30d}$, and $R^{30e}$ is independently selected from hydrogen, methyl, ethyl, and ethenyl. In a still further aspect, each of $R^{30a}$, $R^{30b}$, $R^{30c}$, $R^{30d}$, and $R^{30e}$ is independently selected from hydrogen and methyl.

In various aspects, each of $R^{30a}$, $R^{30b}$, $R^{30c}$, $R^{30d}$, and $R^{30e}$ is independently selected from hydrogen, halogen, —CN, —$NH_2$, —OH, —$NO_2$, C1-C4 haloalkyl, and C1-C4 haloalkoxy. Thus, in various further aspects, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$OCF_3$, —$OCH_2CF_3$, —$OCH_2CH_2CF_3$, and —$OCH(CH_3)CF_3$. In a further aspect, each of $R^{30a}$, $R^{30b}$, $R^{30c}$, $R^{30d}$, and $R^{30e}$ is independently selected from hydrogen, —F, —C1, —$NH_2$, —CN, —OH, —$NO_2$, —$CH_2F$, —$CH_2Cl$, —$CH_2CH_2F$, —$CH_2CH_2Cl$, —$OCF_3$, and —$OCH_2CF_3$. In a still further aspect, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, —$CH_2F$, —$CH_2Cl$, —$OCF_3$, and —$OCH_2CF_3$.

In various aspects, each of $R^{30a}$, $R^{30b}$, $R^{30c}$, $R^{30d}$, and $R^{30e}$ is independently selected from hydrogen, halogen, C1-C4 haloalkyl, and C1-C4 haloalkoxy. Thus, in various further aspects, each of $R^{30a}$, $R^{30b}$, $R^{30c}$, $R^{30d}$, and $R^{30e}$ is independently selected from hydrogen, —F, —Cl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$OCF_3$, —$OCH_2CF_3$, —$OCH_2CH_2CF_3$, and —$OCH(CH_3)CF_3$. In a further aspect, each of $R^{30a}$, $R^{30b}$, $R^{30c}$, $R^{30d}$, and $R^{30e}$ is independently selected from hydrogen, —F, —Cl, —$CH_2F$, —$CH_2Cl$, —$CH_2CH_2F$, —$CH_2CH_2Cl$, —$OCF_3$, and —$OCH_2CF_3$. In a still further aspect, each of $R^{30a}$, $R^{30b}$, $R^{30c}$, $R^{30d}$, and $R^{30e}$ is independently selected from hydrogen, —F, —Cl, —$CH_2F$, —$CH_2Cl$, —$OCF_3$, and —$OCH_2CF_3$.

In various aspects, each of $R^{30a}$, $R^{30b}$, $R^{30c}$, $R^{30d}$, and $R^{30e}$ is independently selected from hydrogen, halogen, —CN, —$NH_2$, —OH, —$NO_2$, and C1-C4 cyanoalkyl. Thus, in various further aspects, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, —$CH_2CN$, —$CH_2CH_2CN$, —$CH_2CH_2CH_2CN$, and —$CH(CH_3)CH_2CN$. In a further aspect, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, —$CH_2CN$, and —$CH_2CH_2CN$. In a still further aspect, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, and —$CH_2CN$.

In various aspects, each of $R^{30a}$, $R^{30b}$, $R^{30c}$, $R^{30d}$, and $R^{30e}$ is independently selected from hydrogen and C1-C4 cyanoalkyl. Thus, in various further aspects, each of $R^{30a}$, $R^{30b}$, $R^{30c}$, $R^{30d}$, and $R^{30e}$ is independently selected from hydrogen, —$CH_2CN$, —$CH_2CH_2CN$, —$CH_2CH_2CH_2CN$, and —$CH(CH_3)CH_2CN$. In a further aspect, each of $R^{30a}$, $R^{30b}$, $R^{30c}$, $R^{30d}$ and $R^{30e}$ is independently selected from hydrogen, —$CH_2CN$, and —$CH_2CH_2CN$. In a still further aspect, each of $R^{30a}$, $R^{30b}$, $R^{30c}$, $R^{30d}$, and $R^{30e}$ is independently selected from hydrogen and —$CH_2CN$.

In various aspects, each of $R^{30a}$, $R^{30b}$, $R^{30c}$, $R^{30d}$, and $R^{30e}$ is independently selected from hydrogen, halogen, —CN, —$NH_2$, —OH, —$NO_2$, C1-C4 hydroxyalkyl, and C1-C4 alkoxy. Thus, in various further aspects, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, —$CH_2OH$, —$CH_2CH_2OH$, —$CH_2CH_2CH_2OH$, —$CH(CH_3)CH_2OH$, —$OCH_3$, —$OCH_2CH_3$, —$OCH_2CH_2CH_3$, and —$OCH(CH_3)CH_3$. In a further aspect, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, —$CH_2OH$, —$CH_2CH_2OH$, —$OCH_3$, and —$OCH_2CH_3$. In a still further aspect, each of $R^{30a}$, $R^{30b}$, $R^{30c}$, $R^{30d}$ and $R^{30e}$ is independently selected from hydrogen, —F, —Cl, —$NH_2$, —CN, —OH, —$NO_2$, —$CH_2OH$, and —$OCH_3$.

In various aspects, each of $R^{30a}$, $R^{30b}$, $R^{30c}$, $R^{30d}$, and $R^{30e}$ is independently selected from hydrogen, C1-C4 hydroxyalkyl, and C1-C4 alkoxy. Thus, in various further aspects, each of $R^{30a}$, $R^{30b}$, $R^{30c}$, $R^{30d}$, and $R^{30e}$ is independently selected from hydrogen, —$CH_2OH$, —$CH_2CH_2OH$, —$CH_2CH_2CH_2OH$, —$CH(CH_3)CH_2OH$, —$OCH_3$, —$OCH_2CH_3$, —$OCH_2CH_2CH_3$, and —$OCH(CH_3)CH_3$. In a further aspect, each of $R^{30a}$, $R^{30b}$, $R^{30c}$, $R^{30d}$ and $R^{30e}$ is independently selected from hydrogen, —$CH_2OH$, —$CH_2CH_2OH$, —$OCH_3$, and —$OCH_2CH_3$. In a still further aspect, each of $R^{30a}$, $R^{30b}$, $R^{30c}$, $R^{30d}$, and $R^{30e}$ is independently selected from hydrogen, —$CH_2OH$, and —$OCH_3$.

In various aspects, each of $R^{30a}$, $R^{30b}$, $R^{30c}$, $R^{30d}$, and $R^{30e}$ is independently selected from hydrogen, halogen, —CN, —$NH_2$, —OH, —$NO_2$, C1-C4 alkylamino, (C1-C4)(C1-C4) dialkylamino, and C1-C4 aminoalkyl. Thus, in various further aspects, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, and —$CH(CH_3)CH_2NH_2$. In a further aspect, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, —$NHCH_3$, —$NHCH_2CH_3$, —$N(CH_3)_2$, —$N(CH_2CH_3)_2$, —$N(CH_3)(CH_2CH_3)$, —$CH_2NH_2$, and —$CH_2CH_2NH_2$. In a still further aspect, each of $R^{30a}$, $R^{30b}$, $R^{30c}$, $R^{30d}$, and $R^{30e}$ is independently selected from hydrogen, —F, —Cl, —$NH_2$, —CN, —OH, —$NO_2$, —$NHCH_3$, —$N(CH_3)_2$, and —$CH_2NH_2$.

In various aspects, each of $R^{30a}$, $R^{30b}$, $R^{30c}$, $R^{30d}$, and $R^{30e}$ is independently selected from hydrogen, C1-C4 alkylamino, (C1-C4)(C1-C4) dialkylamino, and C1-C4 aminoalkyl. Thus, in various further aspects, each of $R^{30a}$, $R^{30b}$, $R^{30c}$, $R^{30d}$, and $R^{30e}$ is independently selected from hydrogen, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, and —$CH(CH_3)CH_2NH_2$. In a further aspect, each of $R^{30a}$, $R^{30b}$, $R^{30c}$, $R^{30d}$, and $R^{30e}$ is independently selected from hydrogen, —$NHCH_3$, —$NHCH_2CH_3$, —$N(CH_3)_2$, —$N(CH_2CH_3)_2$, —$N(CH_3)(CH_2CH_3)$, —$CH_2NH_2$, and —$CH_2CH_2NH_2$. In a still further aspect, each of $R^{30a}$, $R^{30b}$, $R^{30c}$, $R^{30d}$, and $R^{30e}$ is independently selected from hydrogen, —$NHCH_3$, —$N(CH_3)_2$, and —$CH_2NH_2$.

In various aspects, each of $R^{30a}$, $R^{30b}$, $R^{30c}$, $R^{30d}$, and $R^{30e}$ is independently selected from hydrogen, —$C(O)NH_2$, —C(O)NH(C1-C4 alkyl), and —C(O)N(C1-C4 alkyl)(C1-C4 alkyl). Thus, in various aspects, each of $R^{30a}$, $R^{30b}$, $R^{30c}$, $R^{30d}$, and $R^{30e}$ is independently selected from hydrogen, —$C(O)NH_2$, —$C(O)NHCH_3$, —$C(O)NHCH_2CH_3$, —$C(O)NHCH(CH_3)_2$, —$C(O)NHCH_2CH_2CH_3$, —$C(O)N(CH_3)_2$, —$C(O)N(CH_3)(CH_2CH_3)$, —$C(O)N(CH_2CH_3)_2$, —$C(O)N(CH_3)(CH(CH_3)_2)$, and —$C(O)N(CH_3)(CH_2CH_2CH_3)$. In a further aspect, each of $R^{30a}$, $R^{30b}$, $R^{30c}$, $R^{30d}$, and $R^{30e}$ is independently selected from hydrogen, —$C(O)NH_2$, —$C(O)NHCH_3$, —$C(O)NHCH_2CH_3$, —$C(O)N(CH_3)_2$, —$C(O)N(CH_3)(CH_2CH_3)$, and —$C(O)N(CH_2CH_3)_2$. In a still further aspect, each of $R^{30a}$, $R^{30b}$, $R^{30c}$, $R^{30d}$, and $R^{30e}$ is independently selected from hydrogen, —$C(O)NH_2$, —$C(O)NHCH_3$, and —$C(O)N(CH_3)_2$.

In various aspects, at least two of $R^{30a}$, $R^{30b}$, $R^{30c}$, $R^{30d}$, and $R^{30e}$ is hydrogen. In a further aspect, at least three of $R^{30a}$, $R^{30b}$, $R^{30c}$, $R^{30d}$, and $R^{30e}$ is hydrogen. In a still further aspect, at least four of $R^{30a}$, $R^{30b}$, $R^{30c}$, $R^{30d}$, and $R^{30e}$ is hydrogen. In yet a further aspect, each of $R^{30a}$, $R^{30b}$, $R^{30c}$, $R^{30d}$, and $R^{30e}$ is hydrogen.

l. $Cy^1$ Groups

In one aspect, $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is selected from C3-C6 cycloalkyl, C3-C6 heterocycloalkyl, C6-C14 aryl, and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is selected from C3-C6 cycloalkyl, C3-C6 heterocycloalkyl, C6-C14 aryl, and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is selected from C3-C6 cycloalkyl, C3-C6 heterocycloalkyl, C6-C14 aryl, and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is selected from C3-C6 cycloalkyl, C3-C6 heterocycloalkyl, C6-C14 aryl, and C2-C10 heteroaryl, and is unsubstituted.

In various aspects, $Cy^1$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is selected from C3-C6 cycloalkyl and C3-C6 heterocycloalkyl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is selected from C3-C6 cycloalkyl and C3-C6 heterocycloalkyl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is selected from C3-C6 cycloalkyl and C3-C6 heterocycloalkyl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is selected from C3-C6 cycloalkyl and C3-C6 heterocycloalkyl, and is unsubstituted.

In various aspects, $Cy^1$, when present, is C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is C3-C6 cycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is C3-C6 cycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is C3-C6 cycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is unsubstituted C3-C6 cycloalkyl.

In various aspects, $Cy^1$, when present, is cyclobutyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is cyclobutyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is cyclobutyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is cyclobutyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is unsubstituted cyclobutyl.

In various aspects, $Cy^1$, when present, is C3-C6 heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 heterocycloalkyls include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, $Cy^1$, when present, is C3-C6 heterocycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is C3-C6 heterocycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is C3-C6 heterocycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, unsubstituted C3-C6 heterocycloalkyl.

In various aspects, $Cy^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is selected from C6-C14 aryl and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is selected from C6-C14 aryl and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is selected from C6-C14 aryl and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is selected from C6-C14 aryl and C2-C10 heteroaryl, and is unsubstituted.

In various aspects, $Cy^1$, when present, is C6-C14 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, anthracenyl, and phenanthrenyl. In a further aspect, $Cy^1$, when present, is C6-C14 aryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is C6-C14 aryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is C6-C14 aryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is unsubstituted C6-C14 aryl.

In various aspects, $Cy^1$, when present, is phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is phenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is phenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is phenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is unsubstituted phenyl.

In various aspects, $Cy^1$, when present, is C2-C10 heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, thiophene, furan, pyrrole, oxazole, isoxazole, isothiazole, pyridine, pyrimidine, pyridazine, pyrazine, triazine, indole, azaindole, purine, benzofuran, quinolone, isoquinoline, and quinoxaline. In a further aspect, $Cy^1$, when present, is C2-C10 heteroaryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is C2-C10 heteroaryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is C2-C10 heteroaryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is unsubstituted C2-C10 heteroaryl.

In various aspects, $Cy^1$, when present, is pyridinyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is pyridinyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is pyridinyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is pyridinyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is unsubstituted pyridinyl.

In various aspects, $Cy^1$, when present, is thiophenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is thiophenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is thiophenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is thiophenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is unsubstituted thiophenyl.

In various aspects, $Cy^1$, when present, is isoxazolyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is isoxazolyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is isoxazolyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is isoxazolyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is unsubstituted isoxazolyl.

m. $Cy^2$ Groups

In one aspect, $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^2$, when present, is selected from C3-C6 cycloalkyl, C3-C6 heterocycloalkyl, C6-C14 aryl, and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^2$, when present, is selected from C3-C6 cycloalkyl, C3-C6 heterocycloalkyl, C6-C14 aryl, and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^2$, when present, is selected from C3-C6 cycloalkyl, C3-C6 heterocycloalkyl, C6-C14 aryl, and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^2$, when present, is selected from C3-C6 cycloalkyl, C3-C6 heterocycloalkyl, C6-C14 aryl, and C2-C10 heteroaryl, and is unsubstituted.

In various aspects, $Cy^2$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^2$, when present, is selected from C3-C6 cycloalkyl and C3-C6 heterocycloalkyl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^2$, when present, is selected from C3-C6 cycloalkyl and C3-C6 heterocycloalkyl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^2$, when present, is selected from C3-C6 cycloalkyl and C3-C6 heterocycloalkyl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^2$, when present, is selected from C3-C6 cycloalkyl and C3-C6 heterocycloalkyl, and is unsubstituted.

In various aspects, $Cy^2$, when present, is C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^2$, when present, is C3-C6 cycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^2$, when present, is C3-C6 cycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^2$, when present, is C3-C6 cycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^2$, when present, is unsubstituted C3-C6 cycloalkyl.

In various aspects, $Cy^2$, when present, is C3-C6 heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 heterocycloalkyls include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, $Cy^2$, when present, is C3-C6 heterocycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^2$, when present, is C3-C6 heterocycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^2$, when present, is C3-C6 heterocycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^2$, when present, unsubstituted C3-C6 heterocycloalkyl.

In various aspects, $Cy^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^2$, when present, is selected from C6-C14 aryl and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^2$, when present, is selected from C6-C14 aryl and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^2$, when present, is selected from C6-C14 aryl and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^2$, when present, is selected from C6-C14 aryl and C2-C10 heteroaryl, and is unsubstituted.

In various aspects, $Cy^2$, when present, is C6-C14 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, anthracenyl, and phenanthrenyl. In a further aspect, $Cy^2$, when present, is C6-C14 aryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^2$, when present, is C6-C14 aryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^2$, when present, is C6-C14 aryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^2$, when present, is unsubstituted C6-C14 aryl.

In various aspects, $Cy^2$, when present, is phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^2$, when present, is phenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^2$, when present, is phenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^2$, when present, is phenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^2$, when present, is unsubstituted phenyl.

In various aspects, $Cy^2$, when present, is C2-C10 heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, thiophene, furan, pyrrole, oxazole, isoxazole, isothiazole, pyridine, pyrimidine, pyridazine, pyrazine, triazine, indole, azaindole, purine, benzofuran, quinolone, isoquinoline, and quinoxaline. In a further aspect, $Cy^2$, when present, is C2-C10 heteroaryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^2$, when present, is C2-C10 heteroaryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^2$, when present, is C2-C10 heteroaryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^2$, when present, is unsubstituted C2-C10 heteroaryl.

n. $Cy^3$ Groups

In one aspect, $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is selected from C3-C6 cycloalkyl, C3-C6 heterocycloalkyl, C6-C14 aryl, and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is selected from C3-C6 cycloalkyl, C3-C6 heterocycloalkyl, C6-C14 aryl, and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is selected from C3-C6 cycloalkyl, C3-C6 heterocycloalkyl, C6-C14 aryl, and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is selected from C3-C6 cycloalkyl, C3-C6 heterocycloalkyl, C6-C14 aryl, and C2-C10 heteroaryl, and is unsubstituted.

In various aspects, $Cy^3$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is selected from C3-C6 cycloalkyl and C3-C6 heterocycloalkyl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is selected from C3-C6 cycloalkyl and C3-C6 heterocycloalkyl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is selected from C3-C6 cycloalkyl and C3-C6 heterocycloalkyl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is selected from C3-C6 cycloalkyl and C3-C6 heterocycloalkyl, and is unsubstituted.

In various aspects, $Cy^3$, when present, is C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is C3-C6 cycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is C3-C6 cycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is C3-C6 cycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is unsubstituted C3-C6 cycloalkyl.

In various aspects, $Cy^3$, when present, is cyclopropyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is cyclopropyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is cyclopropyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is cyclopropyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is unsubstituted cyclopropyl.

In various aspects, $Cy^3$, when present, is cyclobutyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is cyclobutyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is cyclobutyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is cyclobutyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is unsubstituted cyclobutyl.

In various aspects, $Cy^3$, when present, is C3-C6 heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 heterocycloalkyls include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, $Cy^3$, when present, is C3-C6 heterocycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is C3-C6 heterocycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is C3-C6 heterocycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, unsubstituted C3-C6 heterocycloalkyl.

In various aspects, $Cy^3$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is selected from C6-C14 aryl and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is selected from C6-C14 aryl and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is selected from C6-C14 aryl and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is selected from C6-C14 aryl and C2-C10 heteroaryl, and is unsubstituted.

In various aspects, $Cy^3$, when present, is C6-C14 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, anthracenyl, and phenanthrenyl. In a further aspect, $Cy^3$, when present, is C6-C14 aryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is C6-C14 aryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is C6-C14 aryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is unsubstituted C6-C14 aryl.

In various aspects, $Cy^3$, when present, is phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is phenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is phenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is phenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is unsubstituted phenyl.

In various aspects, $Cy^3$, when present, is C2-C10 heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, thiophene, furan, pyrrole, oxazole, isoxazole, isothiazole, pyridine, pyrimidine, pyridazine, pyrazine, triazine, indole, azaindole, purine, benzofuran, quinolone, isoquinoline, and quinoxaline. In a further aspect, $Cy^3$, when present, is C2-C10 heteroaryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is C2-C10 heteroaryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is C2-C10 heteroaryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is unsubstituted C2-C10 heteroaryl.

In various aspects, $Cy^3$, when present, is pyridinyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is pyridinyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is pyridinyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is pyridinyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is unsubstituted pyridinyl.

o. $Cy^4$ Groups

In one aspect, $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^4$, when present, is selected from C3-C6 cycloalkyl, C3-C6 heterocycloalkyl, C6-C14 aryl, and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is selected from C3-C6 cycloalkyl, C3-C6 heterocycloalkyl, C6-C14 aryl, and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is selected from C3-C6 cycloalkyl, C3-C6 heterocycloalkyl, C6-C14 aryl, and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, is selected from C3-C6 cycloalkyl, C3-C6 heterocycloalkyl, C6-C14 aryl, and C2-C10 heteroaryl, and is unsubstituted.

In various aspects, $Cy^4$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^4$, when present, is selected from C3-C6 cycloalkyl and C3-C6 heterocycloalkyl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is selected from C3-C6 cycloalkyl and C3-C6 heterocycloalkyl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is selected from C3-C6 cycloalkyl and C3-C6 heterocycloalkyl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, is selected from C3-C6 cycloalkyl and C3-C6 heterocycloalkyl, and is unsubstituted.

In various aspects, $Cy^4$, when present, is C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^4$, when present, is C3-C6 cycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is C3-C6 cycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is C3-C6 cycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, is unsubstituted C3-C6 cycloalkyl.

In various aspects, $Cy^4$, when present, is C3-C6 heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 heterocycloalkyls include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, $Cy^4$, when present, is C3-C6 heterocycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is C3-C6 heterocycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is C3-C6 heterocycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, unsubstituted C3-C6 heterocycloalkyl.

In various aspects, $Cy^4$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^4$, when present, is selected from C6-C14 aryl and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is selected from C6-C14 aryl and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is selected from C6-C14 aryl and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, is selected from C6-C14 aryl and C2-C10 heteroaryl, and is unsubstituted.

In various aspects, $Cy^4$, when present, is C6-C14 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, anthracenyl, and phenanthrenyl. In a further aspect, $Cy^4$, when present, is C6-C14 aryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is C6-C14 aryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is C6-C14 aryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, is unsubstituted C6-C14 aryl.

In various aspects, $Cy^4$, when present, is phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^4$, when present, is phenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is phenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is phenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, is unsubstituted phenyl.

In various aspects, $Cy^4$, when present, is C2-C10 heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, thiophene, furan, pyrrole, oxazole, isoxazole, isothiazole, pyridine, pyrimidine, pyridazine, pyrazine, triazine, indole, azaindole, purine, benzofuran, quinolone, isoquinoline, and quinoxaline. In a further aspect, $Cy^4$, when present, is C2-C10 heteroaryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is C2-C10 heteroaryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is C2-C10 heteroaryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, is unsubstituted C2-C10 heteroaryl.

p. $Cy^5$ Groups

In one aspect, $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^5$, when present, is selected from C3-C6 cycloalkyl, C3-C6 heterocycloalkyl, C6-C14 aryl, and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is selected from C3-C6 cycloalkyl, C3-C6 heterocycloalkyl, C6-C14 aryl, and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is selected from C3-C6 cycloalkyl, C3-C6 heterocycloalkyl, C6-C14 aryl, and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, is selected from C3-C6 cycloalkyl, C3-C6 heterocycloalkyl, C6-C14 aryl, and C2-C10 heteroaryl, and is unsubstituted.

In various aspects, $Cy^5$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^5$, when present, is selected from C3-C6 cycloalkyl and C3-C6 heterocycloalkyl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is selected from C3-C6 cycloalkyl and C3-C6 heterocycloalkyl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is selected from C3-C6 cycloalkyl and C3-C6 heterocycloalkyl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, is selected from C3-C6 cycloalkyl and C3-C6 heterocycloalkyl, and is unsubstituted.

In various aspects, $Cy^5$, when present, is C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^5$, when present, is C3-C6 cycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is C3-C6 cycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is C3-C6 cycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-

C4) dialkylamino, and C1-C4 aminoalkyl. In an even further aspect, $Cy^5$, when present, is unsubstituted C3-C6 cycloalkyl.

In various aspects, $Cy^5$, when present, is cyclopropyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^5$, when present, is cyclopropyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is cyclopropyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is cyclopropyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, is unsubstituted cyclopropyl.

In various aspects, $Cy^5$, when present, is cyclobutyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^5$, when present, is cyclobutyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is cyclobutyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is cyclobutyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, is unsubstituted cyclobutyl.

In various aspects, $Cy^5$, when present, is C3-C6 heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 heterocycloalkyls include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, $Cy^5$, when present, is C3-C6 heterocycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is C3-C6 heterocycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is C3-C6 heterocycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, unsubstituted C3-C6 heterocycloalkyl.

In various aspects, $Cy^5$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^5$, when present, is selected from C6-C14 aryl and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is selected from C6-C14 aryl and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is selected from C6-C14 aryl and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, is selected from C6-C14 aryl and C2-C10 heteroaryl, and is unsubstituted.

In various aspects, $Cy^5$, when present, is C6-C14 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, anthracenyl, and phenanthrenyl. In a further aspect, $Cy^5$, when present, is C6-C14 aryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is C6-C14 aryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is C6-C14 aryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, is unsubstituted C6-C14 aryl.

In various aspects, $Cy^5$, when present, is phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^5$, when present, is phenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is phenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is phenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, is unsubstituted phenyl.

In various aspects, $Cy^5$, when present, is C2-C10 heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, thiophene, furan, pyrrole, oxazole, isoxazole, isothiazole, pyridine, pyrimidine, pyridazine, pyrazine, triazine, indole, azaindole, purine, benzofuran, quinolone, isoquinoline, and quinoxaline. In a further aspect, $Cy^5$, when present, is C2-C10 heteroaryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is C2-C10 heteroaryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is C2-C10 heteroaryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, is unsubstituted C2-C10 heteroaryl.

In various aspects, $Cy^5$, when present, is pyridinyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^5$, when present, is pyridinyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^5$, when present, is pyridinyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^5$, when present, is pyridinyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^5$, when present, is unsubstituted pyridinyl.

q. $Cy^6$ Groups

In one aspect, $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^6$, when present, is selected from C3-C6 cycloalkyl and C3-C6 heterocycloalkyl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^6$, when present, is selected from C3-C6 cycloalkyl and C3-C6 heterocycloalkyl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^6$, when present, is selected from C3-C6 cycloalkyl and C3-C6 heterocycloalkyl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^6$, when present, is selected from C3-C6 cycloalkyl and C3-C6 heterocycloalkyl, and is unsubstituted.

In various aspects, $Cy^6$, when present, is C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^6$, when present, is C3-C6 cycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^6$, when present, is C3-C6 cycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^6$, when present, is C3-C6 cycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^6$, when present, is unsubstituted C3-C6 cycloalkyl.

In various aspects, $Cy^6$, when present, is cyclopropyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^6$, when present, is cyclopropyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^6$, when present, is cyclopropyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^6$, when present, is cyclopropyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^6$, when present, is unsubstituted cyclopropyl.

In various aspects, $Cy^6$, when present, is cyclobutyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^6$, when present, is cyclobutyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^6$, when present, is cyclobutyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^6$, when present, is cyclobutyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^6$, when present, is unsubstituted cyclobutyl.

In various aspects, $Cy^6$, when present, is C3-C6 heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 heterocycloalkyls include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, $Cy^6$, when present, is C3-C6 heterocycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^6$, when present, is C3-C6 heterocycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^6$, when present, is C3-C6 heterocycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^6$, when present, is unsubstituted C3-C6 heterocycloalkyl.

r. $Ar^1$ Groups

In one aspect, $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^1$ is selected from C6-C14 aryl and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is selected from C6-C14 aryl and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^1$ is selected from C6-C14 aryl and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^1$ is selected from C6-C14 aryl and C2-C10 heteroaryl, and is unsubstituted.

In various aspects, $Ar^1$ is C6-C14 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-

C4)(C1-C4) dialkylamino, and C1-C4 aminoalkyl. Examples of C6-C14 aryls include, but are not limited to, phenyl, naphthyl, anthracenyl, and phenanthrenyl. In a further aspect, Ar[1] is C6-C14 aryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, AO is C6-C14 aryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar[1] is C6-C14 aryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar[1] is unsubstituted C6-C14 aryl.

In various aspects, Ar[1] is C6-C14 aryl para-substituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, Ar[1] is phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Ar[1] is phenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar[1] is phenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar[1] is phenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar[1] is unsubstituted phenyl.

In various aspects, Ar[1] is C2-C10 heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, thiophene, furan, pyrrole, oxazole, isoxazole, isothiazole, pyridine, pyrimidine, pyridazine, pyrazine, triazine, indole, azaindole, purine, benzofuran, quinolone, isoquinoline, and quinoxaline. In a further aspect, Ar[1] is C2-C10 heteroaryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar[1] is C2-C10 heteroaryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar[1] is C2-C10 heteroaryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar[1] is unsubstituted C2-C10 heteroaryl.

In various aspects, Ar[1] is pyridinyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Ar[1] is pyridinyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar[1] is pyridinyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar[1] is pyridinyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar[1] is unsubstituted pyridinyl.

In various aspects, Ar[1] is thiophenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Ar[1] is thiophenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar[1] is thiophenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar[1] is thiophenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar[1] is unsubstituted thiophenyl.

In various aspects, Ar[1] is thiazolyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^1$ is thiazolyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is thiazolyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^1$ is thiazolyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^1$ is unsubstituted thiazolyl.

In various aspects, $Ar^1$ is isoxazolyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^1$ is isoxazolyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is isoxazolyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^1$ is isoxazolyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^1$ is unsubstituted isoxazolyl.

In various aspects, $Ar^1$ is triazolyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^1$ is triazolyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^1$ is triazolyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^1$ is triazolyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^1$ is unsubstituted triazolyl.

s. $Ar^2$ Groups

In one aspect, $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl). In a further aspect, $Ar^2$, when present, is selected from C6-C14 aryl and C2-C10 heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^2$, when present, is selected from C6-C14 aryl and C2-C10 heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^2$, when present, is selected from C6-C14 aryl and C2-C10 heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^2$, when present, is selected from C6-C14 aryl and C2-C10 heteroaryl, and is unsubstituted.

In various aspects, $Ar^2$, when present, is C6-C14 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, anthracenyl, and phenanthrenyl. In a further aspect, $Ar^2$, when present, is C6-C14 aryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^2$, when present, is C6-C14 aryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^2$, when present, is C6-C14 aryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^2$, when present, is unsubstituted C6-C14 aryl.

In various aspects, $Ar^2$, when present, is phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^2$, when present, is phenyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^2$, when present, is phenyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^2$, when present, is phenyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^2$, when present, is unsubstituted phenyl.

In various aspects, $Ar^2$, when present, is C2-C10 heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, thiophene, furan, pyrrole, oxazole, isoxazole, isothiazole, pyridine, pyrimidine, pyridazine, pyrazine, triazine, indole, azaindole, purine, benzofuran, quinolone, isoquinoline, and quinoxaline. In a further aspect, $Ar^2$, when present, is C2-C10 heteroaryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^2$, when present, is C2-C10 heteroaryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^2$, when present, is C2-C10 heteroaryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^2$, when present, is unsubstituted C2-C10 heteroaryl.

In various aspects, $Ar^2$, when present, is imidazolyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^2$, when present, is imidazolyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^2$, when present, is imidazolyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^2$, when present, is imidazolyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^2$, when present, is unsubstituted imidazolyl.

In various aspects, $Ar^2$, when present, is oxadiazolyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^2$, when present, is oxadiazolyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^2$, when present, is oxadiazolyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^2$, when present, is oxadiazolyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^2$, when present, is unsubstituted oxadiazolyl.

In various aspects, $Ar^2$, when present, is benzoimidazolyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^2$, when present, is benzoimidazolyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^2$, when present, is benzoimidazolyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^2$, when present, is benzoimidazolyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^2$, when present, is unsubstituted benzoimidazolyl.

In various aspects, $Ar^2$, when present, is indolyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Ar^2$, when present, is indolyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Ar^2$, when present, is indolyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Ar^2$, when present, is indolyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Ar^2$, when present, is unsubstituted indolyl.

2. Example Compounds

In one aspect, a compound can be present as one or more of the following structures:

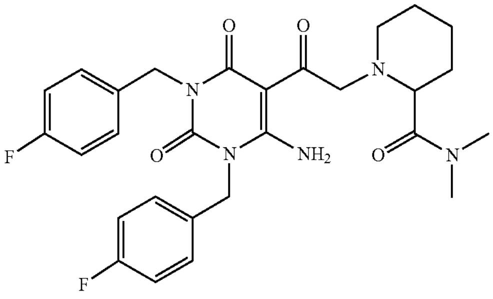
,

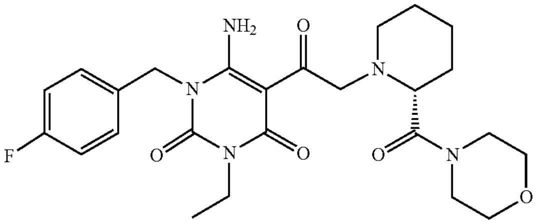
,

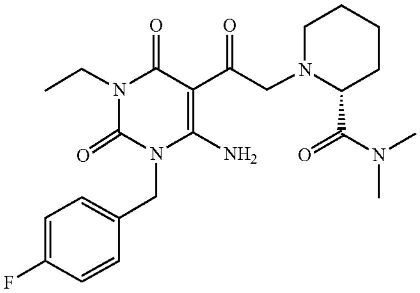
,

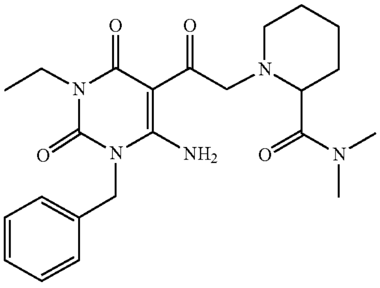
,

-continued

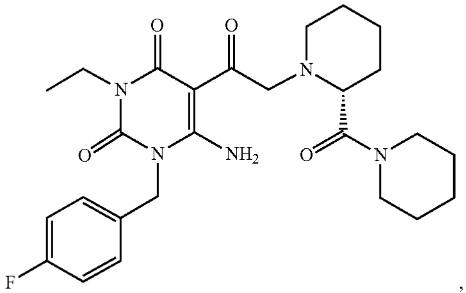
,

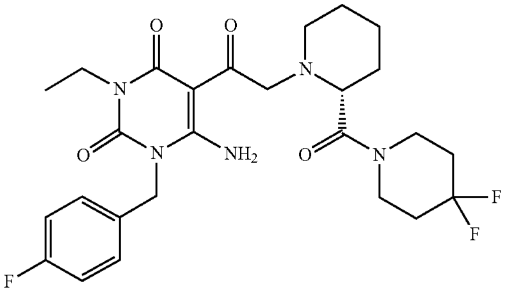
,

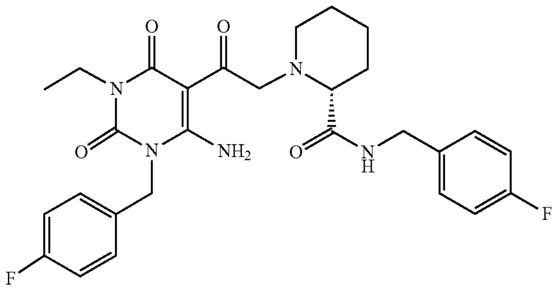
,

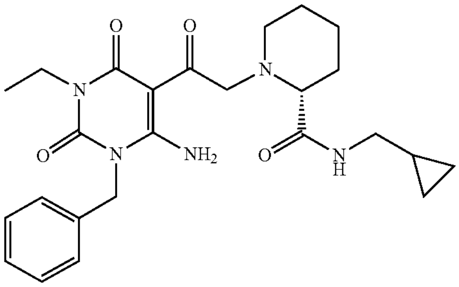
,

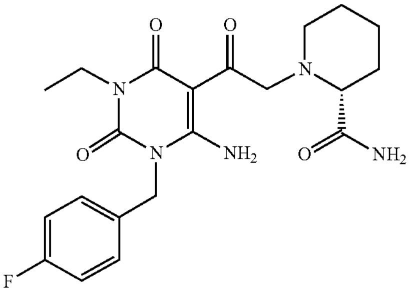
,

-continued
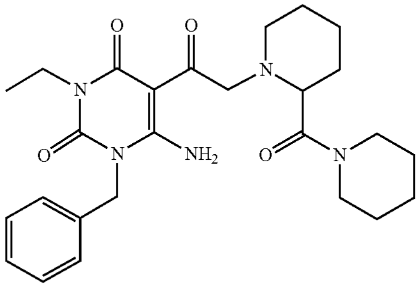
,
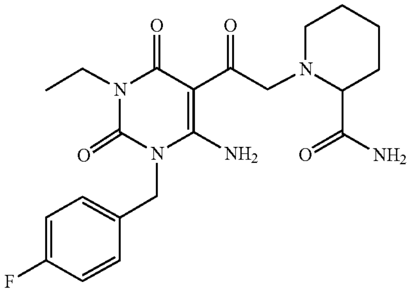
,
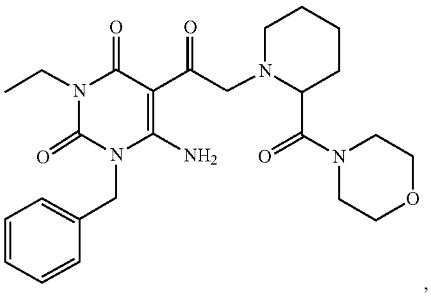
,
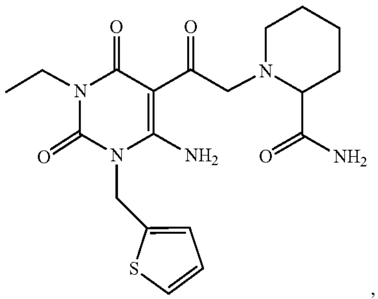
,
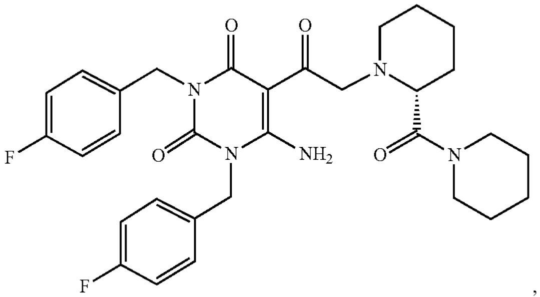
,
-continued
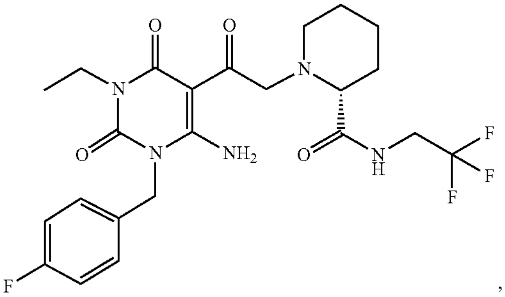
,
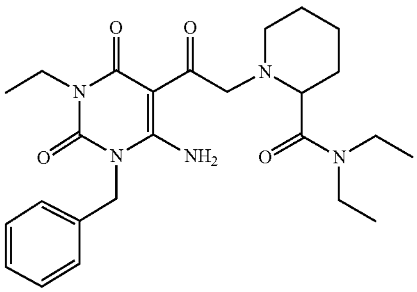
,
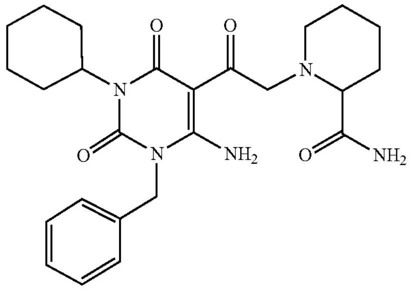
,
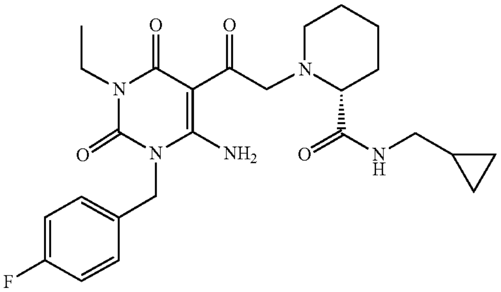
,
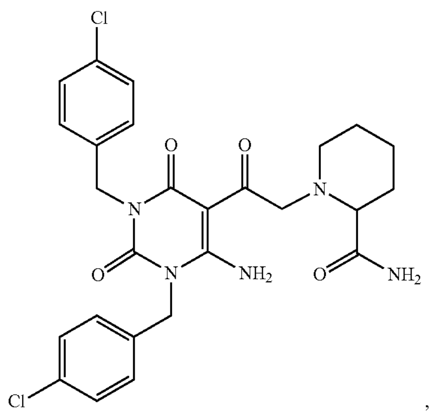
, -continued
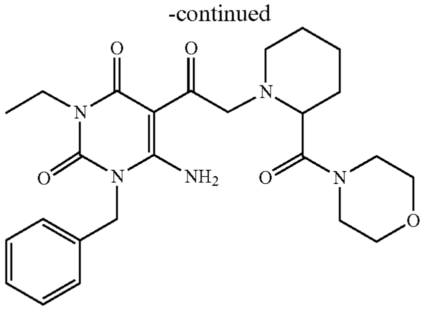
,
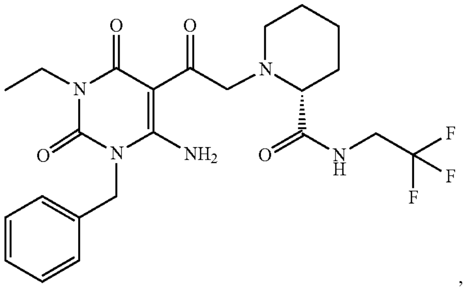
,
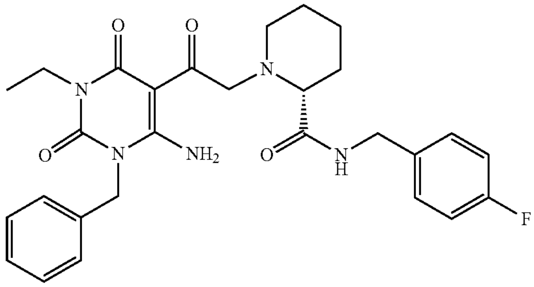
,
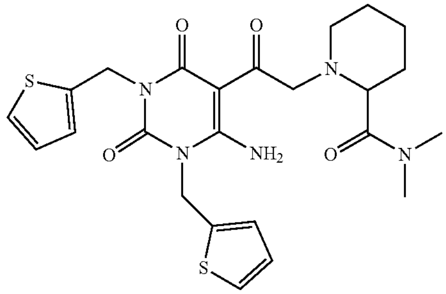
,
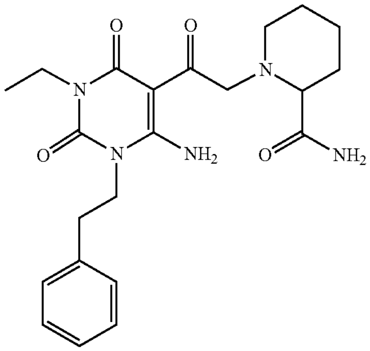
,
-continued
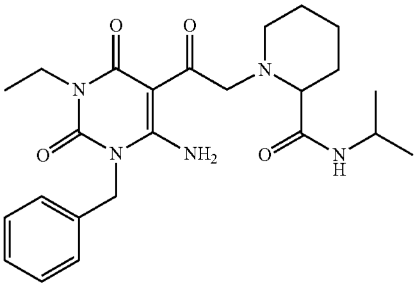
,
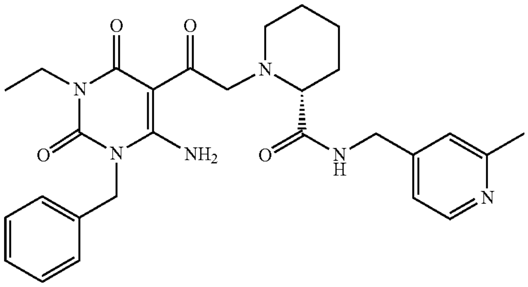
,
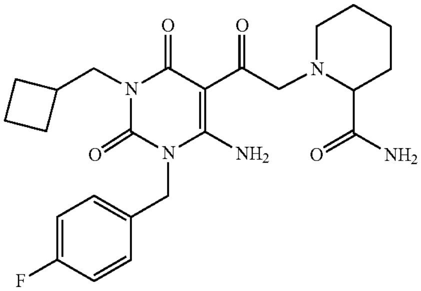
,
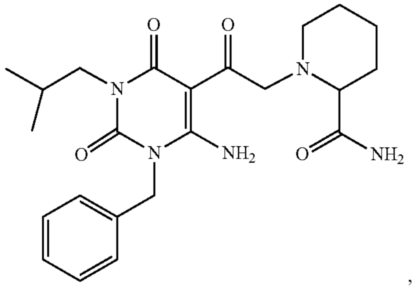
,
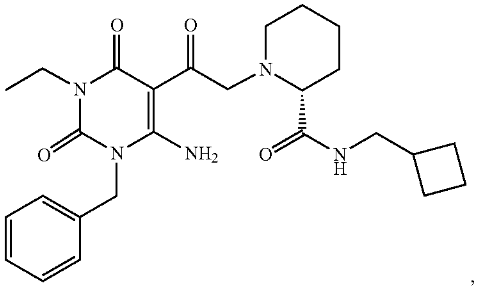
, -continued
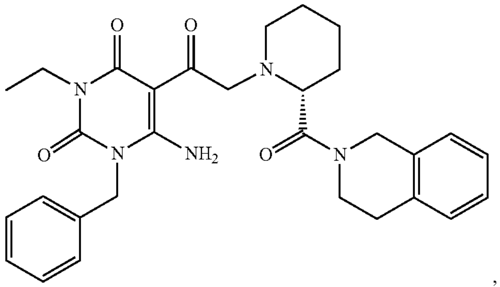
,
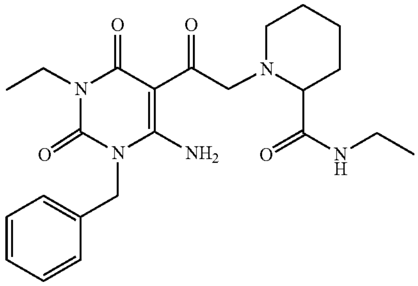
,
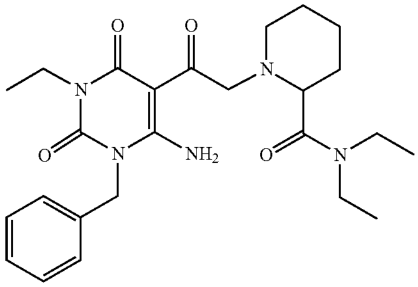
,
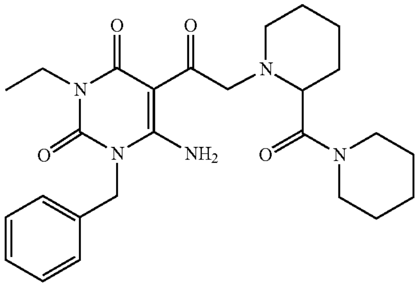
,
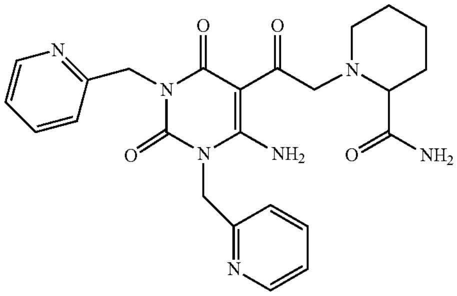
,
-continued
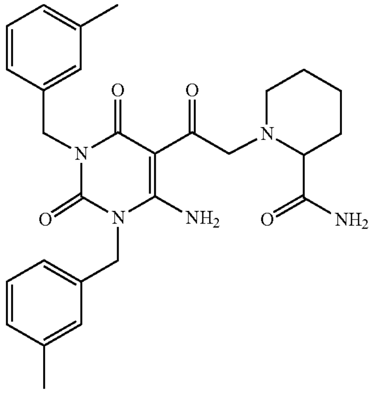
,
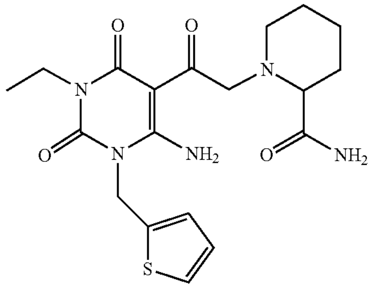
,
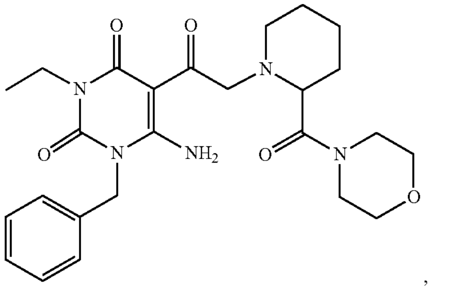
,
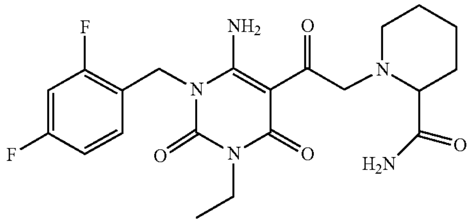
,
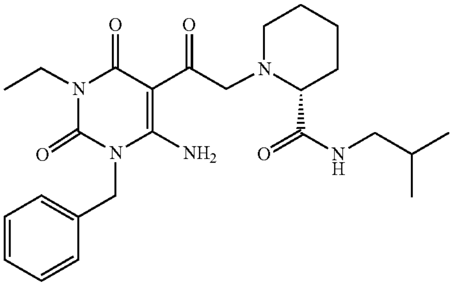
, -continued
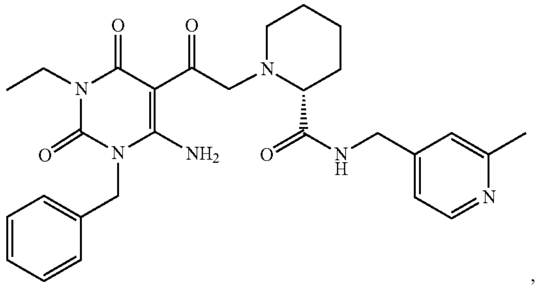
,
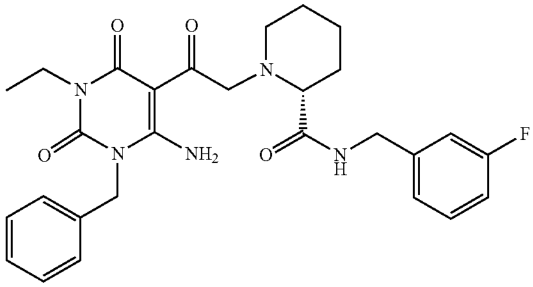
,
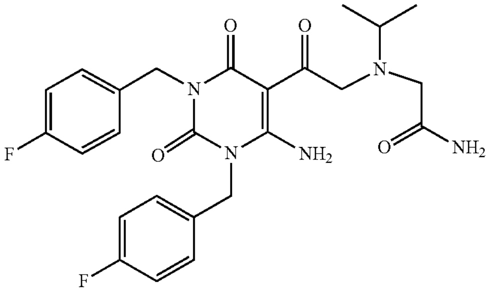
,
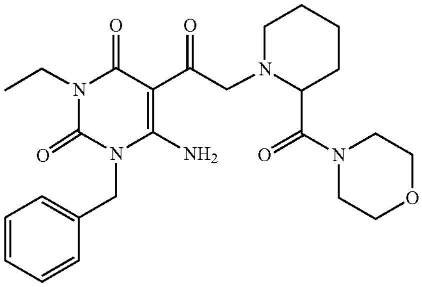
,
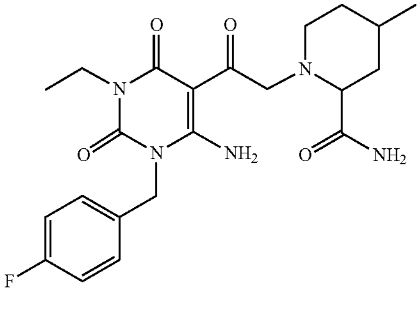
,
-continued
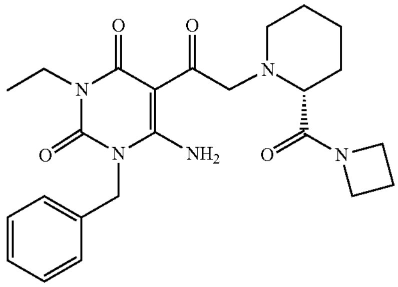
,
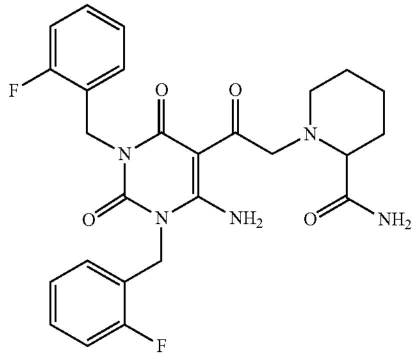
,
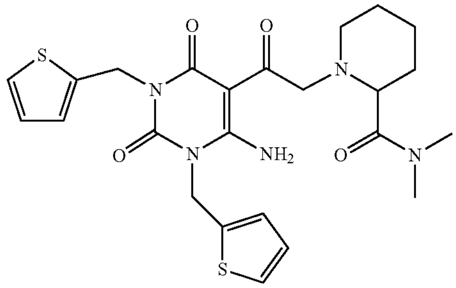
,
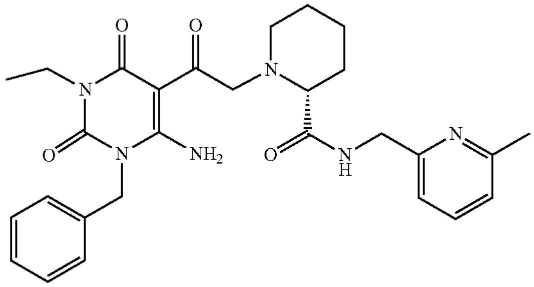
,
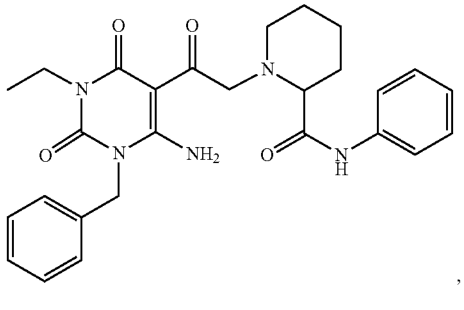
, -continued
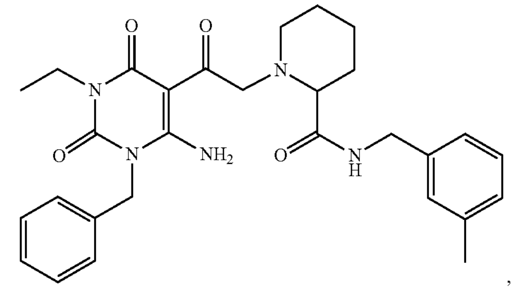
,
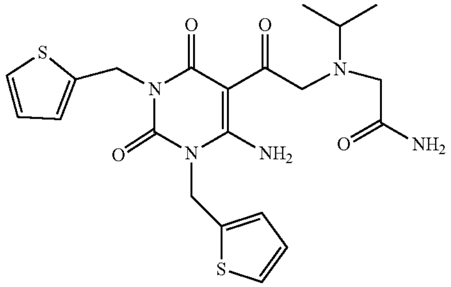
,
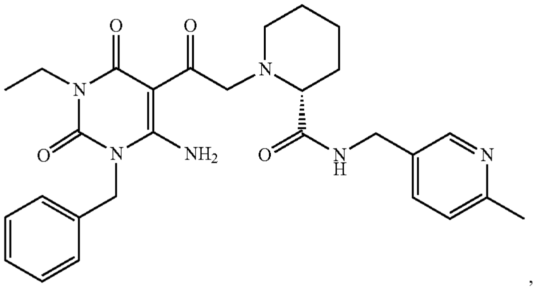
,
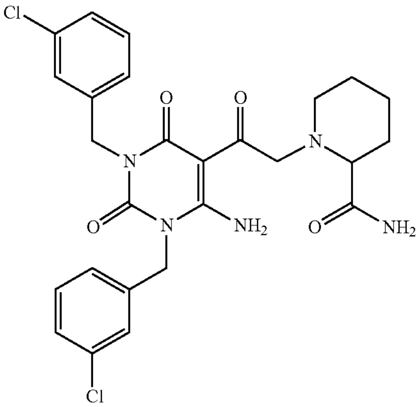
,
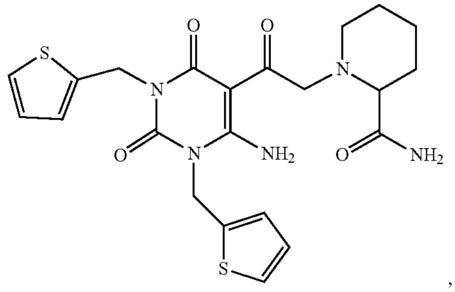
,
-continued
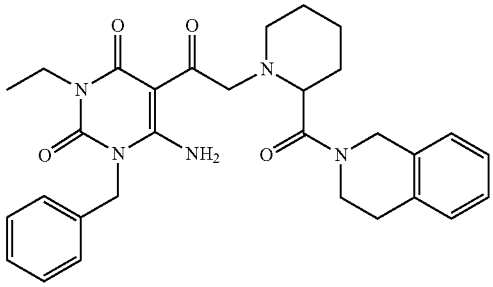
,
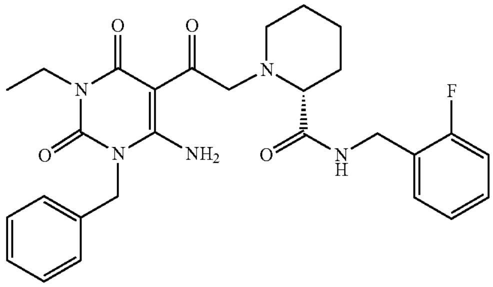
,
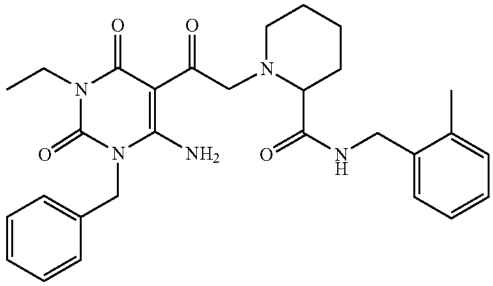
,
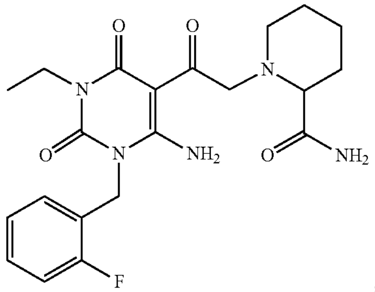
,
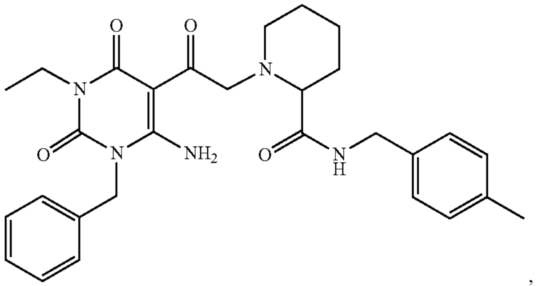
, -continued
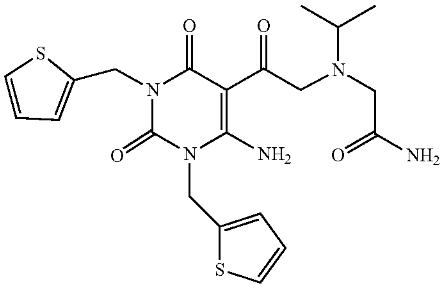
,
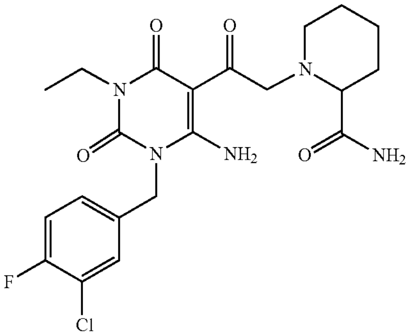
,
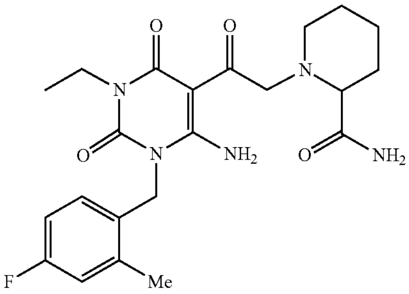
,
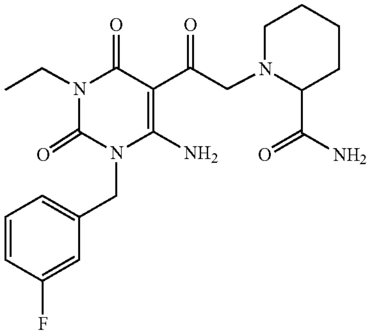
,
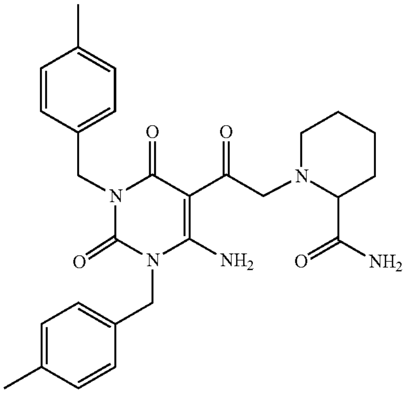
,
-continued
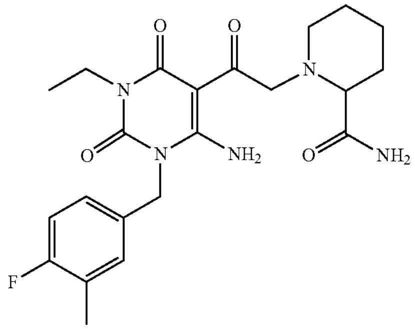
,
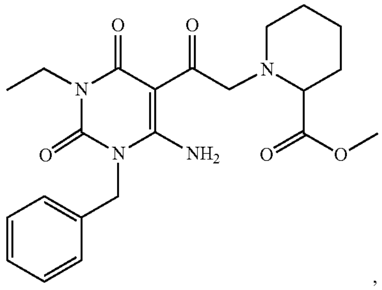
,
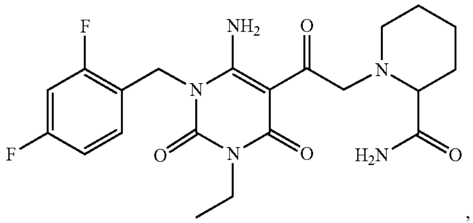
,
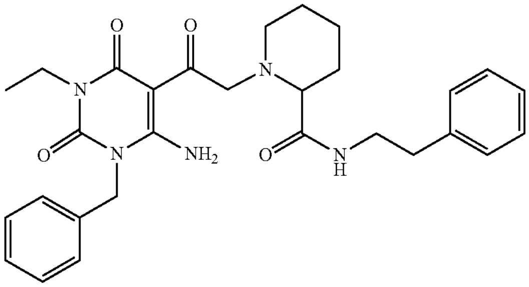
,
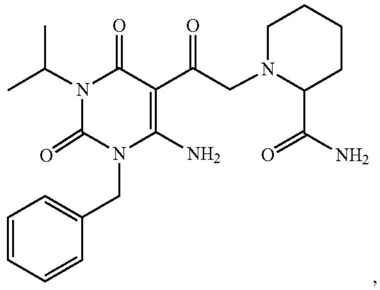
, -continued
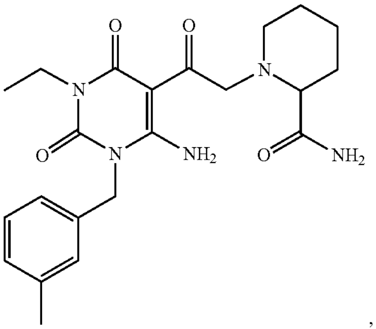
,
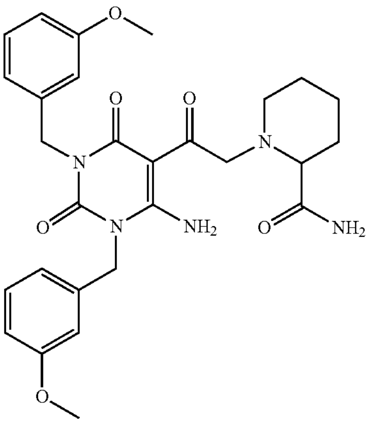
,
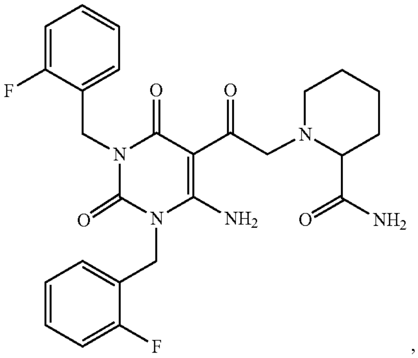
,
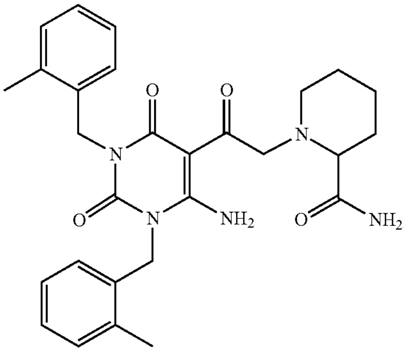
,
-continued
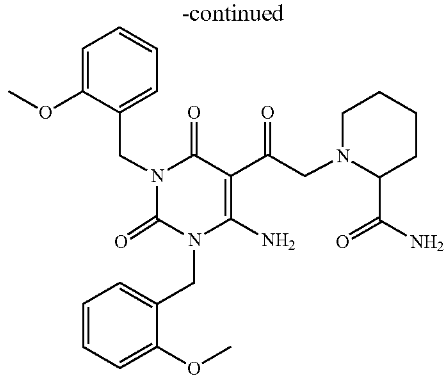
,
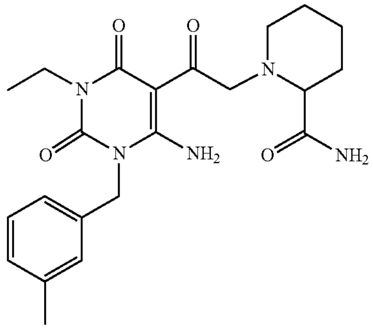
,
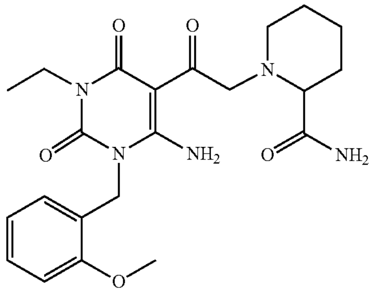
,
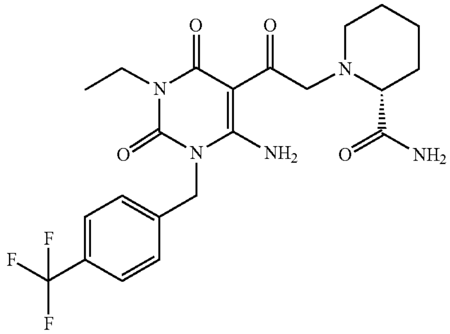
,
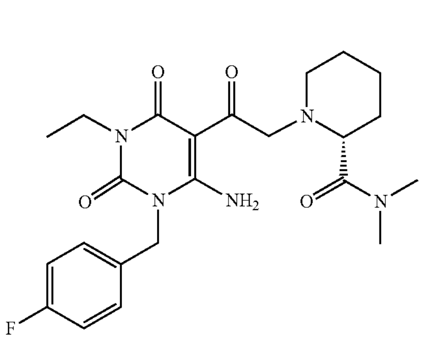
, -continued
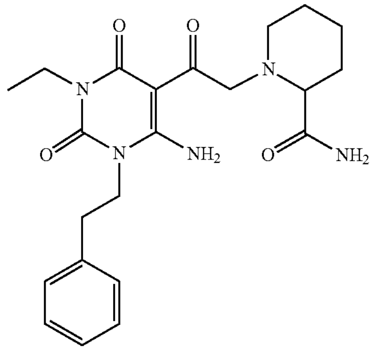
,
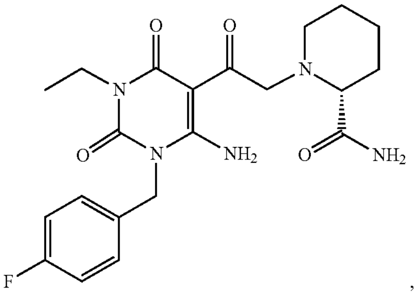
,
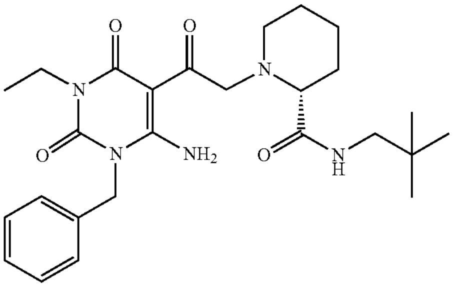
,
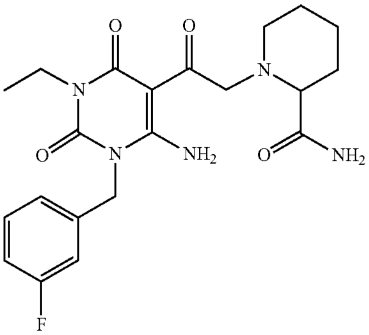
,
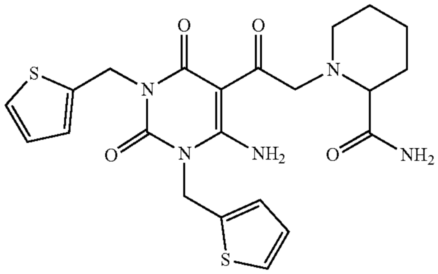
,
-continued
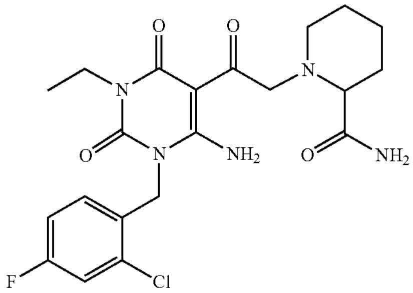
,
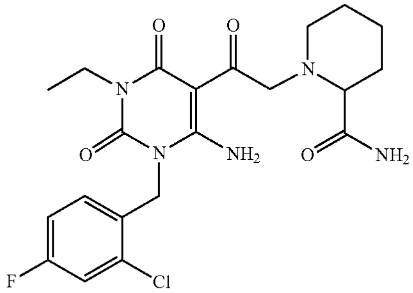
,
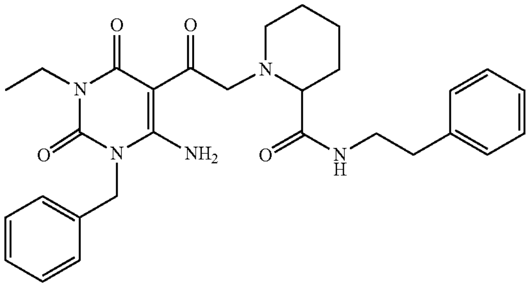
,
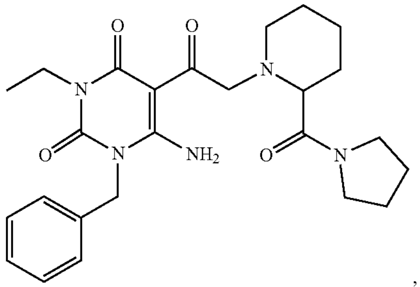
,
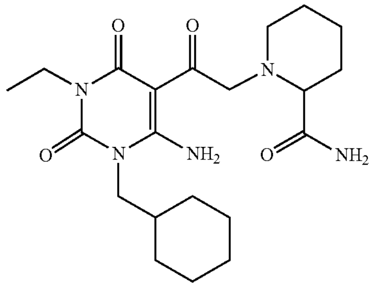
, -continued
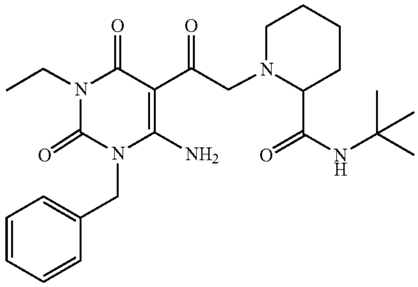
,
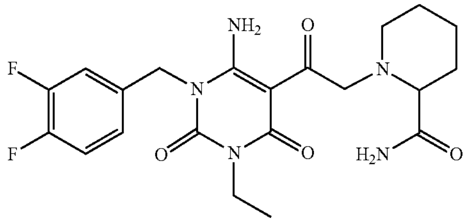
,
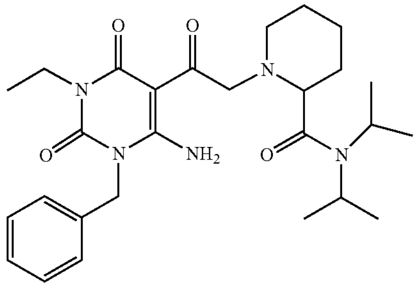
,
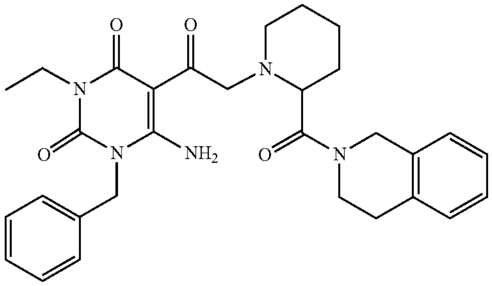
,
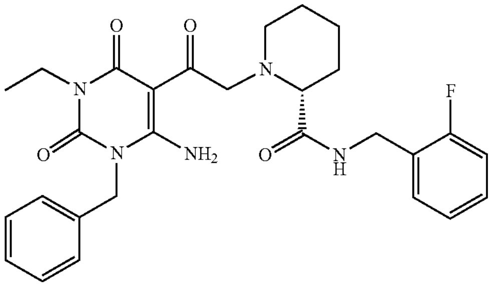
,
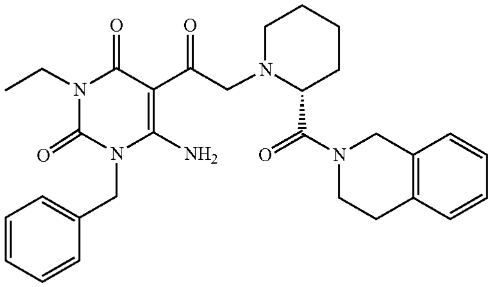
,
-continued
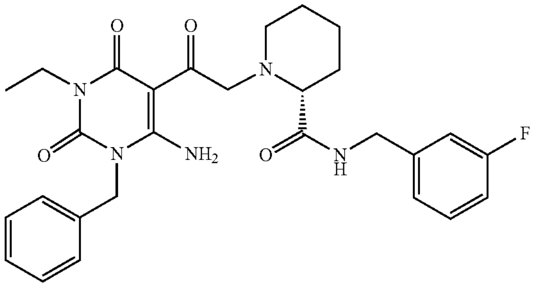
,
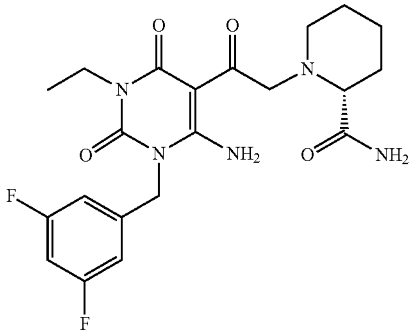
,
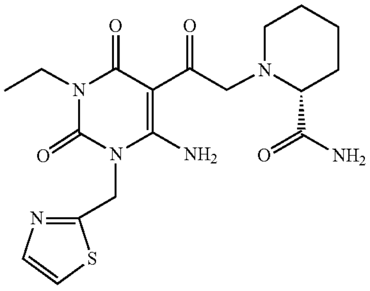
,
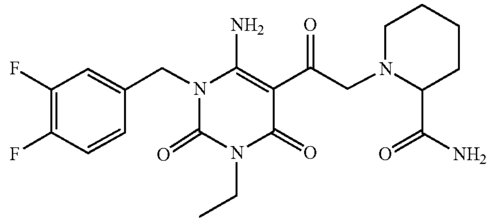
,
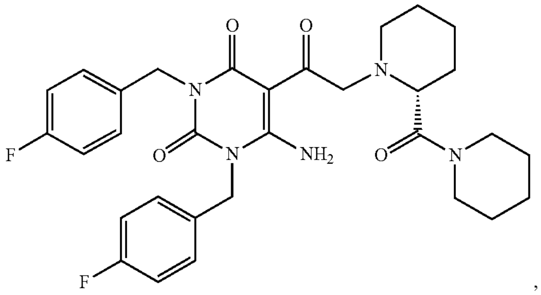
, -continued
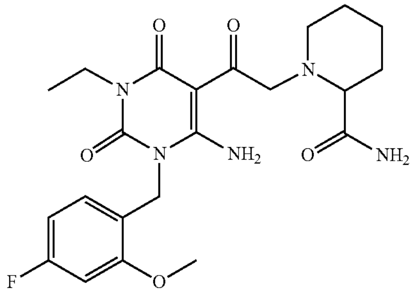
,
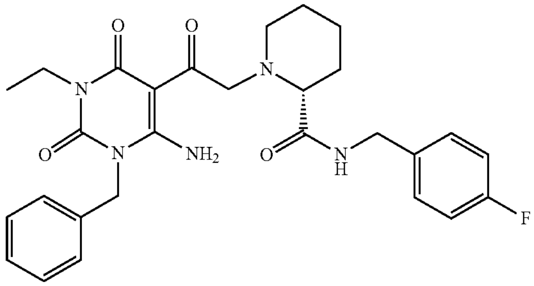
,
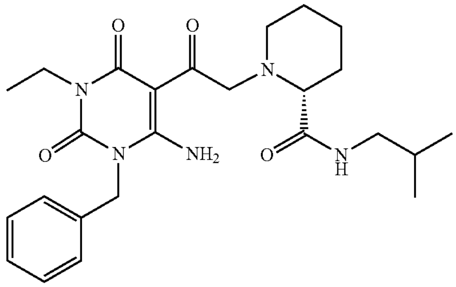
,
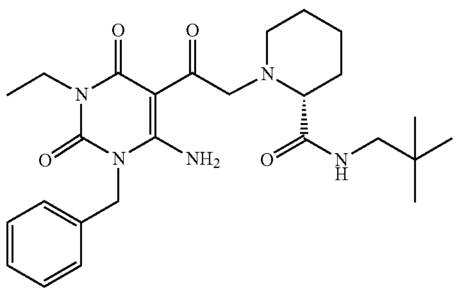
,
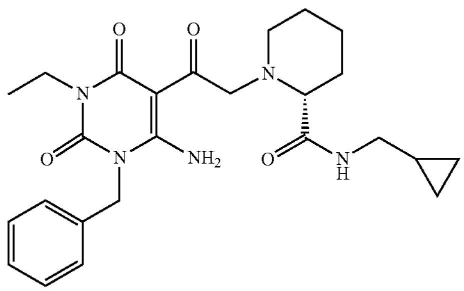
,
-continued
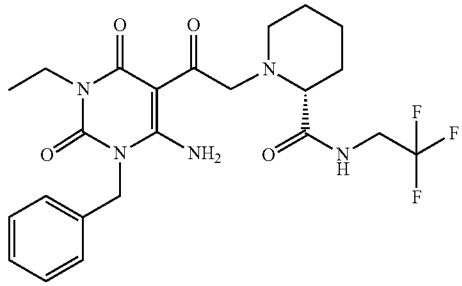
,
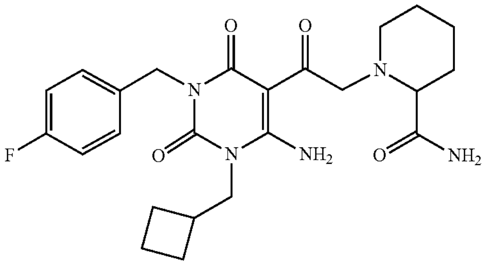
,
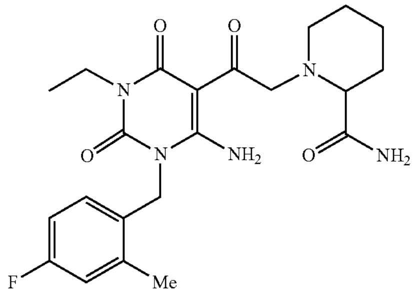
,
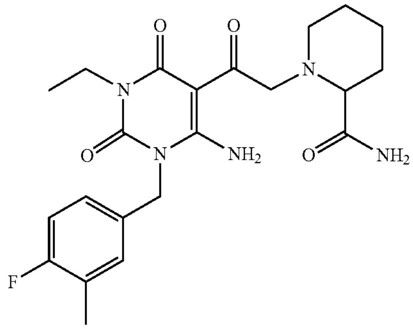
,
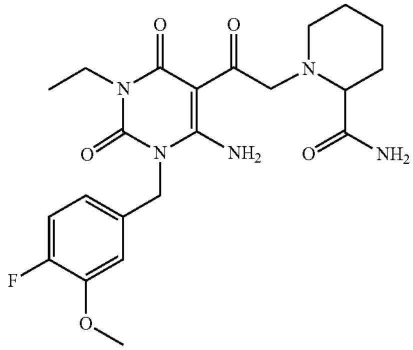
, -continued
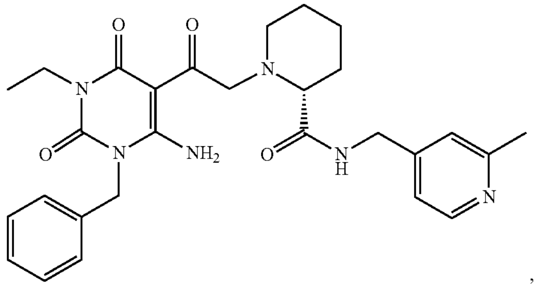
,
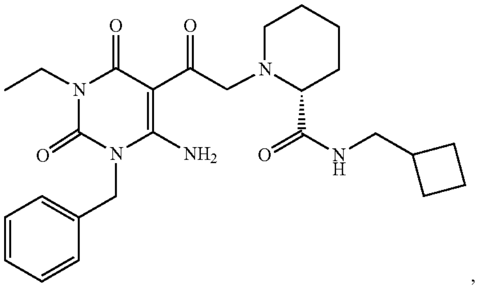
,
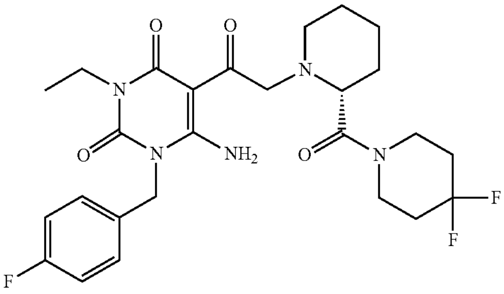
,
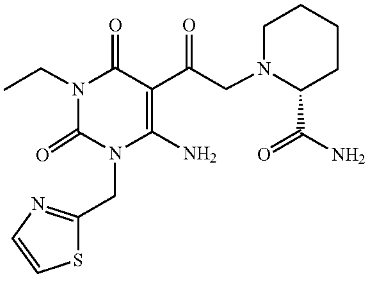
,
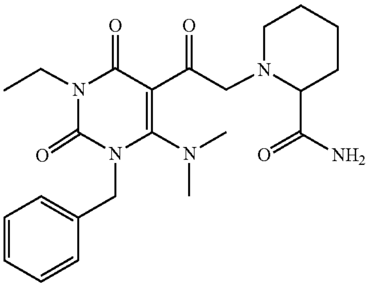
,
-continued
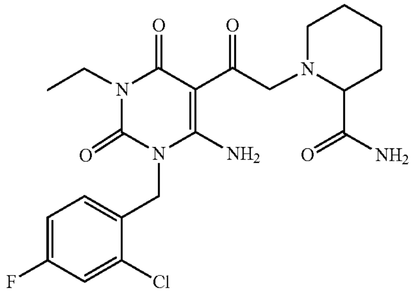
,
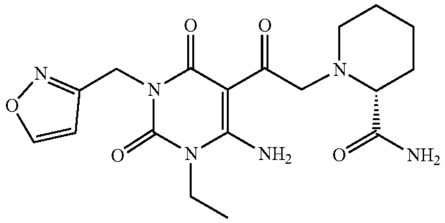
,
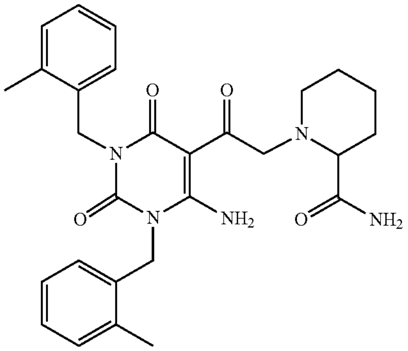
,
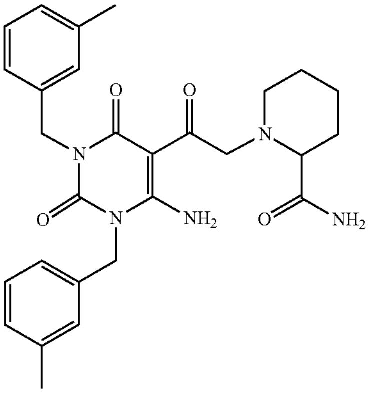
,
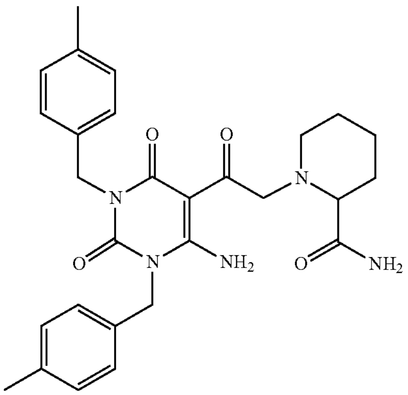
, -continued
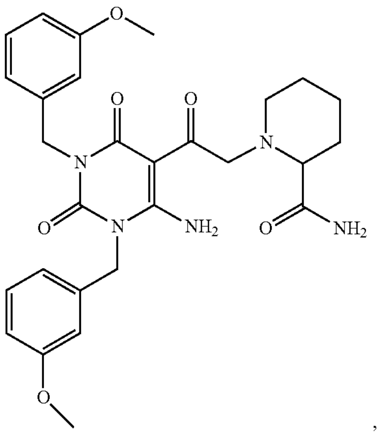
,
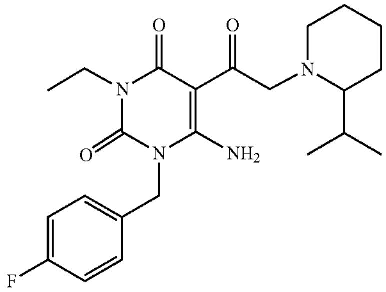
,
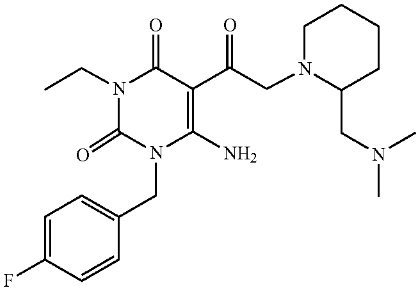
,
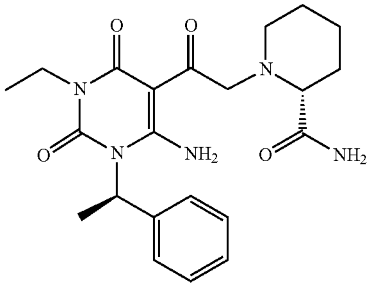
,
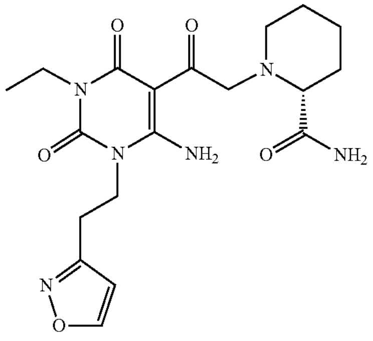
,
-continued
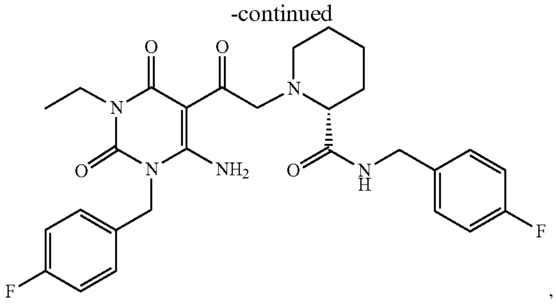
,
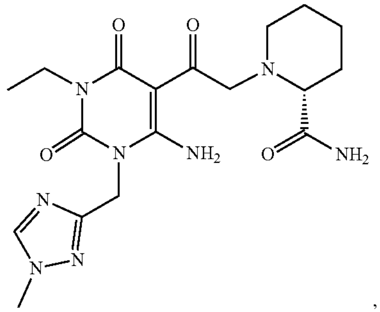
,
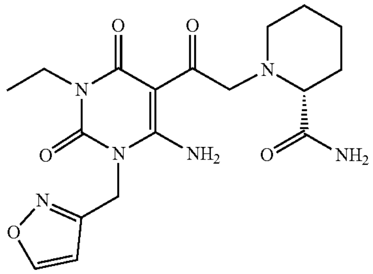
,
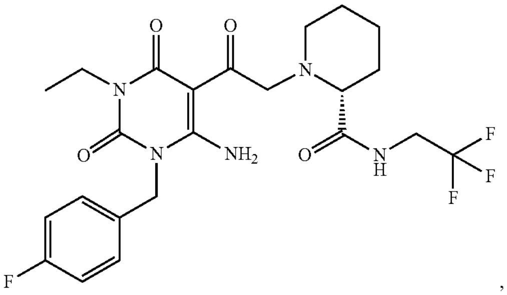
,
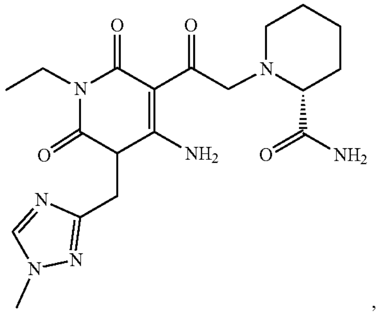
, and -continued
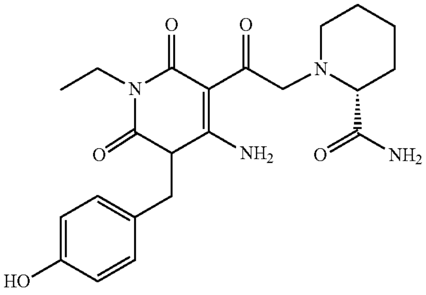
,
or a pharmaceutically acceptable salt thereof.
In one aspect, a compound can be present as one or more of the following structures:
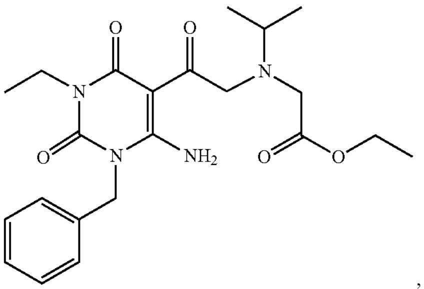
,
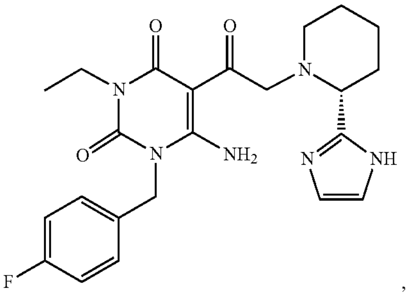
,
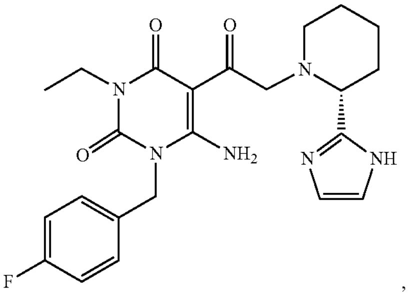
,
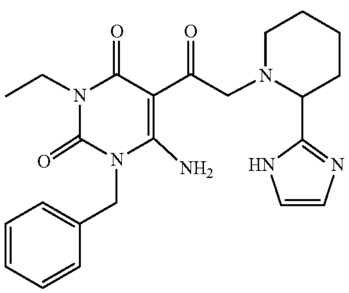
,
-continued
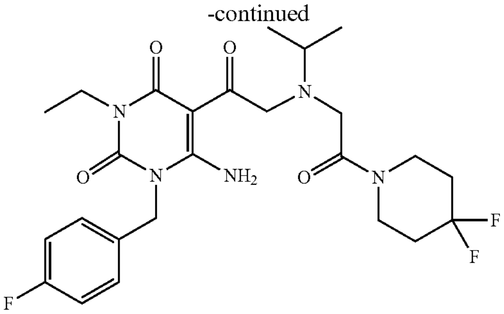
,
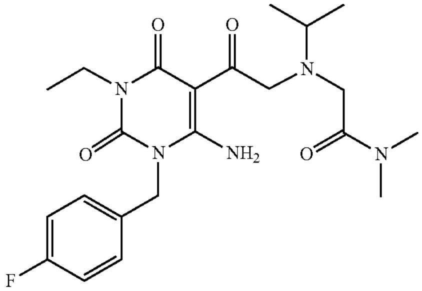
,
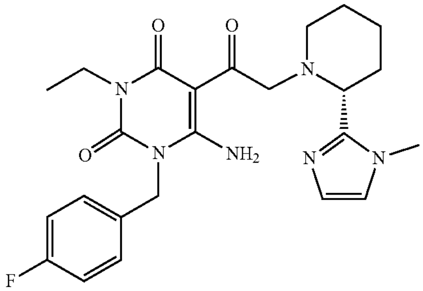
,
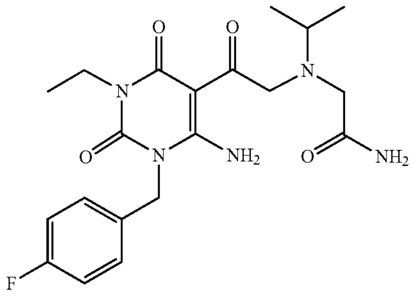
,
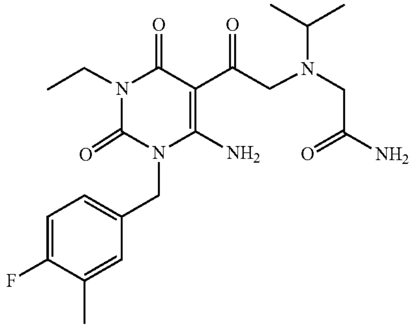
, -continued
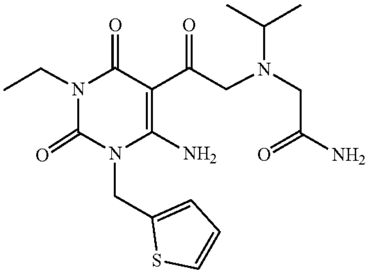
,
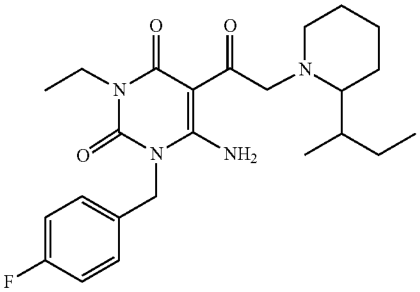
,
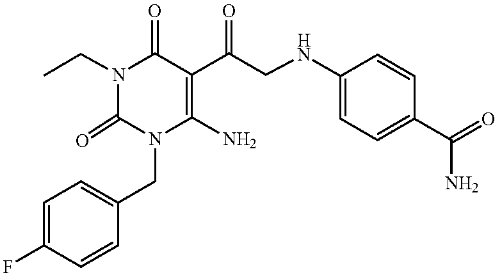
,
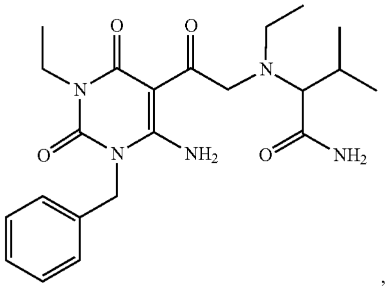
,
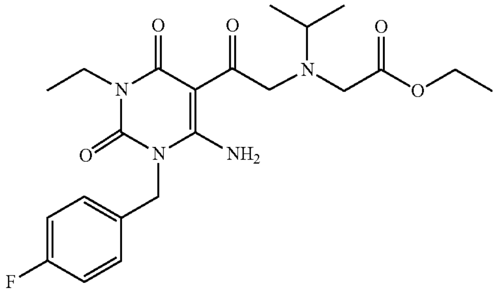
,
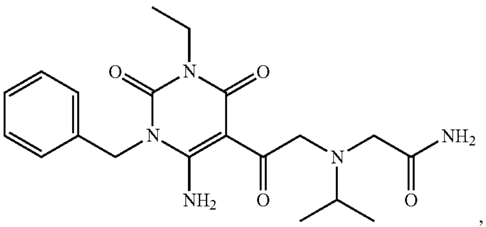
,
-continued
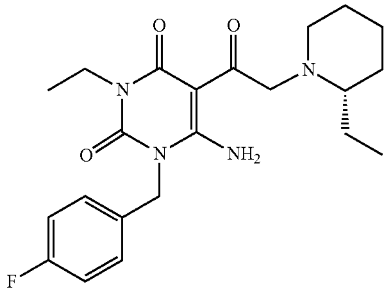
,
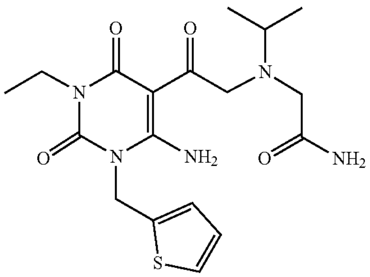
,
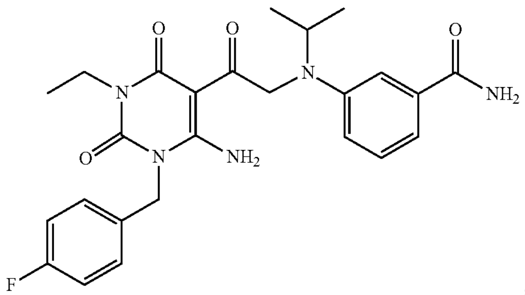
,
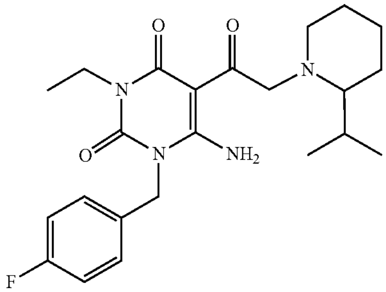
,
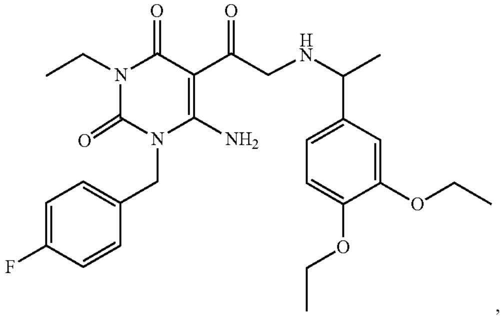
, -continued
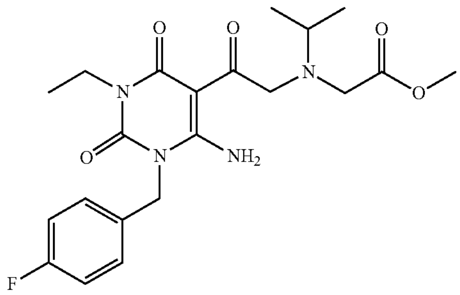
,
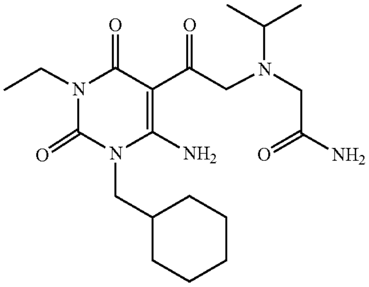
,
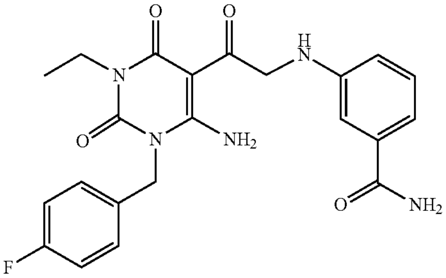
,
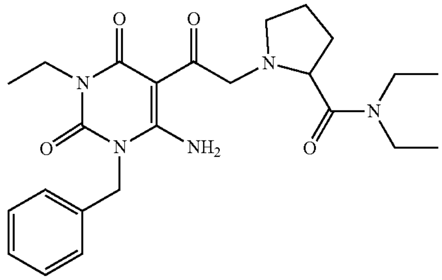
,
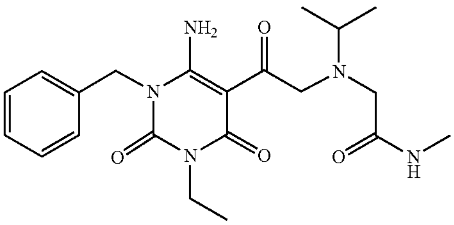
,
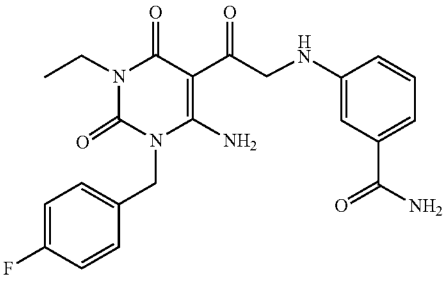
,
-continued
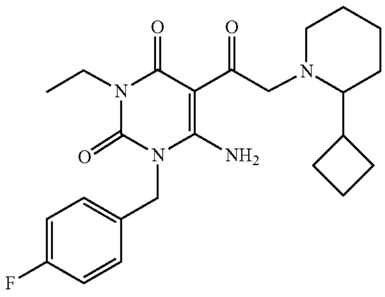
,
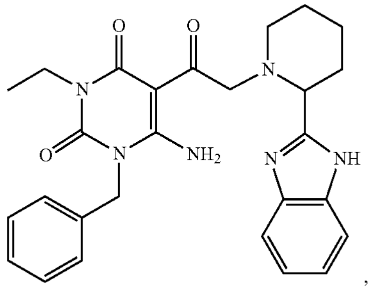
,
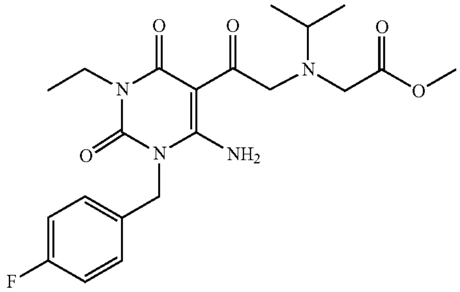
,
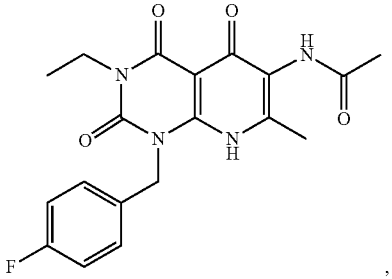
,
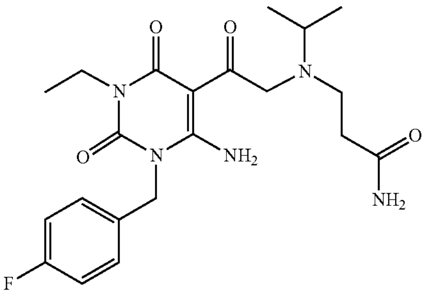
,

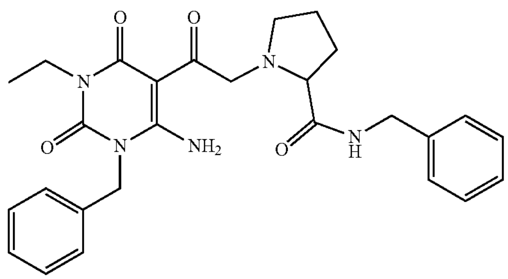
,
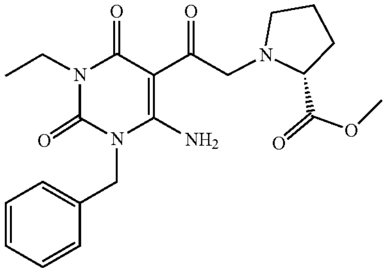
,
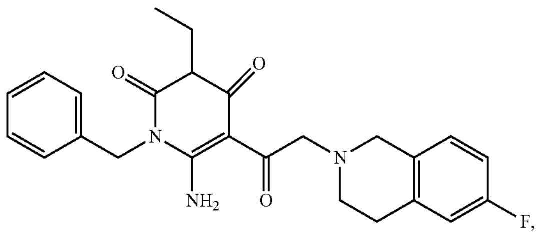
,
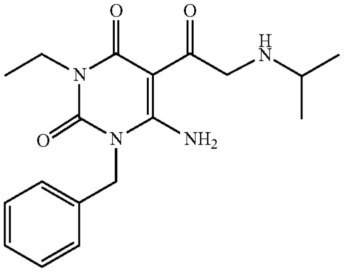
,
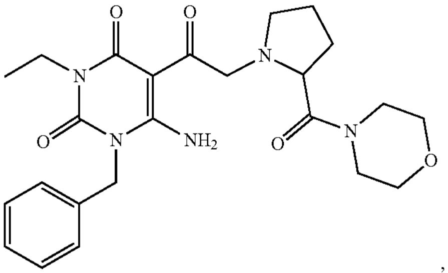
,
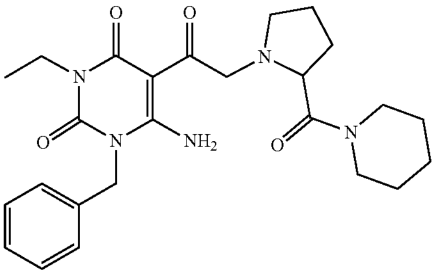
,
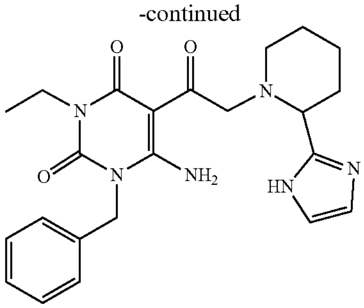
,
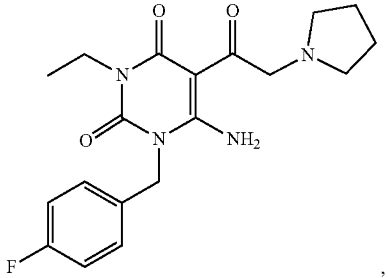
,
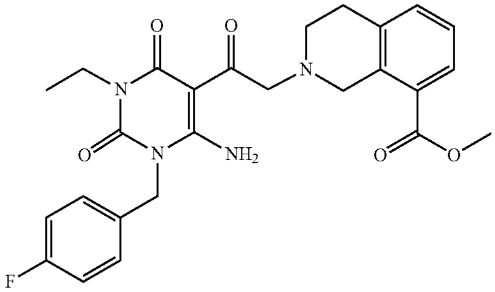
,
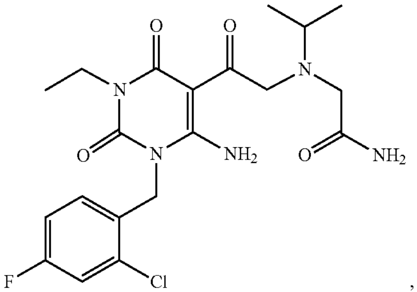
,
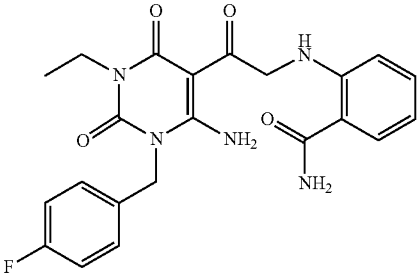
,
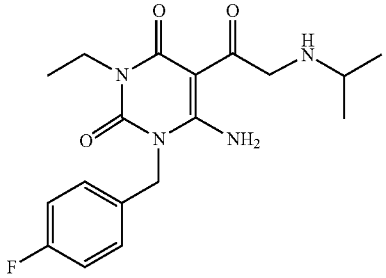
, -continued
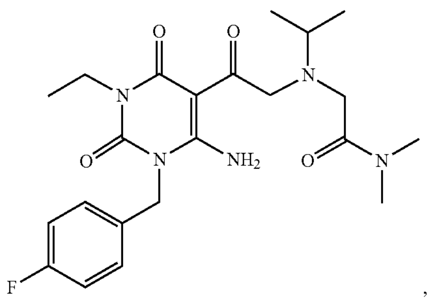
,
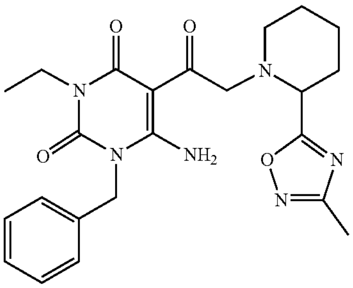
,
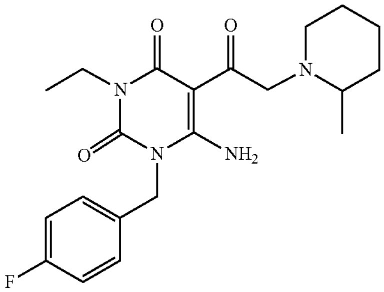
,
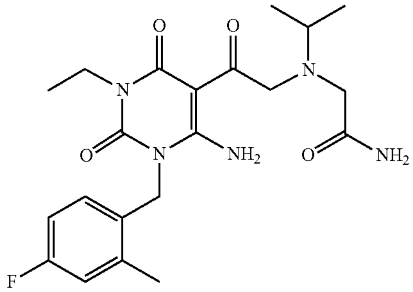
,
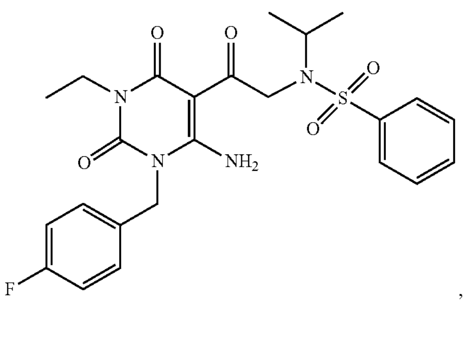
,
-continued
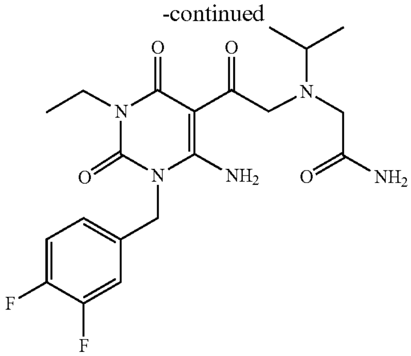
,
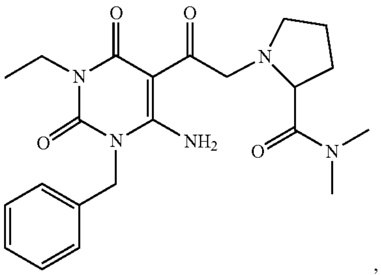
,
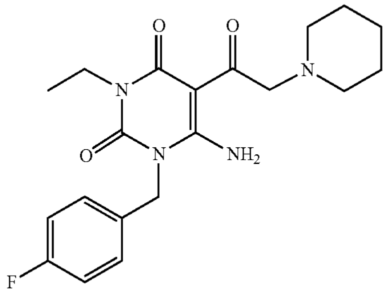
,
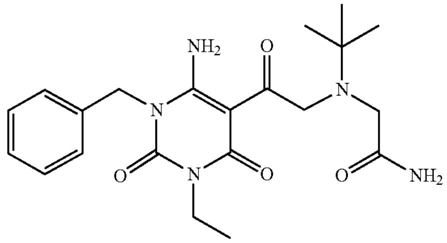
,
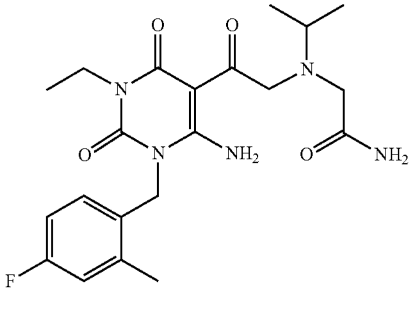
, -continued
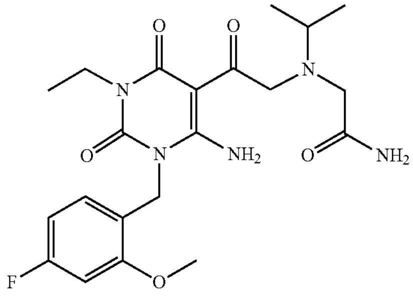
,
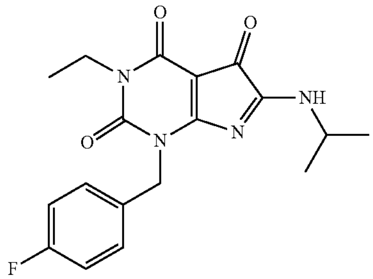
,
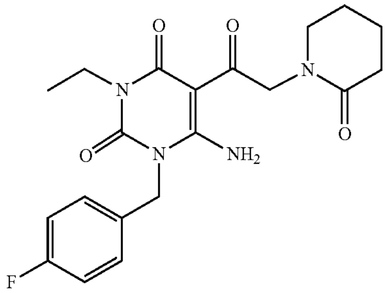
,
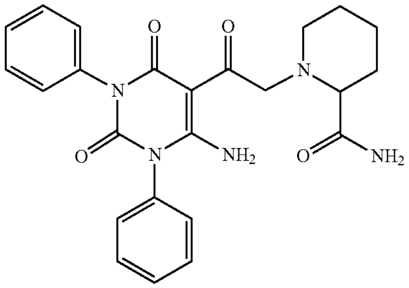
,
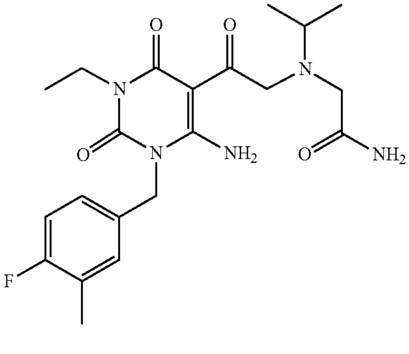
,
-continued
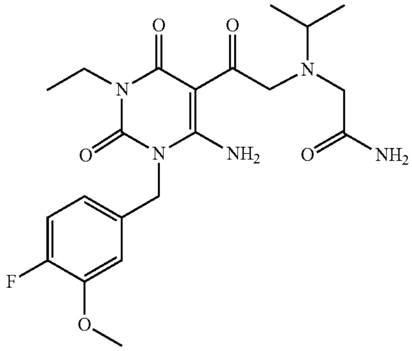
,
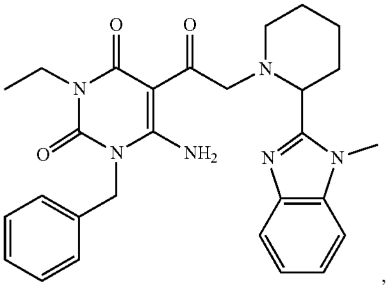
,
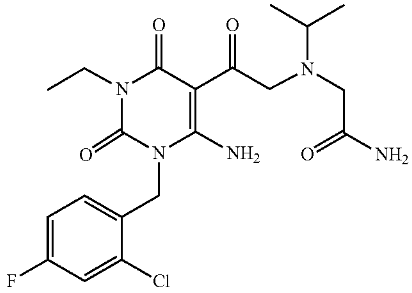
,
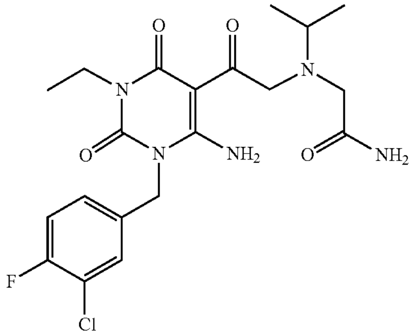
,
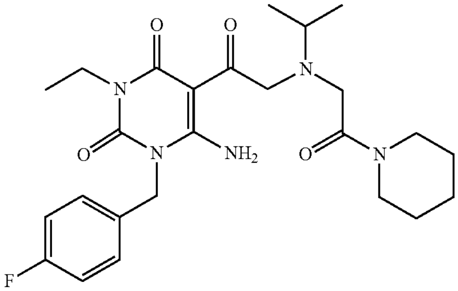
, -continued
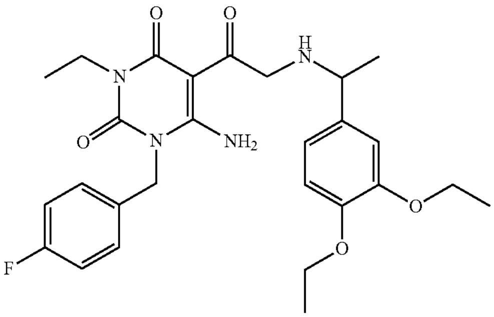
,
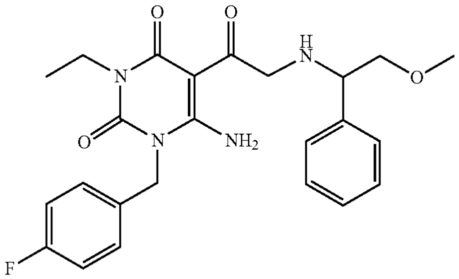
,
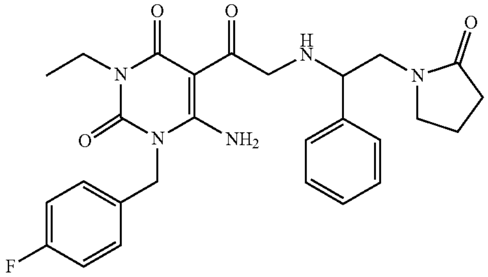
,
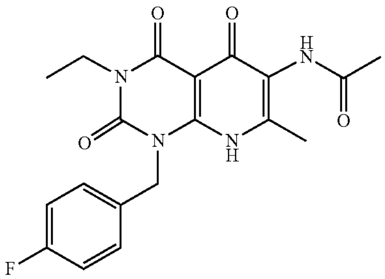
,
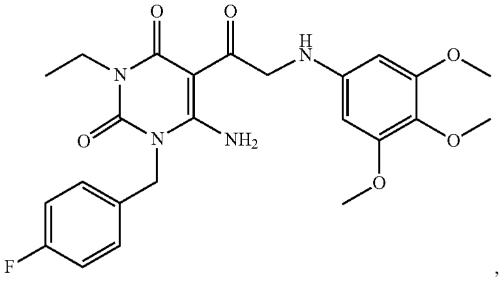
,
-continued
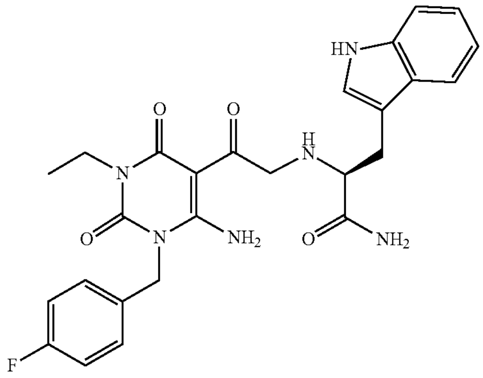
,
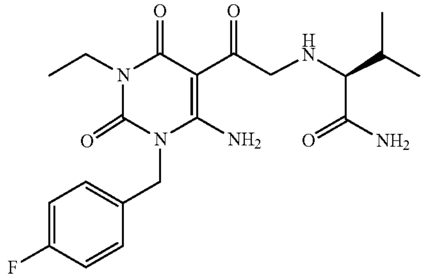
,
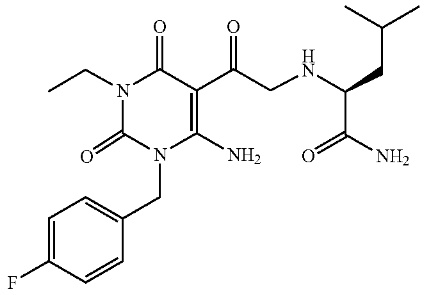
,
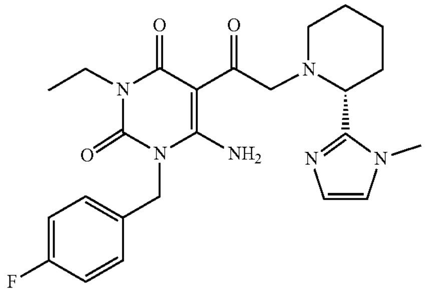
,
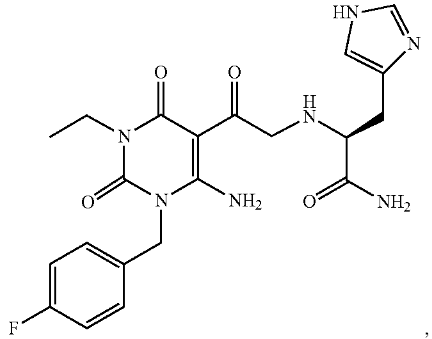
, -continued
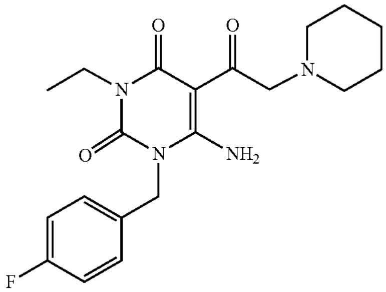
,
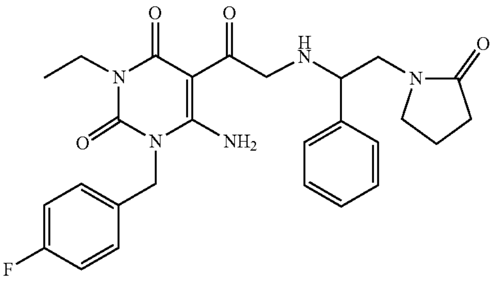
,
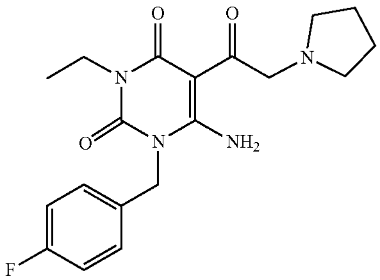
,
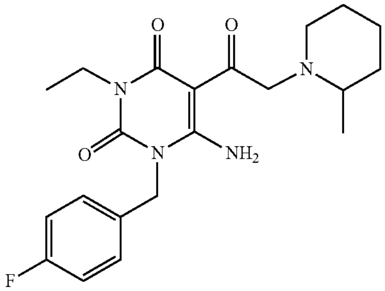
,
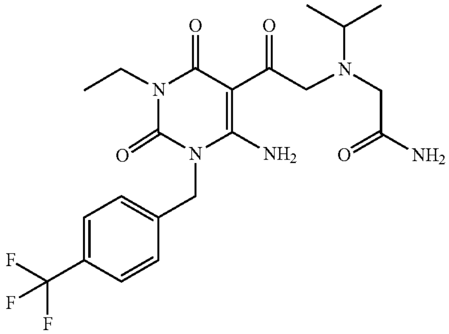
,
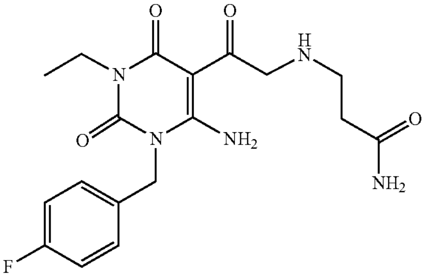
,
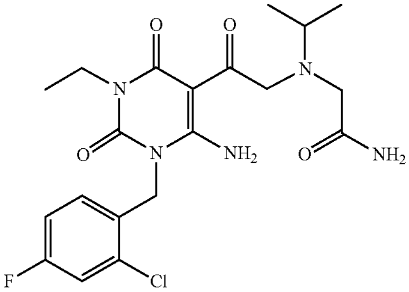
,
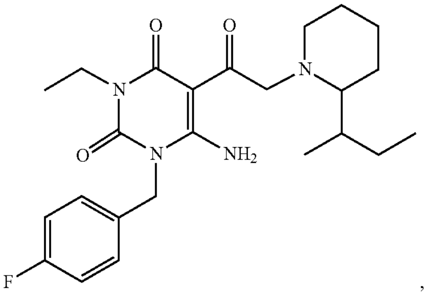
,
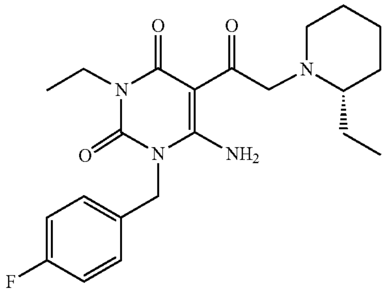
,
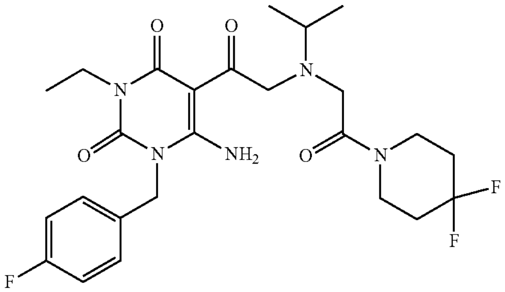
, -continued
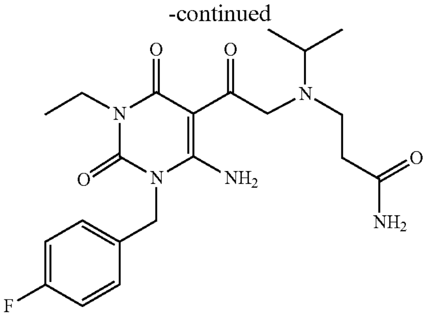
,
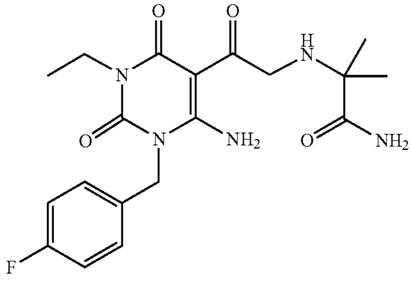
,
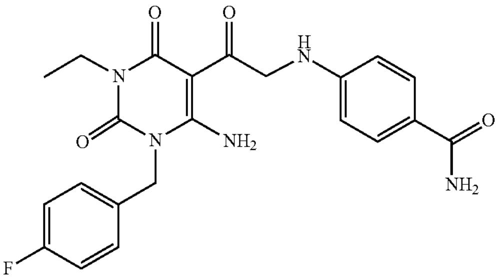
,
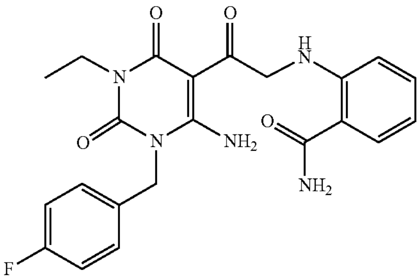
,
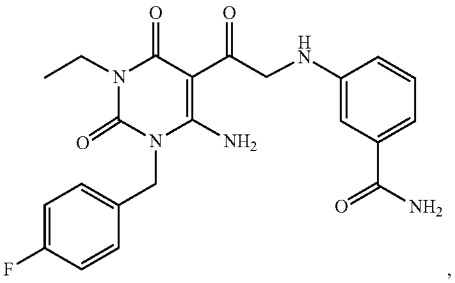
,
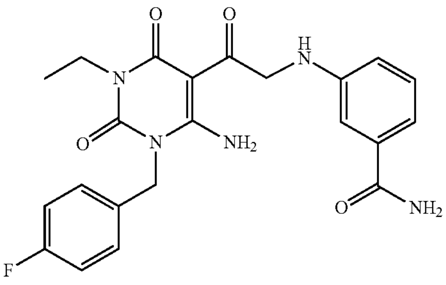
,
-continued
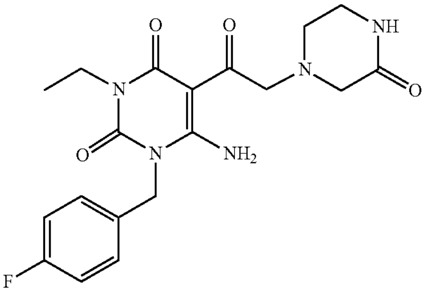
,
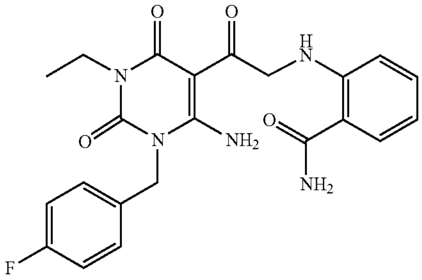
,
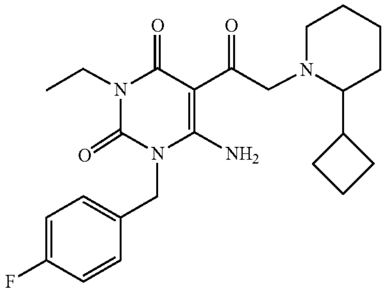
,
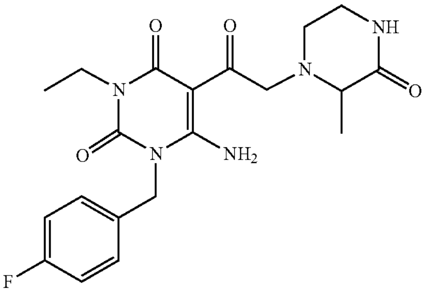
,
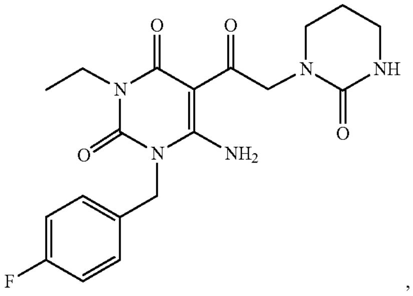
, -continued
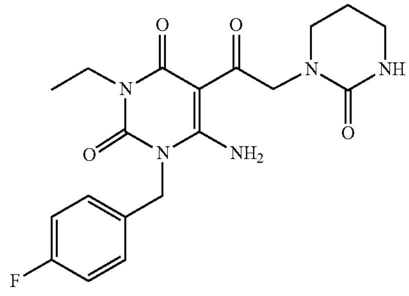
,
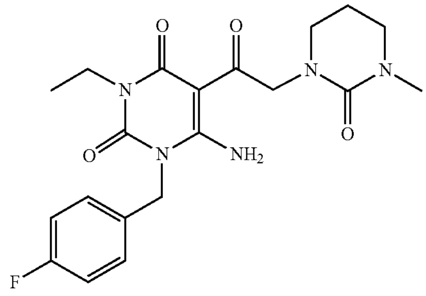
,
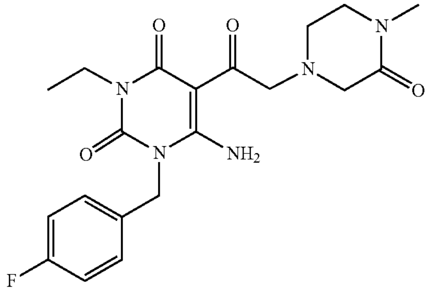
,
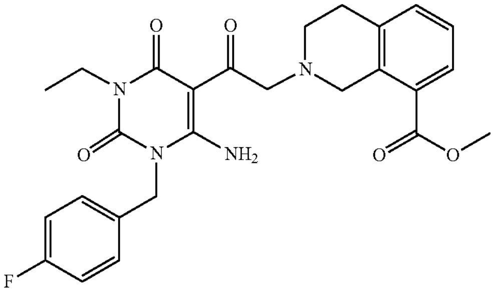
,
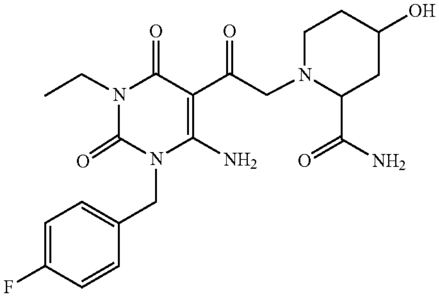
,
-continued
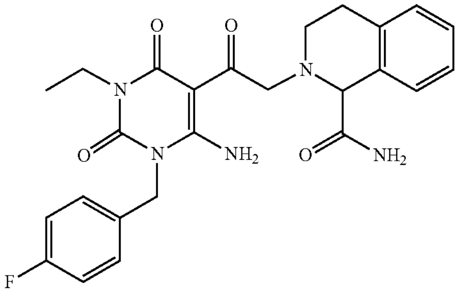
,
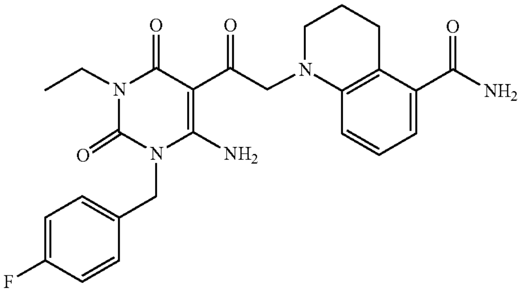
,
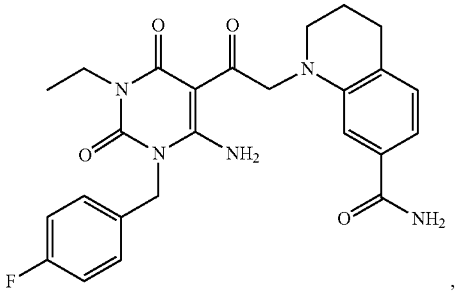 [SMILES: CCn1c(=O)c(C(=O)CN2CCCc3ccc(C(N)=O)cc32)c(N)n(Cc2ccc(F)cc2)c1=O]
,
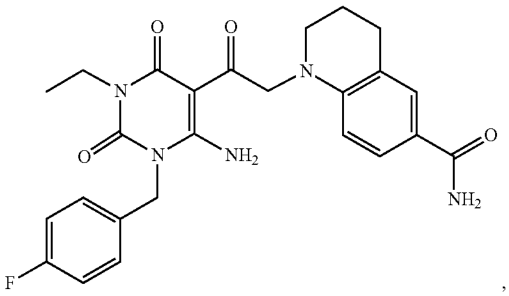
,
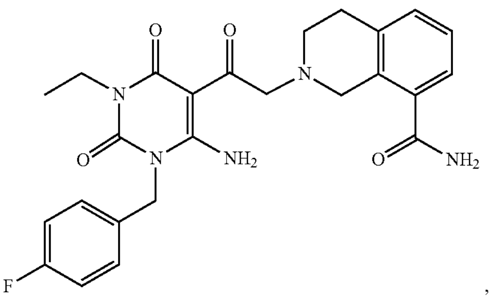
, -continued
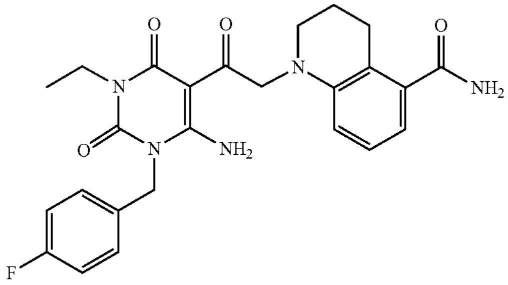
, and
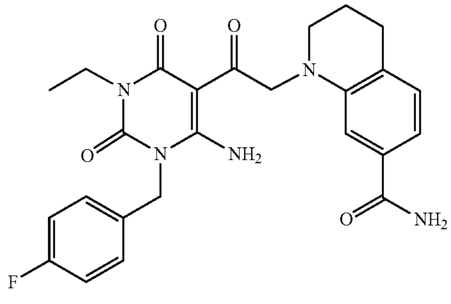
,
or a pharmaceutically acceptable salt thereof.
In one aspect, a compound can be present as one or more of the following structures:
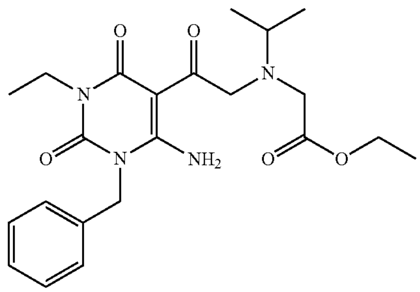
,
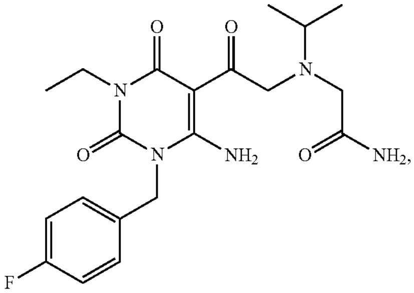
,
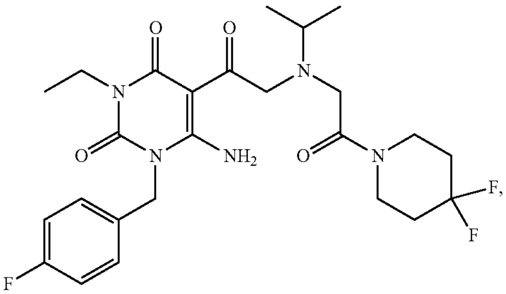
,
-continued
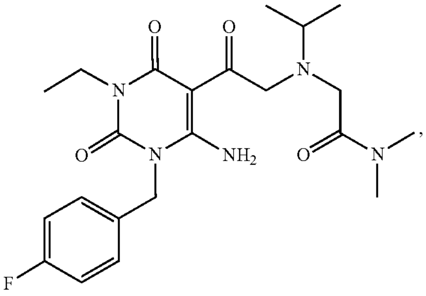
,
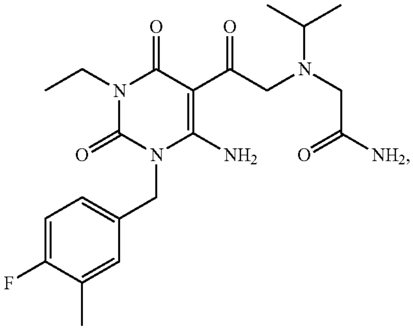
,
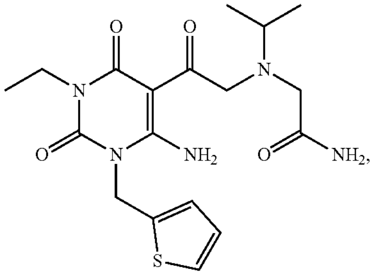
,
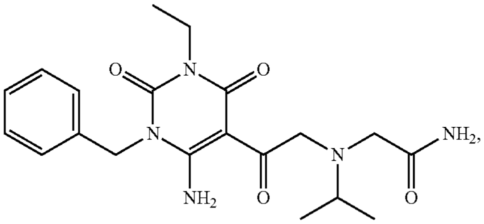
,
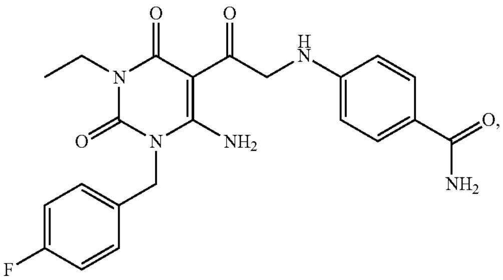
,
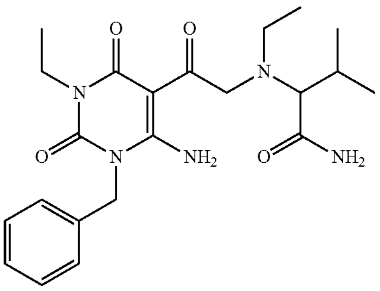
, -continued
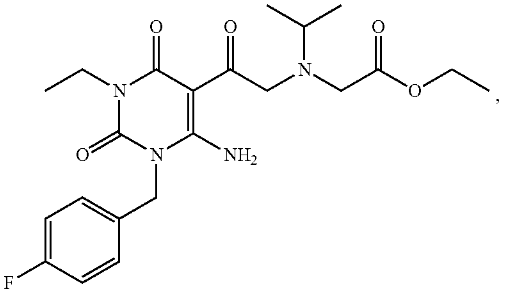
,
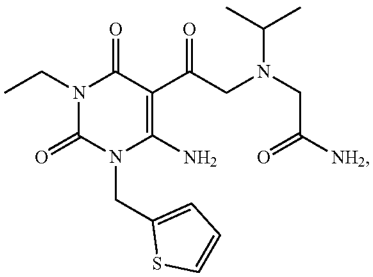
,
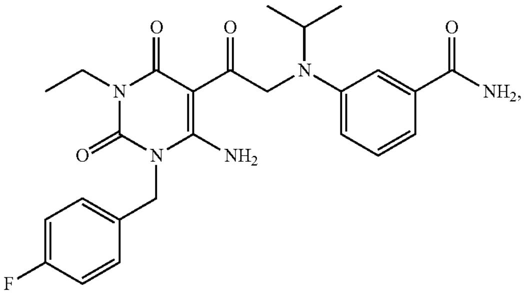
,
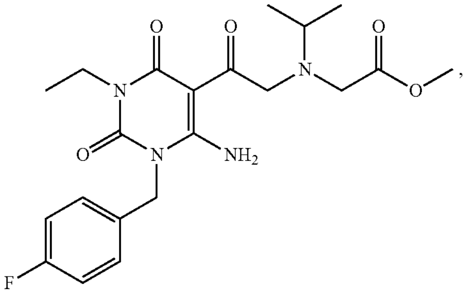
,
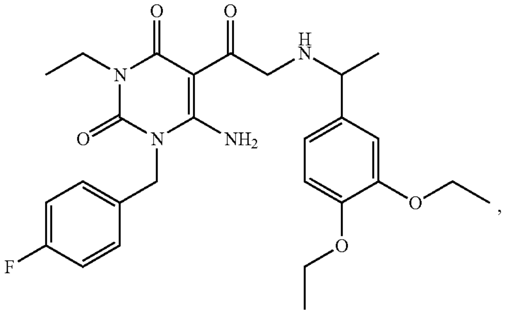
,
-continued
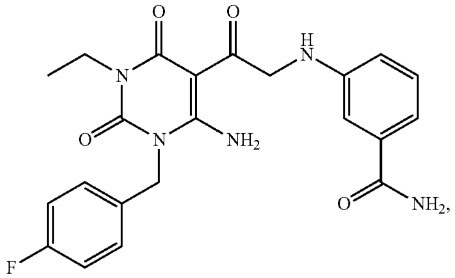
,
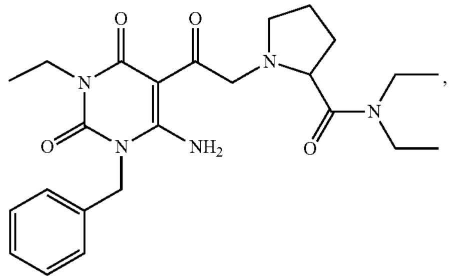
,
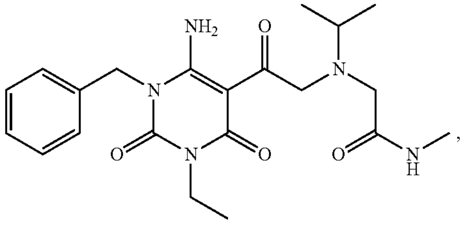
,
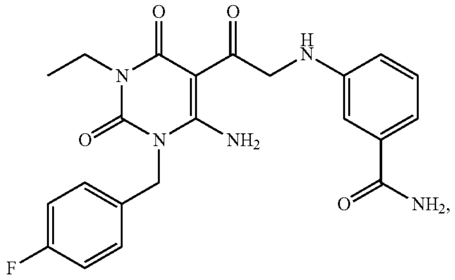
,
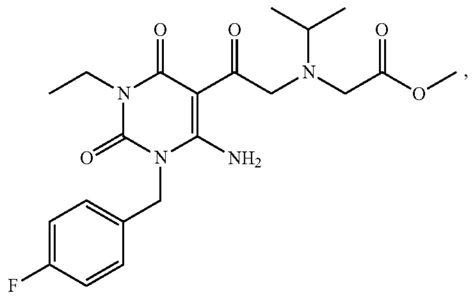
,
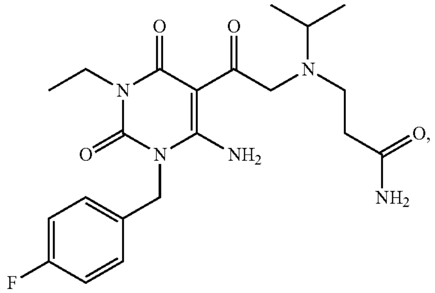
, -continued
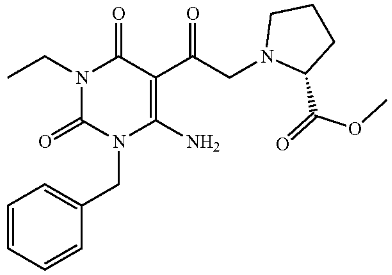
,
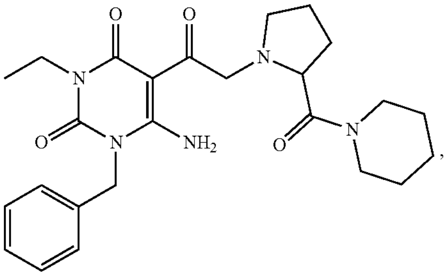
,
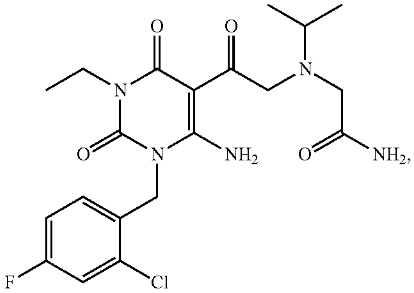
,
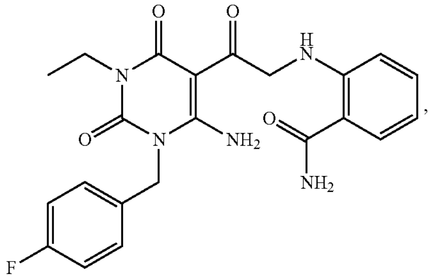
,
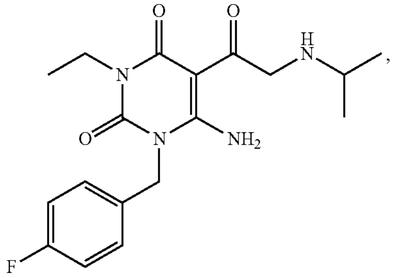
,
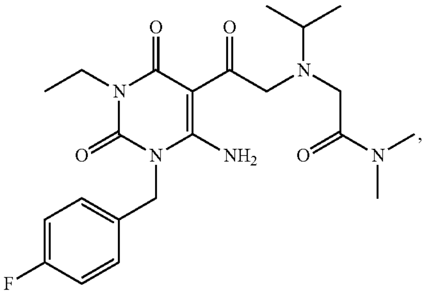
,
-continued
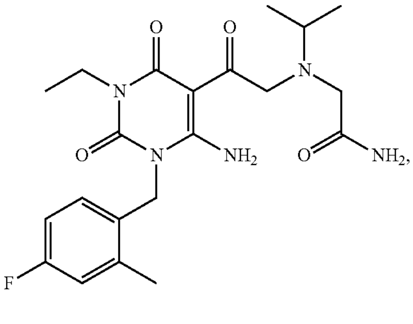
,
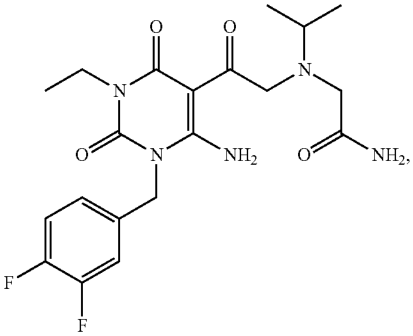
,
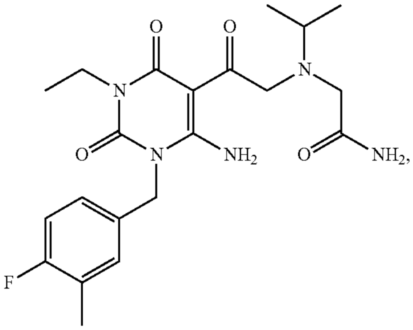
,
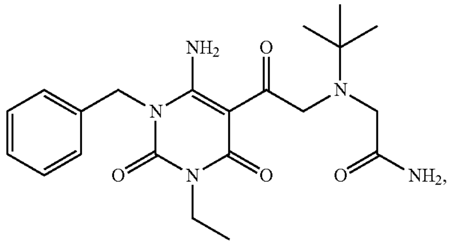
,
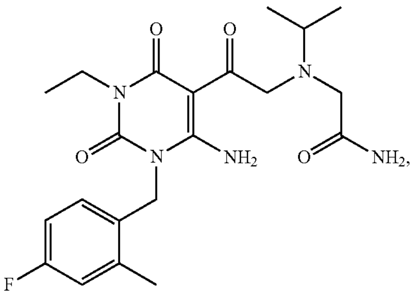
,

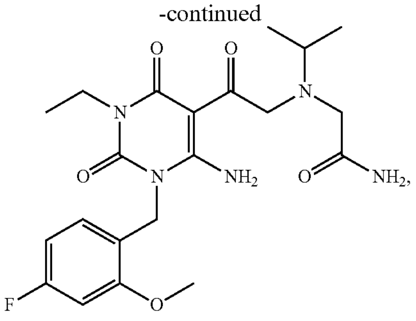
,
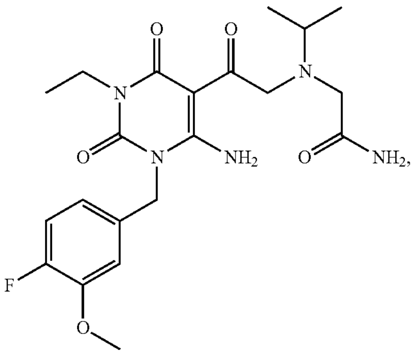
,
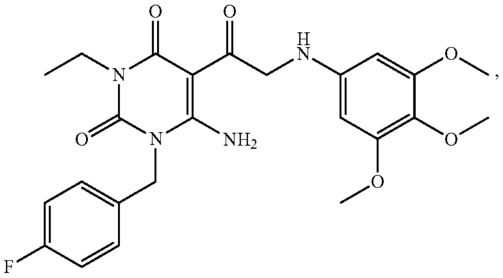
,
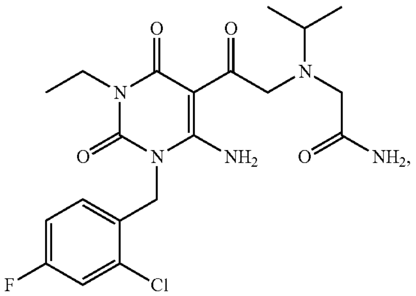
,
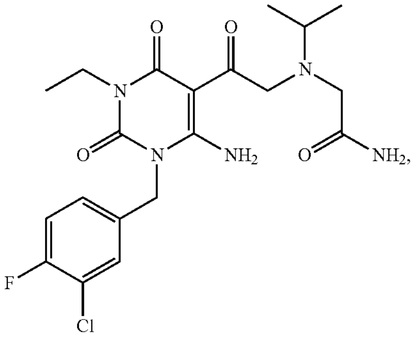
,
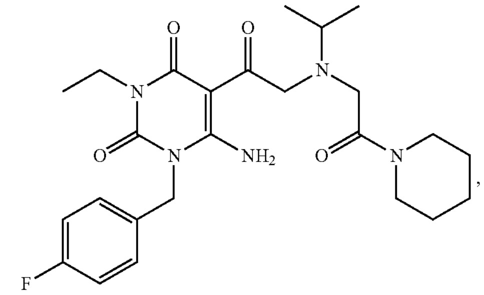
,
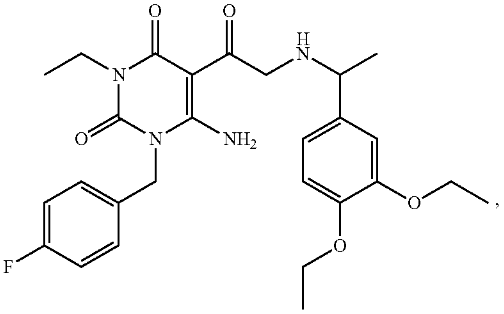
,
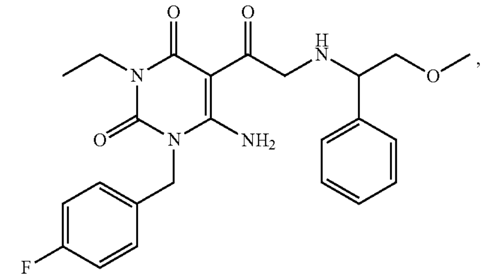
,
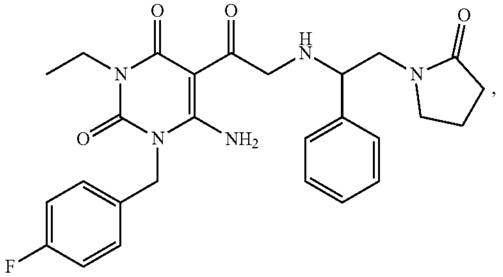
,
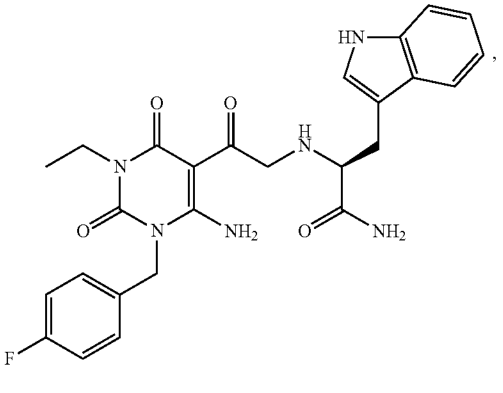
, -continued
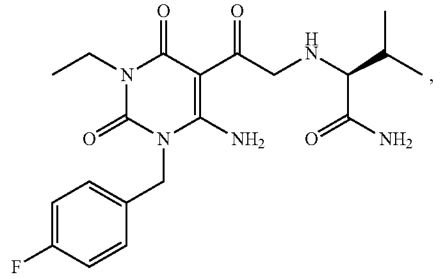
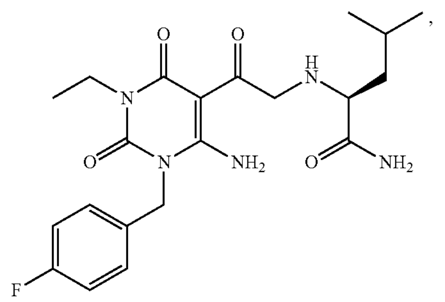
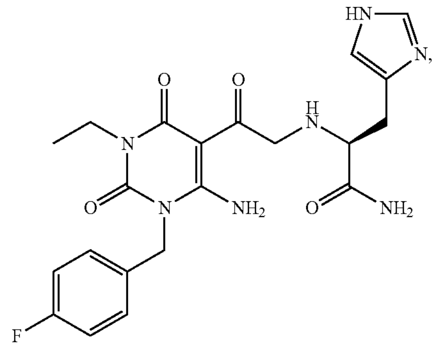
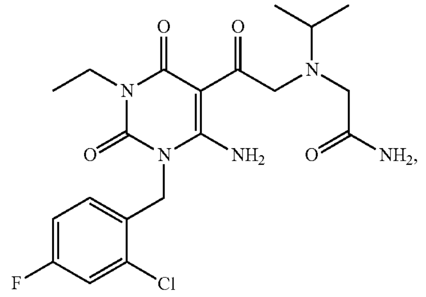
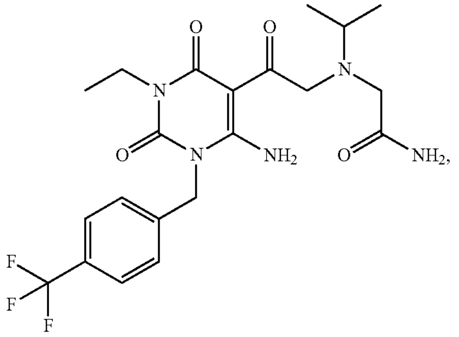
-continued
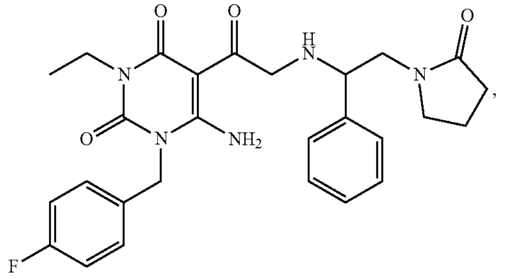
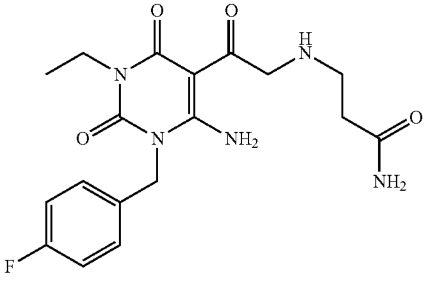
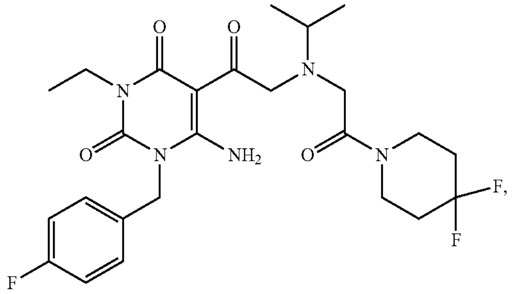
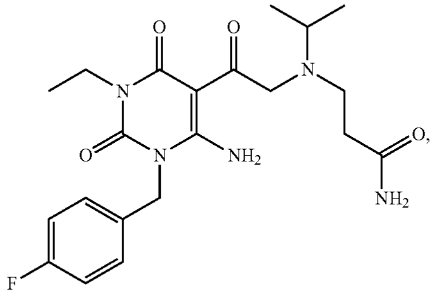
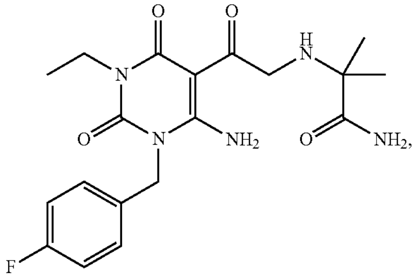
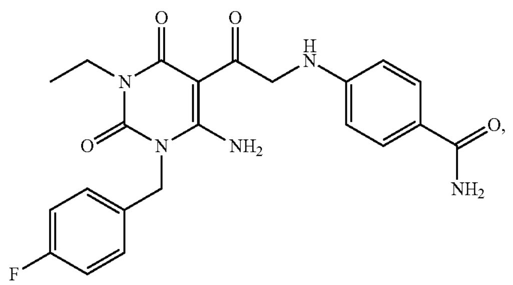

-continued
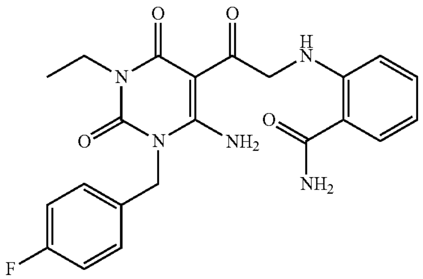
,
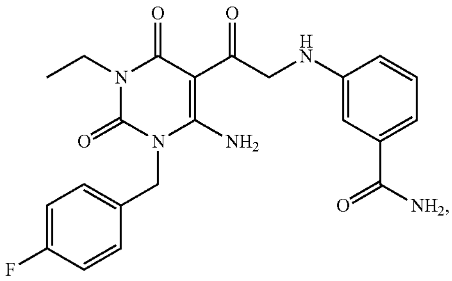
,
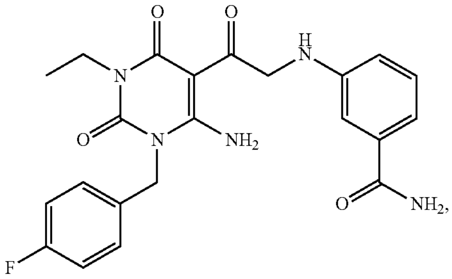
, and
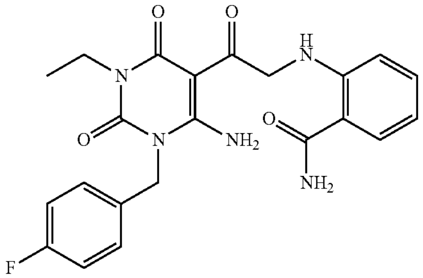
,
or a pharmaceutically acceptable salt thereof.
In one aspect, a compound can be present as one or more of the following structures:
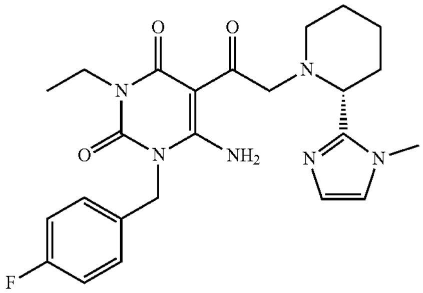
,
-continued
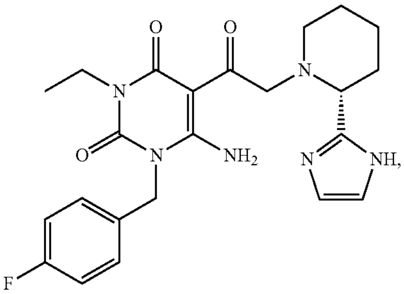
,
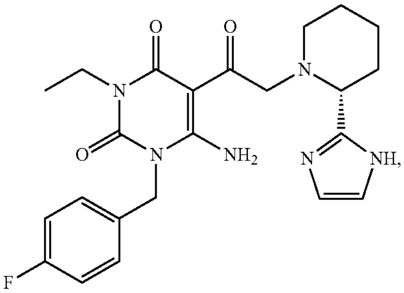
,
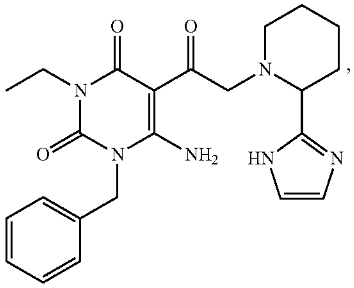
,
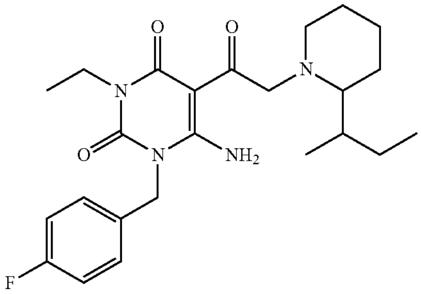
,
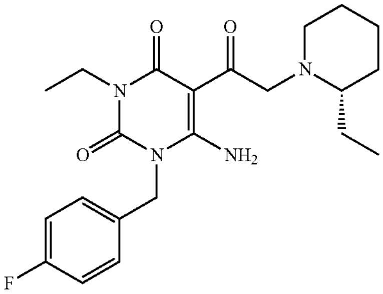
, -continued
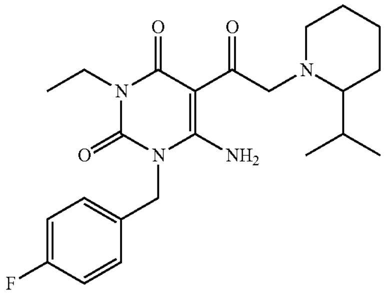
,
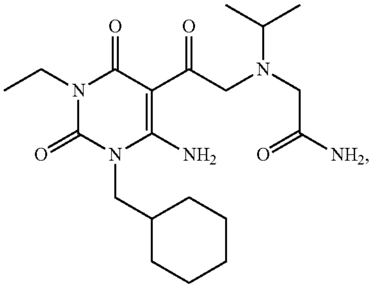
,
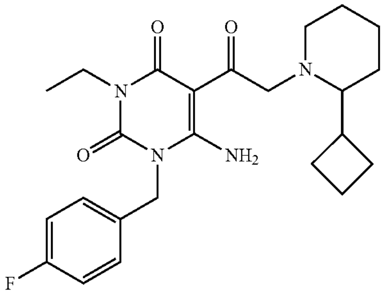
,
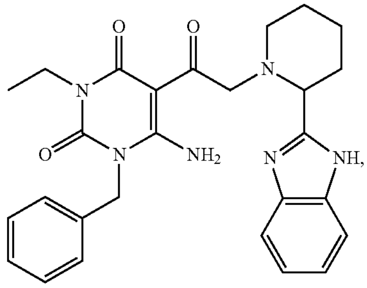
,
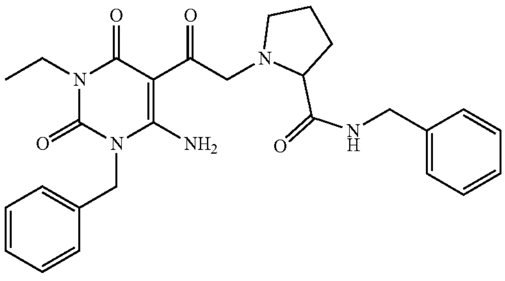
,
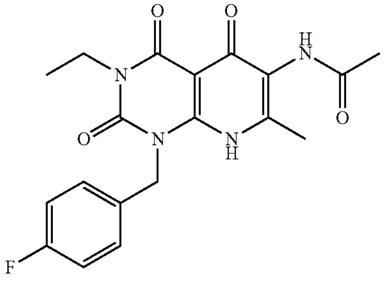
,
-continued
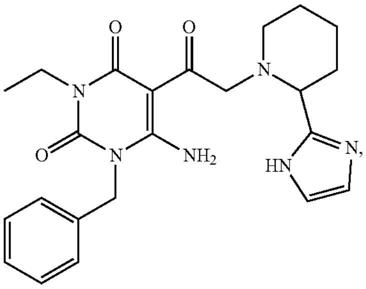
,
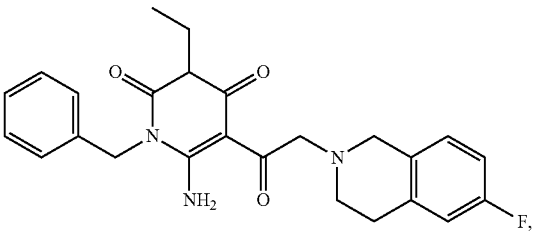
,
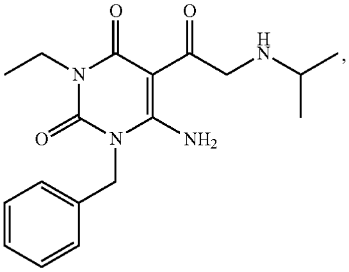
,
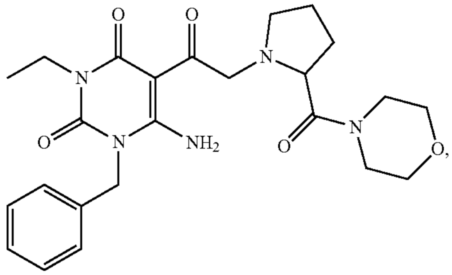
,
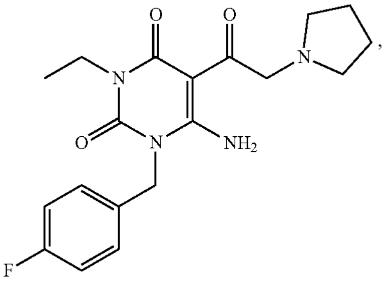
,
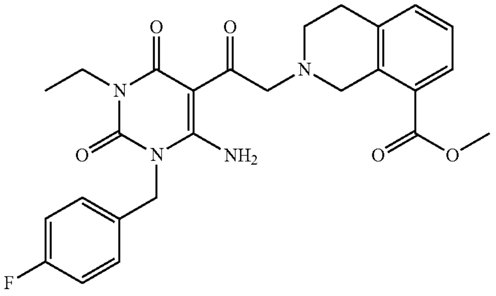
, -continued
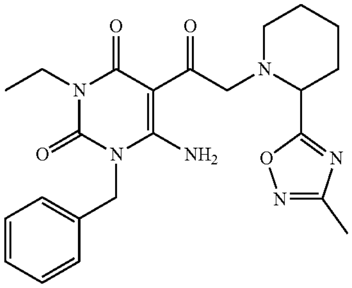
,
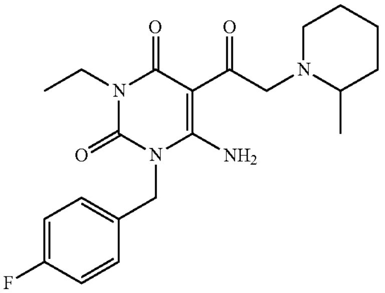
,
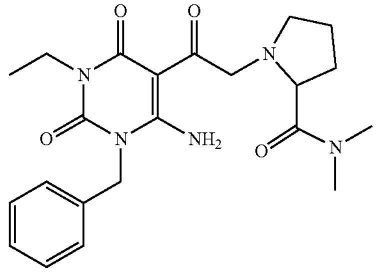
,
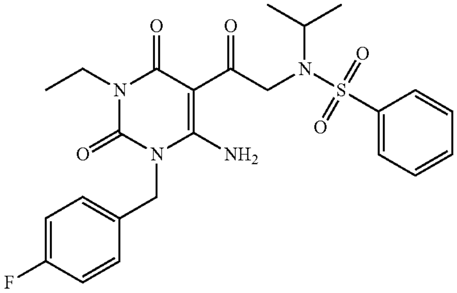
,
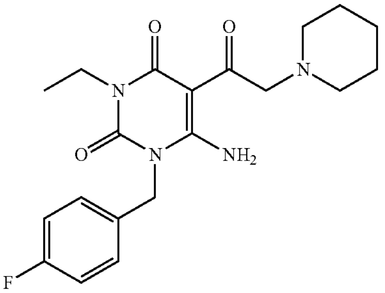
,
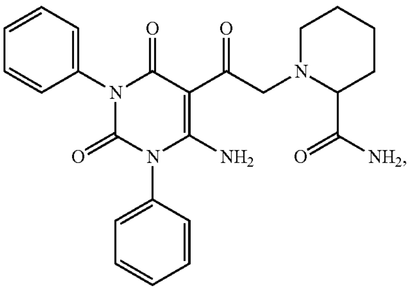
,
-continued
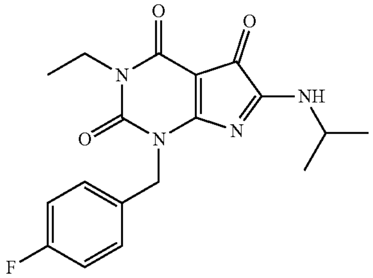
,
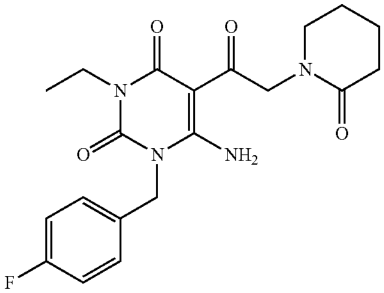
,
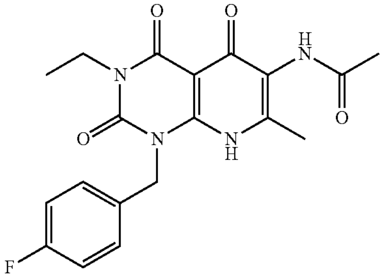
,
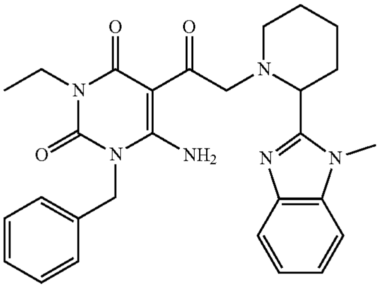
,
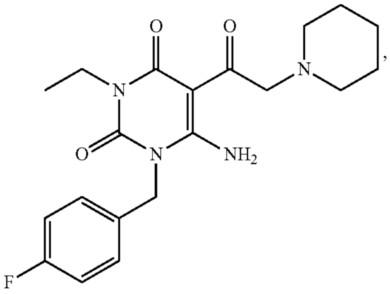
,
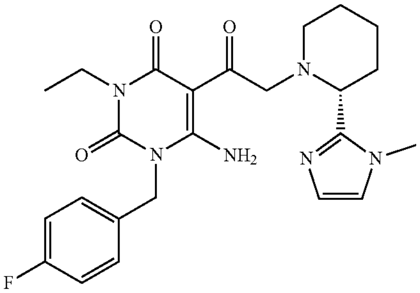
, -continued
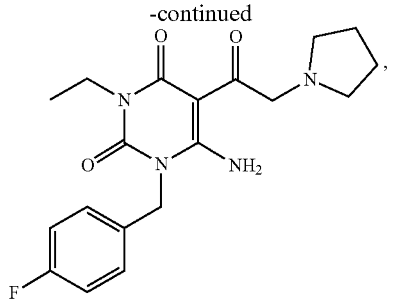
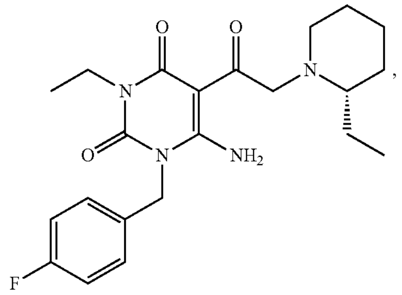
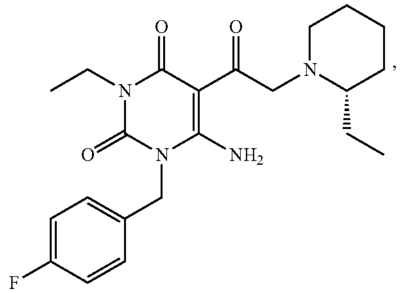
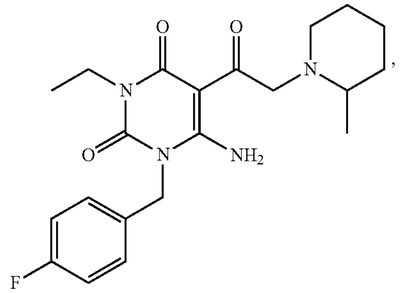
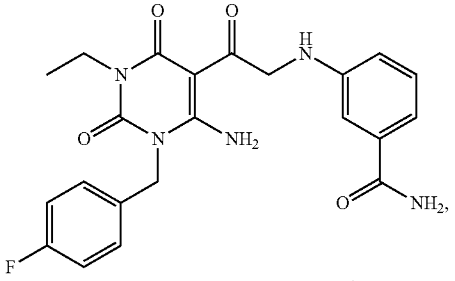
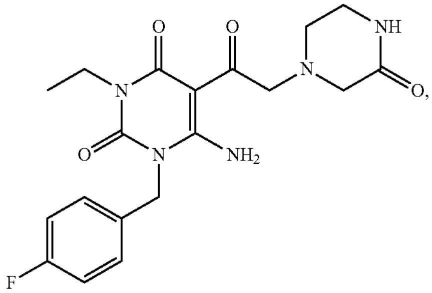
-continued
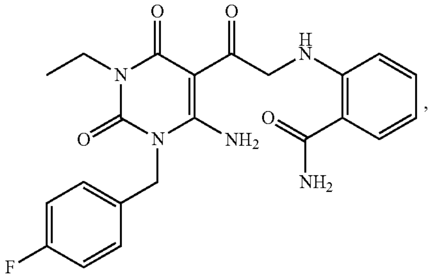
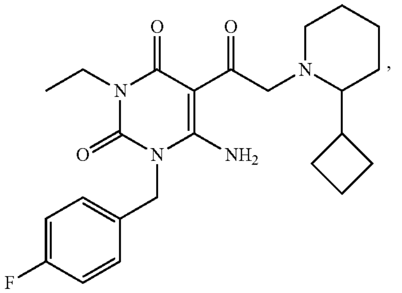
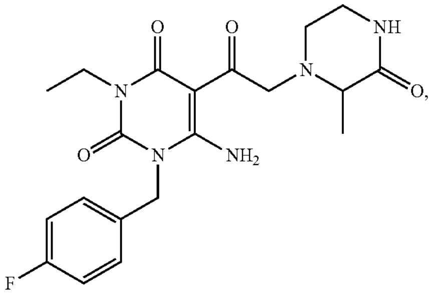
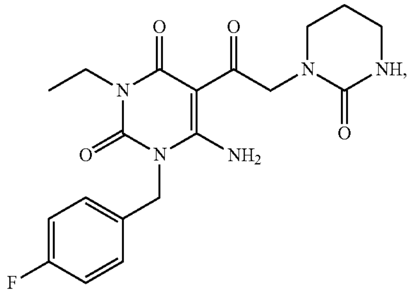
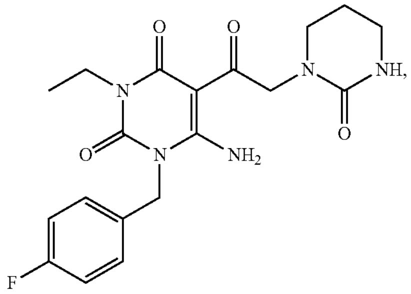

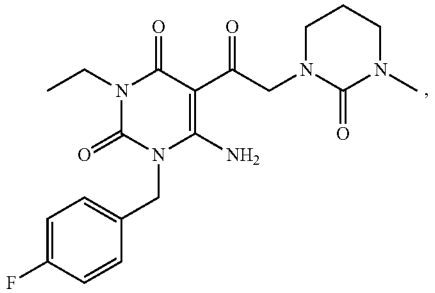
,
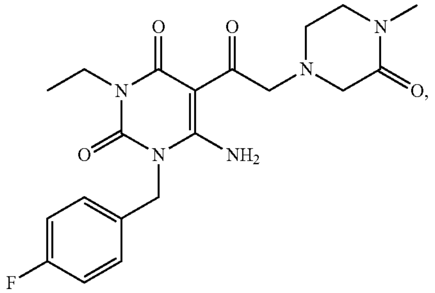
,
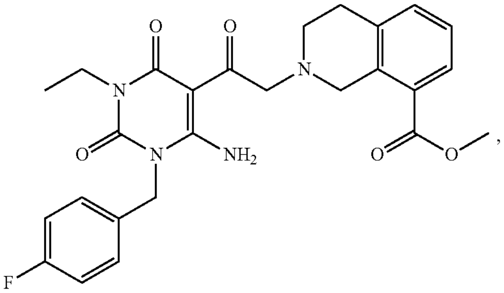
,
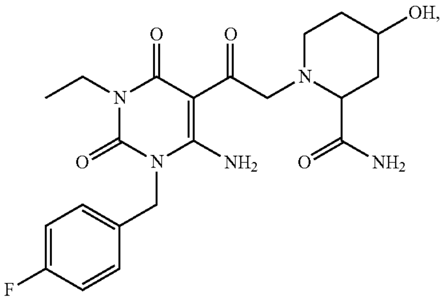
,
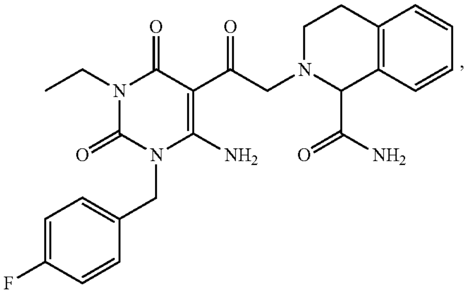
,
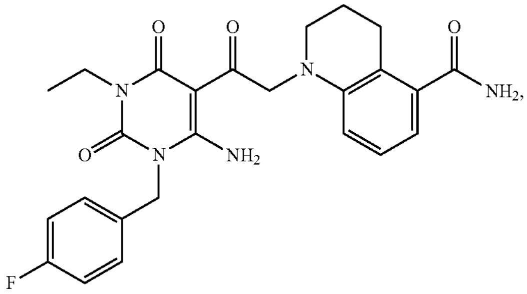
,
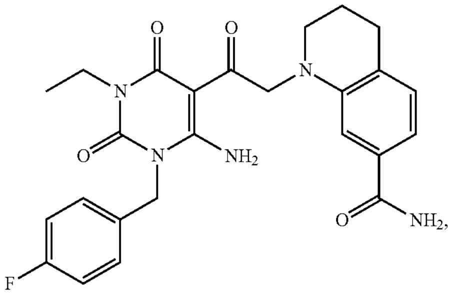
,
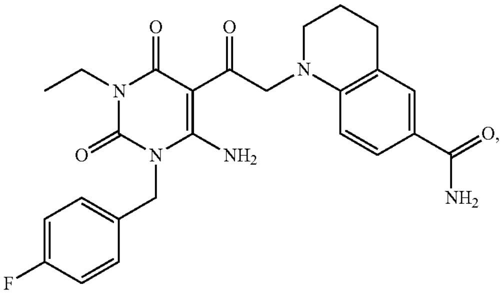
,
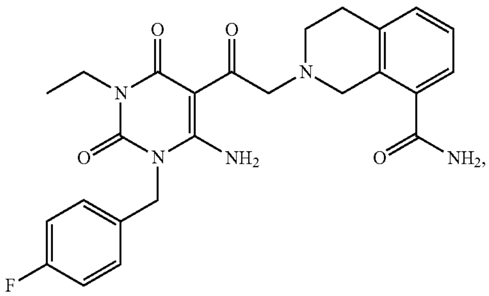
,
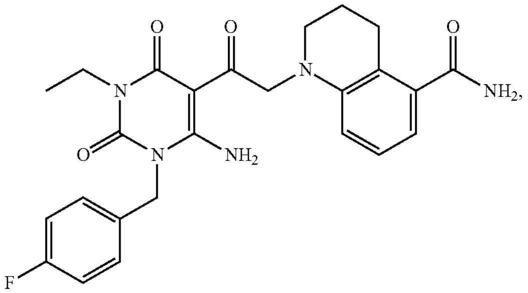
, and -continued
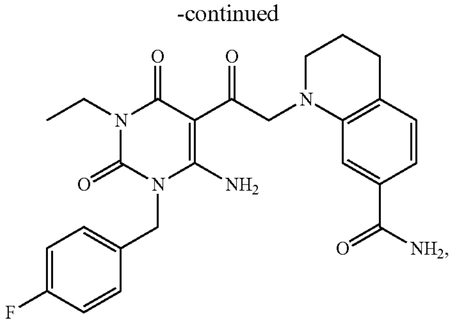
or a pharmaceutically acceptable salt thereof.
In one aspect, a compound can be present as one or more of the following structures:
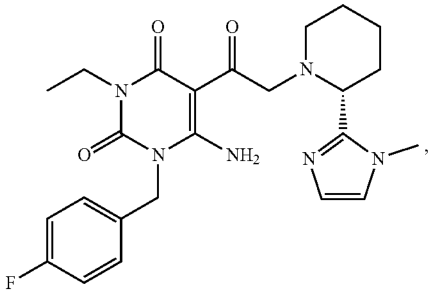
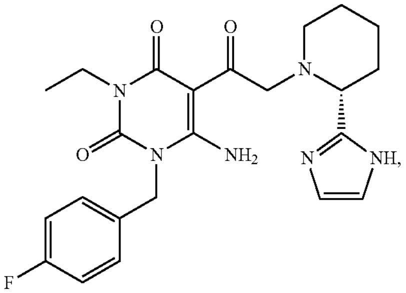
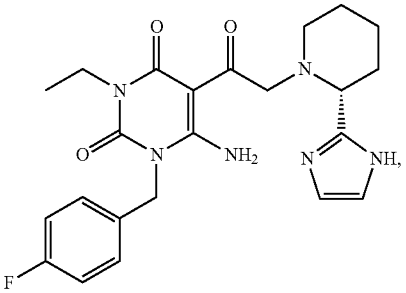
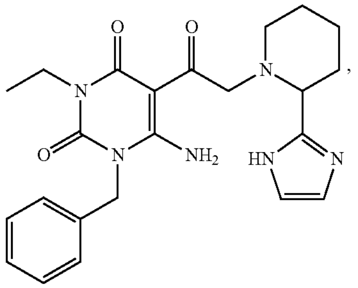
-continued
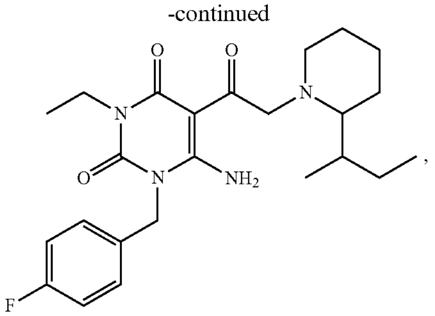
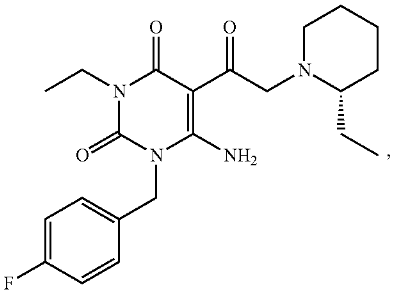
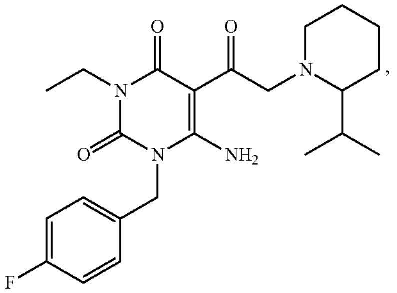
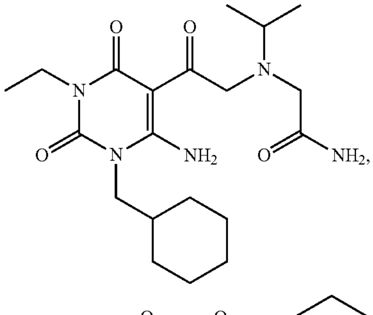
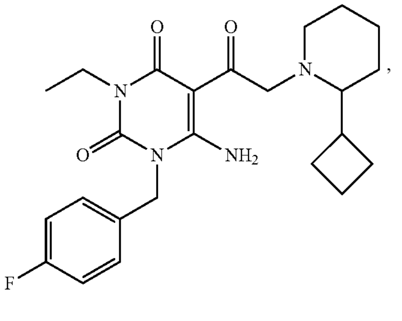

-continued
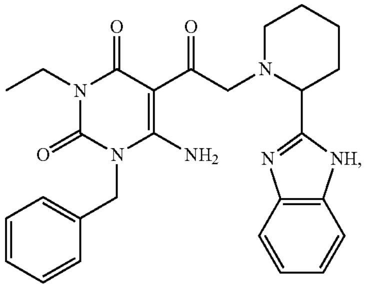
,
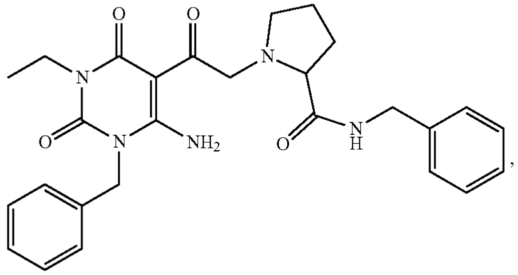
,
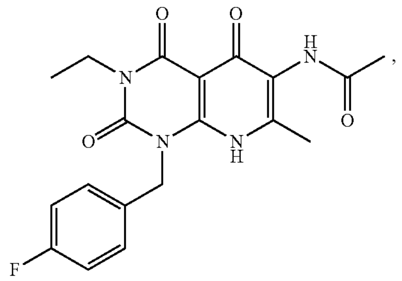
,
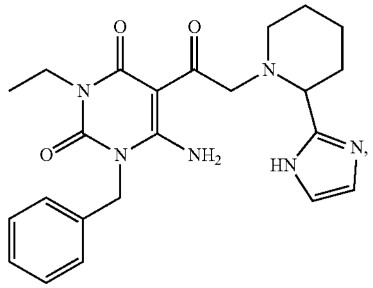
,
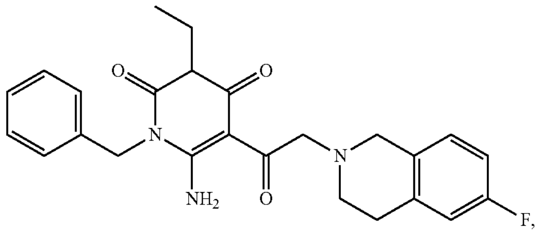
,
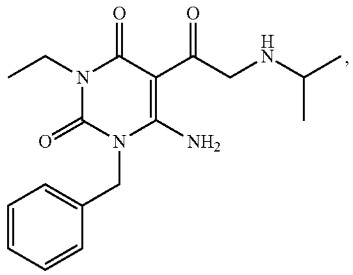
,
-continued
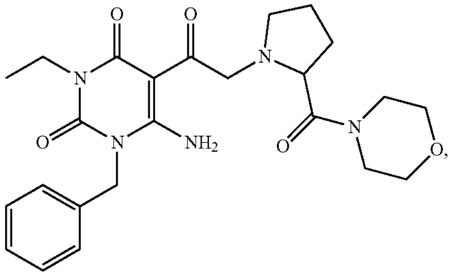
,
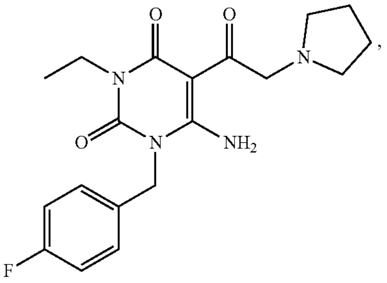
,
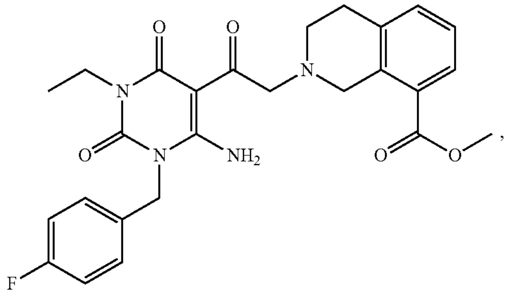
,
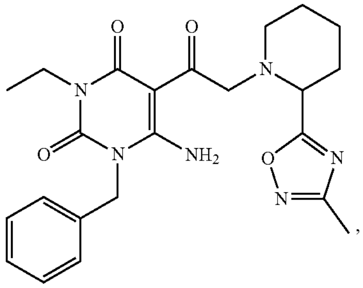
,
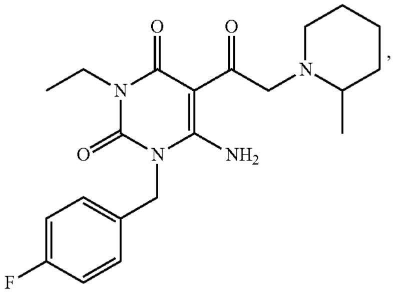
,
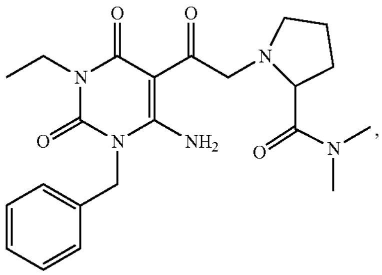
, -continued
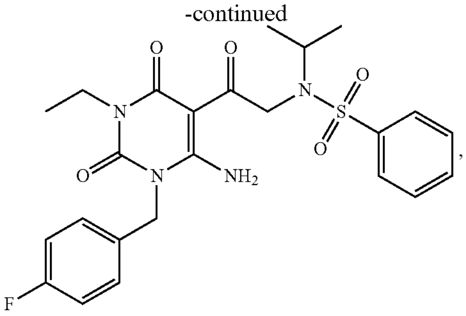,
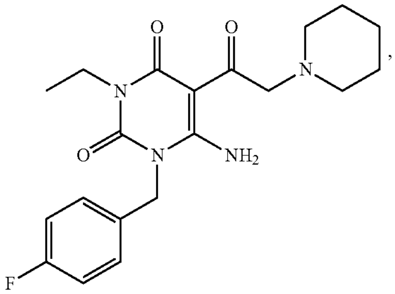,
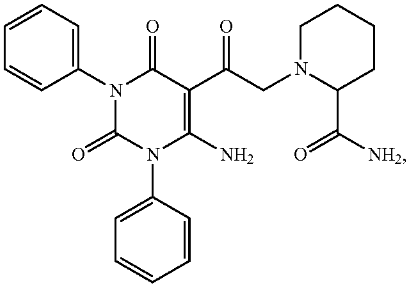,
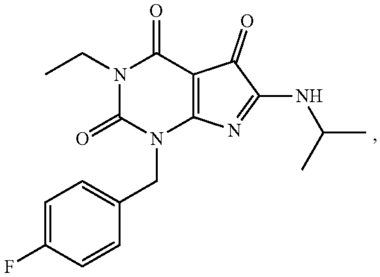,
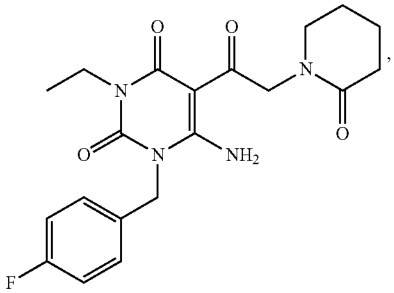,
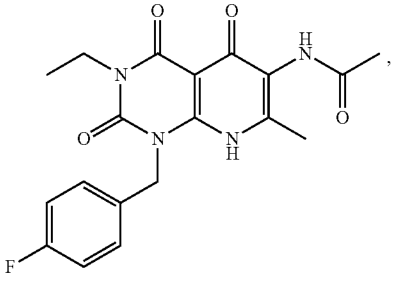,
-continued
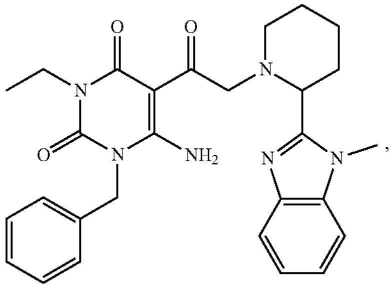,
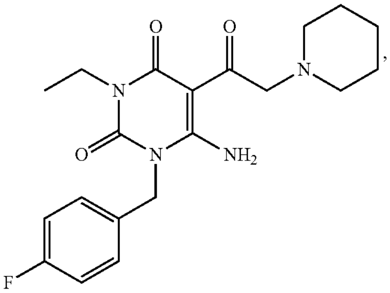,
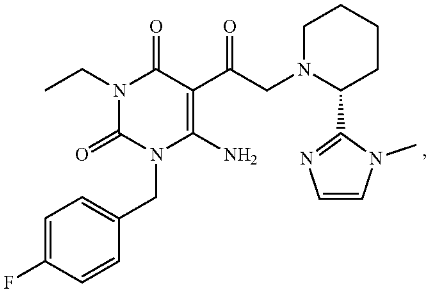,
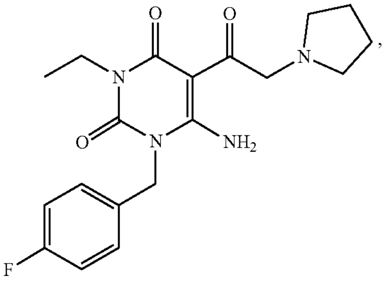,
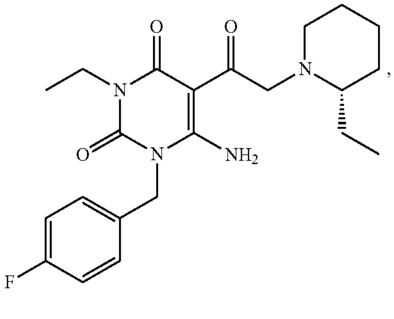, -continued
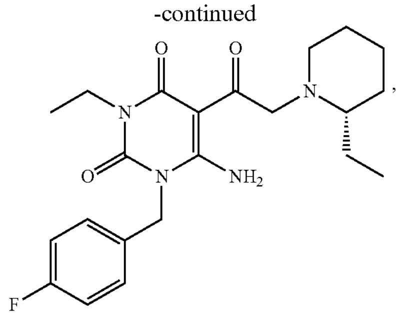
,
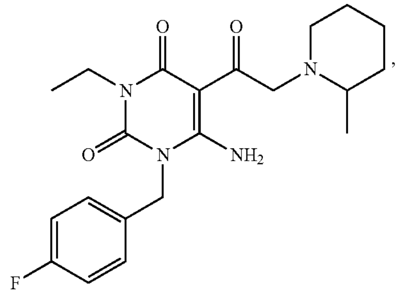
,
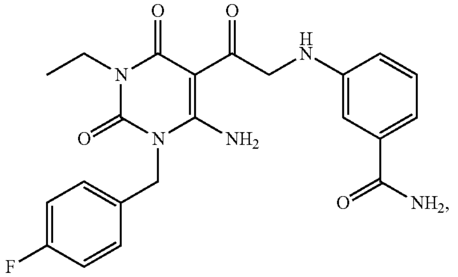
,
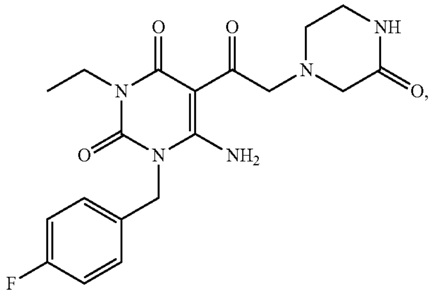
,
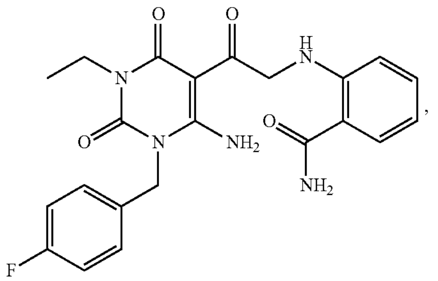
,
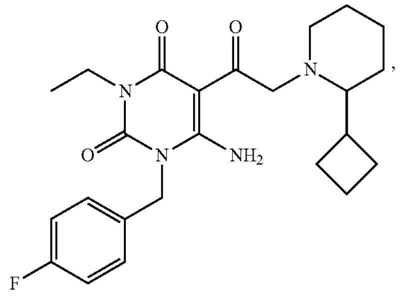
,
-continued
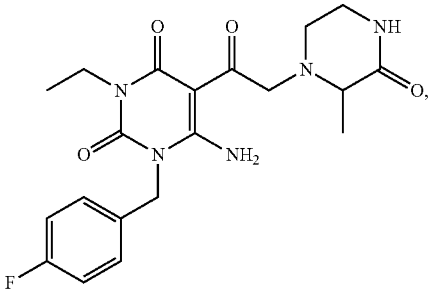
,
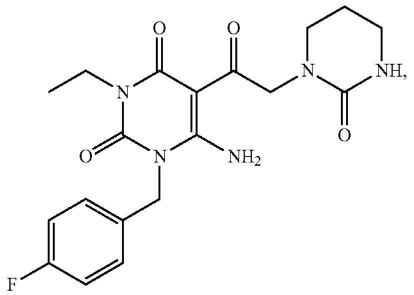
,
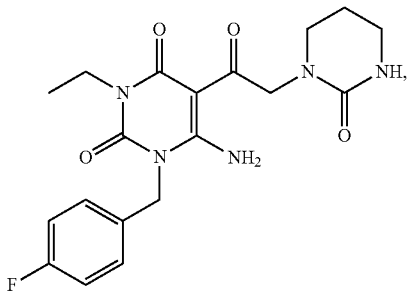
,
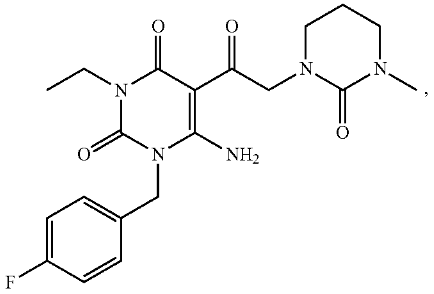
,
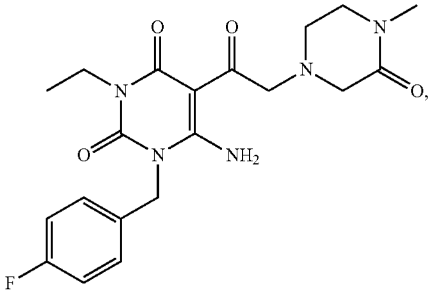
, -continued
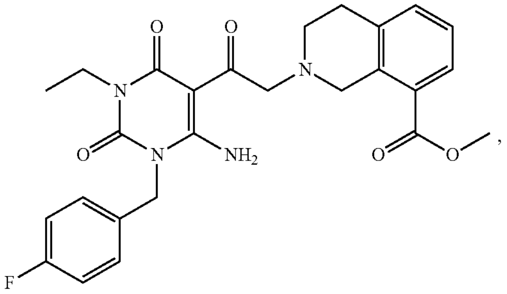
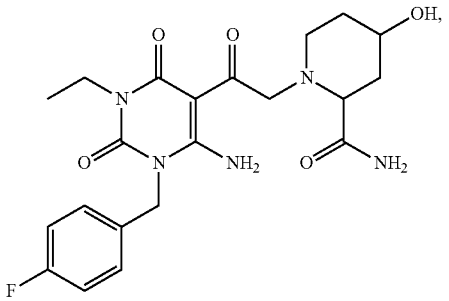
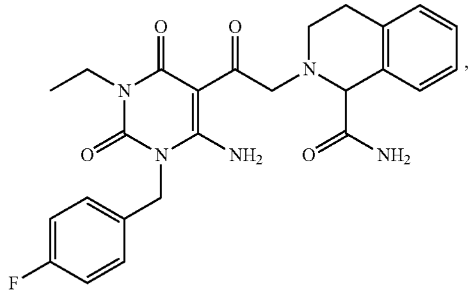
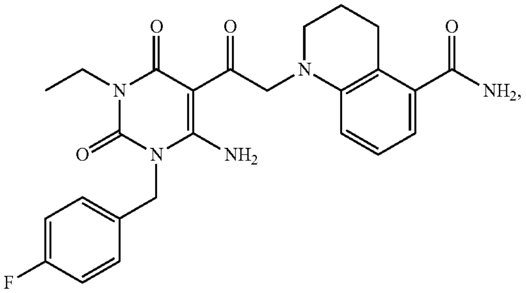
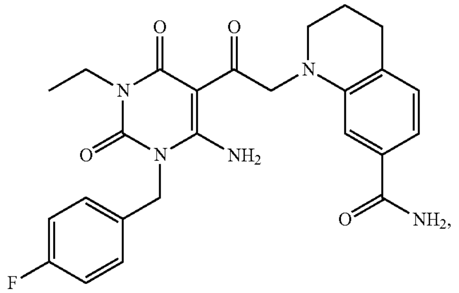
-continued
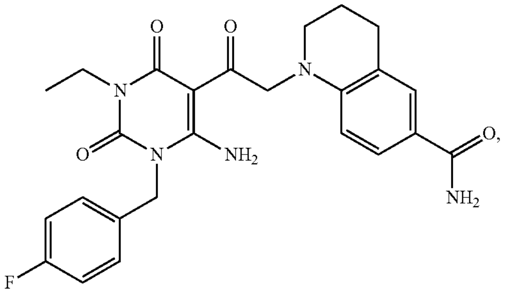
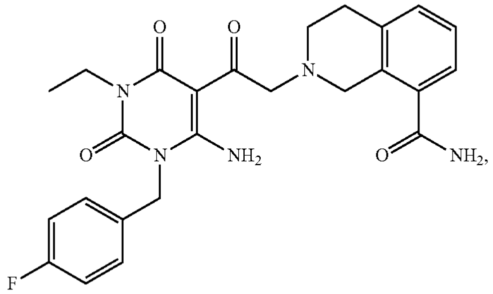
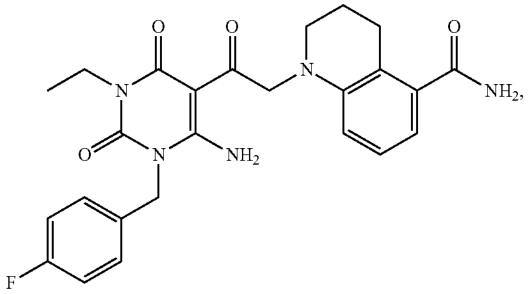
and
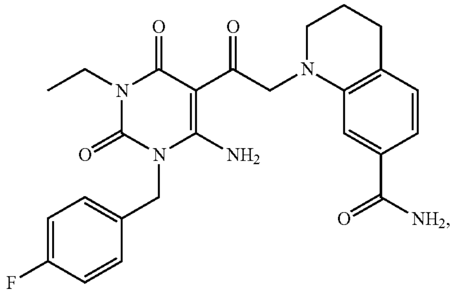
or a pharmaceutically acceptable salt thereof.
In one aspect, a compound can be present as:
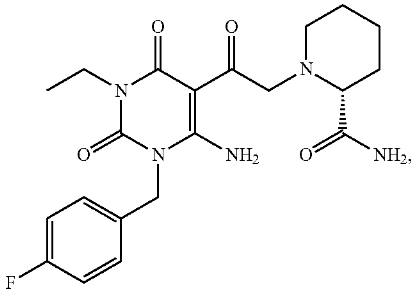 [SMILES: CCn1c(=O)c(C(=O)CN2CCCC[C@@H]2C(N)=O)c(N)n(Cc2ccc(F)cc2)c1=O]
or a pharmaceutically acceptable salt thereof.

C. Pharmaceutical Compositions

In one aspect, disclosed are pharmaceutical compositions comprising a therapeutically effective of a compound having a structure represented by a formula:

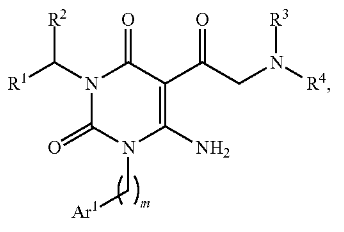

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$, when present, is independently selected from hydrogen and C1-C4 alkyl; wherein $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

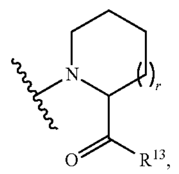

wherein r is 0 or 1; and wherein $R^{13}$ is selected from C1-C4 alkoxy and —$NR^{21a}R^{21b}$; wherein each of $R^{21a}$ and $R^{21b}$ when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.

In one aspect, disclosed are pharmaceutical compositions comprising a therapeutically effective amount of a compound selected from:

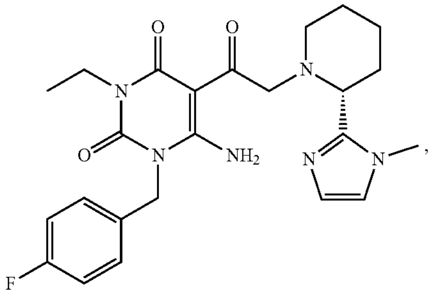
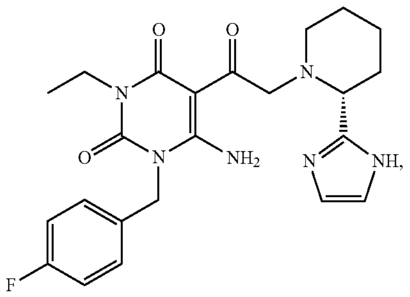
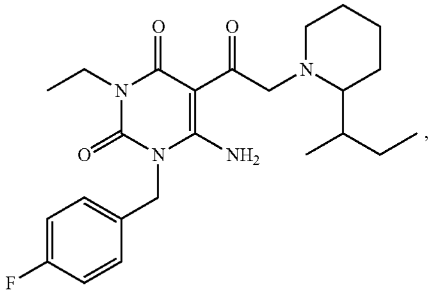
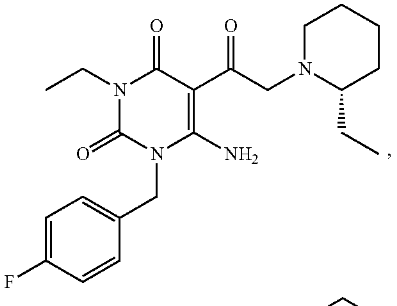
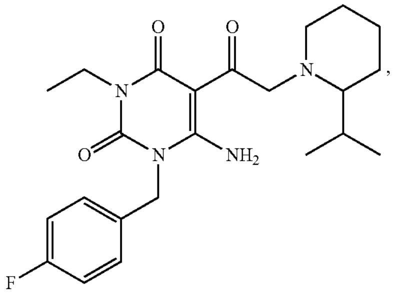
-continued
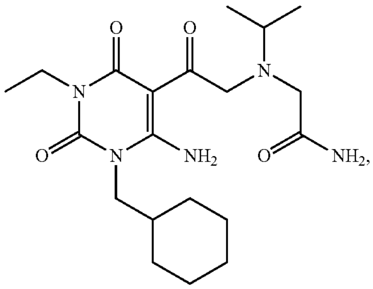
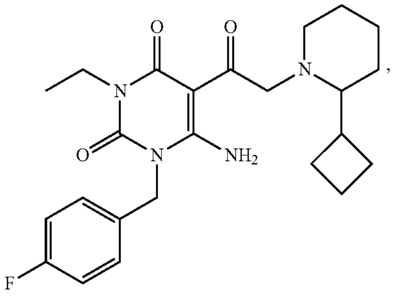
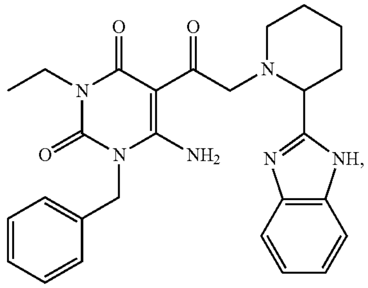
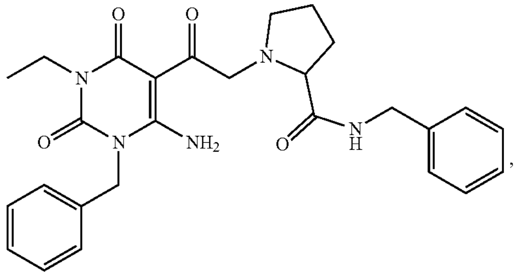
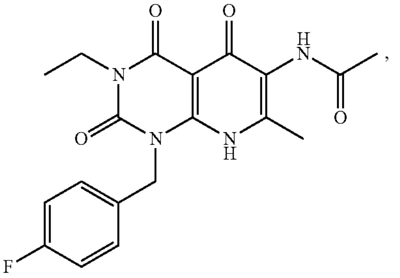
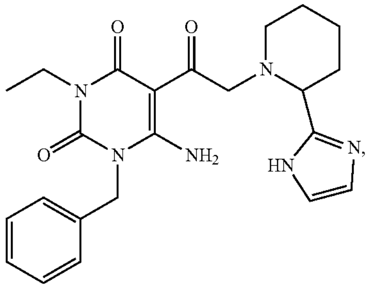

-continued
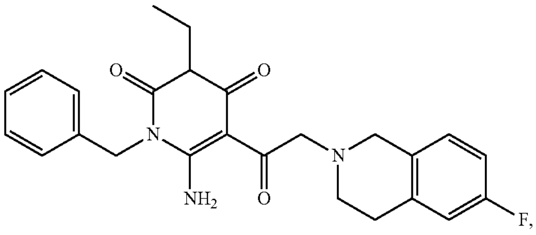
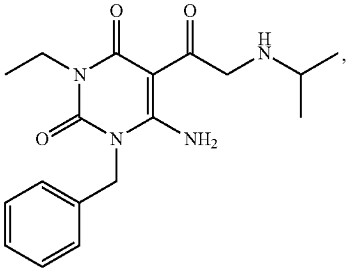
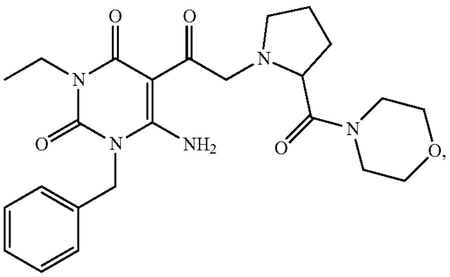
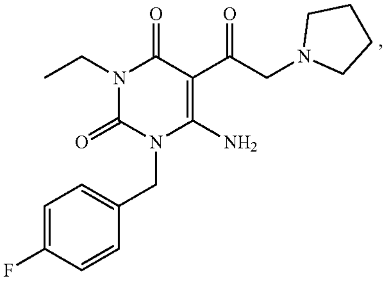
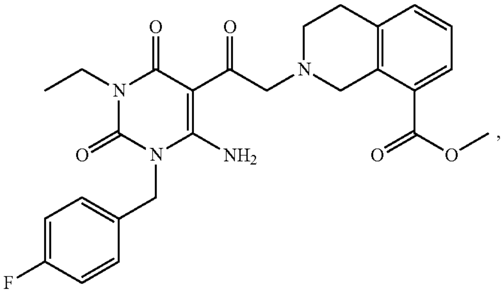
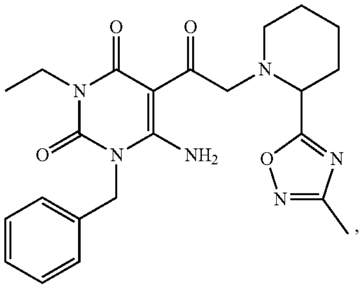
-continued
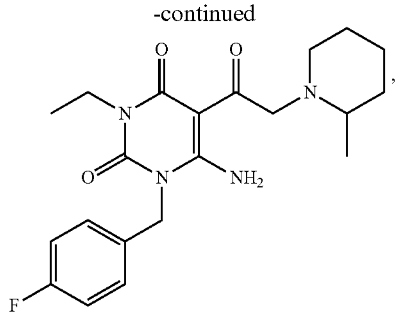
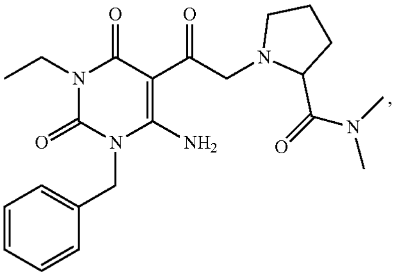
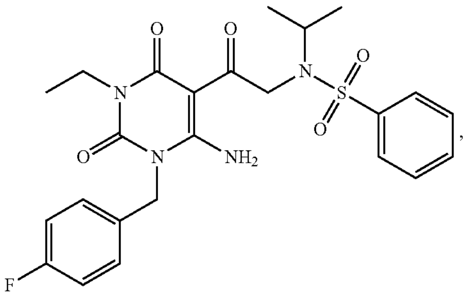
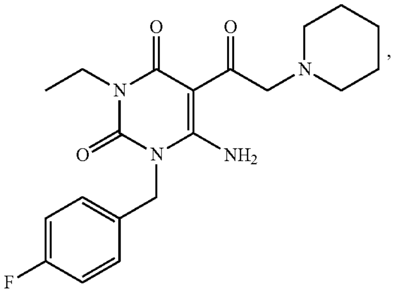
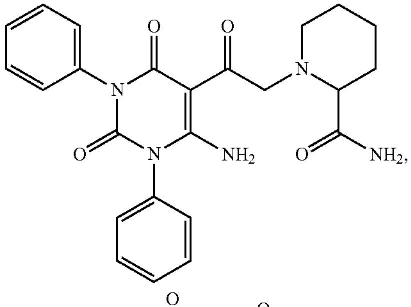
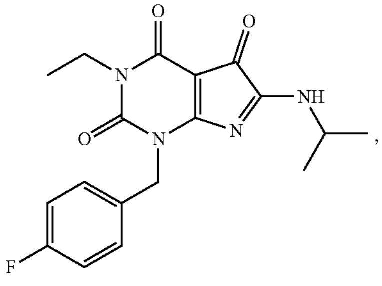

-continued
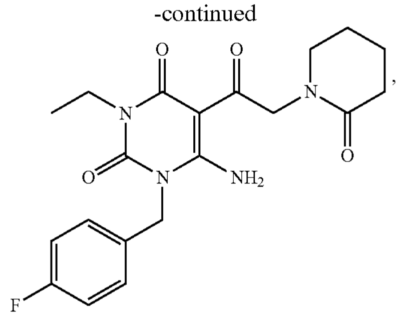
,
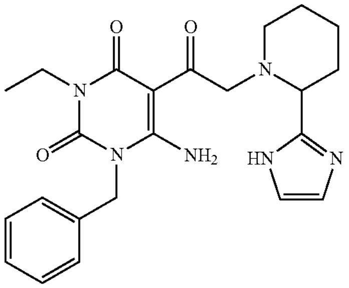
,
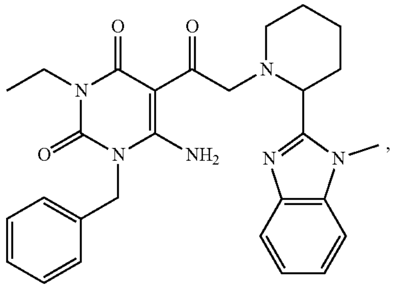
,
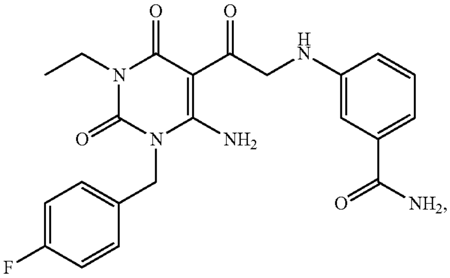
,
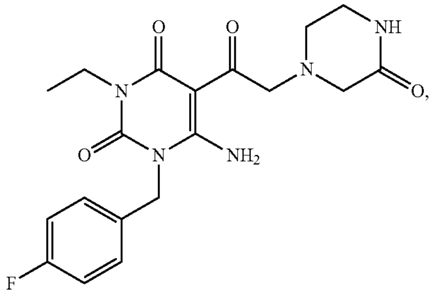
,
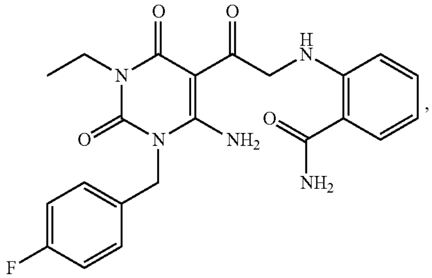
,
-continued
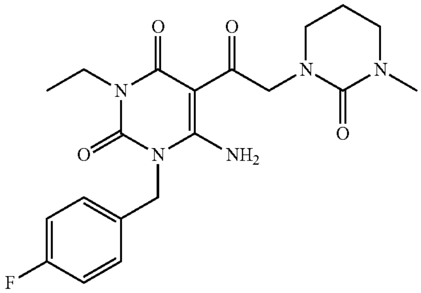
,
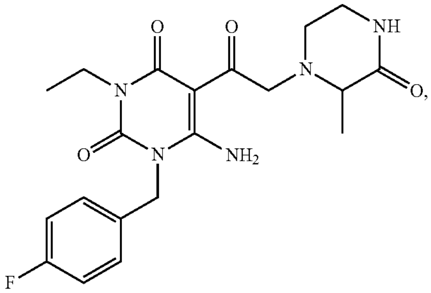
,
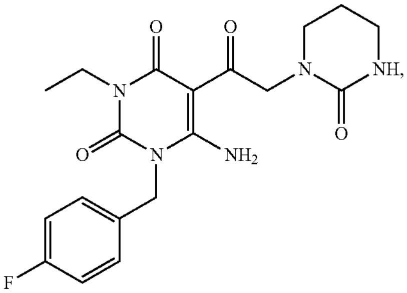
,
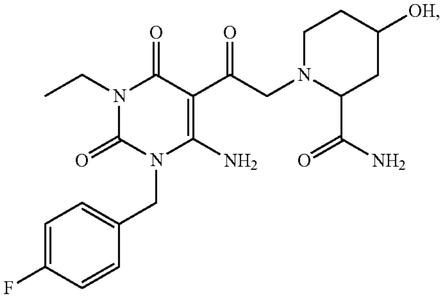
,
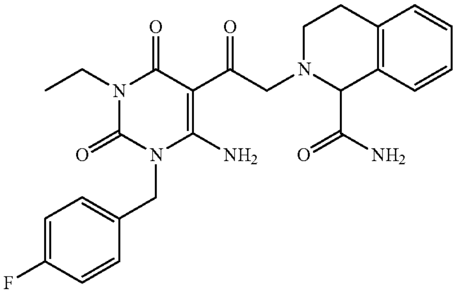
, -continued

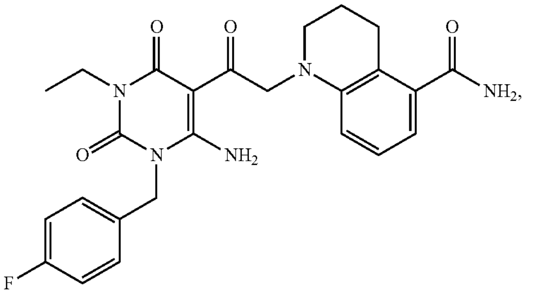

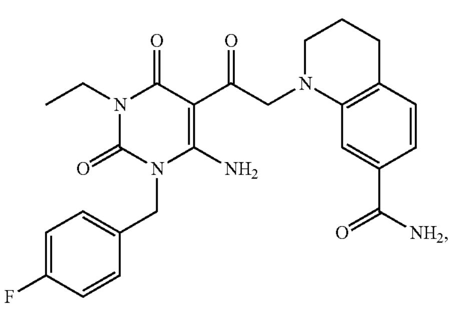

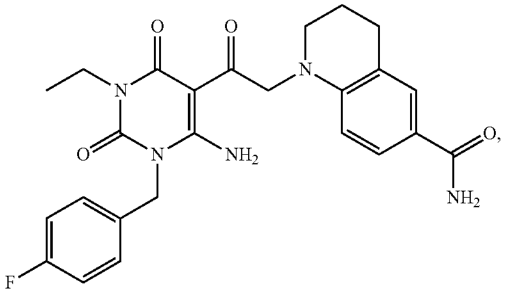

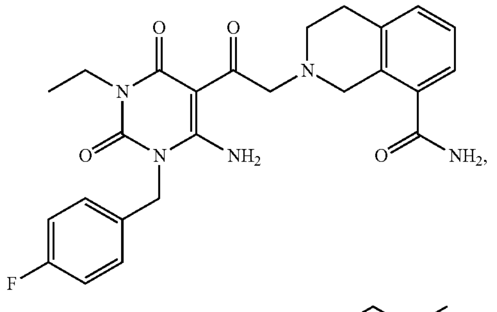

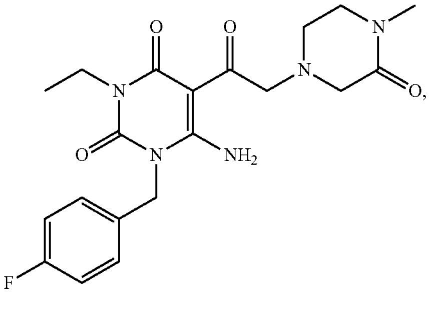

-continued

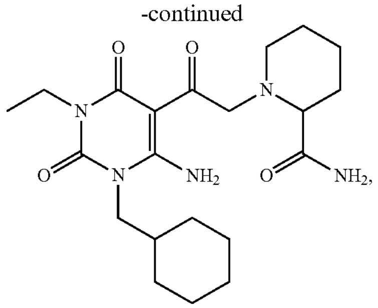

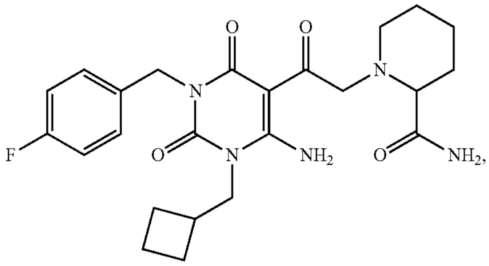

and

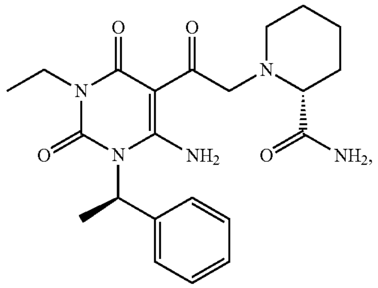

or a pharmaceutically acceptable salt thereof, and a pharmaceutically acceptable carrier.

In one aspect, disclosed are pharmaceutical compositions comprising an effective amount of a compound having a structure represented by a formula:

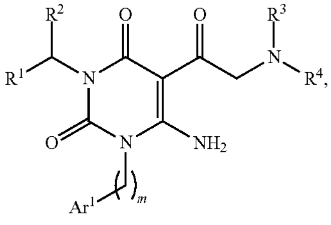

wherein m is 1 or 2; wherein $R^1$ is selected from C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —(C each occurrence of $R^{10b})_n$C(O)$R^{11}$, —CH($R^{12}$)$Ar^2$, and $Ar^2$; wherein n, when present, is 1 or 2; wherein $R^{10a}$, when present, is independently selected from hydrogen and C1-C4 alkyl; wherein each occurrence of $R^{10b}$, when present, is independently selected from hydrogen, C1-C4 alkyl, —(C1-C4 alkyl)O(C1-C4 alkyl), and —$(CH_2)_o$$Cy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein each of $R^{20a}$ and $R^{20b}$, when present, is independently selected from hydrogen, C1-C8 alkyl, C1-C8 haloalkyl, and —$(CH_2)_p$$Cy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O (C1-C4 alkyl), and —$(CH_2)_q$$Cy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

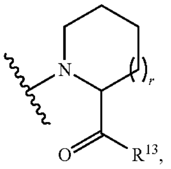

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_s$$Cy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when $R^4$ is —$(CR^{10a}R^{10b})_n$C(O)$R^{11}$, —CH($R^{12}$)$Ar^2$, or $Ar^2$, or when $R^3$ and $R^4$ together comprise a heterocycle having a structure represented by a formula:

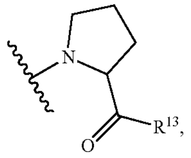

then $R^1$ is $Cy^1$ or $R^1$ and $R^2$ together comprise a C3-C6 cycloalkyl or a C3-C6 heterocycloalkyl, and provided that when $R^1$ is C1-C3 alkyl, $R^3$ and $R^4$ together comprise a heterocycle having a structure represented by a formula:

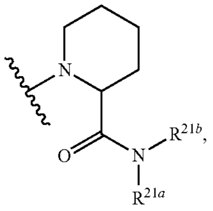

and $Ar^1$ is phenyl, then either (i) $Ar^1$ is substituted with at least one non-hydrogen group; or (ii) at least one of $R^{21a}$ and $R^{21b}$ is hydrogen, or a pharmaceutically acceptable salt thereof, and a pharmaceutically acceptable carrier.

In one aspect, disclosed are pharmaceutical compositions comprising an effective amount of a compound selected from:

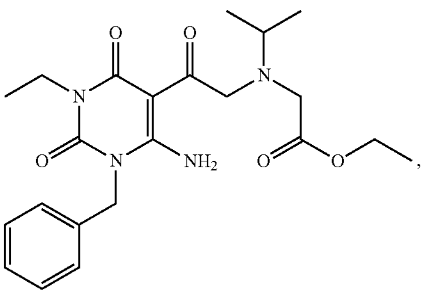
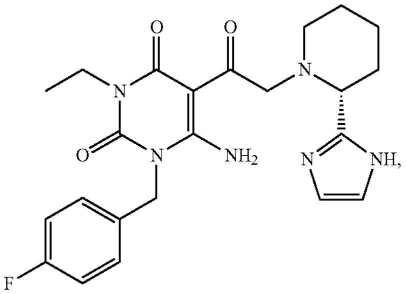
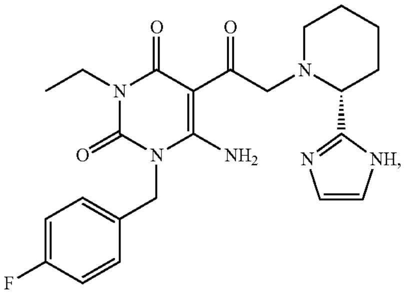
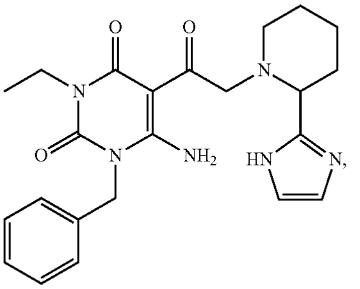
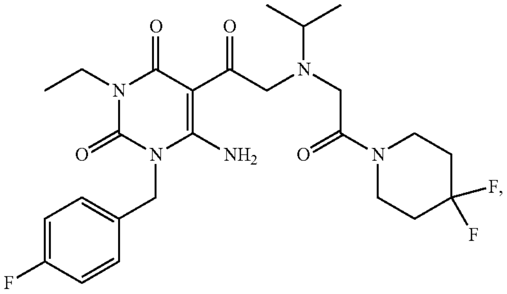
-continued
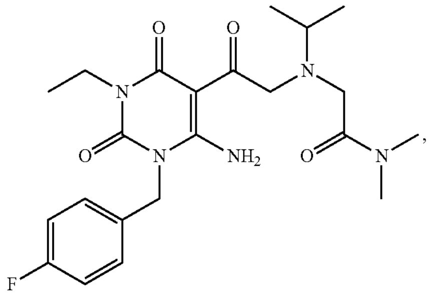
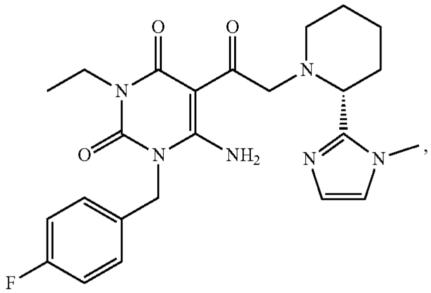
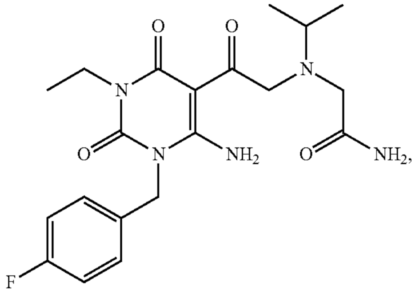
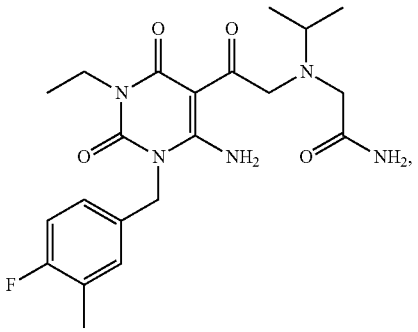
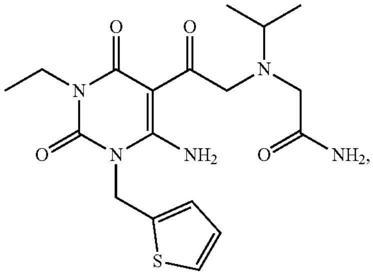

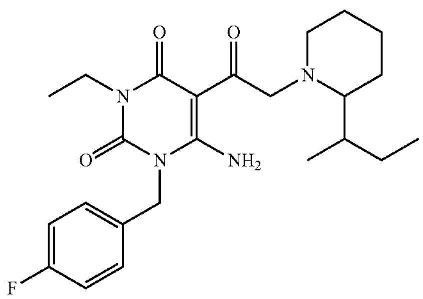
,
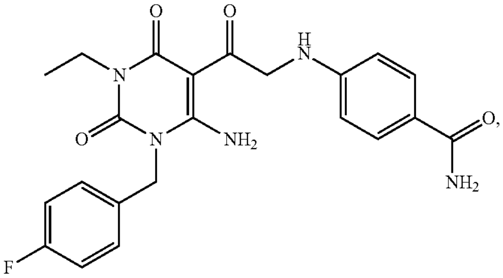
,
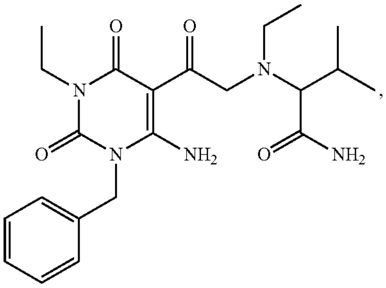
,
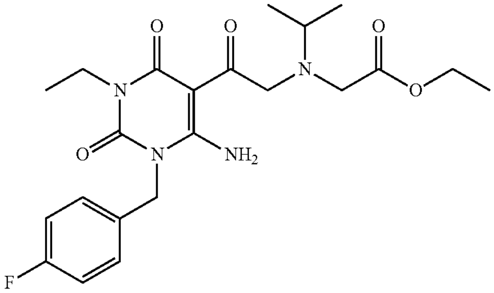
,
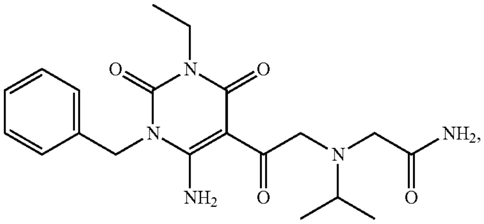
,
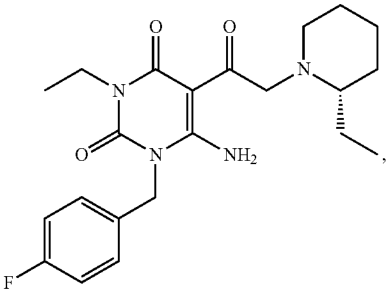
,
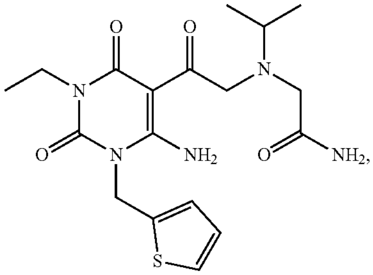
,
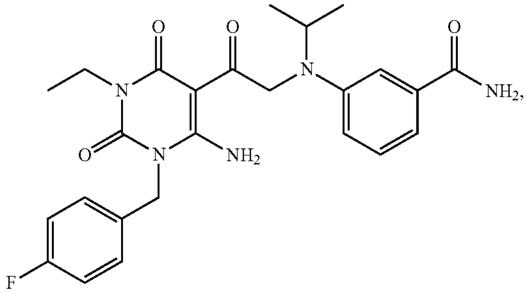
,
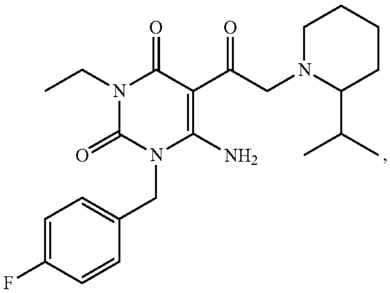
,
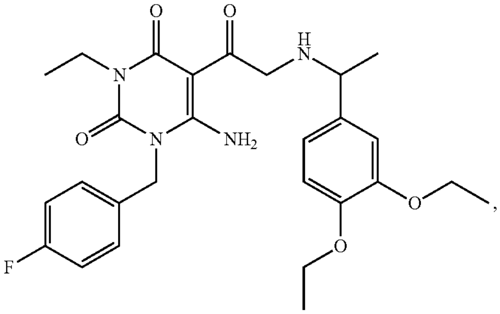
,
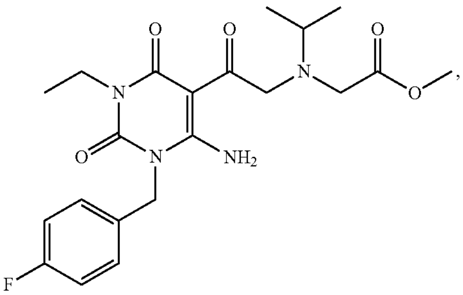
, -continued
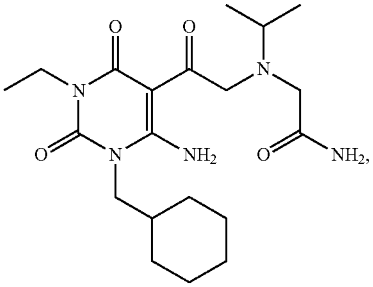
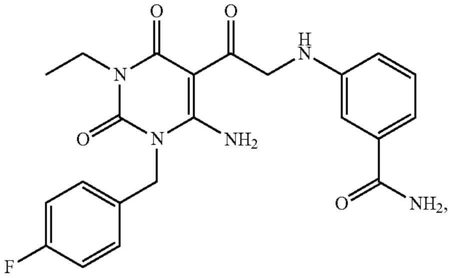
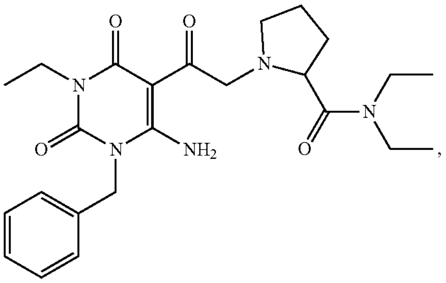
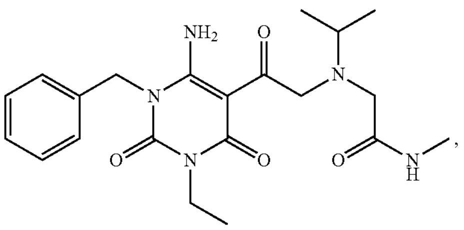
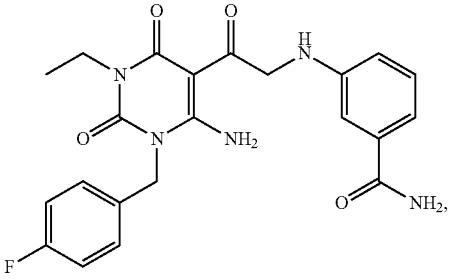
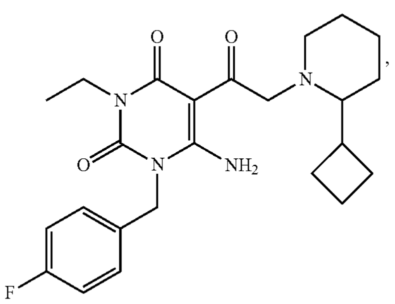
-continued
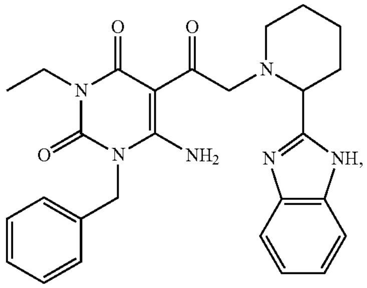
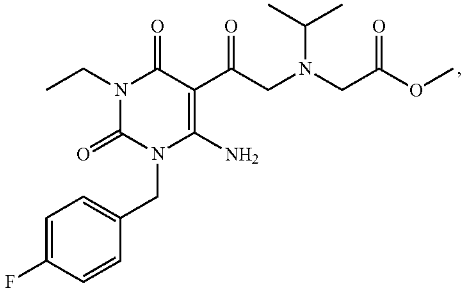
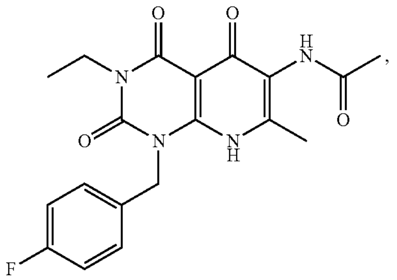
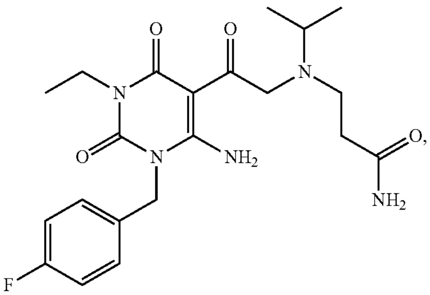
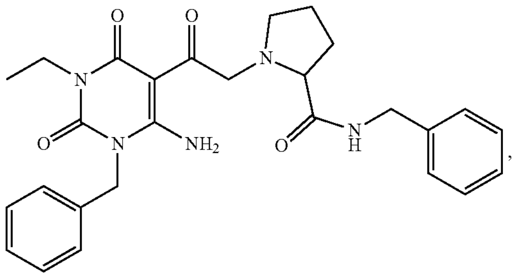
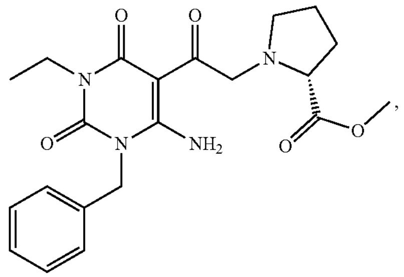

-continued
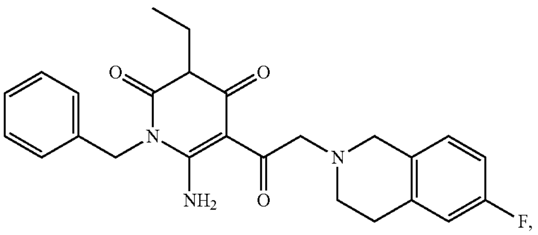
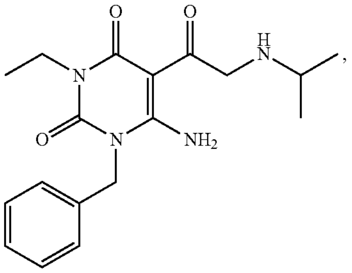
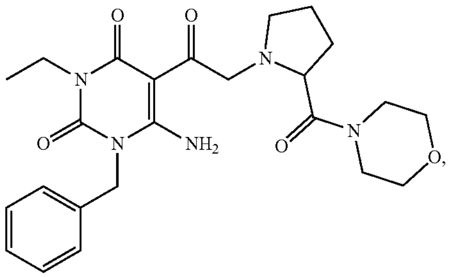
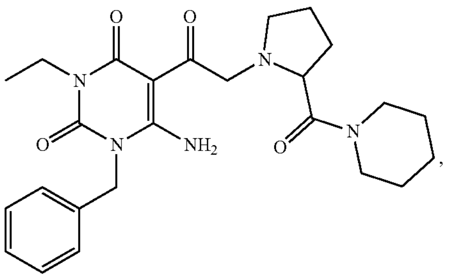
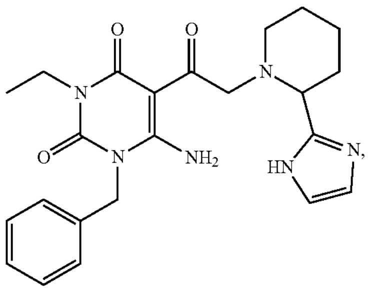
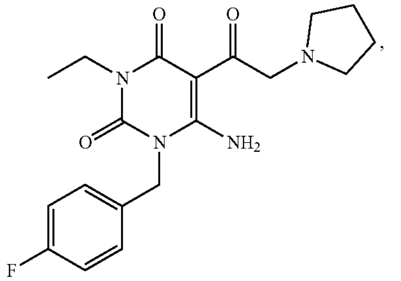
-continued
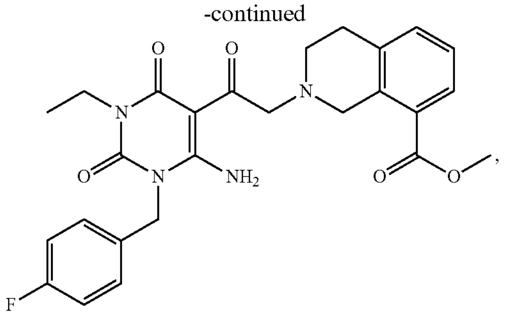
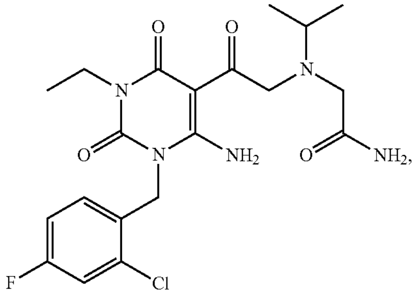
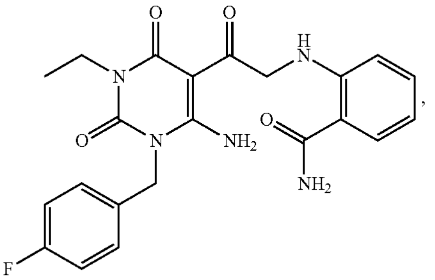
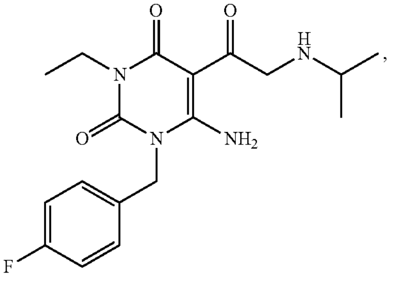
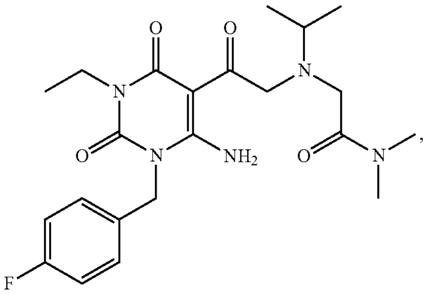
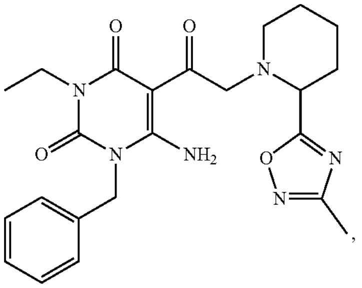

-continued
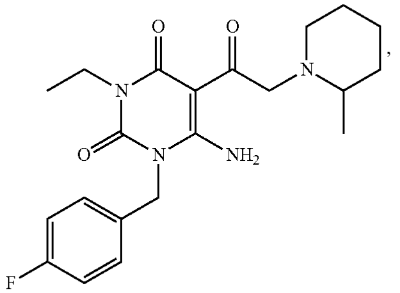
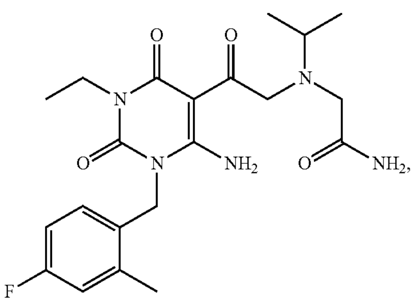
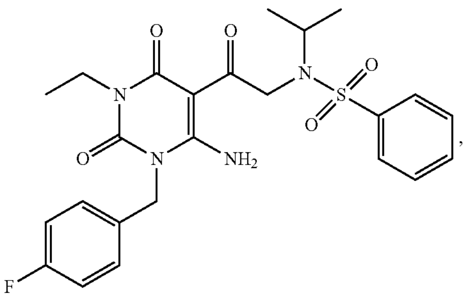
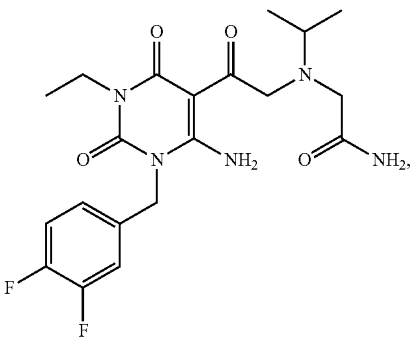
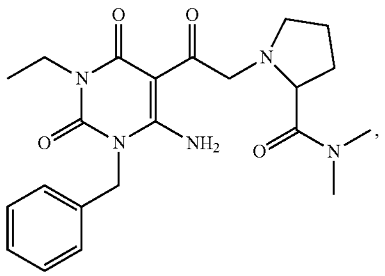
-continued
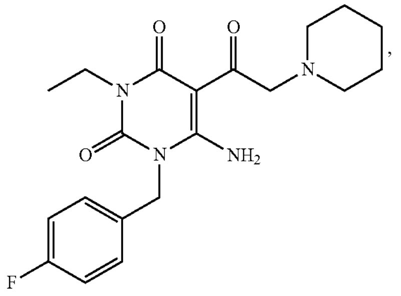
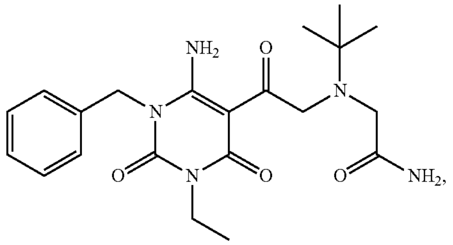
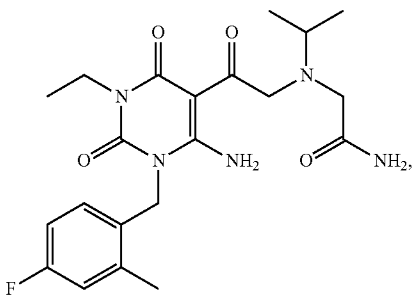
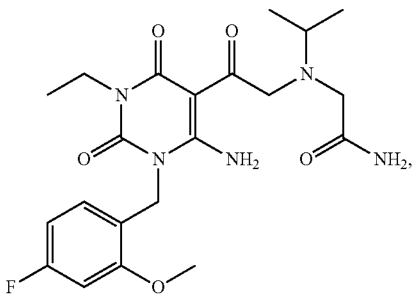
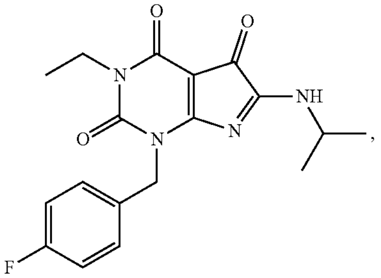
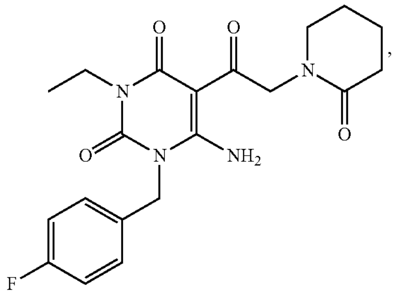

-continued
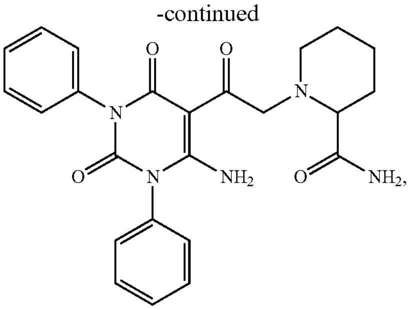
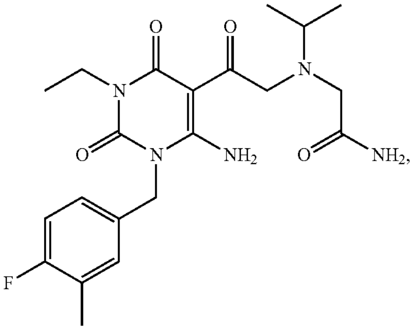
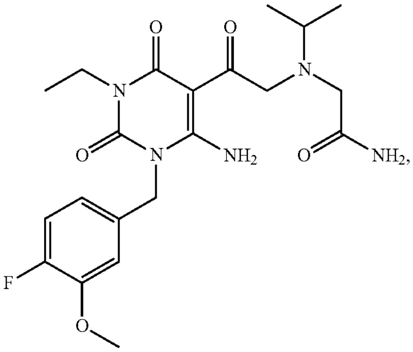
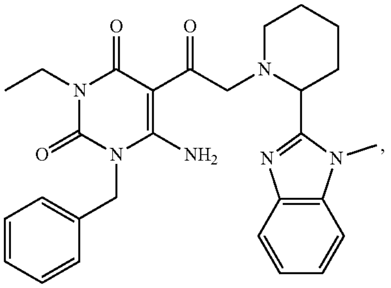
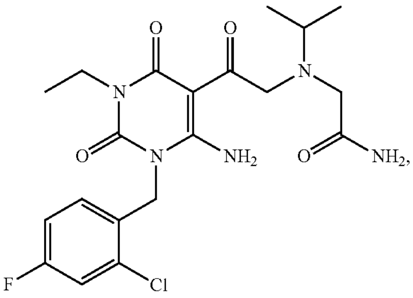
-continued
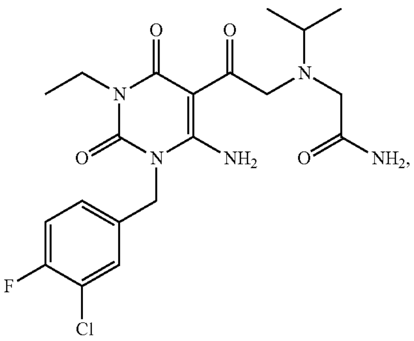
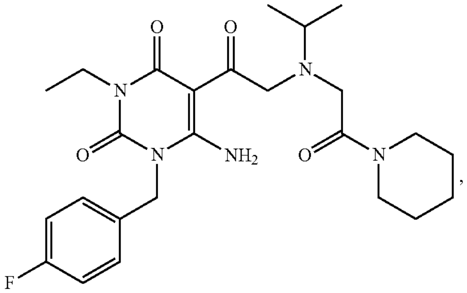
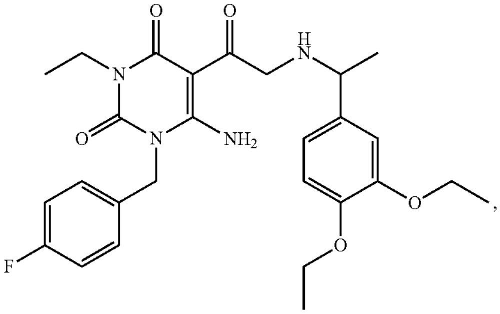
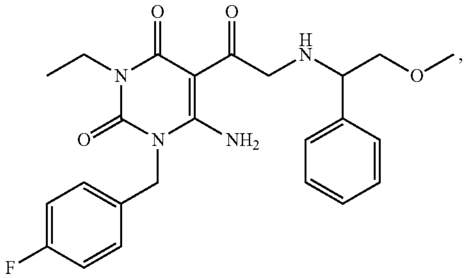
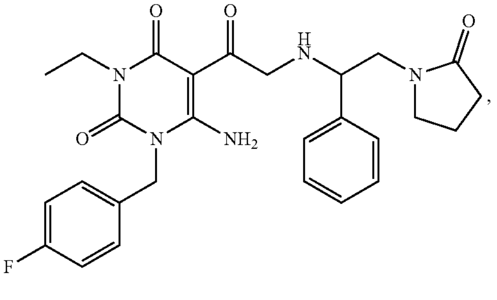

-continued
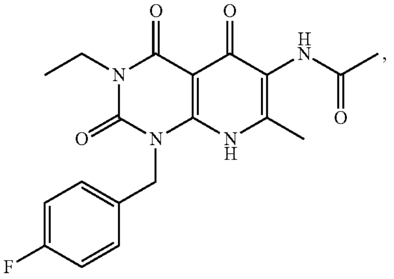
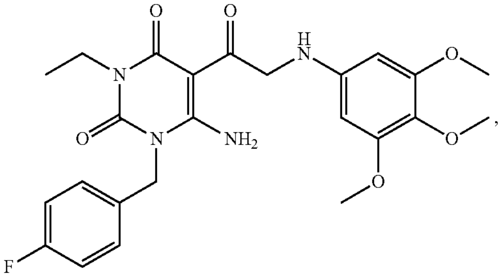
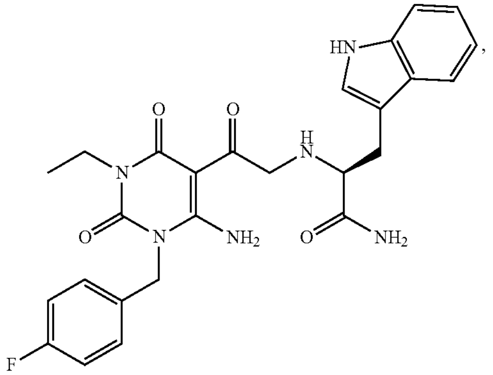
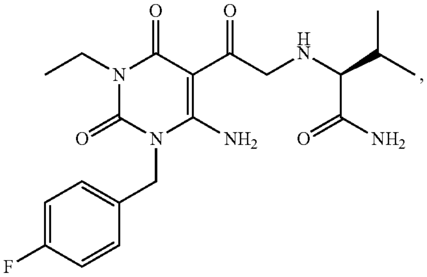
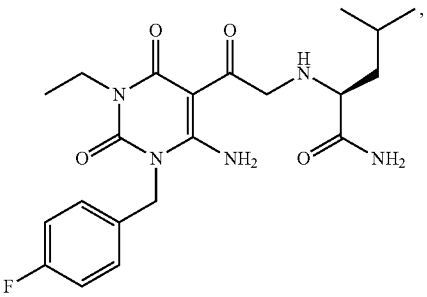
-continued
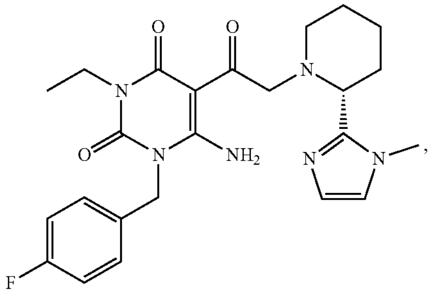
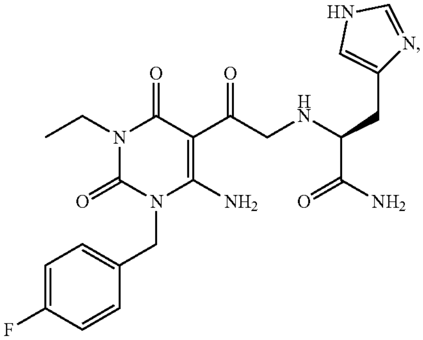
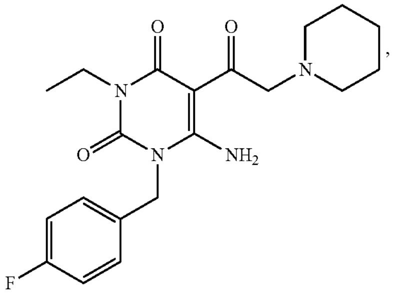
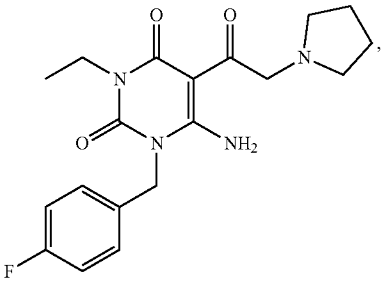
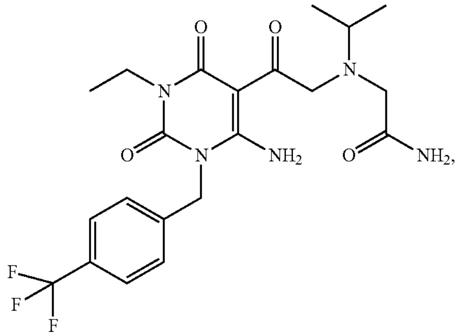

-continued
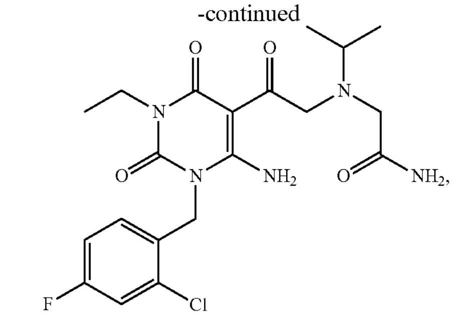
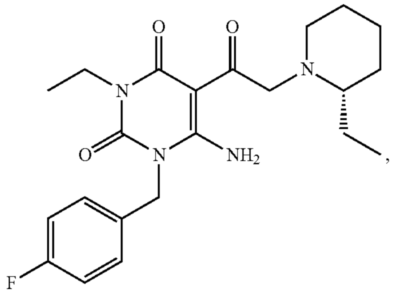
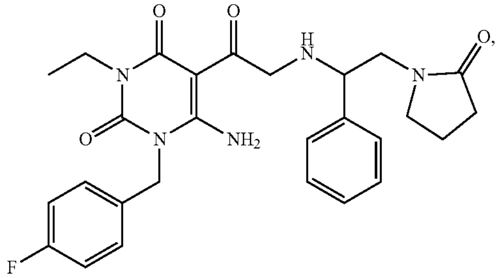
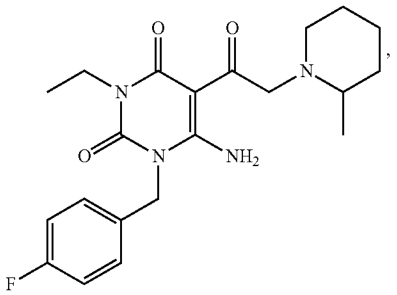
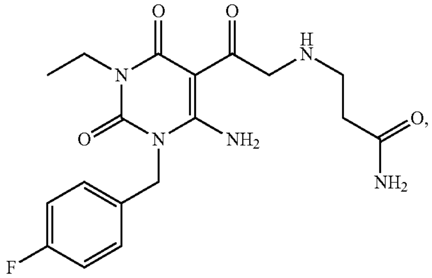
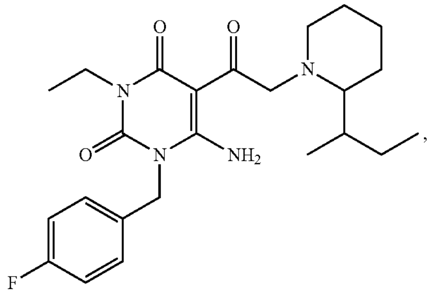
-continued
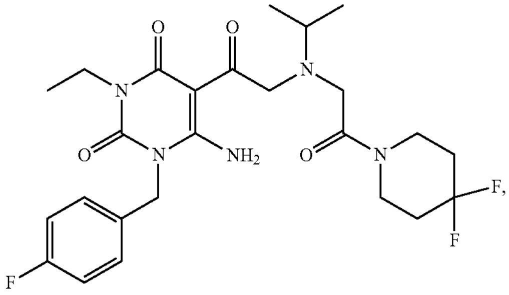
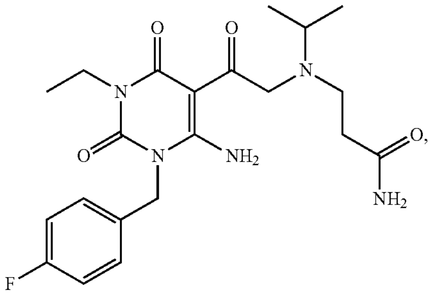
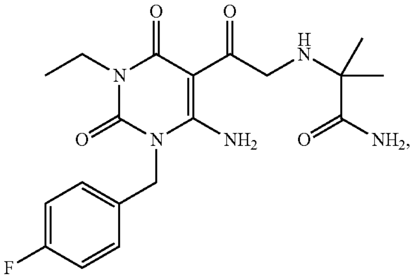
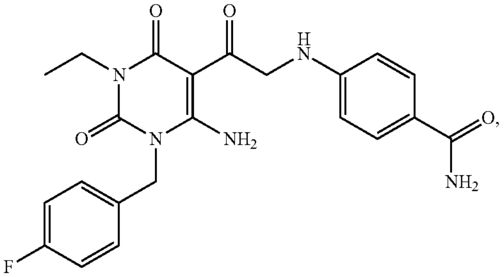
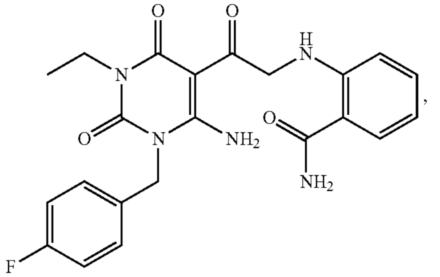
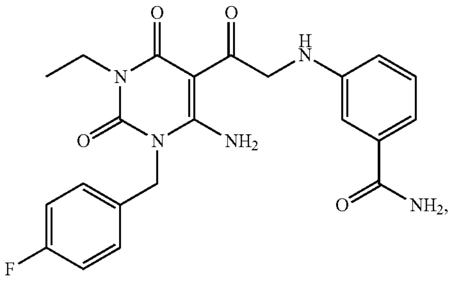

-continued
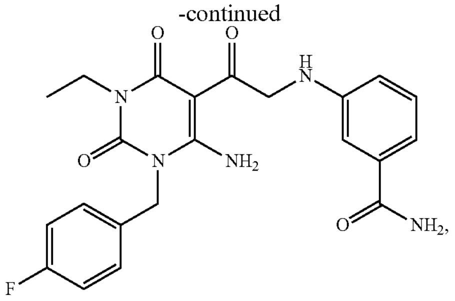
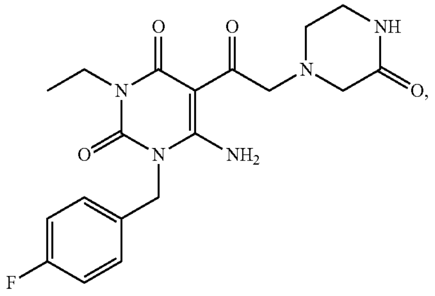
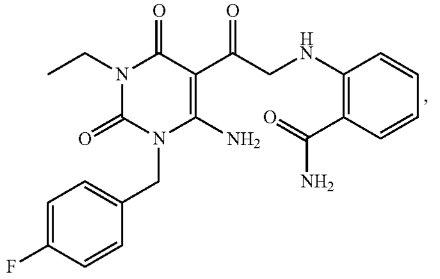
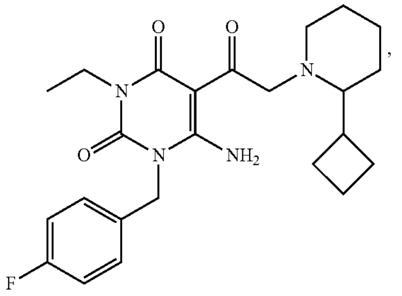
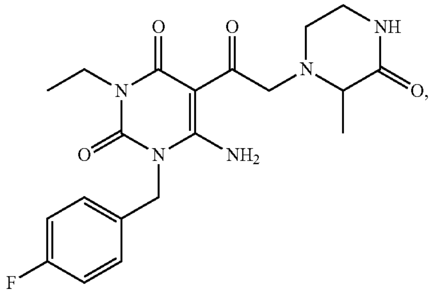
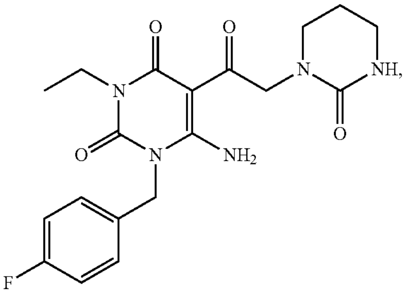
-continued
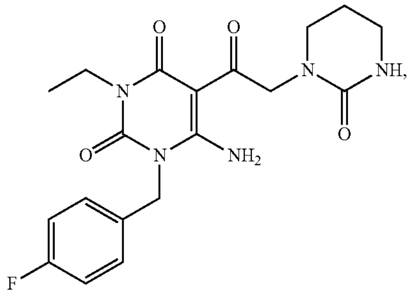
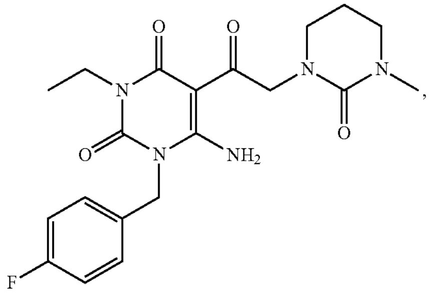
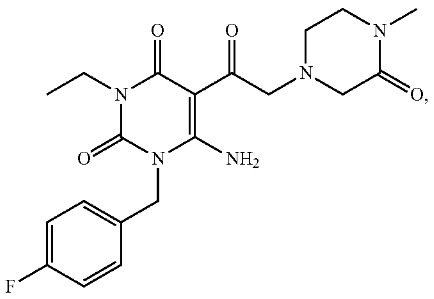
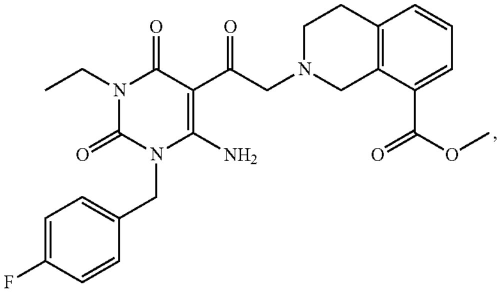
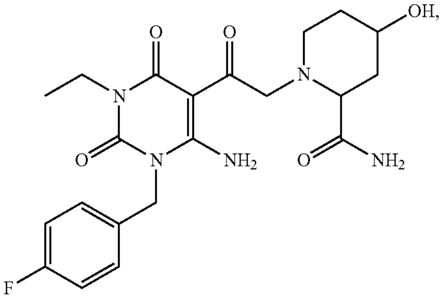

-continued
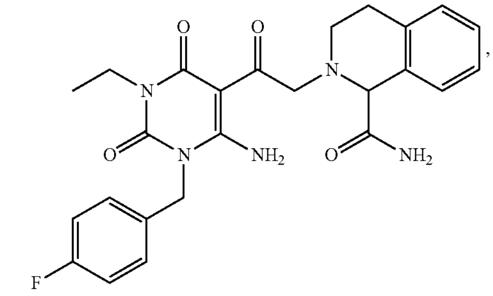
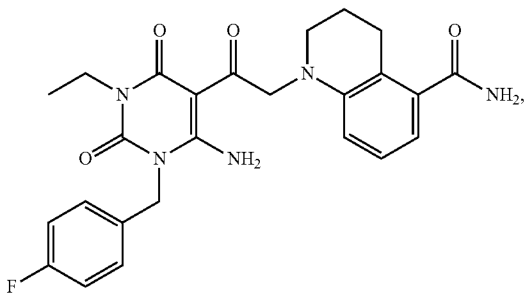
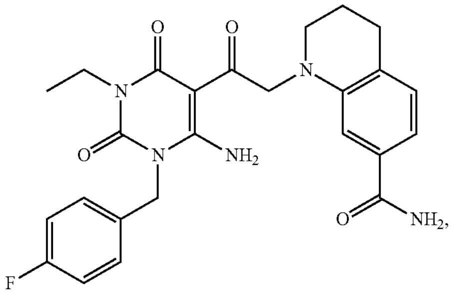
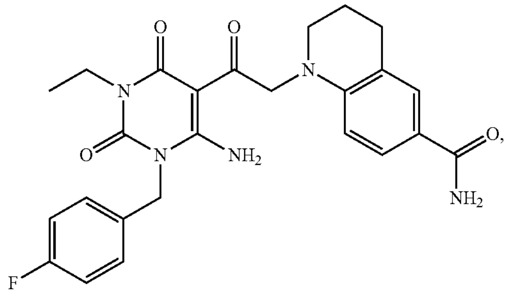
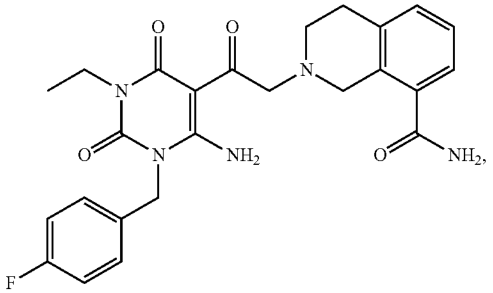
-continued
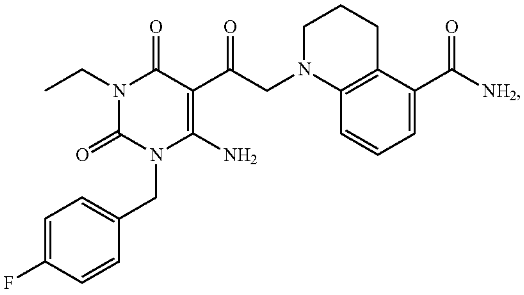
and
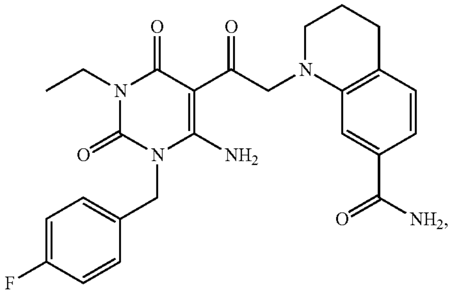
or a pharmaceutically acceptable salt thereof, and a pharmaceutically acceptable carrier.
In various aspects, the compound is selected from:
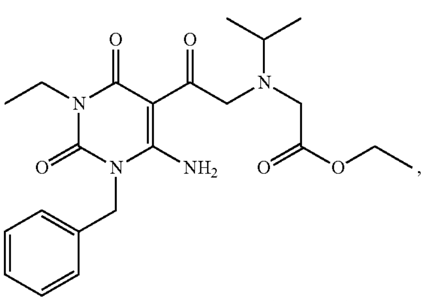
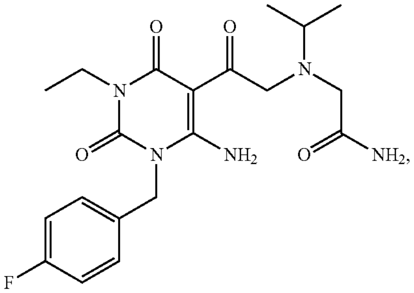
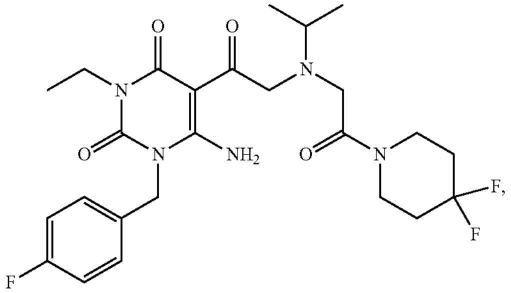

-continued
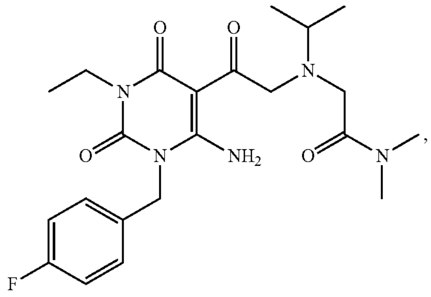
,
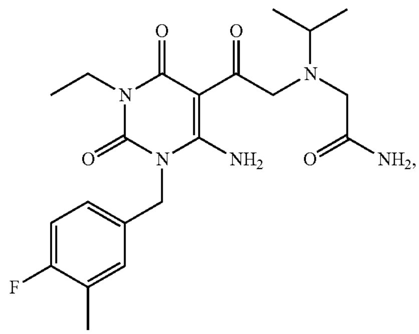
,
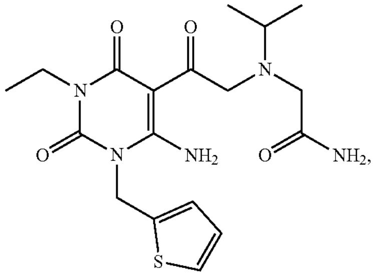
,
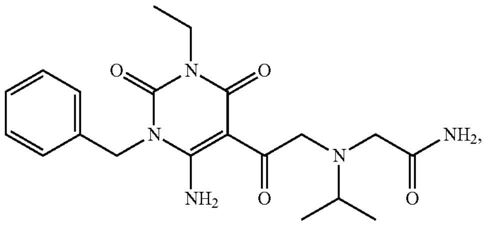
,
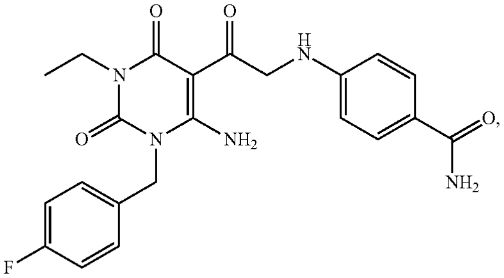
,
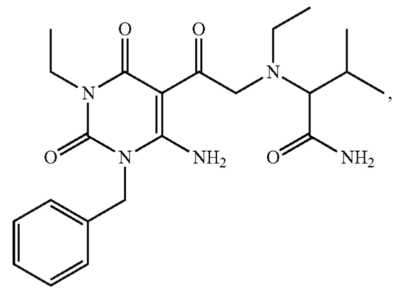
,
-continued
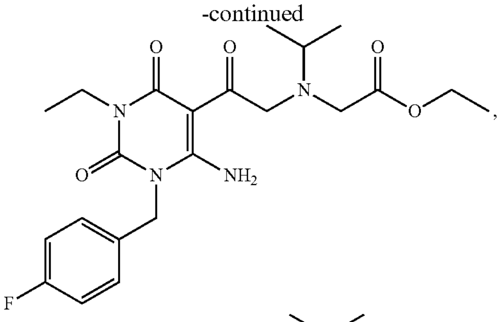
,
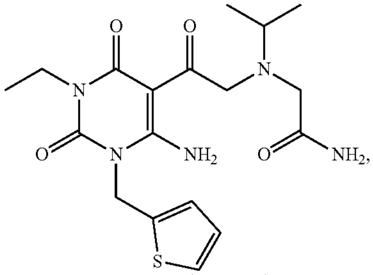
,
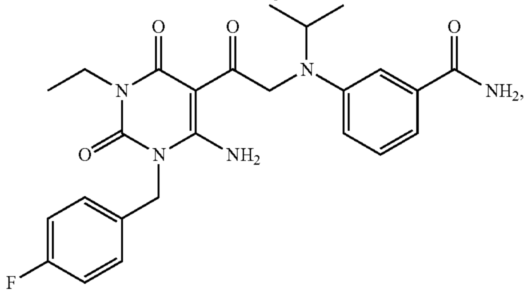
,
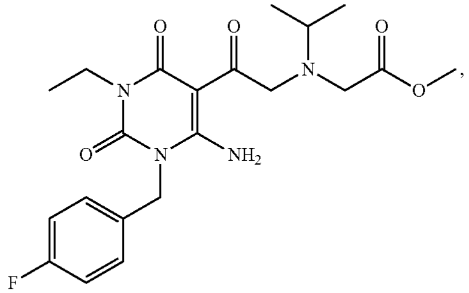
,
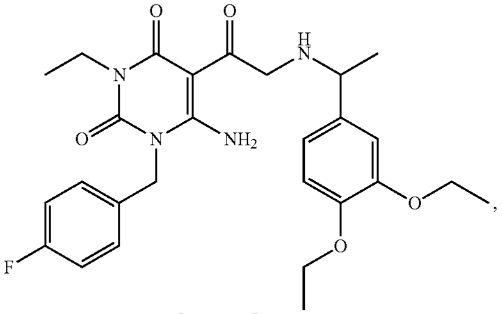
,
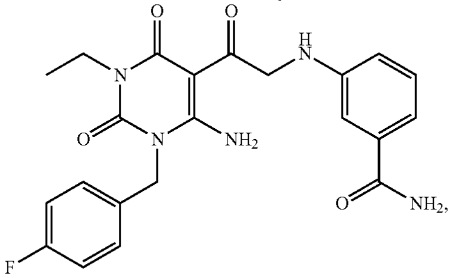
, -continued
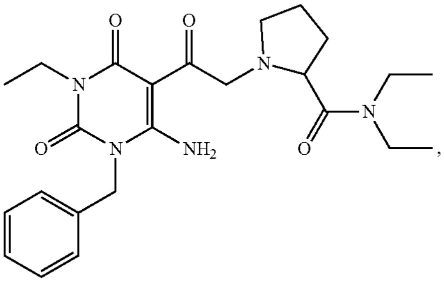,
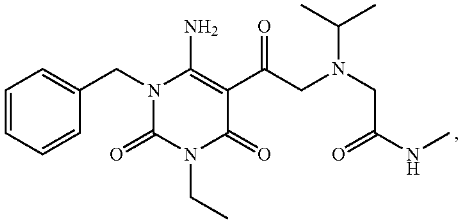,
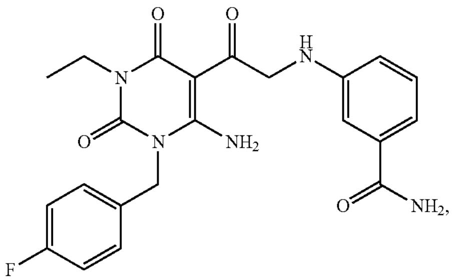,
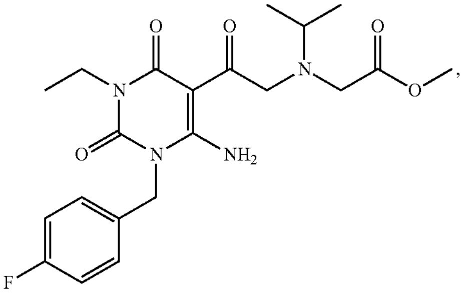,
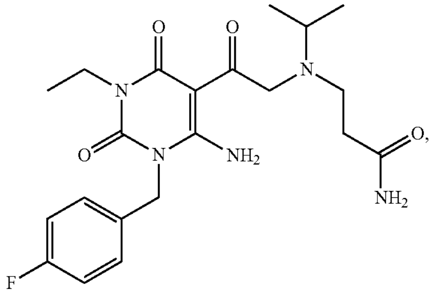,
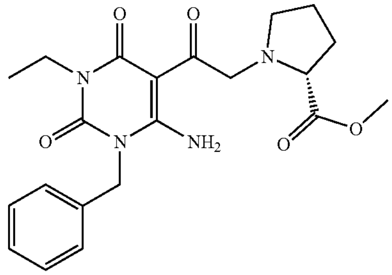,
-continued
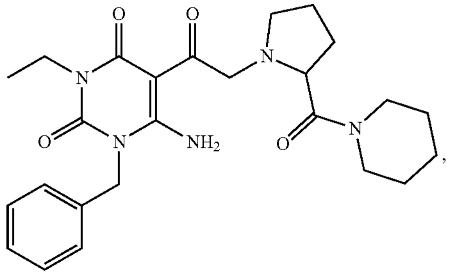,
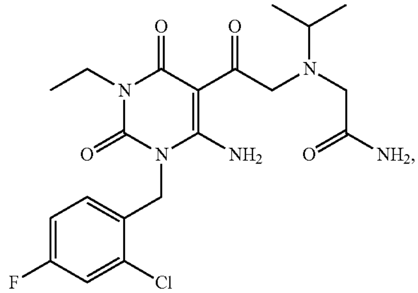,
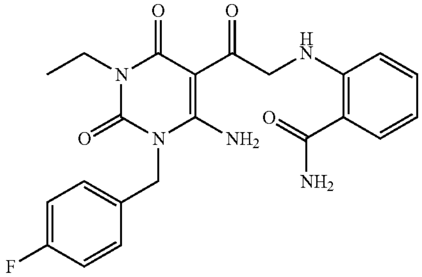,
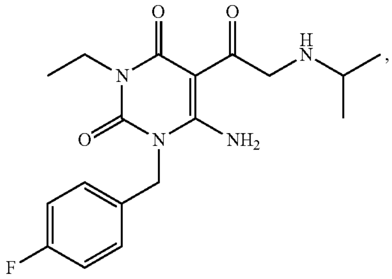,
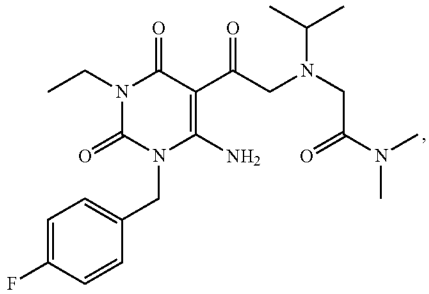,
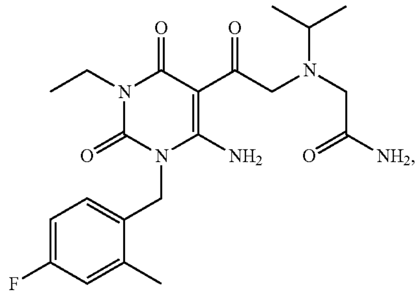, -continued
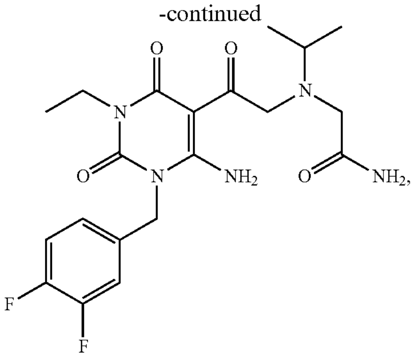
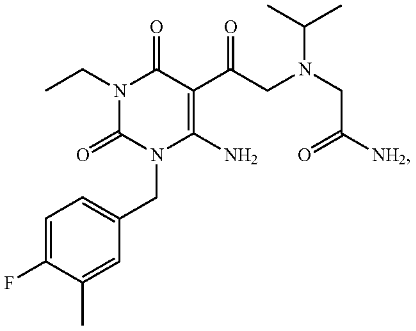
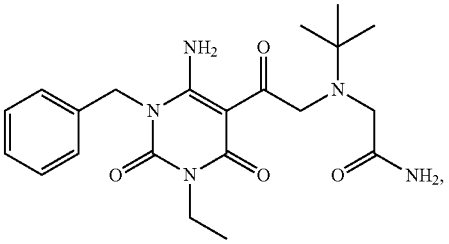
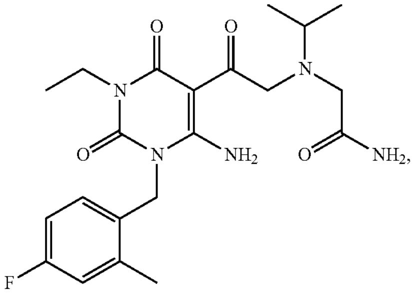
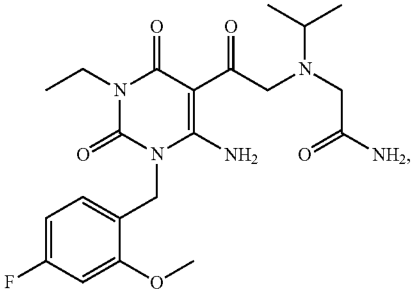
-continued
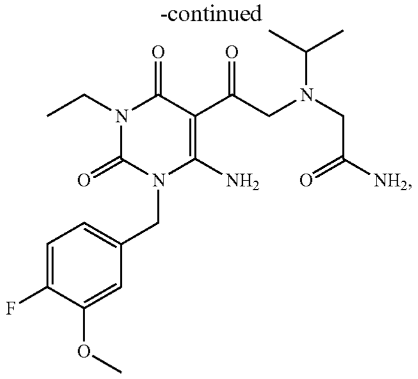
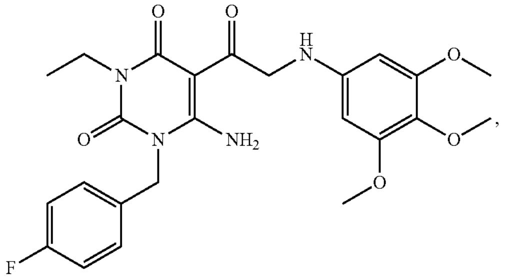
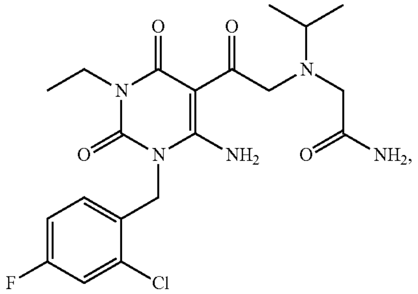
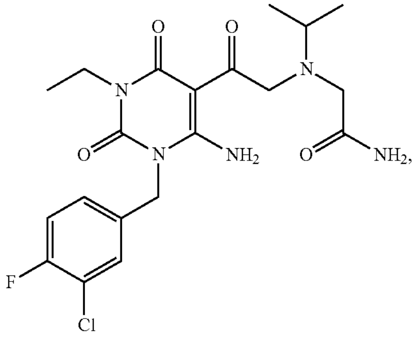
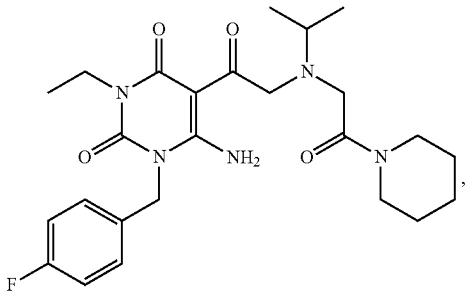

-continued
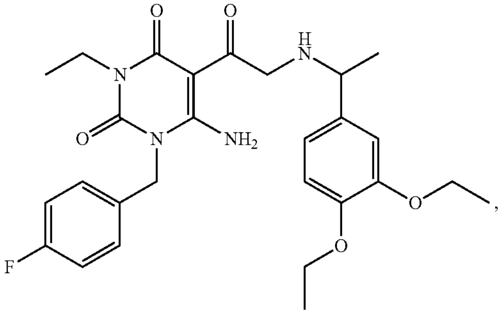
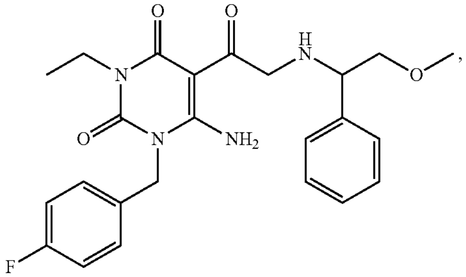
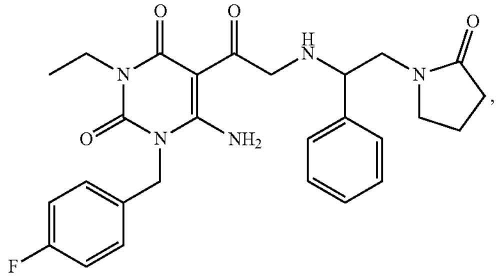
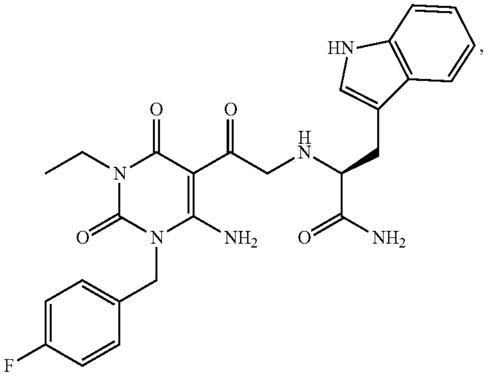
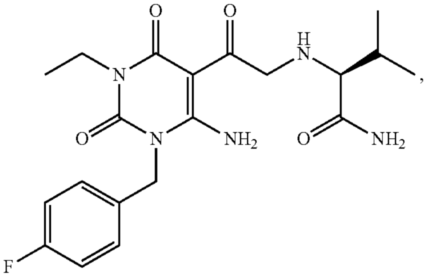
-continued
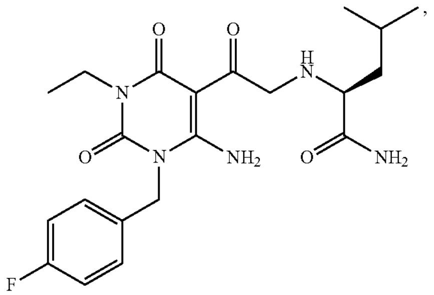
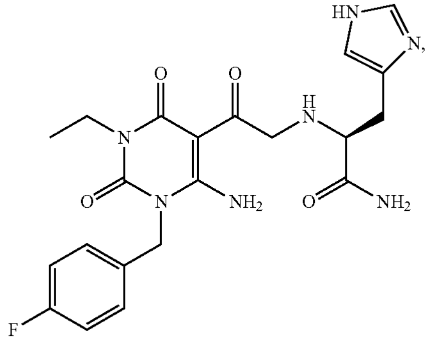
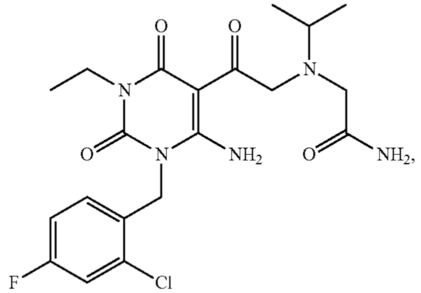
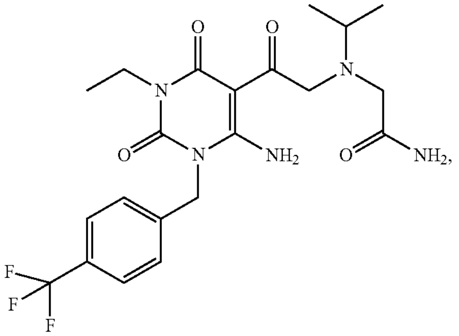
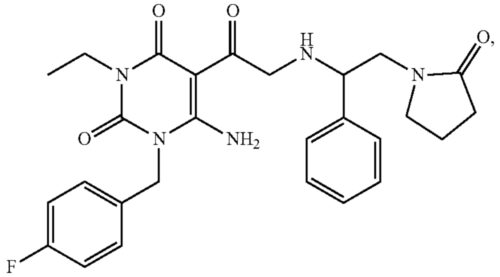

-continued

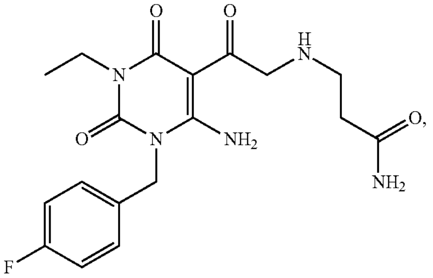

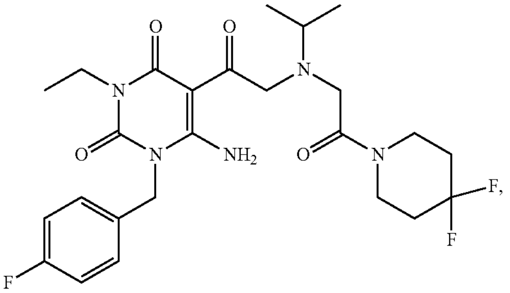

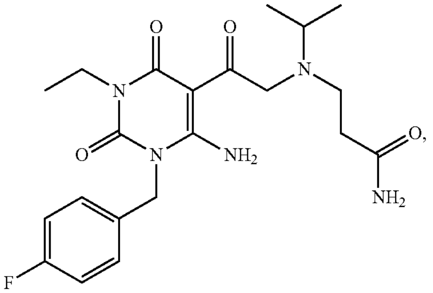

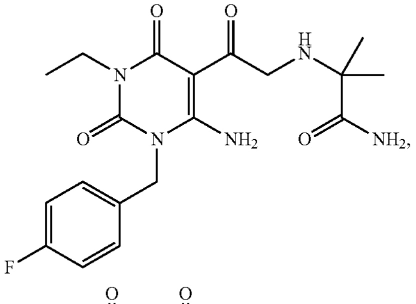

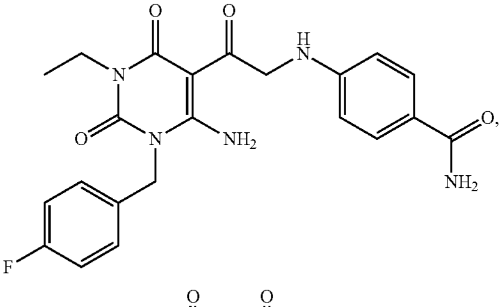

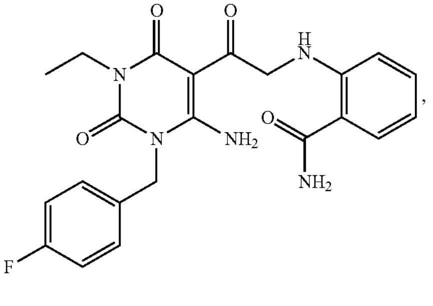

-continued

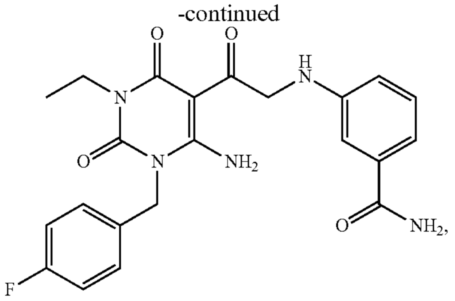

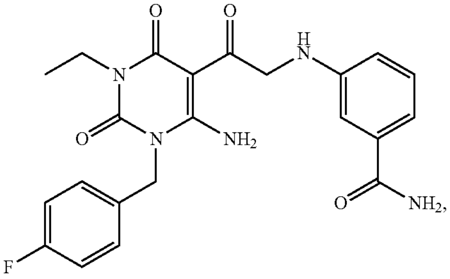

and

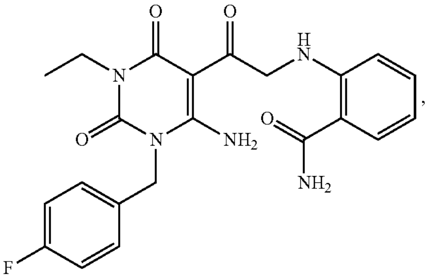

or a pharmaceutically acceptable salt thereof.

In various aspects, the compound is:

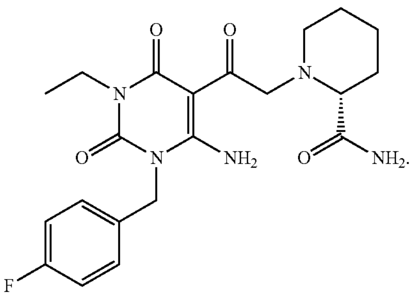

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise a disclosed compound (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the effective amount is a therapeutically effective amount. In a still further aspect, the effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with the presence of a premature termination codon such as, for example, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer. In a still further aspect, the pharmaceutical composition is used to treat a disorder in a subject identified as having a premature termination codon.

It is understood that the disclosed compositions can be prepared from the disclosed compounds. It is also understood that the disclosed compositions can be employed in the disclosed methods of using.

D. Methods of Making a Compound

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I, as described and exemplified below. The following examples are provided so that the invention might be more fully understood, are illustrative only, and should not be construed as limiting.

1. Route I

In one aspect, substituted uracil analogs can be prepared as shown below.

SCHEME 1A

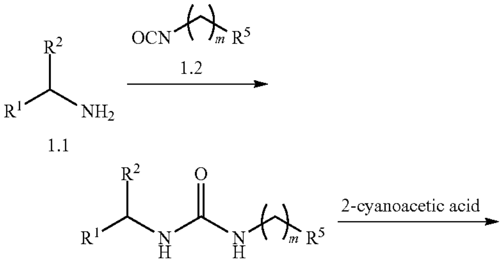

1.1 1.2 1.3

-continued

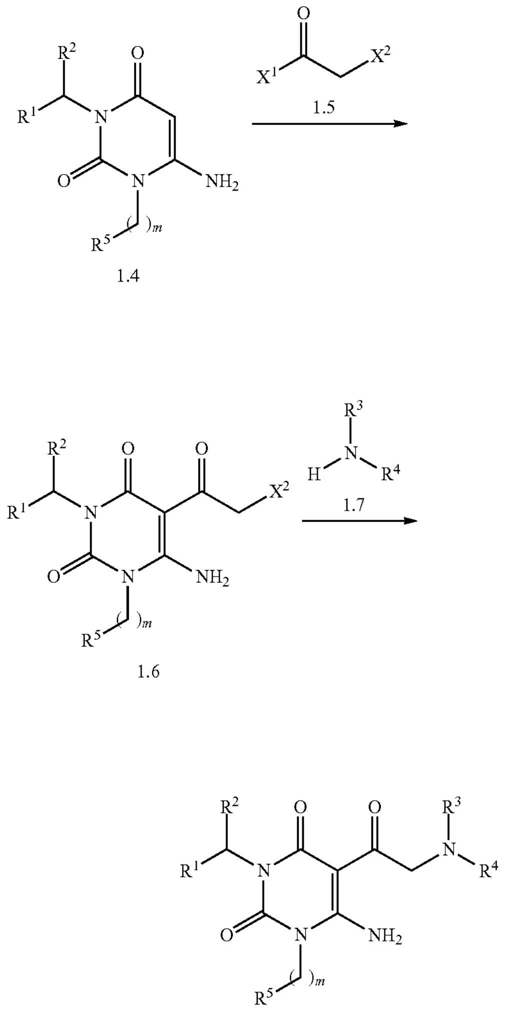

1.4 1.5 1.6 1.7 1.8

Compounds are represented in generic form, wherein $X^1$ and $X^2$ are independently halogen, and with other substituents as noted in compound descriptions elsewhere herein. A more specific example is set forth below.

SCHEME 1B

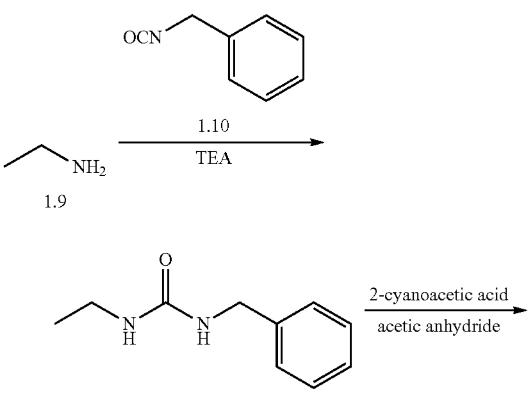

1.9 1.10 1.11

-continued

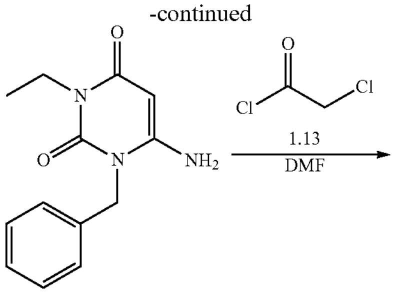

1.12

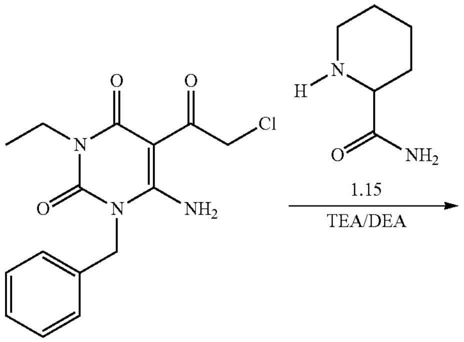

1.14

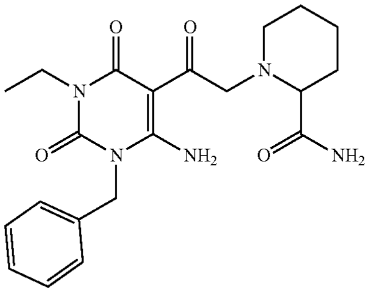

1.16

In one aspect, compounds of type 1.16 and similar compounds can be prepared according to reaction Scheme 1B above. Thus, compounds of type 1.11 can be prepared by coupling an appropriate amine, e.g., 1.9 as shown above, with an appropriate isocyanate, e.g., 1.0 as shown above. Appropriate amines and appropriate isocyanates are commercially available or prepared by methods known to one skilled in the art. The coupling reaction is carried out in the presence of an appropriate base, e.g., triethylamine. Compounds of type 1.12 can be prepared by reacting an appropriate urea, e.g., 1.11 as shown above, with 2-cyanoacetic acid. The cyclization is carried out in the presence of an appropriate dehydrating agent, e.g., acetic anhydride. Compounds of type 1.14 can be prepared by reacting an appropriate uracil derivative, e.g., 1.12 as shown above, with an appropriate acyl halide, e.g., 1.13 as shown above. The reaction is carried out in the presence of an appropriate solvent, e.g., dimethylformamide. Compounds of type 1.16 can be prepared by reacting an appropriate halide, e.g., 1.14, with an appropriate amine, e.g., 1.15 as shown above. The reaction is carried out in the presence of an appropriate base, e.g., triethylamine, N,N-diisopropylamine. As can be appreciated by one skilled in the art, the above reaction provides an example of a generalized approach wherein compounds similar in structure to the specific reactants above (compounds similar to compounds of type 1.1, 1.2, 1.3, 1.4, 1.5, 1.6, and 1.7) can be substituted in the reaction to provide substituted uracil analogs similar to Formula 1.8.

E. Methods of Modulating Read-Through of a Premature Termination Codon in a Subject The compounds and pharmaceutical compositions of the invention are also useful in modulating read-through of a premature termination codon in a subject. Exemplary disorders associated with the presence of a premature termination codon include, but are not limited to, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer.

Nonsense suppression therapy is an approach utilized to treat disorders such as cystic fibrosis in patients who carry a nonsense mutation or a premature termination codon (PTC). Without wishing to be bound by theory, this therapeutic strategy utilizes small molecules to suppress translation termination at in-fram PTCs, allowing partial levels of full-length, functional protein to be restored. PTC suppression agents increase the frequency that aminoacyl tRNAs become incorporated at a PTC, resulting in insertion of an amino acid into the anscent polypeptide at the site of the PTC. This mechanism, termed "readthrough," suppresses translation termination at a PTC, allowing translation elongation to continue downstream of the PTC in the correct reading frame to generate a full-length protein. The instantly disclosed compounds induce readthrough by targeting the translation termination factor, eRF1, to the proteasome for degradation. This results in reduced intracellular eRF1 levels, which promotes a corresponding increase in readthrough of PTCs.

Thus, in one aspect, disclosed are methods for modulating read-through of a premature termination codon in a subject in need thereof, the method comprising administering to the subject an effective amount of a disclosed compound. In a further aspect, disclosed are methods for modulating read-through of a premature termination codon in a subject in need thereof, the method comprising administering to the subject an effective amount of a compound having a structure represented by a formula:

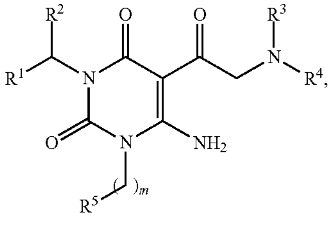

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_n$C(O)$R^{11}$, —CH($R^{12}$)$Ar^2$, and $Ar^2$; wherein n, when present, is 1 or 2; wherein $R^{10a}$, when present, is independently selected from hydrogen and C1-C4 alkyl; wherein $R^{10b}$, when present, is independently selected from hydrogen, C1-C4 alkyl, —(C1-C4 alkyl)O(C1-C4 alkyl), and —$(CH_2)_o Cy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_p Cy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_q Cy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)$NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

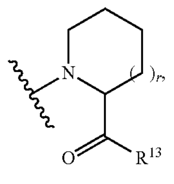

wherein r is 0 or 1; and wherein $R^{13}$ is selected from C1-C4 alkoxy and —$NR^{21a}R^{21b}$; wherein each of $R^{21a}$ and $R^{21b}$ when present, is independently selected from hydrogen, C1-C8 alkyl, C1-C8 haloalkyl, and —$(CH_2)_s Cy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^5$ is selected from $Ar^1$ and $Cy^6$; wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In a further aspect, disclosed are methods for modulating read-through of a premature termination codon in a subject in need thereof, the method comprising administering to the subject an effective amount of a compound selected from:

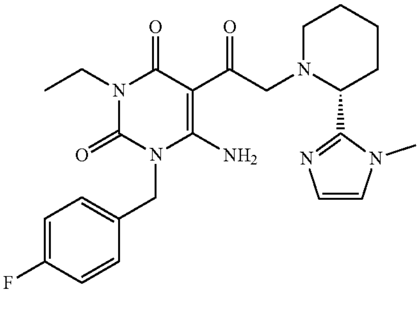
,

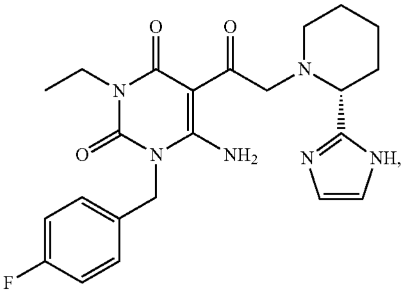
,

-continued
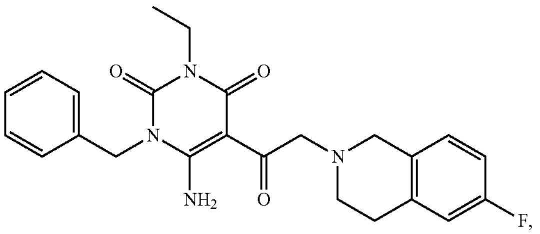
,
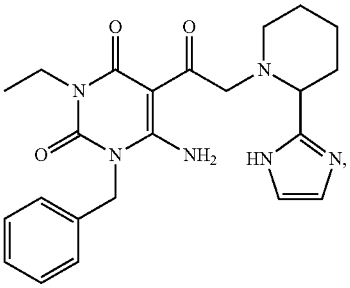
,
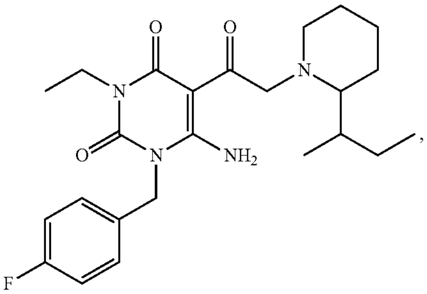
,
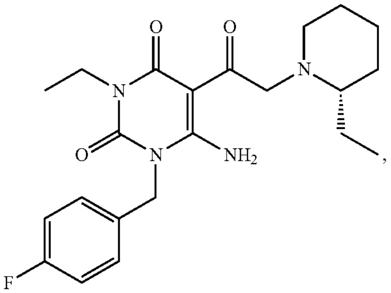
,
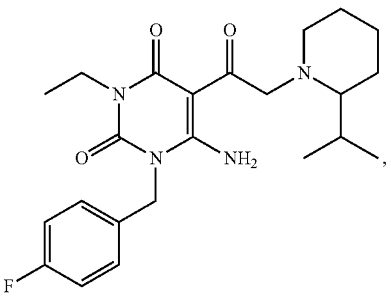
,
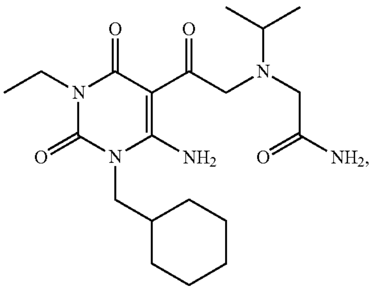
,
-continued
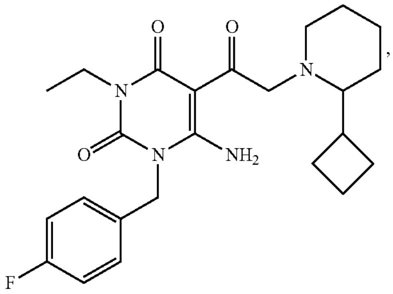
,
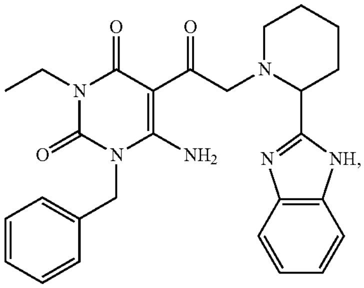
,
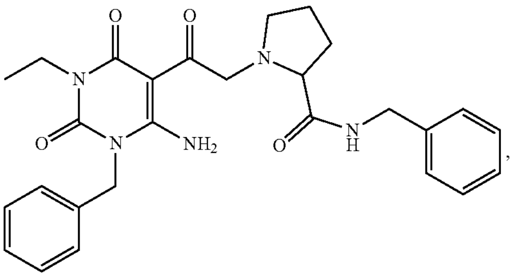
,
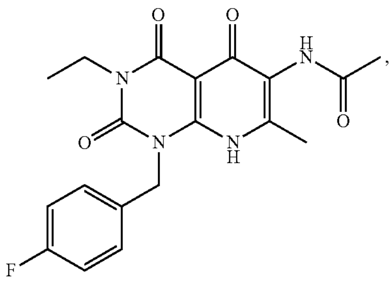
,
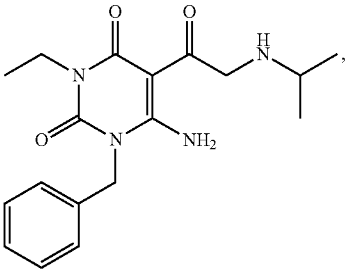
,
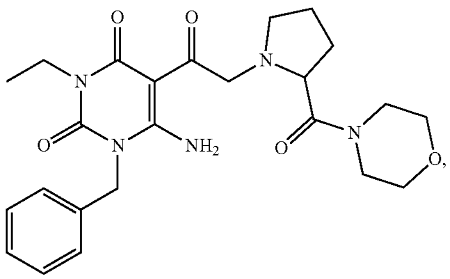
, -continued
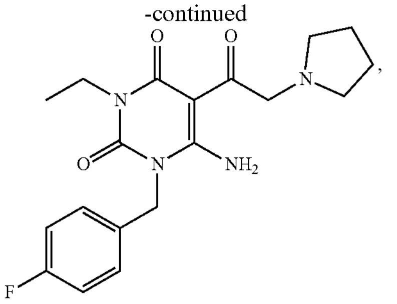
,
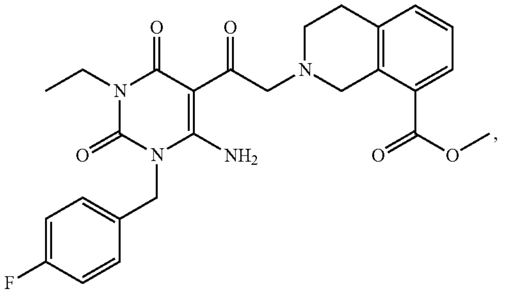
,
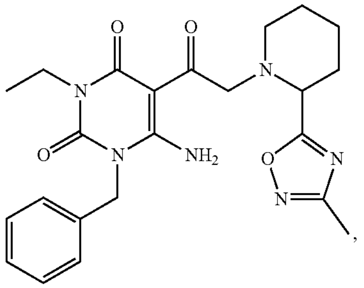
,
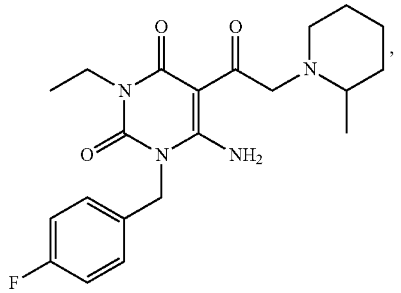
,
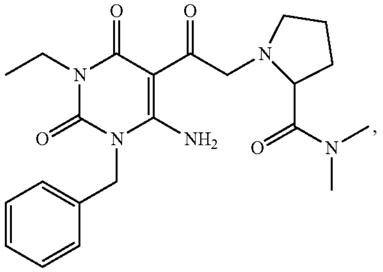
,
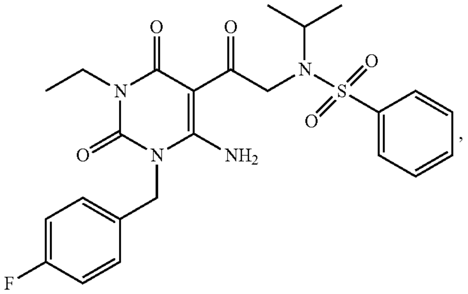
,
-continued
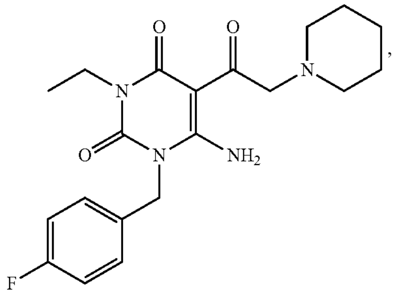
,
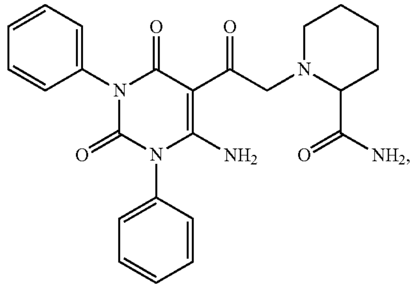
,
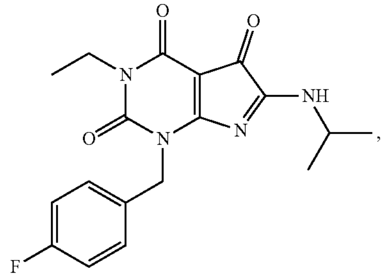
,
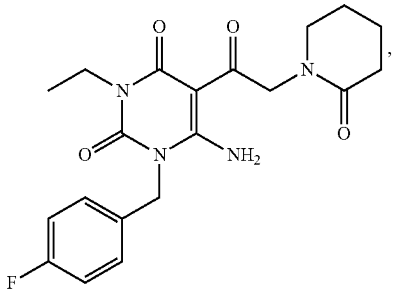
,
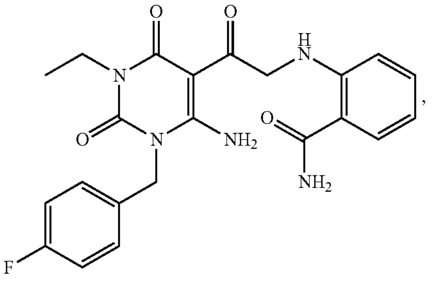
,
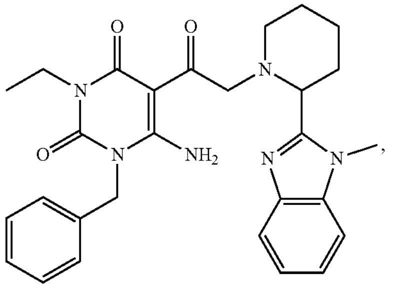
, -continued
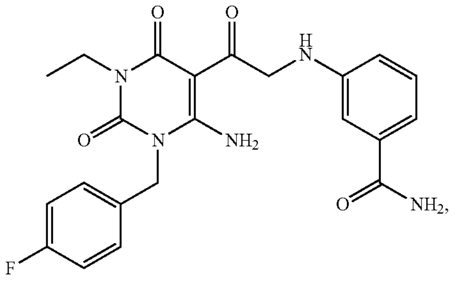
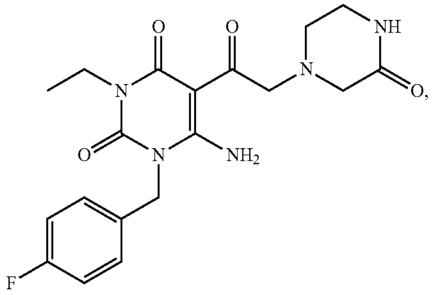
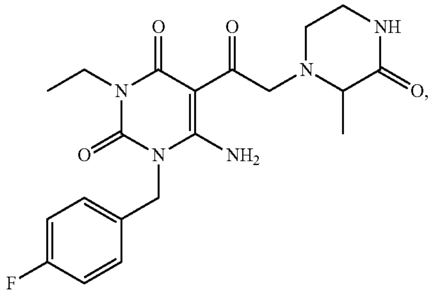
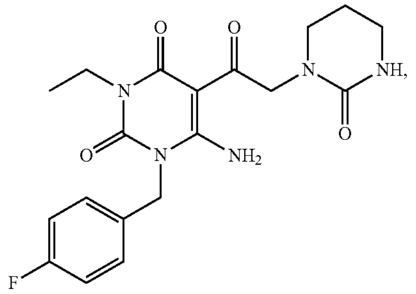
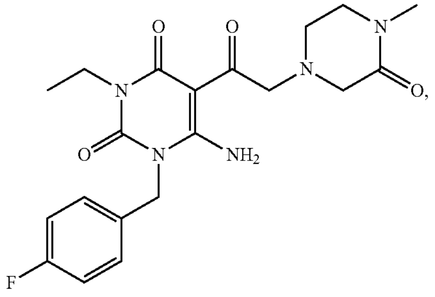
-continued
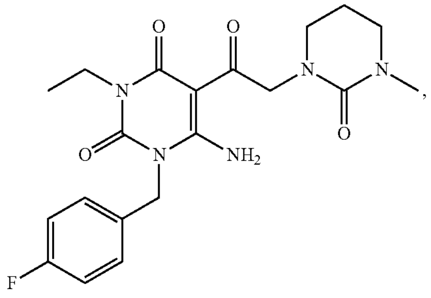
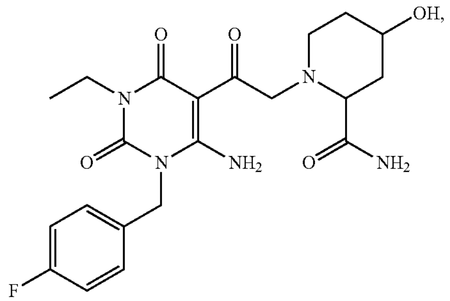
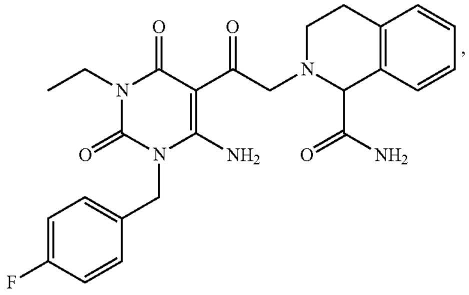
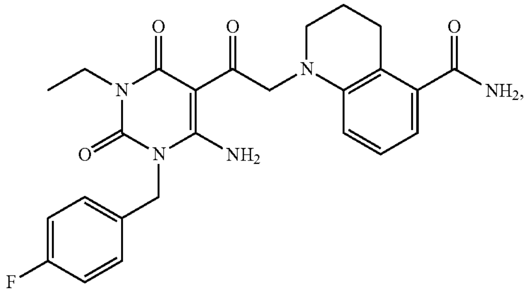
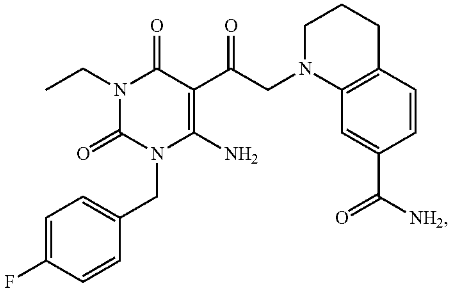

-continued

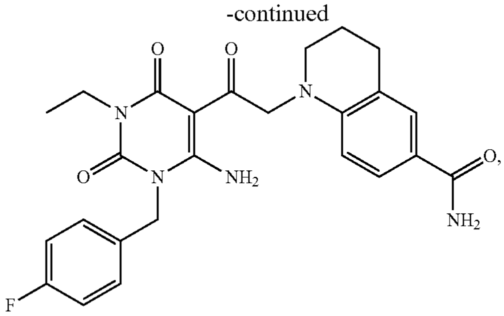

, and

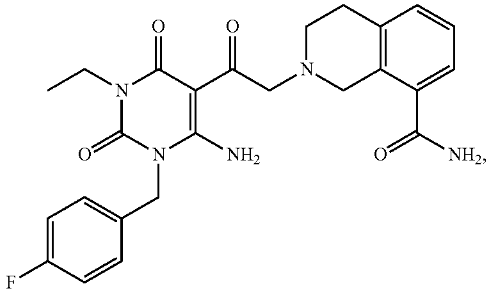

, or a pharmaceutically acceptable salt thereof.

In a further aspect, disclosed are methods for modulating read-through of a premature termination codon in a subject in need thereof, the method comprising administering to the subject an effective amount of a compound having a structure represented by a formula:

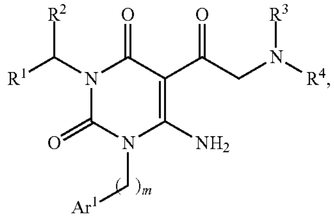

, wherein m is 1 or 2; wherein $R^1$ is selected from C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein each occurrence of $R^{10a}$, when present, is independently selected from hydrogen and C1-C4 alkyl; wherein each occurrence of $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein each of $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O (C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

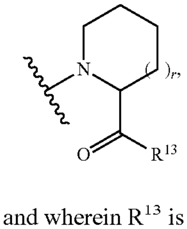

, wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-

C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when $R^4$ is —$(CR^{10a}R^{10b})_nC(O)R^{11}$, —$CH(R^{12})Ar^2$, or $Ar^2$, or when $R^3$ and $R^4$ together comprise a heterocycle having a structure represented by a formula:

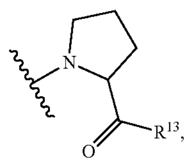

then $R^1$ is $Cy^1$ or $R^1$ and $R^2$ together comprise a C3-C6 cycloalkyl or a C3-C6 heterocycloalkyl, and provided that when $R^1$ is C1-C3 alkyl, $R^3$ and $R^4$ together comprise a heterocycle having a structure represented by a formula:

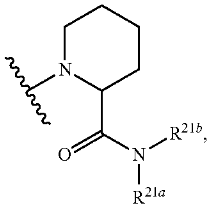

and $Ar^1$ is phenyl, then either (i) $Ar^1$ is substituted with at least one non-hydrogen group; or (ii) at least one of $R^{21a}$ and $R^{21b}$ is hydrogen, or a pharmaceutically acceptable salt thereof.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a disorder associated with the presence of a premature termination codon, such as, for example, cystic fibrosis.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disorder associated with the presence of a premature termination codon, such as, for example, cystic fibrosis.

In a further aspect, modulating is increasing.

In a further aspect, the premature termination codon is selected from E60X, Y122X, Q493X, G542X, G550X, R553X, Y1092X, R1162X, and W1282X.

In a further aspect, the subject has been diagnosed with a disorder selected from cystic fibrosis, Duchenne muscular dystrophy, aniridia, Becker muscular dystrophy, spinal muscular atrophy, Hurler syndrome, hemophilia, epidermolysis bullosa, Usher syndrome, neurofibromatosis, and cancer prior to the administering step. In a still further aspect, the subject has been diagnosed with a need for modulating read-through of a premature termination codon prior to the administering step.

In a further aspect, the subject is a mammal. In a still further aspect, the mammal is a human.

In a further aspect, the method further comprises the step of identifying a subject in need of treatment of a disorder caused by a premature termination codon, wherein the disorder is selected from cystic fibrosis, Duchenne muscular dystrophy, aniridia, Becker muscular dystrophy, spinal muscular atrophy, Hurler syndrome, hemophilia, epidermolysis bullosa, Usher syndrome, neurofibromatosis, and cancer.

In a further aspect, the disorder is cystic fibrosis.

The therapeutically effective amount or dosage of each active agent can vary within wide limits. Such a dosage is adjusted to the individual requirements in each particular case including the specific compound(s) being administered, the route of administration, the condition being treated, as well as the patient being treated. In general, in the case of nasal or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

In a further aspect, the effective amount is a therapeutically effective amount. In a still further aspect, the effective amount is a prophylactically effective amount.

In a further aspect, the compound exhibits activation of read-through of a premature termination codon. Thus, in various aspects, the compound exhibits activation of read-through of a premature termination codon with an $EC_{50}$ of less than 10 μM. In a further aspect, the compound has an $EC_{50}$ of less than 8 μM. In a still further aspect, the compound has an $EC_{50}$ of less than 6 μM. In yet a further aspect, the compound has an $EC_{50}$ of less than 4 μM. In an even further aspect, the compound has an $EC_{50}$ of less than 2 μM. In a still further aspect, the compound has an $EC_{50}$ of less than 1 μM. In yet a further aspect, the compound has an $EC_{50}$ of less than 0.8 μM. In an even further aspect, the compound has an $EC_{50}$ of less than 0.6 μM. In a still further aspect, the compound has an $EC_{50}$ of less than 0.4 μM. In yet a further aspect, the compound has an $EC_{50}$ of less than 0.2 μM. In an even further aspect, the compound has an $EC_{50}$ of less than 0.1 μM.

In a further aspect, the subject is a mammal. In a still further aspect, the subject is a human.

In a further aspect, administering stimulates read-through of the premature termination codon. In a still further aspect, administering increases the stability of an mRNA containing the premature termination codon.

In a further aspect, the effective amount is a therapeutically effective amount. In a still further aspect, the effective amount is a prophylactically effective amount.

In a further aspect, the disorder is selected from cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, neurofibromatosis, and cancer.

In a further aspect, the disorder is cancer. In a still further aspect, the cancer is associated with one or more mutations selected from a P53 mutation and an APC mutation.

In a further aspect, the disorder is cystic fibrosis.

In a further aspect, the subject has been diagnosed with a need for treatment of the disorder prior to the administering step. In a still further aspect, the method further comprises the step of identifying a subject in need of treatment of the disorder. In yet a further aspect, identifying comprises identifying the presence of a premature termination codon in the subject.

Figure 2:
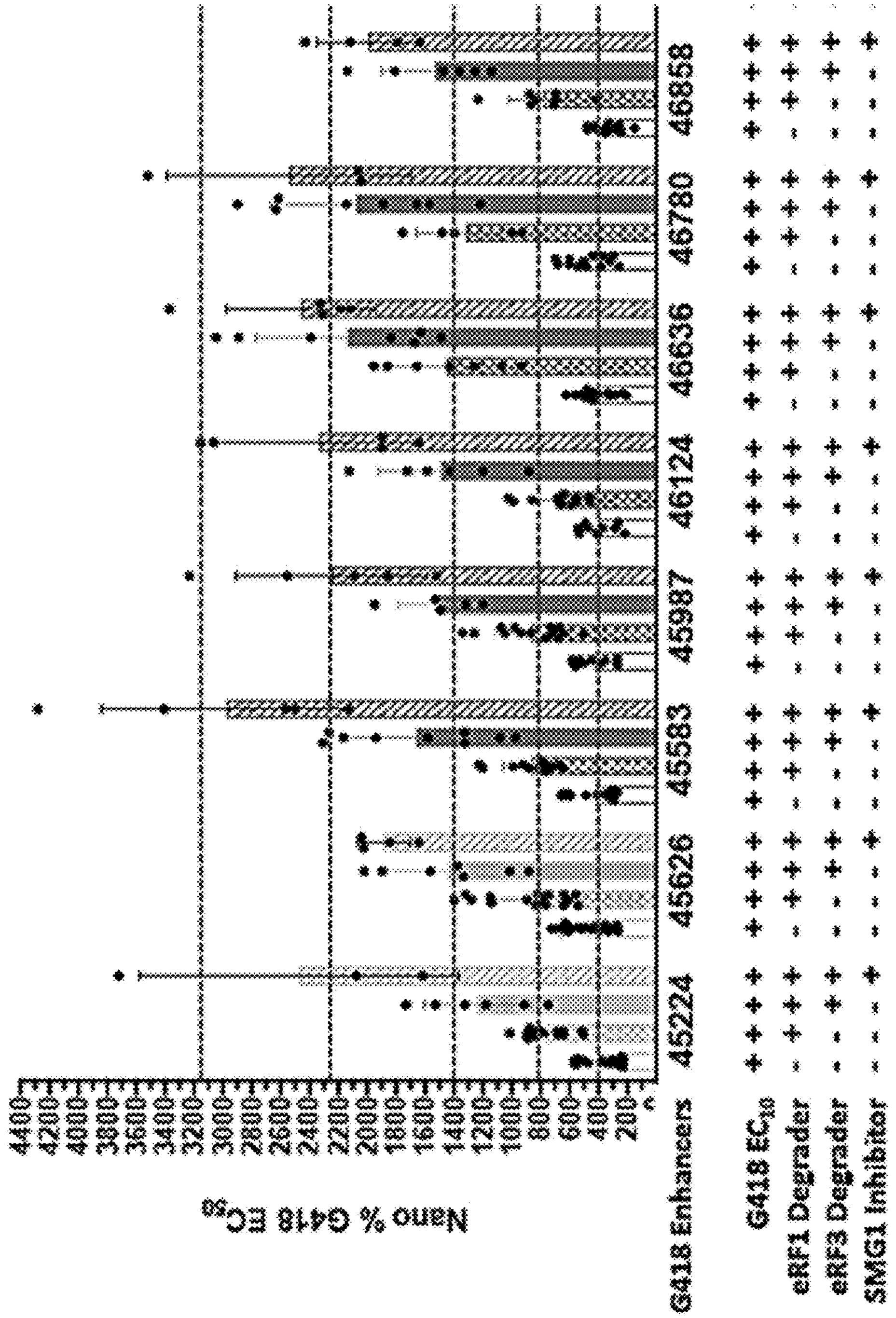
FIG. 2 shows representative data illustrating that readthrough enhancement can be obtained when readthrough compounds from different functional classes are added together.

In a further aspect, the method further comprises administering a second active agent to the subject. While many pharmacological readthrough compounds have been identified, to date, none have been able to rescue the 25-35% of normal CFTR function that is needed to alleviate lung defects in CF patients. In contrast, the instantly disclosed compounds induce modest readthrough alone specifically at PTCs. When combined with aminoglycosides such as G418 (which mediates readthrough by reducing ribosomal proofreading), synergistic increases in readthrough are observed that are significantly higher than either compound alone (see FIG. 1). Without wishing to be bound by theory, this suggests that combining agents that mediate or augment readthrough by different mechanisms is similarly likely to amplify the amount of CFTR function rescued. Additional studies have demonstrated that combining readthrough compounds with distinct mechanisms can promote synergistic PTC suppression that further enhances the level of CFTR production from CFTR alleles containing a nonsense mutation. For examples of this approach using reporter constructs, see the data in FIG. 2. Thus, in various aspects, the second active agent is selected from a CFTR modulator, an NMD inhibitor, and an agent that increases mRNA levels. In yet a further aspect, the CFTR polypeptide modulator is a CFTR potentiator (e.g., ivacaftor, VX-770, PG-01, tetrahydrobenzothiophene, GP-5), a CFTR amplifier, or a CFTR corrector (e.g., elexacaftor, lumacaftor, tezacaftor, Corr-4a, VX-809, C1, C2).

In a further aspect, the second active agent is a NMD inhibitor. Examples of NMD inhibitors include, but are not limited to, NMDI-1, NMDI-9, NMDI-25, and NMDI-14.

In a further aspect, the second active agent is an agent that increases mRNA levels. In a still further aspect, the agent that increases mRNA levels is a histone deacetylase inhibitor. In yet a further aspect, the histone deacetylase inhibitor is selected from vorinostat, romidepsin, panobinostat, and belinostat.

In a further aspect, the second active agent is an agent that increases general pulmonary function. In a still further aspect, the agent that increases general pulmonary function is selected from albuterol, salbuterol, recombinant DNAse, dornase alpha, inhaled tobramycin, amikracin, azithromycin, and hypertonic saline.

In a further aspect, the premature termination codon is in a CFTR.

In a further aspect, the second active agent is an aminoglycoside. Examples of aminoglycosides include, but are not limited to, G418, geneticin, amikacin, tobramycin, ELX-02, NB54, NB124, NB127, and NB83.

In a further aspect, the compound and the second active agent each modulate read-through of a premature termination codon via different mechanism. In a still further aspect, the compound and the second active agent each modulate read-through of a premature termination codon via the same mechanism. In yet a further aspect, the compound modulates read-through of a premature termination codon via degradation of translation termination factor eRF1. In an even further aspect, the second active agent modulates read-through of a premature termination codon via degradation of translation termination factor eRF3 (e.g., CC-9009) or via inhibition of SMG1 (e.g., via a SMG1 inhibitor).

In a further aspect, the second active agent is selected from erythromycin, artesunate, atazanavir, ataluren, genistein, and Y-320.

In a further aspect, the compound and the second active agent are administered sequentially. In a still further aspect, the compound and the second active agent are administered simultaneously.

In a further aspect, the compound and the second active agent are co-formulated. In a still further aspect, the compound and the second active agent are co-packaged.

F. Methods of Modulating Read-Through of a Premature Termination Codon in a Cell The compounds and pharmaceutical compositions of the invention are also useful in modulating read-through of a premature termination codon in a cell. Exemplary disorders associated with the presence of a premature termination codon include, but are not limited to, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer.

Thus, in one aspect, disclosed are methods for modulating read-through of a premature termination codon in a cell, the method comprising contacting the cell with an effective amount of a disclosed compound. In a further aspect, disclosed are methods for modulating read-through of a premature termination codon in a cell, the method comprising contacting the cell with an effective amount of a compound having a structure represented by a formula:

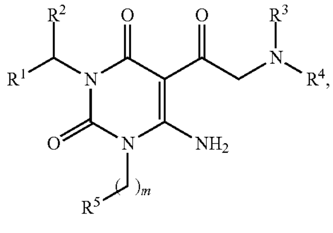

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$, when present, is independently selected from hydrogen and C1-C4 alkyl; wherein $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

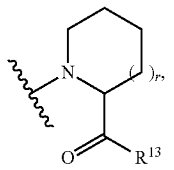

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^5$ is selected from $Ar^1$ and $Cy^6$; wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In a further aspect, disclosed are methods for modulating read-through of a premature termination codon in a call, the method comprising contacting the cell with an effective amount of a compound selected from:

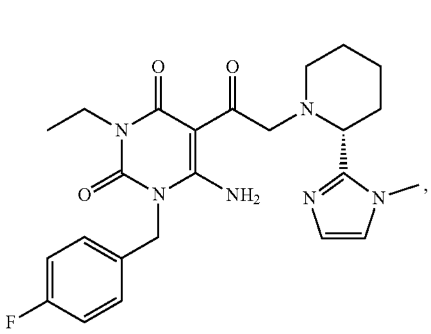
,

-continued
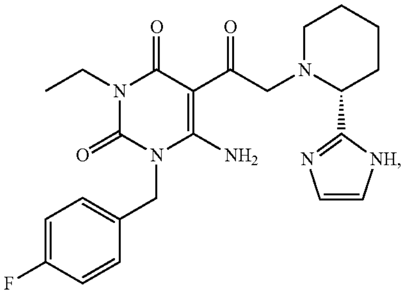
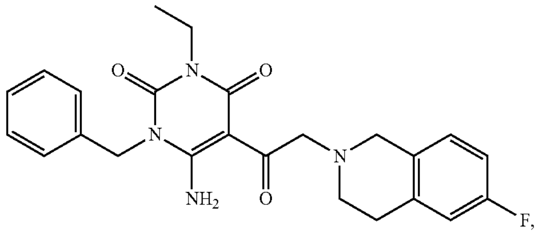
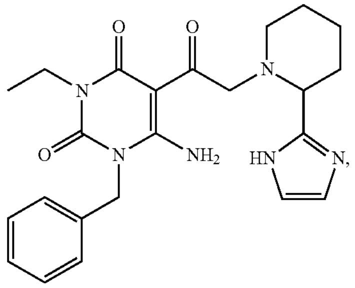
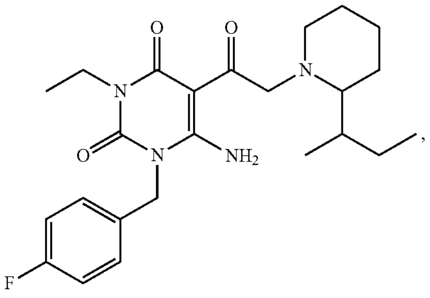
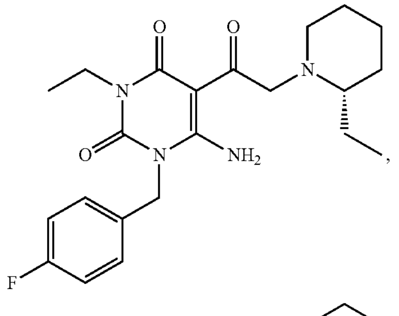
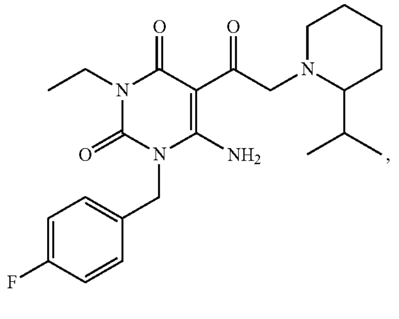
-continued
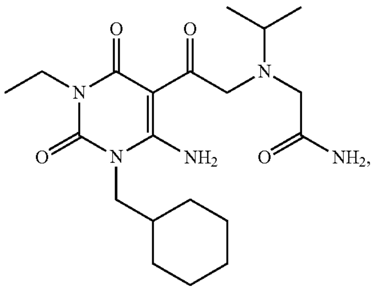
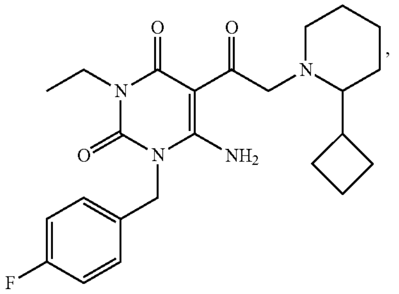
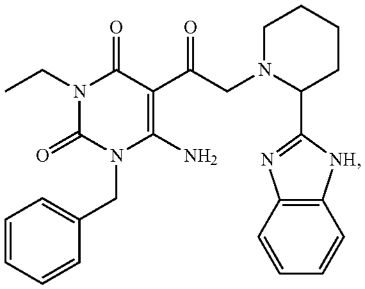
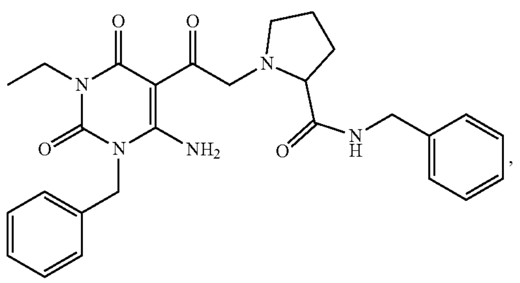
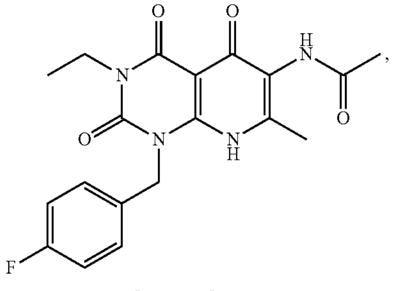
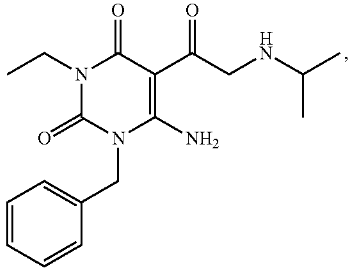

-continued
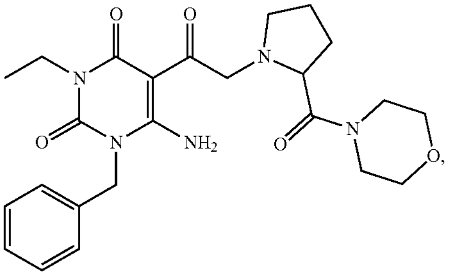
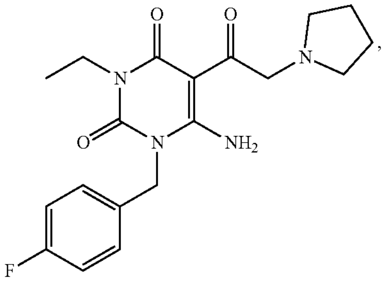
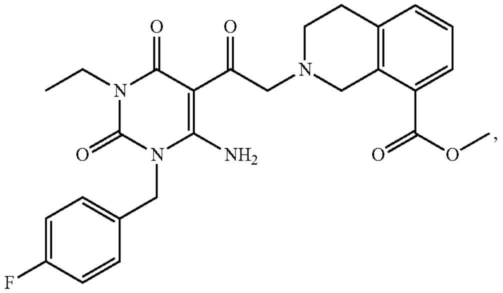
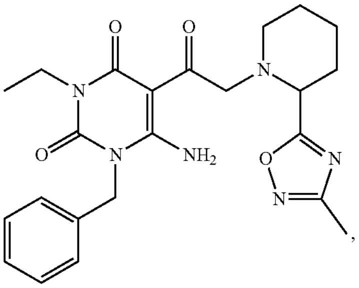
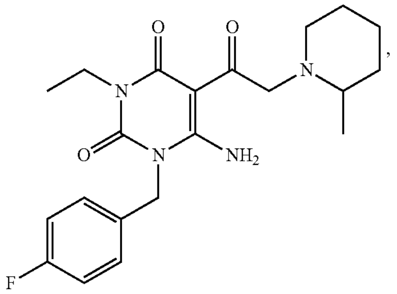
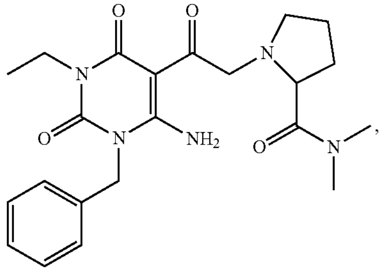
-continued
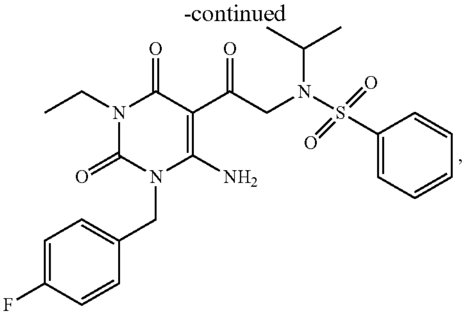
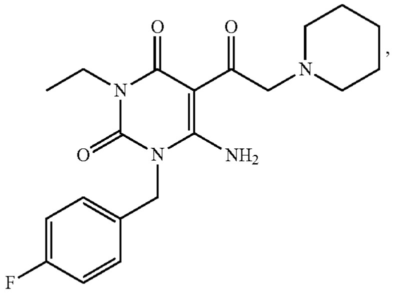
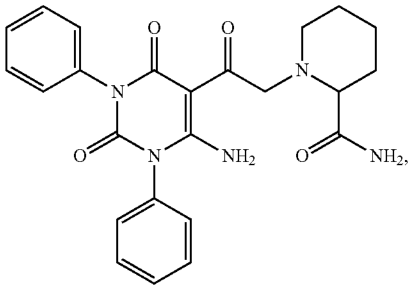
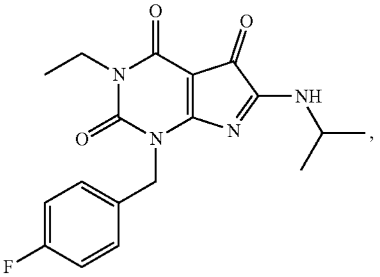
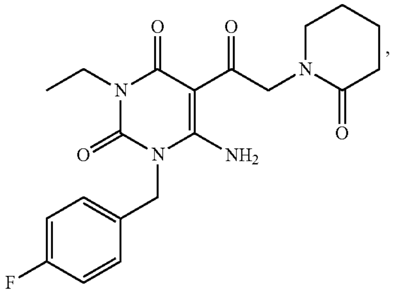
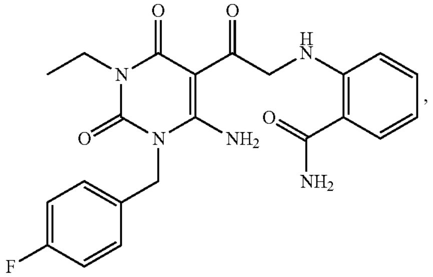

-continued
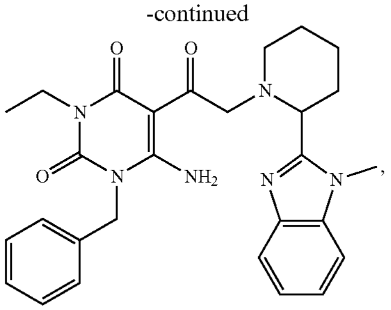
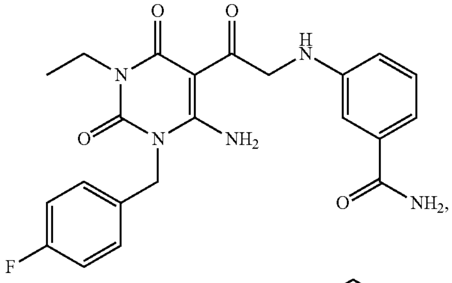
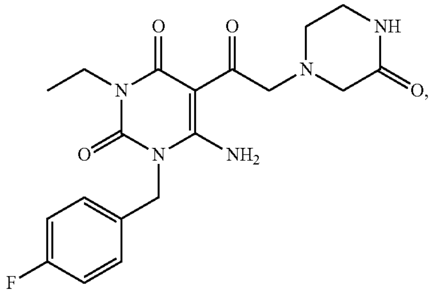
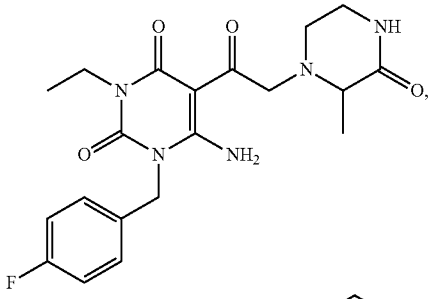
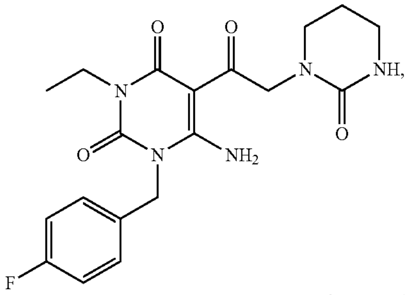
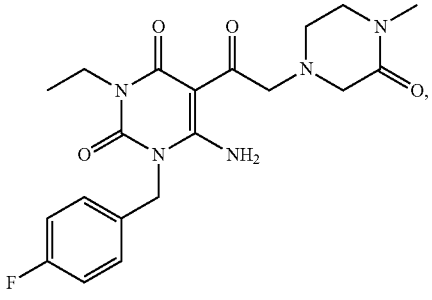
-continued
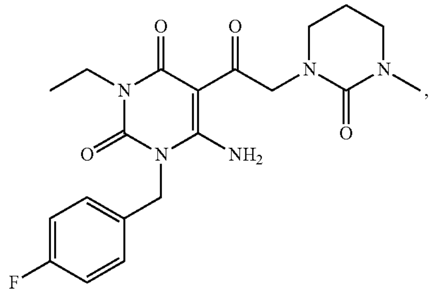
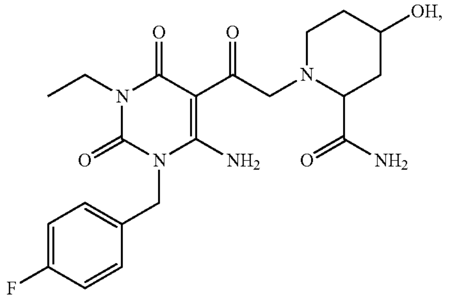
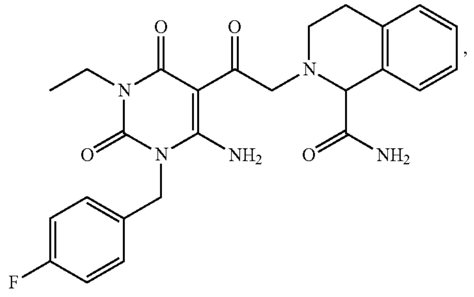
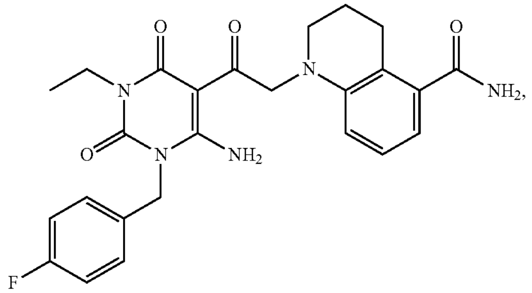
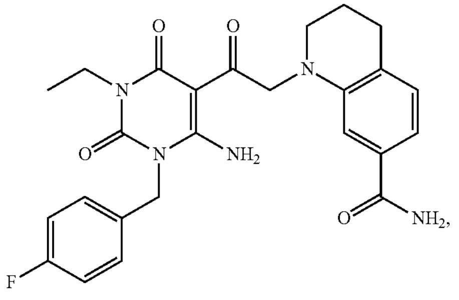

-continued

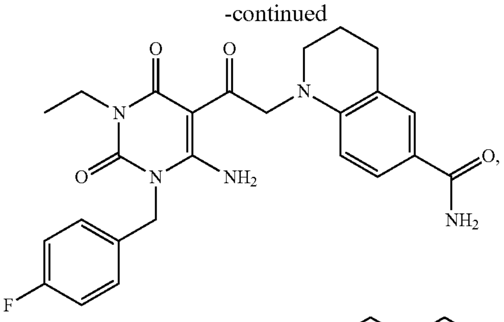 and

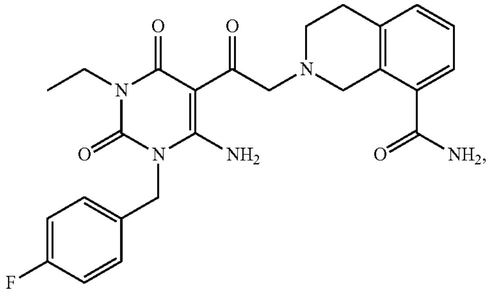

or a pharmaceutically acceptable salt thereof.

In a further aspect, disclosed are methods for modulating read-through of a premature termination codon in a cell, the method comprising contacting the cell with an effective amount of a compound having a structure represented by a formula:

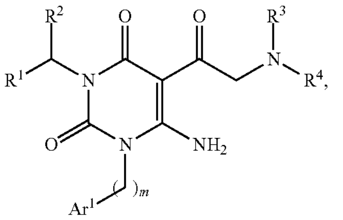

wherein m is 1 or 2; wherein $R^1$ is selected from C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein each occurrence of $R^{10a}$, when present, is independently selected from hydrogen and C1-C4 alkyl; wherein each occurrence of $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein each of $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O (C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

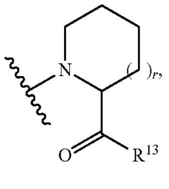

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-

C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when $R^4$ is —$(CR^{10a}R^{10b})_nC(O)R^{11}$, —$CH(R^{12})Ar^2$, or $Ar^2$, or when $R^3$ and $R^4$ together comprise a heterocycle having a structure represented by a formula:

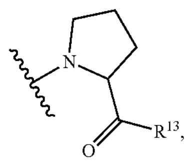

then $R^1$ is $Cy^1$ or $R^1$ and $R^2$ together comprise a C3-C6 cycloalkyl or a C3-C6 heterocycloalkyl, and provided that when $R^1$ is C1-C3 alkyl, $R^3$ and $R^4$ together comprise a heterocycle having a structure represented by a formula:

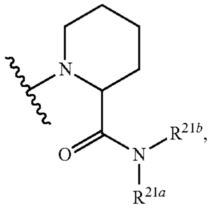

and $Ar^1$ is phenyl, then either (i) $Ar^1$ is substituted with at least one non-hydrogen group; or (ii) at least one of $R^{21a}$ and $R^{21b}$ is hydrogen, or a pharmaceutically acceptable salt thereof.

In a further aspect, modulating is increasing.

In a further aspect, the cell is mammalian. In a still further aspect, the cell is human. In yet a further aspect, the cell has been isolated from a human prior to the contacting step.

In a further aspect, contacting is via administration to a subject. In a still further aspect, the subject has been diagnosed with a need for modulating read-through of a premature termination codon prior to the administering step. In yet a further aspect, the subject has been diagnosed with a need for treatment of cystic fibrosis, Duchenne muscular dystrophy, aniridia, Becker muscular dystrophy, spinal muscular atrophy, Hurler syndrome, hemophilia, epidermolysis bullosa, Usher syndrome, neurofibromatosis, and cancer prior to the administering step.

In a further aspect, the premature termination codon is selected from E60X, Y122X, Q493X, G542X, G550X, R553X, Y1092X, R1162X, and W1282X.

In a further aspect, the compound exhibits activation of read-through of a premature termination codon. Thus, in various aspects, the compound exhibits activation of read-through of a premature termination codon with an $EC_{50}$ of less than 10 μM. In a further aspect, the compound has an $EC_{50}$ of less than 8 μM. In a still further aspect, the compound has an $EC_{50}$ of less than 6 μM. In yet a further aspect, the compound has an $EC_{50}$ of less than 4 μM. In an even further aspect, the compound has an $EC_{50}$ of less than 2 μM. In a still further aspect, the compound has an $EC_{50}$ of less than 1 μM. In yet a further aspect, the compound has an $EC_{50}$ of less than 0.8 μM. In an even further aspect, the compound has an $EC_{50}$ of less than 0.6 μM. In a still further aspect, the compound has an $EC_{50}$ of less than 0.4 μM. In yet a further aspect, the compound has an $EC_{50}$ of less than 0.2 μM. In an even further aspect, the compound has an $EC_{50}$ of less than 0.1 μM.

In a further aspect, the subject is a mammal. In a still further aspect, the subject is a human.

In a further aspect, administering stimulates read-through of the premature termination codon. In a still further aspect, administering increases the stability of a mRNA containing the premature termination codon.

In a further aspect, the effective amount is a therapeutically effective amount. In a still further aspect, the effective amount is a prophylactically effective amount.

In a further aspect, the disorder is selected from cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, neurofibromatosis, and cancer.

In a further aspect, the disorder is cancer. In a still further aspect, the cancer is associated with one or more mutations selected from a P53 mutation and an APC mutation.

In a further aspect, the disorder is cystic fibrosis.

In a further aspect, the subject has been diagnosed with a need for treatment of the disorder prior to the administering step. In a still further aspect, the method further comprises the step of identifying a subject in need of treatment of the disorder. In yet a further aspect, identifying comprises identifying the presence of a premature termination codon in the subject.

In a further aspect, the premature termination codon is selected from E60X, Y122X, Q493X, G542X, G550X, R553X, Y1092X, R1162X, and W1282X.

In a further aspect, the method further comprises administering a second active agent to the subject. In a still further aspect, the second active agent is selected from a CFTR modulator, an NMD inhibitor, and an agent that increases mRNA levels. In yet a further aspect, the CFTR polypeptide modulator is a CFTR potentiator (e.g., ivacaftor, VX-770, PG-01, tetrahydrobenzothiophene, GP-5), a CFTR amplifier, or a CFTR corrector (e.g., elexacaftor, lumacaftor, tezacaftor, Corr-4a, VX-809, C1, C2).

In a further aspect, the second active agent is a NMD inhibitor. Examples of NMD inhibitors include, but are not limited to, NMDI-1, NMDI-9, NMDI-25, and NMDI-14.

In a further aspect, the second active agent is an agent that increases mRNA levels. In a still further aspect, the agent that increases mRNA levels is a histone deacetylase inhibitor. In yet a further aspect, the histone deacetylase inhibitor is selected from vorinostat, romidepsin, panobinostat, and belinostat.

In a further aspect, the second active agent is an agent that increases general pulmonary function. In a still further aspect, the agent that increases general pulmonary function is selected from albuterol, salbuterol, recombinant DNAse, dornase alpha, inhaled tobramycin, amikracin, azithromycin, and hypertonic saline.

In a further aspect, the premature termination codon is in a CFTR.

In a further aspect, the second active agent is an aminoglycoside. Examples of aminoglycosides include, but are not limited to, G418, geneticin, amikacin, tobramycin, ELX-02, NB54, NB124, NB127, and NB83.

In a further aspect, the compound and the second active agent each modulate read-through of a premature termination codon via different mechanism. In a still further aspect, the compound and the second active agent each modulate read-through of a premature termination codon via the same mechanism. In yet a further aspect, the compound modulates read-through of a premature termination codon via degradation of translation termination factor eRF1. In an even further aspect, the second active agent modulates read-through of a premature termination codon via degradation of translation termination factor eRF3 (e.g., CC-9009) or via inhibition of SMG1 (e.g., via a SMG1 inhibitor).

In a further aspect, the second active agent is selected from erythromycin, artesunate, atazanavir, ataluren, genistein, and Y-320.

G. Methods of Treating a Disorder Associated with the Presence of A Premature Termination Codon in a Subject In various aspects, the compounds and pharmaceutical compositions of the invention are useful in treating or controlling disorders associated with the presence of a premature termination codon. See, e.g., Dabrowski et al. (2018) *Molecular Medicine* 24: 25; Lombardi et al. (2020) *Int. J. Mol. Sci.* 21: 9449. Examples of such disorders include, but are not limited to, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer.

Thus, in one aspect, disclosed are methods for treating a disorder associated with the presence of a premature termination codon in a subject in need thereof, the method comprising administering to the subject an effective amount of a disclosed compound, or a pharmaceutically acceptable salt thereof, thereby treating the disorder in the subject. In a further aspect, disclosed are methods for treating a disorder associated with the presence of a premature termination codon in a subject in need thereof, the method comprising administering to the subject an effective amount of a compound having a structure represented by a formula:

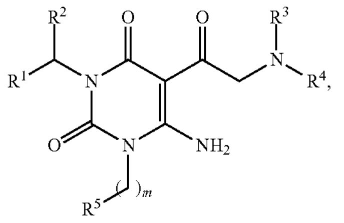

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from $—(CR^{10a}R^{10b})_nC(O)R^{11}$, $—CH(R^{12})Ar^2$, and $Ar^2$; wherein n, when present, is 1 or 2; wherein $R^{10a}$ when present, is independently selected from hydrogen and C1-C4 alkyl; wherein $R^{10b}$ when present, is independently selected from hydrogen, C1-C4 alkyl, —(C1-C4 alkyl)O(C1-C4 alkyl), and $—(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and $—NR^{20a}R^{20b}$; wherein $R^{20a}$ and $R^{20b}$, when present, is independently selected from hydrogen, C1-C8 alkyl, C1-C8 haloalkyl, and $—(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and $—(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $—C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

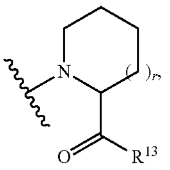

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^5$ is selected from $Ar^1$ and $Cy^6$; wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In a further aspect, disclosed are methods for treating a disorder associated with the presence of a premature termination codon in a subject in need thereof, the method comprising administering to the subject an effective amount of a compound selected from:

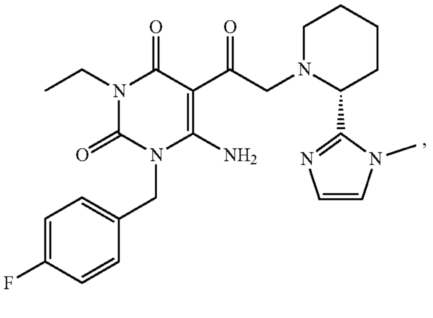

-continued

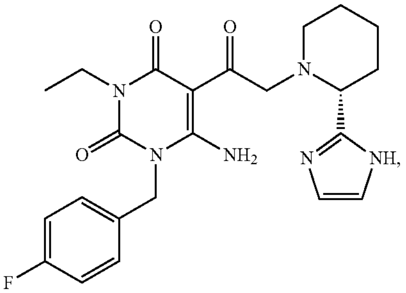

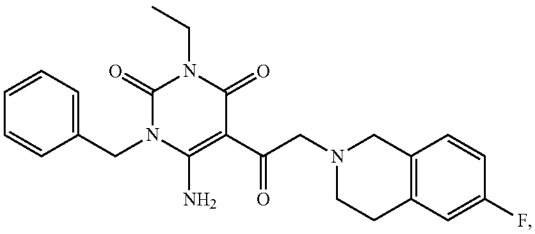

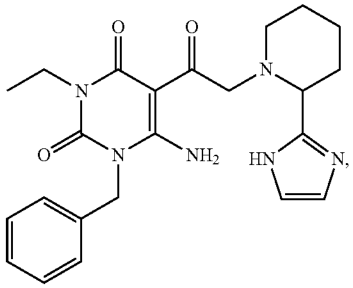

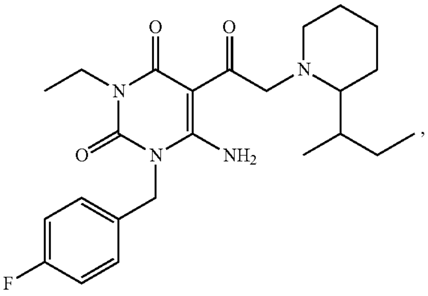

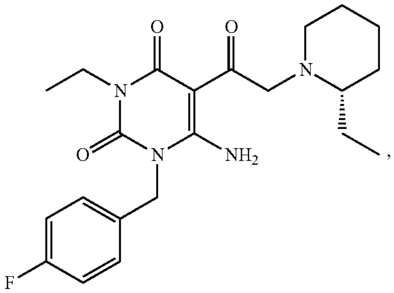

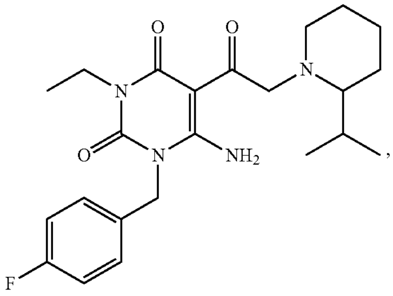

-continued
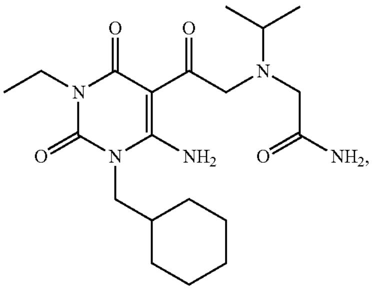
,
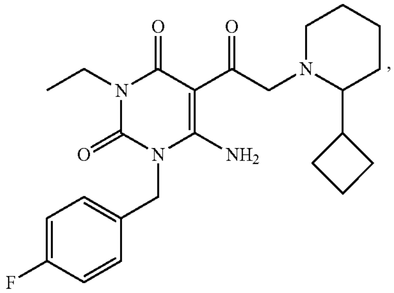
,
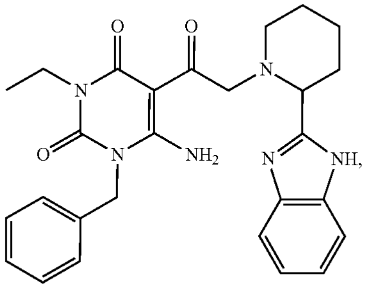
,
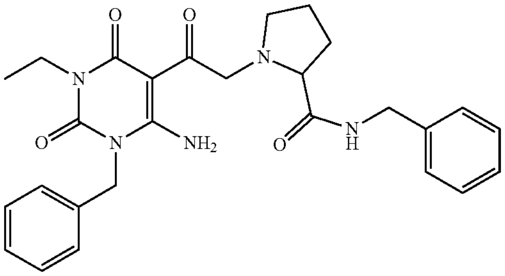
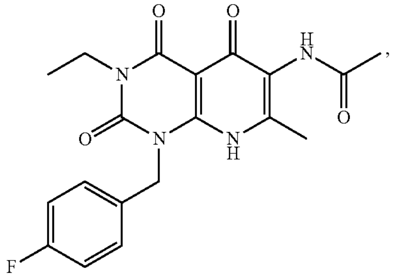
,
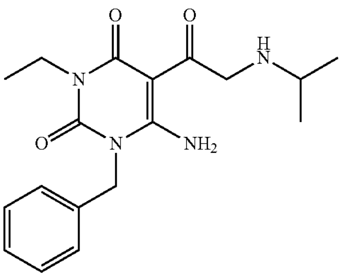
,
-continued
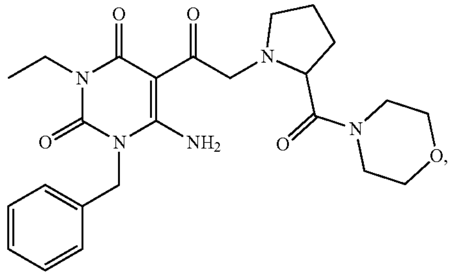
,
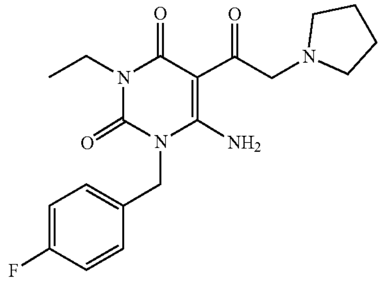
,
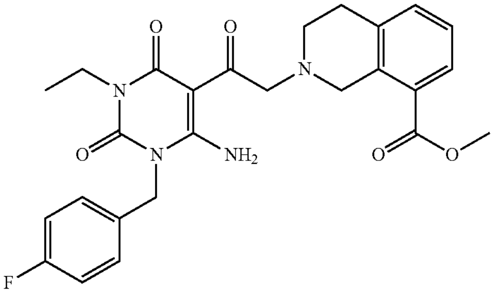
,
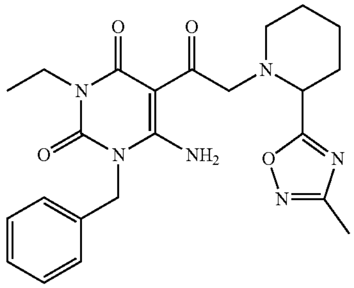
,
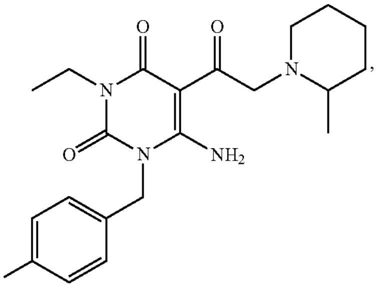
,
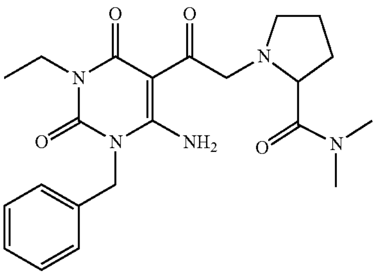
, -continued
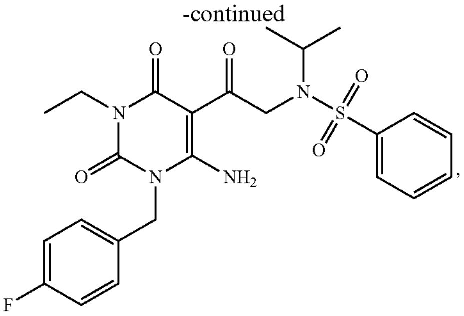
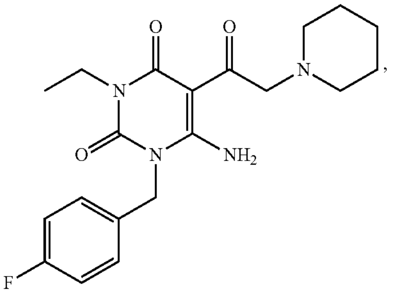
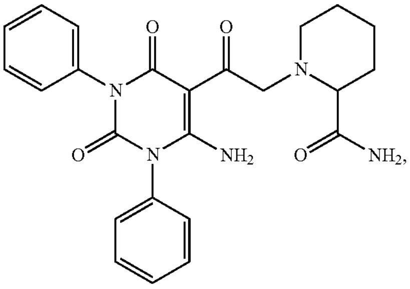
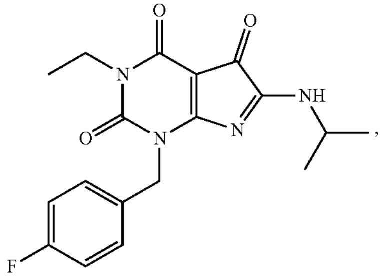
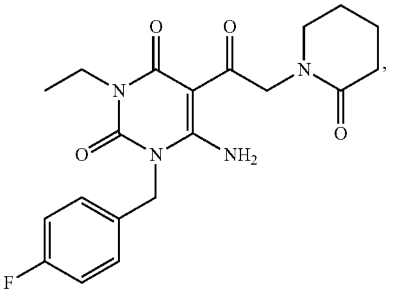
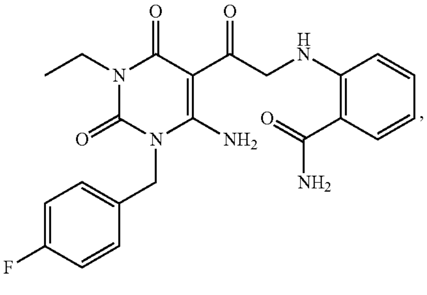
-continued
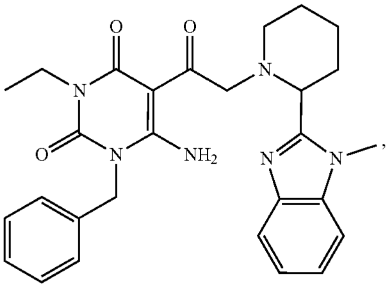
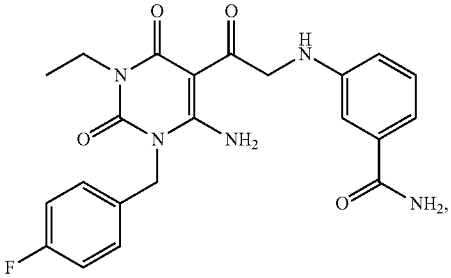
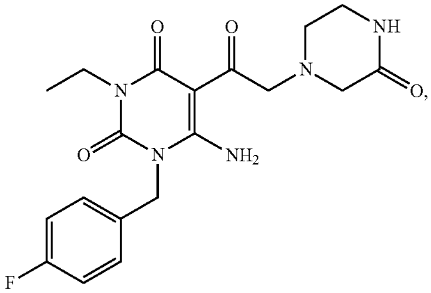
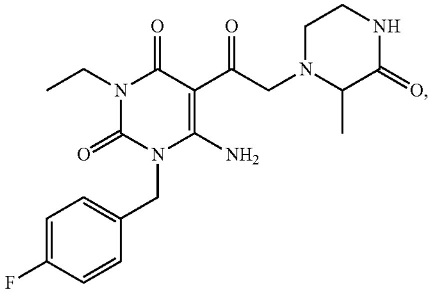
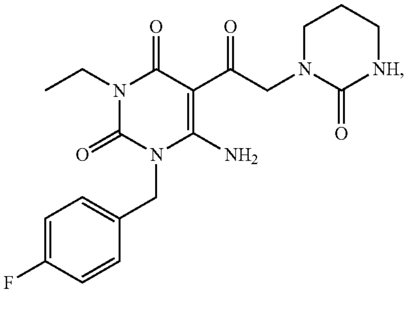

-continued

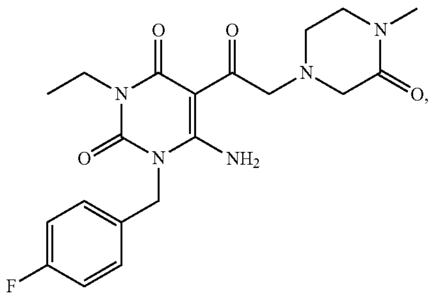

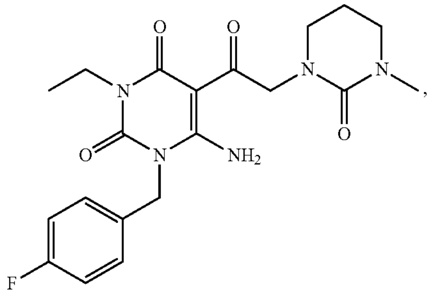

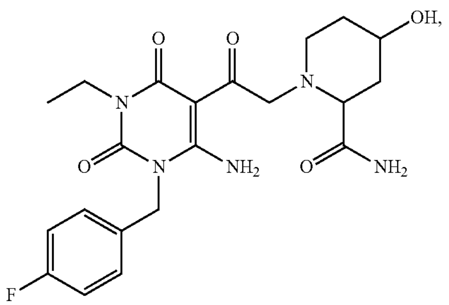

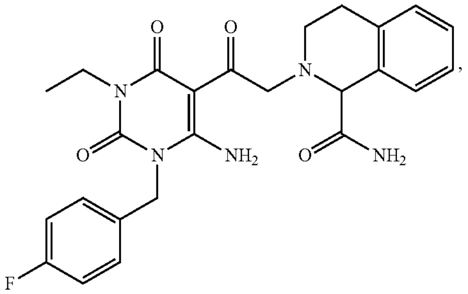

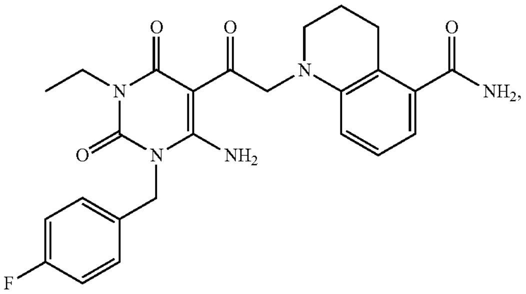

-continued

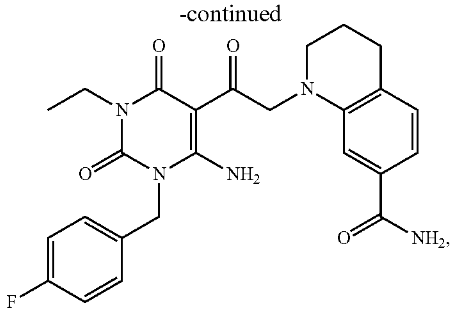

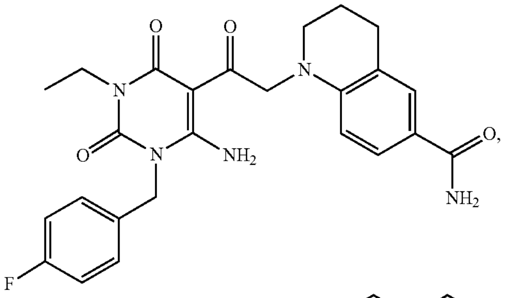

and

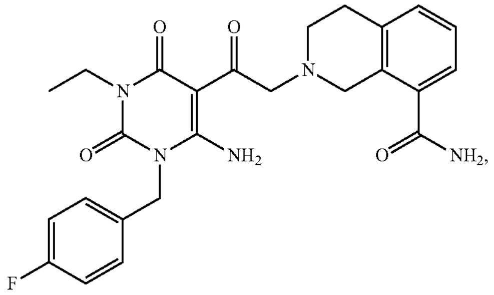

or a pharmaceutically acceptable salt thereof.

In a further aspect, disclosed are methods for treating a disorder associated with the presence of a premature termination codon in a subject in need thereof, the method comprising administering to the subject an effective amount of a compound having a structure represented by a formula:

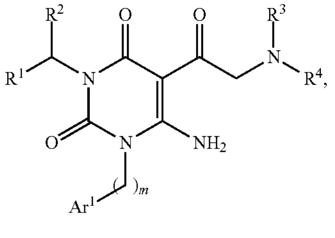

wherein m is 1 or 2; wherein $R^1$ is selected from C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein each occurrence of $R^{10a}$, when present, is independently selected from hydrogen and C1-C4 alkyl; wherein each occurrence of $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein each of $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O (C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

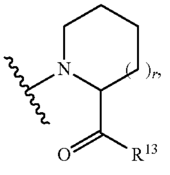

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when $R^4$ is —$(CR^{10a}R^{10b})_nC(O)R^{11}$, —$CH(R^{12})Ar^2$, or $Ar^2$, or when $R^3$ and $R^4$ together comprise a heterocycle having a structure represented by a formula:

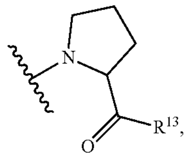

then $R^1$ is $Cy^1$ or $R^1$ and $R^2$ together comprise a C3-C6 cycloalkyl or a C3-C6 heterocycloalkyl, and provided that when $R^1$ is C1-C3 alkyl, $R^3$ and $R^4$ together comprise a heterocycle having a structure represented by a formula:

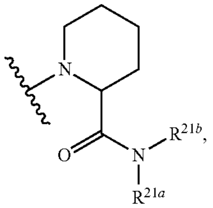

and $Ar^1$ is phenyl, then either (i) $Ar^1$ is substituted with at least one non-hydrogen group; or (ii) at least one of $R^{21a}$ and $R^{21b}$ is hydrogen, or a pharmaceutically acceptable salt thereof.

In a further aspect, the compound exhibits activition of read-through of a premature termination codon. Thus, in various aspects, the compound exhibits activation of read-through of a premature termination codon with an $EC_{50}$ of less than 10 μM. In a further aspect, the compound has an $EC_{50}$ of less than 8 μM. In a still further aspect, the compound has an $EC_{50}$ of less than 6 μM. In yet a further aspect, the compound has an $EC_{50}$ of less than 4 μM. In an even further aspect, the compound has an $EC_{50}$ of less than 2 μM. In a still further aspect, the compound has an $EC_{50}$ of less than 1 μM. In yet a further aspect, the compound has an $EC_{50}$ of less than 0.8 μM. In an even further aspect, the compound has an $EC_{50}$ of less than 0.6 μM. In a still further aspect, the compound has an $EC_{50}$ of less than 0.4 μM. In yet a further aspect, the compound has an $EC_{50}$ of less than 0.2 μM. In an even further aspect, the compound has an $EC_{50}$ of less than 0.1 μM.

In a further aspect, the subject is a mammal. In a still further aspect, the subject is a human.

In a further aspect, administering stimulates read-through of the premature termination codon. In a still further aspect, administering increases the stability of a mRNA containing the premature termination codon.

In a further aspect, the effective amount is a therapeutically effective amount. In a still further aspect, the effective amount is a prophylactically effective amount.

In a further aspect, the disorder is selected from cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, neurofibromatosis, and cancer.

In a further aspect, the disorder is cancer. In a still further aspect, the cancer is associated with one or more mutations selected from a P53 mutation and an APC mutation.

In a further aspect, the disorder is cystic fibrosis.

In a further aspect, the subject has been diagnosed with a need for treatment of the disorder prior to the administering step. In a still further aspect, the method further comprises the step of identifying a subject in need of treatment of the disorder. In yet a further aspect, identifying comprises identifying the presence of a premature termination codon in the subject.

In a further aspect, the premature termination codon is selected from E60X, Y122X, Q493X, G542X, G550X, R553X, Y1092X, R1162X, and W1282X.

In a further aspect, the method further comprises administering a second active agent to the subject. In a still further aspect, the second active agent is selected from a CFTR modulator, an NMD inhibitor, and an agent that increases mRNA levels. In yet a further aspect, the CFTR polypeptide modulator is a CFTR potentiator (e.g., ivacaftor, VX-770, PG-01, tetrahydrobenzothiophene, GP-5), a CFTR amplifier, or a CFTR corrector (e.g., elexacaftor, lumacaftor, tezacaftor, Corr-4a, VX-809, C1, C2).

In a further aspect, the second active agent is a NMD inhibitor. Examples of NMD inhibitors include, but are not limited to, NMDI-1, NMDI-9, NMDI-25, and NMDI-14.

In a further aspect, the second active agent is an agent that increases mRNA levels. In a still further aspect, the agent that increases mRNA levels is a histone deacetylase inhibitor. In yet a further aspect, the histone deacetylase inhibitor is selected from vorinostat, romidepsin, panobinostat, and belinostat.

In a further aspect, the second active agent is an agent that increases general pulmonary function. In a still further aspect, the agent that increases general pulmonary function is selected from albuterol, salbuterol, recombinant DNAse, dornase alpha, inhaled tobramycin, amikracin, azithromycin, and hypertonic saline.

In a further aspect, the premature termination codon is in a CFTR.

In a further aspect, the second active agent is an aminoglycoside. Examples of aminoglycosides include, but are not limited to, G418, geneticin, amikacin, tobramycin, ELX-02, NB54, NB124, NB127, and NB83.

In a further aspect, the compound and the second active agent each modulate read-through of a premature termination codon via different mechanism. In a still further aspect, the compound and the second active agent each modulate read-through of a premature termination codon via the same mechanism. In yet a further aspect, the compound modulates read-through of a premature termination codon via degradation of translation termination factor eRF1. In an even further aspect, the second active agent modulates read-through of a premature termination codon via degradation of translation termination factor eRF3 (e.g., CC-9009) or via inhibition of SMG1 (e.g., via a SMG1 inhibitor).

In a further aspect, the second active agent is selected from erythromycin, artesunate, atazanavir, ataluren, genistein, and Y-320.

H. Methods of Treating a Disorder in a Subject Identified as Having A Premature Termination Codon In various aspects, the compounds and pharmaceutical compositions of the invention are useful in treating or controlling disorders in a subject identified as having a premature termination codon. Exemplary disorders include, but are not limited to, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer.

Thus, in one aspect, disclosed are methods for treating a disorder in a subject identified as having a premature termination codon, the method administering to the subject an effective amount of a disclosed compound, or a pharmaceutically acceptable salt thereof, thereby treating the disorder in the subject. In a further aspect, disclosed are methods for treating a disorder in a subject identified as having a premature termination codon, the method comprising administering to the subject an effective amount of a compound having a structure represented by a formula:

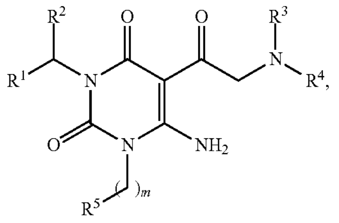

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$, when present, is independently selected from hydrogen and C1-C4 alkyl; wherein $R^{10b}$ when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

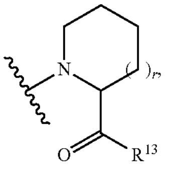

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^5$ is selected from $Ar^1$ and $Cy^6$; wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In a further aspect, disclosed are methods for treating a disorder in a subject identified as having a premature termination codon, the method comprising administering to the subject an effective amount of a compound selected from:

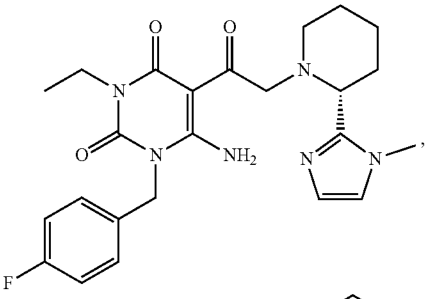

,

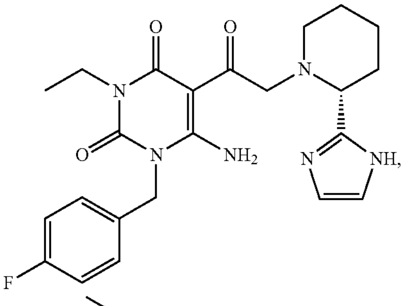

,

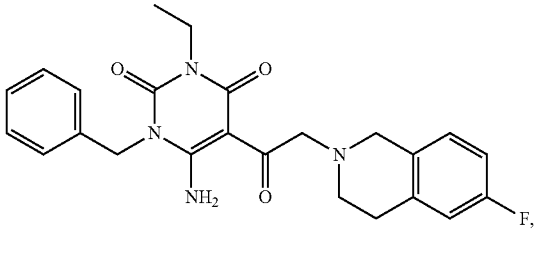

,

-continued
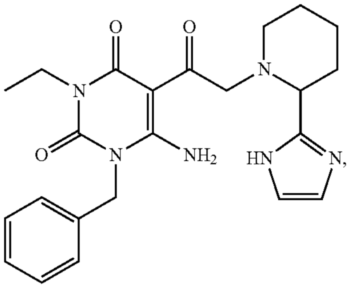
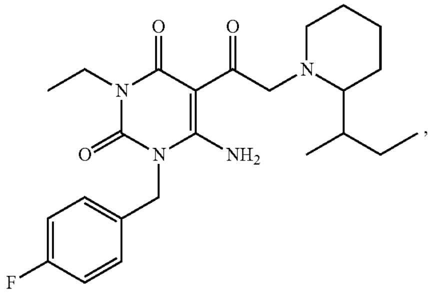
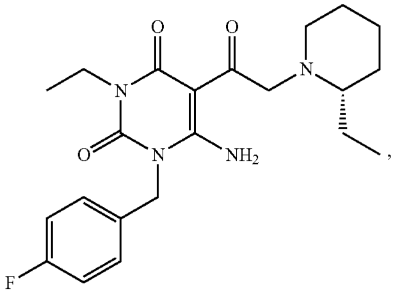
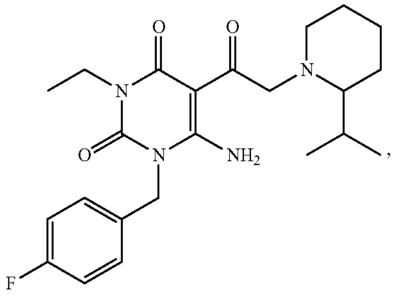
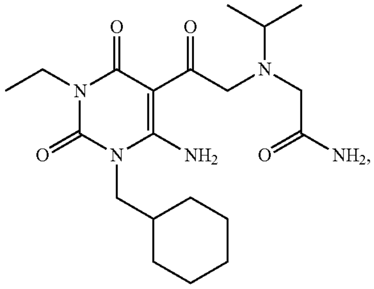
-continued
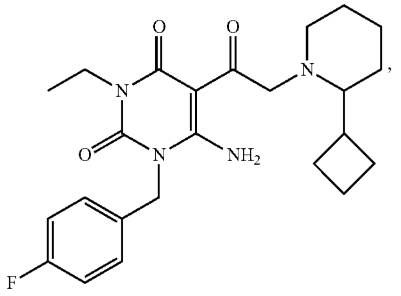
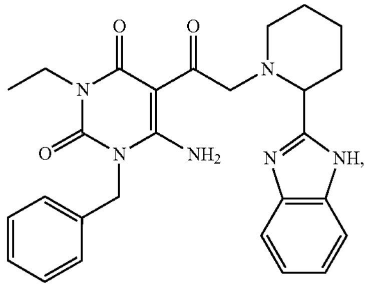
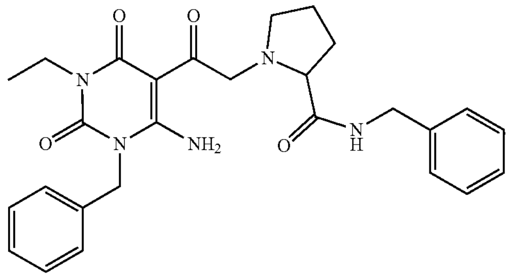
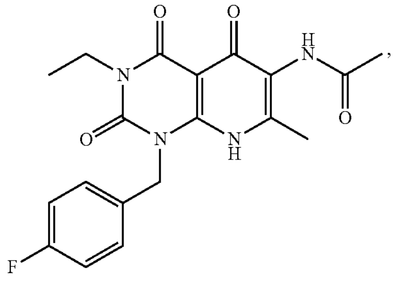
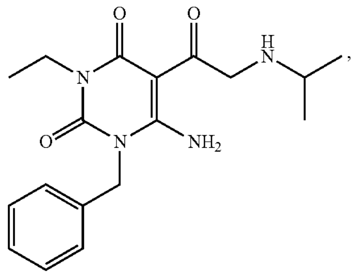
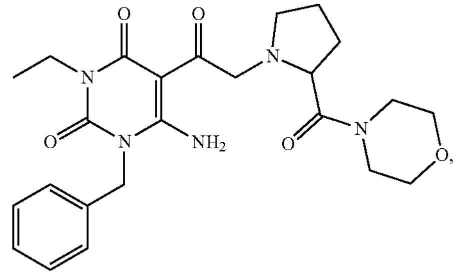

-continued
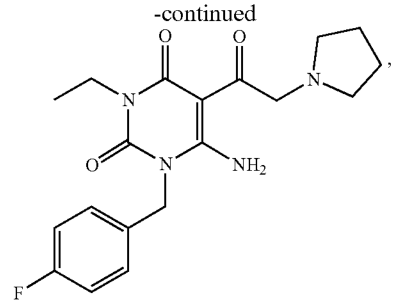
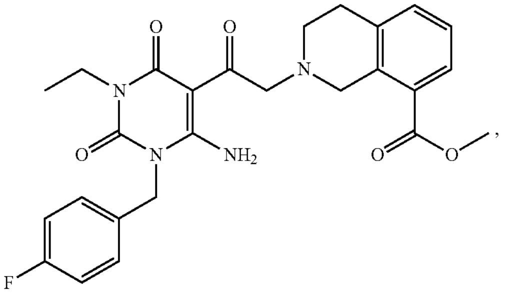
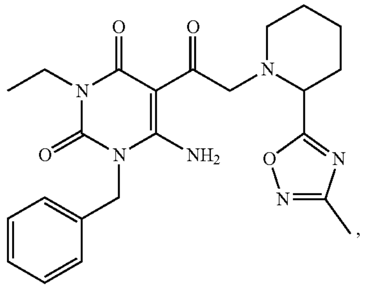
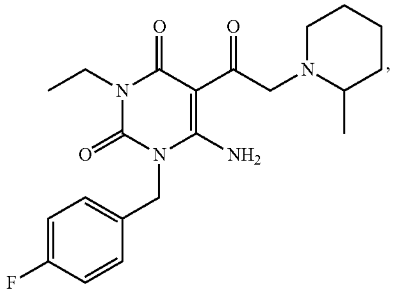
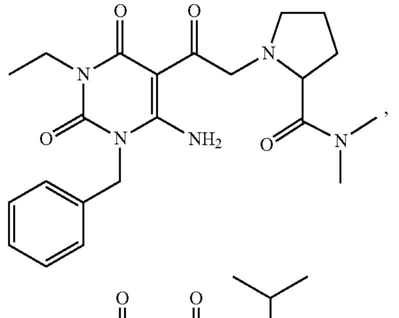
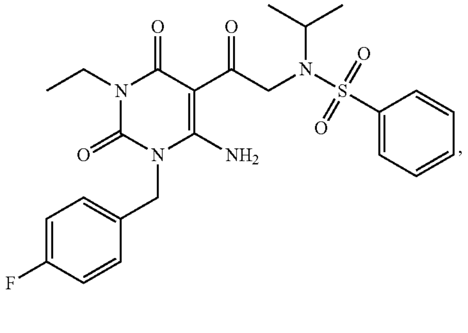
-continued
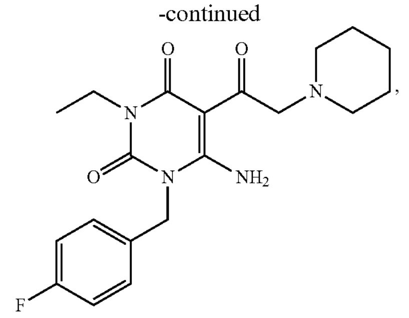
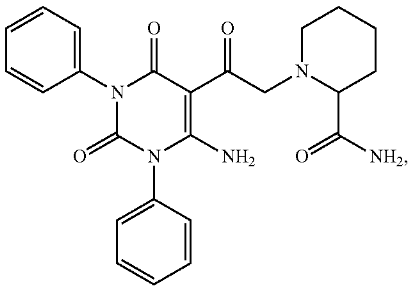
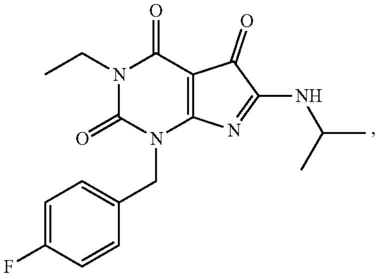
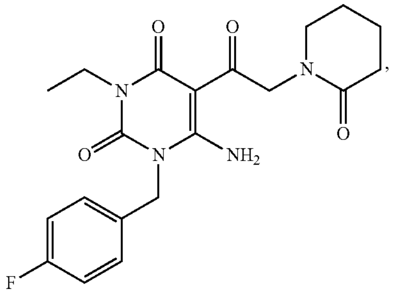
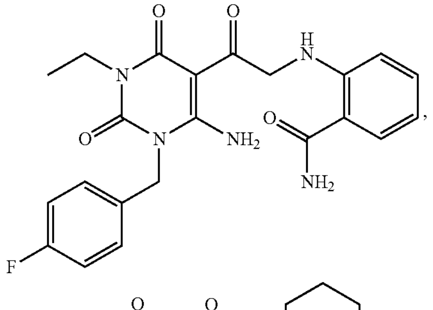
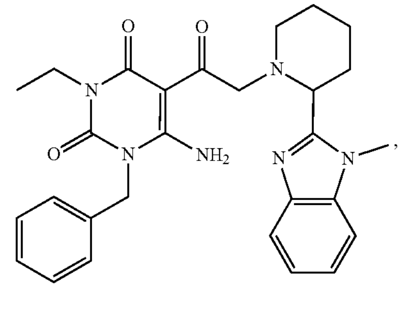

-continued
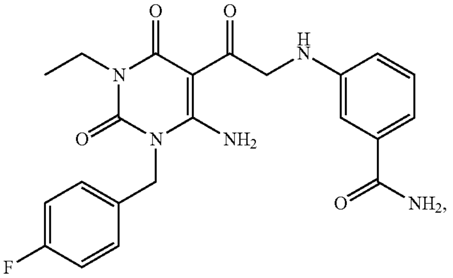,
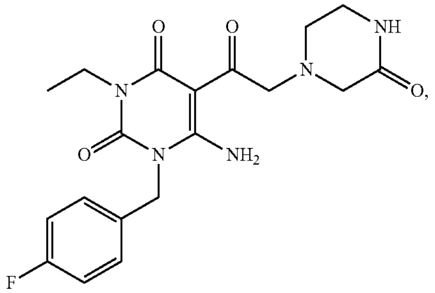,
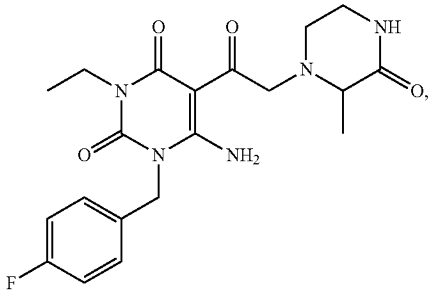,
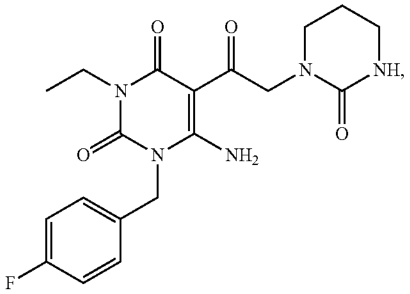,
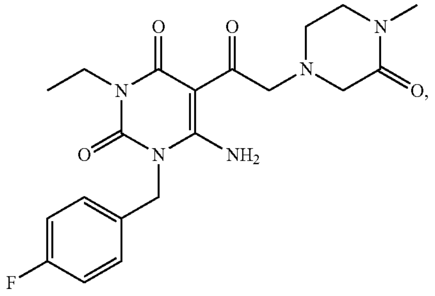,
-continued
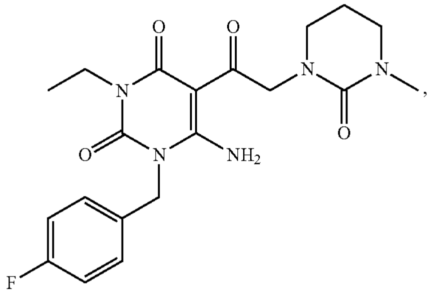,
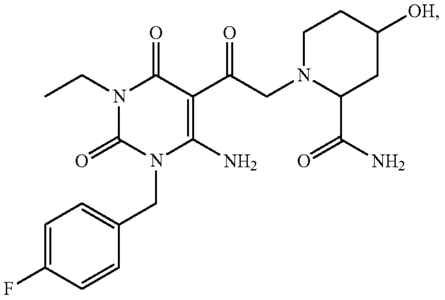,
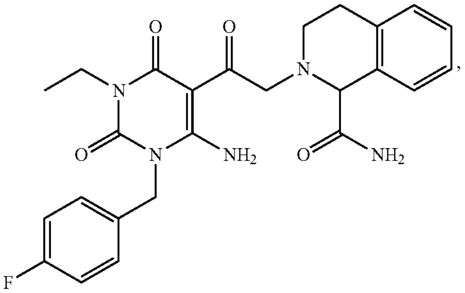,
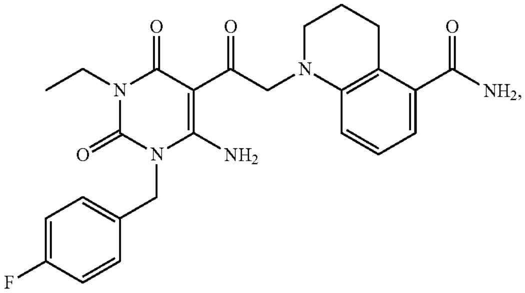,
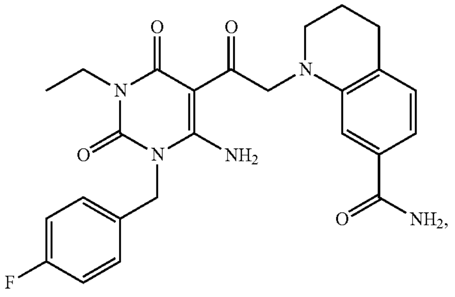, -continued

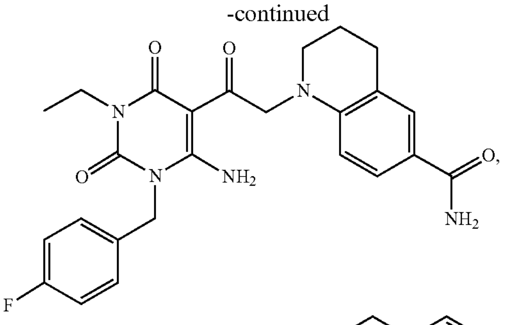

and

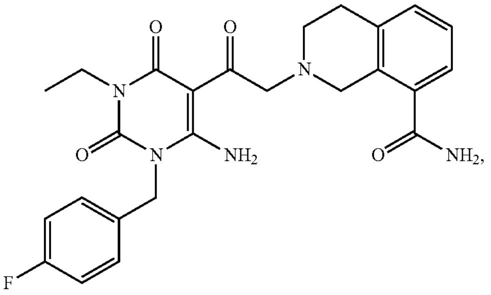

or a pharmaceutically acceptable salt thereof.

In a further aspect, disclosed are methods for treating a disorder in a subject identified as having a premature termination codon, the method comprising administering to the subject an effective amount of a compound having a structure represented by a formula:

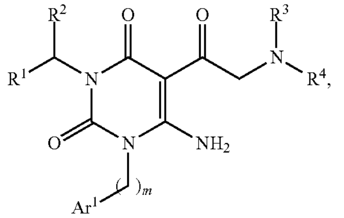

wherein m is 1 or 2; wherein $R^1$ is selected from C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein each occurrence of $R^{10a}$, when present, is independently selected from hydrogen and C1-C4 alkyl; wherein each occurrence of $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein each of $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O (C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

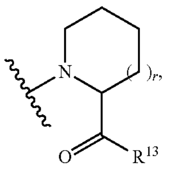

wherein r is 0 or 1; and wherein $R^{13}$ is selected from C1-C4 alkoxy and —$NR^{21a}R^{21b}$; wherein each of $R^{21a}$ and $R^{21b}$, when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-

C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^1$ is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when $R^4$ is —$(CR^{10a}R^{10b})_nC(O)R^{11}$, —$CH(R^{12})Ar^2$, or $Ar^2$, or when $R^3$ and $R^4$ together comprise a heterocycle having a structure represented by a formula:

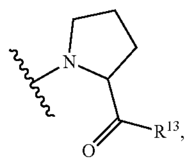

then $R^1$ is $Cy^1$ or $R^1$ and $R^2$ together comprise a C3-C6 cycloalkyl or a C3-C6 heterocycloalkyl, and provided that when $R^1$ is C1-C3 alkyl, $R^3$ and $R^4$ together comprise a heterocycle having a structure represented by a formula:

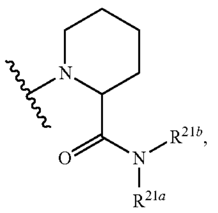

and $Ar^1$ is phenyl, then either (i) $Ar^1$ is substituted with at least one non-hydrogen group; or (ii) at least one of $R^{21a}$ and $R^{21b}$ is hydrogen, or a pharmaceutically acceptable salt thereof.

In a further aspect, the compound exhibits activation of read-through of a premature termination codon. Thus, in various aspects, the compound exhibits activation of read-through of a premature termination codon with an $EC_{50}$ of less than 10 μM. In a further aspect, the compound has an $EC_{50}$ of less than 8 μM. In a still further aspect, the compound has an $EC_{50}$ of less than 6 μM. In yet a further aspect, the compound has an $EC_{50}$ of less than 4 μM. In an even further aspect, the compound has an $EC_{50}$ of less than 2 μM. In a still further aspect, the compound has an $EC_{50}$ of less than 1 μM. In yet a further aspect, the compound has an $EC_{50}$ of less than 0.8 μM. In an even further aspect, the compound has an $EC_{50}$ of less than 0.6 μM. In a still further aspect, the compound has an $EC_{50}$ of less than 0.4 μM. In yet a further aspect, the compound has an $EC_{50}$ of less than 0.2 μM. In an even further aspect, the compound has an $EC_{50}$ of less than 0.1 μM.

In a further aspect, the subject is a mammal. In a still further aspect, the subject is a human.

In a further aspect, administering stimulates read-through of the premature termination codon. In a still further aspect, administering increases the stability of a mRNA containing the premature termination codon.

In a further aspect, the effective amount is a therapeutically effective amount. In a still further aspect, the effective amount is a prophylactically effective amount.

In a further aspect, the disorder is selected from cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, neurofibromatosis, and cancer.

In a further aspect, the disorder is cancer. In a still further aspect, the cancer is associated with one or more mutations selected from a P53 mutation and an APC mutation.

In a further aspect, the disorder is cystic fibrosis.

In a further aspect, the subject has been diagnosed with a need for treatment of the disorder prior to the administering step. In a still further aspect, the method further comprises the step of identifying a subject in need of treatment of the disorder. In yet a further aspect, identifying comprises identifying the presence of a premature termination codon in the subject.

In a further aspect, the premature termination codon is selected from E60X, Y122X, Q493X, G542X, G550X, R553X, Y1092X, R1162X, and W1282X.

In a further aspect, the method further comprises administering a second active agent to the subject. In a still further aspect, the second active agent is selected from a CFTR modulator, an NMD inhibitor, and an agent that increases mRNA levels. In yet a further aspect, the CFTR polypeptide modulator is a CFTR potentiator (e.g., ivacaftor, VX-770, PG-01, tetrahydrobenzothiophene, GP-5), a CFTR amplifier, or a CFTR corrector (e.g., elexacaftor, lumacaftor, tezacaftor, Corr-4a, VX-809, C1, C2).

In a further aspect, the second active agent is a NMD inhibitor. Examples of NMD inhibitors include, but are not limited to, NMDI-1, NMDI-9, NMDI-25, and NMDI-14.

In a further aspect, the second active agent is an agent that increases mRNA levels. In a still further aspect, the agent that increases mRNA levels is a histone deacetylase inhibitor. In yet a further aspect, the histone deacetylase inhibitor is selected from vorinostat, romidepsin, panobinostat, and belinostat.

In a further aspect, the second active agent is an agent that increases general pulmonary function. In a still further aspect, the agent that increases general pulmonary function is selected from albuterol, salbuterol, recombinant DNAse, dornase alpha, inhaled tobramycin, amikracin, azithromycin, and hypertonic saline.

In a further aspect, the premature termination codon is in a CFTR.

In a further aspect, the second active agent is an aminoglycoside. Examples of aminoglycosides include, but are not limited to, G418, geneticin, amikacin, tobramycin, ELX-02, NB54, NB124, NB127, and NB83.

In a further aspect, the compound and the second active agent each modulate read-through of a premature termination codon via different mechanism. In a still further aspect, the compound and the second active agent each modulate read-through of a premature termination codon via the same mechanism. In yet a further aspect, the compound modulates read-through of a premature termination codon via degradation of translation termination factor eRF1. In an even further aspect, the second active agent modulates read-through of a premature termination codon via degradation of translation termination factor eRF3 (e.g., CC-9009) or via inhibition of SMG1 (e.g., via a SMG1 inhibitor).

In a further aspect, the second active agent is selected from erythromycin, artesunate, atazanavir, ataluren, genistein, and Y-320.

I. Use of Compounds

In one aspect, the invention relates to the use of a disclosed compound or a product of a disclosed method. In a further aspect, a use relates to the manufacture of a medicament for the treatment of a disorder associated with the presence of a premature termination codon such as, for example, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder associated with the presence of a premature termination codon in a subject. Also disclosed is the use of a compound for inhibition of read-through of a premature termination codon. In one aspect, the use is characterized in that the subject is a human. In one aspect, the use is characterized in that the disorder is cystic fibrosis.

In a further aspect, the use relates to the manufacture of a medicament for the treatment of a disorder associated with the presence of a premature termination codon in a subject.

In a further aspect, the use relates to modulation of read-through of a premature termination codon in a subject. In a further aspect, the use relates to modulation of read-through of a premature termination codon in a subject. In a still further aspect, the use relates to modulation of read-through of a premature termination codon in a cell. In yet a further aspect, the subject is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a disorder associated with the presence of a premature termination codon in a mammal. In a further aspect, the disorder is selected from cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, and cancer.

J. Manufacture of a Medicament

In one aspect, the invention relates to a method for the manufacture of a medicament for treating a disorder associated with the presence of a premature termination codon in a subject in need thereof, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of read-through of a premature termination codon. The dose administered to an animal, particularly a human, in the context of the present invention should be sufficient to affect a therapeutic response in the animal over a reasonable timeframe. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

K. Kits

In one aspect, disclosed are kits comprising an effective amount of a disclosed compound, or a pharmaceutically acceptable salt thereof, and one or more selected from: (a) at least one agent known for the treatment of a disorder associated with the presence of a premature termination codon; (b) at least one device known for the treatment of a disorder associated with the presence of a premature termination codon; (c) instructions for administering the compound in connection with treating a disorder associated with the presence of a premature termination codon; (d) instructions for administering the compound in connection with reducing the risk of a disorder associated with the presence of a premature termination codon; and (e) instructions for treating a disorder associated with the presence of a premature termination codon.

In one aspect, disclosed are kits comprising a compound having a structure represented by a formula:

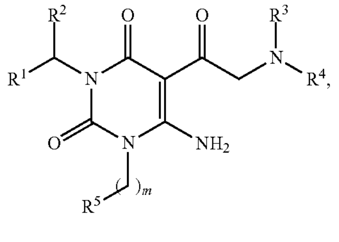

wherein m is 1 or 2; wherein $R^1$ is selected from —C1-C3 alkyl and $Cy^1$; wherein $Cy^1$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is selected from hydrogen and C1-C4 alkyl; or wherein $R^1$ and $R^2$ together comprise a C3-C6 cycloalkyl or a C3-C6 heterocycloalkyl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from hydrogen and C1-C4 alkyl; and wherein $R^4$ is selected from —$(CR^{10a}R^{10b})_nC(O)R^{11}$, —$CH(R^{12})Ar^2$, and $Ar^2$; wherein n, when present, is 1 or 2; wherein $R^{10a}$ when present, is independently selected from hydrogen and C1-C4 alkyl; wherein $R^{10b}$, when present, is independently selected from hydrogen, C1-C4 alkyl, —(C1-C4 alkyl)O(C1-C4 alkyl), and —$(CH_2)_oCy^2$; wherein o, when present, is 0 or 1; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{11}$, when present, is selected from C1-C4 alkoxy and —$NR^{20a}R^{20b}$; wherein $R^{20a}$ and $R^{20b}$, when present, is independently selected from hydrogen, C1-C8 alkyl, C1-C8 haloalkyl, and —$(CH_2)_pCy^3$; wherein p, when present, is 0, 1, or 2; and wherein $Cy^3$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{20a}$ and $R^{20b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{12}$, when present, is selected from hydrogen, C1-C4 alkyl, —(C1-C4 alkyl)O(C1-C4 alkyl), and —$(CH_2)_qCy^4$; wherein q, when present, is 0 or 1; wherein $Cy^4$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, oxo, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —$C(O)NH_2$, —C(O)NH(C1-C4 alkyl), and —C(O)N(C1-C4 alkyl)(C1-C4 alkyl); or wherein $R^3$ and $R^4$ together comprise a heterocycle having a structure represented by a formula:

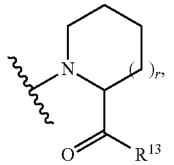

wherein r is 0 or 1; and wherein $R^{13}$ is selected from C1-C4 alkoxy and —$NR^{21a}R^{21b}$; wherein each of $R^{21a}$ and $R^{21b}$ when present, is independently selected from hydrogen, C1-C8 alkyl, C1-C8 haloalkyl, and —$(CH_2)_sCy^5$; wherein s, when present, is 0, 1, or 2; and wherein $Cy^5$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{21a}$ and $R^{21b}$, when present, together comprise a 5- to 10-membered heterocycle substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^5$ is selected from $Ar^1$ and $Cy^6$; wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^6$, when present, is selected from C3-C6 cycloalkyl and C3-C6 heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and one or more selected from: (a) at least one agent known for the treatment of a disorder associated with the presence of a premature termination codon; (b) at least one device known for the treatment of a disorder associated with the presence of a premature termination codon; (c) instructions for administering the compound in connection with treating a disorder associated with the presence of a premature termination codon; (d) instructions for administering the compound in connection with reducing the risk of a disorder associated with the presence of a premature termination codon; and (e) instructions for treating a disorder associated with the presence of a premature termination codon.

In one aspect, disclosed are kits comprising a compound selected from:

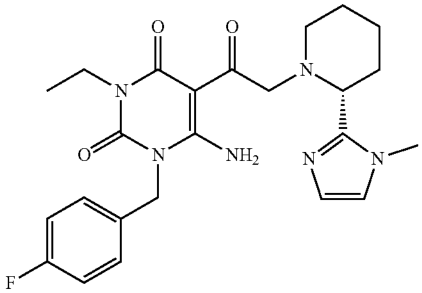
,

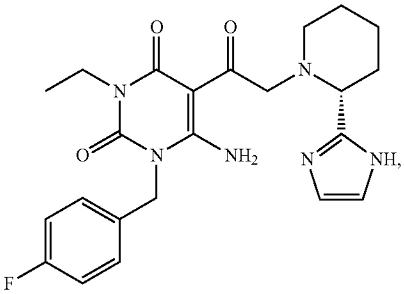
,

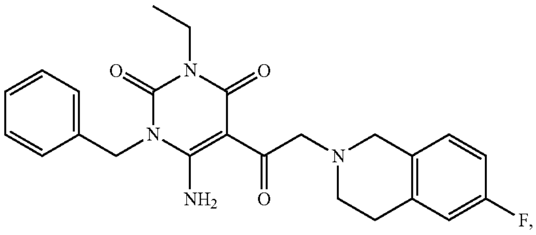
,

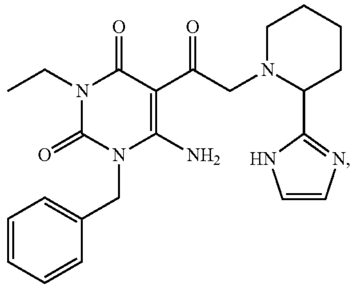
,

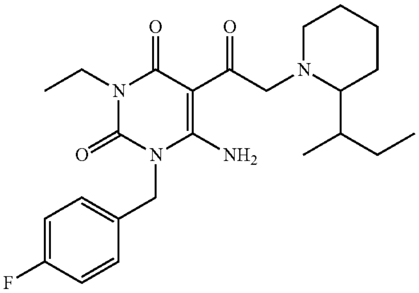
,

-continued

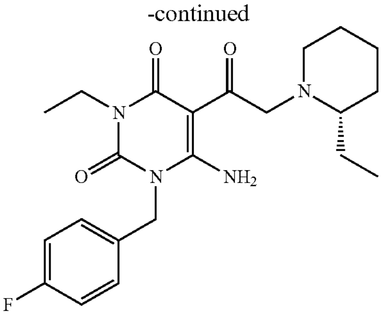
,

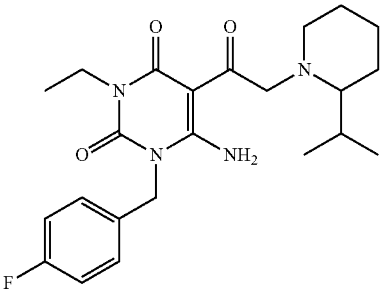
,

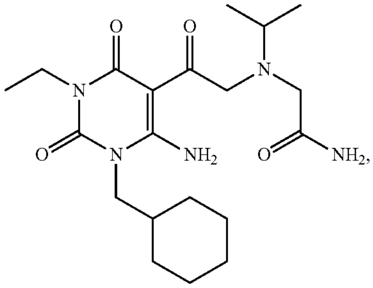
,

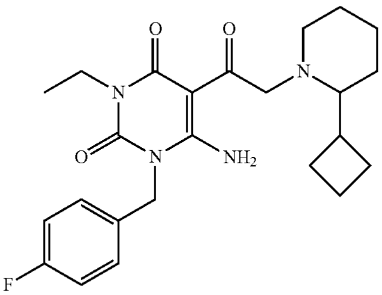
,

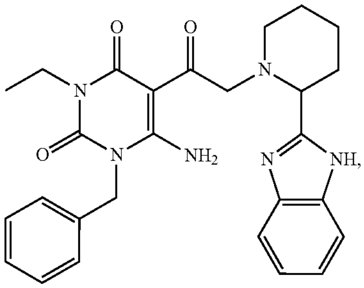
,

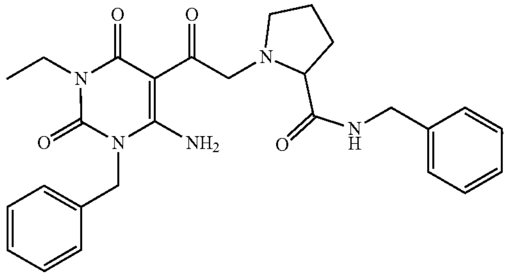

-continued
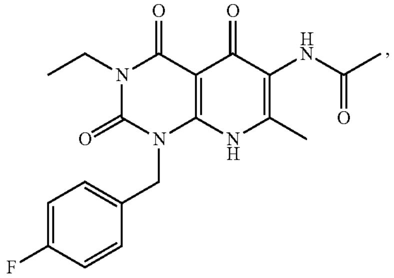
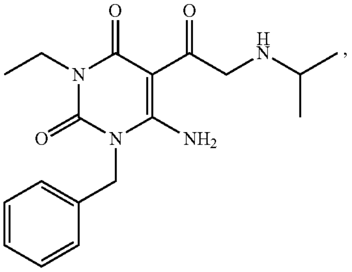
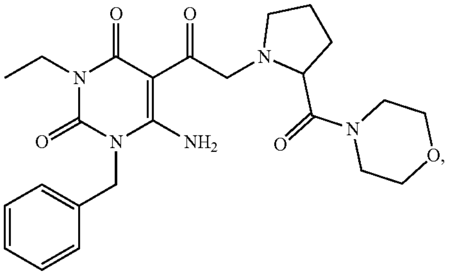
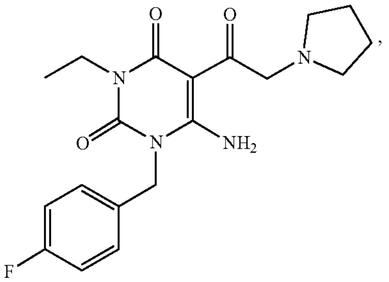
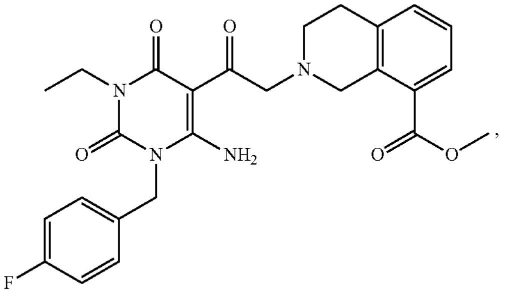
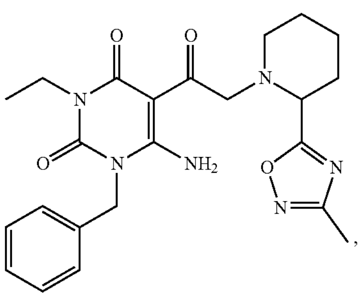
-continued
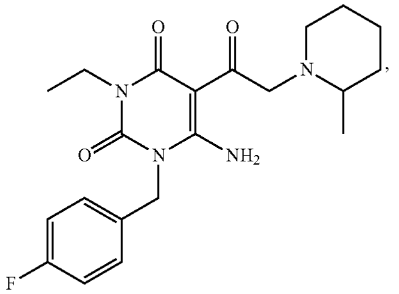
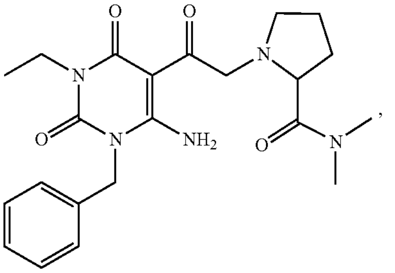
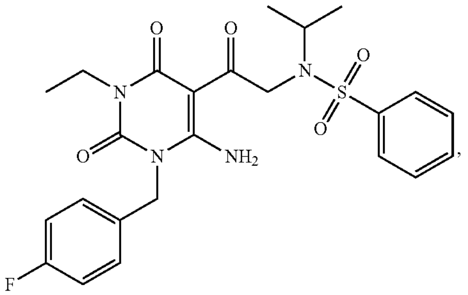
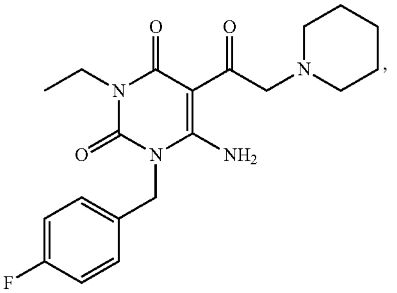
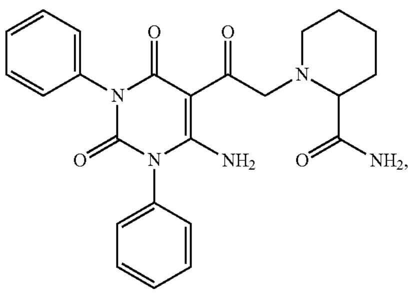
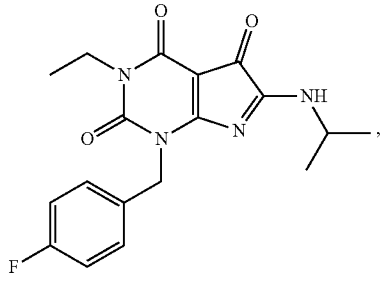

-continued
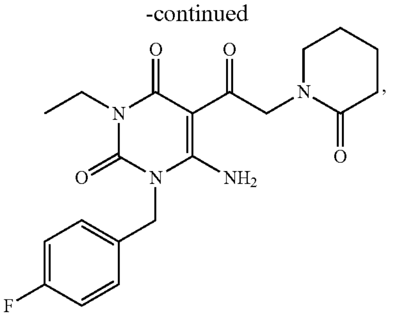
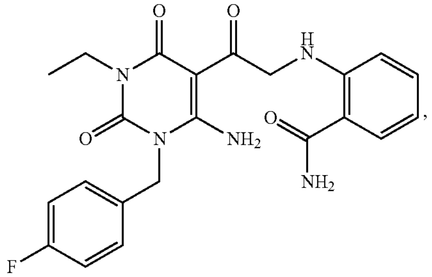
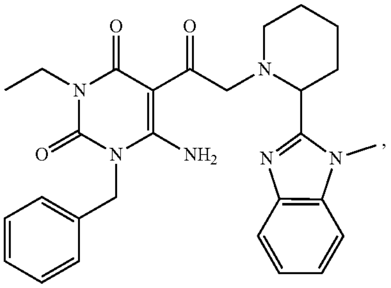
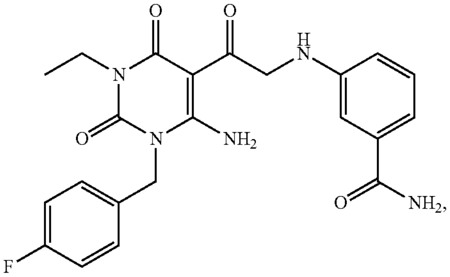
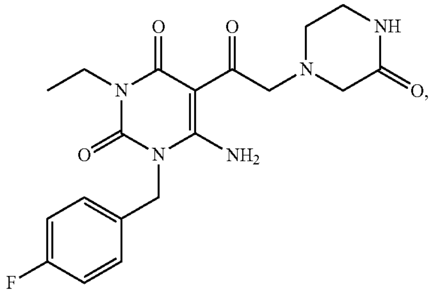
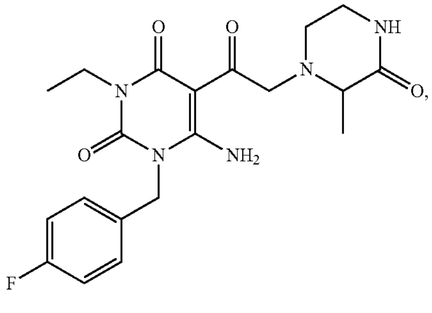
-continued
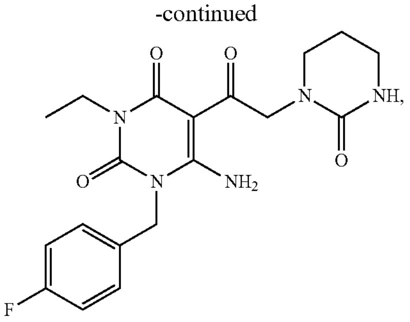
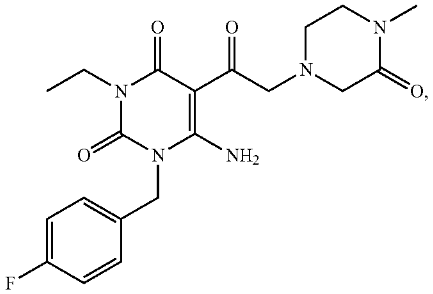
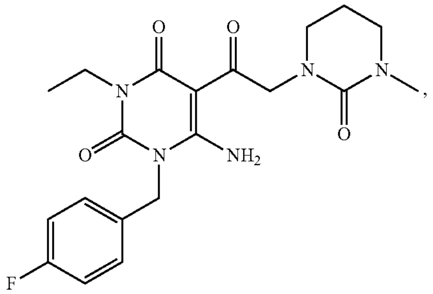
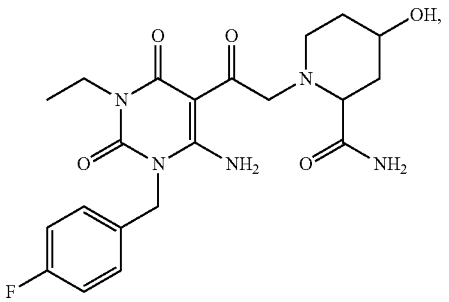
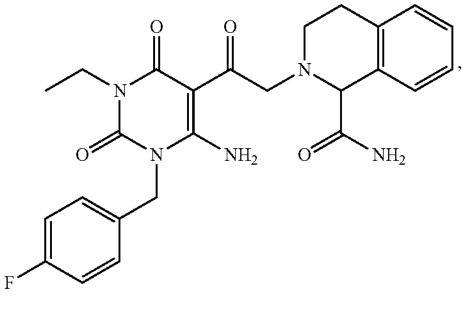

-continued

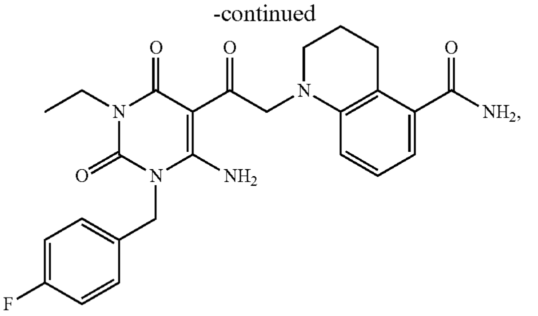

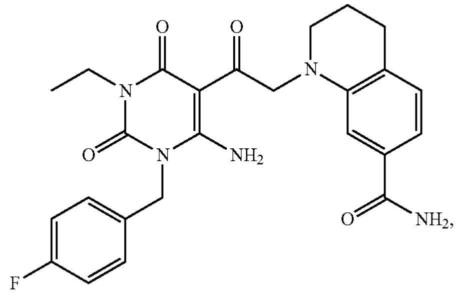

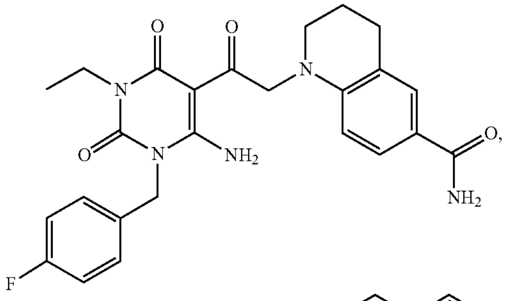

and

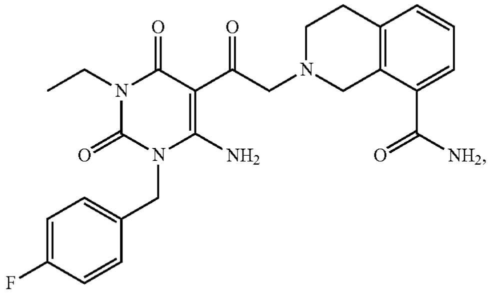

or a pharmaceutically acceptable salt thereof, and one or more selected from: (a) at least one agent known for the treatment of a disorder associated with the presence of a premature termination codon; (b) at least one device known for the treatment of a disorder associated with the presence of a premature termination codon; (c) instructions for administering the compound in connection with treating a disorder associated with the presence of a premature termination codon; (d) instructions for administering the compound in connection with reducing the risk of a disorder associated with the presence of a premature termination codon; and (e) instructions for treating a disorder associated with the presence of a premature termination codon.

Examples of disorders associated with the presence of a premature termination codon include, but are not limited to, cystic fibrosis, Duchenne muscular dystrophy, aniridia, Becker muscular dystrophy, spinal muscular atrophy, Hurler syndrome, hemophilia, epidermolysis bullosa (e.g., dystrophic (DEB) form, junctional (JEB) form), Usher syndrome, neurofibromatosis, and cancer.

In a further aspect, the kit comprises the agent known for the treatment of a disorder associated with the presence of a premature termination codon. In a still further aspec, the agent is a nonsense suppression agent. Examples of nonsense suppression agents include, but are not limited to, eRF3 degraders (e.g., CC-885, CC-9009), aminoglycosides (e.g., G418, gentamicin, paromomycin, amikacin, ELX-02), macrolides (e.g., erythromycin), PRC124 (ataluren), 2,6-diaminopurines, and G418 enhancers (e.g., Y320, CDX5-1). In yet a further aspect, the agent is selected from a CFTR modulator (e.g., a CFTR potentiator, a CFTR amplifier, a CFTR corrector), an NMD inhibitor (e.g., NMDI-1, NMDI-9, NMDI-25, NMDI-14), an agent that increases mRNA levels (e.g., a histone deacetylase inhibitor), an agent that increases general pulmonary function, an aminoglycoside (e.g., G418, geneticin, amikacin, tobramycin, ELX-02, NB54, NB124, NB83), erythromycin, artesunate, atazanavir, ataluren, genistein, Y-320, ELX-02, and CC-9009. In an even further aspect, the agent is known for the treatment of cystic fibrosis. In a still further aspect, the agent is selected from elexacaftor, ivacaftor, tezacaftor, lumacaftor, a mucus thinner (e.g., hypertonic saline, dornase alfa), and a bronchodilator (e.g., a beta-adrenergic bronchodilator such as albuterol, levalbuterol, an epinephrine injection, salmeterol, azithromycin, clarithromycin, and formoterol, an anticholinergic bronchodilator such as ipratropium and tiotropium, a xanthine derivative such as theophylline and aminophylline).

In a further aspect, the kit comprises the device known for the treatment of a disorder associated with the presence of a premature termination codon. In a still further aspect, the device is selected from a nebulizer and a vascular access device. Examples of vascular devices include, but are not limited to, a peripheral intravenous catheter (PIV), a peripherally inserted central catheter (PICC), a centrally inserted central catheter (CICC), a subcutaneous catheter device, and an implanted venous port.

In a further aspect, the compound and the agent are co-packaged. In a still further aspect, the compound and the agent are co-formulated.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

L. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals

A. General Experimental Method

All reactions were carried out in an oven-dried glassware under argon atmosphere using standard gas-tight syringe, cannula, and septa. The reaction temperatures were measured externally. Stirring was achieved with oven dried magnetic bars. All the reactions were done in anhydrous solvents ($CH_2Cl_2$, THF, MeOH) purchased from Sigma-Aldrich. All commercially purchased reagents were used without purification. The reactions were monitored by thin-layer chromatography (TLC) on a pre-coated silica gel (60 F254) glass plates from EMD Millipore and visualized using UV light (254 nm). Purification of the compounds was performed on Teledyne-ISCO Combiflash Rf 200 purification system using Redisep Rf® normal phase silica gel columns 230-400 mesh or Shimadzu HPLC system (Phenomenex Gemini NX-C18). ESI-MS spectra were recorded on a BioTof-2 time-of-flight mass spectrometer. Proton NMR spectra were recorded on a Varian Unity 400 NMR spectrometer operating at 400 MHz calibrated to the solvent peak and TMS peak. The chemical formula and Exact Mass for target compounds were determined from the $(M+H)^+$ by high resolution mass spectroscopy using an Agilent 6210 Electrospray Time of Flight. Determination of % purity was obtained by HPLC using an Agilent 1100 LC equipped with a diode array UV detector and monitored at multiple wavelengths.

A list of exemplary compounds that were prepared as described herein is shown in Table 1 below.

TABLE 1

| No. | Structure | HRMS | HPLC/LC MS Purity (%) | Synthetic Route |
|---|---|---|---|---|
| 1.1 | 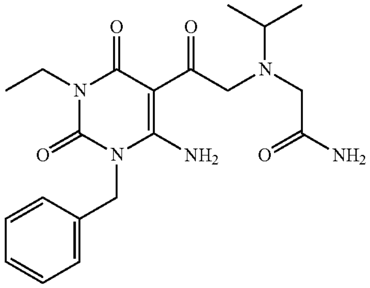 [SMILES: CCn1c(=O)c(C(=O)CN(CC(N)=O)C(C)C)c(N)n(Cc2ccccc2)c1=O] | HRMS calcd for $[C_{20}H_{27}N_5O_4 + H]^+$: 402.2136, Found: 402.2135 | 98.2 | A |
| 1.2 | 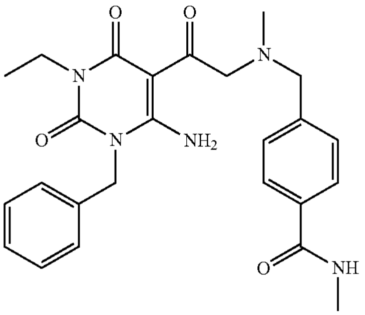 [SMILES: CCn1c(=O)c(C(=O)CN(C)Cc2ccc(C(=O)NC)cc2)c(N)n(Cc2ccccc2)c1=O] | HRMS calcd for $[C_{25}H_{29}N_5O_4 + H]^+$: 464.2292, Found: 464.2290 | 98.7 | A |

TABLE 1-continued
| No. | Structure | HRMS | HPLC/LC MS Purity (%) | Synthetic Route |
|---|---|---|---|---|
| 1.3 | 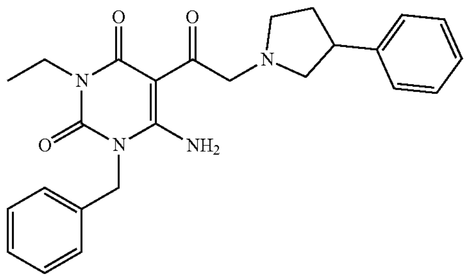 [SMILES: CCn1c(=O)c(C(=O)CN2CCC(c3ccccc3)C2)c(N)n(Cc2ccccc2)c1=O] | HRMS calcd for $[C_{25}H_{28}N_4O_3 + H]^+$: 433.2234, Found: 433.2234 | 97.5 | A |
| 1.4 | 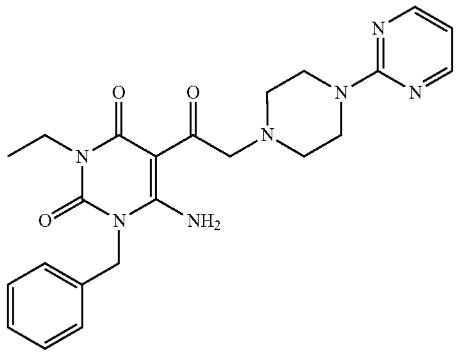 [SMILES: CCn1c(=O)c(C(=O)CN2CCN(c3ncccn3)CC2)c(N)n(Cc2ccccc2)c1=O] | HRMS calcd for $[C_{23}H_{27}N_7O_3 + H]^+$: 450.2248, Found: 450.2257 | 99.0 | A |
| 1.5 | 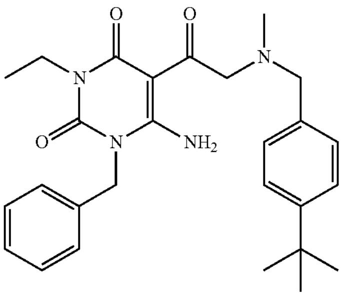 [SMILES: CCn1c(=O)c(C(=O)CN(C)Cc2ccc(C(C)(C)C)cc2)c(N)n(Cc2ccccc2)c1=O] | HRMS calcd for $[C_{27}H_{34}N_4O_3 + H]^+$: 463.2704, Found: 463.2696 | 97.3 | A |
| 1.6 | 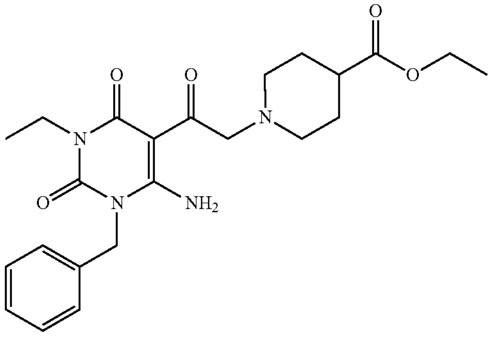 [SMILES: CCOC(=O)C1CCN(CC(=O)c2c(N)n(Cc3ccccc3)c(=O)n(CC)c2=O)CC1] | HRMS calcd for $[C_{23}H_{30}N_4O_5 + H]^+$: 443.2289, Found: 443.2288 | 100 | A |

TABLE 1-continued
| No. | Structure | HRMS | HPLC/LC MS Purity (%) | Synthetic Route |
| --- | --- | --- | --- | --- |
| 1.7 | 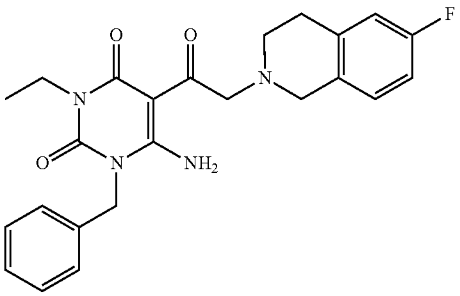 [SMILES: CCn1c(=O)c(C(=O)CN2CCc3cc(F)ccc3C2)c(N)n(Cc2ccccc2)c1=O] | HRMS calcd for $[C_{24}H_{25}FN_4O3 + H]^+$: 437.1983, Found: 437.1982 | 98.5 | A |
| 1.8 | 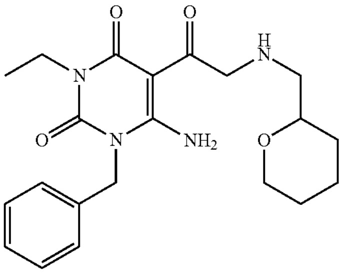 [SMILES: CCn1c(=O)c(C(=O)CNCC2CCCCO2)c(N)n(Cc2ccccc2)c1=O] | HRMS calcd for $[C_{21}H_{28}N_4O_4 + H]^+$: 401.2183, Found: 401.2184 | 97.5 | A |
| 1.9 | 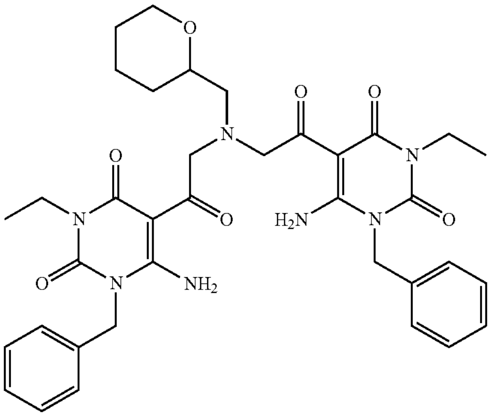 [SMILES: CCn1c(=O)c(C(=O)CN(CC(=O)c2c(N)n(Cc3ccccc3)c(=O)n(CC)c2=O)CC2CCCCO2)c(N)n(Cc2ccccc2)c1=O] | HRMS calcd for $[C_{36}H_{43}N_7O_7 + H]^+$: 686.3297, Found: 686.3288 | 93.5 | A |
| 1.10 | 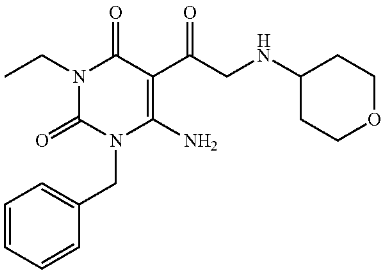 [SMILES: CCn1c(=O)c(C(=O)CNC2CCOCC2)c(N)n(Cc2ccccc2)c1=O] | HRMS calcd for $[C_{20}H_{26}N_4O_4 + H]^+$: 387.2027, Found: 387.2028 | 98.4 | A |

TABLE 1-continued
| No. | Structure | HRMS | HPLC/LC MS Purity (%) | Synthetic Route |
|---|---|---|---|---|
| 1.11 | 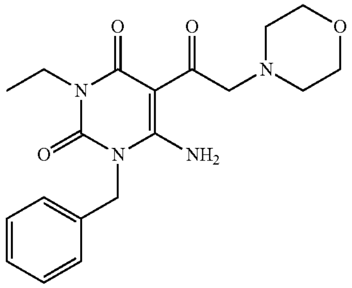 | HRMS calcd for [$C_{190}H_{24}N_4O_4$ + H]$^+$: 373.1870, Found: 373.1874 | 98.9 | A |
| 1.12 | 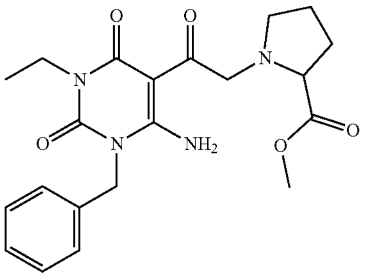 [SMILES: CCn1c(=O)c(C(=O)CN2CCCC2C(=O)OC)c(N)n(Cc2ccccc2)c1=O] | HRMS calcd for [$C_{21}H_{26}N_4O_5$ + H]$^+$: 415.1976, Found: 415.1976 | 98.8 | A |
| 1.13 | 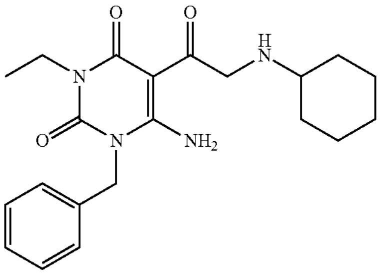 [SMILES: CCn1c(=O)c(C(=O)CNC2CCCCC2)c(N)n(Cc2ccccc2)c1=O] | HRMS calcd for [$C_{21}H_{28}N_4O_3$ + H]$^+$: 385.2234, Found: 385.2231 | 94.9 | A |
| 1.14 | 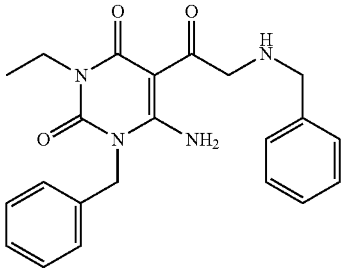 [SMILES: CCn1c(=O)c(C(=O)CNCc2ccccc2)c(N)n(Cc2ccccc2)c1=O] | HRMS calcd for [$C_{22}H_{24}N_4O_3$ + H]$^+$: 393.1921, Found: 393.1922 | 95.6 | A |
| 1.15 | 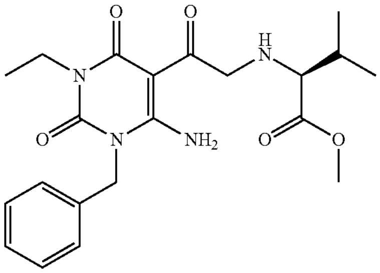 [SMILES: CCn1c(=O)c(C(=O)CN[C@H](C(=O)OC)C(C)C)c(N)n(Cc2ccccc2)c1=O] | HRMS calcd for [$C_{21}H_{28}N_4O_5$ + H]$^+$: 417.2133, Found: 417.2132 | 97.1 | A |

TABLE 1-continued
| No. | Structure | HRMS | HPLC/LC MS Purity (%) | Synthetic Route |
|---|---|---|---|---|
| 1.16 | 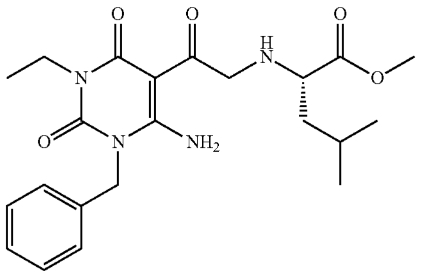 [SMILES: CCn1c(=O)c(C(=O)CN[C@@H](CC(C)C)C(=O)OC)c(N)n(Cc2ccccc2)c1=O] | HRMS calcd for $[C_{22}H_{30}N_4O_5 + H]^+$: 431.2289, Found: 431.2288 | 94.9 | A |
| 1.17 | 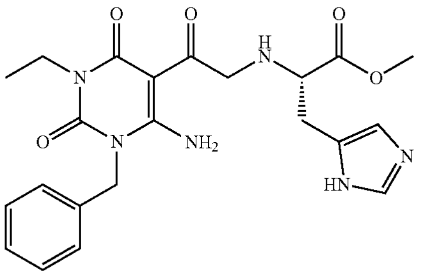 [SMILES: CCn1c(=O)c(C(=O)CN[C@@H](Cc2cnc[nH]2)C(=O)OC)c(N)n(Cc2ccccc2)c1=O] | HRMS calcd for $[C_{22}H_{26}N_6O_5 + H]^+$: 455.2037, Found: 455.2033 | 90.0 | A |
| 1.18 | 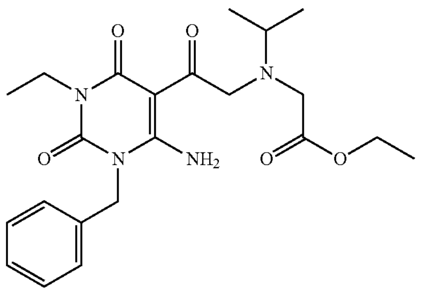 [SMILES: CCOC(=O)CN(CC(=O)c1c(N)n(Cc2ccccc2)c(=O)n(CC)c1=O)C(C)C] | HRMS calcd for $[C_{22}H_{30}N_4O_5 + H]^+$: 431.2289, Found: 431.2282 | 96.1 | A |
| 1.19 | 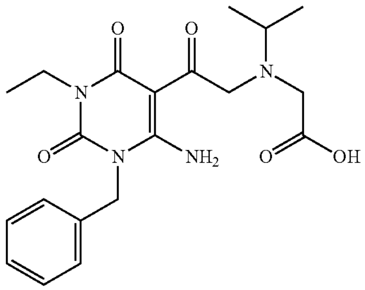 [SMILES: CCn1c(=O)c(C(=O)CN(CC(=O)O)C(C)C)c(N)n(Cc2ccccc2)c1=O] | HRMS calcd for $[C_{22}H_{30}N_4O_5 + H]^+$: 431.2289, Found: 431.2282 | 96.1 | A&B |
| 1.20 | 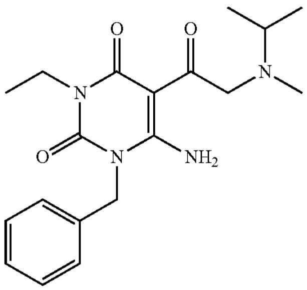 [SMILES: CCn1c(=O)c(C(=O)CN(C)C(C)C)c(N)n(Cc2ccccc2)c1=O] | HRMS calcd for $[C_{19}H_{26}N_4O_3 + H]^+$: 359.2078, Found: 359.2077 | 93.3 | A |

TABLE 1-continued
| No. | Structure | HRMS | HPLC/LC MS Purity (%) | Synthetic Route |
|---|---|---|---|---|
| 1.21 | 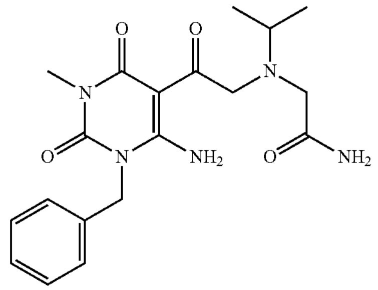 [SMILES: CC(C)N(CC(N)=O)CC(=O)c1c(N)n(Cc2ccccc2)c(=O)n(C)c1=O] | HRMS calcd for $[C_{19}H_{25}N_5O_4 + H]^+$: 388.1979, Found: 388.1980 | 94.4 | A |
| 1.22 | 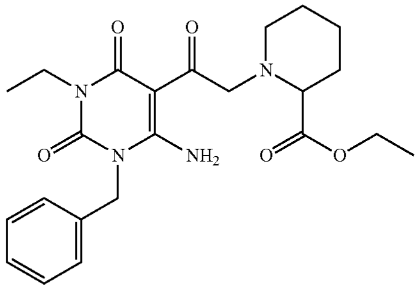 [SMILES: CCOC(=O)C1CCCCN1CC(=O)c1c(N)n(Cc2ccccc2)c(=O)n(CC)c1=O] | HRMS calcd for $[C_{23}H_{30}N_4O_5 + H]^+$: 443.2289, Found: 443.2280 | 95.9 | A |
| 1.23 | 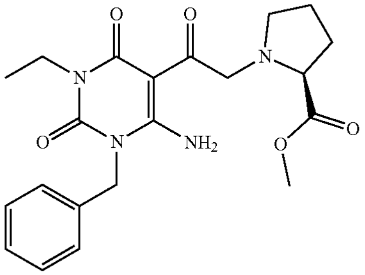 [SMILES: CCn1c(=O)c(C(=O)CN2CCC[C@H]2C(=O)OC)c(N)n(Cc2ccccc2)c1=O] | HRMS calcd for $[C_{21}H_{26}N_4O_5 + H]^+$: 415.1976, Found: 415.1969 | 97.5 | A |
| 1.24 | 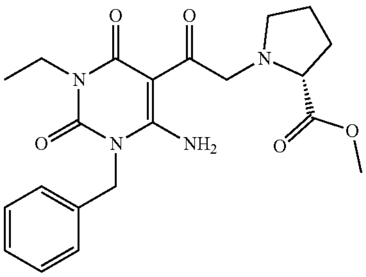 [SMILES: CCn1c(=O)c(C(=O)CN2CCC[C@@H]2C(=O)OC)c(N)n(Cc2ccccc2)c1=O] | ESI-MS m/z for $[C_{21}H_{26}N_4O_5 + H]^+$: 415.1 | 98.4 | A |
| 1.25 | 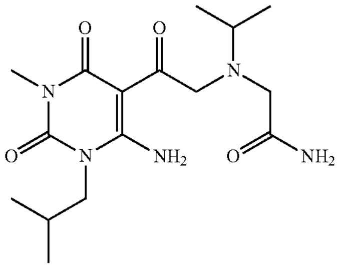 [SMILES: CC(C)Cn1c(N)c(C(=O)CN(CC(N)=O)C(C)C)c(=O)n(C)c1=O] | HRMS calcd for $[C_{16}H_{27}N_5O_4 + H]^+$: 354.2136, Found: 354.2131 | 98.2 | A |

TABLE 1-continued
| No. | Structure | HRMS | HPLC/LC MS Purity (%) | Synthetic Route |
|---|---|---|---|---|
| 1.26 | 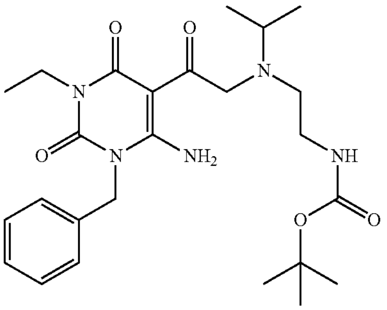 [SMILES: CCn1c(=O)c(C(=O)CN(CCNC(=O)OC(C)(C)C)C(C)C)c(N)n(Cc2ccccc2)c1=O] | HRMS calcd for $[C_{25}H_{37}N_5O_5 + H]^+$: 488.2868, Found: 488.2861 | 95.9 | A |
| 1.27 | 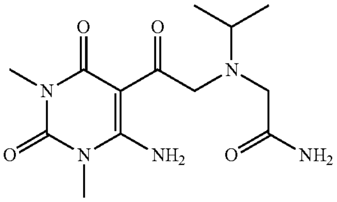 [SMILES: CC(C)N(CC(N)=O)CC(=O)c1c(N)n(C)c(=O)n(C)c1=O] | HRMS calcd for $[C_{14}H_{21}N_5O_4 + H]^+$: 312.1666, Found: 312.1662 | 100 | A |
| 1.28 | 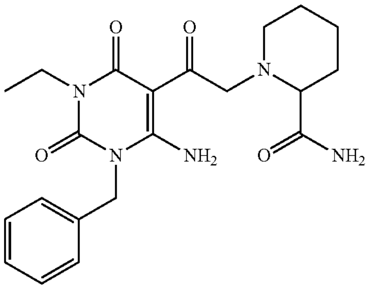 [SMILES: CCn1c(=O)c(C(=O)CN2CCCCC2C(N)=O)c(N)n(Cc2ccccc2)c1=O] | HRMS calcd for $[C_{21}H_{27}N_5O_4 + H]^+$: 414.2136, Found: 414.2132 | 99.5 | A |
| 1.29 | 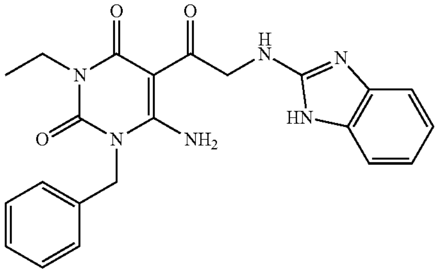 [SMILES: CCn1c(=O)c(C(=O)CNc2nc3ccccc3[nH]2)c(N)n(Cc2ccccc2)c1=O] | ESI-MS m/z for $[C_{22}H_{22}N_6O_3 + H]^+$: 419.2 | 96.2 | A |
| 1.30 | 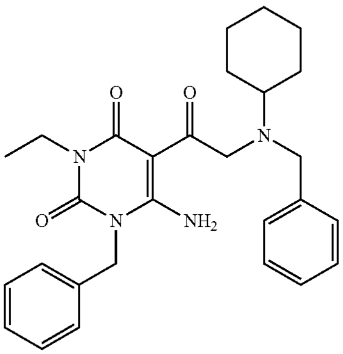 [SMILES: CCn1c(=O)c(C(=O)CN(Cc2ccccc2)C2CCCCC2)c(N)n(Cc2ccccc2)c1=O] | ESI-MS m/z for $[C_{28}H_{34}N_4O_3 + H]^+$ 475.2 | — | A |

TABLE 1-continued
| No. | Structure | HRMS | HPLC/LC MS Purity (%) | Synthetic Route |
| --- | --- | --- | --- | --- |
| 1.31 | 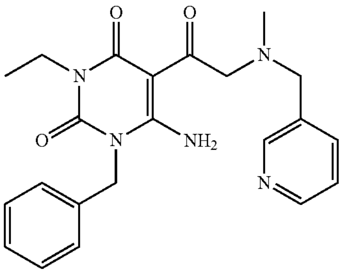 | HRMS calcd for $[C_{221}H_{25}N_5O_3 + H]^+$: 408.2030, Found: 408.2025 | 99.5 | A |
| 1.32 | 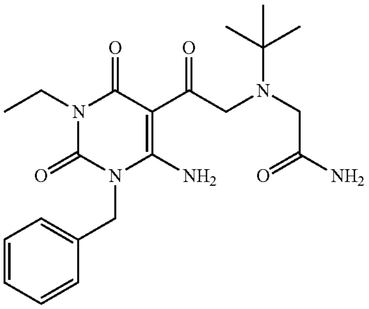 [SMILES: CCn1c(=O)c(C(=O)CN(CC(N)=O)C(C)(C)C)c(N)n(Cc2ccccc2)c1=O] | HRMS calcd for $[C_{21}H_{29}N_5O_4 + H]^+$: 416.2292, Found: 416.2287 | 95.0 | A |
| 1.33 | 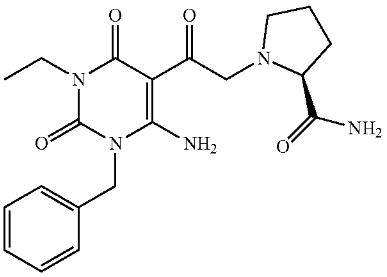 [SMILES: CCn1c(=O)c(C(=O)CN2CCC[C@H]2C(N)=O)c(N)n(Cc2ccccc2)c1=O] | HRMS calcd for $[C_{20}H_{25}N_5O_4 + H]^+$: 400.1979, Found: 400.1983 | 97.0 | A |
| 1.34 | 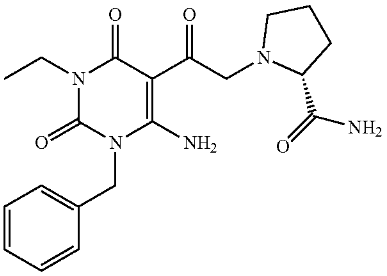 [SMILES: CCn1c(=O)c(C(=O)CN2CCC[C@@H]2C(N)=O)c(N)n(Cc2ccccc2)c1=O] | HRMS calcd for $[C_{20}H_{25}N_5O_4 + H]^+$: 400.1979, Found: 400.1971 | 97.0 | A |
| 1.35 | 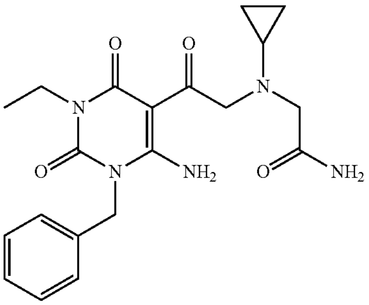 [SMILES: CCn1c(=O)c(C(=O)CN(CC(N)=O)C2CC2)c(N)n(Cc2ccccc2)c1=O] | HRMS calcd for $[C_{20}H_{25}N_5O_4 + H]^+$: 400.1979, Found: 400.1983 | 98.8 | A |

TABLE 1-continued
| No. | Structure | HRMS | HPLC/LC MS Purity (%) | Synthetic Route |
|---|---|---|---|---|
| 1.36 | 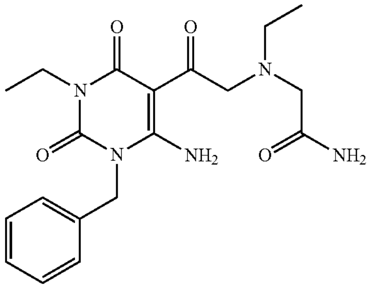 [SMILES: CCN(CC(N)=O)CC(=O)c1c(N)n(Cc2ccccc2)c(=O)n(CC)c1=O] | HRMS calcd for $[C_{19}H_{25}N_5O_4 + H]^+$: 388.1979, Found: 388.1971 | 97.5 | A |
| 1.37 | 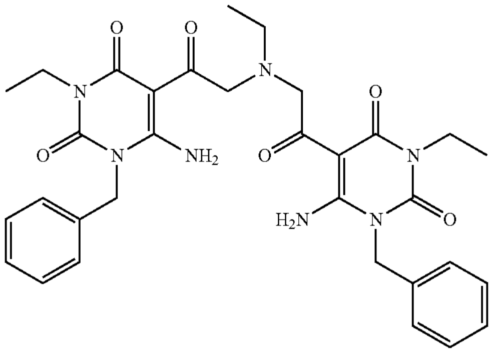 [SMILES: CCN(CC(=O)c1c(N)n(Cc2ccccc2)c(=O)n(CC)c1=O)CC(=O)c1c(N)n(Cc2ccccc2)c(=O)n(CC)c1=O] | ESI-MS m/z for $[C_{32}H_{37}N_7O_6 + H]^+$: 616.3 | 96.7 | A |
| 1.38 | 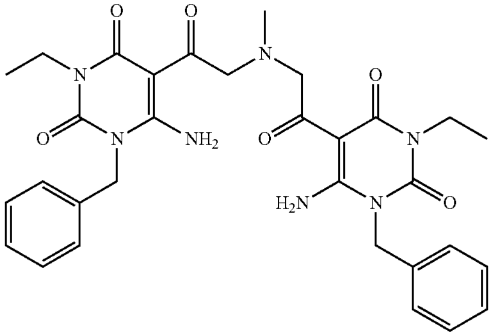 [SMILES: CCn1c(=O)c(C(=O)CN(C)CC(=O)c2c(N)n(Cc3ccccc3)c(=O)n(CC)c2=O)c(N)n(Cc2ccccc2)c1=O] | HRMS calcd for $[C_{31}H_{35}N_7O_6 + H]^+$: 602.2722, Found: 602.2710 | 95.5 | A |
| 1.39 | 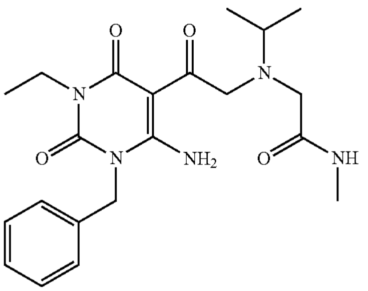 [SMILES: CCn1c(=O)c(C(=O)CN(CC(=O)NC)C(C)C)c(N)n(Cc2ccccc2)c1=O] | HRMS calcd for $[C_{21}H_{29}N_5O_4 + H]^+$: 416.2292, Found: 416.2287 | 92.3 | A |

TABLE 1-continued
| No. | Structure | HRMS | HPLC/LC MS Purity (%) | Synthetic Route |
|---|---|---|---|---|
| 1.40 | 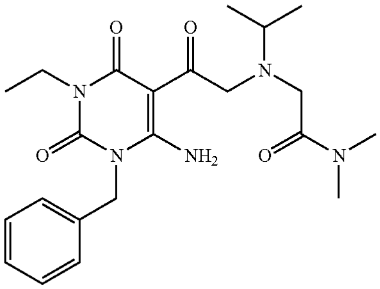 [SMILES: CCn1c(=O)c(C(=O)CN(CC(=O)N(C)C)C(C)C)c(N)n(Cc2ccccc2)c1=O] | HRMS calcd for $[C_{22}H_{31}N_5O_4 + H]^+$: 430.2449, Found: 430.2445 | 89.7 | A |
| 1.41 | 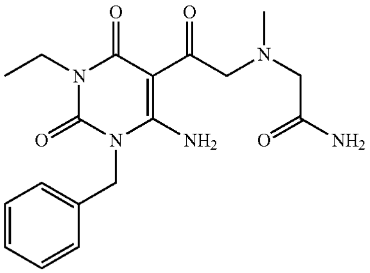 [SMILES: CCn1c(=O)c(C(=O)CN(C)CC(N)=O)c(N)n(Cc2ccccc2)c1=O] | HRMS calcd for $[C_{18}H_{23}N_5O_4 + H]^+$: 374.1823, Found: 374.1825 | 96.8 | A |
| 1.42 | 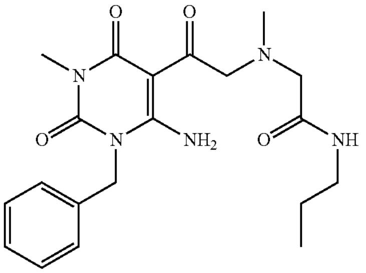 [SMILES: CCCNC(=O)CN(C)CC(=O)c1c(N)n(Cc2ccccc2)c(=O)n(C)c1=O] | ESI-MS m/z for $[C_{20}H_{27}N_5O_4 + H]^+$: 402.47 | 95.6 | Commercial compound |
| 1.43 | 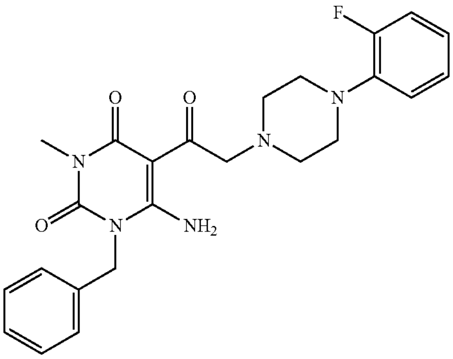 [SMILES: Cn1c(=O)c(C(=O)CN2CCN(c3ccccc3F)CC2)c(N)n(Cc2ccccc2)c1=O] | ESI-MS m/z for $[C_{24}H_{26}FN_5O_3 + H]^+$: 452.50 | 97.6 | Commercial compound |
| 1.44 | 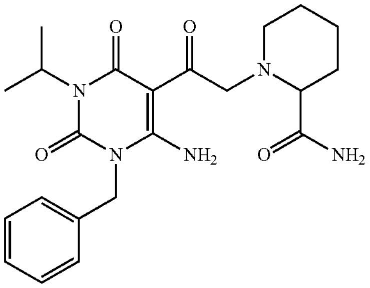 [SMILES: CC(C)n1c(=O)c(C(=O)CN2CCCCC2C(N)=O)c(N)n(Cc2ccccc2)c1=O] | HRMS calcd for $[C_{22}H_{29}N_5O_4 + H]^+$: 428.2292, Found: 428.2286 | 98.1 | A |

TABLE 1-continued
| No. | Structure | HRMS | HPLC/LC MS Purity (%) | Synthetic Route |
| --- | --- | --- | --- | --- |
| 1.45 | 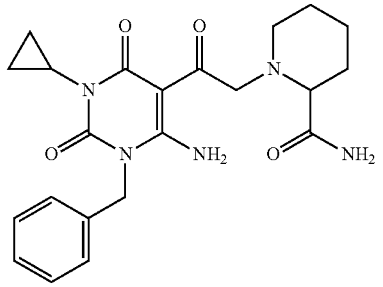 [SMILES: NC(=O)C1CCCCN1CC(=O)c1c(N)n(Cc2ccccc2)c(=O)n(C2CC2)c1=O] | HRMS calcd for $[C_{22}H_{27}N_5O_4 + H]^+$: 426.2136, Found: 426.2132 | 96.8 | A |
| 1.46 | 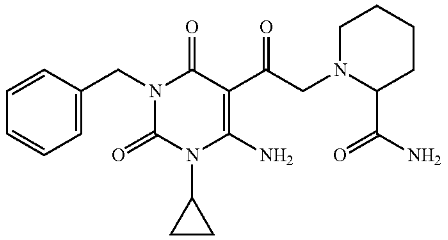 [SMILES: NC(=O)C1CCCCN1CC(=O)c1c(N)n(C2CC2)c(=O)n(Cc2ccccc2)c1=O] | HRMS calcd for $[C_{22}H_{27}N_5O_4 + H]^+$: 426.2136, Found: 426.2133 | 90.2 | A |
| 1.47 | 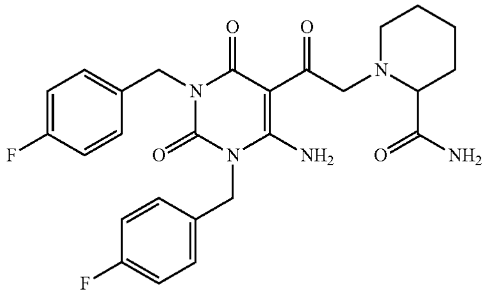 [SMILES: NC(=O)C1CCCCN1CC(=O)c1c(N)n(Cc2ccc(F)cc2)c(=O)n(Cc2ccc(F)cc2)c1=O] | HRMS calcd for $[C_{26}H_{27}F_2N_5O_4 + H]^+$: 512.2104, Found: 512.2099 | 99.0 | C |
| 1.48 | 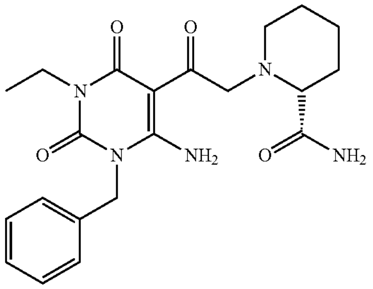 | HRMS calcd for $[C_{21}H_{27}N_5O_4 + H]^+$: 414.2136, Found: 414.2142 | 94.2 | A |
| 1.49 | 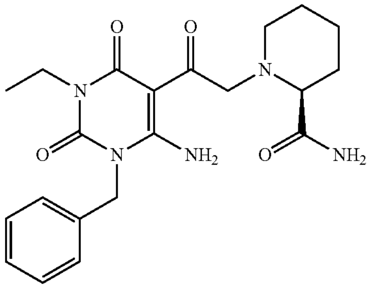 [SMILES: CCn1c(=O)c(C(=O)CN2CCCC[C@H]2C(N)=O)c(N)n(Cc2ccccc2)c1=O] | HRMS calcd for $[C_{21}H_{27}N_5O_4 + H]^+$: 414.2136, Found: 414.2133 | 95.4 | A |

TABLE 1-continued
| No. | Structure | HRMS | HPLC/LC MS Purity (%) | Synthetic Route |
| --- | --- | --- | --- | --- |
| 1.50 | 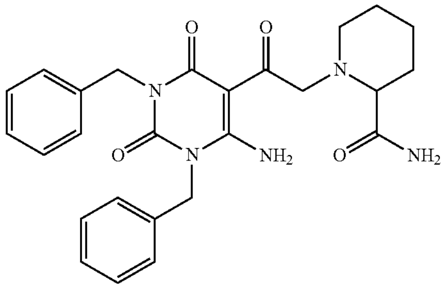 [SMILES: NC(=O)C1CCCCN1CC(=O)c1c(N)n(Cc2ccccc2)c(=O)n(Cc2ccccc2)c1=O] | HRMS calcd for $[C_{26}H_{29}N_5O_4 + H]^+$: 476.2292, Found: 476.2285 | 96.4 | C |
| 1.51 | 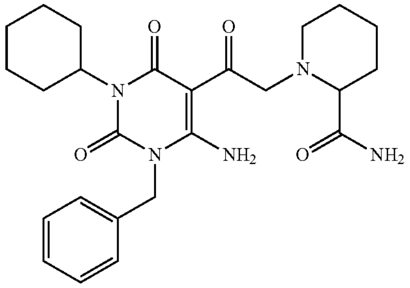 [SMILES: NC(=O)C1CCCCN1CC(=O)c1c(N)n(Cc2ccccc2)c(=O)n(C2CCCCC2)c1=O] | HRMS calcd for $[C_{25}H_{33}N_5O_4 + H]^+$: 468.2605, Found: 468.2594 | 95.3 | A |
| 1.52 | 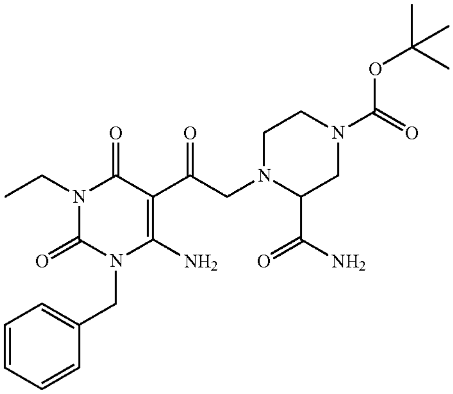 [SMILES: CCn1c(=O)c(C(=O)CN2CCN(C(=O)OC(C)(C)C)CC2C(N)=O)c(N)n(Cc2ccccc2)c1=O] | ESI-MS m/z for $[C_{25}H_{34}N_6O_6 + H]^+$: 515.2 | 99.6 | A |
| 1.53 | 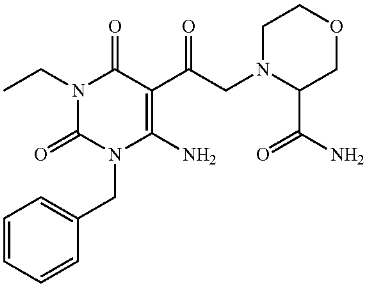 [SMILES: CCn1c(=O)c(C(=O)CN2CCOCC2C(N)=O)c(N)n(Cc2ccccc2)c1=O] | ESI-MS m/z for $[C_{20}H_{25}N_5O_5 + H]^+$: 415.1 | 99.3 | A |
| 1.54 | 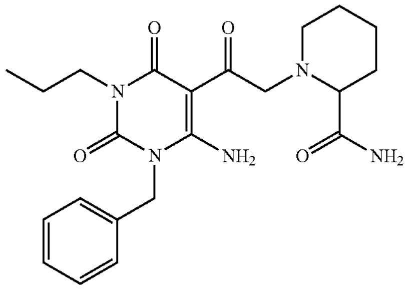 [SMILES: CCCn1c(=O)c(C(=O)CN2CCCCC2C(N)=O)c(N)n(Cc2ccccc2)c1=O] | HRMS calcd for $[C_{22}H_{29}N_5O_4 + H]^+$: 428.2292, Found: 428.2287 | 97.0 | A |

TABLE 1-continued
| No. | Structure | HRMS | HPLC/LC MS Purity (%) | Synthetic Route |
|---|---|---|---|---|
| 1.55 | 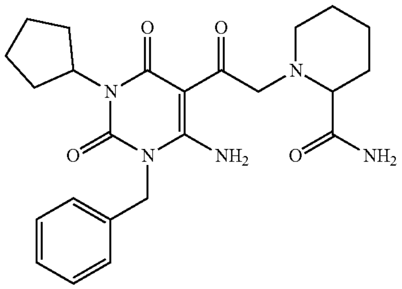 [SMILES: NC(=O)C1CCCCN1CC(=O)c1c(N)n(Cc2ccccc2)c(=O)n(C2CCCC2)c1=O] | HRMS calcd for $[C_{24}H_{31}N_5O_4 + H]^+$: 454.2449, Found: 454.2455 | 95.1 | A |
| 1.56 | 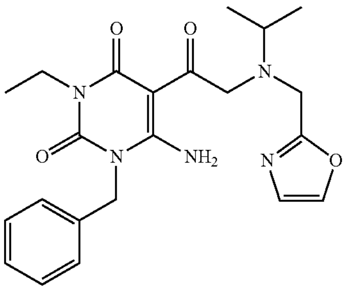 [SMILES: CCn1c(=O)c(C(=O)CN(Cc2ncco2)C(C)C)c(N)n(Cc2ccccc2)c1=O] | ESI-MS m/z for $[C_{20}H_{25}N_5O_5 + H]^+$: 426.2 | 99.2 | A |
| 1.57 | 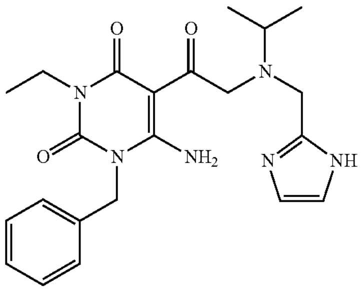 [SMILES: CCn1c(=O)c(C(=O)CN(Cc2ncc[nH]2)C(C)C)c(N)n(Cc2ccccc2)c1=O] | ESI-MS m/z for $[C_{20}H_{25}N_5O_5 + H]^+$: 425.1 | 95.6 | A |
| 1.58 | 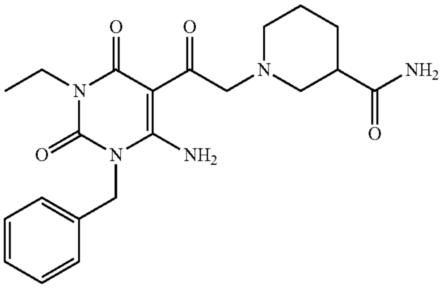 [SMILES: CCn1c(=O)c(C(=O)CN2CCCC(C(N)=O)C2)c(N)n(Cc2ccccc2)c1=O] | ESI-MS m/z for $[C_{21}H_{27}N_5O_4 + H]^+$: 414.2 | 96.9 | Commercial compound |
| 1.59 | 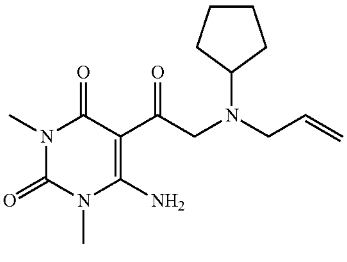 [SMILES: C=CCN(CC(=O)c1c(N)n(C)c(=O)n(C)c1=O)C1CCCC1] | ESI-MS m/z for $[C_{16}H_{24}N_4O_3 + H]^+$: 321.2 | 96.1 | Commercial compound |

TABLE 1-continued
| No. | Structure | HRMS | HPLC/LC MS Purity (%) | Synthetic Route |
|---|---|---|---|---|
| 1.60 | 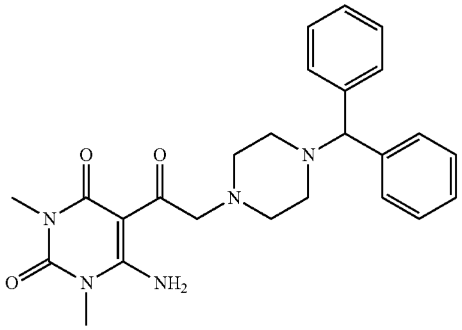 [SMILES: Cn1c(N)c(C(=O)CN2CCN(C(c3ccccc3)c3ccccc3)CC2)c(=O)n(C)c1=O] | ESI-MS m/z for $[C_{25}H_{29}N_5O_3 + H]^+$: 448.2 | 96.3 | Commercial compound |
| 1.61 | 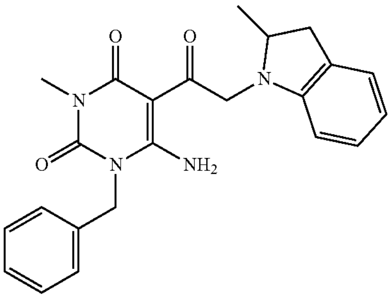 [SMILES: CC1Cc2ccccc2N1CC(=O)c1c(N)n(Cc2ccccc2)c(=O)n(C)c1=O] | ESI-MS m/z for $[C_{23}H_{24}N_4O_3 + H]^+$: 405.2 | | Commercial compound |
| 1.62 | 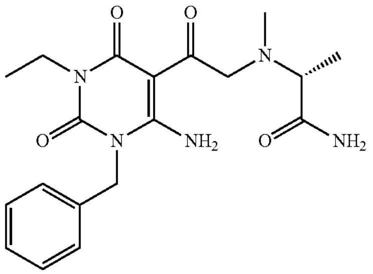 [SMILES: CCn1c(=O)c(C(=O)CN(C)[C@H](C)C(N)=O)c(N)n(Cc2ccccc2)c1=O] | ESI-MS m/z for $[C_{19}H_{25}N_5O_4 + H]^+$: 388.2 | — | Commercial compound |
| 1.63 | 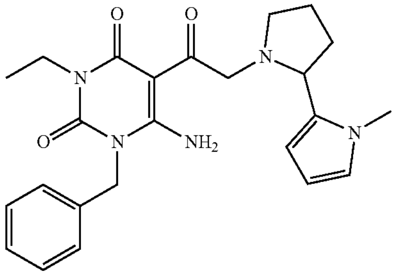 [SMILES: CCn1c(=O)c(C(=O)CN2CCCC2c2cccn2C)c(N)n(Cc2ccccc2)c1=O] | ESI-MS m/z for $[C_{24}H_{29}N_5O_3 + H]^+$: 436.3 | — | Commercial compound |
| 1.64 | 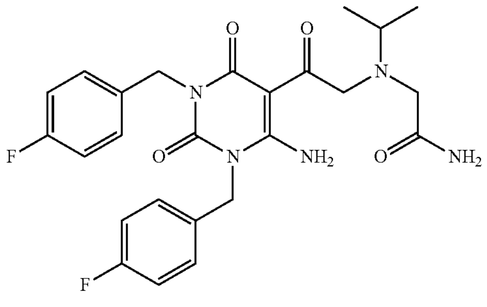 [SMILES: CC(C)N(CC(N)=O)CC(=O)c1c(N)n(Cc2ccc(F)cc2)c(=O)n(Cc2ccc(F)cc2)c1=O] | HRMS calcd for $[C_{25}H_{27}F_2N_5O_4 + H]^+$: 500.2104, Found: 500.2102 | 94.3 | C |

TABLE 1-continued
| No. | Structure | HRMS | HPLC/LC MS Purity (%) | Synthetic Route |
|---|---|---|---|---|
| 1.65 | 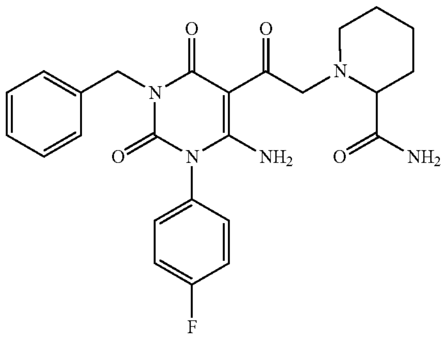 [SMILES: NC(=O)C1CCCCN1CC(=O)c1c(N)n(-c2ccc(F)cc2)c(=O)n(Cc2ccccc2)c1=O] | HRMS calcd for $[C_{25}H_{26}FN_5O_4 + H]^+$: 480.2042, Found: 480.2035 | 97.4 | A |
| 1.66 | 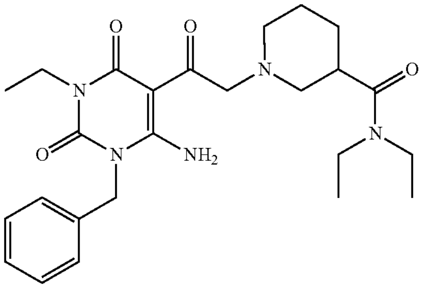 [SMILES: CCN(CC)C(=O)C1CCCN(CC(=O)c2c(N)n(Cc3ccccc3)c(=O)n(CC)c2=O)C1] | HRMS calcd for $[C_{25}H_{35}N_5O_4 + H]^+$: 470.2762, Found: 470.2758 | 98.5 | A |
| 1.67 | 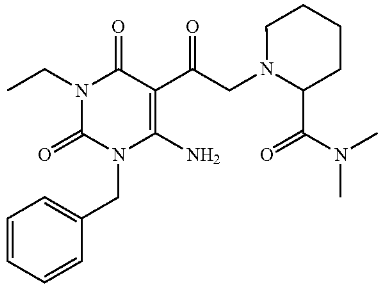 [SMILES: CCn1c(=O)c(C(=O)CN2CCCCC2C(=O)N(C)C)c(N)n(Cc2ccccc2)c1=O] | HRMS calcd for $[C_{23}H_{31}N_5O_4 + H]^+$: 442.2449, Found: 442.2443 | 97.3 | A |
| 1.68 | 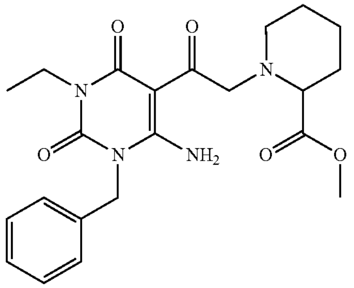 [SMILES: CCn1c(=O)c(C(=O)CN2CCCCC2C(=O)OC)c(N)n(Cc2ccccc2)c1=O] | ESI-MS m/z for $[C_{22}H_{28}N_4O_5 + H]^+$: 429.2 | 99.7 | A |
| 1.69 | 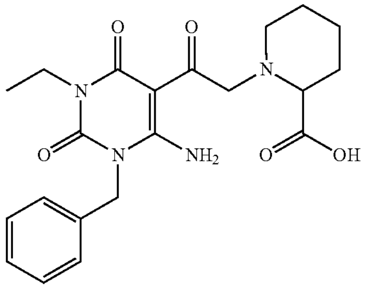 [SMILES: CCn1c(=O)c(C(=O)CN2CCCCC2C(=O)O)c(N)n(Cc2ccccc2)c1=O] | ESI-MS m/z for $[C_{21}H_{26}N_4O_5 + H]^+$: 415.1 | 99.0 | A |

TABLE 1-continued
| No. | Structure | HRMS | HPLC/LC MS Purity (%) | Synthetic Route |
|---|---|---|---|---|
| 1.70 | 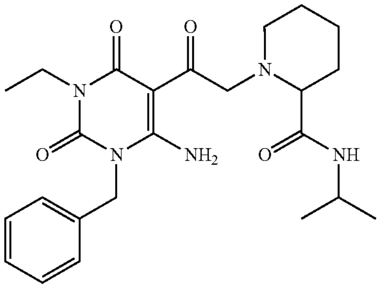 [SMILES: CCn1c(=O)c(C(=O)CN2CCCCC2C(=O)NC(C)C)c(N)n(Cc2ccccc2)c1=O] | ESI-MS m/z for $[C_{24}H_{33}N_5O_4 + H]^+$: 456.2 | 98.4 | A |
| 1.71 | 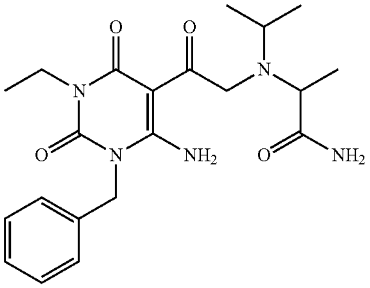 [SMILES: CCn1c(=O)c(C(=O)CN(C(C)C)C(C)C(N)=O)c(N)n(Cc2ccccc2)c1=O] | ESI-MS m/z for $[C_{21}H_{29}N_5O_4 + H]^+$: 416.1 | 99.9 | A |
| 1.72 | 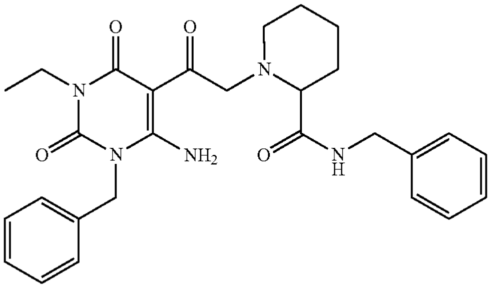 [SMILES: CCn1c(=O)c(C(=O)CN2CCCCC2C(=O)NCc2ccccc2)c(N)n(Cc2ccccc2)c1=O] | ESI-MS m/z for $[C_{28}H_{33}N_5O_4 + H]^+$: 504.2 | 99.6 | A |
| 1.73 | 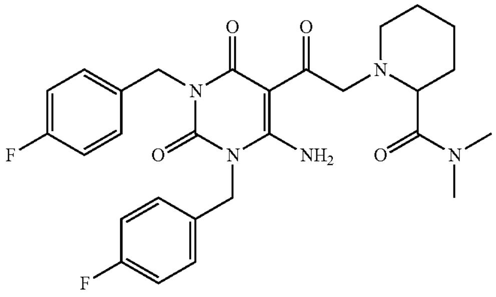 [SMILES: CN(C)C(=O)C1CCCCN1CC(=O)c1c(N)n(Cc2ccc(F)cc2)c(=O)n(Cc2ccc(F)cc2)c1=O] | HRMS calcd for $[C_{28}H_{31}F_2N_5O_4 + H]^+$: 540.2417, Found: 540.2413 | 99.6 | C |
| 1.74 | 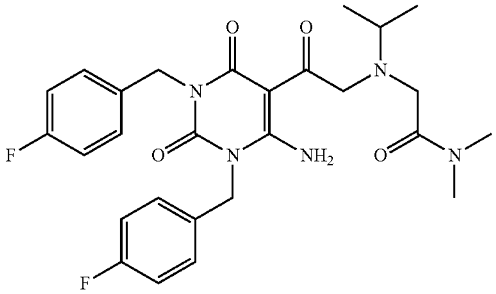 [SMILES: CC(C)N(CC(=O)c1c(N)n(Cc2ccc(F)cc2)c(=O)n(Cc2ccc(F)cc2)c1=O)CC(=O)N(C)C] | HRMS calcd for $[C_{27}H_{31}F_2N_5O_4 + H]^+$: 528.2417, Found: 528.2412 | 95.6 | C |

TABLE 1-continued
| No. | Structure | HRMS | HPLC/LC MS Purity (%) | Synthetic Route |
|---|---|---|---|---|
| 1.75 | 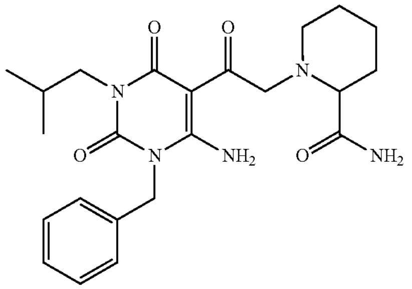 [SMILES: CC(C)Cn1c(=O)c(C(=O)CN2CCCCC2C(N)=O)c(N)n(Cc2ccccc2)c1=O] | HRMS calcd for $[C_{23}H_{31}N_5O_4 + H]^+$: 442.2449, Found: 442.2456 | 88.6 | A |
| 1.76 | 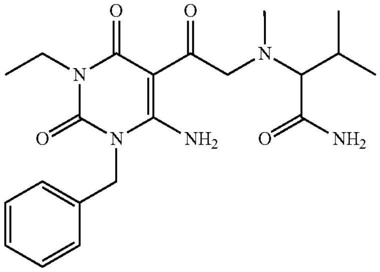 [SMILES: CCn1c(=O)c(C(=O)CN(C)C(C(N)=O)C(C)C)c(N)n(Cc2ccccc2)c1=O] | ESI-MS m/z for $[C_{21}H_{29}N_5O_4 + H]^+$: 416.2 | 95.6 | A |
| 1.77 | 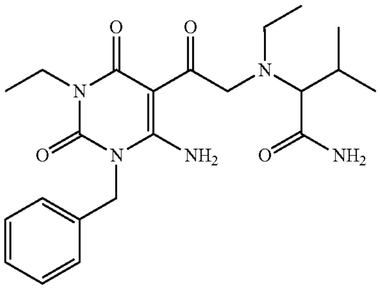 [SMILES: CCN(CC(=O)c1c(N)n(Cc2ccccc2)c(=O)n(CC)c1=O)C(C(N)=O)C(C)C] | ESI-MS m/z for $[C_{22}H_{31}N_5O_4 + H]^+$: 430.2 | 98.6 | A |
| 1.78 | 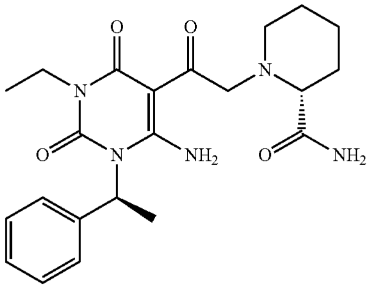 [SMILES: CCn1c(=O)c(C(=O)CN2CCCC[C@@H]2C(N)=O)c(N)n([C@@H](C)c2ccccc2)c1=O] | HRMS calcd for $[C_{22}H_{29}N_5O_4 + H]^+$: 428.2292, Found: 428.2291 | 99.6 | A |
| 1.79 | 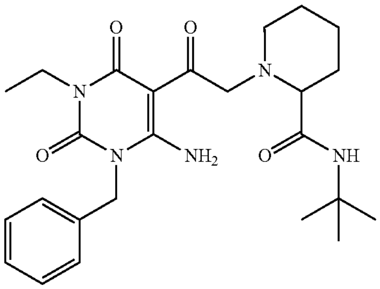 [SMILES: CCn1c(=O)c(C(=O)CN2CCCCC2C(=O)NC(C)(C)C)c(N)n(Cc2ccccc2)c1=O] | ESI-MS m/z for $[C_{25}H_{35}N_5O_4 + H]^+$: 470.2 | 99.4 | A |

TABLE 1-continued
| No. | Structure | HRMS | HPLC/LC MS Purity (%) | Synthetic Route |
|---|---|---|---|---|
| 1.80 | 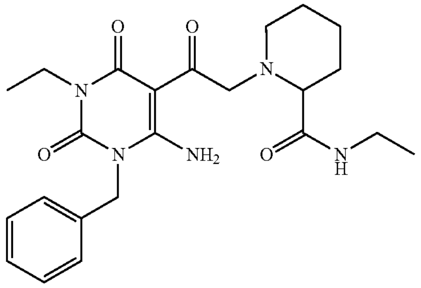 [SMILES: CCNC(=O)C1CCCCN1CC(=O)c1c(N)n(Cc2ccccc2)c(=O)n(CC)c1=O] | ESI-MS m/z for $[C_{23}H_{31}N_5O_4 + H]^+$: 442.2 | 99.4 | A |
| 1.81 | 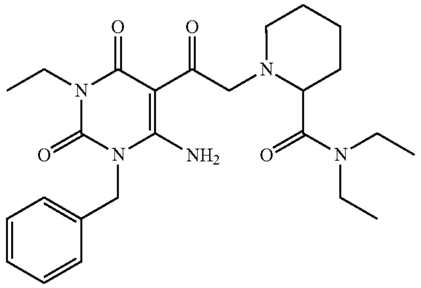 [SMILES: CCN(CC)C(=O)C1CCCCN1CC(=O)c1c(N)n(Cc2ccccc2)c(=O)n(CC)c1=O] | ESI-MS m/z for $[C_{25}H_{35}N_5O_4 + H]^+$: 470.0 | 99.5 | A |
| 1.82 | 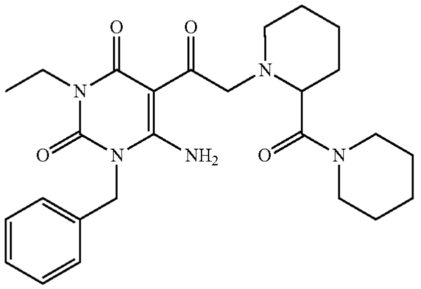 [SMILES: CCn1c(=O)c(C(=O)CN2CCCCC2C(=O)N2CCCCC2)c(N)n(Cc2ccccc2)c1=O] | ESI-MS m/z for $[C_{26}H_{35}N_5O_4 + H]^+$: 482.0 | 98.9 | A |
| 1.83 | 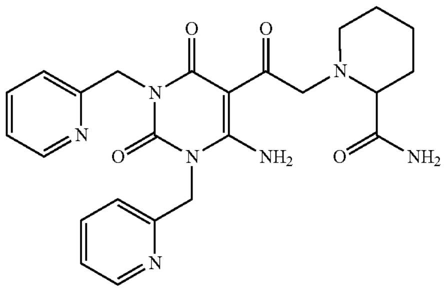 [SMILES: NC(=O)C1CCCCN1CC(=O)c1c(N)n(Cc2ccccn2)c(=O)n(Cc2ccccn2)c1=O] | HRMS calcd for $[C_{24}H_{27}N_7O_4 + H]^+$: 478.2197, Found: 478.2189 | 98.1 | C |
| 1.84 | 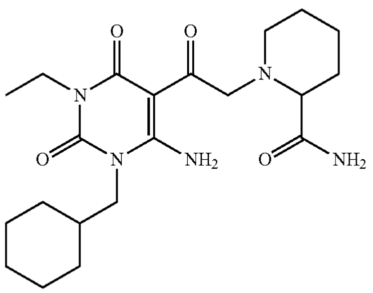 [SMILES: CCn1c(=O)c(C(=O)CN2CCCCC2C(N)=O)c(N)n(CC2CCCCC2)c1=O] | HRMS calcd for $[C_{21}H_{33}N_5O_4 + H]^+$: 420.2605, Found: 420.2608 | 100 | A |

TABLE 1-continued
| No. | Structure | HRMS | HPLC/LC MS Purity (%) | Synthetic Route |
|---|---|---|---|---|
| 1.85 | 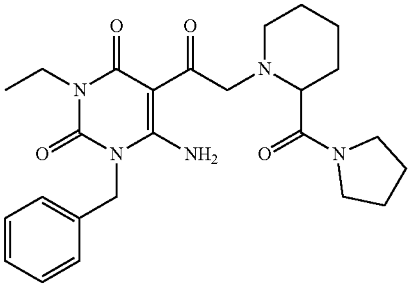 [SMILES: CCn1c(=O)c(C(=O)CN2CCCCC2C(=O)N2CCCC2)c(N)n(Cc2ccccc2)c1=O] | ESI-MS m/z for $[C_{25}H_{33}N_5O_4 + H]^+$: 468.0 | 98.1 | A |
| 1.86 | 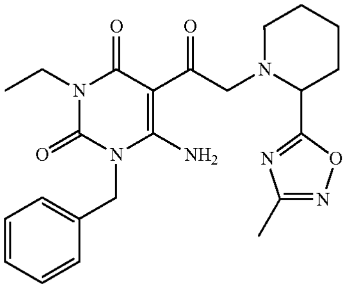 [SMILES: CCn1c(=O)c(C(=O)CN2CCCCC2c2nc(C)no2)c(N)n(Cc2ccccc2)c1=O] | ESI-MS m/z for $[C_{23}H_{28}N_6O_4 + H]^+$: 453.0 | 94.1 | A |
| 1.87 | 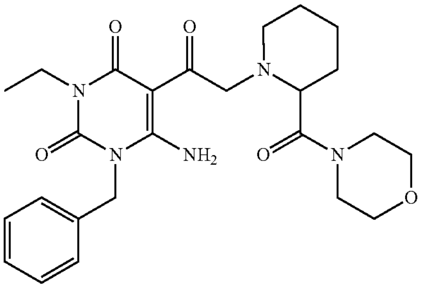 [SMILES: CCn1c(=O)c(C(=O)CN2CCCCC2C(=O)N2CCOCC2)c(N)n(Cc2ccccc2)c1=O] | ESI-MS m/z for $[C_{25}H_{33}N_5O_5 + H]^+$: 484.0 | 98.7 | A |
| 1.88 | 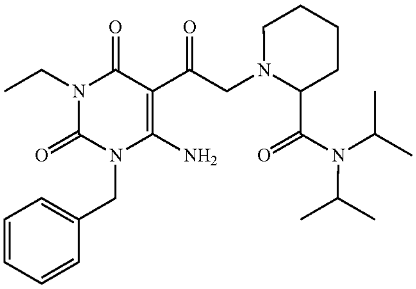 [SMILES: CCn1c(=O)c(C(=O)CN2CCCCC2C(=O)N(C(C)C)C(C)C)c(N)n(Cc2ccccc2)c1=O] | ESI-MS m/z for $[C_{27}H_{39}N_5O_4 + H]^+$: 498.0 | 97.9 | A |
| 1.89 | 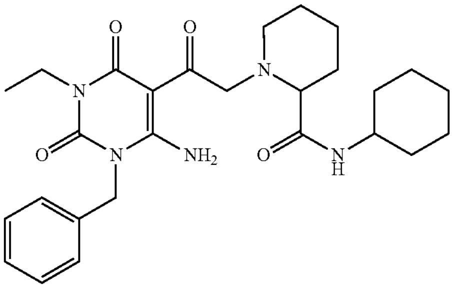 [SMILES: CCn1c(=O)c(C(=O)CN2CCCCC2C(=O)NC2CCCCC2)c(N)n(Cc2ccccc2)c1=O] | ESI-MS m/z for $[C_{27}H_{37}N_5O_4 + H]^+$: 496.0 | 97.3 | A |

TABLE 1-continued
| No. | Structure | HRMS | HPLC/LC MS Purity (%) | Synthetic Route |
|---|---|---|---|---|
| 1.90 | 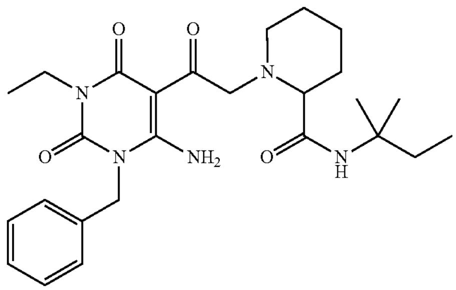 [SMILES: CCn1c(=O)c(C(=O)CN2CCCCC2C(=O)NC(C)(C)CC)c(N)n(Cc2ccccc2)c1=O] | ESI-MS m/z for $[C_{26}H_{37}N_5O_4 + H]^+$: 484.0 | 96.4 | A |
| 1.91 | 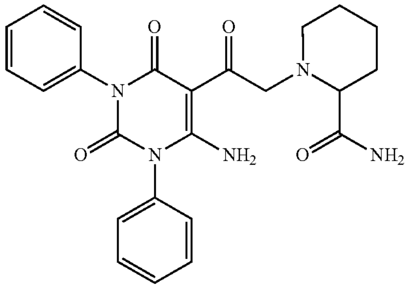 [SMILES: NC(=O)C1CCCCN1CC(=O)c1c(N)n(-c2ccccc2)c(=O)n(-c2ccccc2)c1=O] | HRMS calcd for $[C_{24}H_{25}N_5O_4 + H]^+$: 448.1979, Found: 448.1980 | 98.0 | A |
| 1.92 | 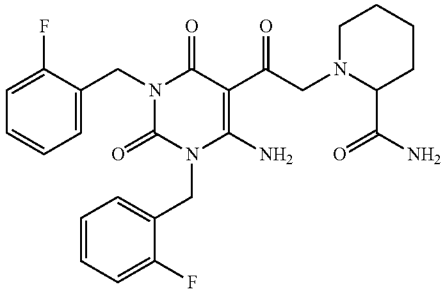 [SMILES: NC(=O)C1CCCCN1CC(=O)c1c(N)n(Cc2ccccc2F)c(=O)n(Cc2ccccc2F)c1=O] | ESI-MS m/z for $[C_{26}H_{27}F_2N_5O_4 + H]^+$: 512.0 | 97.0 | C |
| 1.93 | 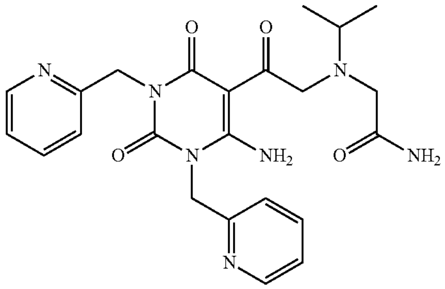 [SMILES: CC(C)N(CC(N)=O)CC(=O)c1c(N)n(Cc2ccccn2)c(=O)n(Cc2ccccn2)c1=O] | HRMS calcd for $[C_{23}H_{27}N_7O_4 + H]^+$: 466.2197, Found: 466.2188 | 100 | C |
| 1.94 | 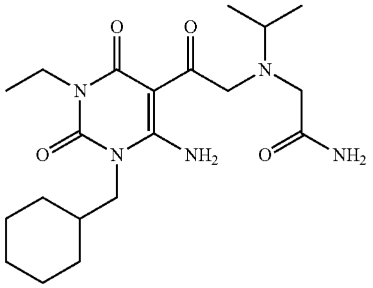 [SMILES: CCn1c(=O)c(C(=O)CN(CC(N)=O)C(C)C)c(N)n(CC2CCCCC2)c1=O] | HRMS calcd for $[C_{20}H_{33}N_5O_4 + H]^+$: 408.2605, Found: 408.2611 | 97.7 | A |

TABLE 1-continued
| No. | Structure | HRMS | HPLC/LC MS Purity (%) | Synthetic Route |
| --- | --- | --- | --- | --- |
| 1.95 | 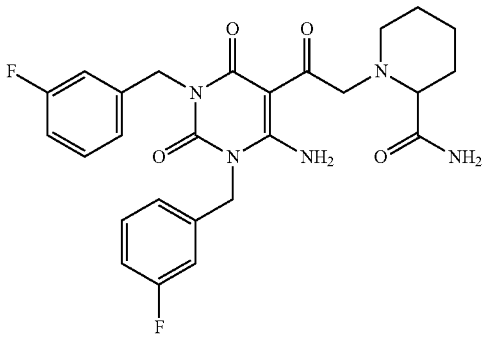 [SMILES: NC(=O)C1CCCCN1CC(=O)c1c(N)n(Cc2cccc(F)c2)c(=O)n(Cc2cccc(F)c2)c1=O] | ESI-MS m/z for $[C_{26}H_{27}F_2N_5O_4 + H]^+$: 512.0 | 98.8 | C |
| 1.96 | 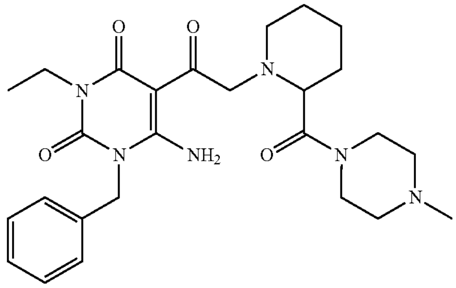 [SMILES: CCn1c(=O)c(C(=O)CN2CCCCC2C(=O)N2CCN(C)CC2)c(N)n(Cc2ccccc2)c1=O] | ESI-MS m/z for $[C_{26}H_{36}N_6O_4 + H]^+$: 497.0 | 99.8 | A |
| 1.97 | 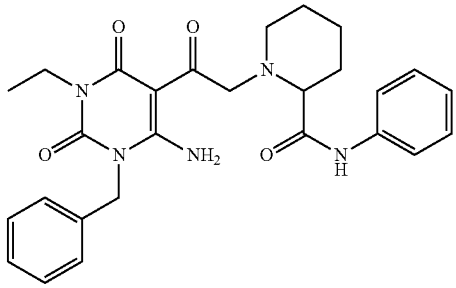 [SMILES: CCn1c(=O)c(C(=O)CN2CCCCC2C(=O)Nc2ccccc2)c(N)n(Cc2ccccc2)c1=O] | ESI-MS m/z for $[C_{27}H_{31}N_5O_4 + H]^+$: 490.2 | 96.9 | A |
| 1.98 | 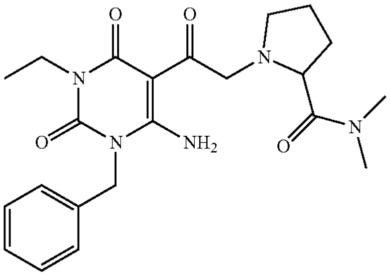 [SMILES: CCn1c(=O)c(C(=O)CN2CCCC2C(=O)N(C)C)c(N)n(Cc2ccccc2)c1=O] | ESI-MS m/z for $[C_{22}H_{29}N_5O_4 + H]^+$: 428.0 | 99.0 | A |
| 1.99 | 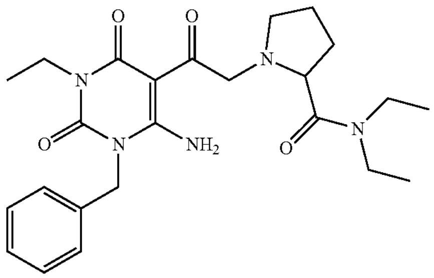 [SMILES: CCN(CC)C(=O)C1CCCN1CC(=O)c1c(N)n(Cc2ccccc2)c(=O)n(CC)c1=O] | ESI-MS m/z for $[C_{24}H_{33}N_5O_4 + H]^+$: 456.0 | 99.6 | A |

TABLE 1-continued
| No. | Structure | HRMS | HPLC/LC MS Purity (%) | Synthetic Route |
|---|---|---|---|---|
| 1.100 | 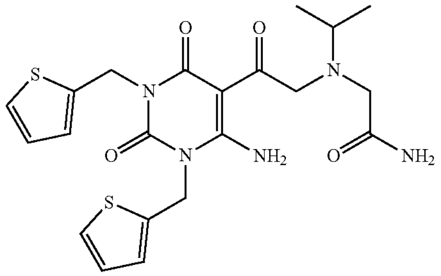 [SMILES: CC(C)N(CC(N)=O)CC(=O)c1c(N)n(Cc2cccs2)c(=O)n(Cc2cccs2)c1=O] | HRMS calcd for $[C_{21}H_{25}N_5O_4S_2 + H]^+$: 476.1421, Found: 476.1421 | 97.8 | C |
| 1.101 | 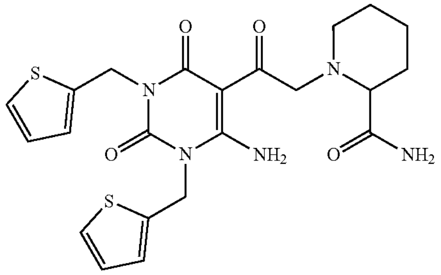 [SMILES: NC(=O)C1CCCCN1CC(=O)c1c(N)n(Cc2cccs2)c(=O)n(Cc2cccs2)c1=O] | HRMS calcd for $[C_{22}H_{25}N_5O_4S_2 + H]^+$: 488.1421, Found: 488.1424 | 98.7 | C |
| 1.102 | 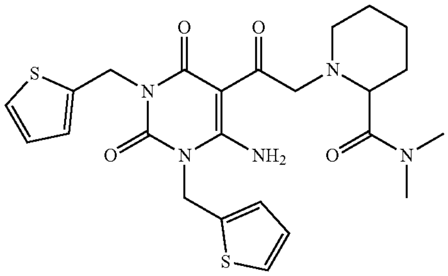 [SMILES: CN(C)C(=O)C1CCCCN1CC(=O)c1c(N)n(Cc2cccs2)c(=O)n(Cc2cccs2)c1=O] | HRMS calcd for $[C_{24}H_{29}N_5O_4S_2 + H]^+$: 516.1734, Found: 516.1727 | 100 | C |
| 1.103 | 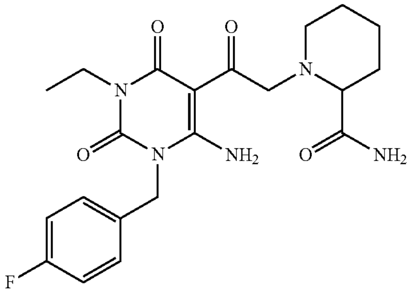 [SMILES: CCn1c(=O)c(C(=O)CN2CCCCC2C(N)=O)c(N)n(Cc2ccc(F)cc2)c1=O] | HRMS calcd for $[C_{21}H_{26}FN_5O_4 + H]^+$: 432.2042, Found: 432.2037 | 98.3 | A |
| 1.104 | 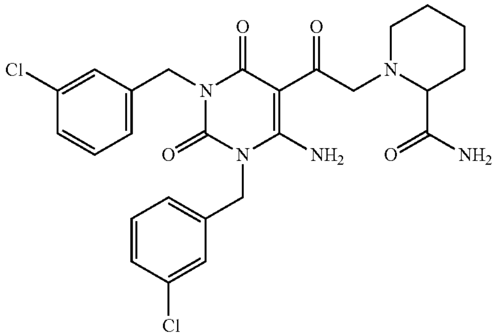 [SMILES: NC(=O)C1CCCCN1CC(=O)c1c(N)n(Cc2cccc(Cl)c2)c(=O)n(Cc2cccc(Cl)c2)c1=O] | ESI-MS m/z for $[C_{26}H_{27}C_{12}N_5O_4 + H]^+$: 544.1 | 97.2 | C |

TABLE 1-continued
| No. | Structure | HRMS | HPLC/LC MS Purity (%) | Synthetic Route |
|---|---|---|---|---|
| 1.105 | 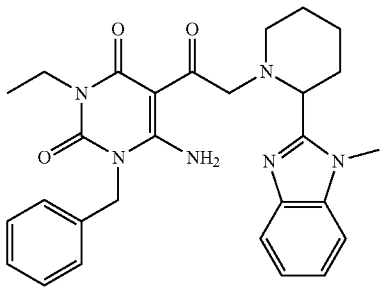 [SMILES: CCn1c(=O)c(C(=O)CN2CCCCC2c2nc3ccccc3n2C)c(N)n(Cc2ccccc2)c1=O] | ESI-MS m/z for $[C_{28}H_{32}N_6O_3 + H]^+$: 501.59 | 96.4 | A |
| 1.106 | 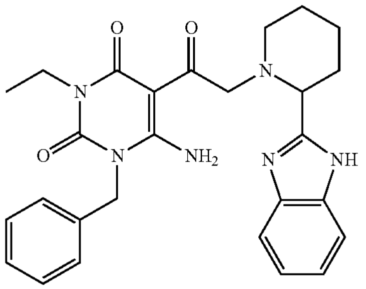 [SMILES: CCn1c(=O)c(C(=O)CN2CCCCC2c2nc3ccccc3[nH]2)c(N)n(Cc2ccccc2)c1=O] | ESI-MS m/z for $[C^{27}H^{30}N^{6}O^{3} + H]^+$: 485.58 | 98.5 | A |
| 1.107 | 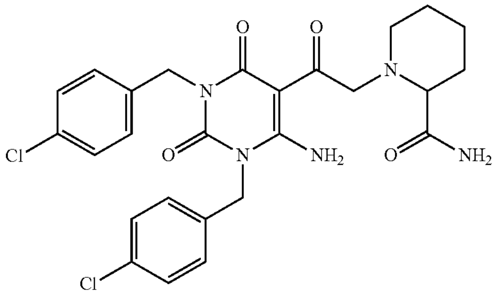 [SMILES: NC(=O)C1CCCCN1CC(=O)c1c(N)n(Cc2ccc(Cl)cc2)c(=O)n(Cc2ccc(Cl)cc2)c1=O] | ESI-MS m/z for $[C_{26}H_{27}C_{12}N_5O_4 + H]^+$: 544.1 | 96.6 | C |
| 1.108 | 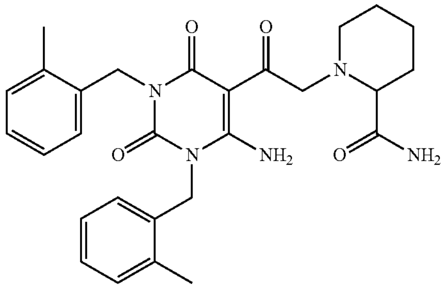 [SMILES: Cc1ccccc1Cn1c(N)c(C(=O)CN2CCCCC2C(N)=O)c(=O)n(Cc2ccccc2C)c1=O] | ESI-MS m/z for $[C_{28}H_{33}N_5O_4 + H]^+$: 504.2 | 97.8 | C |
| 1.109 | 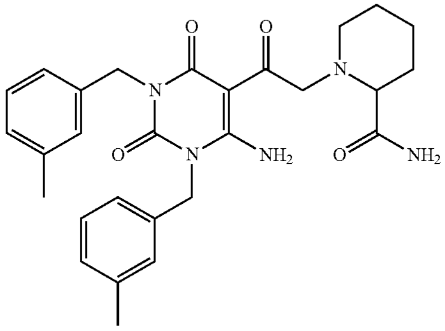 [SMILES: Cc1cccc(Cn2c(N)c(C(=O)CN3CCCCC3C(N)=O)c(=O)n(Cc3cccc(C)c3)c2=O)c1] | ESI-MS m/z for $[C_{28}H_{33}N_5O_4 + H]^+$: 504.2 | 97.8 | C |

TABLE 1-continued
| No. | Structure | HRMS | HPLC/LC MS Purity (%) | Synthetic Route |
|---|---|---|---|---|
| 1.110 | 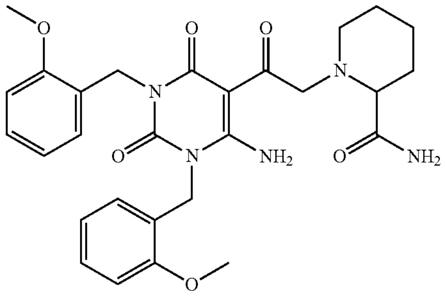 [SMILES: COc1ccccc1Cn1c(N)c(C(=O)CN2CCCCC2C(N)=O)c(=O)n(Cc2ccccc2OC)c1=O] | ESI-MS m/z for $[C_{28}H_{33}N_5O_6 + H]^+$: 536.2 | 97.9 | C |
| 1.111 | 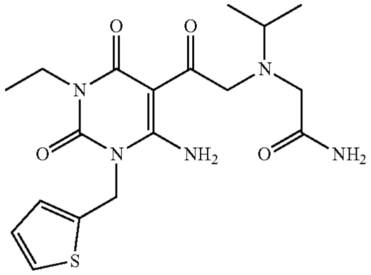 [SMILES: CCn1c(=O)c(C(=O)CN(CC(N)=O)C(C)C)c(N)n(Cc2cccs2)c1=O] | HRMS calcd for $[C_{18}H_{25}N_5O_4S + H]^+$: 408.1700, Found: 408.1706 | 98 | A |
| 1.112 | 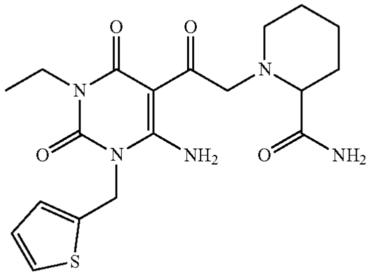 [SMILES: CCn1c(=O)c(C(=O)CN2CCCCC2C(N)=O)c(N)n(Cc2cccs2)c1=O] | HRMS calcd for $[C_{19}H_{25}N_5O_4S + H]^+$: 420.1700, Found: 420.1696 | 99 | A |
| 1.113 | 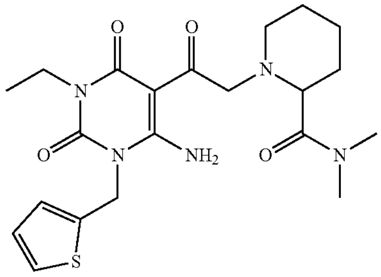 [SMILES: CCn1c(=O)c(C(=O)CN2CCCCC2C(=O)N(C)C)c(N)n(Cc2cccs2)c1=O] | HRMS calcd for $[C_{21}H_{29}N_5O_4S + H]^+$: 448.2013, Found: 448.2014 | 100 | A |
| 1.114 | 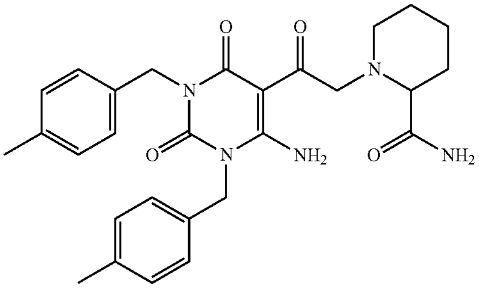 [SMILES: Cc1ccc(Cn2c(N)c(C(=O)CN3CCCCC3C(N)=O)c(=O)n(Cc3ccc(C)cc3)c2=O)cc1] | ESI-MS m/z for $[C_{28}H_{33}N_5O_4 + H]^+$: 504.2 | 98.2 | C |

TABLE 1-continued
| No. | Structure | HRMS | HPLC/LC MS Purity (%) | Synthetic Route |
|---|---|---|---|---|
| 1.115 | 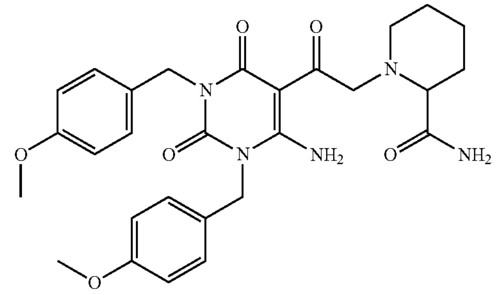 [SMILES: COc1ccc(Cn2c(N)c(C(=O)CN3CCCCC3C(N)=O)c(=O)n(Cc3ccc(OC)cc3)c2=O)cc1] | ESI-MS m/z for $[C_{28}H_{33}N_5O_6 + H]^+$: 536.2 | 97.9 | C |
| 1.116 | 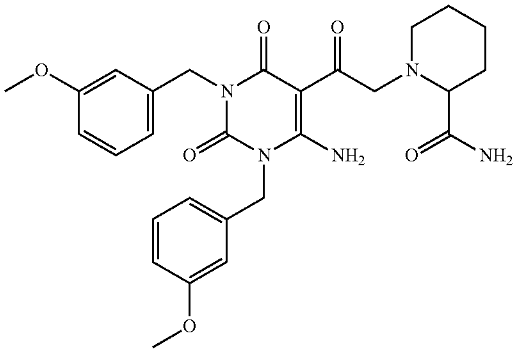 [SMILES: COc1cccc(Cn2c(N)c(C(=O)CN3CCCCC3C(N)=O)c(=O)n(Cc3cccc(OC)c3)c2=O)c1] | ESI-MS m/z for $[C_{28}H_{33}N_5O_6 + H]^+$: 536.2 | 98.5 | C |
| 1.117 | 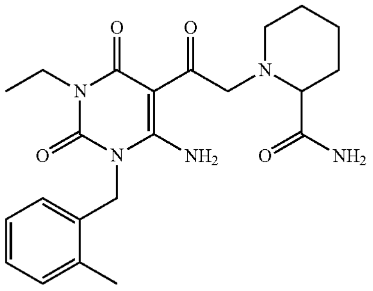 [SMILES: CCn1c(=O)c(C(=O)CN2CCCCC2C(N)=O)c(N)n(Cc2ccccc2C)c1=O] | HRMS calcd for $[C_{22}H_{29}N_5O_4 + H]^+$: 428.2292, Found: 428.2290 | 99 | A |
| 1.118 | 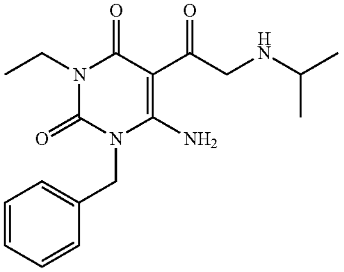 [SMILES: CCn1c(=O)c(C(=O)CNC(C)C)c(N)n(Cc2ccccc2)c1=O] | HRMS calcd for $[C_{18}H_{24}N_4O_3 + H]^+$: 345.1921, Found: 345.1917 | 99.2 | A |
| 1.119 | 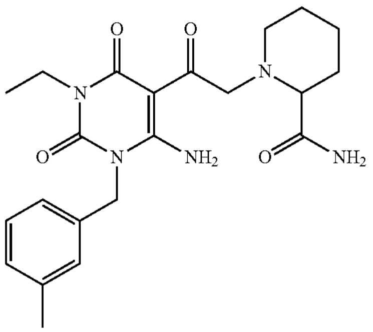 [SMILES: CCn1c(=O)c(C(=O)CN2CCCCC2C(N)=O)c(N)n(Cc2cccc(C)c2)c1=O] | HRMS calcd for $[C_{22}H_{29}N_5O_4 + H]^+$: 428.2292, Found: 428.2295 | 97.3 | A |

TABLE 1-continued
| No. | Structure | HRMS | HPLC/LC MS Purity (%) | Synthetic Route |
|---|---|---|---|---|
| 1.120 | 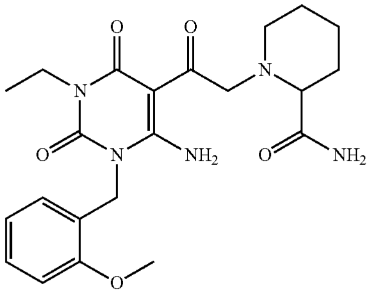 [SMILES: CCn1c(=O)c(C(=O)CN2CCCCC2C(N)=O)c(N)n(Cc2ccccc2OC)c1=O] | HRMS calcd for $[C_{22}H_{29}N_5O_5 + H]^+$: 444.2242, Found: 444.2244 | 96.7 | A |
| 1.121 | 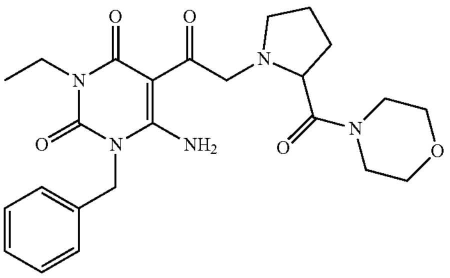 [SMILES: CCn1c(=O)c(C(=O)CN2CCCC2C(=O)N2CCOCC2)c(N)n(Cc2ccccc2)c1=O] | ESI-MS m/z for $[C_{24}H_{31}N_5O_5 + H]^+$: 470.1 | 99.1 | A |
| 1.122 | 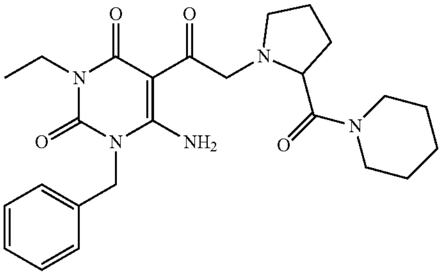 [SMILES: CCn1c(=O)c(C(=O)CN2CCCC2C(=O)N2CCCCC2)c(N)n(Cc2ccccc2)c1=O] | ESI-MS m/z for $[C_{25}H_{33}N_5O_4 + H]^+$: 468.0 | 99.7 | A |
| 1.123 | 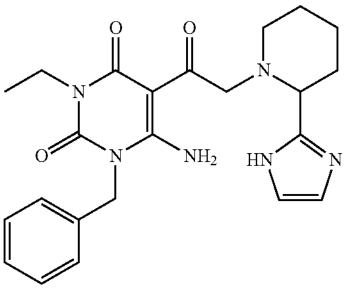 | ESI-MS m/z for $[C_{22}H_{26}N_6O_3 + H]^+$: 423.2 | 99.1 | A |
| 1.124 | 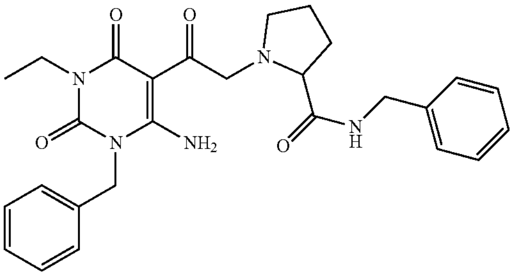 [SMILES: CCn1c(=O)c(C(=O)CN2CCCC2C(=O)NCc2ccccc2)c(N)n(Cc2ccccc2)c1=O] | ESI-MS m/z for $[C_{27}H_{31}N_5O_4 + H]^+$: 490.2 | 99.4 | A |

TABLE 1-continued
| No. | Structure | HRMS | HPLC/LC MS Purity (%) | Synthetic Route |
|---|---|---|---|---|
| 1.125 | 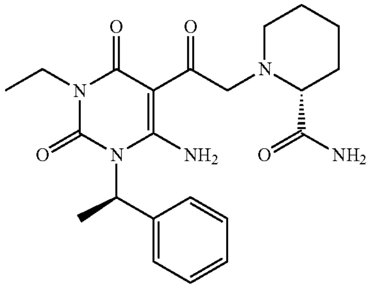 [SMILES: CCn1c(=O)c(C(=O)CN2CCCC[C@@H]2C(N)=O)c(N)n([C@H](C)c2ccccc2)c1=O] | HRMS calcd for $[C_{22}H_{29}N_5O_4 + H]^+$: 428.2292, Found: 428.2293 | 100 | A |
| 1.126 | 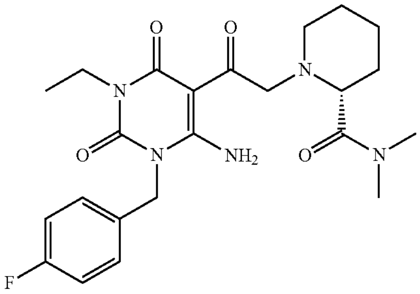 [SMILES: CCn1c(=O)c(C(=O)CN2CCCC[C@@H]2C(=O)N(C)C)c(N)n(Cc2ccc(F)cc2)c1=O] | HRMS calcd for $[C_{23}H_{30}FN_5O_4 + H]^+$: 460.2355, Found: 460.2348 | 100 | A |
| 1.127 | 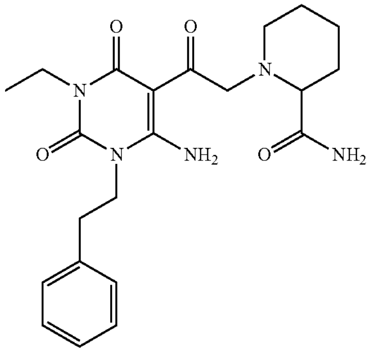 [SMILES: CCn1c(=O)c(C(=O)CN2CCCCC2C(N)=O)c(N)n(CCc2ccccc2)c1=O] | HRMS calcd for $[C_{22}H_{29}N_5O_4 + H]^+$: 428.2292, Found: 428.2287 | 95.4 | A |
| 1.128 | 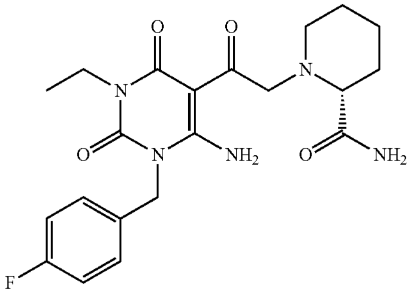 | HRMS calcd for $[C_{21}H_{26}FN_5O_4 + H]^+$: 432.2042, Found: 432.2041 | 97 | A |
| 1.129 | 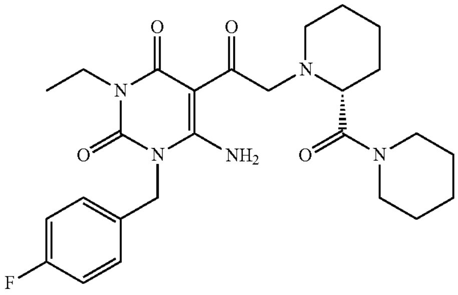 [SMILES: CCn1c(=O)c(C(=O)CN2CCCC[C@@H]2C(=O)N2CCCCC2)c(N)n(Cc2ccc(F)cc2)c1=O] | HRMS calcd for $[C_{26}H_{34}FN_5O_4 + H]^+$: 500.2668, Found: 500.2668 | 99.7 | A |

TABLE 1-continued
| No. | Structure | HRMS | HPLC/LC MS Purity (%) | Synthetic Route |
|---|---|---|---|---|
| 1.130 | 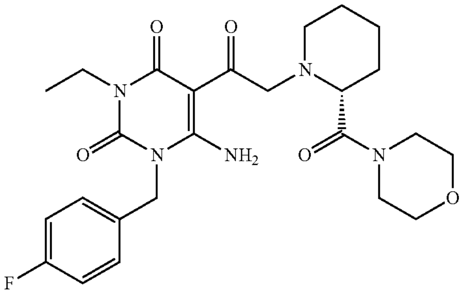 [SMILES: CCn1c(=O)c(C(=O)CN2CCCC[C@@H]2C(=O)N2CCOCC2)c(N)n(Cc2ccc(F)cc2)c1=O] | HRMS calcd for $[C_{25}H_{32}FN_5O_5 + H]^+$: 502.2460, Found: 502.2459 | 100 | A |
| 1.131 | 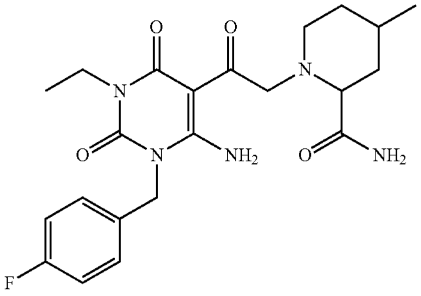 [SMILES: CCn1c(=O)c(C(=O)CN2CCC(C)CC2C(N)=O)c(N)n(Cc2ccc(F)cc2)c1=O] | HRMS calcd for $[C_{22}H_{28}FN_5O_4 + H]^+$: 446.2198, Found: 446.2202 | 99.5 | A |
| 1.132 | 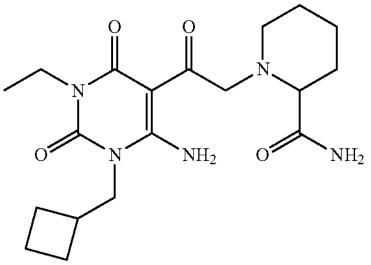 [SMILES: CCn1c(=O)c(C(=O)CN2CCCCC2C(N)=O)c(N)n(CC2CCC2)c1=O] | HRMS calcd for $[C_{19}H_{29}N_5O_4 + H]^+$: 392.2292, Found: 392.2294 | 99.6 | A |
| 1.133 | 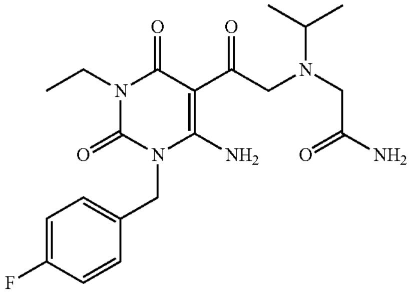 [SMILES: CCn1c(=O)c(C(=O)CN(CC(N)=O)C(C)C)c(N)n(Cc2ccc(F)cc2)c1=O] | HRMS calcd for $[C_{20}H_{26}FN_5O_4 + H]^+$: 420.2042, Found: 420.2042 | 98.5 | A |
| 1.134 | 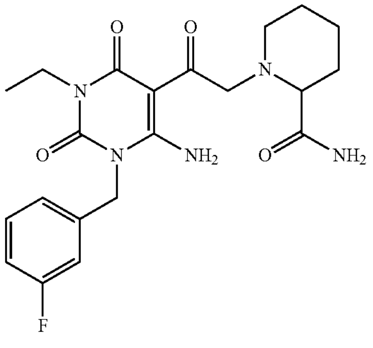 [SMILES: CCn1c(=O)c(C(=O)CN2CCCCC2C(N)=O)c(N)n(Cc2cccc(F)c2)c1=O] | HRMS calcd for $[C_{21}H_{26}FN_5O_4 + H]^+$: 432.2042, Found: 432.2044 | 99.3 | A |

TABLE 1-continued
| No. | Structure | HRMS | HPLC/LC MS Purity (%) | Synthetic Route |
|---|---|---|---|---|
| 1.135 | 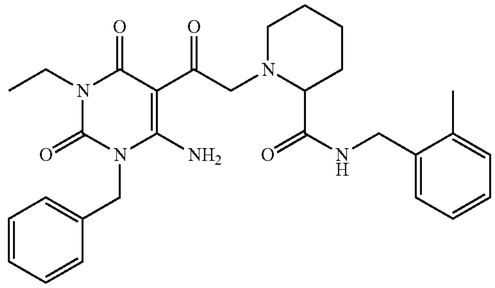 [SMILES: CCn1c(=O)c(C(=O)CN2CCCCC2C(=O)NCc2ccccc2C)c(N)n(Cc2ccccc2)c1=O] | ESI-MS m/z for $[C_{29}H_{35}N_5O_4 + H]^+$: 518.2 | 98.9 | A |
| 1.136 | 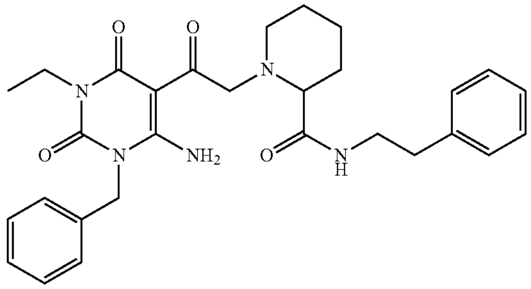 [SMILES: CCn1c(=O)c(C(=O)CN2CCCCC2C(=O)NCCc2ccccc2)c(N)n(Cc2ccccc2)c1=O] | ESI-MS m/z for $[C_{29}H_{35}N_5O_4 + H]^+$: 518.2 | 99.7 | A |
| 1.137 | 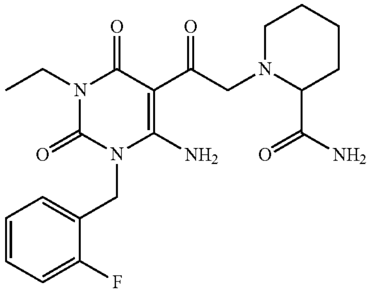 [SMILES: CCn1c(=O)c(C(=O)CN2CCCCC2C(N)=O)c(N)n(Cc2ccccc2F)c1=O] | ESI-MS m/z for $[C_{21}H_{26}FN_5O_4 + H]^+$: 432.2 | 99.3 | A |
| 1.138 | 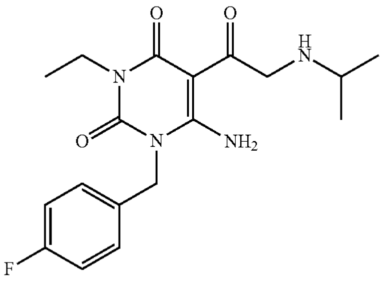 [SMILES: CCn1c(=O)c(C(=O)CNC(C)C)c(N)n(Cc2ccc(F)cc2)c1=O] | ESI-MS m/z for $[C_{21}H_{26}FN_5O_4 + H]^+$: 363.1 | 98.2 | A |
| 1.139 | 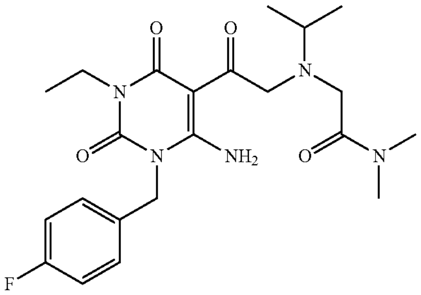 [SMILES: CCn1c(=O)c(C(=O)CN(CC(=O)N(C)C)C(C)C)c(N)n(Cc2ccc(F)cc2)c1=O] | HRMS calcd for $[C_{22}H_{30}FN_5O_4 + H]^+$: 448.2355, Found: 448.2359 | 100 | A |

TABLE 1-continued
| No. | Structure | HRMS | HPLC/LC MS Purity (%) | Synthetic Route |
| --- | --- | --- | --- | --- |
| 1.140 | 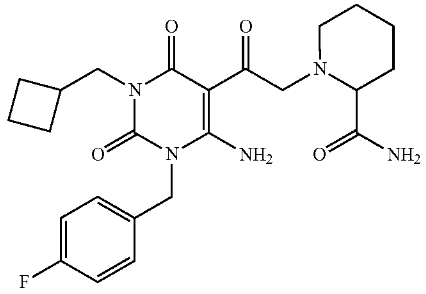 [SMILES: NC(=O)C1CCCCN1CC(=O)c1c(N)n(Cc2ccc(F)cc2)c(=O)n(CC2CCC2)c1=O] | HRMS calcd for $[C_{24}H_{30}FN_5O_4 + H]^+$: 472.2355, Found: 472.2359 | 95.8 | A |
| 1.141 | 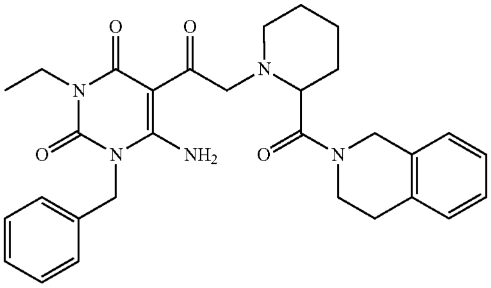 [SMILES: CCn1c(=O)c(C(=O)CN2CCCCC2C(=O)N2CCc3ccccc3C2)c(N)n(Cc2ccccc2)c1=O] | ESI-MS m/z for $[C_{30}H_{35}N_5O_4 + H]^+$: 530.2 | 99.8 | A |
| 1.142 | 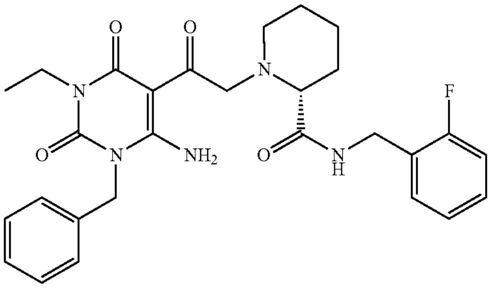 [SMILES: CCn1c(=O)c(C(=O)CN2CCCC[C@@H]2C(=O)NCc2ccccc2F)c(N)n(Cc2ccccc2)c1=O] | ESI-MS m/z for $[C_{28}H_{32}FN_5O_4 + H]^+$: 522.1 | 97.4 | A |
| 1.143 | 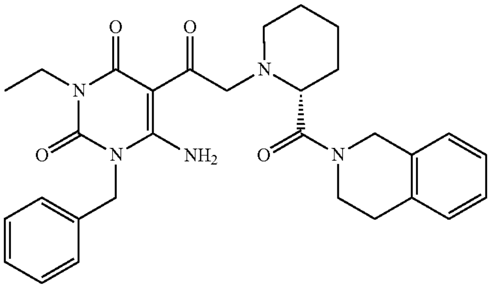 [SMILES: CCn1c(=O)c(C(=O)CN2CCCC[C@@H]2C(=O)N2CCc3ccccc3C2)c(N)n(Cc2ccccc2)c1=O] | ESI-MS m/z for $[C_{30}H_{35}N_5O_4 + H]^+$: 530.1 | 99.4 | A |
| 1.144 | 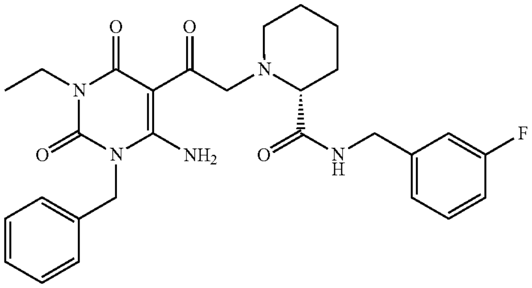 [SMILES: CCn1c(=O)c(C(=O)CN2CCCC[C@@H]2C(=O)NCc2cccc(F)c2)c(N)n(Cc2ccccc2)c1=O] | ESI-MS m/z for $[C_{28}H_{32}FN_5O_4 + H]^+$: 522.1 | 98.3 | A |

TABLE 1-continued
| No. | Structure | HRMS | HPLC/LC MS Purity (%) | Synthetic Route |
|---|---|---|---|---|
| 1.145 | 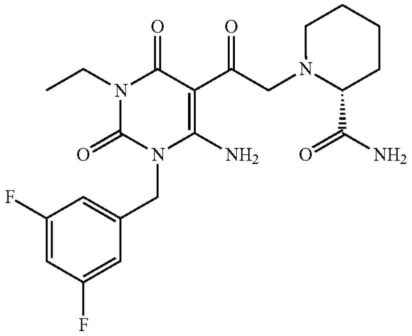 [SMILES: CCn1c(=O)c(C(=O)CN2CCCC[C@@H]2C(N)=O)c(N)n(Cc2cc(F)cc(F)c2)c1=O] | ESI-MS m/z for $[C_{21}H_{25}F_2N_5O_4 + H]^+$: 450.0 | 97.3 | A |
| 1.146 | 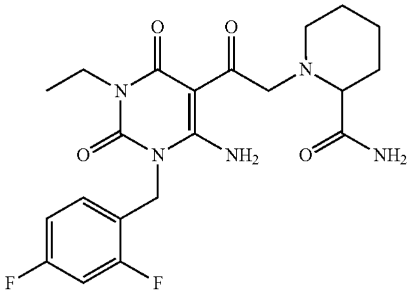 | ESI-MS m/z for $[C_{21}H_{25}F_2N_5O_4 + H]^+$: 450.0 | 95.0 | A |
| 1.147 | 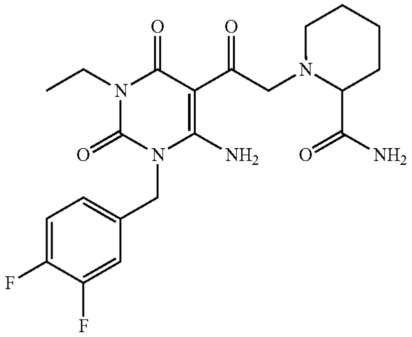 [SMILES: CCn1c(=O)c(C(=O)CN2CCCCC2C(N)=O)c(N)n(Cc2ccc(F)c(F)c2)c1=O] | ESI-MS m/z for $[C_{21}H_{25}F_2N_5O_4 + H]^+$: 450.1 | 99.6 | A |
| 1.148 | 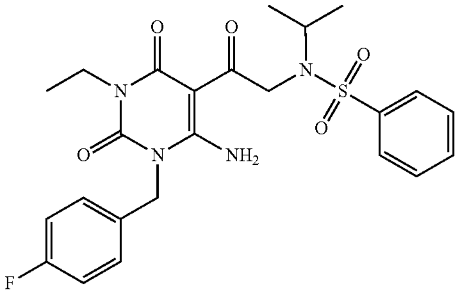 [SMILES: CCn1c(=O)c(C(=O)CN(C(C)C)S(=O)(=O)c2ccccc2)c(N)n(Cc2ccc(F)cc2)c1=O] | HRMS calcd for $[C_{24}H_{27}FN_4O_5S + H]^+$: 503.1759, Found: 503.1752 | 97.5 | D |
| 1.149 | 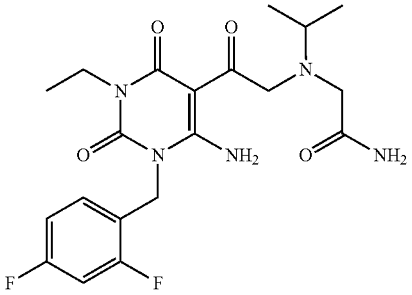 | ESI-MS m/z for $[C_{20}H_{25}F_2N_5O_4 + H]^+$: 438.0 | 99.3 | A |

TABLE 1-continued
| No. | Structure | HRMS | HPLC/LC MS Purity (%) | Synthetic Route |
| --- | --- | --- | --- | --- |
| 1.150 | 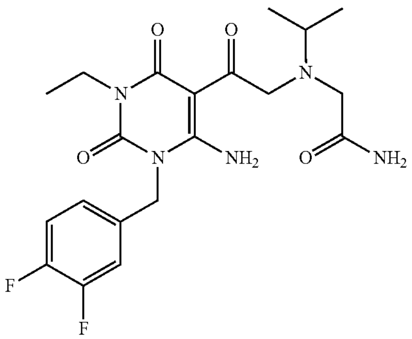 [SMILES: CCn1c(=O)c(C(=O)CN(CC(N)=O)C(C)C)c(N)n(Cc2ccc(F)c(F)c2)c1=O] | ESI-MS m/z for $[C_{20}H_{25}F_2N_5O_4 + H]^+$: 438.0 | 97.0 | A |
| 1.151 | 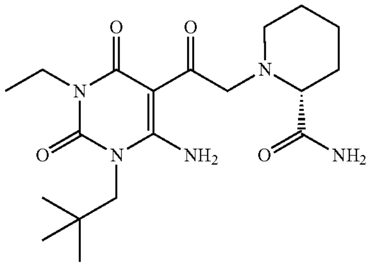 [SMILES: CCn1c(=O)c(C(=O)CN2CCCC[C@@H]2C(N)=O)c(N)n(CC(C)(C)C)c1=O] | ESI-MS m/z for $[C_{19}H_{31}F_2N_5O_4 + H]^+$: 394.0 | 99.9 | A |
| 1.152 | 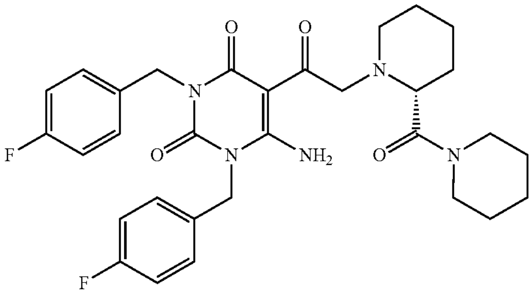 [SMILES: Nc1c(C(=O)CN2CCCC[C@@H]2C(=O)N2CCCCC2)c(=O)n(Cc2ccc(F)cc2)c(=O)n1Cc1ccc(F)cc1] | HRMS calcd for $[C_{31}H_{35}F_2N_5O_4 + H]^+$: 580.2730, Found: 580.2724 | 100 | A |
| 1.153 | 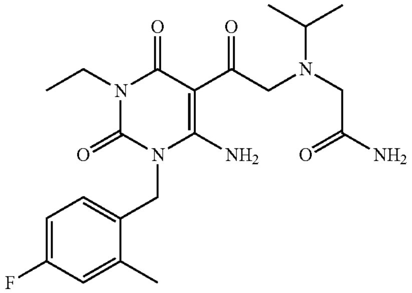 [SMILES: CCn1c(=O)c(C(=O)CN(CC(N)=O)C(C)C)c(N)n(Cc2ccc(F)cc2C)c1=O] | ESI-MS m/z for $[C_{21}H_{28}FN_5O_4 + H]^+$: 434.0 | 97.9 | A |
| 1.154 | 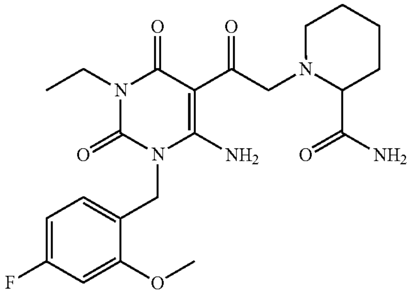 [SMILES: CCn1c(=O)c(C(=O)CN2CCCCC2C(N)=O)c(N)n(Cc2ccc(F)cc2OC)c1=O] | ESI-MS m/z for $[C_{22}H_{28}FN_5O_5 + H]^+$: 462.0 | 97.9 | A |

TABLE 1-continued
| No. | Structure | HRMS | HPLC/LC MS Purity (%) | Synthetic Route |
|---|---|---|---|---|
| 1.155 | 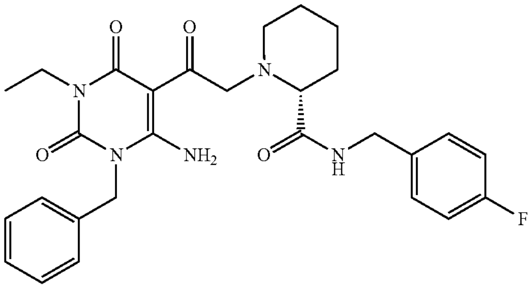 [SMILES: CCn1c(=O)c(C(=O)CN2CCCC[C@@H]2C(=O)NCc2ccc(F)cc2)c(N)n(Cc2ccccc2)c1=O] | ESI-MS m/z for $[C_{28}H_{32}FN_5O_4 + H]^+$: 522.1 | 98.8 | A |
| 1.156 | 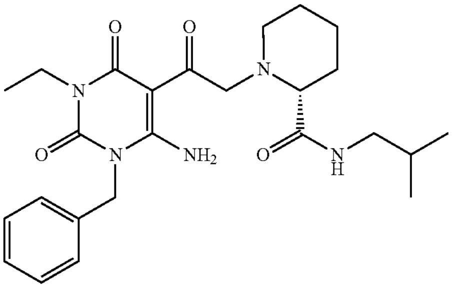 [SMILES: CCn1c(=O)c(C(=O)CN2CCCC[C@@H]2C(=O)NCC(C)C)c(N)n(Cc2ccccc2)c1=O] | ESI-MS m/z for $[C_{25}H_{35}N_5O_4 + H]^+$: 470.1 | 99.3 | A |
| 1.157 | 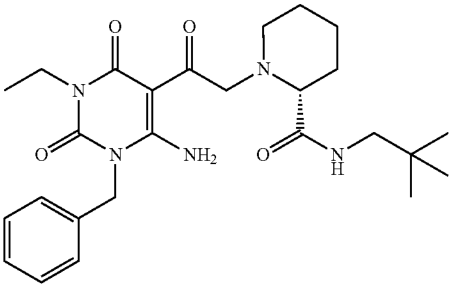 [SMILES: CCn1c(=O)c(C(=O)CN2CCCC[C@@H]2C(=O)NCC(C)(C)C)c(N)n(Cc2ccccc2)c1=O] | ESI-MS m/z for $[C_{26}H_{37}N_5O_4 + H]^+$: 484.1 | 99.0 | A |
| 1.158 | 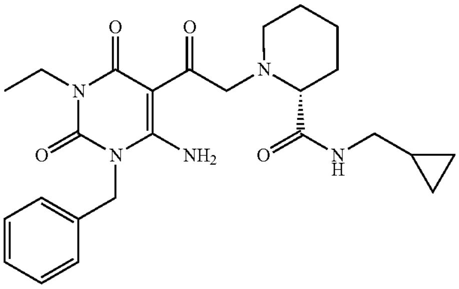 [SMILES: CCn1c(=O)c(C(=O)CN2CCCC[C@@H]2C(=O)NCC2CC2)c(N)n(Cc2ccccc2)c1=O] | ESI-MS m/z for $[C_{25}H_{33}N_5O_4 + H]^+$: 468.0 | 99.5 | A |
| 1.159 | 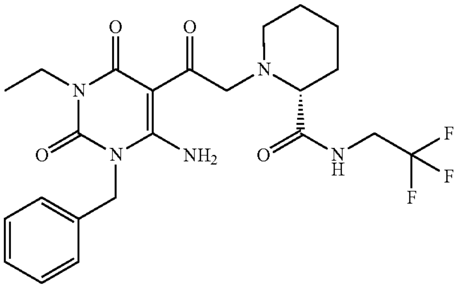 [SMILES: CCn1c(=O)c(C(=O)CN2CCCC[C@@H]2C(=O)NCC(F)(F)F)c(N)n(Cc2ccccc2)c1=O] | ESI-MS m/z for $[C_{23}H_{28}F_3N_5O_4 + H]^+$: 496.0 | 97.3 | A |

TABLE 1-continued
| No. | Structure | HRMS | HPLC/LC MS Purity (%) | Synthetic Route |
|---|---|---|---|---|
| 1.160 | 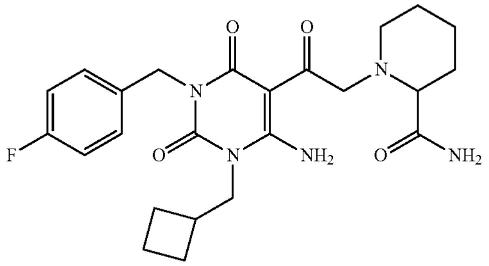 [SMILES: NC(=O)C1CCCCN1CC(=O)c1c(N)n(CC2CCC2)c(=O)n(Cc2ccc(F)cc2)c1=O] | HRMS calcd for $[C_{24}H_{30}FN_5O_4 + H]^+$: 472.2355, Found: 472.2362 | 98.7 | A |
| 1.161 | 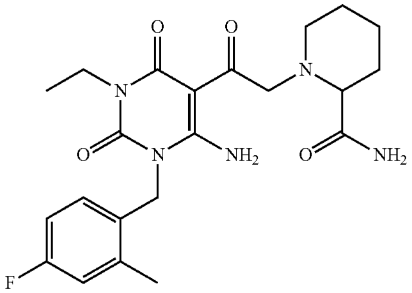 [SMILES: CCn1c(=O)c(C(=O)CN2CCCCC2C(N)=O)c(N)n(Cc2ccc(F)cc2C)c1=O] | ESI-MS m/z for $[C_{22}H_{28}FN_5O_4 + H]^+$: 446.0 | 96.4 | A |
| 1.162 | 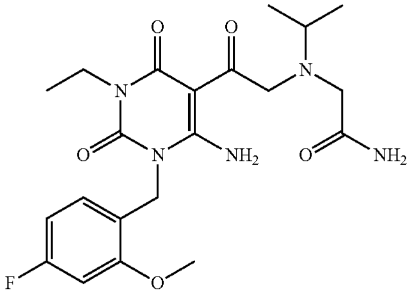 [SMILES: CCn1c(=O)c(C(=O)CN(CC(N)=O)C(C)C)c(N)n(Cc2ccc(F)cc2OC)c1=O] | ESI-MS m/z for $[C_{21}H_{28}FN_5O_5 + H]^+$: 450.0 | 97.8 | A |
| 1.163 | 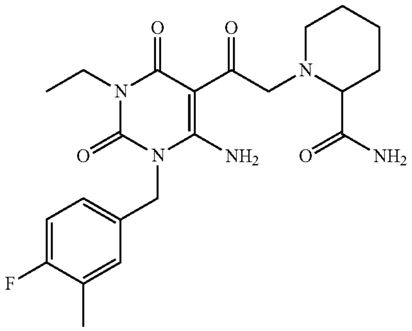 [SMILES: CCn1c(=O)c(C(=O)CN2CCCCC2C(N)=O)c(N)n(Cc2ccc(F)c(C)c2)c1=O] | ESI-MS m/z for $[C_{22}H_{28}FN_5O_4 + H]^+$: 446.0 | 97.6 | A |
| 1.164 | 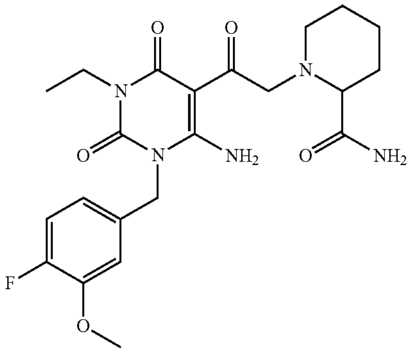 [SMILES: CCn1c(=O)c(C(=O)CN2CCCCC2C(N)=O)c(N)n(Cc2ccc(F)c(OC)c2)c1=O] | ESI-MS m/z for $[C_{22}H_{28}FN_5O_5 + H]^+$: 462.0 | 95.7 | A |

TABLE 1-continued
| No. | Structure | HRMS | HPLC/LC MS Purity (%) | Synthetic Route |
|---|---|---|---|---|
| 1.165 | 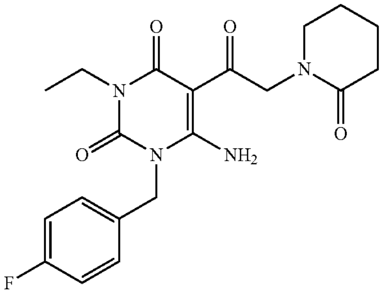 [SMILES: CCn1c(=O)c(C(=O)CN2CCCCC2=O)c(N)n(Cc2ccc(F)cc2)c1=O] | HRMS calcd for $[C_{20}H_{23}FN_4O_4 + H]^+$: 403.1776, Found: 403.1785 | 98.5 | A |
| 1.166 | 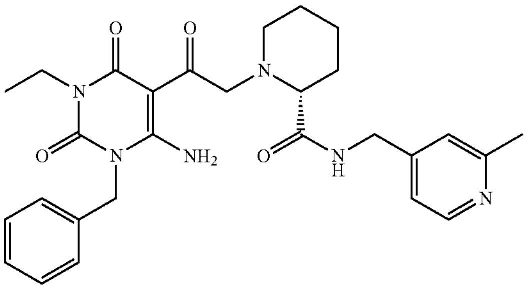 [SMILES: CCn1c(=O)c(C(=O)CN2CCCC[C@@H]2C(=O)NCc2ccnc(C)c2)c(N)n(Cc2ccccc2)c1=O] | ESI-MS m/z for $[C_{28}H_{34}N_6O_4 + H]^+$: 519.3 | 99.0 | A |
| 1.167 | 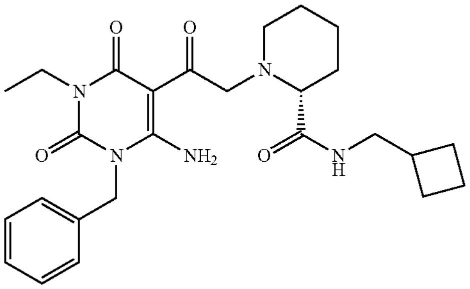 [SMILES: CCn1c(=O)c(C(=O)CN2CCCC[C@@H]2C(=O)NCC2CCC2)c(N)n(Cc2ccccc2)c1=O] | ESI-MS m/z for $[C_{26}H_{35}N_5O_4 + H]^+$: 482.1 | 99.5 | A |
| 1.168 | 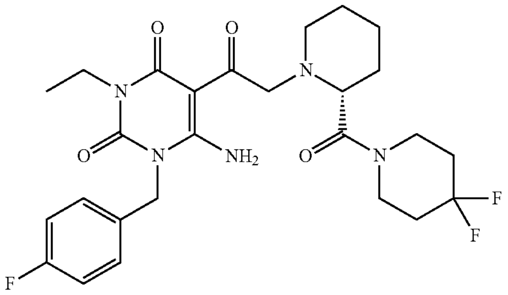 [SMILES: CCn1c(=O)c(C(=O)CN2CCCC[C@@H]2C(=O)N2CCC(F)(F)CC2)c(N)n(Cc2ccc(F)cc2)c1=O] | HRMS calcd for $[C_{26}H_{32}F_3N_5O_4 + H]^+$: 536.2479, Found: 536.2480 | 99.0 | A |
| 1.169 | 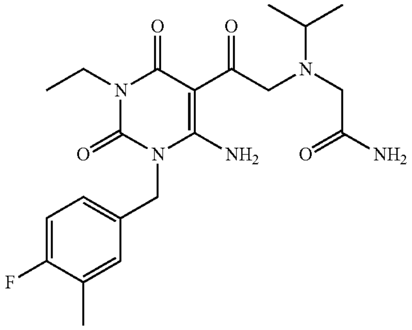 [SMILES: CCn1c(=O)c(C(=O)CN(CC(N)=O)C(C)C)c(N)n(Cc2ccc(F)c(C)c2)c1=O] | ESI-MS m/z for $[C_{21}H_{28}FN_5O_4 + H]^+$: 434.2 | 99.6 | A |

TABLE 1-continued
| No. | Structure | HRMS | HPLC/LC MS Purity (%) | Synthetic Route |
|---|---|---|---|---|
| 1.170 | 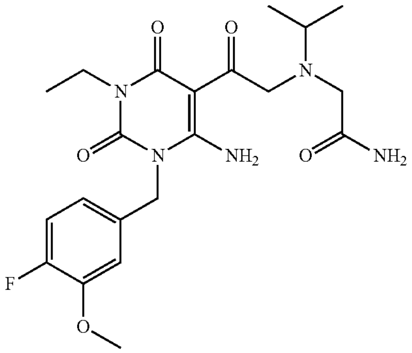 [SMILES: CCn1c(=O)c(C(=O)CN(CC(N)=O)C(C)C)c(N)n(Cc2ccc(F)c(OC)c2)c1=O] | ESI-MS m/z for $[C_{21}H_{28}FN_5O_5 + H]^+$: 450.2 | 96.5 | A |
| 1.171 | 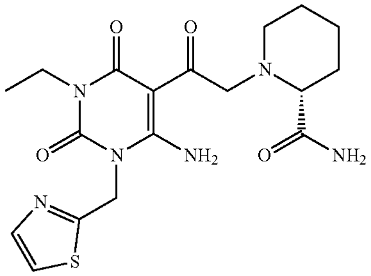 [SMILES: CCn1c(=O)c(C(=O)CN2CCCC[C@@H]2C(N)=O)c(N)n(Cc2nccs2)c1=O] | ESI-MS m/z for $[C_{18}H_{24}N_6O_4S + H]^+$: 421.0 | 99.4 | A |
| 1.172 | 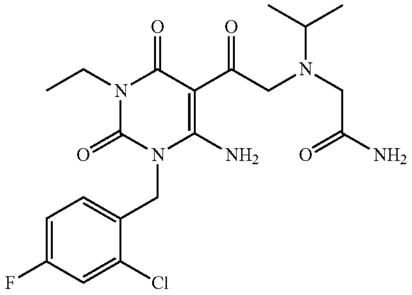 | ESI-MS m/z for $[C_{20}H_{25}ClFN_5O_4 + H]^+$: 454.1 | 94.7 | A |
| 1.173 | 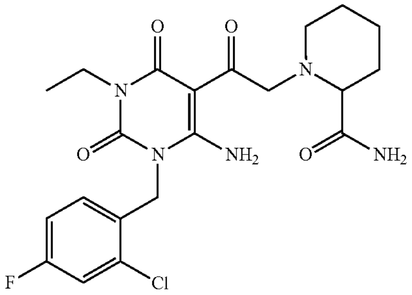 [SMILES: CCn1c(=O)c(C(=O)CN2CCCCC2C(N)=O)c(N)n(Cc2ccc(F)cc2Cl)c1=O] | ESI-MS m/z for $[C_{21}H_{25}ClFN_5O_4 + H]^+$: 466.1 | 97.8 | A |
| 1.174 | 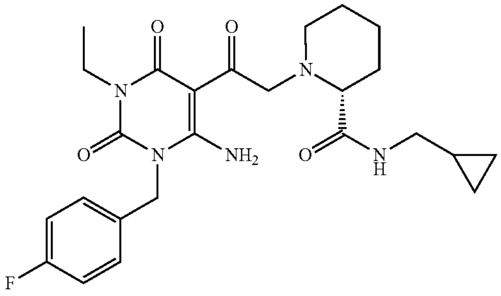 [SMILES: CCn1c(=O)c(C(=O)CN2CCCC[C@@H]2C(=O)NCC2CC2)c(N)n(Cc2ccc(F)cc2)c1=O] | ESI-MS m/z for $[C_{25}H_{32}FN_5O_4 + H]^+$: 486.56 | 98.9 | A |

TABLE 1-continued
| No. | Structure | HRMS | HPLC/LC MS Purity (%) | Synthetic Route |
|---|---|---|---|---|
| 1.175 | 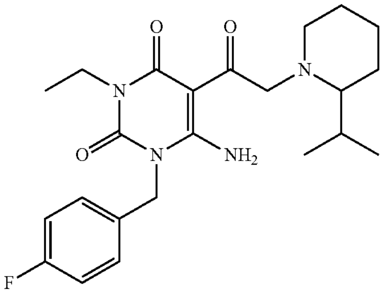 [SMILES: CCn1c(=O)c(C(=O)CN2CCCCC2C(C)C)c(N)n(Cc2ccc(F)cc2)c1=O] | HRMS calcd for $[C_{23}H_{31}FN_4O_3 + H]^+$: 431.2453, Found: 431.2461 | 92.8 | A |
| 1.176 | 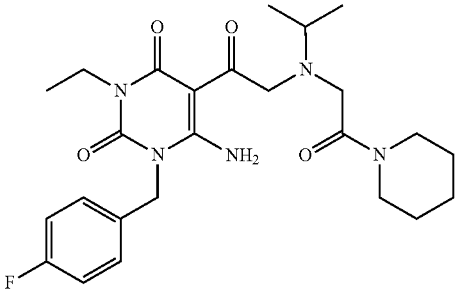 [SMILES: CCn1c(=O)c(C(=O)CN(CC(=O)N2CCCCC2)C(C)C)c(N)n(Cc2ccc(F)cc2)c1=O] | HRMS calcd for $[C_{25}H_{34}FN_5O_4 + H]^+$: 488.2668, Found: 488.2675 | 94.1 | A |
| 1.177 | 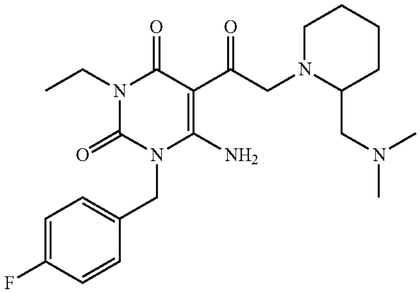 [SMILES: CCn1c(=O)c(C(=O)CN2CCCCC2CN(C)C)c(N)n(Cc2ccc(F)cc2)c1=O] | HRMS calcd for $[C_{23}H_{32}FN_5O_3 + H]^+$: 446.2562, Found: 446.2555 | 97.4 | A |
| 1.178 | 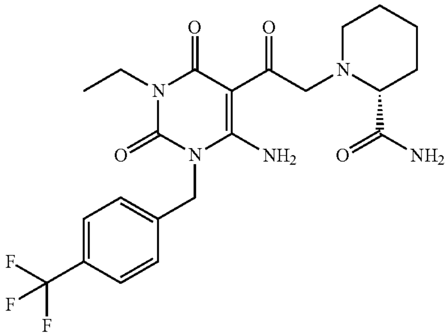 [SMILES: CCn1c(=O)c(C(=O)CN2CCCC[C@@H]2C(N)=O)c(N)n(Cc2ccc(C(F)(F)F)cc2)c1=O] | HRMS calcd for $[C_{22}H_{26}F_3N_5O_4 + H]^+$: 482.2010, Found: 482.2010 | 99.4 | A |
| 1.179 | 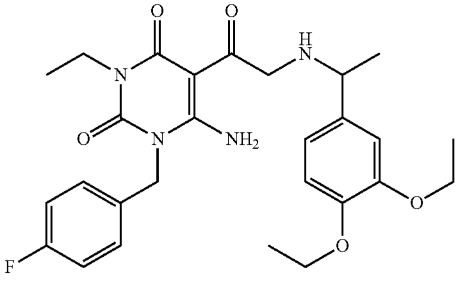 [SMILES: CCOc1ccc(C(C)NCC(=O)c2c(N)n(Cc3ccc(F)cc3)c(=O)n(CC)c2=O)cc1OCC] | HRMS calcd for $[C_{27}H_{33}FN_4O_5 + H]$+: 513.2508, Found: 513.2511 | 98.3 | A |

TABLE 1-continued
| No. | Structure | HRMS | HPLC/LC MS Purity (%) | Synthetic Route |
|---|---|---|---|---|
| 1.180 | 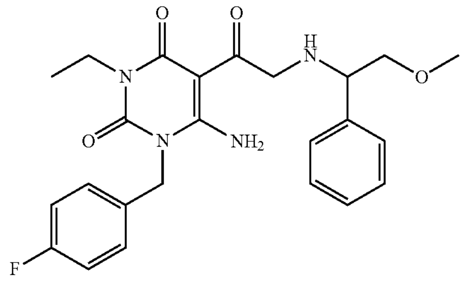 [SMILES: CCn1c(=O)c(C(=O)CNC(COC)c2ccccc2)c(N)n(Cc2ccc(F)cc2)c1=O] | HRMS calcd for $[C_{24}H_{27}FN_4O_4 + H]^+$: 455.2090, Found: 455.2091 | 96.9 | A |
| 1.181 | 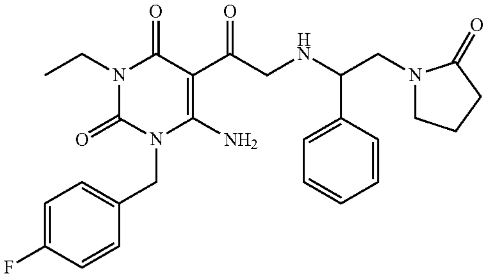 [SMILES: CCn1c(=O)c(C(=O)CNC(CN2CCCC2=O)c2ccccc2)c(N)n(Cc2ccc(F)cc2)c1=O] | HRMS calcd for $[C_{27}H_{30}FN_5O_4 + H]^+$: 508.2355, Found: 508.2361 | 98.2 | A |
| 1.182 | 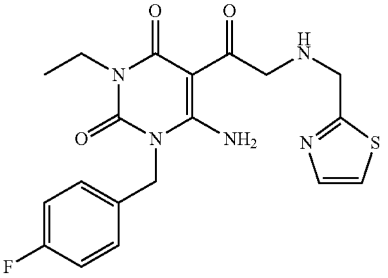 [SMILES: CCn1c(=O)c(C(=O)CNCc2nccs2)c(N)n(Cc2ccc(F)cc2)c1=O] | HRMS calcd for $[C_{19}H_{20}FN_5O_3S + H]^+$: 418.1344, Found: 418.1353 | 96.4 | A |
| 1.183 | 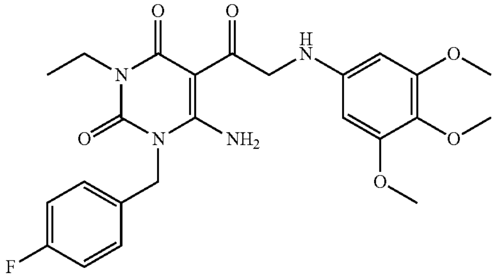 [SMILES: CCn1c(=O)c(C(=O)CNc2cc(OC)c(OC)c(OC)c2)c(N)n(Cc2ccc(F)cc2)c1=O] | HRMS calcd for $[C_{24}H_{27}FN_4O_6 + H]^+$: 486.1909, Found: 486.1914 | 99.0 | A |
| 1.184 | 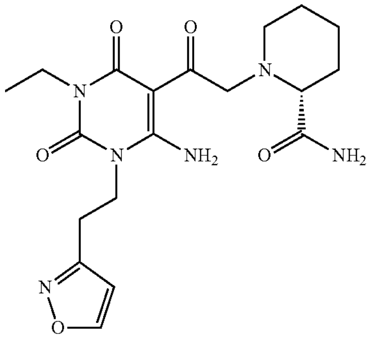 [SMILES: CCn1c(=O)c(C(=O)CN2CCCC[C@@H]2C(N)=O)c(N)n(CCc2ccon2)c1=O] | ESI-MS m/z for $[C_{19}H_{26}N_6O_5 + H]^+$: 419.41 | 99.4 | A |

TABLE 1-continued
| No. | Structure | HRMS | HPLC/LC MS Purity (%) | Synthetic Route |
|---|---|---|---|---|
| 1.185 | 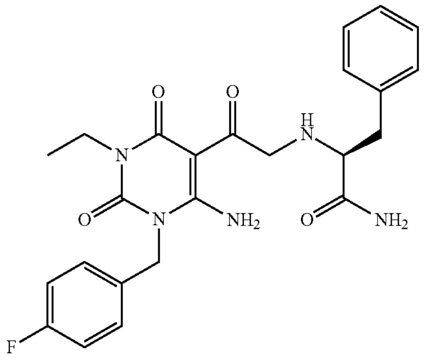 [SMILES: CCn1c(=O)c(C(=O)CN[C@@H](Cc2ccccc2)C(N)=O)c(N)n(Cc2ccc(F)cc2)c1=O] | HRMS calcd for $[C_{24}H_{26}FN_5O_4 + H]^+$: 468.2042, Found: 468.2046 | 99.6 | A |
| 1.186 | 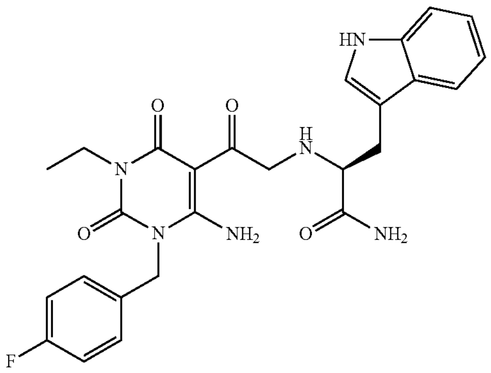 [SMILES: CCn1c(=O)c(C(=O)CN[C@@H](Cc2c[nH]c3ccccc23)C(N)=O)c(N)n(Cc2ccc(F)cc2)c1=O] | HRMS calcd for $[C_{26}H_{27}FN_6O_4 + H]^+$: 507.2151, Found: 507.2152 | 94.7 | A |
| 1.187 | 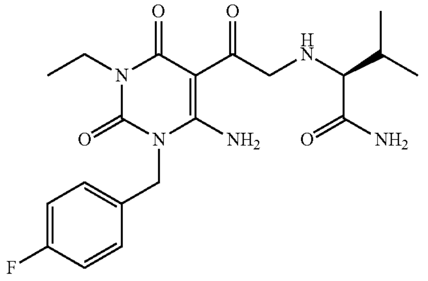 [SMILES: CCn1c(=O)c(C(=O)CN[C@H](C(N)=O)C(C)C)c(N)n(Cc2ccc(F)cc2)c1=O] | HRMS calcd for $[C_{20}H_{26}FN_5O_4 + H]^+$: 420.2042, Found: 420.2044 | 100 | A |
| 1.188 | 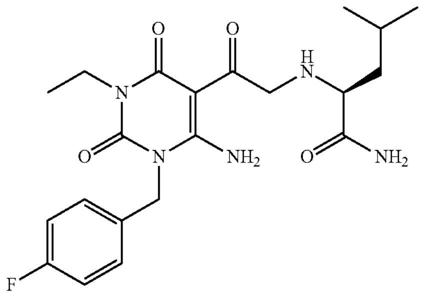 [SMILES: CCn1c(=O)c(C(=O)CN[C@@H](CC(C)C)C(N)=O)c(N)n(Cc2ccc(F)cc2)c1=O] | HRMS calcd for $[C_{21}H_{28}FN_5O_4 + H]^+$: 434.2198, Found: 434.2199 | 99.6 | A |

TABLE 1-continued
| No. | Structure | HRMS | HPLC/LC MS Purity (%) | Synthetic Route |
|---|---|---|---|---|
| 1.189 | 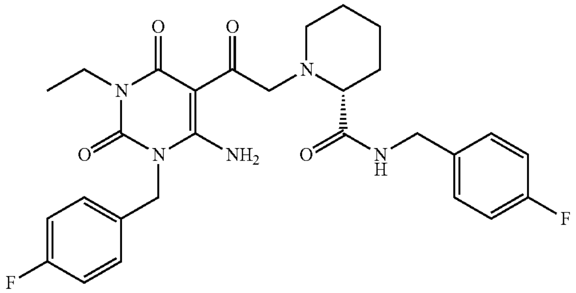 [SMILES: CCn1c(=O)c(C(=O)CN2CCCC[C@@H]2C(=O)NCc2ccc(F)cc2)c(N)n(Cc2ccc(F)cc2)c1=O] | ESI-MS m/z for $[C_{28}H_{31}F_2N_5O_4 + H]^+$: 540.4 | 97.6 | A |
| 1.190 | 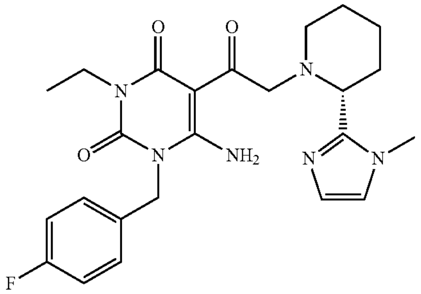 [SMILES: CCn1c(=O)c(C(=O)CN2CCCC[C@@H]2c2nccn2C)c(N)n(Cc2ccc(F)cc2)c1=O] | ESI-MS m/z for $[C_{24}H_{29}FN_6O_3 + H]^+$: 469.0 | 99.5 | A |
| 1.191 | 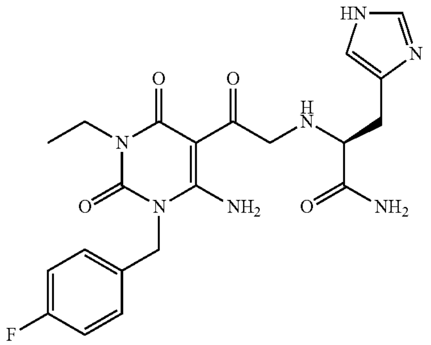 [SMILES: CCn1c(=O)c(C(=O)CN[C@@H](Cc2c[nH]cn2)C(N)=O)c(N)n(Cc2ccc(F)cc2)c1=O] | HRMS calcd for $[C_{21}H_{24}FN_7O_4 + H]^+$: 458.1947, Found: 458.1949 | 97.6 | A |
| 1.192 | 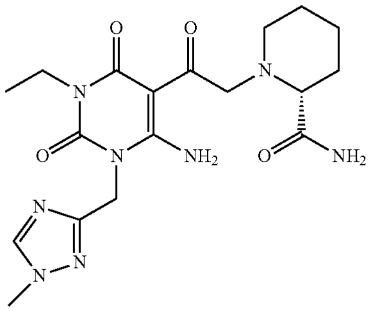 [SMILES: CCn1c(=O)c(C(=O)CN2CCCC[C@@H]2C(N)=O)c(N)n(Cc2ncn(C)n2)c1=O] | ESI-MS m/z for $[C_{18}H_{26}N_8O_4 + H]^+$: 419.0 | 99.3 | A |
| 1.193 | 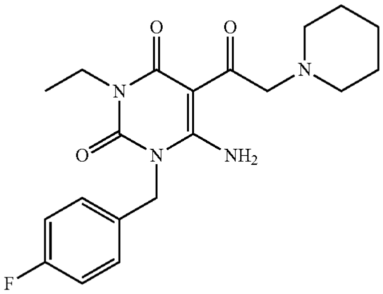 [SMILES: CCn1c(=O)c(C(=O)CN2CCCCC2)c(N)n(Cc2ccc(F)cc2)c1=O] | HRMS calcd for $[C_{20}H_{25}FN_4O_3 + H]^+$: 389.1984, Found: 389.1988 | 98.7 | A |

TABLE 1-continued
| No. | Structure | HRMS | HPLC/LC MS Purity (%) | Synthetic Route |
|---|---|---|---|---|
| 1.194 | 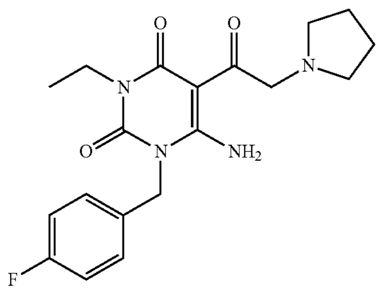 [SMILES: CCn1c(=O)c(C(=O)CN2CCCC2)c(N)n(Cc2ccc(F)cc2)c1=O] | HRMS calcd for $[C_{19}H_{23}FN_4O_3 + H]^+$: 375.1827, Found: 375.1823 | 99.6 | A |
| 1.195 | 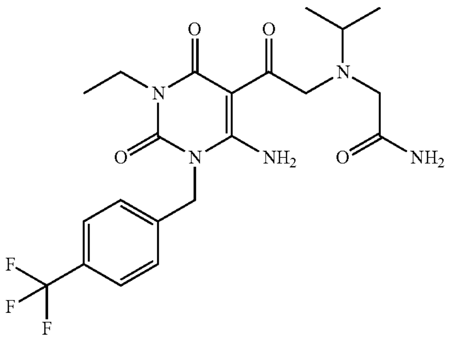 [SMILES: CCn1c(=O)c(C(=O)CN(CC(N)=O)C(C)C)c(N)n(Cc2ccc(C(F)(F)F)cc2)c1=O] | HRMS calcd for $[C_{21}H_{26}F_3N_5O_4 + H]^+$: 470.2010, Found: 470.2007 | 97.3 | A |
| 1.196 | 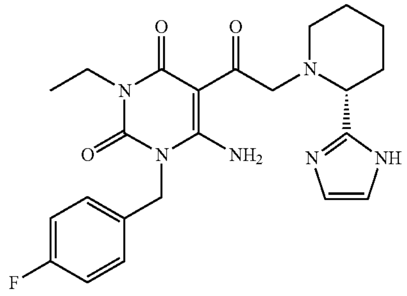 [SMILES: CCn1c(=O)c(C(=O)CN2CCCC[C@@H]2c2ncc[nH]2)c(N)n(Cc2ccc(F)cc2)c1=O] | ESI-MS m/z for $[C_{23}H_{27}FN_6O_3 + H]^+$: 455.2 | 99.5 | A |
| 1.197 | 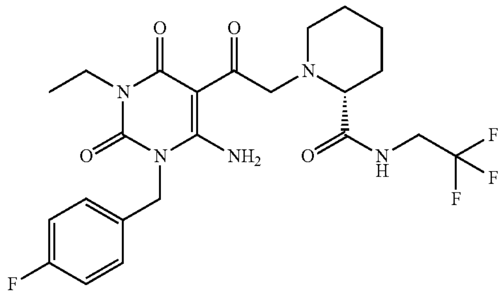 [SMILES: CCn1c(=O)c(C(=O)CN2CCCC[C@@H]2C(=O)NCC(F)(F)F)c(N)n(Cc2ccc(F)cc2)c1=O] | ESI-MS m/z for $[C_{23}H_{27}F_4N_5O_4 + H]^+$: 514.1 | 97.0 | A |
| 1.198 | 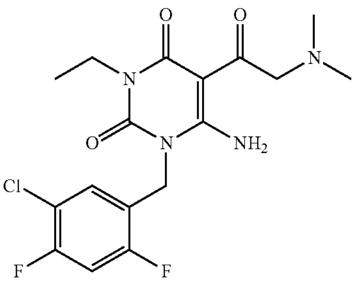 [SMILES: CCn1c(=O)c(C(=O)CN(C)C)c(N)n(Cc2cc(Cl)c(F)cc2F)c1=O] | ESI-MS m/z for $[C_{17}H_{19}ClF_2N_4O_3 + H]^+$: 401.0 | — | A |

TABLE 1-continued
| No. | Structure | HRMS | HPLC/LC MS Purity (%) | Synthetic Route |
|---|---|---|---|---|
| 1.199 | 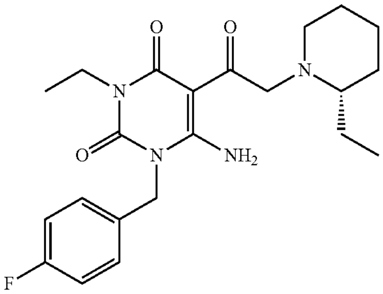 [SMILES: CC[C@H]1CCCCN1CC(=O)c1c(N)n(Cc2ccc(F)cc2)c(=O)n(CC)c1=O] | HRMS calcd for $[C_{22}H_{29}FN_4O_3 + H]^+$: 417.2297, Found: 417.2299 | 99.7 | A |
| 1.200 | 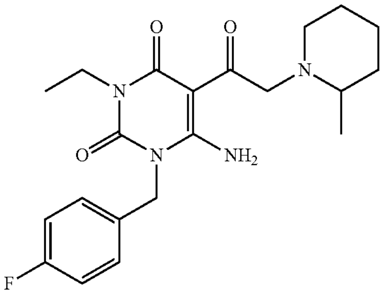 | HRMS calcd for $[C_{21}H_{27}FN_4O_3 + H]^+$: 403.2140, Found: 403.2141 | 100 | A |
| 1.201 | 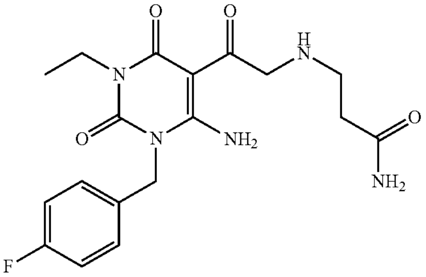 [SMILES: CCn1c(=O)c(C(=O)CNCCC(N)=O)c(N)n(Cc2ccc(F)cc2)c1=O] | ESI-MS m/z for $[C_{18}H_{22}FN_5O_4 + H]^+$: 392.3 | 95.3 | A |
| 1.202 | 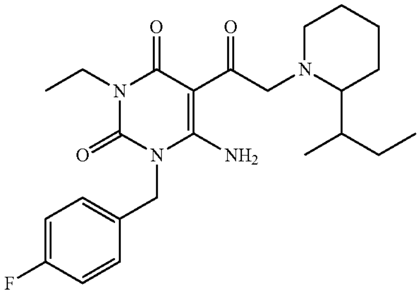 [SMILES: CCC(C)C1CCCCN1CC(=O)c1c(N)n(Cc2ccc(F)cc2)c(=O)n(CC)c1=O] | HRMS calcd for $[C_{24}H_{33}FN_4O_3 + H]^+$: 445.2610, Found: 445.2613 | 98.2 | A |
| 1.203 | 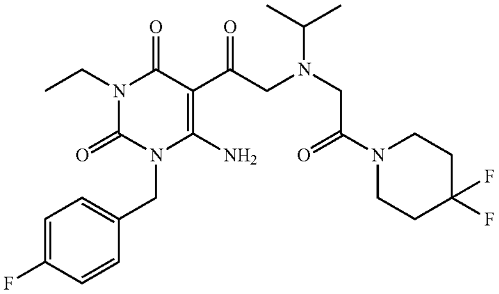 [SMILES: CCn1c(=O)c(C(=O)CN(CC(=O)N2CCC(F)(F)CC2)C(C)C)c(N)n(Cc2ccc(F)cc2)c1=O] | HRMS calcd for $[C_{25}H_{32}F_3N_5O_4 + H]^+$: 524.2479, Found: 524.2485 | 100 | A |

TABLE 1-continued
| No. | Structure | HRMS | HPLC/LC MS Purity (%) | Synthetic Route |
|---|---|---|---|---|
| 1.204 | 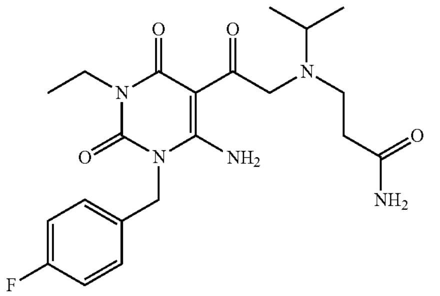 [SMILES: CCn1c(=O)c(C(=O)CN(CCC(N)=O)C(C)C)c(N)n(Cc2ccc(F)cc2)c1=O] | ESI-MS m/z for $[C_{21}H_{28}FN_5O_4 + H]^+$: 434.2 | 99.0 | A |
| 1.205 | 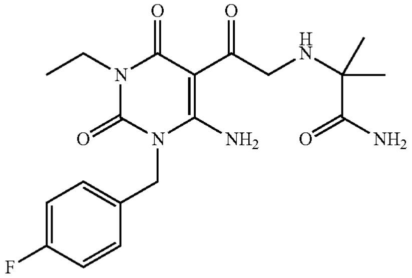 [SMILES: CCn1c(=O)c(C(=O)CNC(C)(C)C(N)=O)c(N)n(Cc2ccc(F)cc2)c1=O] | ESI-MS m/z for $[C_{19}H_{24}FN_5O_4 + H]^+$: 406.1 | 97.9 | A |
| 1.206 | 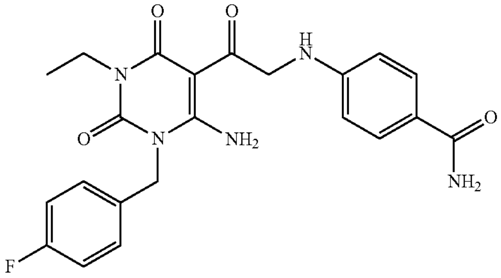 [SMILES: CCn1c(=O)c(C(=O)CNc2ccc(C(N)=O)cc2)c(N)n(Cc2ccc(F)cc2)c1=O] | ESI-MS m/z for $[C_{22}H_{22}FN_5O_4 + H]^+$: 440.2 | 99.5 | A |
| 1.207 | 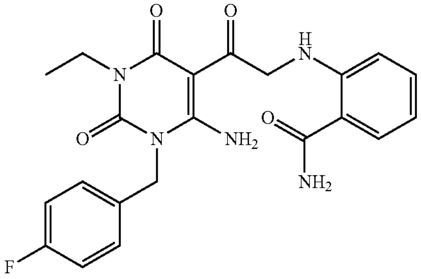 [SMILES: CCn1c(=O)c(C(=O)CNc2ccccc2C(N)=O)c(N)n(Cc2ccc(F)cc2)c1=O] | ESI-MS m/z for $[C_{22}H_{22}FN_5O_4 + H]^+$: 440.3 | 100 | A |
| 1.208 | 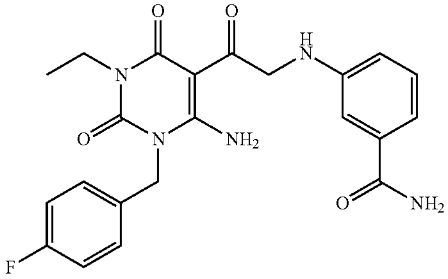 [SMILES: CCn1c(=O)c(C(=O)CNc2cccc(C(N)=O)c2)c(N)n(Cc2ccc(F)cc2)c1=O] | ESI-MS m/z for $[C_{22}H_{22}FN_5O_4 + H]^+$: 440.2 | 96.6 | A |

TABLE 1-continued
| No. | Structure | HRMS | HPLC/LC MS Purity (%) | Synthetic Route |
| --- | --- | --- | --- | --- |
| 1.209 | 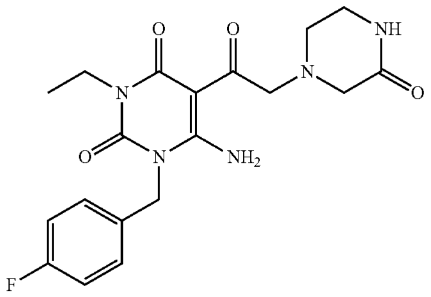 [SMILES: CCn1c(=O)c(C(=O)CN2CCNC(=O)C2)c(N)n(Cc2ccc(F)cc2)c1=O] | ESI-MS m/z for $[C_{19}H_{22}FN_5O_4 + H]^+$: 404.1 | 99.6 | A |
| 1.210 | 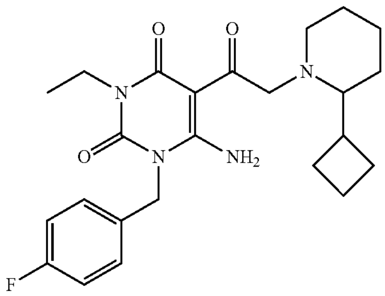 [SMILES: CCn1c(=O)c(C(=O)CN2CCCCC2C2CCC2)c(N)n(Cc2ccc(F)cc2)c1=O] | HRMS calcd for $[C_{24}H_{31}FN_4O_3 + H]^+$: 443.2453, Found: 443.2460 | 100 | A |
| 1.211 | 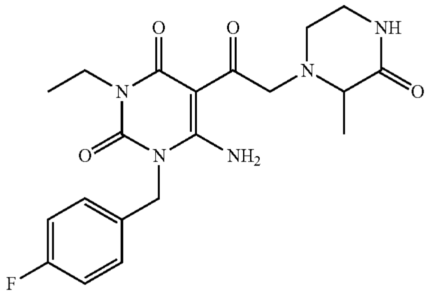 [SMILES: CCn1c(=O)c(C(=O)CN2CCNC(=O)C2C)c(N)n(Cc2ccc(F)cc2)c1=O] | ESI-MS m/z for $[C_{20}H_{24}FN_5O_4 + H]^+$: 418.1 | 99.6 | A |
| 1.212 | 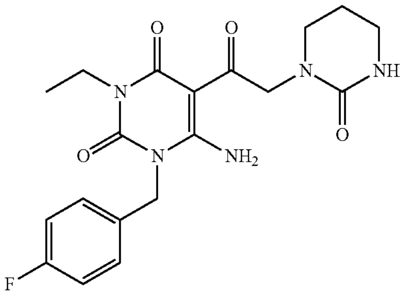 [SMILES: CCn1c(=O)c(C(=O)CN2CCCNC2=O)c(N)n(Cc2ccc(F)cc2)c1=O] | ESI-MS m/z for $[C_{19}H_{22}FN_5O_4 + H]^+$: 404.3 | 98.1 | A |
| 1.213 | 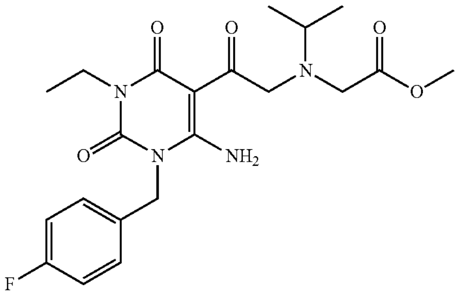 [SMILES: CCn1c(=O)c(C(=O)CN(CC(=O)OC)C(C)C)c(N)n(Cc2ccc(F)cc2)c1=O] | HRMS calcd for $[C_{21}H_{27}FN_4O_5 + H]^+$: 435.2038, Found: 435.2034 | 97.9 | A |

TABLE 1-continued
| No. | Structure | HRMS | HPLC/LC MS Purity (%) | Synthetic Route |
| --- | --- | --- | --- | --- |
| 1.214 | — | HRMS calcd for $[C_{22}H_{29}FN_4O_5 + H]^+$: 449.2195, Found: 449.2195 | 98.9 | A |
| 1.215 | 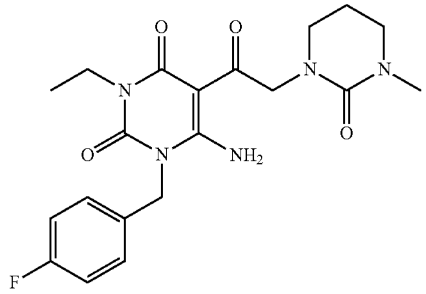 [SMILES: CCn1c(=O)c(C(=O)CN2CCCN(C)C2=O)c(N)n(Cc2ccc(F)cc2)c1=O] | ESI-MS m/z for $[C_{20}H_{24}FN_5O_4 + H]^+$: 418.4 | 98.7 | A |
| 1.216 | 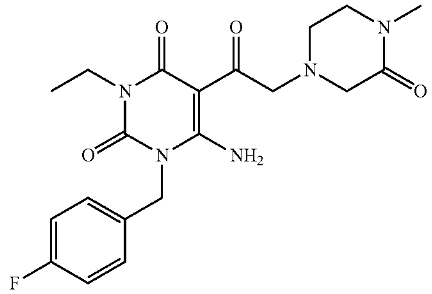 [SMILES: CCn1c(=O)c(C(=O)CN2CCN(C)C(=O)C2)c(N)n(Cc2ccc(F)cc2)c1=O] | ESI-MS m/z for $[C_{20}H_{24}FN_5O_4 + H]^+$: 418.3 | 99.8 | A |
| 1.217 | 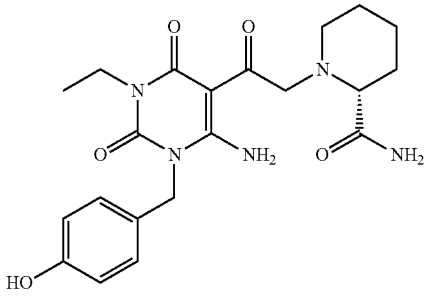 [SMILES: CCn1c(=O)c(C(=O)CN2CCCC[C@@H]2C(N)=O)c(N)n(Cc2ccc(O)cc2)c1=O] | ESI-MS m/z for $[C_{21}H_{27}N_5O_5 + H]^+$: 430.4 | 99.7 | A |
| 1.218 | 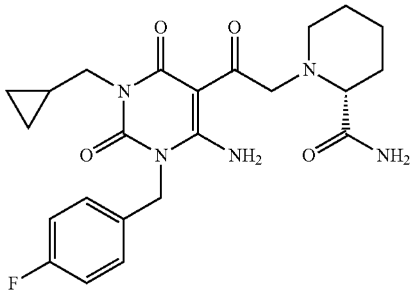 [SMILES: NC(=O)[C@H]1CCCCN1CC(=O)c1c(N)n(Cc2ccc(F)cc2)c(=O)n(CC2CC2)c1=O] | ESI-MS m/z for $[C_{23}H_{28}FN_5O_4 + H]^+$: 458.4 | 99.3 | A |

TABLE 1-continued
| No. | Structure | HRMS | HPLC/LC MS Purity (%) | Synthetic Route |
|---|---|---|---|---|
| 1.219 | 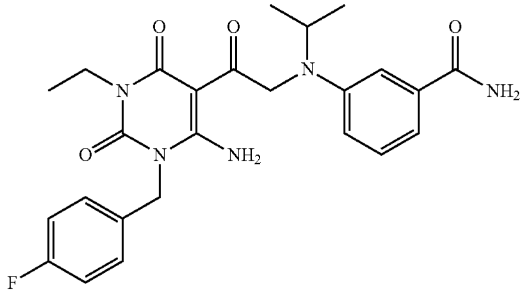 [SMILES: CCn1c(=O)c(C(=O)CN(c2cccc(C(N)=O)c2)C(C)C)c(N)n(Cc2ccc(F)cc2)c1=O] | ESI-MS m/z for $[C_{25}H_{28}FN_5O_4 + H]^+$: 482.3 | 99.7 | A |
| 1.220 | 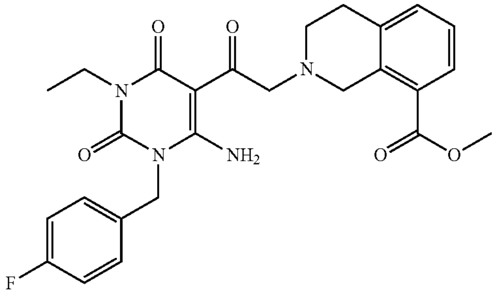 [SMILES: CCn1c(=O)c(C(=O)CN2CCc3cccc(C(=O)OC)c3C2)c(N)n(Cc2ccc(F)cc2)c1=O] | ESI-MS m/z for $[C_{26}H_{27}FN_4O_5 + H]^+$: 495.4 | 93.3 | A |
| 1.221 | 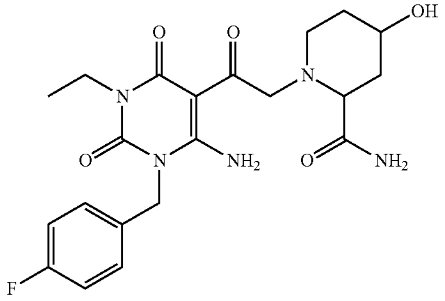 [SMILES: CCn1c(=O)c(C(=O)CN2CCC(O)CC2C(N)=O)c(N)n(Cc2ccc(F)cc2)c1=O] | ESI-MS m/z for $[C_{21}H_{26}FN_5O_5 + H]^+$: 448.2 | 95.9 | A |
| 1.222 | 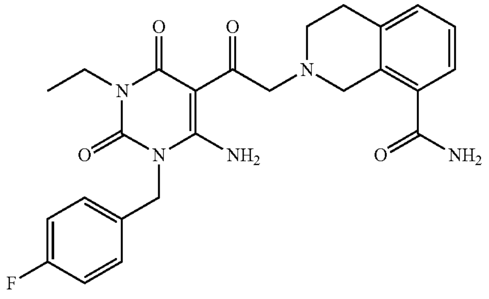 [SMILES: CCn1c(=O)c(C(=O)CN2CCc3cccc(C(N)=O)c3C2)c(N)n(Cc2ccc(F)cc2)c1=O] | ESI-MS m/z for $[C_{25}H_{26}FN_5O_4 + H]^+$: 480.4 | 98.6 | A |
| 1.223 | 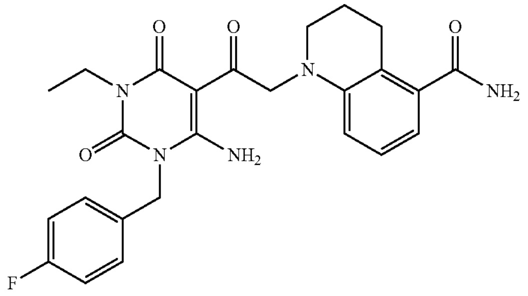 [SMILES: CCn1c(=O)c(C(=O)CN2CCCc3c(C(N)=O)cccc32)c(N)n(Cc2ccc(F)cc2)c1=O] | ESI-MS m/z for $[C_{25}H_{26}FN_5O_4 + H]^+$: 480.3 | 99.9 | A |

TABLE 1-continued
| No. | Structure | HRMS | HPLC/LC MS Purity (%) | Synthetic Route |
|---|---|---|---|---|
| 1.224 | 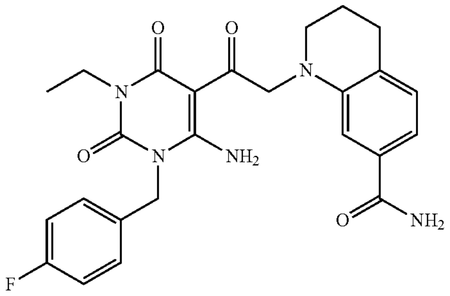 [SMILES: CCn1c(=O)c(C(=O)CN2CCCc3ccc(C(N)=O)cc32)c(N)n(Cc2ccc(F)cc2)c1=O] | ESI-MS m/z for $[C_{25}H_{26}FN_5O_4 + H]^+$: 480.3 | 99.3 | A |
| 1.225 | 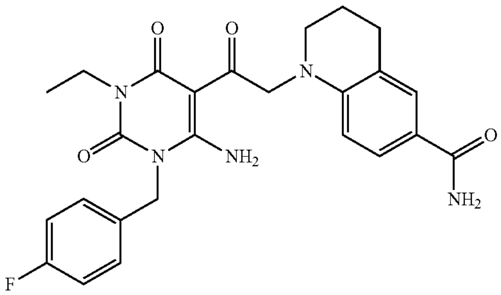 [SMILES: CCn1c(=O)c(C(=O)CN2CCCc3cc(C(N)=O)ccc32)c(N)n(Cc2ccc(F)cc2)c1=O] | ESI-MS m/z for $[C_{25}H_{26}FN_5O_4 + H]^+$: 480.3 | 95.2 | A |
| 1.226 | 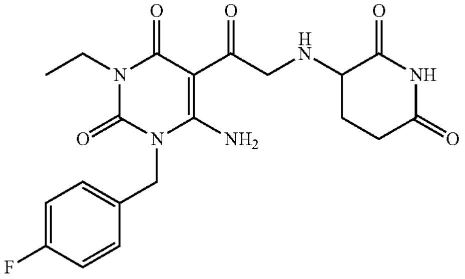 [SMILES: CCn1c(=O)c(C(=O)CNC2CCC(=O)NC2=O)c(N)n(Cc2ccc(F)cc2)c1=O] | HRMS calcd for $[C_{20}H_{22}FN_5O_5 + H]^+$: 432.1678, Found: 432.1681 | 99.8 | A |
| 1.227 | 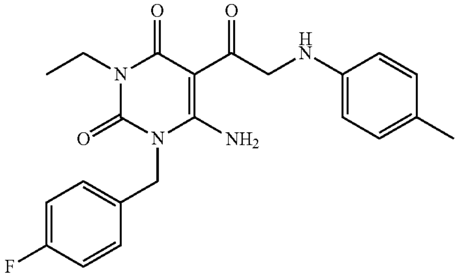 [SMILES: CCn1c(=O)c(C(=O)CNc2ccc(C)cc2)c(N)n(Cc2ccc(F)cc2)c1=O] | ESI-MS m/z for $[C_{22}H_{23}FN_4O_3 + H]^+$: 410.9 | 99.7 | A |
| 1.228 | 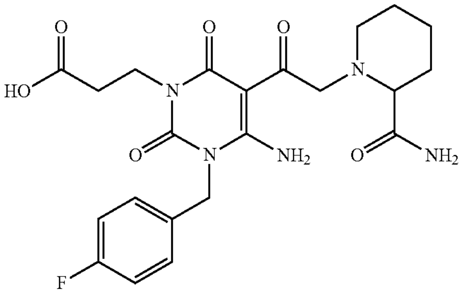 [SMILES: NC(=O)C1CCCCN1CC(=O)c1c(N)n(Cc2ccc(F)cc2)c(=O)n(CCC(=O)O)c1=O] | ESI-MS m/z for $[C_{22}H_{26}FN_5O_6 + H]^+$: 476.3 | 98.6 | A2. |

TABLE 1-continued
| No. | Structure | HRMS | HPLC/LC MS Purity (%) | Synthetic Route |
|---|---|---|---|---|
| 2.1 | 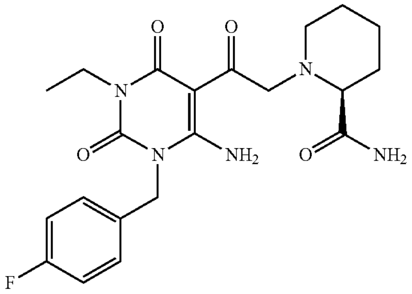 [SMILES: CCn1c(=O)c(C(=O)CN2CCCC[C@H]2C(N)=O)c(N)n(Cc2ccc(F)cc2)c1=O] | | | |
| 2.2 | 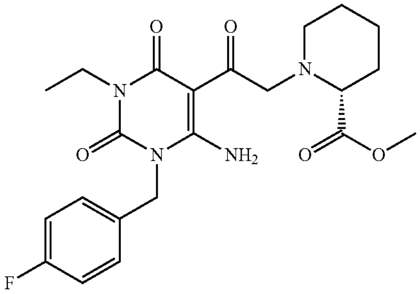 | | | |
| 2.3 | 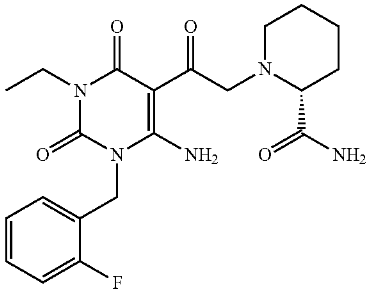 [SMILES: CCn1c(=O)c(C(=O)CN2CCCC[C@@H]2C(N)=O)c(N)n(Cc2ccccc2F)c1=O] | | | |
| 2.4 | 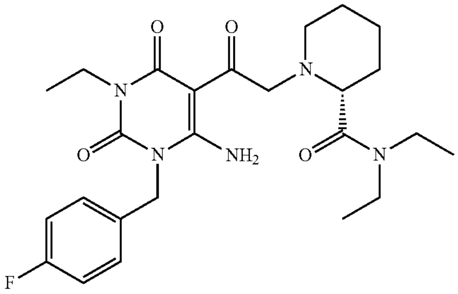 [SMILES: CCN(CC)C(=O)[C@H]1CCCCN1CC(=O)c1c(N)n(Cc2ccc(F)cc2)c(=O)n(CC)c1=O] | | | |
| 2.5 | 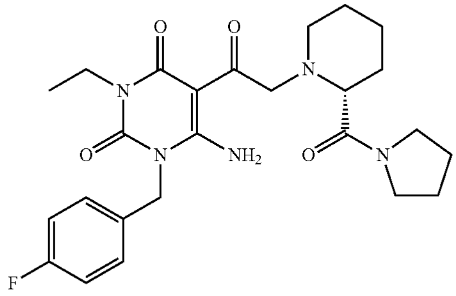 [SMILES: CCn1c(=O)c(C(=O)CN2CCCC[C@@H]2C(=O)N2CCCC2)c(N)n(Cc2ccc(F)cc2)c1=O] | | | |

TABLE 1-continued
| No. | Structure | HRMS | HPLC/LC MS Purity (%) | Synthetic Route |
|---|---|---|---|---|
| 2.6 | 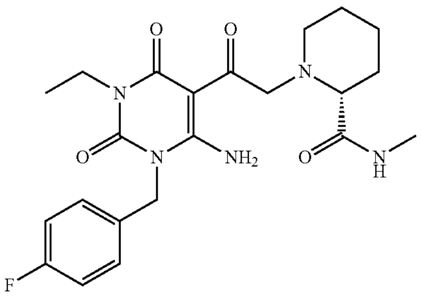 | | | |
| 2.7 | 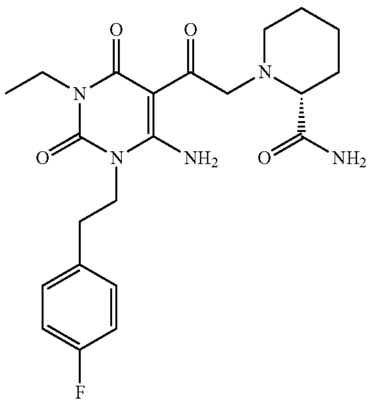 [SMILES: CCn1c(=O)c(C(=O)CN2CCCC[C@@H]2C(N)=O)c(N)n(CCc2ccc(F)cc2)c1=O] | | | |
| 2.8 | 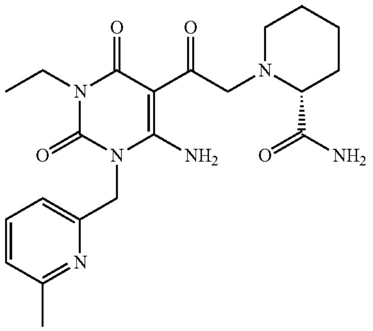 [SMILES: CCn1c(=O)c(C(=O)CN2CCCC[C@@H]2C(N)=O)c(N)n(Cc2cccc(C)n2)c1=O] | | | |
| 2.9 | 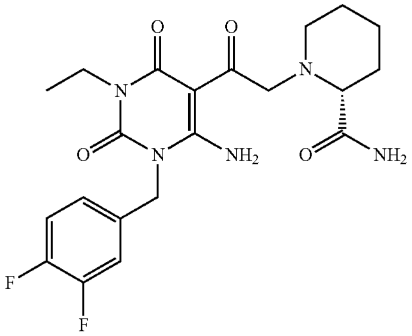 | | | |

TABLE 1-continued
| No. | Structure | HRMS | HPLC/LC MS Purity (%) | Synthetic Route |
| --- | --- | --- | --- | --- |
| 2.10 | 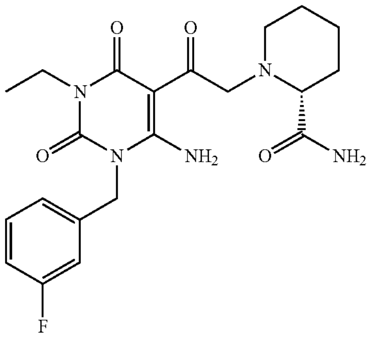 [SMILES: CCn1c(=O)c(C(=O)CN2CCCC[C@@H]2C(N)=O)c(N)n(Cc2cccc(F)c2)c1=O] | | | |
| 2.11 | 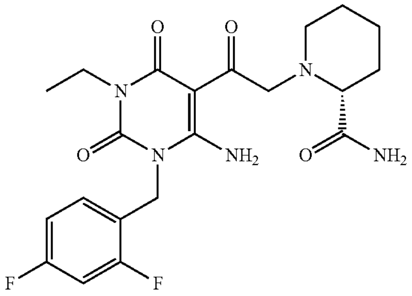 | | | |
| 2.12 | 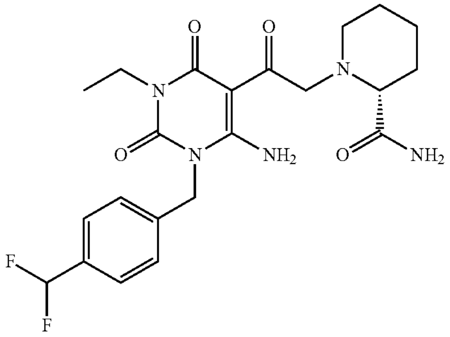 [SMILES: CCn1c(=O)c(C(=O)CN2CCCC[C@@H]2C(N)=O)c(N)n(Cc2ccc(C(F)F)cc2)c1=O] | | | |
| 2.13 | 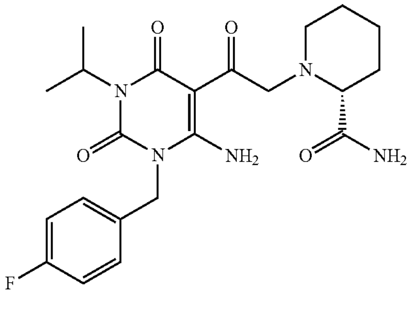 | | | |

TABLE 1-continued
| No. | Structure | HRMS | HPLC/LC MS Purity (%) | Synthetic Route |
|---|---|---|---|---|
| 2.14 | 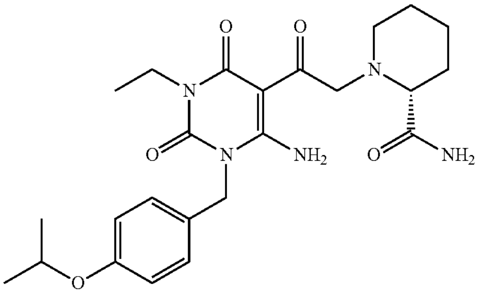 [SMILES: CCn1c(=O)c(C(=O)CN2CCCC[C@@H]2C(N)=O)c(N)n(Cc2ccc(OC(C)C)cc2)c1=O] | | | |
| 2.15 | 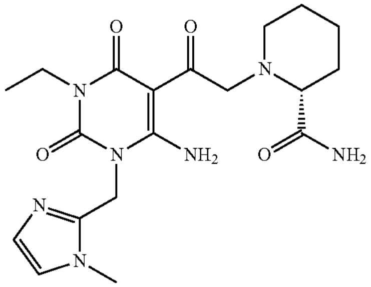 [SMILES: CCn1c(=O)c(C(=O)CN2CCCC[C@@H]2C(N)=O)c(N)n(Cc2nccn2C)c1=O] | | | |
| 2.16 | 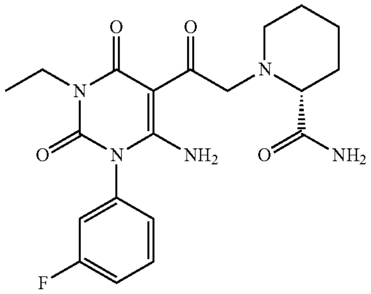 [SMILES: CCn1c(=O)c(C(=O)CN2CCCC[C@@H]2C(N)=O)c(N)n(-c2cccc(F)c2)c1=O] | | | |
| 2.17 | 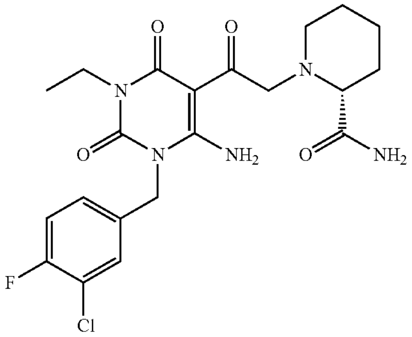 | | | |
| 2.18 | 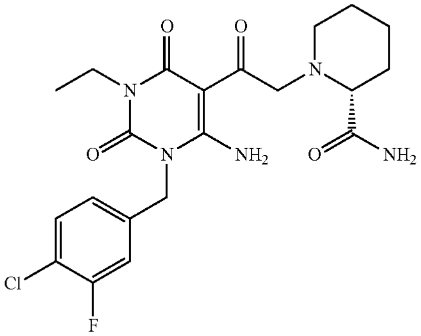 [SMILES: CCn1c(=O)c(C(=O)CN2CCCC[C@@H]2C(N)=O)c(N)n(Cc2ccc(Cl)c(F)c2)c1=O] | | | |

TABLE 1-continued
| No. | Structure | HRMS | HPLC/LC MS Purity (%) | Synthetic Route |
|---|---|---|---|---|
| 2.19 | 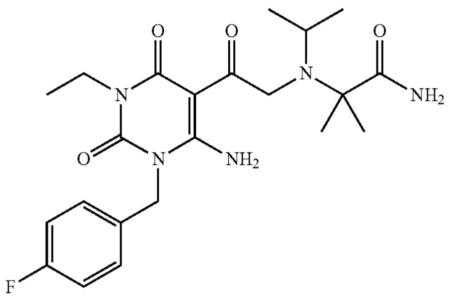 [SMILES: CCn1c(=O)c(C(=O)CN(C(C)C)C(C)(C)C(N)=O)c(N)n(Cc2ccc(F)cc2)c1=O] | | | |
| 2.20 | 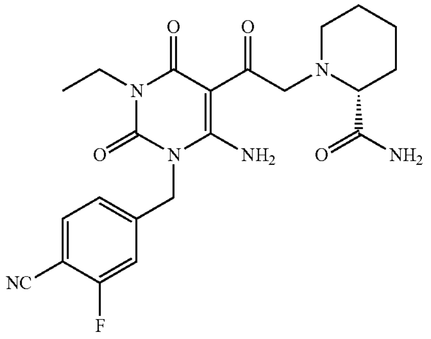 [SMILES: CCn1c(=O)c(C(=O)CN2CCCC[C@@H]2C(N)=O)c(N)n(Cc2ccc(C#N)c(F)c2)c1=O] | | | |
| 2.21 | 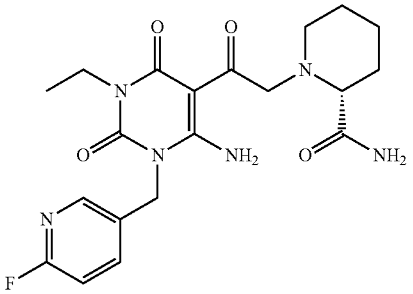 | | | |
| 2.22 | 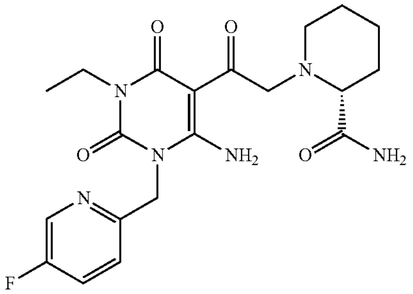 | | | |
| 2.23 | 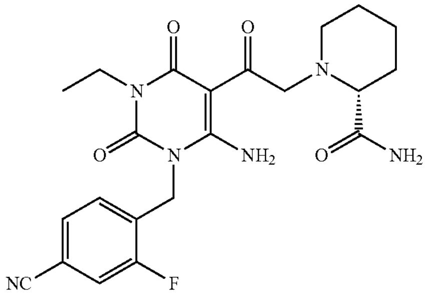 [SMILES: CCn1c(=O)c(C(=O)CN2CCCC[C@@H]2C(N)=O)c(N)n(Cc2ccc(C#N)cc2F)c1=O] | | | |

TABLE 1-continued

| No. | Structure | HRMS | HPLC/LC MS Purity (%) | Synthetic Route |
| --- | --- | --- | --- | --- |
| 2.24 | 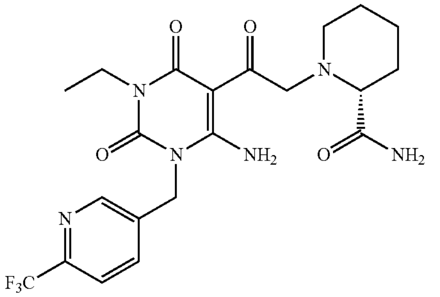 [SMILES: CCn1c(=O)c(C(=O)CN2CCCC[C@@H]2C(N)=O)c(N)n(Cc2ccc(C(F)(F)F)nc2)c1=O] | | | |

b. GENERAL SYNTHETIC SCHEME A

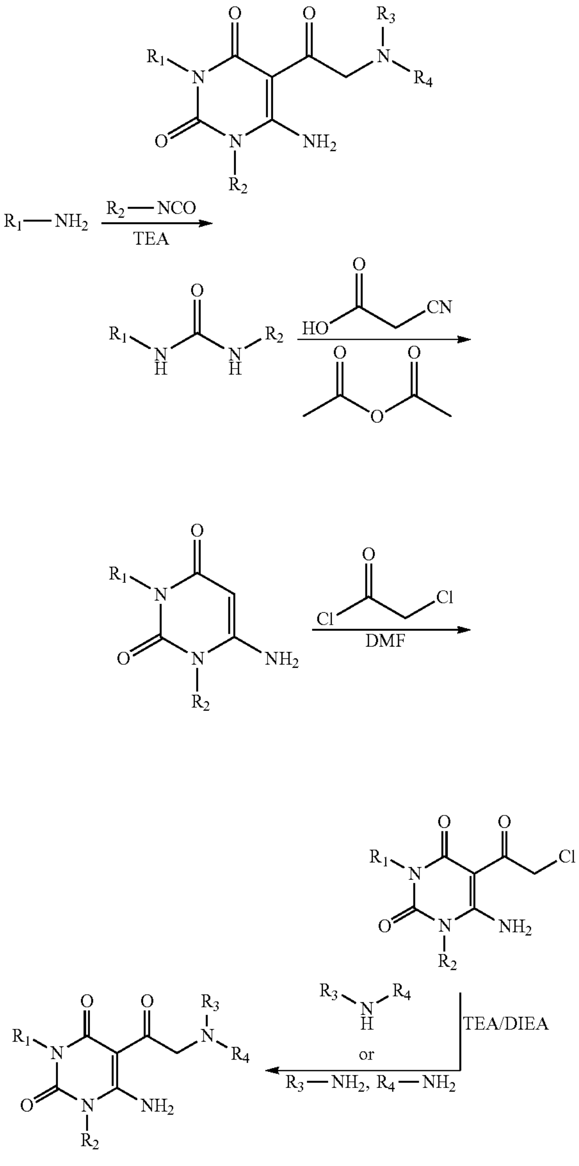

i. Synthesis of Representative Example SRI-41765 (1.128)

1.128

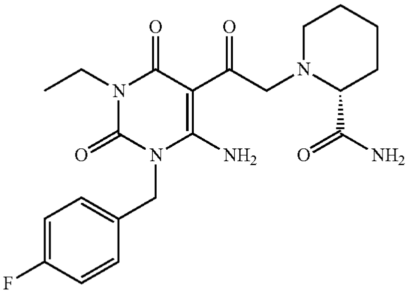

1-Ethyl-3-[(4 fluorophenyl)methyl]urea (1.128a): To a 500 ml RB flask were added 4-fluorobenzylamine (8.80 g, 70.34 mmol) and triethylamine (7.12 g, 70.34 mmol) and DCM (200 mL). The resulted reaction mixture was stirred at room temperature and the ethane, isocyanato- (5.0 g, 70.34 mmol) was added dropwise and then allowed to stir at room temperature for 4 hours, a solid formed as the reaction progressed. It was allowed to stir overnight and then added more DCM (50 ml) and filtered the white solid off and rinsed the solid with hexane 150 mL and then dried under high vacuum provided 1-ethyl-3-[(4-fluorophenyl)methyl]urea (10.2 g, 72%) as a white solid. $^1$H NMR (400 MHz, DMSO): δ 7.29-7.20 (m, 2H), 7.14-7.06 (m, 2H), 6.27 (t, J=6.0 Hz, 1H), 5.86 (t, J=5.7 Hz, 1H), 4.14 (dd, J=6.2, 0.9 Hz, 2H), 3.00 (qd, J=7.2, 5.6 Hz, 2H), 0.97 (t, J=7.2 Hz, 3H).

6-Amino-3-ethyl-1-[(4 fluorophenyl)methyl]pyrimidine-2,4-dione (1.128b): To a solution of 1-ethyl-3-[(4-fluorophenyl)methyl]urea (981 mg, 5 mmol) in ethyl acetate (15 mL) was added cyanoacetic acid (850.6 mg, 10 mmol) and acetic anhydride (1.04 mL, 11 mmol) and was stirred at 90° C. overnight. The reaction was concentrated in vacuo. The crude oil was diluted with water, treated with 5% aqueous NaOH to reach pH=10, then extracted with EtOAc (3×). The organic layers were washed with brine, dried over anhydrous $Na_2SO_4$, filtered, and concentrated in vacuo. The solid suspended in ether was filtered, and dried under high vacuum to give 6-amino-3-ethyl-1-[(4-fluorophenylmethyl]pyrimidine-2,4-dione (553 mg, 42.01%) as an off-white solid. $^1$H NMR (400 MHz, DMSO): δ 7.29-7.22 (m, 2H), 7.21-7.13 (m, 2H), 6.81 (s, 2H), 5.04 (s, 2H), 4.72 (s, 1H), 3.76 (q, J=7.0 Hz, 2H), 1.04 (t, J=6.9 Hz, 3H).

6-Amino-5-(2-chloroacetyl)-3-ethyl-1-[(4-fluorophenyl)methyl]pyrimidine-2,4-dione (1.128c): To a solution of 6-amino-3-ethyl-1-[(4-fluorophenyl)methyl]pyrimidine-2,4-dione (932 mg, 3.54 mmol) in DMF (30 mL) was added dropwise chloroacetyl chloride (0.56 mL, 7.08 mmol). The reaction was stirred at room temperature for 5 h. The reaction was then quenched by addition of ice water. The solids were collected by filtration, washed with water, and dried under high vacuum to give 6-amino-5-(2-chloroacetyl)-3-ethyl-1-[(4-fluorophenyl)methyl]pyrimidine-2,4-dione 1.06 g, 88%) as a light tan solid. $^1$H NMR (400 MHz, DMSO): δ 10.93 (s, 1H), 8.44 (s, 1H), 7.29 (dd, J=8.6, 5.5 Hz, 2H), 7.22-7.15 (m, 2H), 5.19 (s, 2H), 4.95 (s, 2H), 3.85 (q, J=6.9 Hz, 2H), 1.10 (t, J=7.0 Hz, 3H).

(2R)-1-[2-[4-amino-1-ethyl-3-[(4 fluorophenyl)methyl]-2,6-dioxo pyrimidin-5-yl]-2-oxo-ethyl]piperidine-2-carboxamide (1.128): To a 10 dram vial was added 6-amino-5-(2-chloroacetyl)-3-ethyl-1-[(4-fluorophenyl)methyl] pyrimidine-2,4-dione (1060 mg, 3.12 mmol) and (2R)-piperidine-2-carboxamide (400 mg, 3.12 mmol) along with triethylamine (2 mL) and DMF (6 mL). The resulted reaction mixture was stirred over night at 60° C. and the progress of the reaction was monitored by LCMS. After completion of the reaction, sodium bicarbonate was added and extracted with ethyl acetate (3× The combined organic layer was dried over anhydrous $Na_2SO_4$ and the solid was filtered off. Solvent was removed from the filtrate in vacuum and the crude product was purified and recrystallized from hexane ethyl acetate to give (2R)-1-[2-[4-amino-1-ethyl-3-[(4-fluorophenyl)methyl]-2,6-dioxo-pyrimidin-5-yl]-2-oxo-ethyl] piperidine-2-carboxamide (350 mg, 25%) as a white solid. HPLC Purity: 97%. LCMS: m/z 432 $(M+H)^+$. $^1$H NMR (400 MHz, DMSO): δ 11.18 (s, 1H), 8.23 (s, 1H), 7.25 (ddd, J=8.6, 5.5, 2.6 Hz, 2H), 7.21-7.10 (m, 2H), 7.00 (d, J=3.3 Hz, 1H), 6.92 (d, J=3.3 Hz, 1H), 5.14 (s, 2H), 3.94-3.67 (m, 4H), 2.98-2.79 (m, 2H), 2.22 (td, J=10.9, 3.1 Hz, 1H), 1.65 (ddd, J=35.2, 11.3, 4.8 Hz, 2H), 1.54-1.33 (m, 3H), 1.22 (dd, J=24.3, 13.1 Hz, 1H), 1.06 (t, J=7.0 Hz, 3H). HRMS calcd for $[C_{21}H_{26}FN_5O_4]$: 432.2042, Found: 432.2041.

C. Synthesis of N-(2-(6-amino-1-benzyl-3-ethyl-2,4-dioxo-1,2,3,4-tetrahydropyrimidin-5-yl)-2-oxo-ethyl)-N-isopropylglycine SRI-39929 (1.19)

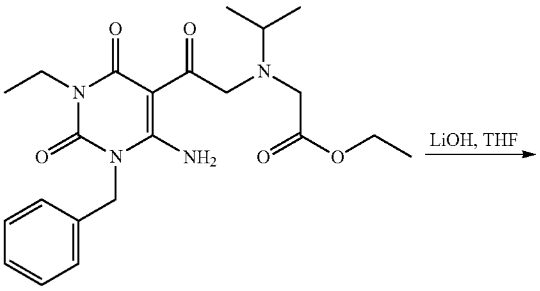

1.18

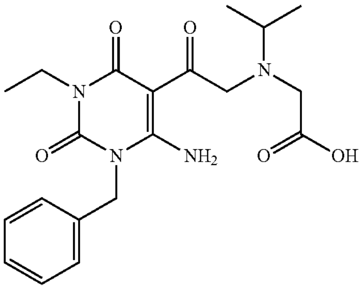

1.19

To a solution of ethyl 2-((2-(6-amino-1-benzyl-3-ethyl-2,4-dioxo-1,2,3,4-tetrahydropyrimidin-5-yl)-2-oxoethyl)(isopropyl)amino)acetate, 1.18 (100 mg, 0.232 mmol) in 5 ml of methanol was added lithium hydroxide (55.6 mg, 2.323 mmol) along with 1 ml of water and the solution was stirred at room temperature for 2 hours. Progress of the reaction was monitored by TLC which indicated that starting material was completely consumed. Acidified the reaction mixture with concentrated HCl and extracted with ethyl acetate (3×). Combined the organic layer was dried over $MgSO_4$ and filtered. The filtrate was concentrated in vacuo to give N-(2-(6-amino-1-benzyl-3-ethyl-2,4-dioxo-1,2,3,4-tetrahydropyrimidin-5-yl)-2-oxoethyl)-N-isopropylglycine (92 mg, 100%) as white solid. HPLC Purity: 96.4%. LCMS: m/z 403 $(M+H)^+$. $^1$H NMR (400 MHz, DMSO): δ 10.63 (s, 1H), 8.74 (s, 1H), 7.44-7.14 (m, 6H), 5.26 (s, 2H), 4.61 (s, 2H), 4.09-3.94 (m, 2H), 3.86 (q, J=7.0 Hz, 2H), 3.60 (p, J=6.6 Hz, 1H), 1.21 (d, J=6.6 Hz, 6H), 1.12 (q, J=7.2 Hz, 3H). HRMS calcd for $[C_{21}H_{26}FN_5O_4]$: 403.1969, Found: 403.1976.

d. GENERAL SYNTHETIC SCHEME C

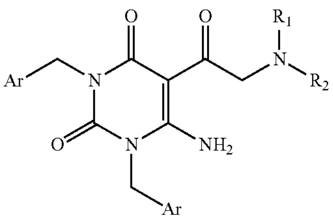

-continued

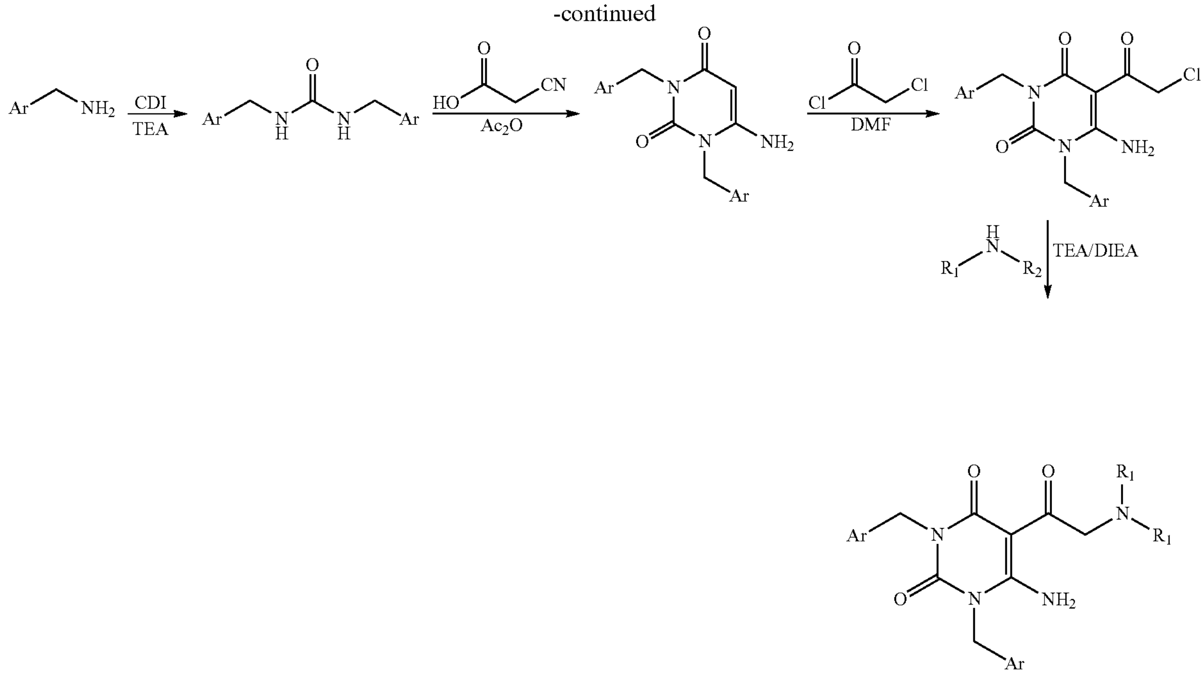

ii. Synthesis of a Representative Example, SRI-40354 (1.47)

1.47

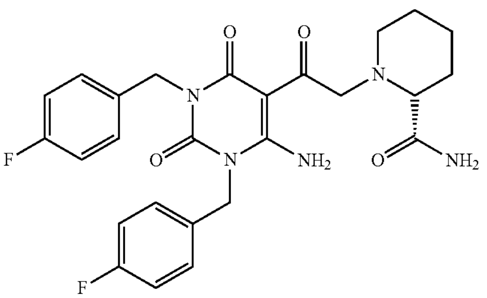

1,3-Bis[(4 fluorophenyl)methyl]urea (1.47a): 4-Fluorobenzylamine (2.08 g, 16.65 mmol) was dissolved in DCM (35 mL) and was added 1,1'-Carbonyldiimidazole (2.7 g, 16.65 mmol) followed by triethylamine (7.1 mL, 50.93 mmol) at room temperature under nitrogen atmosphere. The resulted reaction mixture was stirred for 30 minutes, then additional 4-fluorobenzylamine (2.1 g, 16.65 mmol) was added and stirring was continued for another 18 hours under same reaction conditions. The solids were collected by vacuum filtration and washed with diethyl ether to afford 1,3-bis[(4-fluorophenyl)methyl]urea (3.96 g, 86.1%) as a white solid. LCMS: m/z 277 $(M+H)^+$.

6-Amino-1,3-bis[(4 fluorophenyl)methyl]pyrimidine-2,4-dione (1.47b): 1,3-Bis[(4-fluorophenyl)methyl]urea (3.9 g, 14.12 mmol) and cyanoacetic acid (1.44 g, 16.94 mmol) in acetic anhydride (50 mL) was heated at 90° C. for 2.5 hours. The solvent was removed and water (25 mL) and 25% NaOH (10 mL) were added. The resulted reaction mixture was stirred at room temperature for 18 hours. The solids formed were collected by filtration and suspended in 50 mL of water and placed in an ultrasonic bath for 20 minutes. The solids were collected by vacuum filtration and dried to afford 6-amino-1,3-bis[(4-fluorophenyl)methyl]pyrimidine-2,4-dione (4.5 g, 92.9%) as a tan solid $^{1}$H NMR (400 MHz, DMSO): δ 7.32-7.20 (m, 4H), 7.20-7.04 (m, 4H), 6.91 (s, 2H), 5.03 (s, 2H), 4.89 (s, 2H), 4.76 (s, 1H).

6-Amino-5-(2-chloroacetyl)-1,3-bis[(4 fluorophenyl) methyl]pyrimidine-2,4-dione (1.47c): 6-Amino-1,3-bis[(4-fluorophenyl)methyl]pyrimidine-2,4-dione (120 mg, 0.35 mmol) was dissolved in DMF (2 mL) and chloroacetyl chloride (0.07 mL, 0.87 mmol) was added and the mixture was stirred at room temperature for 48 hours. The solvent was removed and the brown solid was triturated with DCM to afford 6-amino-5-(2-chloroacetyl)-1,3-bis[(4-fluorophenyl)methyl]pyrimidine-2,4-dione (92 mg, 62.7%) as a white solid. LCMS: m/z 420.8 $(M+H)^+$.

(2R)-1-[2-[4-Amino-1,3-bis[(4 fluorophenyl)methyl]-2,6-dioxo pyrimidin-5-yl]-2-oxo-ethyl]piperidine-2-carboxamide (1.47): A solution of 6-amino-5-(2-chloroacetyl)-1,3-bis[(4-fluorophenyl)methyl]pyrimidine-2,4-dione (90. mg, 0.21 mmol), (2R)-piperidine-2-carboxamide (33 mg, 0.26 mmol) and N,N-diisopropylethylamine (0.11 mL, 0.64 mmol) in DMF (1.8 mL) was heated at 55° C. for 18 hours. The crude reaction mixture was purified on Shimadzu HPLC system (Phenomenex Gemini NX-C18, 21.2×150 mm, Sum, Flow rate 22 ml/min; $CH_3CN$+0.1% TFA/$H_2O$+0.1% TFA; 5 to 95 over 18.4 minutes) and the pure fractions were concentrated to dryness. The pure residue was dissolved in MeOH and treated with MP-carbonate for 1 h and the mixture was filtered and solvent was removed from the filtrate. The residue was triturated with ether and filtered to afford (2R)-1-[2-[4-amino-1,3-bis[(4-fluorophenyl)methyl]-2,6-dioxo-pyrimidin-5-yl]-2-oxo-ethyl]piperidine-2-carboxamide (63 mg, 53.4%) as a white solid. HPLC Purity: 99%. $^{1}$H NMR (400 MHz, DMSO): δ 11.23 (s, 1H), 8.34 (s, 1H), 7.40-6.75 (m, 10H), 5.17 (s, 2H), 4.95 (s, 2H), 3.88 (d, J=3.6 Hz, 2H), 2.90 (bs, 2H), 2.31 (bs, 1H), 1.75-2.82 (m, 6H). HRMS calcd for $[C_{26}H_{27}F_2N_5O_4+H]^+$: 512.2104, Found: 512.2099.

e. Synthesis of N-(2-(6-amino-3-ethyl-1-(4-fluorobenzyl)-2,4-dioxo-1,2,3,4-tetrahydropyrimidin-5-yl)-2-oxoethyl)-N-isopropylbenzenesulfonamide, SRI-42116 (1.148)

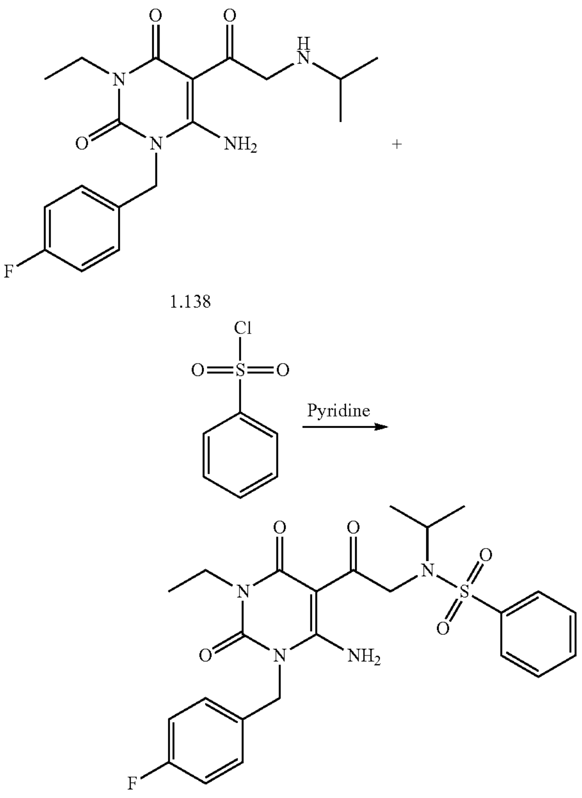

1.138

1.148

A solution of 6-amino-3-ethyl-1-[(4-fluorophenyl)methyl]-5-[2-(isopropylamino)acetyl]pyrimidine-2,4-dione, 1.138 (100 mg, 0.28 mmol) in pyridine (3 mL) was added benzenesulfonyl chloride (0.042 mL, 0.33 mmol) at room temperature under nitrogen atmosphere and was stirred for 18 hrs. Solvent was removed under vacuum and the crude product was purified on the ACCQPrep HPLC system (Phenomenex Gemini NX-C18, 30×250 mm, Sum, Flow rate 42 ml/min; $CH_3CN$+0.1% TFA/$H_2O$+0.1% TFA; 5 to 95% over 30 minutes) to afford N-[2-[4-amino-1-ethyl-3-[(4-fluorophenyl)methyl]-2,6-dioxo-pyrimidin-5-yl]-2-oxo-ethyl]-N-isopropyl-benzenesulfonamide (45 mg, 0.087 mmol, 31.5%) as a yellow solid. HPLC Purity: 97%. $^1H$ NMR (400 MHz, DMSO): δ 11.06 (s, 1H), 8.31 (s, 1H), 7.92-7.74 (m, 2H), 7.70-7.49 (m, 3H), 7.28 (ddd, J=8.5, 5.4, 2.6 Hz, 2H), 7.23-7.10 (m, 2H), 5.17 (s, 2H), 4.59 (s, 2H), 3.87 (dq, J=13.8, 6.8 Hz, 3H), 1.10 (t, J=7.0 Hz, 3H), 0.85 (d, J=6.7 Hz, 6H). HRMS calcd for $[C_{24}H_{28}FN_4O_5S+H]^+$: 503.1759, Found: 503.17524.

2. Evaluation of Compound Activity

The compounds shown in Table 1 were evaluated for their ability to stimulate read-through of a premature termination codon, and their respective activities are shown in Tables 2 and 3 below.

TABLE 2

| | W134X-CF#14 FRT data | |
|---|---|---|
| No. | $EC_{50+G418}$ (μM) | $E_{max+G418}$ |
| 1.1 | 19.70 | 2773.7 |
| | 10.60 | 2479.1 |
| | 9.35 | 2180.9 |
| | 10.87 | 2342.2 |
| 1.2 | 108.81 | 14.7 |
| 1.3 | 22.72 | 96.0 |
| 1.4 | 99.94 | 60.7 |
| 1.5 | 180 | 147.5 |
| 1.6 | 180 | −0.62 |
| 1.7 | 32.15 | 161.1 |
| 1.8 | 165.67 | 106.2 |
| 1.9 | 180 | 58.0 |
| 1.10 | 180 | 3.5 |
| 1.11 | 180 | −3.9 |
| 1.12 | 46.02 | 320.0 |
| 1.13 | 173.80 | 12.5 |
| 1.14 | 12.29 | 90.0 |
| 1.15 | 180 | 14.2 |
| 1.16 | 180 | 8.5 |
| 1.17 | 180 | −0.33 |
| 1.18 | 25.54 | 1555.6 |
| | 0.35 | 3635.5 |
| 1.19 | 27.14 | 28.45 |
| | 180 | −0.11 |
| 1.21 | 43.19 | 1472.5 |
| 1.22 | 83.23 | 1039.8 |
| 1.23 | 180 | −1.36 |
| 1.24 | 23.05 | 746.2 |
| 1.25 | 180 | 1.8 |
| 1.26 | 155.04 | 74.3 |
| 1.27 | 180 | −0.32 |
| 1.28 | 6.46 | 1428.8 |
| | 3.99 | 2055.7 |
| 1.29 | 11.66 | 252.5 |
| 1.30 | 67.54 | 309.7 |
| 1.31 | 180 | 12.3 |
| 1.32 | 72.26 | 275.1 |
| 1.33 | 180 | −1.52 |
| 1.34 | 52.97 | 2262.9 |
| 1.35 | 180 | 4.19 |
| 1.36 | 93.86 | 7275.3 |
| 1.37 | 12.94 | 620.3 |
| 1.38 | 11.92 | 602.2 |
| 1.39 | 11.48 | 13352.0 |
| | 8.26 | 1139.0 |
| 1.40 | 5.62 | 1254.5 |
| | 7.08 | 12356.0 |
| 1.41 | 157.35 | 434.1 |
| 1.42 | 180 | 8.2 |
| 1.43 | 49.29 | 373.7 |
| 1.44 | 22.71 | 5879.7 |
| 1.45 | 100 | 6.86 |
| | 12.32 | 12.39 |
| | 100 | 1.59 |
| | 100 | 3.77 |
| 1.46 | 100 | 2.12 |
| | 100 | 5.02 |
| | 17.50 | 11.16 |
| | 100 | 4.32 |
| 1.47 | 2.78 | 4301.5 |
| | 3.19 | 3501.5 |
| | 3.19 | 2434.8 |
| 1.48 | 2.72 | 1876.4 |
| | 3.82 | 1650.2 |
| | 100 | 3895.3 |
| 1.49 | 59.36 | 3312.6 |
| 1.50 | 100 | 2137.7 |
| 1.51 | 28.23 | 142.1 |
| | 20.81 | 153.9 |
| 1.52 | 100 | 1.9 |
| | 100 | 4.7 |
| 1.53 | 100 | 5.1 |
| | 100 | 5.6 |
| 1.54 | 11.59 | 3761.9 |
| | 7.15 | 2608.6 |

TABLE 2-continued

| | W134X-CF#14 FRT data | |
|---|---|---|
| No. | $EC_{50+G418}$ (μM) | $E_{max+G418}$ |
| 1.55 | 27.09 | 106.34 |
| | 26.95 | 49.75 |
| 1.56 | 100 | 15.8 |
| | 100 | 8.8 |
| 1.57 | 15.41 | 5215.9 |
| 1.58 | 100 | 3.5 |
| 1.59 | 100 | 3.3 |
| 1.60 | 100 | 115.6 |
| 1.61 | 32.33 | 104.6 |
| 1.62 | 100 | 504.7 |
| 1.63 | 79.94 | 269.7 |
| 1.64 | 13.91 | 381.0 |
| | 9.46 | 352.3 |
| 1.65 | 100 | 14.5 |
| 1.66 | 100 | 10.1 |
| 1.67 | 3.10 | 5064.4 |
| | 3.27 | 1116.2 |
| 1.68 | 19.65 | 636.3 |
| 1.69 | 100 | 0.3 |
| 1.70 | 27.93 | 1122.1 |
| 1.71 | 70.40 | 2554.0 |
| 1.72 | 8.20 | 1473.0 |
| | 5.17 | 2000.4 |
| 1.73 | 1.21 | 1544.8 |
| | 0.82 | 2020.5 |
| 1.74 | 1.65 | 2171.1 |
| | 1.64 | 1089.2 |
| 1.75 | 28.02 | 1566.4 |
| 1.76 | 100 | −0.3 |
| 1.77 | 31.19 | 140.5 |
| 1.78 | 100 | −6.0 |
| 1.79 | 49.27 | 119.0 |
| 1.80 | 3.89 | 2634.6 |
| 1.81 | 3.92 | 2241.1 |
| 1.82 | 6.18 | 1470.6 |
| | 3.27 | 1822.8 |
| 1.83 | 100 | −1.7 |
| 1.84 | 48.16 | 1700.7 |
| 1.85 | 28.06 | 2535.9 |
| 1.86 | 56.07 | 20.4 |
| 1.87 | 3.33 | 2067.4 |
| | 4.74 | 1060.2 |
| 1.88 | 53.80 | 1527.2 |
| 1.89 | 100 | 10.5 |
| 1.90 | 100 | 4.6 |
| 1.91 | 100 | 0.9 |
| 1.92 | 24.19 | 2318.8 |
| 1.93 | 100 | 4.8 |
| 1.94 | 100 | 64.1 |
| 1.95 | 21.05 | 2494.8 |
| 1.96 | 58.51 | 1909.4 |
| 1.97 | 62.45 | 39.3 |
| 1.98 | 43.15 | 1890.0 |
| 1.99 | 28.33 | 1782.0 |
| 1.100 | 16.53 | 2116.7 |
| 1.101 | 12.82 | 2460.5 |
| 1.102 | 6.20 | 1790.3 |
| 1.107 | 4.52 | 62.0 |
| 1.108 | 25.00 | 76.8 |
| 1.109 | 7.47 | 76.1 |
| 1.110 | 25.00 | 63.3 |
| 1.111 | 5.19 | 1782.4 |
| 1.112 | 3.46 | 1734.7 |
| 1.113 | 5.79 | 1630.9 |
| 1.114 | 18.08 | 105.3 |
| 1.115 | 31.87 | 69.0 |
| 1.116 | 23.88 | 20.2 |
| 1.117 | 100 | 4.0 |
| 1.118 | 100 | 28.4 |
| 1.119 | 13.35 | 2057.0 |
| 1.120 | 100 | −1.0 |
| 1.121 | 61.34 | 1794.3 |
| 1.122 | 30.40 | 2022.6 |
| 1.123 | 2.31 | 1729.3 |
| 1.124 | 24.07 | 205.2 |
| 1.125 | 100 | −1.3 |

TABLE 2-continued

| | W134X-CF#14 FRT data | |
|---|---|---|
| No. | $EC_{50+G418}$ (μM) | $E_{max+G418}$ |
| 1.126 | 1.56 | 1530.0 |
| | 0.84 | 1116.9 |
| 1.127 | 100 | 1.6 |
| 1.128 | 1.04 | 1655.5 |
| | 1.56 | 2416.1 |
| | 0.82 | 3222.9 |
| | 0.79 | 2262.2 |
| 1.129 | 1.65 | 1181.9 |
| | 0.39 | 1725.8 |
| 1.130 | 3.13 | 1442.0 |
| | 0.82 | 980.0 |
| 1.131 | 4.70 | 1648.4 |
| 1.132 | 100 | 0.2 |
| 1.133 | 2.74 | 1349.4 |
| | 2.73 | 3132.7 |
| | 1.71 | 1765.6 |
| 1.134 | 17.37 | 2135.6 |
| 1.135 | 13.52 | 127.4 |
| 1.136 | 8.25 | 1913.0 |
| 1.137 | 5.08 | 1666.9 |
| 1.138 | 79.09 | 111.5 |
| 1.140 | 6.34 | 664.2 |
| 1.141 | 12.94 | 877.0 |
| 1.142 | 13.11 | 825.4 |
| 1.143 | 6.48 | 877.7 |
| 1.144 | 9.35 | 901.0 |
| 1.145 | 100 | 3.2 |
| 1.146 | 8.50 | 731.2 |
| 1.147 | 52.53 | 791.2 |
| 1.148 | 100 | 78.9 |
| 1.149 | 3.20 | 1899.3 |
| 1.150 | 100 | 883.9 |
| 1.151 | 100 | −2.6 |
| 1.152 | 3.13 | 1358.4 |
| 1.153 | 64.79 | 18.6 |
| 1.154 | 68.52 | 57.5 |
| 1.155 | 3.16 | 1876.9 |
| 1.156 | 11.42 | 2052.1 |
| 1.157 | 19.49 | 1702.5 |
| 1.158 | 2.59 | 1884.1 |
| 1.159 | 4.91 | 1870.9 |
| 1.160 | 28.37 | 59.6 |
| 1.161 | 13.87 | 91.0 |
| 1.162 | 100 | −2.2 |
| 1.163 | 8.05 | 1915.5 |
| 1.164 | 100 | 1979.4 |
| 1.165 | 100 | 9.0 |
| | 100 | 3.7 |
| 1.166 | 4.79 | 847.6 |
| | 6.33 | 1581.2 |
| 1.167 | 6.42 | 1808.2 |
| | 5.77 | 1208.7 |
| 1.168 | 1.73 | 896.7 |
| | 2.55 | 1748.9 |
| 1.169 | 6.39 | 1840.3 |
| | 4.20 | 941.9 |
| 1.170 | 100 | 152.4 |
| | 100 | 94.1 |
| 1.171 | 65.30 | 612.2 |
| | 70.42 | 689.3 |
| 1.172 | 50.59 | 247.0 |
| | 35.57 | 495.6 |
| 1.173 | 42.08 | 1406.1 |
| 1.175 | 8.49 | 1789.5 |
| 1.176 | 1.63 | 1132.7 |
| 1.177 | 65.07 | 1458.1 |
| 1.178 | 21.16 | 2143.5 |
| 1.179 | 10.10 | 18.1 |
| 1.180 | 100 | 23.0 |
| 1.181 | 100 | 4.7 |
| 1.182 | 100 | 6.1 |
| 1.183 | 25.70 | 39.9 |
| 1.184 | 100 | 1.7 |
| 1.185 | 100 | 1.8 |
| 1.186 | 100 | 1.8 |
| 1.187 | 100 | 4.2 |

TABLE 2-continued

| | W134X-CF#14 FRT data | |
|---|---|---|
| No. | $EC_{50+G418}$ (μM) | $E_{max+G418}$ |
| 1.188 | 100 | 8.3 |
| 1.189 | 2.56 | 701.6 |
| 1.190 | 3.26 | 950.0 |
| 1.191 | 100 | 1.5 |
| 1.192 | 100 | 7.5 |
| 1.193 | 47.24 | 2766.3 |
| 1.194 | 29.72 | 2248.9 |
| 1.195 | 100 | 146.0 |
| 1.196 | 1.56 | 3241.6 |
| 1.197 | 3.91 | 3513.5 |
| 1.198 | 100 | −0.5 |
| 1.199 | 9.50 | 3015.1 |
| 1.200 | 34.92 | 2261.0 |
| 1.201 | 100 | 4.6 |
| 1.202 | 5.51 | 2373.3 |
| 1.203 | 4.10 | 3935.7 |
| 1.204 | 12.50 | 3133.9 |
| 1.205 | 100 | 5.8 |
| 1.206 | 12.95 | 130.3 |
| 1.207 | 35.66 | 33.7 |
| 1.208 | 11.38 | 472.2 |
| 1.209 | 100 | 4.4 |
| 1.210 | 6.68 | 1763.6 |
| 1.211 | 100 | 18.1 |
| 1.212 | 100 | 7.4 |
| 1.213 | 10.25 | 1909.2 |
| 1.214 | 4.70 | 1895.1 |

TABLE 3

| | G542X#10-HBE5x5 | |
|---|---|---|
| No. | $EC_{50+G418}$ | $E_{max+G418}$ |
| 1.1 | 100 | 41.95 |
| 1.2 | 100 | 35.61 |
| 1.3 | 100 | 59.52 |
| 1.4 | 100 | 27.21 |
| 1.6 | 100 | 41.39 |
| 1.7 | 100 | 40.65 |
| 1.8 | 100 | 34.21 |
| 1.10 | 100 | 32.57 |
| 1.11 | 100 | 45.54 |
| 1.12 | 100 | 29.76 |
| 1.14 | 100 | 45.78 |
| 1.15 | 100 | 29.58 |
| 1.17 | 100 | 36.66 |
| 1.18 | 100 | 30.85 |
| | 100 | 31.95 |
| 1.20 | 100 | 29.91 |
| 1.22 | 100 | 34.85 |
| 1.23 | 100 | 48.18 |
| 1.24 | 100 | 41.51 |
| 1.29 | 62.33 | 66.01 |
| 1.30 | 90.55 | 50.71 |
| 1.35 | 100 | 31.27 |
| 1.36 | 100 | 35.17 |
| 1.39 | 100 | 32.81 |
| 1.40 | 100 | 43.15 |
| 1.42 | 100 | 35.09 |
| 1.47 | 50 | 55.81 |
| 1.48 | 100 | 39.72 |
| 1.50 | 29.97 | 94.24 |
| 1.51 | 100 | 91.02 |
| 1.53 | 100 | 29.91 |
| 1.56 | 100 | 31.63 |
| 1.57 | 100 | 33.56 |
| 1.65 | 100 | 41.49 |
| 1.66 | 100 | 31.06 |
| 1.67 | 100 | 37.25 |
| 1.73 | 62.90 | 405.95 |
| 1.74 | 100 | 379.05 |
| 1.86 | 100 | 29.47 |

TABLE 3-continued

| | G542X#10-HBE5x5 | |
|---|---|---|
| No. | $EC_{50+G418}$ | $E_{max+G418}$ |
| 1.87 | 100 | 33.06 |
| 1.96 | 100 | 33.14 |
| 1.103 | 100 | 45.82 |
| 1.104 | 25 | 60.87 |
| 1.105 | 100 | 32.73 |
| 1.106 | 100 | 28.33 |
| 1.107 | 7.03 | 112.88 |
| 1.112 | 100 | 35.25 |
| 1.113 | 100 | 29.12 |
| 1.123 | 100 | 34.37 |
| 1.125 | 100 | 31.14 |
| 1.126 | 100 | 85.22 |
| 1.128 | 99.24 | 98.6 |
| | 100 | 125.55 |
| | 100 | 101.77 |
| | 67.58 | 114.41 |
| | 44.41 | 163.61 |
| | 100 | 111.82 |
| 1.129 | 100 | 48.3 |
| 1.130 | 100 | 58.82 |
| 1.131 | 100 | 40.02 |
| | 100 | 76.17 |
| 1.133 | 50.51 | 61.36 |
| 1.138 | 100 | 53.79 |
| 1.139 | 100 | 48.86 |
| 1.140 | 100 | 83.17 |
| 1.148 | 100 | 30.77 |
| | 38.30 | 123.80 |
| 1.149 | 41.68 | 188.62 |
| 1.152 | 25 | 90.08 |
| 1.158 | 100 | 27.78 |
| 1.164 | 100 | 67.54 |
| 1.165 | 100 | 47.47 |
| 1.168 | 100 | 39.07 |
| 1.174 | 100 | 53.58 |
| 1.175 | 100 | 31.85 |
| 1.176 | 100 | 38.65 |
| 1.177 | 100 | 45.98 |
| 1.180 | 73.18 | 86.83 |
| 1.181 | 100 | 40.62 |
| 1.183 | 100 | 30.08 |
| 1.187 | 100 | 27.06 |
| 1.190 | 100 | 44.76 |
| 1.194 | 100 | 44.5 |
| 1.196 | 100 | 67.88 |
| 1.198 | 100 | 36.87 |
| 1.201 | 100 | 31.84 |
| 1.203 | 100 | 36.03 |
| 1.206 | 18.13 | 100.24 |
| 1.207 | 26.19 | 83.24 |
| 1.208 | 100 | 33.48 |
| | 29.08 | 189.47 |
| 1.209 | 100 | 29.94 |
| | 100 | 25.47 |
| 1.212 | 100 | 34.56 |
| 1.214 | 100 | 33.39 |
| 1.215 | 100 | 27.90 |
| 1.216 | 100 | 32.08 |
| 1.217 | 100 | 28.84 |
| 1.218 | 100 | 32.6 |
| 1.219 | 48.51 | 93.50 |
| 1.220 | 100 | 55.91 |
| 1.221 | 100 | 33.39 |
| | 100 | 35.15 |
| 1.222 | 100 | 30.5 |
| 1.223 | 100 | 32.71 |
| | 100 | 30.02 |
| 1.224 | 100 | 29.56 |
| | 100 | 28.66 |
| 1.225 | 32.85 | 64.94 |
| | 100 | 39.74 |
| 1.226 | 100 | 41.53 |
| 1.227 | 100 | 207.62 |
| 1.228 | 100 | 27.93 |
| 2.1 | 30 | 18.5 |
| | 30 | 2.67 |

TABLE 3-continued

| | G542X#10-HBE5x5 | |
|---|---|---|
| No. | $EC_{50+G418}$ | $E_{max+G418}$ |
| | 30 | |
| 2.2 | 30 | |
| | 30 | 42.31 |
| | 30 | 3.44 |
| | 30 | |
| 2.3 | 30 | |
| | 30 | 1.71 |
| | 30 | |
| | 30 | 22.61 |
| 2.4 | 30 | 25.7 |
| | 30 | |
| | 30 | |
| | 30 | 3.08 |
| 2.5 | 30 | 16.01 |
| | 30 | |
| | 30 | 1.43 |
| | 30 | |
| 2.6 | 30 | |
| | 30 | 40.23 |
| | 30 | |
| | 30 | 5.42 |
| 2.7 | 30 | 1.74 |
| | 30 | |
| | 30 | 19.12 |
| | 30 | |
| 2.8 | 30 | |
| | 30 | 0.6000 |
| | 30 | |
| | 30 | 22.49 |
| 2.9 | 6.06 | 56.01 |
| | 30 | |
| | 30 | |
| | 30 | 1.5 |
| 2.10 | 30 | |
| | 30 | |
| | 30 | 3.16 |
| | 30 | 42.41 |
| 2.11 | 30 | |
| | 18.243 | 72.68 |
| | 30 | |
| | 30 | 10.24 |
| 2.12 | 30 | |
| | 30 | |
| | 30 | 5.48 |
| | 30 | 40.23 |
| 2.13 | 30 | 4.5 |
| | 30 | |
| | 30 | 49.07 |
| | 30 | |
| 2.14 | 30 | |
| | 30 | |
| | 30 | 6.42 |
| | 30 | 40.08 |
| 2.15 | 30 | 1.9 |
| | 30 | |
| | 30 | |
| | 30 | 40.73 |
| 2.16 | 30 | 19.4 |
| | 30 | |
| | 30 | 2.91 |
| | 30 | |
| 2.17 | 30 | |
| | 30 | |
| | 30 | 29.96 |
| | 30 | 32.35 |
| 2.18 | 30 | |
| | 30 | |
| | 30 | 31.62 |
| | 30 | 3.99 |
| 2.19 | 30 | 3.01 |
| | 30 | |
| | 30 | |
| | 30 | 17.72 |
| 2.20 | 30 | |
| | 30 | |
| | 30 | 2.66 |
| | 30 | 30.5 |
| 2.21 | 30 | |
| | 30 | 17.38 |
| | 30 | |
| | 30 | 0.8800 |
| 2.22 | 30 | 1.13 |
| | 30 | |
| | 30 | 24.31 |
| | 30 | |
| 2.23 | 30 | 1.28 |
| | 30 | |
| | 30 | 24.18 |
| | 30 | |
| 2.24 | 30 | |
| | 30 | 25.82 |
| | 30 | 1.44 |
| | 30 | |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound selected from:

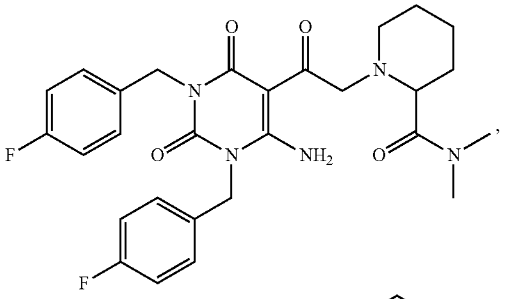

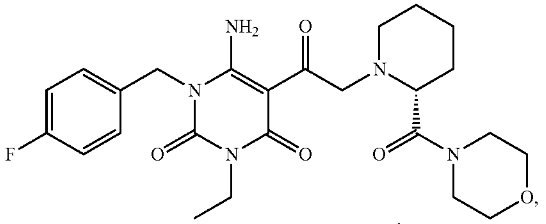

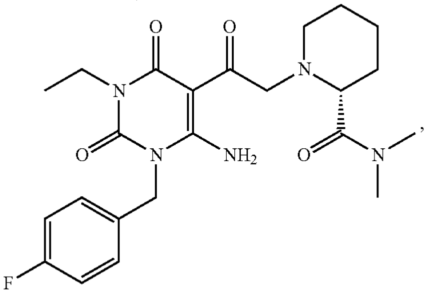

-continued
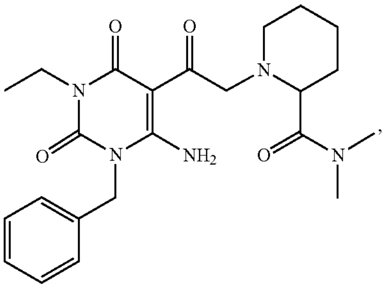
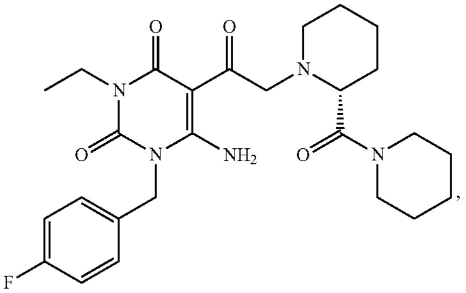
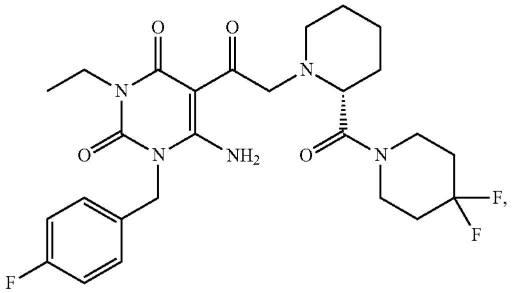
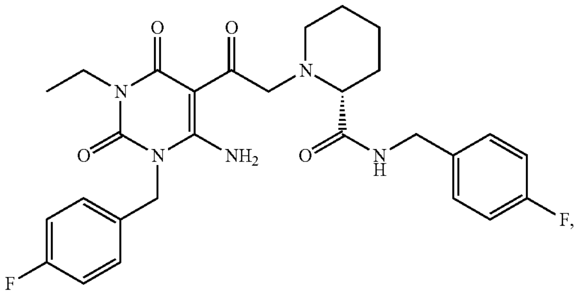
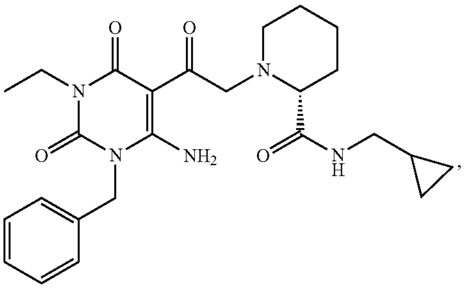
-continued
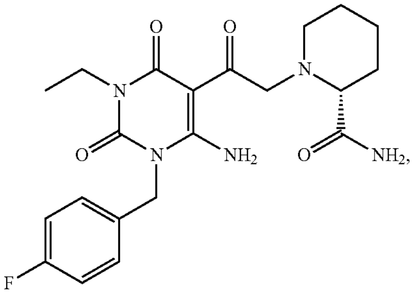
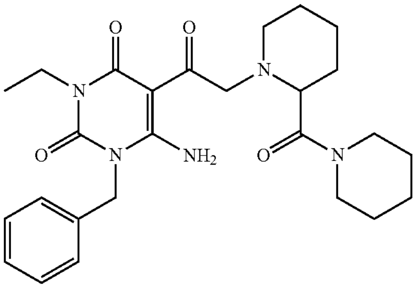
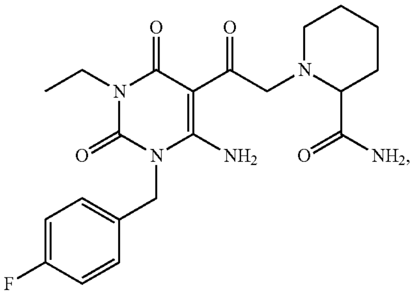
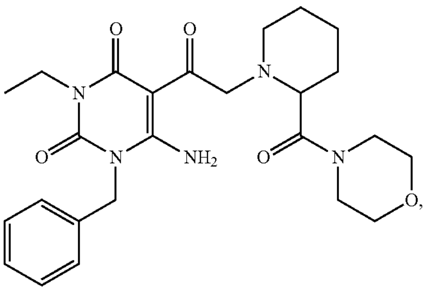
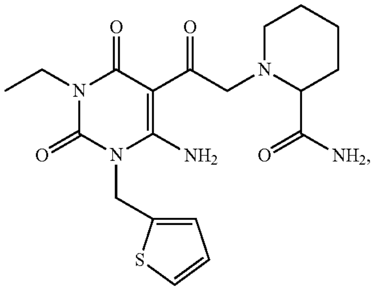

-continued
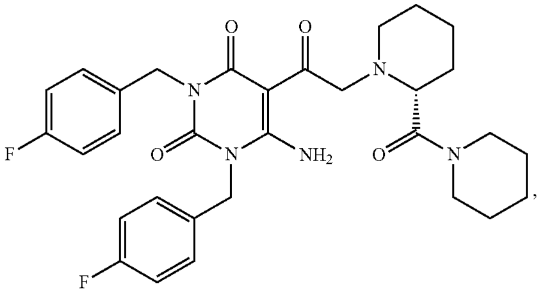
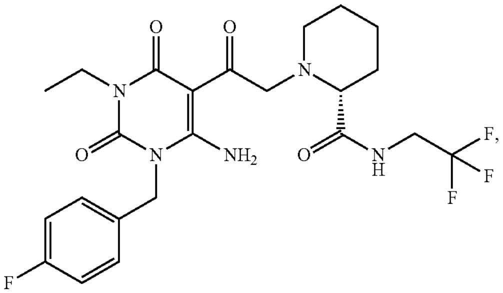
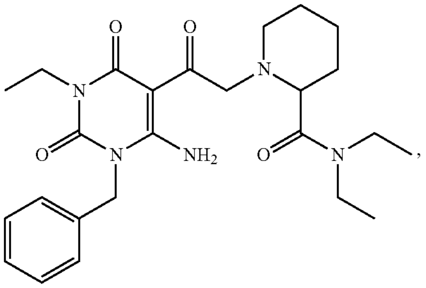
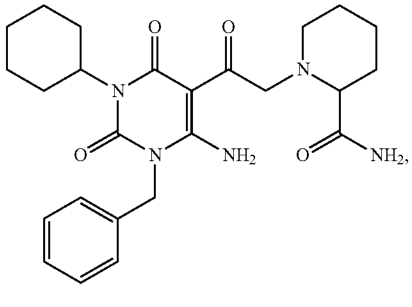
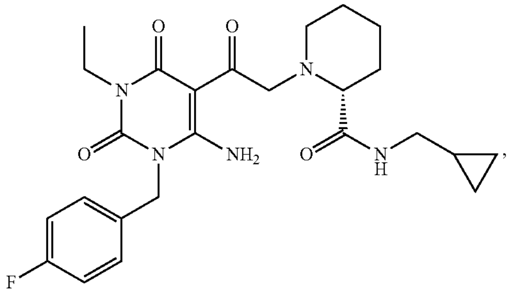
-continued
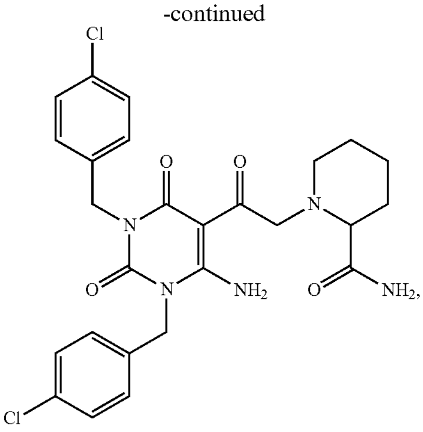
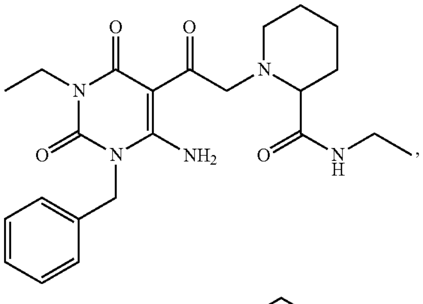
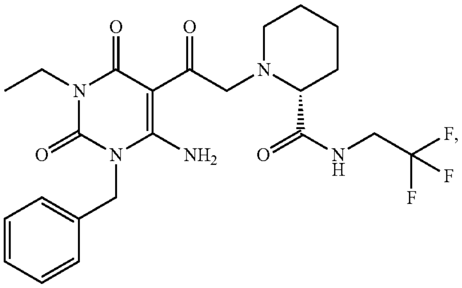
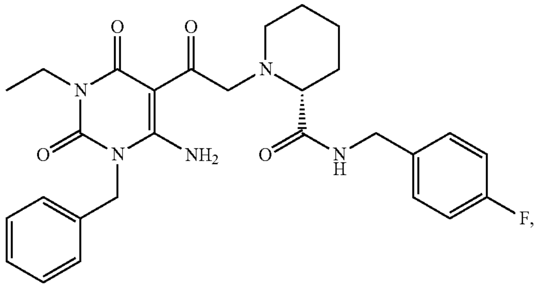
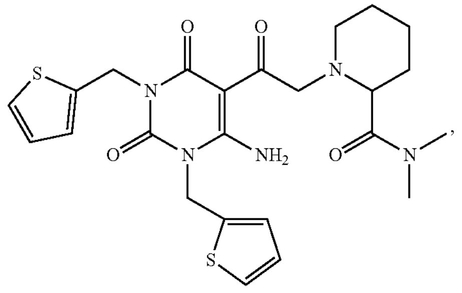

-continued
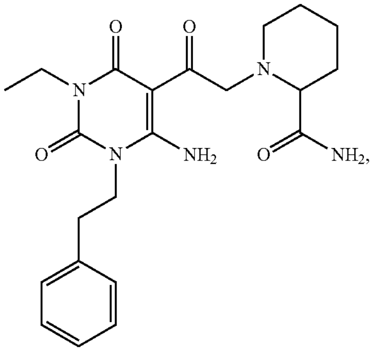
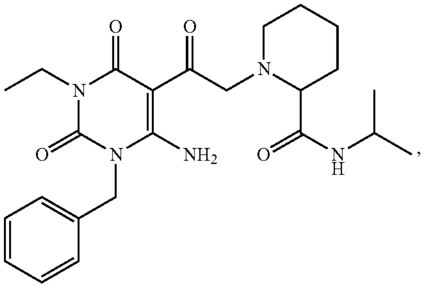
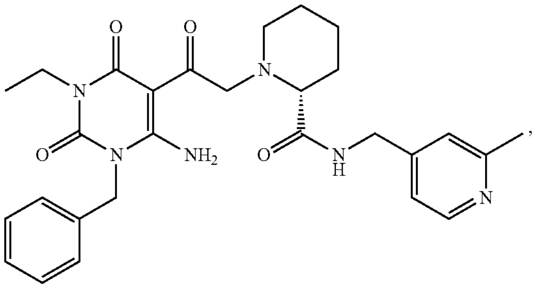
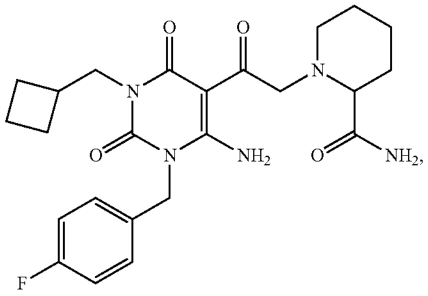
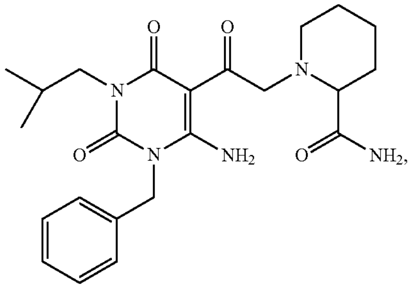
-continued
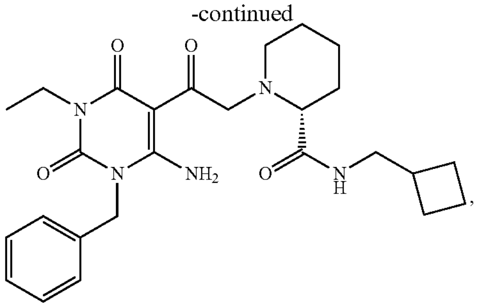
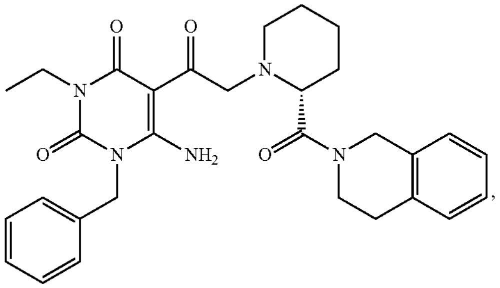
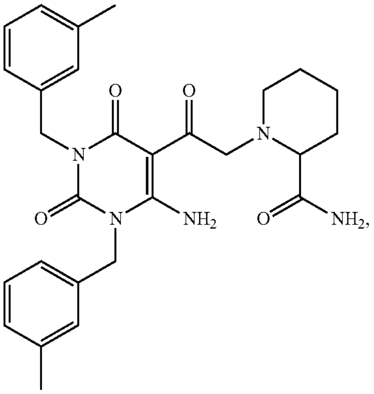
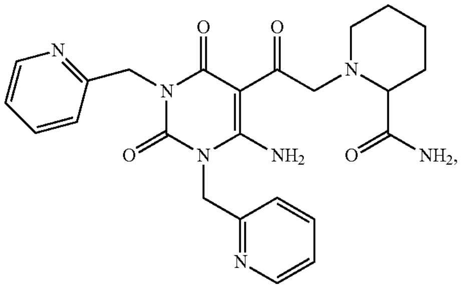
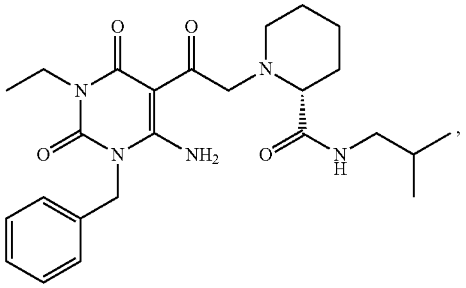

-continued
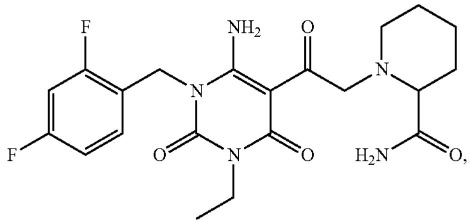
,
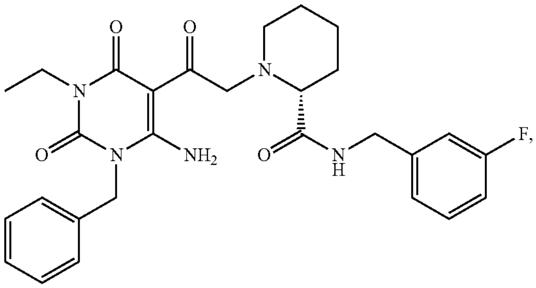
,
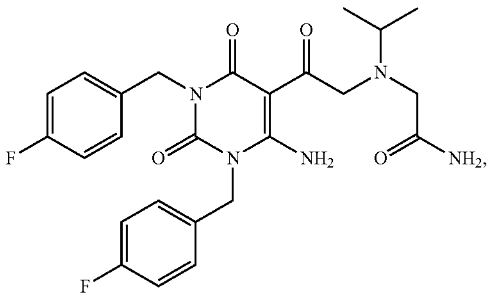
,
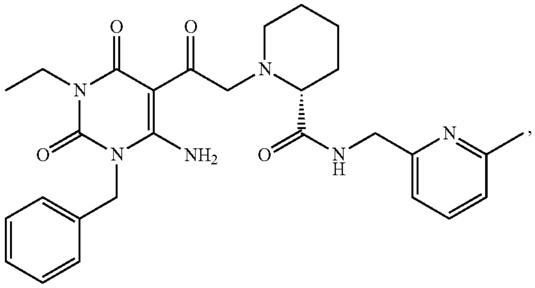
,
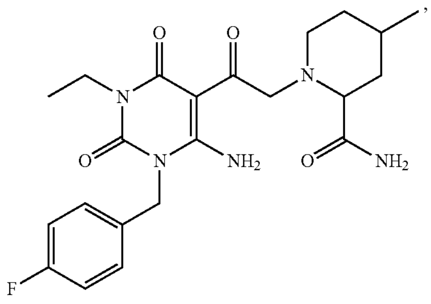
,
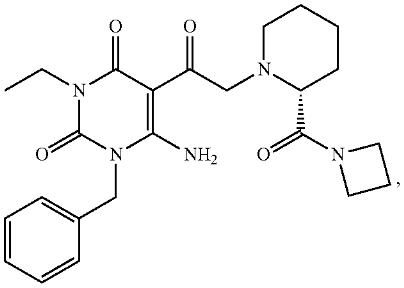
,
-continued
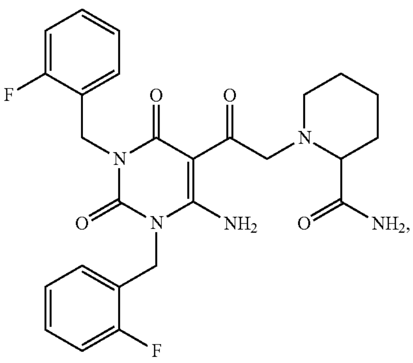
,
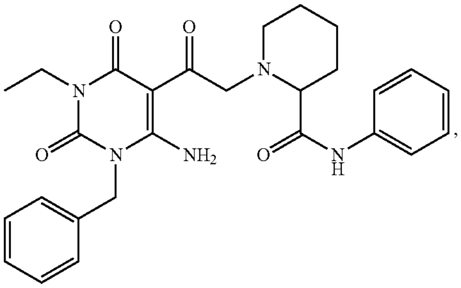
,
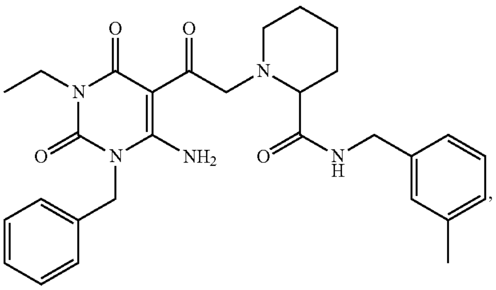
,
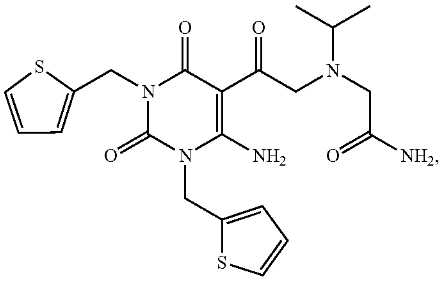
,
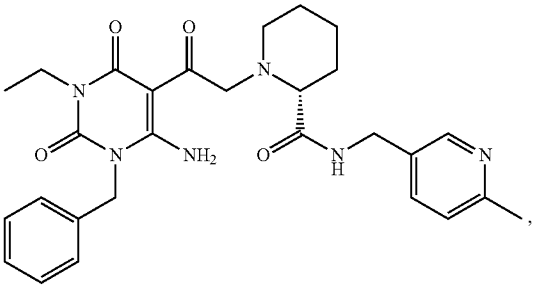
, -continued
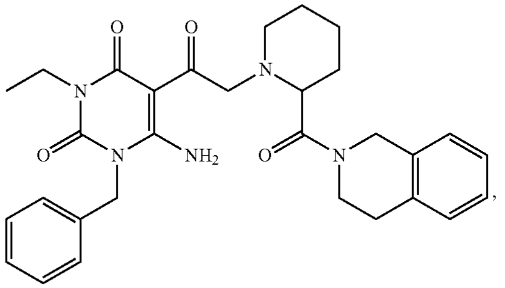
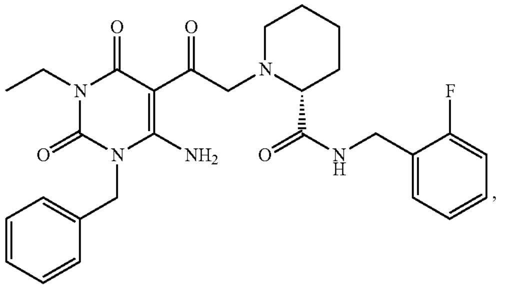
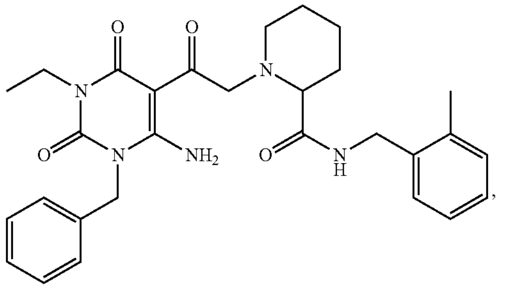
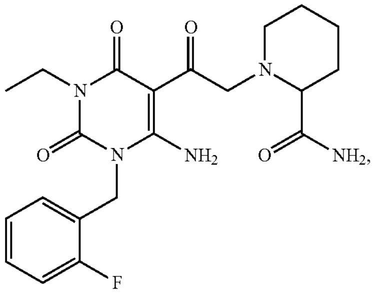
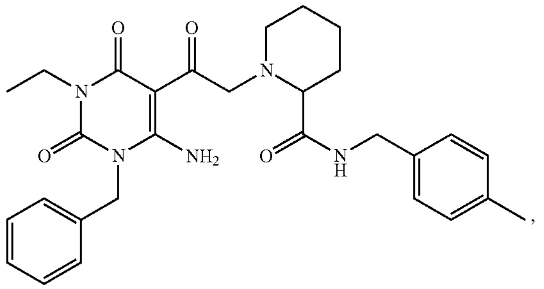
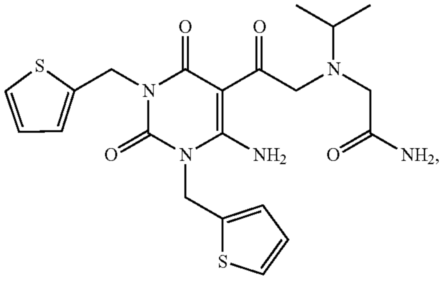
-continued
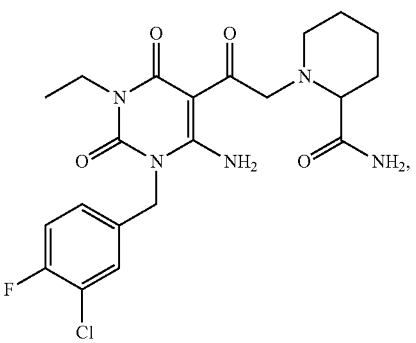
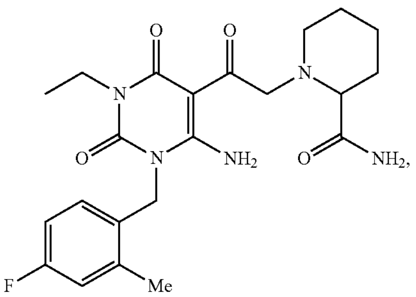
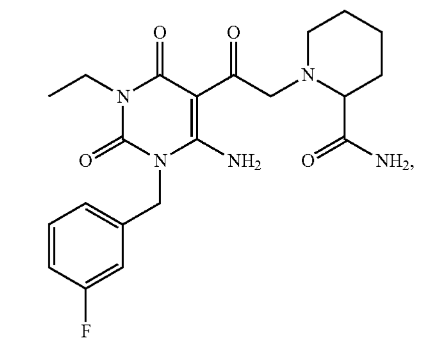
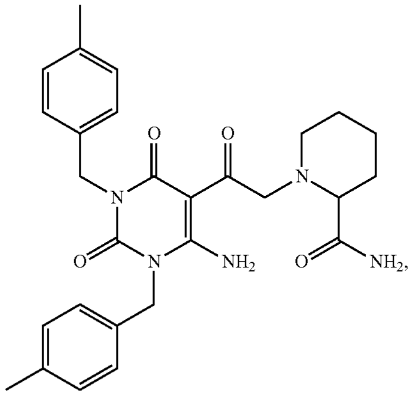
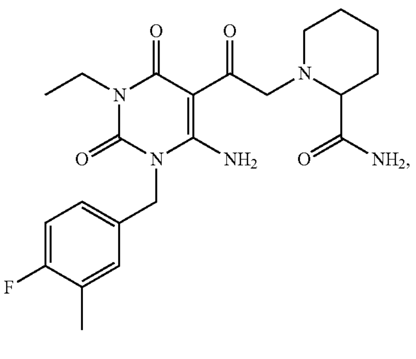

-continued
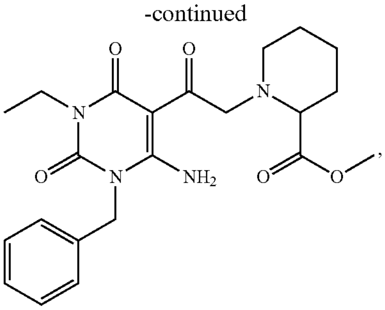
,
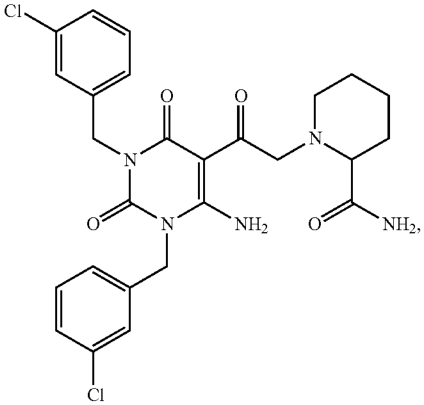
,
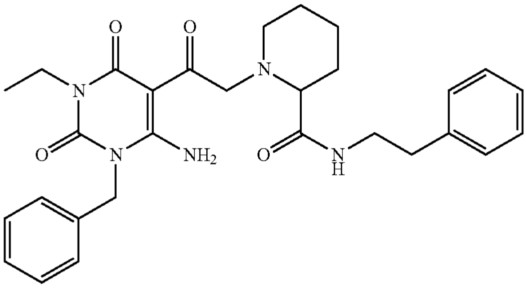
,
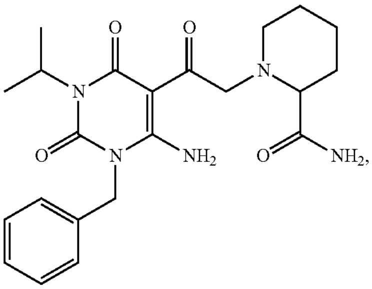
,
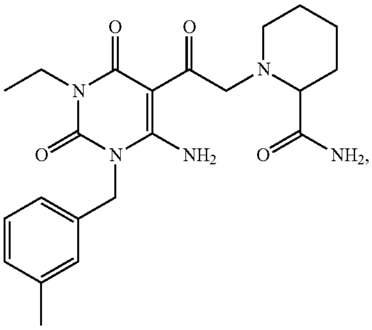
,
-continued
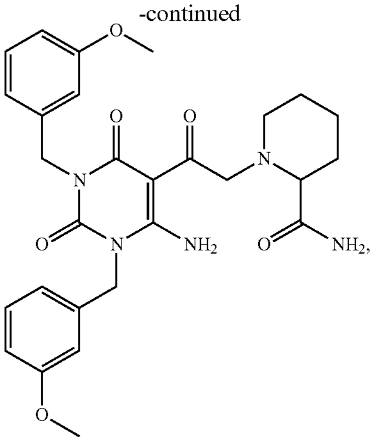
,
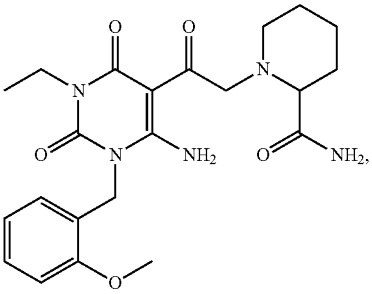
,
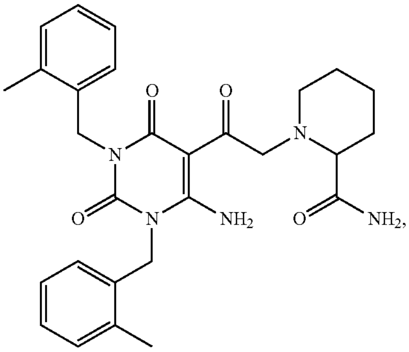
,
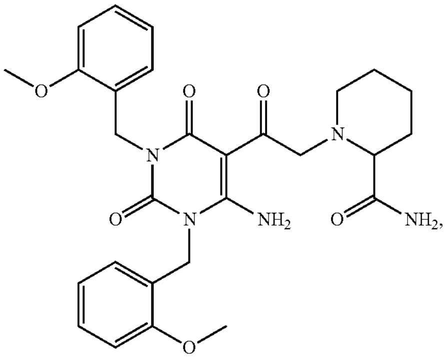
, -continued
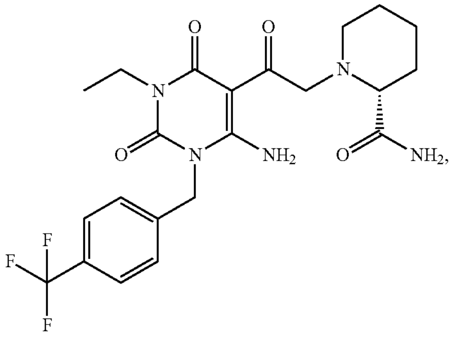
,
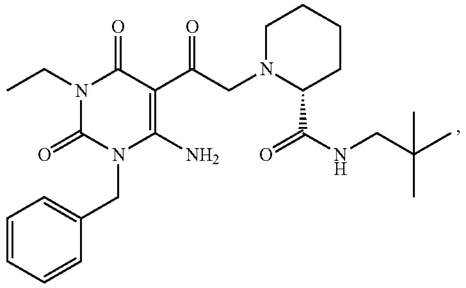
,
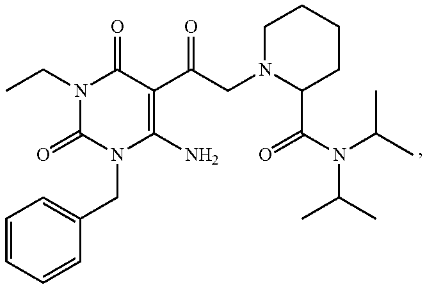
,
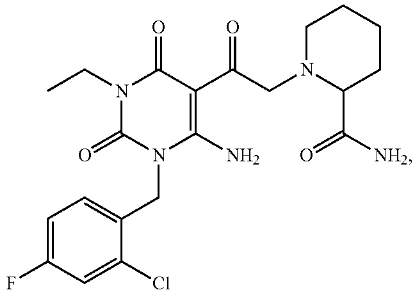
,
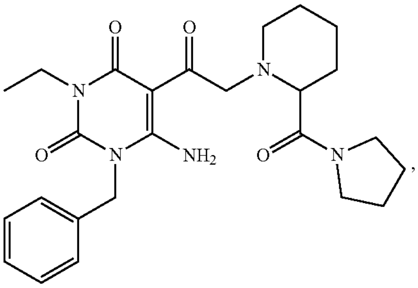
,
-continued
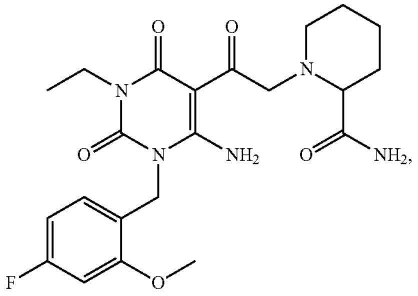
,
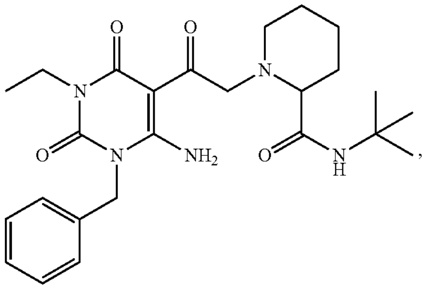
,
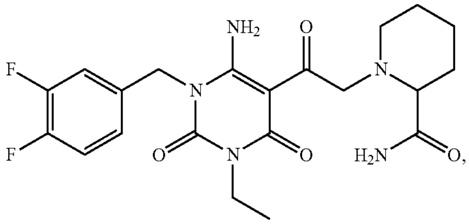
,
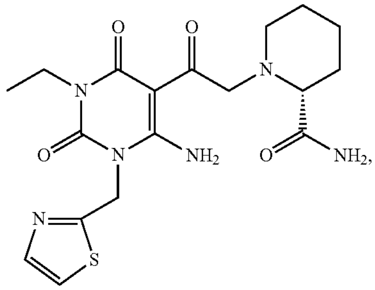
,
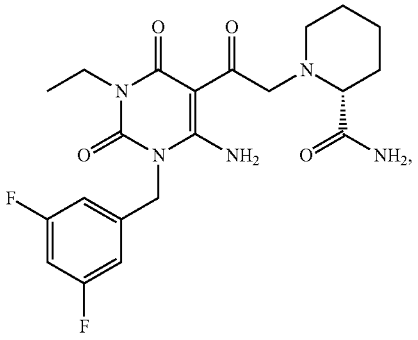
,
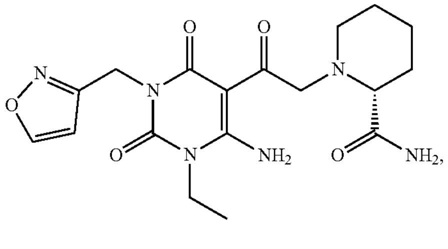
, -continued
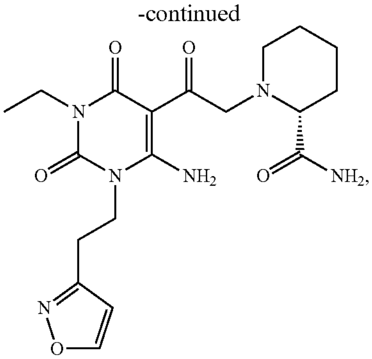
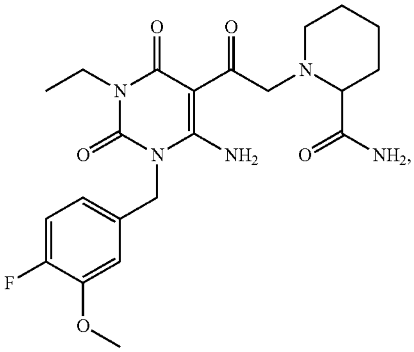
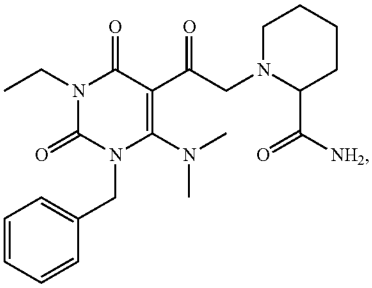
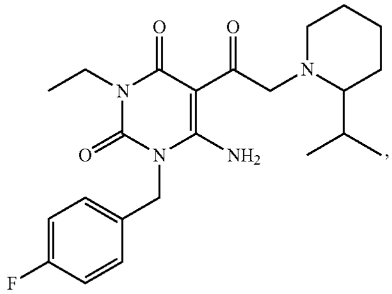
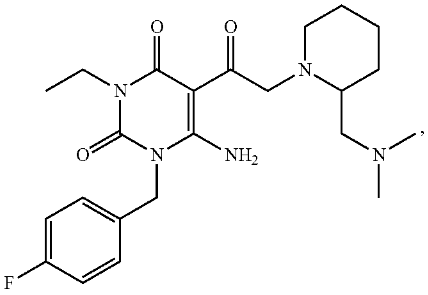
-continued
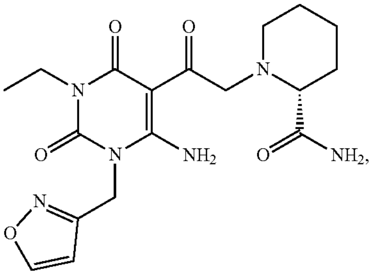
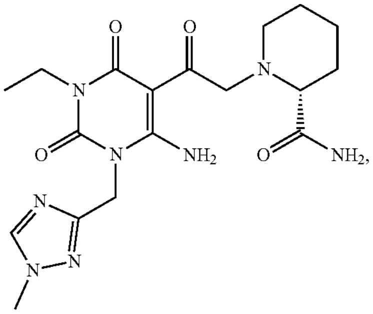
and
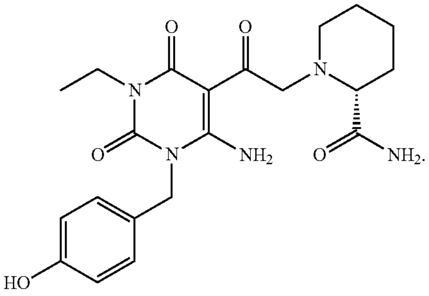 [SMILES: CCn1c(=O)c(C(=O)CN2CCCC[C@@H]2C(N)=O)c(N)n(Cc2ccc(O)cc2)c1=O]
2. The compound of claim 1, wherein the compound is:
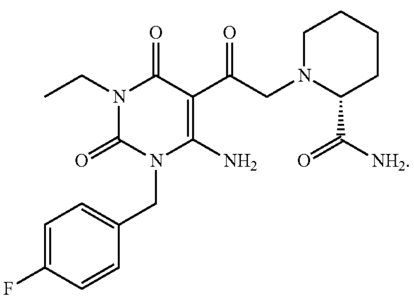
* * * * *